(12) United States Patent
Kersten et al.

(10) Patent No.: US 12,241,072 B2
(45) Date of Patent: Mar. 4, 2025

(54) BIOSYNTHETIC APPROACH FOR HETEROLOGOUS PRODUCTION AND DIVERSIFICATION OF BIOACTIVE LYCIUMIN CYCLIC PEPTIDES

(71) Applicant: Whitehead Institute for Biomedical Research, Cambridge, MA (US)

(72) Inventors: Roland D. Kersten, Arlington, MA (US); Jing-Ke Weng, Belmont, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 402 days.

(21) Appl. No.: 16/963,099

(22) PCT Filed: Jan. 21, 2019

(86) PCT No.: PCT/US2019/014430
§ 371 (c)(1),
(2) Date: Jul. 17, 2020

(87) PCT Pub. No.: WO2019/144083
PCT Pub. Date: Jul. 25, 2019

(65) Prior Publication Data
US 2020/0347396 A1    Nov. 5, 2020

Related U.S. Application Data

(60) Provisional application No. 62/732,957, filed on Sep. 18, 2018, provisional application No. 62/620,420, filed on Jan. 22, 2018, provisional application No. 62/619,905, filed on Jan. 21, 2018.

(51) Int. Cl.
C12N 15/82    (2006.01)
C07K 7/64     (2006.01)
C07K 14/415   (2006.01)

(52) U.S. Cl.
CPC ............ C12N 15/8241 (2013.01); C07K 7/64 (2013.01); C07K 14/415 (2013.01)

(58) Field of Classification Search
None
See application file for complete search history.

(56) References Cited

U.S. PATENT DOCUMENTS

| | | |
|---|---|---|
| 2002/0055186 A1 | 5/2002 | Barry et al. |
| 2007/0277269 A1* | 11/2007 | Alexandrov et al. .................. C07K 14/415 536/23.6 |
| 2009/0311284 A1 | 12/2009 | Liang et al. |
| 2010/0100988 A1 | 4/2010 | Tranel et al. |
| 2012/0011598 A1 | 1/2012 | Troukhan et al. |
| 2012/0096584 A1 | 4/2012 | Alexandrov et al. |
| 2013/0333061 A1* | 12/2013 | Wu et al. ............. C07K 14/415 800/300 |
| 2014/0283201 A1 | 9/2014 | Flasinski et al. |
| 2017/0240883 A1 | 8/2017 | Christiansen |

FOREIGN PATENT DOCUMENTS

| | | | |
|---|---|---|---|
| WO | WO 2014/057284 A2 | | 4/2014 |
| WO | WO 2017/054044 A | * | 6/2017 |
| WO | WO2017/054044 A1 | * | 6/2017 |
| WO | PCT/US2019/014430 | * | 4/2019 |

OTHER PUBLICATIONS

Potterat (2009) Planta Medica 76(1):7-19.*
Written Opinion of Intn'l Searching Authority (WOSA) PCT/US2019/014430 (2019).*
NCBI Reference Sequence: NP_001235780.2 (2021).*
Chigumba et al. (2022) Nat Chem Biol 18:18-28.*
Morita et al. (1996) Tetrahedron 52(8):2795-2802.*
Written Opinion of the International Searching Authority for PCT Application Serial No. US2019/014430 (2019).*
Potterat (2009) Planta Med 76: 7-19.*
Buckley & Haydon (2024) Sci 383(6683):589-90.*
International Preliminary Report on Patentability for International Application No. PCT/US2019/014430, entitled: "A Biosynthetic Approach For Heterologous Production and Diversification of Bioactive Lyciumin Cyclic Peptides," dated Jul. 21, 2020.
Potterat, O. et al., "Goji (Lycium barbarum and L. Chinese): Phytochemistry, Pharmacology and Safety in the Perspective of Traditional Uses and Recent Popularity," Planta Med, vol. 76; 7-19 (2009).
Notification of Transmittal of the International Search Report and the Written Opinion of International Application No. PCT/US2019/014430, entitled: "A Biosynthetic Approach For Heterologous Production and Diversification of Bioactive Lyciumin Cyclic Peptides," mailed Apr. 18, 2019.

\* cited by examiner

*Primary Examiner* — Russell T Boggs
(74) *Attorney, Agent, or Firm* — HAMILTON, BROOK, SMITH & REYNOLDS, P.C.

(57) ABSTRACT

Lyciumin cyclic peptides and methods of producing lyciumin cyclic peptides are described. A host cell can include a transgene encoding a lyciumin precursor peptide, or a biologically-active fragment thereof. The lyciumin precursor peptide, or biologically-active fragment thereof, can include one or more core lyciumin peptide domains. The transgene can be expressed in the host cell to thereby produce a lyciumin precursor peptide, or biologically-active fragment thereof. The lyciumin precursor peptide, or biologically-active fragment thereof, can be converted to one or more lyciumin cyclic peptides in the host cell. A library of nucleic acids encoding lyciumin precursor peptides, or biologically-active fragments thereof, can be generated.

26 Claims, 62 Drawing Sheets
Specification includes a Sequence Listing.

*Lycium barbarum*

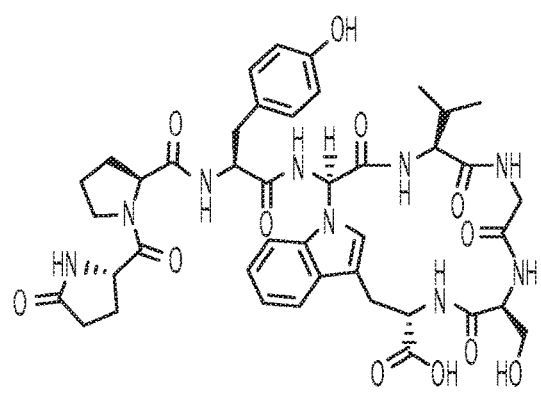
Lyciumin A
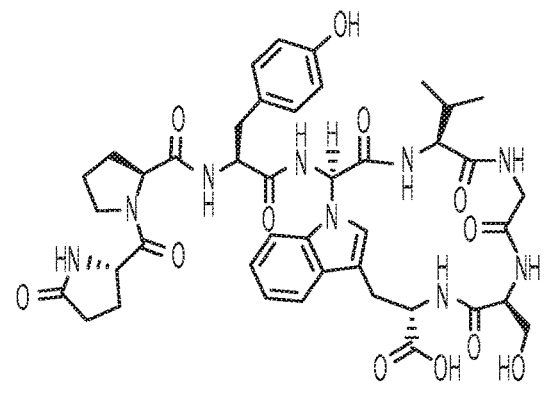
Lyciumin C
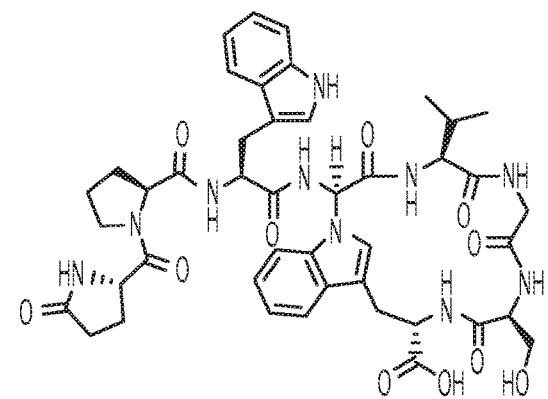
Lyciumin B
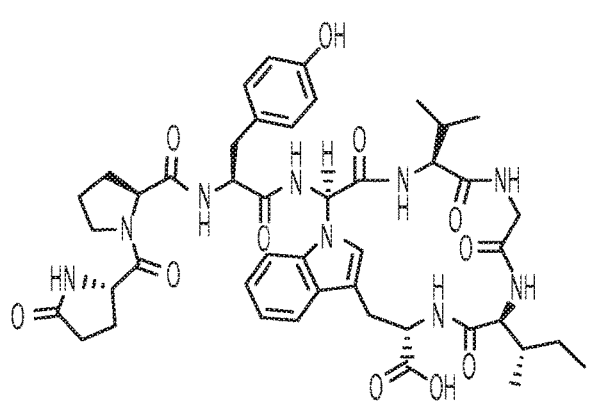
Lyciumin D
FIG. 1B >LbaLycA
MELHHHYFFILLSLAFIASHAANLSPEVYWKVKLPNTPMPRP
IKDALHYSEASEGDVHKLRQPWGVGSWYQAANEGDIKKLR*QP*
*YGVGIWY*QAANEGDVKKLRQPWGVGSWYQAANEGDVKKLRQP
WGVGSWYQAANEGDVKKLRQPWGVGSWYQAANEGDANEGDVK
KLR*PYGVGIWY*QAANEGDVKKLRQPWGVGSWYQAANEGDVK
KLRQPWGVGSWYQAANEGDVKKLHQPWGVGSWYQAANEGDVK
KLPQPWGVGSWYQAANEGDVKKLR*PYGVGIWY*EAANEGQVK
KLR*QPYGVGSW*YNTATKKDVNENLPVTPYFFETDLHQGKKMN
LPSLKNYNPAPILPRKVADSIPFSSDKIEEILKHFSIDKDSE
GAKMIKKTIKMCEEQAGNGEKKYCATSLESMVDFTSSYLGTN
NIIALSTLVEKETPEVQIYTIEEVKEKANGKGVICHKVAYPY
AIHYCHSVGSTRTFMVSMVGSDGTKVNAVSECHEDTAPMNPK
ALPFQLLNVKPGDKPICHFILDDQIALVPSQDATQVSEN (SEQ ID NO: 1)

FIG. 1C

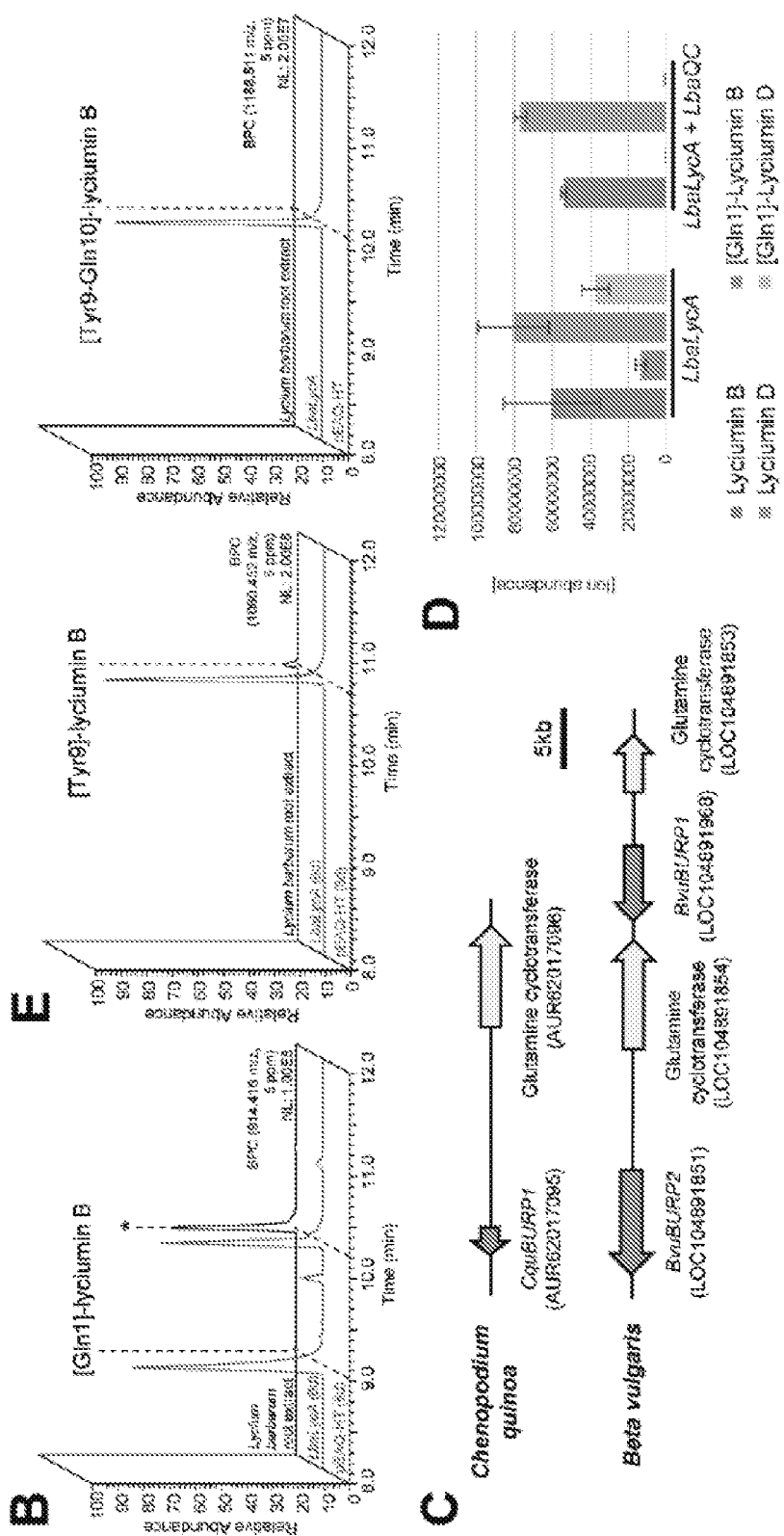
FIGs. 3B-E

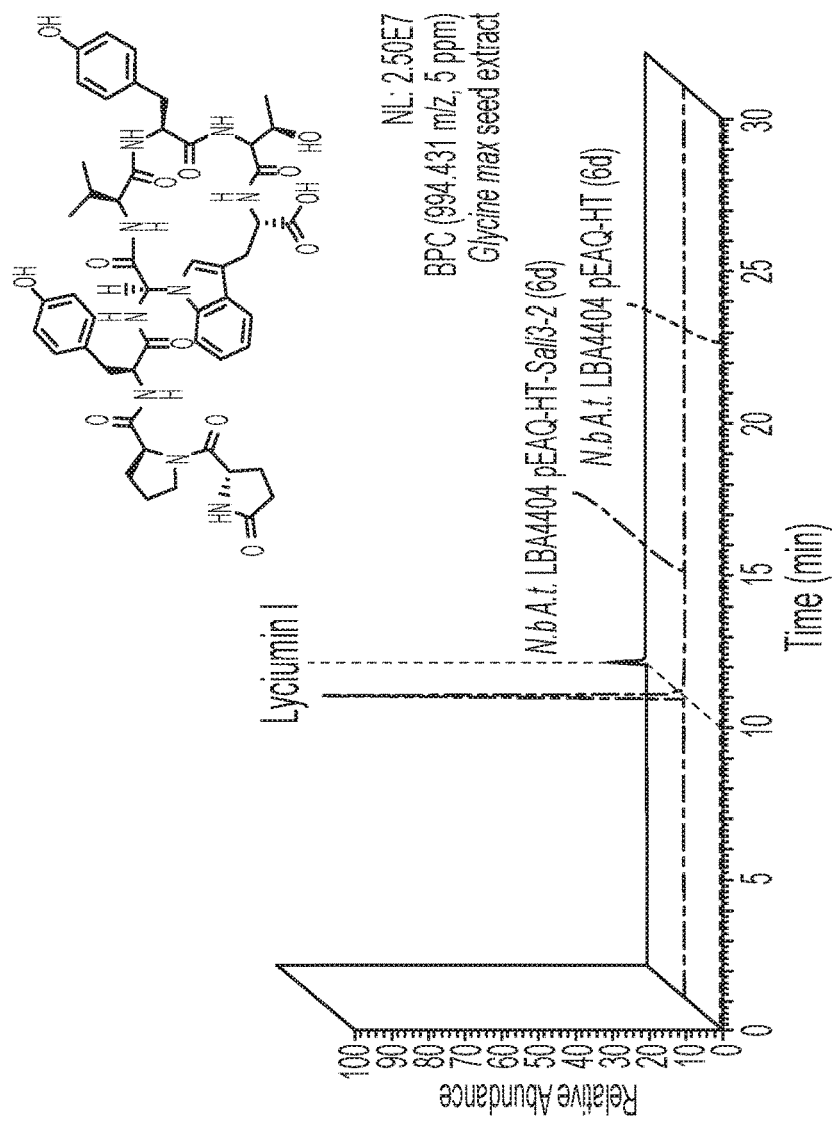

FIG. 4A

```
>Glyma.12G217400 (Glycine max, Sali3-2)
MEFRCSVISFTILFSLALAGESHVASLPEEDYWEAVWP
NTPIPTAIRELLKPLPAGVETDELPKQIDDTQYPKTFFY
KEDLHPGKTMKVQFTKRPYAQPYGVYTWLTDIKDTSKEG
YSFTETCIKKEAFEGEEKFCAKSLGTVTGFAISKLGKNI
QVLSSSFVNKQEQYTVEGVQNLGDKAVMCHGLNFRTAVF
YCHKVRETTAFMVPLVAGDGTKTQALAVCHSDTSGMNHH
MLHELMGVDPGTNPVCHFLGSKATIWPNLSMDTAYQTIN
VVV
                                  (SEQ ID NO: 2)
```

| Name | | | | | | | | | |
|---|---|---|---|---|---|---|---|---|---|
| Glycine max lyciumin I [Ala1] | | P | Y | G | V | Y | T | W | yes |
| Glycine max lyciumin I [Ala2] | Q | | Y | G | V | Y | T | W | yes |
| Glycine max lyciumin I [Ala3] | Q | P | | G | V | Y | T | W | yes |
| Glycine max lyciumin I [Ala4] | Q | P | Y | | V | Y | T | W | yes |
| Glycine max lyciumin I [Ala5] | Q | P | Y | G | | Y | T | W | yes (low yield) |
| Glycine max lyciumin I [Ala6] | Q | P | Y | G | V | | T | W | yes |
| Glycine max lyciumin I [Ala7] | Q | P | Y | G | V | Y | | W | yes |
| Glycine max lyciumin I [Ala8] | Q | P | Y | G | V | Y | T | | no |
| Glycine max lyciumin I [Thr4] | Q | P | Y | T | V | Y | T | W | yes |
| Glycine max lyciumin I [9aa-(5aa-cyclic)] | Q | P | Y | G | V | Y | T | W | no |
| Glycine max lyciumin I [7aa-(4aa-cyclic)] | Q | P | Y | G | V | Y | T |  | no |
| Glycine max lyciumin I [Ala1 & 4aa linear N-terminus] |  |  |  |  | V | Y | T | W | no |
| Glycine max lyciumin I [7aa-(5aa-cyclic)] |  | P | Y | G | V | Y | T | W | no |
| Glycine max lyciumin I [6aa-(5aa-cyclic)] |  |  | Y | G | V | Y | T | W | no |
| Glycine max lyciumin H | Q | P | Y | G | V | Y | A | W | yes |
| Solanum tuberosum lyciumin K | Q | P | Y | G | V | Y | S | W | yes (low yield) |
| M. truncatula predicted lyciumin (Medtr8g045890) | Q | P | Y | G | V | Y | T | W | yes |
| M. truncatula predicted lyciumin (Medtr2g081590) | Q | P | Y | G | V | Y | T | W | yes |
| Nicotiana attenuata predicted lyciumin precursor (XP_019246232.1) | Q | P | Y | G | V | Y | T | W | yes |
| Glycine max lyciumin I [Phe3] | Q | P | F | G | V | Y | T | W | no |
| Glycine max lyciumin I [Trp3] | Q | P | W | G | V | Y | T | W | no |
| Glycine max lyciumin I [Phe8] | Q | P | Y | G | V | Y | T | F | no |
| Glycine max lyciumin I [His8] | Q | P | Y | G | V | Y | T | H | no |
| Glycine max lyciumin I [Tyr8] | Q | P | Y | G | V | Y | T | Y | no |
| Capsicum annuum precursor (XP_016572294.1) | Q | P | Y | G | V | Y | T | W | yes |

FIG. 4B

```
>TRINITY_DN33942_c0_g1_i2_m.67 TRINITY_DN33942_c0_g1_i2_g.67 type:5prime_partial        (SEQ ID NO:
len:297 gc:universal TRINITY_DN33942_c0_g1_i2:2-892(+)                                  130)
EGDVKKLF░░░░░YQAANEGDVKKLR░░░░░YEAANEGDVKKLR░░░░░VNTATKKDVNEMLPVTFYFFETILRQGK
KMNLPSLKNVNPAPILPRKVADSIPFSSDKIEEILKHFSIDKDSEGARMIRKTIKMCEEQAGNGEKKYCATSLESMVDFTSSYLGT
MNIIALSTIVEKETPEVQITTEEVKEKANGKSVICHKVAYPYAIHYCHSVGSTRTFMVSMVGSDGTKVNAVSECHEDTAPMNFKA
LPFQLLMVKPGDKPICHFILDEQIALVFSQDATQVSEN*
>TRINITY_DN32732_c0_g2_i11m.98 TRINITY_DN32732_c0_g2_i11g.98 type:internal len:130      (SEQ ID NO:
gc:universal TRINITY_DN32732_c0_g2_i1:309-3(-)                                          131)
GIKQQTRVMLKNVIANHGEWVPGIKQQTRVMLKNYTNHGEWVPGIKQQTRVMLKNYPAHGEWVPGIKQQTRVMLKNYAMPELVYGM
KQQTRVLKKLR░░░░░YQAANEGDVKKIP░░░░░YQ
>TRINITY_DN32732_c0_g2_i31m.101 TRINITY_DN32732_c0_g2_i3ig.101 type:5prime_partial      (SEQ ID NO:
len:345 gc:universal TRINITY_DN32732_c0_g2_i3:1216-182(-)                               132)
MVYQAANEGDVKKLR░░░░░YQAANEGDVKKLR░░░░░V
ERAANEGDVKKLR░░░░░VNTATKKDVNEMLPVTFYFFETDLRQGKKMMLPSLKNVMPAPILPRKVADSIPFSSDKIEEILKHF
SIDKDSEGARMIKTIRMCEEQAGMGEKKYCATSLESMVDFTSSYLGTMNIIALSTIVEKETPEVQITTEEVKEKANGKGVICHK
VAYPYAIHYCHSVGSTRTFMVSMVGSDGTKVNAVSECHEDTAPMNFKALPFQLLMVZPGDKPICHFILDDQIALVFSQDATQVSEN
```

| Transcript | Lycium chemotype | Gene expression (RSEM (TPM)) in tissues/conditions | | | | | | |
|---|---|---|---|---|---|---|---|---|
| | | Cotyledon | Developing embryo | Drought | Leaf | Mature seed | Root | Stem | Flower |
| AHYPO_007393-RA | Lycumin A & C | 37339 | | 60460 | | | | 15572 | |
| References (SRA) | | SRR1598915 | SRR1598909 | SRR1598914 | SRR1598912 | SRR1598916 | SRR1598913 | SRR1598911 | SRR1598910 |

FIG. 8B

| Transcript | Lycium chemotype | Gene expression (RSEM (TPM)) in tissues/conditions | | | | | | | | | | | | | | |
|---|---|---|---|---|---|---|---|---|---|---|---|---|---|---|---|---|
| | | Flower 1 | Flower 2 | Flower 3 | Leaf 1 | Leaf 2 | Leaf 3 | Seed 1 | Seed 2 | Seed 3 | Stem 1 | Stem 2 | Stem 3 | Seedling 1 | Seedling 2 | Seedling 3 |
| AIR62017095 | Lycumin F & G | 1777.8 | 1384.4 | 1095.6 | | | | 270.1 | 355.2 | 207.5 | | | | 184.7 | 159.4 | 165.18 |
| Reference (SRA) | | SRR5974430 | SRR5974427 | SRR5974436 | SRR5974438 | SRR5974437 | SRR5974435 | SRR5974426 | SRR5974424 | SRR5974431 | SRR5974432 | SRR5974433 | SRR5974425 | SRR5974428 | SRR5974429 | SRR5974434 |

FIG. 8C

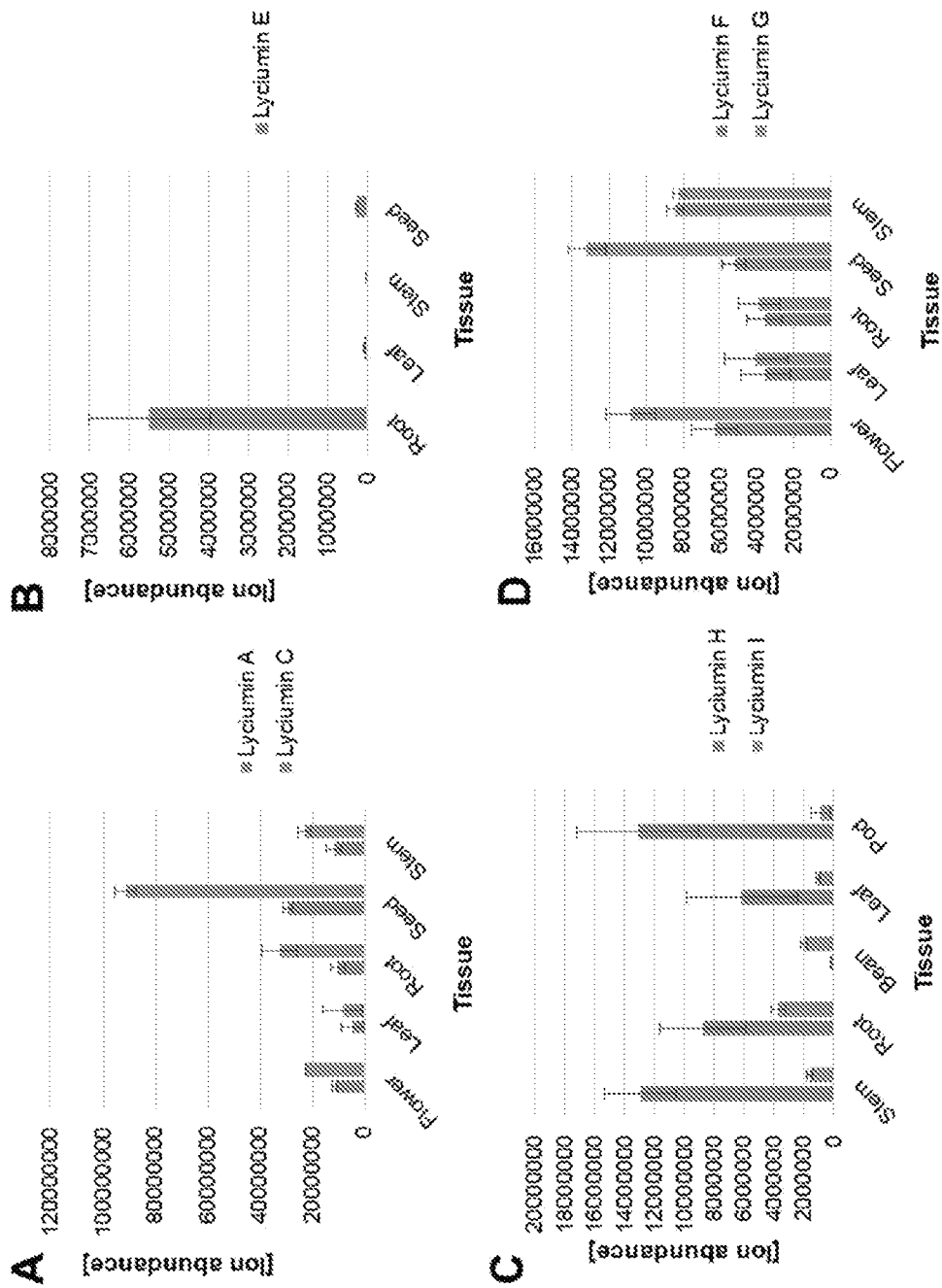
FIGs. 9A-D

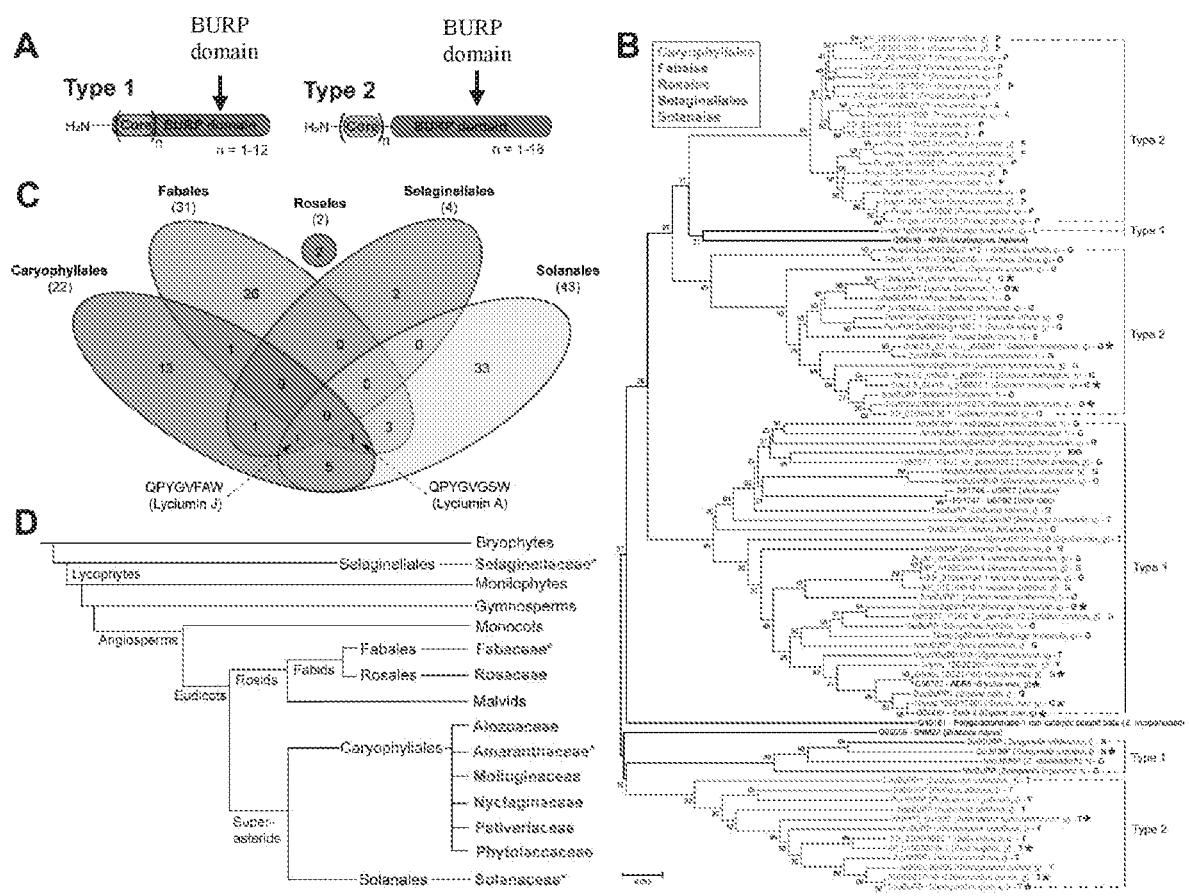
FIGs. 10A-D

>AHYPO_007393 Org_Ahypochondriacus peptide:
AHYPO_007393-RA
MAMDLRLQFPALFLLTFLALHASSCKQEDYWKMKLPKVPMPEAIKQSL
LHSGGENKLKDDSALKQPYTVGSWKYDVDTNKVKDDSVVKQPYTVGSW
KYDADKNKVPDESALK*QPYTVFSW*KYDAGENKVKDESALK*QPYTVGSW*
KYDAGENKVKDESALK*QPYTVFSW*KYDAGENKVKDESALK*QPYTVGSW*
KYDAGENKVKDESALK*QPYTVFSW*KYDAGENKVKDESALK*QPYTVGSW*
KYDAGENKVKDESALK*QPYTVFSW*KYDAGENKVKDESALK*QPYTVGSW*
KYDAGENKVKDESALK*QPYTVFSW*KYDAGENKVKDESALK*QPYTVGSW*
KYDAGENKVKDESALK*QPYTVFSW*KYDAGENKVKDESALKQPYTVGSW
KYDAGENKVKDESALKQPYTVGSWKYNENDESKQASPHHLHHHKLMHD
NVNSKDQEDLTDGSVFFVEKSLHIGSKLKHDFQKTPKTSFLSKQEAQS
IPFSMEKIGDILNLTCAQSMEDIVDFVVGELGTNEVEIKMMNNNIEVP
NGIQDYVLSKVEKLVVPGNTAVACHRMSYPYIVYYCHHQQDIGQYNVT
LVSPSTGAAFQTTAVCHYDTYAWQPDVVALKYLGIRPGDAPVCHFSAI
NDMFWNRKNNDFKSLDMVQ (SEQ ID NO: 34)

FIG. 12A

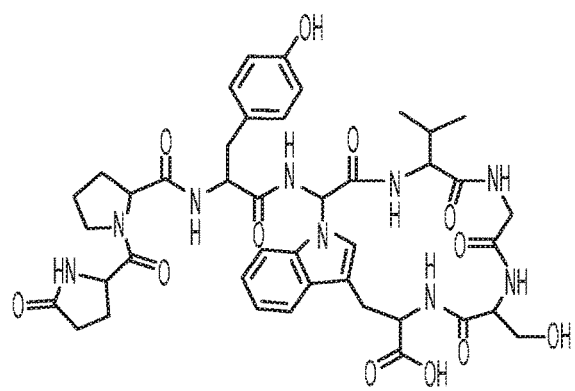
Lyciumin A
(QPYTVGSW)
(SEQ ID NO: 41)

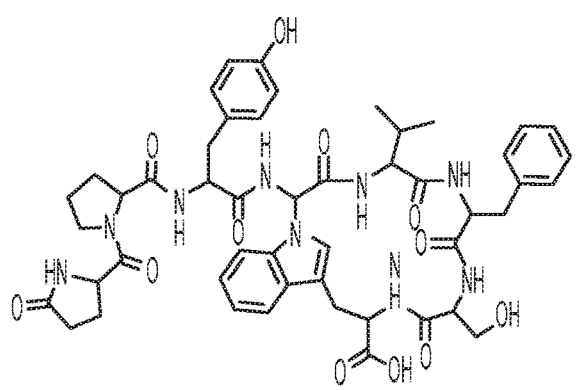
Lyciumin C
(QPYTVFSW)
(SEQ ID NO: 42)

FIG. 12B

```
>XP_010676059.1 PREDICTED: BURP domain protein USPL1-like
[Beta vulgaris subsp. vulgaris]
MGKQLWGQLQYIETKEKLANFDKPYTAKKDKIVASENQPFTISAWHYNPETGANVVEPV
SHDVATTKKDKTVASENQPFTISAWRYNSDTNANAVEPVSDGATTDTVTTKKDKTVASE
NQPWTVAAWRYNPDNINEKYSIKASHNHHHFMHNANSKDSEVKEENLNGGSVFFVEESL
RLGMKLKHDFQKTKKRPYLPKKIAQSIPFSVDKVAEIVNLFSIKSESAEATAIKETLGI
CLQRPKVKKENRTCAQSMEDIVDFVVKELGTNDVELRMMRNNIEVPHGIQDYVVTKVKK
LVVPGNTAAACHRMVYPYVVYYCHHQQDIGHYDVTLVSPTFGNAIQTTAVCHYDTYAWQ
PDVLALRYLGIRPGDAPVCHFSAINDMFWSIKPNSKYISRHGSVKRVIES
```

(SEQ ID NO: 133)

FIG. 13A

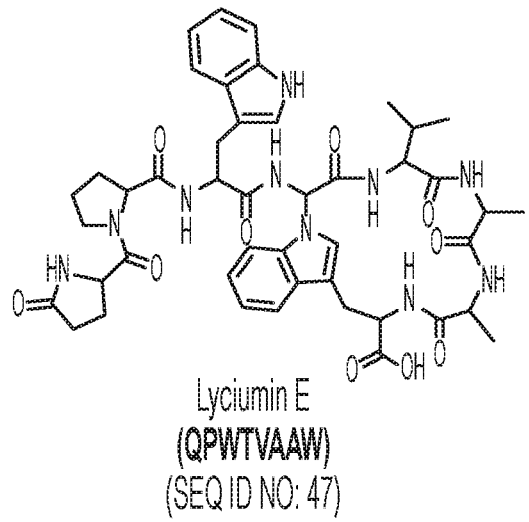

Lyciumin E
(QPWTVAAW)
(SEQ ID NO: 47)

FIG. 13B

>AUR62017095 Org_Cquinoaearly-release peptide: AUR62017095-RA BURP5: BURP domain-containing protein 5 (Chenopodium quinoa)
MSLYSNDADKAKKANTN*QPFTVVGW*KYNADGAKERVGMS*QPYTVMAW*KYNVDDAKERVGI
D*QPYTVWGW*NYNTDSANKEKVKEAYKPLSIETNTKKTGID*QPYTVWGW*NYNTNSANKEKV
KEAEKPLSIETNTKKTGVD*QPYTVWGW*NYNTNNANKEKVKEAEKPLSIETNTKKTGID*QP*
*YTVWGW*NYNTDSANKEKVKEANKPLSIETDTKKTGID*QPYTVWGW*NYNTDSANKEKVKEA
EKSLSIETNTKKTGID*QPYTVWGW*NYNTNSGNKEKVKEADKVFTMDTSTKKAGTK*QPYTV*
*MGWK*YNADNGKREKVGHEVSVGSVFFIEKSLRLGDKLKHDFQKTPSVPFLPKHIAKSIPF
SEDKFTEILNLFSIKPGSVEATGIKGTLDVCLHRPKVEKENRTCAQSMEDVVDFVVRELG
SNDVELRMMKNDIEVPKGIQDYVITKVKKLVVPGNTAAACHRMSYPYVVYYCHHQQDIGH
YDVTLVSPTTGNAIQTTAVCHYDTYAWKPNVPALQYLGIRPGDAPVCHFSAINDMFWSLK
ANSKSLDMVV (SEQ ID NO: 35)

FIG. 14A

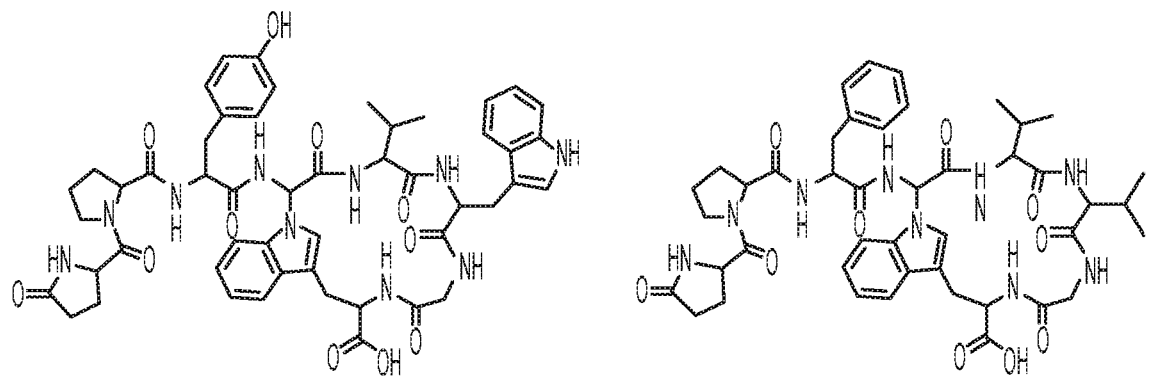

Lyciumin F
(QPYTVWGW)
(SEQ ID NO: 55)

Lyciumin G
(QPFTVVGW)
(SEQ ID NO: 53)

FIG. 14B

>Glyma.12G217300 DEHYDRATION-RESPONSIVE PROTEIN RD22
(Glycine max)
MALRCLVMSLSVLFTLGLARESHARDEDFWHAVWPNTPIPSSLRDLLKPGPASVEIDD
HPMQIEETQYPKTFFYKEDLHPGKTMKVQFSKPPFQQPWGVGTWLKEIKDTTKEGYSF
EELCIKKEAIEGEEKFCAKSLGTVIGFAISKLGKNIQVLSSSFVNKQDQYTVEGVQNL
GDKAVMCHRLNFRTAVFYCHEVRETTAFMVPLVAGDGTKTQALAICHSNTSGMNHQML
HQLMGVDPGTNPVCHFLGSKAILWVPNLSVDTAYQTNIVA (SEQ ID NO: 36)

FIG. 15A

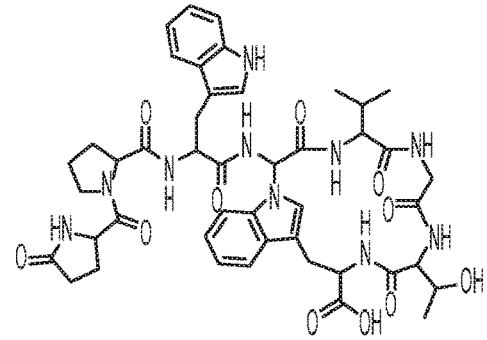

Lyciumin H
(QPWGVGTW)
(SEQ ID NO: 61)

FIG. 15B

>Glyma.12G217400 (Sali3-2, Glycine max)
MEFRCSVISFTILFSLALAGESHVHASLPEEDYWEAVWPNTPIPTALRELLKPL
PAGVEIDELPKQIDDTQYPKTFFYKEDLHPGKTMKVQFTKRPYAQPYGVYTWLT
DIKDTSKEGYSFEEICIKKEAFEGEEKFCAKSLGTVIGFAISKLGKNIQVLSSS
FVNKQEQYTVEGVQNLGDKAVMCHGLNFRTAVFYCHKVRETTAFMVPLVAGDGT
KTQALAVCHSDTSGMNHEMLHELMGVDPGTNPVCHFLGSKAILWVPNLSMDTAY
QTNVVV (SEQ ID NO: 2)

FIG. 15C

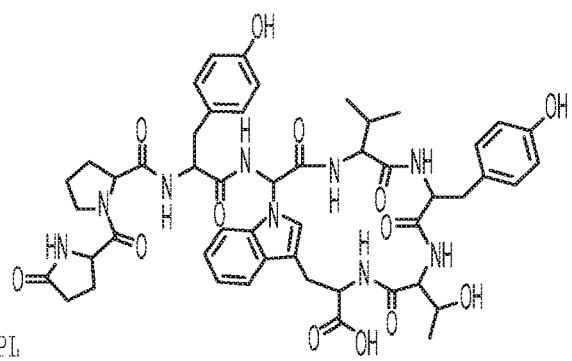

Lyciumin I
(QPYGVYTW)
(SEQ ID NO: 43)

FIG. 15D

>SmeBURP (extended BAP00548.1, *Solanum melongena*)
MELYFFTLFSVIFVVSHAANLSPEVYWKVTLPNTPMPKPIKDALHISEEKLKPEDELDKL
RQWGVYARYDGVPKSELRKLHQPYGVYTWYRGAAEDPVYARYHDASENELHKVHQPSLKD
HKENHLVMPYFFETHLHQGKQLNLLSLKNNNPAPFLPRKIVDSIPFSSDKIEEIFSYFSV
DKDSKPAEMIGKTIKLCEGPAGNGEVKYCATSLESMIEFTLSHVGTNNIIAISTEVEKET
PEVQTYTIEKVEEKANGKGVICHKVAYPYAVHYCHDVGSTRVFMVSMVGADGTKVNGVSV
CHEDTTPMNPEALPFQLLNVKPGEKPICHFTLDDQIVLFPSPNVLLQVTDN (SEQ ID NO: 134)

FIG. 16A

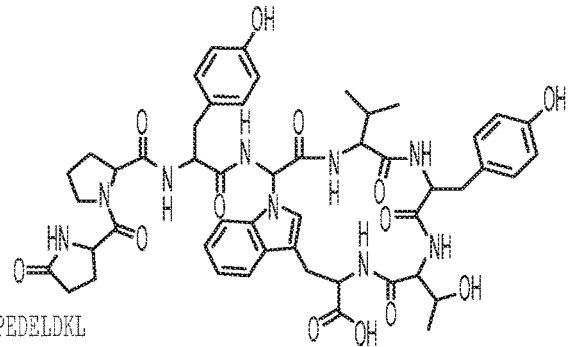

Lyciumin I
(QPYGVYTW)
(SEQ ID NO: 43)

FIG. 16B

>Sme2.5_02115.1_g00002.1 unnamed protein product (*Solanum melongena*)
MCDVYTSQLVLVASQAANLSPEVYWKVKLPNTPMPKPIKDALHISEKTAYNGDKSTKISQ
PWGVGSWYQAAPENDLHKVRQPWGVLGWYHDAPENELHKLRQPWGVGSWYQAALGNELHK
LRQPWGVGSWYHDAPENELHKLRQPWGVGSWYQAAPENELYKVRQPWGVLGWSHVPLRMS
FTNCANRGEWAHDLHQGKAMNLLSLKNYNPAPILPRKVVDSIFFSSDKIEEILSHFSADK
DSERAEMIKKTIKMCEDPAGNGEVKHCATSLESMLDFTVSHLGTNNIIAISTEVEKETPE
VQTYTIEKVEEKANGKGVVCHKVAYPYSVHFCHDVGSTRTFMVSMVGADGTKVNAVSVCH
EDTAPMNPKALPFQLLNVKPGDKPICHFTLDDQIALFPSPNVPLQVTKN (SEQ ID NO: 135)

FIG. 16C

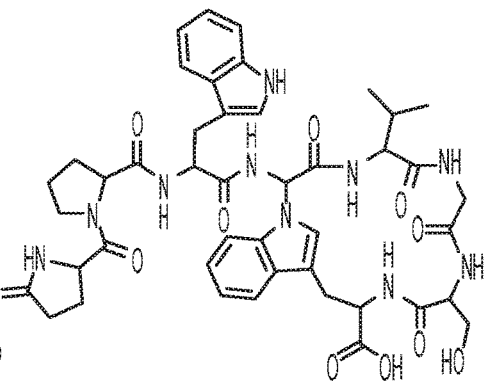

Lyciumin B
(QPWGVGSW)
(SEQ ID NO: 50)

FIG. 16D

```
>Medtr2g081610 - DEHYDRATION-RESPONSIVE PROTEIN RD22
(Medicago truncatula)
MELKHILIFISVLSLALAGGSHASLPEEEYWEAVWPNTPIPSSLRELLKPGPE
GVEIDDLPMEVDDTQYPKTFFYEHELYPGKTMKVQFSKRPFAQPYGVYTWMRE
IKDIEKEGYTFNEVCVKKAAAEGEQKFCAKSLGTLIGFSISKLGKNIQALSSS
FIDKHEQYKIESVQNLGEKAVMCHRLNFQKVVFYCHEIHGTTAFMVPLVANDG
RKTQALAVCHFDTSGMNHEMLQQIMKADPGSKPVCHFLGNKAILWVPNLGLDN
AYGANAAV
```

(SEQ ID NO: 40)

FIG. 17A

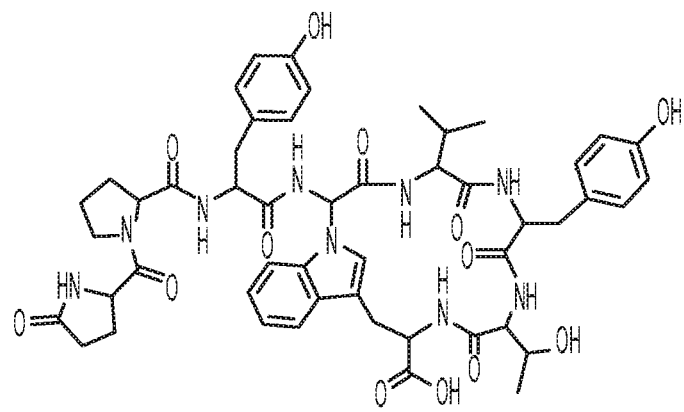

Lyciumin I
(QPYGVYTW)
(SEQ ID NO: 43)

FIG. 17B

Predicted precursor peptide from Solanum tuberosum genome (JGI Phytozome, v4.03)
>PGSC0003DMG400047074 Org_Stuberosum peptide: PGSC0003DMP400069178 BURP domain-containing protein
(PAC:37467747)
MELHHQYFFTFFSVIFVVSHAANLSPEVYWRVKLPNTPMPTPIKDALHISDGIRLPLRTSFKYANHGEWVDGIRLPFENELHKVRQPWGVDSWYQAAPENEL
HKVRQPYGVGVWYNDAAKKDLNDNHPVTPYFFETDLHQGKKMNLQSLKNYNPAPILPRKVVDSTAFSSDKIEEILNHFSVDKDSERAKDIKKTKCEPAGNG
EVKHCATSLESMIDFTLSHLGTNNIIAMSTEVEKETPEVQYTTEKVEEKANGKGVVCHKVAYPIAVHFCHDVGSTRTFMVSMVGADGTKVNAVSVCHEDTASM
NPKALFQLLNVRPGDKPICHFTLDDQIALFPSQNAVIQVAEN
(SEQ ID NO: 38)

FIG. 18A

LbalycA blastp hits of Trinity (v2.4) de novo transcriptome assembly:
>lcl|Potato_tuber|TRINITY_DN47721_c0_g1_i1 (5' partial)
VRQPFGVGRWNDASENELHKVRQPFGVGWYQAASENELHKVRQPYGVGVFGWYNDAAKKDLNDNHPVTPYFFETDLHQGKMNLESLKNYNPAPILPRKVVDSI
AFSSDKIEEILNHFSVDKDSERAKDIKKTKMCEDPAGNGEVKHCATSLESMIDFTLSHLGTNNIIATSTEVEKETPEVQTYTTEKVEEKANGKGVVCHKVAYP
YAVHFCHDVGSTRTFMVSMVGADGTKVNAVSVCHEDTASMNPKALPFQLLNVRPGDKPICHFTLDDQIALFPSQNALAEN (SEQ ID NO: 136)

>lcl|Potato_tuber|TRINITY_DN47721_c1_g2_i3 (5' partial)
APENELQKVRQPWGVGRWYNDAPENELQKVRQPWGVGRWYNDAAKKDLNDNHPVTPYFFETDLHQGKOMNLQSLKNYNPAPIL
PRKVVDSTAFSSDKIEEILNHFSVDKDSERAKDIKKTKMCEDPAGNGEVKHCATSLESMIDFTLSHLGTNNIIAMSTEVEKETPEVQTYTTEKVEEKANGKGV
VCHKVAYPYAVHFCHDVGSTRTFMVSMVGADGTKVNAVSVCHEDTASMNPKALPFQLLNVKPGDKPICHFTLDDQIALFPSQNALAEN
(SEQ ID NO: 137)

>lcl|Potato_tuber|TRINITY_DN47721_c1_g2_i4 (5' partial)
MGSWYQAAPENELHKVRQPFGVGVFAWYKAATENELHKVRQPYGVFAWYKAASENVLH
KTIKMCEDPAGNGEVKHCATSLESMIDFTLSHLGTNNIIAMSTEVEKETPEVQTYTTEKVEEKANGKGVVCHKVAYPIAVHFCHDVGSTRTFMVSMVGADGTKV
NAVSVCHEDTASMNPKALFQLLNVRPGDKPICHFTLDDQALFPSQNALAEN (SEQ ID NO: 138)

>lcl|Potato_tuber|TRINITY_DN48305_c1_g2_i2 (3' partial)
MELHHQYFFTFFSVIFVVSHAANLSPEVYWRVKLPNTPMPTPIKDALHISEKTAYNGDGNTKISQPYGVFAWYKAASENVLH
KVRQPYG (SEQ ID NO: 139)

FIG. 18B

LbalycA hits of rnaSPAdes (v1.0) de novo transcriptome assembly (kmer 25,75):
>lcl|Potato_tuber|NODE_10739_length_1460_cov_677.901_ID_21479
MELHHQYFFTLFSVIFLVSHAANLSPEVYWRVKLPNTPMPTPIKDALHISENELHKVRQPYGVLAHQAASENELHKVRQPY
GVLAHQAAPENELHKVRQPYGVRWYQAASENELHKVRQPYGVYRWYQAAPENELHKVRQPYGVSRWYNDAATKDINDHPV
TPYFFETDLHQGKKMNLQSLKNYNPAPTLPRKVVDSTAFSSDKTEILNHFSVRDKDSERAKDIKKTKMCEDPAGNGEVKHCATSLESMIDFTLSHLGTNNITA
ISTEVEKETPEVQTYTLRKVEEKANGKGVVCHKVAYPYAVHFCHDVGSTRTFMVSMVGADGTKVNAVSVCHEDTASMNPKAIPFQILNVRPGDKPICHFTLDDQ
TALEPSQNALAEN*
(SEQ ID NO: 140)

>lcl|Potato_tuber|NODE_29201_length_620_cov_26.9761_ID_58407
MELHHQYFFTLFSVIFFVSHAANLSPEVYWRVKLPNTPMPTPIKDALHISEKTAYNGDNTKISQPWGVAWYQDAPENELHKVRQPYGVDSWYQASPENKLH
KVRQPWGVSWYQAASENELHKVRQPYGVRWYQAAPENELHKVRQPWGVSWYQAASENELHKVRQPNG (SEQ ID NO: 141)

>lcl|Potato_tuber|NODE_26964_length_666_cov_44.9932_ID_53933
MELHHQYFFTLFSVIFFVSHAANLSPEVYWRVKLPNTPMPTPIKDALHISEKTAYNGDNTKISQPYGVTAWYQAASENELHKVRQPYGVDSWYQASENELH
KVRQPYGVTAWYQAAPENELHKVRQPWGVSWYQAASENELHKVRQPYGVTAWYKAASENELHKVRQPYGVTAWYNDAAKKDINDHPVTPYFFETDLHQGKKM
(SEQ ID NO: 142)

>lcl|Potato_tuber|NODE_40653_length_459_cov_9.7474_ID_81309
IKDALHISEKTAYNGDNTKISQPWGVGAWYQDAPENELHKVRQPWGVGSWYQAAPENELHKVRQPYGVGAWYQAASENELHKVRQPYGVDSWYQAASENELHK
VRQPYGVFRWYQPWGVGSWYQDASENELHKVRQPNG
(SEQ ID NO: 143)

FIG. 18C

Core peptides from BURP domain precursor peptide genes:
Genome sequence (v4.03): QPWGVDSW (SEQ ID NO: 97), QPYGVGVW (SEQ ID NO: 98)
Trinity transcriptome assembly: QPFGVGRW (SEQ ID NO: 99), QPFGVFGW (SEQ ID NO: 83), QPYGVFGW (SEQ ID NO:
82), QPWGVGRW (SEQ ID NO: 100), QPFGVVAW (SEQ ID NO: 101), QPWGVRW (SEQ ID NO: 78)
rnaSPAdes assembly: QPYGVLAW (SEQ ID NO: 102), QPYGVRW (SEQ ID NO: 89), QPYGVSRW (SEQ ID NO: 103)
QPWGVGAW (SEQ ID NO: 87), QPYGVTAW (SEQ ID NO: 104), QPWGVGSW (SEQ ID NO: 50), QPYGVFRW (SEQ ID NO:
105), QPYGVFAW (SEQ ID NO: 78), QPYGVDGW (SEQ ID NO: 106)

FIG. 18D

\>StuBURP (*Solanum tuberosum* 'Russett')
MELLHQYYFFTPFSVIFVVSHAANLSPEVYWRVKLPNTPMPT
PIKDALHISEKTAYNGDGNTKISQPYGVFAWYQAASENELHK
VRQPYGVDGWYKAASENELHKVRQPYGVFAWYKAITENELHK
VRPYGVFAWYKAATENELHKVRQPYGVFAWYKAASENVLHK
VRQPYGVFAWYNDAAKKDLNDNHPVTPYFFETDLHQGKKMNL
QSLKNYNPAPILPRKVVDSIAFSSDKIEEILNHFSVDKDSER
AKDIKKTIKMCEEPAGNGEVKHCATSLESMIDFTLSHLGTNN
IVAISTEVDKETPEVQTYTIEKVEEKANGKGVVCHKVAYPYA
VHFCHDVGSTRTFVVSMVGADGTKVNAVSVCHEDTASMNPKA
LPFQLLNVKPGDKPICHFTLDDQIALPPSQNALLQVAEN (SEQ ID NO: 126)

FIG. 19A

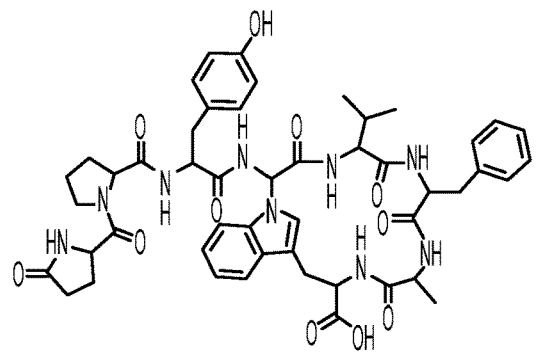

Lyciumin J
(QPYGVFAW)
(SEQ ID NO: 78)

FIG. 19B

\>lcl|Potato_tuber|NODE_29201_length_620_co
v_26.9761_ID_58407
MELLHQYYFFTLFSVIFVVSHAANLSPEVYWRVKLPNTPMPT
PIKDALHISEKTAYNGDGNTKISQPWGVGAWYQDAPENELHK
VRQPWGVGSWYQASPENKLHKVRQPWGVVAWYQAASENKLHK
VRQPWGVGSWYQAAPENELHKVRQPYGVFRWYQAASENELHK
VRQPWGVGSWYQDASENELHKVRQPWG (SEQ ID NO: 144)

FIG. 19C

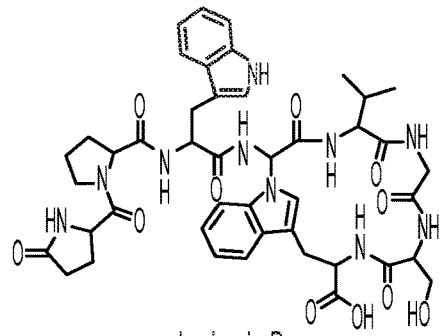

Lyciumin B
(QPWGVGSW)
(SEQ ID NO: 50)

FIG. 19D

\>lcl|Potato_tuber|NODE_29201_length_620_co
v_26.9761_ID_58407
MELLHQYYFFTLFSVIFVVSHAANLSPEVYWRVKLPNTPMPT
PIKDALHISEKTAYNGDGNTKISQPWGVGAWYQDAPENELHK
VRQPWGVGSWYQASPENKLHKVRQPWGVVAWYQAASENKLHK
VRQPWGVGSWYQAAPENELHKVRQPYGVFRWYQAASENELHK
VRQPWGVGSWYQDASENELHKVRQPWG (SEQ ID NO: 144)

FIG. 19E

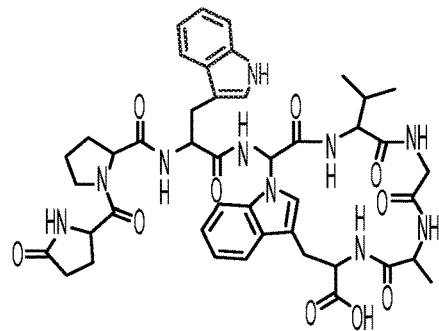

Lyciumin K
(QPWGVGAW)
(SEQ ID NO: 87)

FIG. 19F

```
>lcl|Potato_tuber|NODE_29201_length_620_co
v_26.9761_ID_58407
MELLHQYYFFTLFSVIFVVSHAANLSPEVYWRVKLPNTPMPT
PIKDALHISEKTAYNGDGNTKISQPWGVGAWYQDAPENELHK
VRQPWGVGSWYQASPENKLHKVRQPWGVVAWYQAASENKLHK
VRQPWGVGSWYQAAPENELHKVRQPYGVFRWYQAASENELHK
VRQPWGVGSWYQDASENELHKVRQPWG
```

(SEQ ID NO: 144)

FIG. 19G

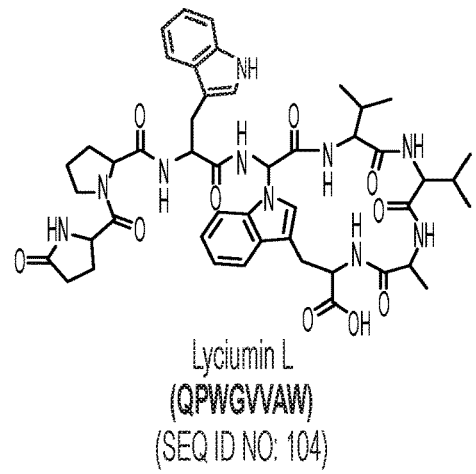

Lyciumin L
(QPWGVVAW)
(SEQ ID NO: 104)

FIG. 19H

```
>lcl|Potato_tuber|NODE_10739_length_1460_cov_677.901_
ID_21479
MELHHQYYFFTLFSVIFLVSHAANLSPEVYWRVKLPNTPMPTPIKDALHISEN
ELHKVRQPYGVLAWYQAASENELHKVRQPYGVLALHQAASENELHKVRQPYGV
LALHQAAPENELHKVRQPYGVYRWYQAASENELHKVRQPYGVYRWYQAASENE
LHKVRQPYGVYRWYQAAPENKLHKVRQPYGVSRWYNDAATKDLNDNHPVTPYF
FETDLHQGKKMNLQSLKNYNPAPILPRKVVDSIAFSSDKIEEILNHFSVDKDS
ERAKDIKKTIKMCEDPAGNGEVKHCATSLESMIDFTLSHLGTNNIIAISTEVE
KETPEVQTYTIEKVEEKANGKGVVCHKVAYPYAVHFCHDVGSTRTFMVSMVGA
DGTKVNAVSVCHEDFASMNPKALPFQLLNVKPGDKPICHFTLDDQIALFPSQN
ALAEN
```

(SEQ ID NO: 145)

FIG. 19I

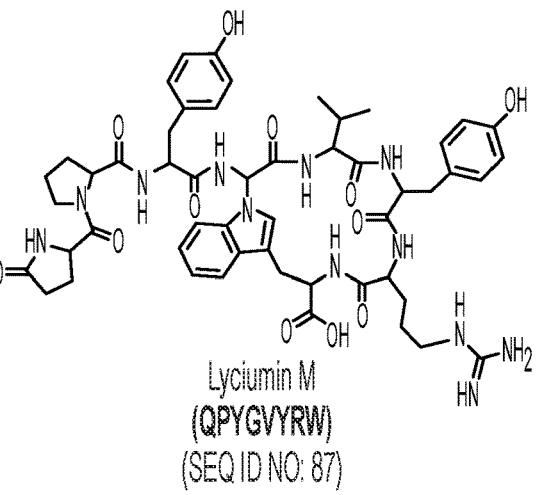

Lyciumin M
(QPYGVYRW)
(SEQ ID NO: 87)

FIG. 19J

```
>lcl|Potato_tuber|NODE_10739_length_1460_cov_677.901_
ID_21479
MELHHQYYFFTLFSVIFLVSHAANLSPEVYWRVKLPNTPMPTPIKDALHISEN
ELHKVRQPYGVLAWYQAASENELHKVRQPYGVLALHQAASENELHKVRQPYGV
LALHQAAPENELHKVRQPYGVYRWYQAASENELHKVRQPYGVYRWYQAASENE
LHKVRQPYGVYRWYQAAPENKLHKVRQPYGVSRWYNDAATKDLNDNHPVTPYF
FETDLHQGKKMNLQSLKNYNPAPILPRKVVDSIAFSSDKIEEILNHFSVDKDS
ERAKDIKKTIKMCEDPAGNGEVKHCATSLESMIDFTLSHLGTNNIIAISTEVE
KETPEVQTYTIEKVEEKANGKGVVCHKVAYPYAVHFCHDVGSTRTFMVSMVGA
DGTKVNAVSVCHEDFASMNPKALPFQLLNVKPGDKPICHFTLDDQIALFPSQN
ALAEN
```

(SEQ ID NO: 145)

FIG. 19K

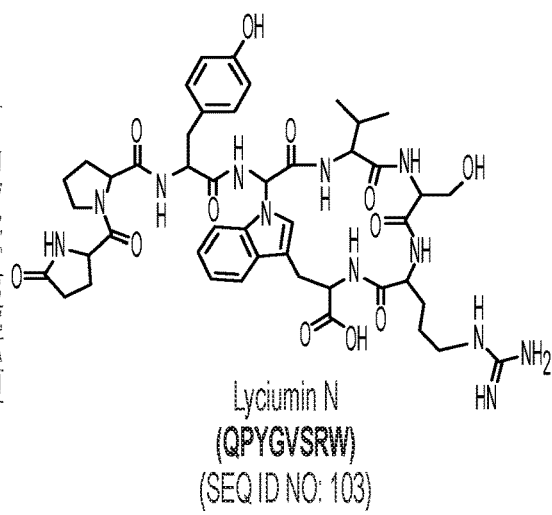

Lyciumin N
(QPYGVSRW)
(SEQ ID NO: 103)

```
>lcl|Potato_tuber|NODE_10739_length_1460_cov_677.901_
ID_21479
MELRKQYYFFTLFSVIFLVSHAANLSPEVYERVKLFNTPMPTPIKDALHISEN
ELHKVRQFYGVLAFYQAASENELHKVRQFYGVLALHQAASENELHKVRQFYGV
LALHQAAPENELHKVRQPYGVYRNYQAASENELHKVRQPYGVYRNYQAASENE
LHKVRQPYGVYRNYQAAPENKLHKVRQPYGVSRNYNDAATKDLNEDHPVTFYF
FETDLHQGKKMYLQSLKNTNPAPILSRKVVDSIAFSSDKIEEILNHFSVDKDS
ERAKDIKNYIKMCEDFASNGKVKHCATELESMIDFTLSRLGTNRKIAISTSYS
NETPKVQYIYIENVEKKANEGYYCHKVAIFYAVHFCHHVGSTRTFMVSNVSA
LGKEVNAYSYCHEDTASMNFKALPFZLLMYKFGDKFICFYLODKYALFSGN
ALKEN
```

(SEQ ID NO: 145)

FIG. 19N

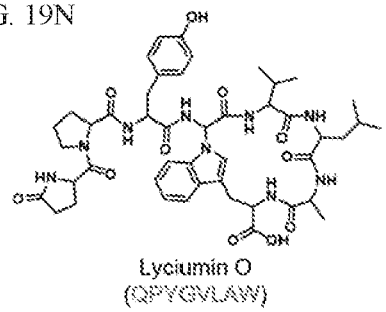

Lyciumin O
(QPYGVLAW)

(SEQ ID NO: 102)

FIG. 19O

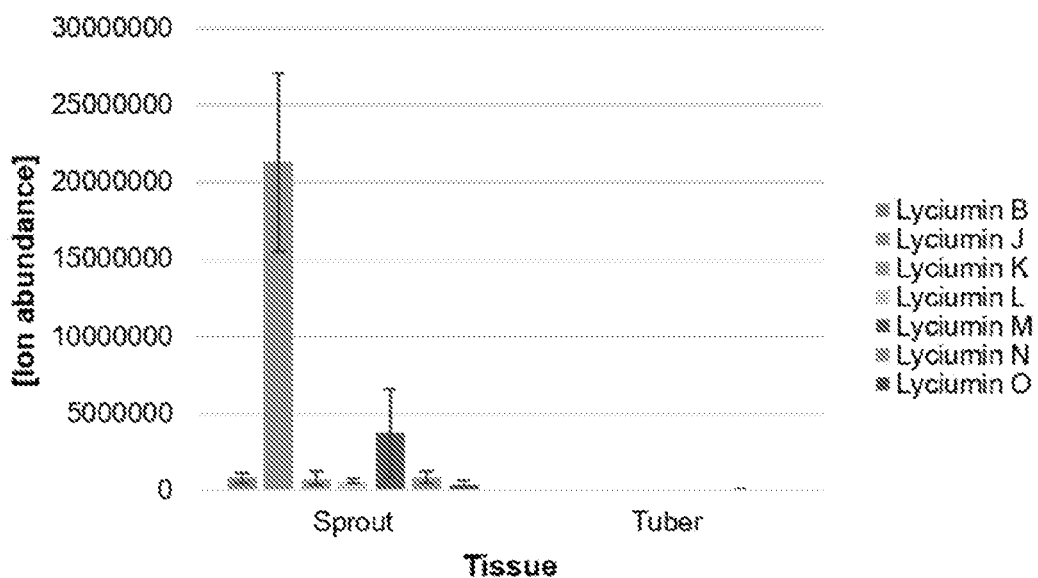

>SunBURP (Selaginella uncinata)
TLFLSPSPTSNWVNKQPYSVFAWT
NEDQPSKWFNKQPYSVFAWTNEDQ
PSKWFNKQPFGEHPKQKLESLPTK
GRAFRFASAQAGKSILLPPITPLL
SNKLIHPHLEDVLPFNKESLSQVL
RSFNLSANSGMGQSMEFALDMGKS
TNNGVEFRKSVATTKEMVDFVGGV
LCKEKGDCHVKSIAQSFENKESKM
VKVVDVELVSKDPVACHTVPFPYK
YYVCHKIKDSPVYKVNMMVEGGKT
LSTPFICHWDTSKFRTNHQAFEDL
NIKPGQGEICHWLGYETIVWYV (SEQ ID NO: 106)

FIG. 20A

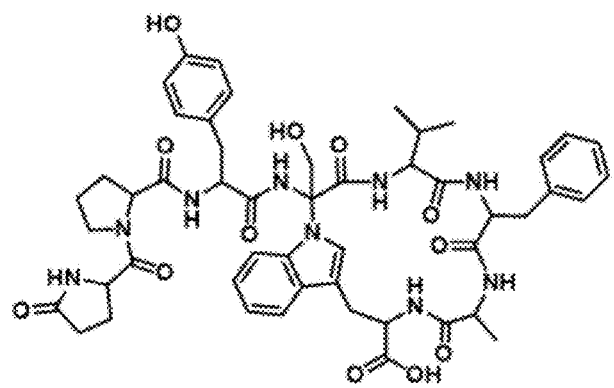

Lyciumin-[QPYSVFAW]
(Lyciumin P)

(SEQ ID NO: 147)

FIG. 20B

FIG. 21A    (SEQ ID NO: 7)

A  >LbaQC
MPLLNPRFLVISLIVLLSITVFREAEASYRVYKVKVVNEFPHDPQAYTQGLLYAENNTLFESTGLYGKSSVRKVALLDGKVERLHEMESSY
FGEGLTLLGERLFQLTWLLDTGFIYDRYNFSKFKKFTHHMQDGWGLATDGKVLFGSDSTSTLYKIDPKTMKVIRKQVVKSQGHEVRYLNEL
EYVKAEVWANVYVTDCIARISPKDGTVIGWILLQSLREELISRGYKDFEVLNGIAWDRDGDRIFVTGKLWPKLFEIKLLPLTPNDPLAGEI
NNLCIPKTSFLLEI

B

| Gene | Size [aa] | RSEM [TPM] | Transcript rank (Total transcript #) | Similarity/identity [%/%] to precursor co-localized Chenopodium quinoa QC (AUR62017096-RA) |
|---|---|---|---|---|
| LbaQC | 287 | 42 | 3365 (100355) | 72/61 |
| LbaLycA | 543 | 13397 | 13 (100355) | - |

FIG. 21B

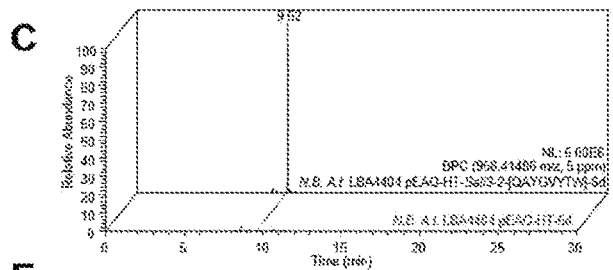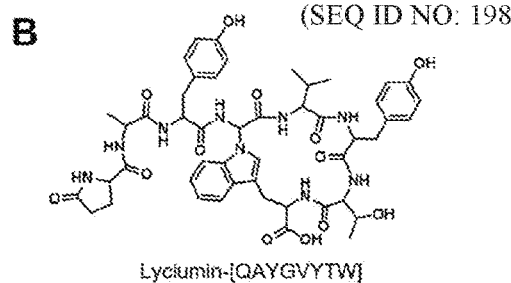
FIGs. 22A-E

>Glyma.12G217400-[QPAGVYTW]
MEFRCSVISFTILFSLALAGESHVHASLPEEDYWEAVWPNTPIPT
ALRELLKPLPAGVEIDELPKQIDDTQYPKTFFYKEDLHPGKTMKV
QFTKRPYAQPAGVYTWLTDIKDTSKEGYSFEEICIKKEAFEGEEK
FCAKSLGTVIGFAISKLGKNIQVLSSSFVNKQEQYTVEGVQNLGD
KAVMCHGLNFRTAVFYCHKVRETTAFMVPLVAGDGTKTQALAVCH
SDTSGMNHHMLHELMGVDPGTNPVCHFLGSKAILWVPNLSMDTAY
QTNVVV (SEQ ID NO: 254)

FIG. 23A

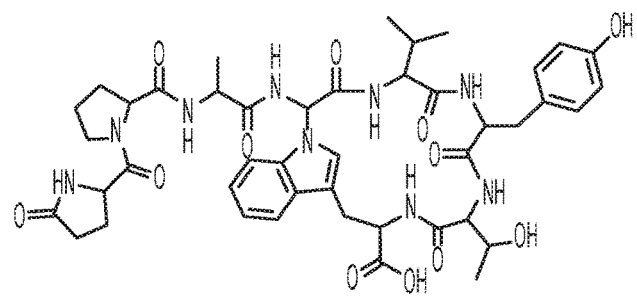

Lyciumin-[QPAGVYTW]
(SEQ ID NO: 255)

FIG. 23B

>Glyma.12G217400-[QPYAVYTW]
MEFRCSVISFTILFSLALAGESHVHASLPEEDYWEAVWPNTPIPT
ALRELLKPLPAGVEIDELPKQIDDTQYPKTFFYKEDLHPGKTMKV
QFTKRPYAQPYAVYTWLTDIKDTSKEGYSFEEICIKKEAFEGEEK
FCAKSLGTVIGFAISKLGKNIQVLSSSFVNKQEQYTVEGVQNLGD
KAVMCHGLNFRTAVFYCHKVRETTAFMVPLVAGDGTKTQALAVCH
SDTSGMNHHMLHELMGVDPGTNPVCHFLGSKAILWVPNLSMDTAY
QTNVVV (SEQ ID NO: 265)

FIG. 24A

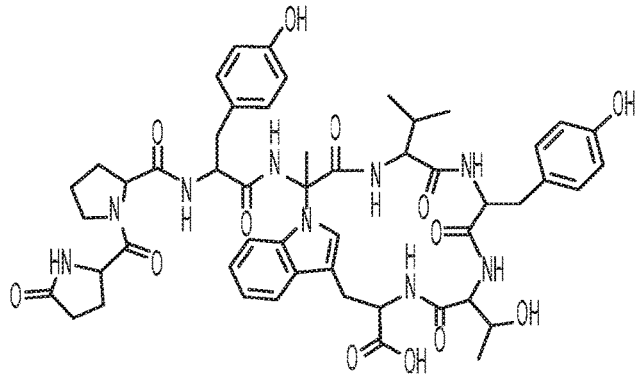

Lyciumin-[QPYAVYTW]
(SEQ ID NO: 257)

FIG. 24B

>Glyma.12G217400-[QPYGAYTW]
MEFRCSVISFTILFSLALAGESHVHASLPEEDYWEAVWPNTPIPT
ALRELLKPLPAGVEIDELPKQIDDTQYPKTFFYKEDLHPGKTMKV
QFTKRPYAQPYGAYTWLTDIKDTSKEGYSFEEICIKKEAFEGEEK
FCAKSLGTVIGFAISKLGKNIQVLSSSFVNKQEQYTVEGVQNLGD
KAVMCHGLNFRTAVFYCHKVRETTAFMVPLVAGDGTKTQALAVCH
SDTSGMNHHMLHELMGVDPGTNPVCHFLGSKAILWVPNLSMDTAY
QTNVVV (SEQ ID NO: 258)

FIG. 25A

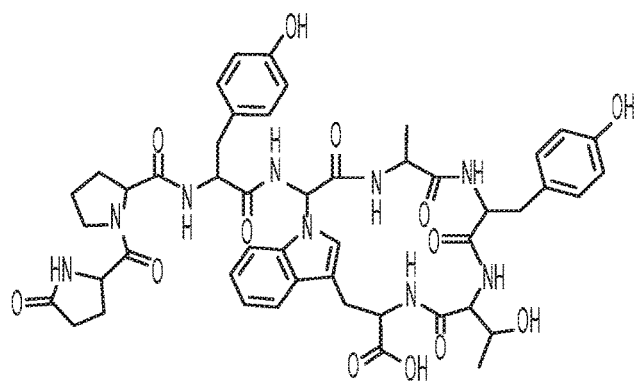

Lyciumin-[QPYGAYTW]
(SEQ ID NO: 259)

FIG. 25B

>Glyma.12G217400-[QPYGVATW]
MEFRCSVISFTILFSLALAGESHVHASLPEEDYWEAVWPNTPIPT
ALRELLKPLPAGVEIDELPKQIDDTQYPKTFFYKEDLHPGKTMKV
QFTKRPYAQPYGVATWLTDIKDTSKEGYSFEEICIKKEAFEGEEK
FCAKSLGTVIGFAISKLGKNIQVLSSSFVNKQEQYTVEGVQNLGD
KAVMCHGLNFRTAVFYCHKVRETTAFMVPLVAGDGTKTQALAVCH
SDTSGMNHHMLHELMGVDPGTNPVCHFLGSKAILWVPNLSMDTAY
QTNVVV (SEQ ID NO: 260)

FIG. 26A

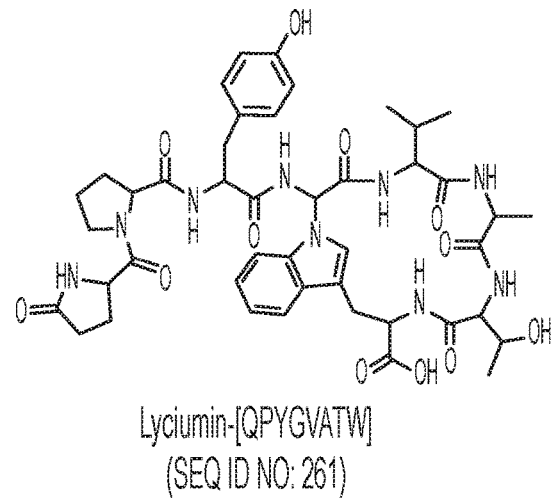

Lyciumin-[QPYGVATW]
(SEQ ID NO: 261)

FIG. 26B

>Glyma.12G217400-[QPYGVYAW]
MEFRCSVISFTILFSLALAGESHVHASLPEEDYWEAVWPNTPIPT
ALRELLKPLPAGVEIDELPKQIDDTQYPKTFFYKEDLHPGKTMKV
QFTKRPYAQPYGVYAWLTDIKDTSKEGYSFEEICIKKEAFEGEEK
FCAKSLGTVIGFAISKLGKNIQVLSSSFVNKQEQYTVEGVQNLGD
KAVMCHGLNFRTAVFYCHKVRETTAFMVPLVAGDGTKTQALAVCH
SDTSGMNHHMLHELMGVDPGTNPVCHFLGSKAILWVPNLSMDTAY
QTNVVV (SEQ ID NO: 262)

FIG. 27A

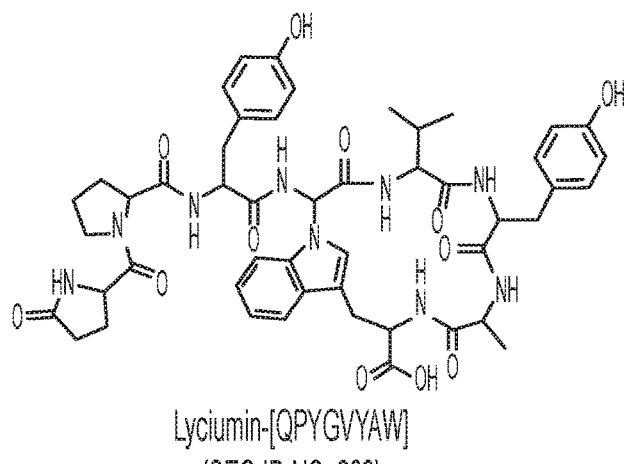

Lyciumin-[QPYGVYAW]
(SEQ ID NO: 263)

FIG. 27B

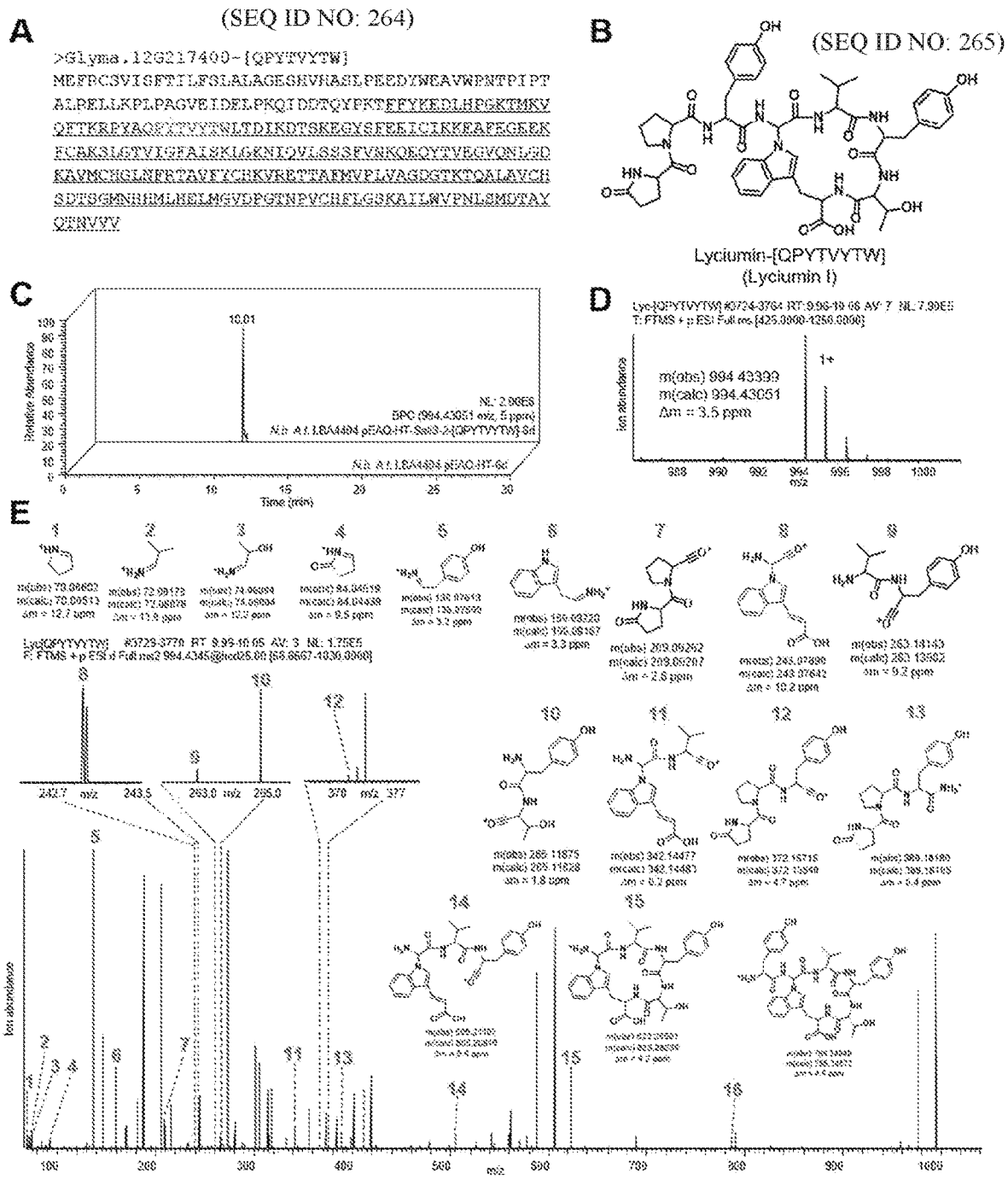
FIGs. 28A-E

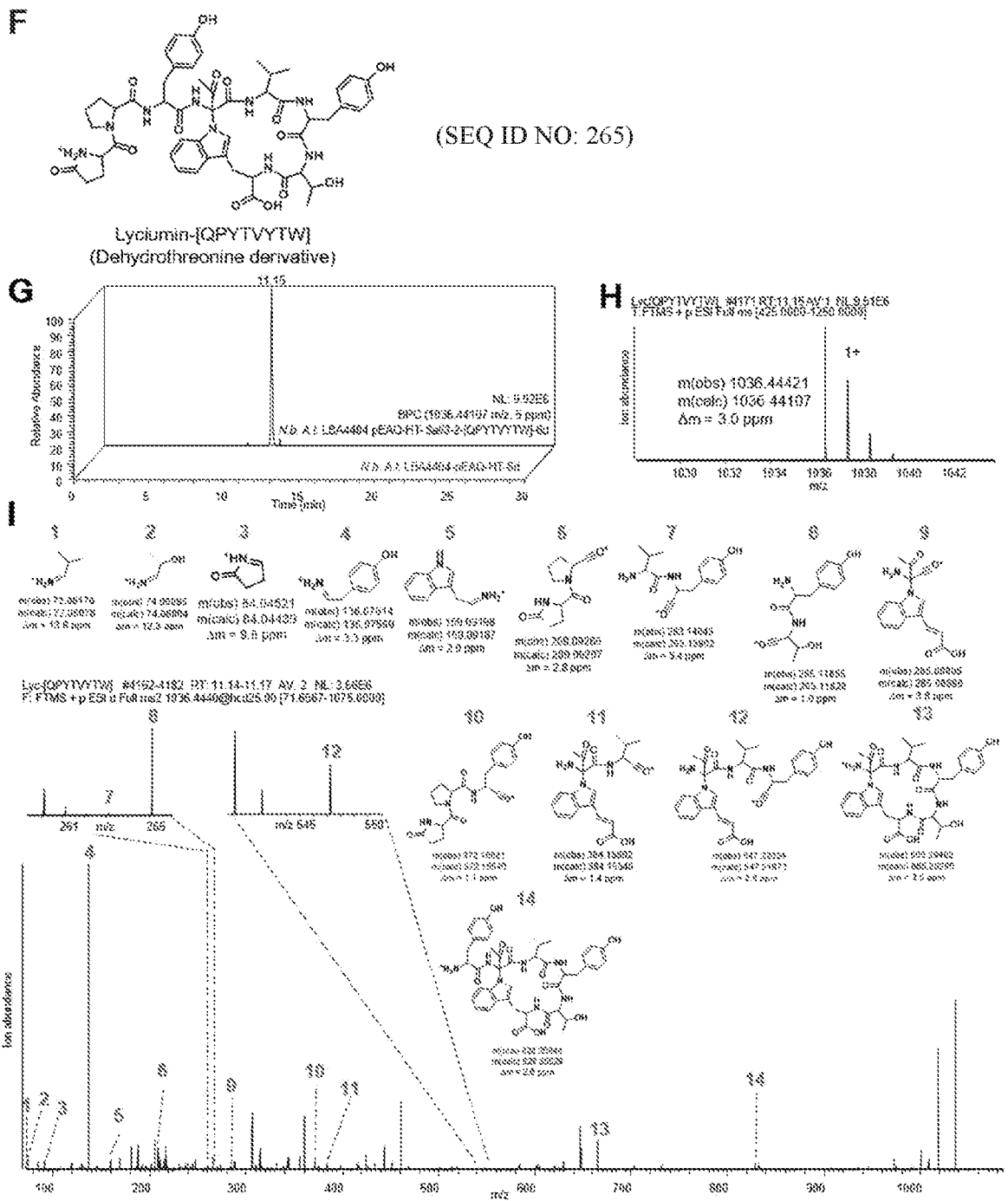
FIGs. 28F-I

>Glyma.12G217400-[QPYGVYTY]
MEFRCSVISFTILFSIALAGESHVHASLPEEDYWEAVWPNTPIPT
ALRELLKPLPAGVEIDELPKQIDDTQYPKTFFYKEDLHPGKTMKV
QFTKRPYAQPYGVYTYLTDIKDTSKEGYSFEEICIKKEAFEGEEK
FCAKSLGTVIGFAISKLGKNIQVLSSSFVNKQEQYTVEGVQNLGD
KAVMCHGLNFRTAVFYCHKVRETTAFMVPLVAGDGTKTQALAVCH
SDTSGMNHHMLHELMGVDPGTNPVCHFLGSKAILWVPNLSMDTAY
QTNVVV (SEQ ID NO: 266)

FIG. 29A

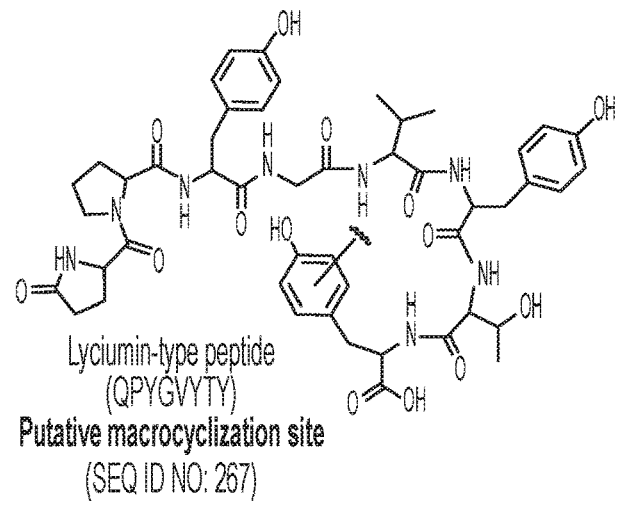

Lyciumin-type peptide
(QPYGVYTY)
Putative macrocyclization site
(SEQ ID NO: 267)

FIG. 29B

>CanBURP (XP_016572294.1 [*Capsicum annuum*])
MAMLYQYYFFTLLSLVFVVISHAANLSPEVYWKIKLPNTPMPKPIK
DALHISEKTSQPYGGLTWDWFHVFSKNELHKLHQLSQPYGVYFYGV
SLKNLNEDHLVPRFFFETDLHQGKKVNLKSLKNNNPAPLLPRKVVD
SISFSSNRIEEILDHFSVDNNSEDAKVIKRTVELCEQPAADGEIKY
CATSLESIIDFASSRLETNNILAIHTEVEKETPVLQTYTIKEVKEK
ANGKCVICHKVPYPYAVHFCHDVGSTRAFRVTMVGADGTKVNAVSV
CHEDTASMNPKALVFQLLNIKPGDKPICHFIMDDQIALFPSQNAVL
QMAEG (SEQ ID NO: 3)

FIG. 30A

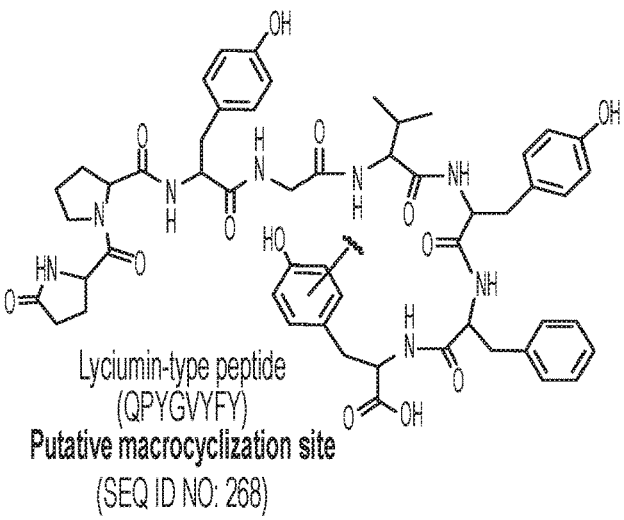

Lyciumin-type peptide
(QPYGVYFY)
Putative macrocyclization site
(SEQ ID NO: 268)

FIG. 30B

>Glyma.12G217400-[QPWGVGTW]
MEFRCSVISFTILFSIALAGESHVHASLPEEDYWEAVWPNTPIPT
ALRELLKPLPAGVEIDELPKQIDDTQYPKTFFYKEDLHPGKTMKV
QFTKRPYAQPWGVGTWLTDIKDTSKEGYSFEEICIKKEAFEGEEK
FCAKSLGTVIGFAISKLGKNIQVLSSSFVNKQEQYTVEGVQNLGD
KAVMCHGLNFRTAVFYCHKVRETTAFMVPLVAGDGTKTQALAVCH
SDTSGMNHHMLHELMGVDPGTNPVCHFLGSKAILWVPNLSMDTAY
QTNVVV (SEQ ID NO: 269)

FIG. 31A

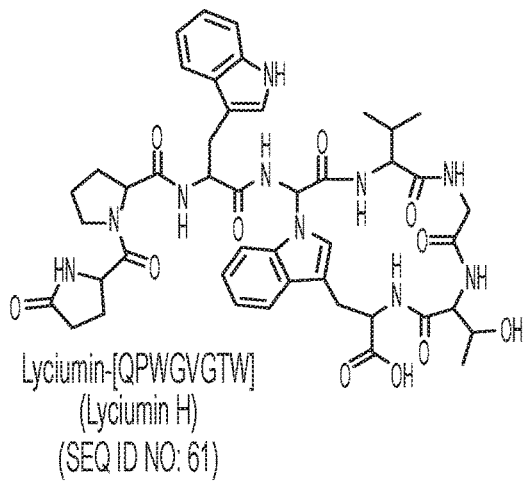

Lyciumin-[QPWGVGTW]
(Lyciumin H)
(SEQ ID NO: 61)

FIG. 31B

>Glyma.12G217400-[QPWGVGAW]
MEFRCSVISFTILFSLALAGESHVHASLPEEDYWEAVWPNTPIPT
ALRELLKPLPAGVEIDELPKQIDDTQYPKTFFYKEDLHPGKTMKV
QFTKRPYAQPWGVGAWLTDIKDTSKEGYSFEEICIKKEAFEGEEK
FCAKSLGTVIGFAISKLGKNIQVLSSSFVNKQEQYTVEGVQNLGD
KAVMCHGLNFRTAVFYCHKVRETTAFMVPLVAGDGTKTQALAVCH
SDTSGMNHHMLHELMGVDPGTNPVCHFLGSKAILWVPNLSMDTAY
QTNVVV (SEQ ID NO: 270)

FIG. 32A

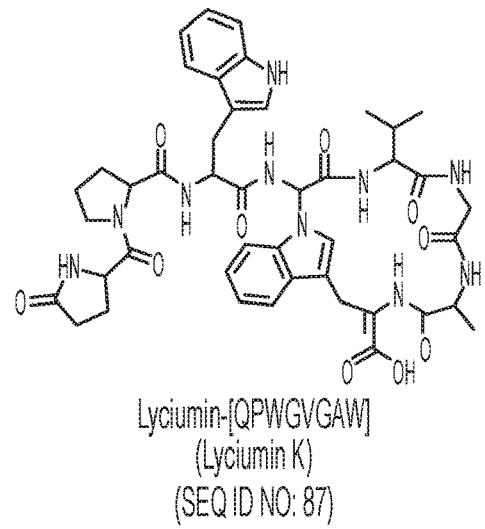

Lyciumin-[QPWGVGAW]
(Lyciumin K)
(SEQ ID NO: 87)

FIG. 32B

>Glyma.12G217400-[QPWGVYTW]
MEFRCSVISFTILFSLALAGESHVHASLPEEDYWEAVWPNTPIPT
ALRELLKPLPAGVEIDELPKQIDDTQYPKTFFYKEDLHPGKTMKV
QFTKRPYAQPWGVYTWLTDIKDTSKEGYSFEEICIKKEAFEGEEK
FCAKSLGTVIGFAISKLGKNIQVLSSSFVNKQEQYTVEGVQNLGD
KAVMCHGLNFRTAVFYCHKVRETTAFMVPLVAGDGTKTQALAVCH
SDTSGMNHHMLHELMGVDPGTNPVCHFLGSKAILWVPNLSMDTAY
QTNVVV (SEQ ID NO: 271)

FIG. 33A

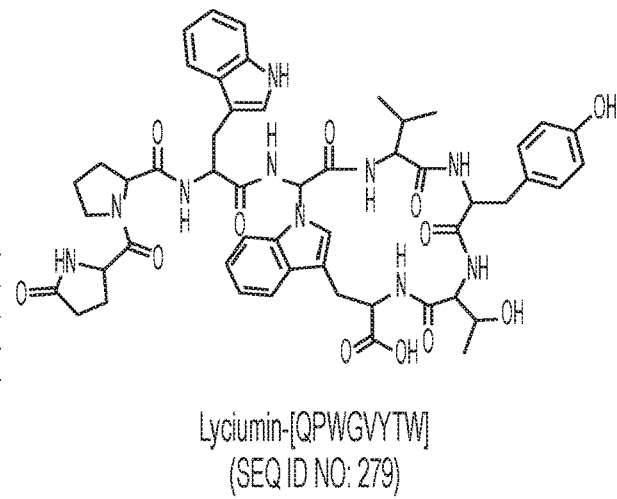

Lyciumin-[QPWGVYTW]
(SEQ ID NO: 279)

FIG. 33B

>Glyma.12G217400-[QPFGVYTW]
MEFRCSVISFTILFSLALAGESHVHASLPEEDYWEAVWPNTPIPT
ALRELLKPLPAGVEIDELPKQIDDTQYPKTFFYKEDLHPGKTMKV
QFTKRPYAQPFGVYTWLTDIKDTSKEGYSFEEICIKKEAFEGEEK
FCAKSLGTVIGFAISKLGKNIQVLSSSFVNKQEQYTVEGVQNLGD
KAVMCHGLNFRTAVFYCHKVRETTAFMVPLVAGDGTKTQALAVCH
SDTSGMNHHMLHELMGVDPGTNPVCHFLGSKAILWVPNLSMDTAY
QTNVVV (SEQ ID NO: 272)

FIG. 34A

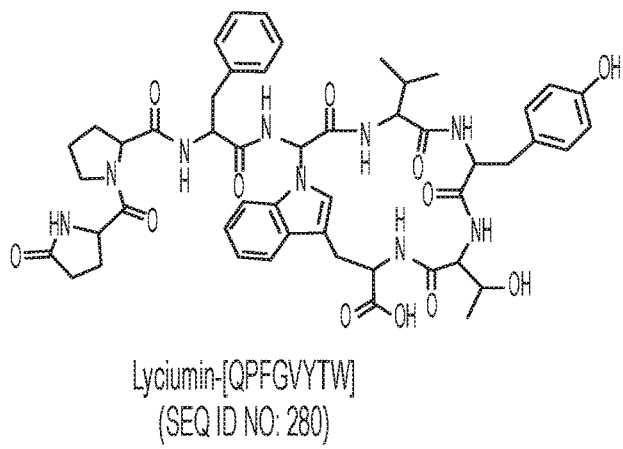

Lyciumin-[QPFGVYTW]
(SEQ ID NO: 280)

FIG. 34B

```
>Glyma.12G217400-[QPFGFFSW]
MEFRCSVISFTILFSLALAGESHVHASLPEEDYWEAVWPNTPIPT
ALRELLKPLPAGVEIDELPKQIDDTQYPKTFFYKEDLHPGKTMKV
QFTKRPYAQPFGFFSWLTDIKDTSKEGYSFEEICIKKEAFEGEEK
FCAKSLGTVIGFAISKLGKNIQVLSSSFVNKQEQYTVEGVQNLGD
KAVMCHGLNFRTAVFYCHKVRETTAFMVPLVAGDGTKTQALAVCH
SDTSGMNHHMLHELMGVDPGTNPVCHFLGSKAILWVPNLSMDTAY
QTNVVV
```
(SEQ ID NO: 273)

FIG. 35A

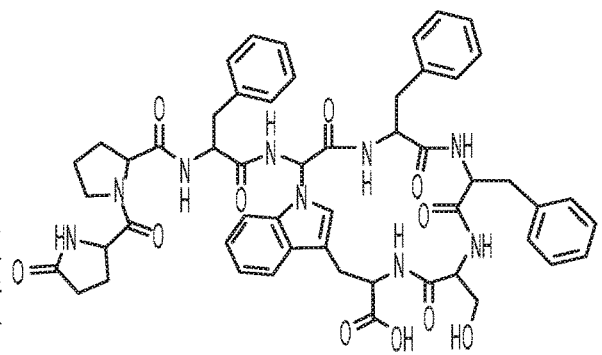

Lyciumin-[QPFGFFSW]
(SEQ ID NO: 69)

FIG. 35B

```
>Glyma.12G217400-[QPWGVYSW]
MEFRCSVISFTILFSLALAGESHVHASLPEEDYWEAVWPNTPIPT
ALRELLKPLPAGVEIDELPKQIDDTQYPKTFFYKEDLHPGKTMKV
QFTKRPYAQPWGVYSWLTDIKDTSKEGYSFEEICIKKEAFEGEEK
FCAKSLGTVIGFAISKLGKNIQVLSSSFVNKQEQYTVEGVQNLGD
KAVMCHGLNFRTAVFYCHKVRETTAFMVPLVAGDGTKTQALAVCH
SDTSGMNHHMLHELMGVDPGTNPVCHFLGSKAILWVPNLSMDTAY
QTNVVV
```
(SEQ ID NO: 274)

FIG. 36A

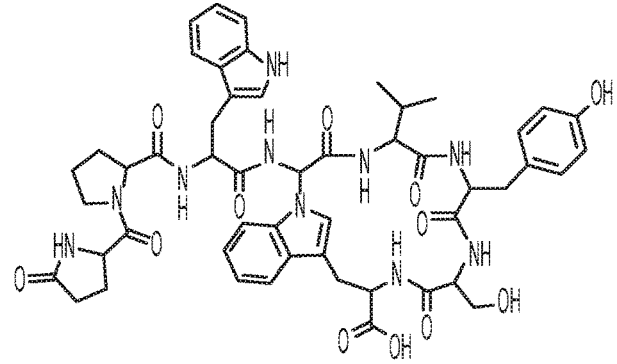

Lyciumin-[QPWGVYSW]
(SEQ ID NO: 77)

FIG. 36B

```
>Glyma.12G217400-[QPYGVYFW]
MEFRCSVISFTILFSLALAGESHVHASLPEEDYWEAVWPNTPIPT
ALRELLKPLPAGVEIDELPKQIDDTQYPKTFFYKEDLHPGKTMKV
QFTKRPYAQPYGVYFWLTDIKDTSKEGYSFEEICIKKEAFEGEEK
FCAKSLGTVIGFAISKLGKNIQVLSSSFVNKQEQYTVEGVQNLGD
KAVMCHGLNFRTAVFYCHKVRETTAFMVPLVAGDGTKTQALAVCH
SDTSGMNHHMLHELMGVDPGTNPVCHFLGSKAILWVPNLSMDTAY
QTNVVV
```
(SEQ ID NO: 275)

FIG. 37A

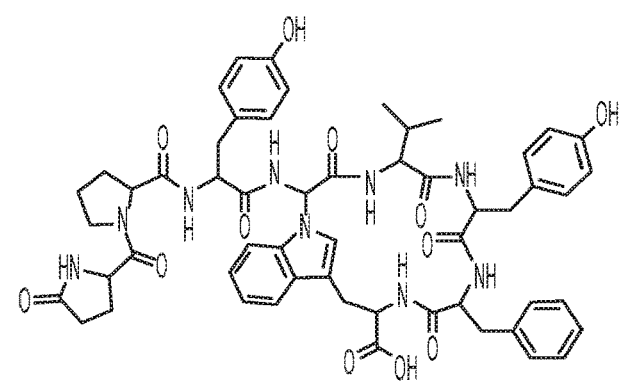

Lyciumin-[QPYGVYFW]
(SEQ ID NO: 63)

FIG. 37B

LycA-1x-QPWGVGSW nucleotide sequence (SEQ ID NO: 112):
ATGGAGTTGCATCACCATTACTTCTTCATACTTCTTTCTCTTGCTTTTATAGCAAG
TCATGCAGCTAATTTATCTCCTGAGGTGTATTGGAAAGTCAAGCTGCCCAACACT
CCTATGCCCAGACCCATTAAGGATGCTCTACACTATTCTGAAGCCTCCGAGGGTG
ACGTTCACAAGTTGCGCCAACCATGGGGAGTGGGTTCGTGGTATAATACTGCTAC
AAAGAAAGATGTTAATGAAAACCTCCCAGTCACCCCTTACTTTTTTGAAACAGAT
TTACATCAAGGGAAAAAGATGAATCTTCCATCTCTCAAAAATTATAATCCAGCTC
CCATTTTGCCTCGCAAAGTTGCAGATTCCATCCCCTTCTCATCAGACAAGATTGA
AGAAATTCTAAAGCACTTTTCCATTGATAAGGACTCAGAGGGGGCTAAAATGAT
CAAGAAAACTATCAAAATGTGTGAGGAGCAAGCGGGTAATGGCGAGAAGAAAT
ATTGTGCCACTTCCTTAGAATCAATGGTTGATTTCACCTCATCTTATCTGGGAACA
AATAATATTATAGCACTTTCCACTTTAGTAGAGAAGGAAACTCCAGAGGTGCAA
ATATATACCATCGAAGAAGTGAAAGAGAAAGCAAATGGCAAAGGCGTGATATG
CCACAAAGTGGCTTACCCGTATGCGATACATTATTGCCATAGTGTAGGAAGCACA
AGGACCTTTATGGTCTCAATGGTGGGTTCTGATGGAACAAAAGTTAATGCAGTAT
CAGAGTGTCATGAGGATACTGCACCCATGAACCCTAAGGCATTGCCTTTTCAATT
GCTCAACGTTAAGCCAGGAGATAAACCTATTTGCCATTTCATATTGGATGATCAG
ATTGCCTTAGTTCCTTCTCAAGACGCAACTCAAGTGTCTGAAAACTAA LycA-1x-QPWGVGSW amino acid (SEQ ID NO: 113):
MELHHHYFFILLSLAFIASHAANLSPEVYWKVKLPNTPMPRPIKDALHYSEASEGDV
HKLRQPWGVGSWYNTATKKDVNENLPVTPYFFETDLHQGKKMNLPSLK LycA-5x-QPWGVGSW nucleotide sequence (SEQ ID NO: 114):
ATGGAGTTGCATCACCATTACTTCTTCATACTTCTTTCTCTTGCTTTTATAGCAAG
TCATGCAGCTAATTTATCTCCTGAGGTGTATTGGAAAGTCAAGCTGCCCAACACT
CCTATGCCCAGACCCATTAAGGATGCTCTACACTATTCTGAAGCCTCCGAGGGTG
ACGTTCACAAGTTGCGCCAACCATGGGGAGTGGGTTCGTGGTATCAAGCAGCAA
ACGAGGGTGATGTTAAAAAATTACGCCAGCCTTGGGGTGTTGGCTCTTGGTATAA
GGCTGCCCCAGAGGACGAGCTTCACAAAATACGCCAGCCCTGGGGCGTCGGATC
CTGGTATCAAGCTGCCAAAGAGAATGACCTACCCAGAATGTCCCAGCCGTGGGG
GGTAGGGAGTTGGTATCAGGCTGCCCCCGAGAACGAGCTTCACAAAGTACGGCA
GCCATGGGGCGTCGGAAGCTGGTACCAACCCGCAGCAGAAGGGGATTTACACAA
GCTCCGATATAATACTGCTAC LycA-10x-QPWGVGSW nucleotide sequence (SEQ ID NO: 116):
ATGGAGTTGCATCACCATTACTTCTTCATACTTCTTTCTCTTGCTTTTATAGCAAG
TCATGCAGCTAATTTATCTCCTGAGGTGTATTGGAAAGTCAAGCTGCCCAACACT
CCTATGCCCAGACCCATTAAGGATGCTCTACACTATTCTGAAGCCTCCGAGGGTG
ACGTTCACAAGTTGCGCCAACCATGGGGAGTGGGTTCGTGGTATCAAGCAGCAA
ACGAGGGTGATGTTAAAAAATTACGCCAGCCTTGGGGTGTTGGCTCTTGGTATAA
GGCTGCCCCAGAGGACGAGCTTCACAAAATACGCCAACCCTGGGGCGTCGGATC
CTGGTATCAAGCTGCCAAAGAGAATGACCTACCCAGAATGTCCCAGCCGTGGGG
GGTAGGGAGTTGGTATCAGGCTGCCCCCGAGAACGAGCTTCACAAAGTACGGCA
ACCATGGGGCGTCGGAAGCTGGTACCAACCCGCAGCAGAAGGGGATTTACACAA
GCTCCGACAGCCTTGGGGCGTGGGGAGTTGGTACAACGACGCACCAGAGAATGA
ACTCCATAAGTTCCGTCAACCCTGGGGAGTTGGATCGTGGTACAGGGCAGCTACT
GAAGGGGACGTTCAAAAGCTGCGTCAGCCGTGGGGCGTCGGCTCATGGTACCAA
GCAGCAAACGAGGGAGACATTAAGAAGCTACGGCAGCCATGGGGAGTCGGCTCT
TGGTACAGAGCCGCTACTGAGGGTGACGTTCAGAAGCTAAGACAGCCCTGGGGG
GTCGGTAGTTGGTATAATACTGCTACAAAGAAAGATGTTAATGAAAACCTCCCA
GTCACCCCTTACTTTTTTGAAACAGATTTACATCAAGGGAAAAAGATGAATCTTC
CATCTCTCAAAAATTATAATCCAGCTCCCATTTTGCCTCGCAAAGTTGCAGATTC
CATCCCCTTCTCATCAGACAAGATTGAAGAAATTCTAAAGCACTTTTCCATTGAT
AAGGACTCAGAGGGGGCTAAAATGATCAAGAAAACTATCAAAATGTGTGAGGA
GCAAGCGGGTAATGGCGAGAAGAAATATTGTGCCACTTCCTTAGAATCAATGGT
TGATTTCACCTCATCTTATCTGGGAACAAATAATATTATAGCACTTTCCACTTTAG
TAGAGAAGGAAACTCCAGAGGTGCAAATATATACCATCGAAGAAGTGAAAGAG
AAAGCAAATGGCAAAGGCGTGATATGCCACAAAGTGGCTTACCCGTATGCGATA
CATTATTGCCATAGTGTAGGAAGCACAAGGACCTTTATGGTCTCAATGGTGGGTT
CTGATGGAACAAAAGTTAATGCAGTATCAGAGTGTCATGAGGATACTGCACCCA
TGAACCCTAAGGCATTGCCTTTTCAATTGCTCAACGTTAAGCCAGGAGATAAACC
TATTTGCCATTTCATATTGGATGATCAGATTGCCTTAGTTCCTTCTCAAGACGCAA
CTCAAGTGTCTGAAAACTAA LycA-10x-QPWGVGSW amino acid (SEQ ID NO: 117):
MELHHHYFFILLSLAFIASHAANLSPEVYWKVKLPNTPMPRPIKDALHYSEASEGDV
HKLRQPWGVGSWYQAANEGDVKKLRQPWGVGSWYKAAPEDELHKIRQPWGVGS
WYQAAKENDLPRMSQPWGVGSWYQAAPENELHKVRQPWGVGSWYQPAAEGDLH
KLRQPWGVGSWYNDAPENELHKFRQPWGVGSWYRAATEGDVQKLRQPWGVGSW
YQAANEGDIKKLRQPWGVGSWYRAATEGDVQKLRQPWGVGSWYNTATKKDVNE
NLPVTPYFFETDLHQGKKMNLPSLKNYNPAPILPRKVADSIPFSSDKIEEILKHFSIDK
DSEGAKMIKKTIKMCEEQAGNGEKKYCATSLESMVDFTSSYLGTNNIIALSTLVEKE
TPEVQIYTIEEVKEKANGKGVICHKVAYPYAIHYCHSVGSTRTFMVSMVGSDGTKV
NAVSECHEDTAPMNPKALPFQLLNVKPGDKPICHFILDDQIALVPSQDATQVSEN*

FIG. 38D

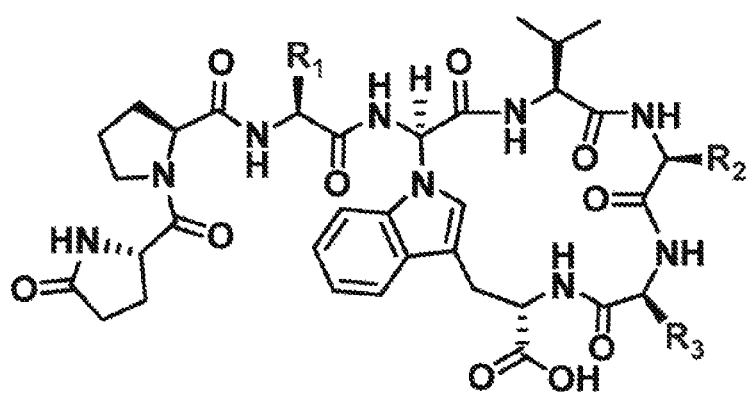
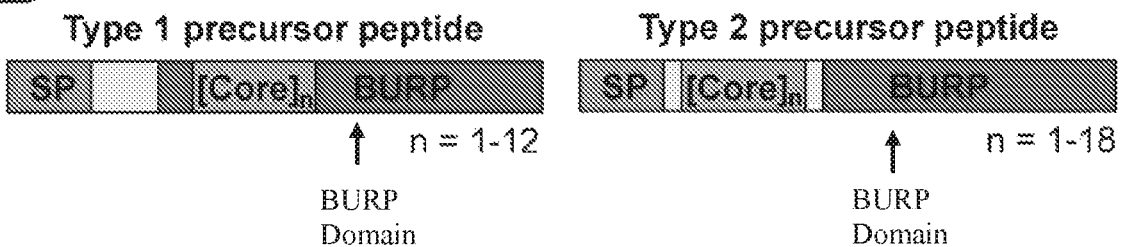
FIGs. 39A-B

SunBURP
MASNLLYLLFLVASAGSAIGALGYQFDIPDTLTNAKSPLDDSTAKFLKS
LLEGGLVLNTPDVCHSLGFFCADEISSSSSEAPEVPKRSLGTRKLLNAA
FESHPNWVSKQPYSVFAWTNEEQPSPTSNWVNKQPYSVFAWTNEEQPSK
WFNKPTSSWVNKQPYSVFAWTNEEQPSKWFNKPTSNWVNKQPYSVFAWT
NEDQPSKWFNKQPYSVFAWTNEDQPSKWFNKQPFGEHPKQKLESLPTKG
RAFRFASAQAGKSILLPPITPLLSNKLIHPHLEDVLPFNKESLSQVLRA
FNLSANSGMGQSMEFALDMGKSTNNGVEFRKSVATTKEMVDFVGGVLCK
EKGDCHVKSIAQSFENKESKMVKVVDVELVSKDPVACHTVPFPYKVYVC
HKIKDSPVYKVNMMVEGGKTLSTPFICHWDTSKFRTNHQAFEDLNMKPG
QGEICHWLGYETIVW (SEQ ID NO: 276)

FIG. 40A

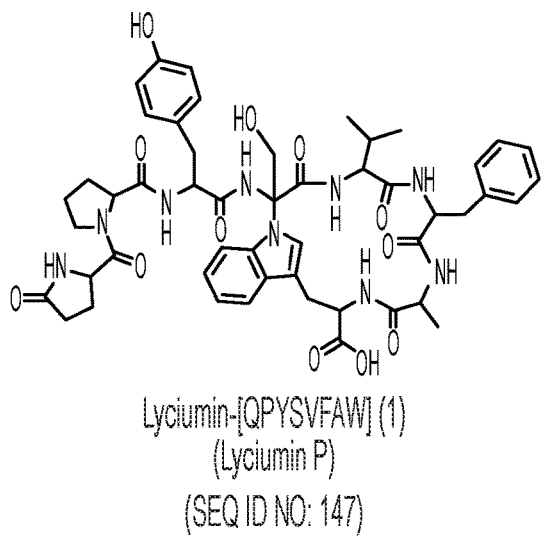

Lyciumin-[QPYSVFAW] (1)
(Lyciumin P)
(SEQ ID NO: 147)

FIG. 40B

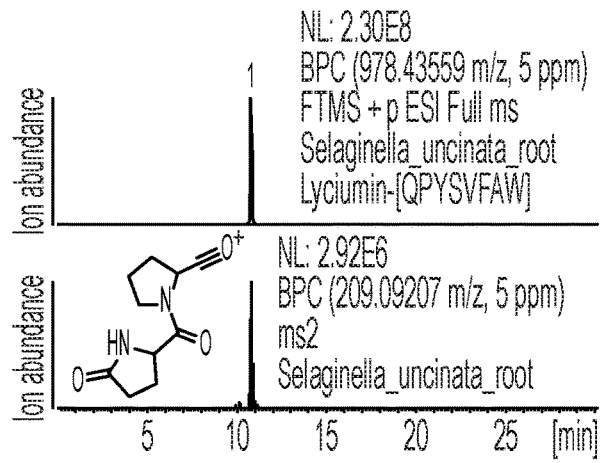

FIG. 40C

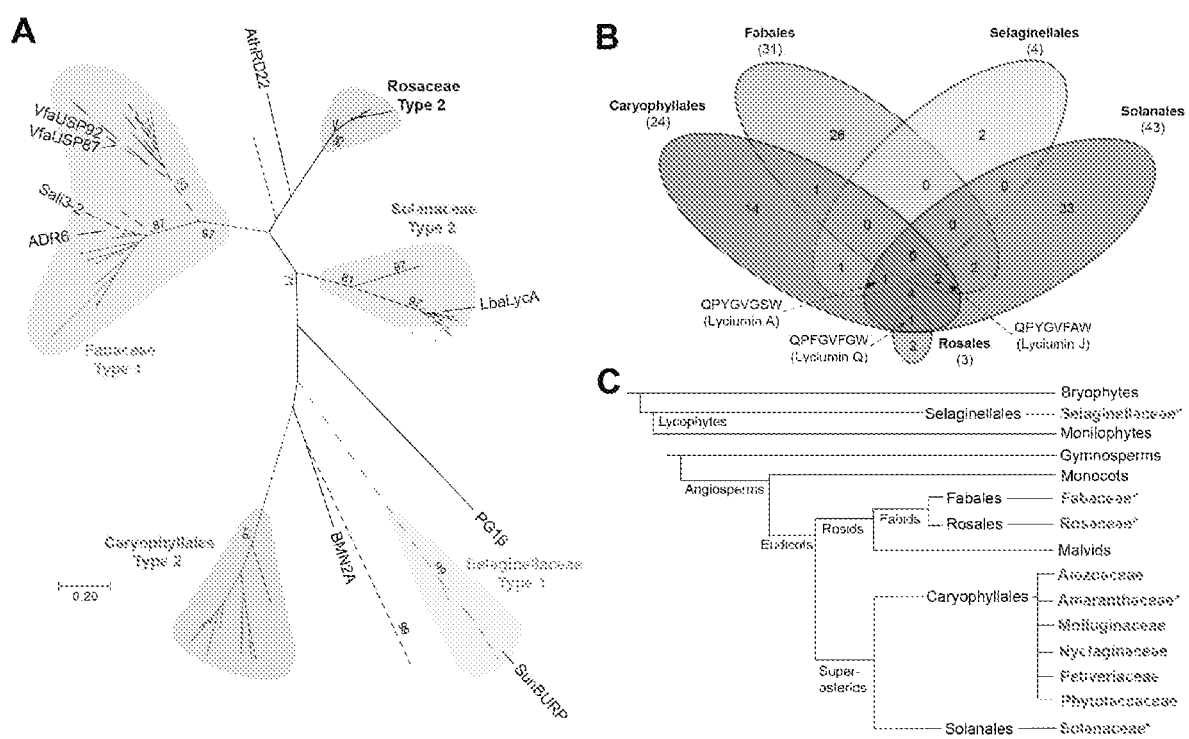
FIGs. 41A-C

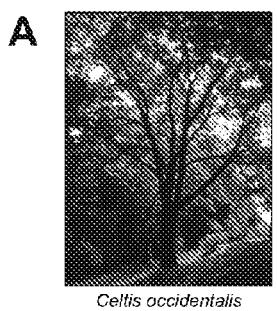
Celtis occidentalis

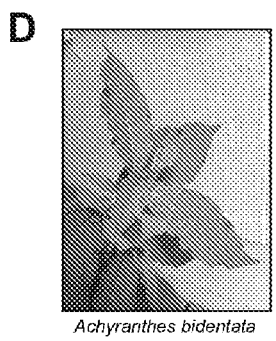
Achyranthes bidentata

A *Celtis occidentalis*
B (SEQ ID NO: 250)

>CocDUF2775
MAESELSSRSVIVALLSLLLSVSTA
ESRKNPAEYWKFVMKDQPMPELIRE
LVBPELFEQEKFDHNEGRVDKKSDK
SFTKESESSISNLDNIKDSQKIAKD
FELDTDSQSSGVFGWVKDSQKFAKD
FELDKRSQPFGVFGWAKDSQKFVND
FELDTNSQPFGVFGWAKDSQKFTND
FGPNPHQRIEGNAKA

Type 3 precursor peptide
[SP][Core][DUF2775] ← DUF2775 Domain

>AbiBURP
MALSFLSFFFLLFSFFFVLSCEQEKYWQMKLPNV
PMPQAIRDNLFHSSGKYEADNNPKVKAEDGVEPFTLHS
NKKSSTNQPFPVFGWKYYVDNKLKDKAEDVVKPFILGS
ETKVGTNQPFPVFGWGYDVGNKPKDKAEDVVESLTLNS
NKKAGTNQPFPVFGWNYDANHKLKEKSQDVVERFTLDS
NTKVGTNQFFPVFGWGYDAGNKPKDKVENVLESLTLDS
NKKAGTNQPFPVFGWNYDANHKLKEKSQDVVEPFTFDS
NTKVGTNQPFPVFGWGYDAGNKPKDKVENVLESLTLDS
NKKAGTNQPFPVFGWKYDANHKLKEKSQDVVEPFIHDL
NTKVGTNQFFPVFGWGYEVGNNPKGKDEDVVESLSLDS
NKKARTNQPFPVFGWKYDANHKLKDKSQSLESNTKVGT
NQPFPVFGWNYAFENLKSKAGDVVKAPDMKETSHDHYF
HFLNKNKNSNEEDPNGGSLFFVEKSLRLGMILKHDFQK
TPKIPFLPKKIAQTIPFKVEKVTDILNLFSLDSESTEG
IAIKETLDVCLQRPKVKKENRTCAQSMEDVVDFVVGEL
GTNDVKVRMMMNNIEVPNGIQDYLITKVKKLEVTNMNG
VACHRMSYPYVVYCHHQKDIGHYDVTLVSPTSGSRPI
QTTAVCHYDTYAWQPDVPALQHLGIRPGDAPVCHFSAI
NDMFWSVKVGSKSLDMVQ (SEQ ID NO: 249)

C (SEQ ID NO: 83)

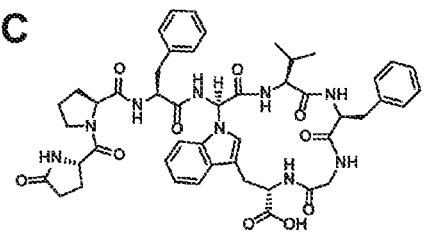
Lyciumin-[QPFGVFGW]
(2, Lyciumin Q)

F
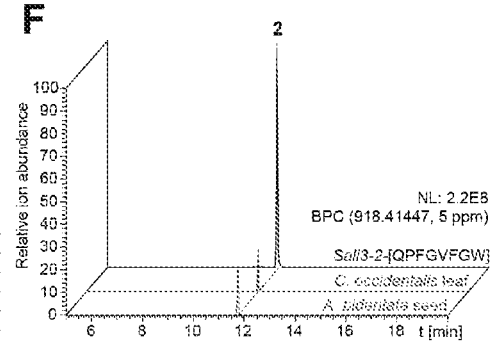

FIGs. 42A-F

\>SwiBURP (*Selaginella willdenowii*) (SEQ ID NO: 199)
MAAHLLYLLFLVAGSAAGALGYQFDIPDTLTNAKSPLDESTAKSLKGLLERGLVLNTPDVCH
SLGFFCEHEISSSSEPEVPKQSLGTRKLLDAALESHLGHPESANQPSPSKWMNKQPYSVFAW
TNENQPSKWFNKQPYSVFAWTNEDQAPSKWFNKQPYSVFAWTNKDQSPSKWFNKQPYSVFAW
TNEDQAPSKWFNKQPYSVFAWTNEDQSPKWFNKQRFARANGEHPKQKSESLPTKGRAFRFAS
AQAGKSILLPPITSLLSNKLIHPHLEDVLTFNKESLSQVLRAFNIPANSGMGQSMEFALDMG
KPTNNGVELRKAVTTTKEMVDFVGGVLCKEKEDCHVKSISQSFENKESKMVKVVDLELVSKD
PVACHTVPFPYKVYVCHKIKDSPVYKVNMMLEGGKTLSTPFICHWDTSKFRTNHQSFEDLNM
KPGEGEICHWLGYETIVWYV \>SbrBURP (*Selaginella bryopteris*) (SEQ ID NO: 200)
PYGVGSWVSKQPYGVGSWVSKQPYGVGSWVNKQPYGVGSWVHKQPYGVGSWVDKQPYGVIRW
VSKKSEEEGLPKGRAFRFASLQSGKSILLPSIIPLVSNKFIHQLLRDVMPFTAESLPQVLTT
LNLPVDSEMAWSMHLALEMGEDCNNEVEVKKSILSTEEMVDFVGGLVCKGSSECHLKSISQS
FDNKDPKMVEIVDVQQLSKHPVACHTVPFAYKVYVCHTIKDSPIYKVTMLEDGKETTVPVMC
HWDTSNFRPDHQAFKDLNMKPGDGEICHWMAYETIVWYA \>SmoBURP (*Selaginella moellendorffii*) (SEQ ID NO: 201)
VKEPFGVGTWVKEPFGVGTWVKEQPYGVGAWVKEQPAPQQEEKNMLGRAFRFASAQAGEILL
PPITALLSNKLMHPHLEDALPFSMKSLPQVLRAFNLSSDSEMAQSMMQSLHMGRPTKNDVEI
RKSVVTAEQMVELAGELLCEGKGEDCHLKSVAQSFENKEPTAKMVKVANIELVSKDPLACHT
VPFPYKVYVCHKIKDSPVYKVTMTLESGETVTTPVVCHWDTTKFRPNHPAFEELNMKPGEGE
ICHWLAYETVVWYA \>SunBURP (*Selaginella uncinata*) (SEQ ID NO: 202)
TLFLSPSPTSNWVNKQPYSVFAWTNEDQPSKWFNKQPYSVFAWTNEDQPSKWFNKQPFGEHP
KQKLESLPTKGRAFRFASAQAGKSILLPPITPLLSNKLIHPHLEDVLPFNKESLSQVLRSFN
LSANSGMGQSMEFALDMGKSTNNGVEFRKSVATTKEMVDFVGGVLCKEKGDCHVKSIAQSFE
NKESKMVKVVDVELVSKDPVACHTVPFPYKVYVCHKIKDSPVYKVNMMVEGGKTLSTPFICH
WDTSKFRTNHQAFEDLNIKPGQGEICHWLGYETIVWYV \>AbeBURP1 (*Atropa belladonna*) (SEQ ID NO: 203)
MELHHHCFFILLSLAFVSSHAANLSPEVYWKVKLPNTPMPRPIKDALHYSEASEGDIHKLSQ
PYGVFSWYRAATEGDVQKLCQPYGVGFWYQAATEGDVQKLRQPYGVGSWYNSAPNKDLNENS
PVTPYFFETDLHKGKKMNLPSLKNYNPAPILPRKVADSIPFSSDKIEEILDHFSIDKDSEGA
KMFKKTIKMCEEPAGNGEEKYCATSLESMIDFTSSYLGTNNILAISTEVEKETPEVQTYIIE
EVKEKANGKGVICHKVAYPYAVHYCHSVGRTRTFMVSMVGADGTKVNAVSECHEDTAPMNPK
ALPFQLLNVKPGDKPICHFILDDQIALVPSHGATQVAQN

FIG. 43A

\>AbeBURP2 (*Atropa belladonna*) (SEQ ID NO: 204)
MELHHQYYFFALLSLVFVVSHAANLSPEVYWKVKLPNTPMPTPIKDALHISEKPAAHNGDGN
IKMSQPWEVFSWYHAATENELSTFHQPWGVFSRYNGVGKKDLNENHRVTQYFFETDLHKGKK
MNLPSLKNYNPAPILSRKVIDSIPFSSDKIEEILDHFSIDKDSESAQTIMKTIKMCEEPAGN
GEVKYCATSLESMVDFTSSQLGTNSILAIFTEVEKETPEVQTYIIQQVKEKTNGNGIVCHKM
AYPYGVHFCHNVGSTRTFMVSMVGADGTIVNAVSICHEDTAYMNPKSLPFQLLHVKPGDKPI
CHFILDDEIAMFPSQNKTLLSD \>SptBURP (*Solanum ptychanthum*) (SEQ ID NO: 205)
MELHHQYYFFTLFSLVFVASHAANLSPEVYWRVKFPNTPMPTPIKDALHISEKTANNGDGNT
KIRQPYGVFAWYHDAPKNELHKLHQPYGVFAWYHDAPENELHKLRQ \>SduBURP (*Solanum dulcamara*) (SEQ ID NO: 206)
MELYHQYYFFTLFSIVFVVSHAANLSPEVYWKVKLPNTPMPTPIKDCLYISEKTTSNGDGST
KVRQPYGVSIWYKAASENELHKVRQPWGVGSWYKAASENELHKVRQPYGVFSWYKAASENEL
HKVRQPYGVGIWYKAASENELHKVRQPYGVFSWYNGANKKDLNENHQVTPYFFETDLHQGKK
MNLQSLKNYNPAPILPRKVVDSIPFSSDKIEEILNNFSVDKDSERAKVIKKTIKMCEEPAGN
GEVKHCATSLESMVEFTLSHLGTNNIIAISTEVEKETPEVQTYTIEKVEEKANGKGVVCHKV
AYPYAVHFCHDVGSTRTFMVSMVGADGTKVNAVSVCHEDTASMNPKALPFQLLNVKPGDKPI
CHFILDDQIALFPSQNAVLQVAEN \>SsiBURP (*Solanum sisymbriifolium*) (SEQ ID NO: 207)
MELHHQYYFLTLFSVVFVVSHAANLSPEVYWKVTMPNTPMPKPIKDALHISEKTAYNGDGNT
KISQPYDAYSWYHASLESELHKIRVPFGVGSWYNGAATKDLNENHLVTPYFFETDLHKGKQM
NLPSLKNYNPAPILPRKVVDSIPFSSNKIEEILSHFSVDKDSERAEAIKKTIKMCEDPAGKG
EVKHCATSLESMVDFTLSHLGTNNIIAMSTEVEKETPEV \>SviBURP1 (*Solanum virginianum*) (SEQ ID NO: 208)
MELYHQYYFFTLFSVIFVVSDAANLSPEVYWKVKLPNTPMPTPIKDALHISEKNLKPKDELH
ELRQWGVYALHHYAPKAELRKLPQPYGVYSWFHGAPEDPVYARYLEAENELHKVHQPSQYDG
AAKKDVNENHLVTPYFFETNLHQG \>SviBURP2 (*Solanum virginianum*) (SEQ ID NO: 209)
SPEVYWKVKLPNTLMPKPIKDALHISEKTAYNGDKNTKISQPYGVYGWYHDAPEDKLHKLRQ
PYGVYVWYQDAPKDELHNLRQPWGVGSQYSGAAKKDLNENHQVTPYFFETNLHK \>LbaBURP1 (*Lycium barbarum*) (SEQ ID NO: 210)
LRQPYGVGSWYQAATEGEVKKLRQPYGVGSWYNTATKKDVNENLPVTPYFFETDLHQGKKMN
LPSLKNYNPAPILPRKVADSTPFSSDKIEEILNHFSIDKDSEGAKMIKKTIKMCEEPAGNGE
KKYCATSLESMVDFTSSYLGTNNIIALSTLVEKETPEVQIYTIEEVKEKANGKGVICHKVAY
PYAIHYCHSVGSTRTFMVSMVGSDGTKVNAVSECHEDTAPMNPKALPFQLLNVKPGDKPICH
FILDDQIALVPSQDATQVSEN

FIG. 43B

>LbaBURP2 (*Lycium barbarum*) (SEQ ID NO: 211)
MELHHYFFILLSLAFIASHAANLSPEVYWKVKLPNTPMRPIKDALHYSEASEGDVHKLRQ
PYGVGSWYQAATEGDVQKLRQPYGVGSWYQAATEGEVKKLRQPYGVFSWYQAANEGDVKKLR
QPWGVGSWYQAAIEGDVQKLQPFGVGSWQAATEGDVQKLRQPYGVGSWYQA >SchBURP1 (*Solanum cheesmaniae*) (SEQ ID NO: 212)
VIFVVSHAANLSPEVYWKVTLPNTPMPKPIKDALHISEEKLKPEDELDKLRQWGVYARYDGV
PKSELRKLHQPYGVYTWYRGAAEDPVYARYLDASRYLDASEKELHKVHPPSLKDDNENHLVM
PYFFETHLHQGQQLNLLSLKNNNPAPFLPRKIVDSIPFSLDKIEEIFSYFSVDKDSKPAEMI
SKTIKLCEGPAGNGEVKYCATSLESMIEFTLSHVGTNNIIAISSEVEKETPEVQTYTIERVE
EKANGKGVICHKVAYPYAVHYCHDVGSTRVFMVSMVGADGTKVNGVSVCHEDTAPMNPEALP
FQLLNVKPGEKPICHFTLDDQIVLFPSPNVLLQVTDN >SchBURP2 (*Solanum cheesmaniae*) (SEQ ID NO: 213)
PYGVYSWYQAAPENELHKVHQPWGVGSWYNHAAKKDLNDNHPVTPYFFETDLHQGKKMNLES
LKNYNPAPILPRKVVDSIAFSSDKIEEILNHFSADKDSERAKDIKKTIKMCEEPAGNGEVKH
CATSLESMIDFTLSHLGTNKIIAISTEVEKETPEVQTYTIEKVEEKANGKGVVCHKVAYPYA
VHFCHDVGSTRT >SlaBURP1 (*Solanum lasiophyllum*) (SEQ ID NO: 214)
KPAYNGDGNTKISQPWGVGAWYKAAPEDELHKIRQPYGVYSWYQAAPENELHKVHQPWGVGS
WYNHAAKKDLNDNHPVTPYFFETDLHQGKKMNLESLKNYNPAPILPRKVVDSIAFSSDKIEE
ILNHFSADKDSERAKDIKKTIKMCEEPAGNGEVKHCATSLESMIDFTLSHLGTNKIIAISTE
VEKETPEVQTYTIEKVEEKANGKGVVCHKVAYPYAVHFCHDVGS >SlaBURP2 (*Solanum lasiophyllum*) (SEQ ID NO: 215)
LLRNLPLAEKPAYNGDGNTKISQPWGVGAWYKADPEDELHKIRQPWGVYRWYQAAPEDELHK
IRQPYGVYRWYQAAPEDELHKIRQPYGVYSWYQA >BbiBURP (*Bituminaria bituminosa*) (SEQ ID NO: 216)
MESWNLGFCILVLFSLALAGESHGRNWQAVWPNTPIPDSLKDLLEPGQSGVENEDVPMKVDD
TQYPTDFFFNKELYPGKTMNIEFSTHHLTQPYGVLYWVHGSDVKDIEKEGYTPEQLCLRKGP
KGEDKYCAKSLDTLMEFVTSKLGKNVQPFTSSFVSKQGQYTVKGAQNLGDKAVMCHRLNFQK
PMFYCHEIHATTAFLVPLVAGDGTKTHAVAVCHFDTSVLNFQLFRQITKVDPGTNPLCHFLG
NKSILWVPNSAMPYQTN >GleBURP (*Glycyrrhiza lepidota*) (SEQ ID NO: 217)
MDFRHPLISILVLFSLALAGESHARASLPEEEYWDAVWPNTPIPTALRELLKPGPQGVDIDN
LPMEIDDTQYPKTFFYEHDLYPGKRMNVQFSKRPFAQPYGVYTWMREIKDIDKEGYTFNEVC
VKKGAAKGEHKYCAKSLGTLIGFAISKLGKNIQSLSSSFPDAQEQYTVESVQNLGDKAVMCH
RLNFQKVVFYCHEINATTAFMVPLVASDGTKTQALAVCHKDTSGMNHDMLHQILKADPGTNP
VCHFLGNKAILWVPNLALDSGYQTNVVV

FIG. 43C

>GsoBURP1 (Glycine soja) (SEQ ID NO: 218)
MALRCLVMSLSVLFTLGLARESHARDEDFWHAVWPNTPIPSSLRDLLKPGPASVEIDDHPMQ
IEETQYPKTFFYKEDLHPGKTMKVQFSKPPFPQPWGVGTWLKEIKDTSKEGYSFEEICIKKE
AFEGEEKFCAKSLGTVIGFAISKLGKNIQVLSSSFVNKQEQYTVEGVQNLGDKAVMCHGLNF
RTAVFYCHKVRETTAFMVPLVAGDGTKTQALAVCHSDTSGMNHHMLHELMGVDPGTNPVCHF
LGSKAILWVPNLSMDTAYQTNVVV >GsoBURP2 (Glycine soja) (SEQ ID NO: 219)
MEFRCSVISFTILFSLALAGESHVHASLPEEDYWEAVWPNTPIPTALRELLKPLPAGVEIDE
LPKQIDDTQYPKTFFYKEDLHPGKTMKVQFTKRPYAQPYGVYTWLTDIKDTSKEGYSFEEIC
IKKEAFEGEEKFCAKSLGTVIGFAISKLGK >ApyBURP (Acacia pycnantha) (SEQ ID NO: 220)
MDLRRRFGVLALLLCLALAESDVTSSRSAEEYWRSIWPDTSMPKNLEYLLGSSVSDAENTDN
TQYPYTSFFEQDLHAGKKMDIIFNSPYADKEQKSNPTEKYPKKSSWKRNTKNEDSEKSASPQ
PWGVGTWRRNTMNEDSKKSASPQPWGVGTWRRNAMNEDSEKSASPQPWGVGTWRRNTMNEDS
EKSGSPQPWGVGTWRRNEMNEDSEKSTYPQPWGVGTWRRNAMNEESEKSASPQPWGVGTWRR
NTMNEDSKKSASPQPWGVGTWRRNAMNEDSEKSGSPQPWGVGTWRRNTMNEYSEKSGSPQPW
GVGTLRRNAMNEDSEKSTYPQPWGVGTWRRDAMNEESEKSASPQPWGVGTWRRNTMNEDSER
SASPLPWGVGTWRRNADSEKSAFPQPWGVGTWKRNTMKNVHEHLSMEAICNTKERFVGEDDK
FCAESVESLIDFVISKLGKDIEALTSSFVPHQTQYKILEGIQRVSSEGVMCHKLNFEKPLFY
CHQVNATITYIVPMEASDGTRTSIVALCHRDTRGLDPHKLFHQLKVKPGTVPVCHLLGSGAI
SWVPKNNELKAAF >AarBURP (Acacia argyrophylla) (SEQ ID NO: 221)
RNADSEKSAFPQPWGVGTWKRNTMKNVHEHLSMEAICNTKERFVGEDDKFCAESVESLIDFV
ISKLGKDIEALTSSFVPHQTQYKILEGIQRVSSEGVMCHKLNFEKPLFYCHQVNATITYIVP
MEASDGTRTSIVALCHRDTRGLDPHKLFHQLKVKPGTVPVCHFLGSGAISWVPRNNELKAAF >AtrBURP1 (Amaranthus tricolor) (SEQ ID NO: 222)
MLSLLAHINRIPNSRSLHYLNSYFLPNMAMDLRLQVPALFLLTFLAIHVSSCKQEDYWKMKL
PKVPMPEAIKHSLLHSGGENKLKDEYTIKQPYTVGSWKYDVDKNKVVDESALKQPFTVGSWK
YDADKNKVKDDSALKQPFTVGSWKYDVDKNKVKDDSALKQPYT >AtrBURP2 (Amaranthus tricolor) (SEQ ID NO: 223)
ADKNKVVDESALKQPYTVGSWKYDVDKNKVKDDSALKQPFTVGSWKYDADKNKVKDDSALRQ
PYTVGSWKYDVDKNEVKDDSALKQPYTVGSWKYNENDESKQASPHHLHHQKLMHENVNSNDK
EDLTDGSVFFVEKSLHIGSKLKHDFQKTPEMSFLSKQEAQSIPFSMEKIGDILNLFSLKSNS
AEANAIKGTLDICLYRPKVSKENRTCAQSMEDIVDFVVGELGTNEVEIKMMNNNIEVPNGIQ
DYLLSKVEKLFVPGNTAVACHRMSYPYIVYYCHQQDIGQYNVTLVSPSTGAAFQTTAVCHY
DTYAWQPDVVALKYLGIRPGDAPVCHFSAINDMFWTLKDEPKSLDMVQ

FIG. 43D

>AhoBURP (Atriplex hortensis) (SEQ ID NO: 224)
SENGKERVGIDQPFTVGAWKYNSKNAKERVGINQPFTVGAWKYNSENRKERVGINQPFTVGA
WKYNSENGKERVGIDQPFTVGAWKYNSENANNKNNGDKEKDNDVRMG >AprBURP1 (Atriplex prostrata) (SEQ ID NO: 225)
WKYNSENGKERVGMDQPFTVGAWKYNSKNGKERVAIDQPFTVGAWKYNSKNANNKDNGDKEK
DNDLRMGSVFFIEKSLRLGAKLKHDFQKTPSVPFLPKHFVQSIPFSDNKFTEILDLFSIKPG
SPEATGIKGTLNICLHRPKVEKENRTCAQSMEDVVDFVVRELGSNDVELRMMRNDIEVPKGI
QDYVVTKVKKLSVPSNTAAACHRMVYPYVVYYCHHQKDIGHYDVTLVNPTTNTAFQTTAVCH
YDTYAWKPNVPALRYLEIRPGDAPVCHFSAINDMWWNLKPNSKSLDMVV >AprBURP2 (Atriplex prostrata) (SEQ ID NO: 226)
MAMHFGLGLGLQVHAIFLLVFLAFHASSCEQEDYWQMKLPKVPMPQAIKDNLFHPKGSYVDD
AKKNVDVDQPFTVGAWKYNSDNGKERVGIDQPFTVGAWKYNSKNGKERVAIDQPFTVGAWKY
NSKNGKERVGIDQPFTVGAWKYNSENGKERVGIDQPFTVGAWKYNSDNGKERLVNTNS >AprBURP3 (Atriplex prostrata) (SEQ ID NO: 227)
SENGKERVGIDQPFTVGAWKYNSENGKERVGIDQPFTVGAWKYNSDNGKERVGVDQPFTVGA
WKYNSENGKERVGIDQPFTVGAWKYNSENGKERVGVDQPFTVGAWKYNSENGKERVGIDQPF
TVGAWKYNSENGKERVGIDQPFTVGAWKYNSENGKERVGIDQPFTFRAWKYNSNNGKERVGI
DQPFTVGAWKYNSENGKERVGIDQPFTVGAWKYNSENGKERVGIDQPFTVGA >CquBURP (Chenopodium quinoa) (SEQ ID NO: 228)
MAMHFGLPRLLLHAIFLLVFLAFHASSCEQEDYWQMKLPKVPMPQAIKDNLFHPKDKMSMMT
PSIETKDKAAHGNDADKAKKANTNQPFTVVGWKYNADGAKERVGMSQPYTVMAWKYNVDDAK
ERVGIDQPYTVWGWNYNTDSANKEKVKEAYKPLSIETNTKKTGIDQPYTVWGWNYNTNSANK
EKVKEAEKPLSIETNTKKTGVDQPYTVWGWNYNTNNANKEKVKEAEKPLSIETNTKKTGIDQ
PYTVWGWNYNTDSANKEKVKEAEKSLSIETDTKKTGIDQPYTVWGWNYNTDSANKEKVKEAE
KSLSIETNTKKTGIDQPYTVWGWNYNTNSGNKEKVKEADKVFTMDTSTKKAGTKQPYTVMGW
KYNADNGKREKVGHEVSVGSVFFIEKSLRLGDKLKHDFQKTPSVPFLPKHIAKSIPFSEDKF
TEILNLFSIKPGSVEATGIKGTLDVCLHRPKVEKENRTCAQSMEDVVDFVVRELGSNDVELR
MMKNDIEVPKGIQDYVITKVKKLVVPGNTAAACHRMSYPYVVYYCHHQQDIGHYDVTLVSPT
TGNAIQTTAVCHYDTYAWKPNVPALQYLGIRPGDAPVCHFSAINDMFWSLKANSKSLDMVV >AbrBURP (Alternanthera brasiliana) (SEQ ID NO: 229)
AQDAEPQEMESLSLDDNKKMSSRTNQPYTVGAWKYDDAGKSKKVEQIVDPFSSDKTKKMSSR
TNQPYTVGAWKYVQDVEPQEKVKQVGNLLSLDNSKKTISHTNQPYTVGAWKYDEAGKPQEKV
EQVVDPLSLDKNKKMTSYTNQPYTVGAWKYDSDKPKIKSEDTSHHDLMHNNIKSDQEDGGS
VFFIEKSLSPGMILKHDFQKTPYVPFLPKHISQNVPFEVENFSEILNLFSLDPKSTEATAIK
ETLEICLQRPKVKKENRTCAQSVEDVVDFVIGELGTNDVKLRMMNNNIEVRNGIQDYVLTKV
KKLEVPGYNAVACHRMSYPYVVYYCHHQQDIGHFDVTLVDPTSGSAIQTTAVCHYDTYAWKP
NVPALRYLKINPGDAPVCHFSAINDMFWSLKDDTNKSLLKVQ

FIG. 43E

>AseBURP (*Alternanthera sessilis*) (SEQ ID NO: 230)
MAMHFGLGLGLQVHAIFLLVFLAFHASSCEQEDYWQMKLPKVPMPQAIKDNLFHPKGSYVDD
AKKNVDVDQPFTVGAWKYNSDNGKERVGIDQPFTVGAWKYNSE >HceBURP (*Hypertelis cerviana*) (SEQ ID NO: 231)
MATPVIILRAFLIVALMVFHGSSCSQEDYWKMKLPEVTMPQALKDNLLHEISNSQKEPIITQ
ASSLHDVKDKVDINDMTSTTQPFTVLGWKYNRDASEKEDVTMQPSLHDFKENVDVKDMTATK
QPFTVFGWKYNKDASEKQNVDVKDMTATKQPFTVFGWKYNKDASEKQNVDVKDMTTTKQPFT
VFGWKYNGDSIEKENVDVKDMTATKQPFTVFGWKYNKDDSEKAEEVDRPKKHTKDVTTMENH
KSHHHVMHHHVHNSGEDNNVAGSVFFKEGSLYLRAKLKHDFQNTSKVVFLPRNEVELIPFSM
DKYMEILNRLSIKPGSLEAIGVKGTLAICLEKPNVHKENRTCARSLEEMVDFVTKELGTNKV
HVTMMRNTDNTEIPNGIQEYEVISLKKLVIPDNTAVACHKMSYPYAVYYCHHQQDIGHYSVT
VRNSDGVLVDTTAVCHYDTYAWEADVPALKYLKIAPGDAPVCHFSAVNDIFWTTKADSYIRK
FLDKDQ >BspBURP1 (*Bougainvillea spectabilis*) (SEQ ID NO: 232)
MAKNLLILRSFLLVCLVAYASSCKQAEYWKMKLPRVPLPKALENNLHYFHHDEKATIAQPYT
VGSWSYKSDKPTIAHPYTVGSWSYKQNNQDKSTISQPFTVGSWSYKQDNQDKSTISQTYTVG
SRSYKQNDQEKPTIAQPFTVGSWSYKQDNQDKSTISQTYTVGSRSYKQNDQEKPTIAQPFTV
GSWSYKQDNQDKSTISQPFTVGSWSYKQSNQDKSTISQPFTVGSWSYKQNDQEKPTIAQPFT
VGSWSYKQDNQDKSTISQPYTVGSWSYKQSNQDKSTISQPFTVGSWSYKQNDQEKPTIAQPY
TVGAWWYKADKNQQNHK >BspBURP2 (*Bougainvillea spectabilis*) (SEQ ID NO: 233)
PYTVGAWWYKADKNQQNHHHHFDASDNNGIKSSNKGNQDDDQDMVGGSVFFTEEHLRVGMKQ
THDFQKSGKVKFLPRDVVQSIPFAVDKLPEILNILSVNPKSAQAMAIKDTLTTCLDRPRVKK
ENRTCTQSLESIVDFVINELGTNNVKLKMMGQPEEKVPTGMQEYLITKVTKLDVPGNNGVAC
HRMIYPYAVYWCHHQKDIGQYSVTLVD >BspBURP3 (*Bougainvillea spectabilis*) (SEQ ID NO: 234)
LPYLFHRSTHSPKMAKNLLILRLFFLVCLVAYASSCKQAEYWKMKLPKVPLPKALENNLQYS
HPDEKATIAQPCTVGAWLYKQTDQDKPSIAQPYTVGGWSYKKDKSTIAQPYTVGAWSYKQNN
QDKST >PalBURP (*Petiveria alliacea*) (SEQ ID NO: 235)
PKSHFLSLHGNKEDNEGKSTIAQPYTVGAWKYVVEKEKDKLTMPQQPYTVGAWKYDVEKEKD
KLTMPQESFLVTSRKYKEDNEGKSTIAQPYTVGAWRYKMNDANNHKFHNHFMNQFHTVDGDK
LLGSSKQGNQDQDLDGGSIFFTKQNLCVGMQRHDFQKSGKVKFWPKNMVESIPFALDKVFE
ILGHLSINTNSFEAKTIKETLITCLERPLVKKENRTCAQSLESIVDFVQELGTDNVKVRMM
SQTENEVPNGMQVYEVTKVEKLDIPGNNGVACHKMLYPYAVYWCHHQQDIGQYAVTLKTSQG
NLVDTTAVCHYDTYAWDPNVPALKYLKLNPGDAHVCHFSGINDMFWSLNTPKITNRKVTLDA
TA

FIG. 43F

>PboBURP (*Phytolacca bogotensis*) (SEQ ID NO: 236)
DKEKPMINHKEDNEKEMPMTNQPYTVFAWKYKQDDQEKPMINYKEDNEKEMPMTNQPYTVFS
WKYKQDDQDKPMINYKENNEKEMPMTNQPYTVFAWKYKQDDKEKPTIAQPYTSADDSNTNNH
KLHDHLMHHMGSVDDRNTLTPSNEENQDKDLIGGSVFFVEEKLRVGMKQRHDFQKIEKVSFL
PKDMVDTIPFGVDRLPEALNRLSINPDSVEATSMKETLTTCLERPRVKKENRTCAQSLEDIV
DFVIRELGSDNVKVRMMSMPEDEVPIGMHEFEITKVDKLEVPGQNGVGCHKMVYPYAVYWCH
HQQDIGQYAVTLVSPEGVKVETTAVCHYDTYAWDPNVLALRYLKIRPGDAPICHFSGFNDMF
WSLNTALQGKVGRSGNRKLDLLQ >MdeBURP (*Microtea debilis*) (SEQ ID NO: 237)
ENTIDTTKKPSTSQPYTVFAWGYGKENANEKTTDTTEKPSTSQPYTVFAWGYGKENANEKTI
DTTEKPSTSQPYTVFAWRYKDKNAKETIIDNTKGSVGTSHEVPHQHFMHKMSSAVDANEEDA
SGGSFFFMEKDLSLGNKLKHDFQKSERVSFLPRDVAESIPFSVDKYGEILNILSLKPESIDA
KAIRETLGLCLEKPMAKEENRTCATSLEALVDFVIGELGTNDVKVTTMSKKFEEVPNGPMKY
KITRLRKLETPSNTAVACHKMSYPYVVYYCHHQQNIGYYAATLLSPGGVSVDTTAICHYDTY
AWDPEVPALRYLNIKPGDSPVCHFS >HlaBURP (*Hilleria latifolia*) (SEQ ID NO: 238)
MGKNFILLRAFFLLSIVAIHASSCKQEEYWKMKLPNVPIPNAVKNNLLHSDKNEKHKPTISQ
PYTVGSWKYNEGEKKQNPITNQPYTVGSWKYGEKEEEKPSINQPYTVGSWKYNEDKEKKPSI
NQLYTVSAWKYNEDKDREKPTINQPYTVGSWKYNEEKEKKKLNINQPYTVGSWKYNEKNMKV
KPTINQPYTVGSWKYNEDEEKEKFIINQPYTVGSWKYNENEEKEKLSINQPYIAILWKNNED
KEEEKPSINQPYTVGSWKYKEDKERDKPTIDQPYTVGSWKYNEDKEKMKLIINQPYTVGSWK
YNEENMKVKPTINQP >DecBURP1 (*Delosperma echinatum*) (SEQ ID NO: 239)
TTQPWTVSLWKYNADEKKYDVNNAKQDGSIHHHIHNHDGEMAGASVFFIEKDFHVGAKLKHD
FQKRPKAPLLSSEIARSIPFSIDRIPEILQRFSISPESSEATIIKETLSLCLERPIVKIENR
TCAQSLESLVEFAVQELGTNDIKATMMNNLNHIRSGLQEYTVTKIKKMSTGLEGNALVTCHR
MNYPYVIYYCHQRAIGLFSVTLVDPKGVAVDTSATCHYDTYAWQPDVPALRYLNIKPGDSP
VCHFAGATDISWTINKSNHLIMATEA >DecBURP2 (*Delosperma echinatum*) (SEQ ID NO: 240)
KEKTTPTTTTTTQPWTVSSWKYNADEKEKITTPTTTTTTQPWTVSSWKYNADEKEKTTPT
TTTTQPWTVSSWKYNADEKEKTTPTTTTTTQPWTVSSWKYNA >AmeBURP1 (*Astragalus membranaceus*) (SEQ ID NO: 241)
MEFTRLSVLALLCLALVGSDASKSEEDYWHSVWPNTPLPKTLSDLLMPYSEIPIKAKEEKQY
WTVFFEHDLYPGKQMSLGVQKHSDIHHEHFQSRITKASQPFGARTWETREKESQPFGARTWE
ARKQVSQPFGARTWETSEKVSQPFGARTWETSEKISQPFGARTWEARKDVIQPFGARTWETN
EKVSQPFGARTWEARKEVSQPFGARTWETSEKASQPFGARTWEAHKEVSQPFGARTWETNQK
VSQPFGARTWETLEKLNQPFGARTWETREKENQPFGTSTLGPEKDSIDDYCGKPSAIGEEKH
CALSLKSMMDFAISKLGTNIKVISSSFAQNRDQYVVEEVKKIGDKAVMCHRLNFEKVVFYCH
QVNATTSYMVPLVAFDGIKAEALTICHHDTRGMNPDVLYDVLKVKPGTVPVCHFVGNKAVAW
VPNRDASNESNDHPCVI

FIG. 43G

>AmeBURP2 (*Astragalus membranaceus*) (SEQ ID NO: 242)
MELTRPSLLALICLVVGSDASKSGEDYWHSVWPNTPLPKIISDLLLPYSEMPIKAKEEKQY
WTLFFEHDLYPGKQMSLGIHGHSEIQPFGALVWRKREEPSQPFGALVWRKREEPSQPFGGFA
WRKREEPSQPFGARDRWTREEPSQHFRAHTQKLEKDIIDEFCGASAIGEDKYCALSLEAMMD
FAISKLGTNIKVISSSLSKNQDQYVVQEVKKIGNKAVMCHRMNFEKVLFYCHEVNATTAYMV
QLVAPDGTKAEALTICHHDTRGMDPNVLYKVLKVKPGTIPVCHFVGNKAVAWVPNRDASHES
SDHLCVT >AmeBURP4 (*Astragalus membranaceus*) (SEQ ID NO: 243)
MELTRLYVLALICLGLVGSNASQGEDYWHSVWPNTPLPKILSDLLLPYSEMPIKAKEEKQYW
TVFFEHDLYPGKQMSLGIHEHSEIQHFQSRVTKAKHPLGILVWGGTREKETQPFGVPTQGAR
EKSNQPFGFLIWEQREKASQPFRARTLGTHKKESKPLAADTRRIEKDIIDEFCVNPSAIGED
KYCALSLESMMEFAISKLGTNIKVISSSFAKNQDQYVVEEVKKIGDKAVMCHRMNFEKVFFY
CHEVNATTAYMVPLVAPDGTKAEALTICHHDTRGMD >KzaBURP1 (*Xanthocercis zambesiaca*) (SEQ ID NO: 244)
MRIYILLQLALVGGSHAHESIPDADYWQAIWPNIPIPSALCELLKPGAADAEISNLPMKIDD
TQYPETFFFEHDLYPGKIMNLQFSKRPYAQPYGVYSWGRLTNLKNLETEGFTYEEVCVKNPN
AKGEHNYCAKSLGTLIGFAISKLGKNIQVLSSSFVDKQNQYTIEGVHNLGDKAVMCRRLNFQ
KVVFYCQEIHKTTAFMVPLVAADGTKTKALAVCHSDTSGMNAEVLYELLKIKPGTASACHFL
GSKAILWVPNFVVDNFYNNNEAS >LsaBURP (*Lathyrus sativus*) (SEQ ID NO: 245)
MGFTHLSLLALLCLVFVGINASKSDEEYWKSIWPNTPIPRPLLDLLLPDSKTSVPIRDYEEN
QYWTVFFEHDLHPGKKMSLGIHKHSKTHVSVETRNQPFGINSWWDRKSSEKASQGFETHRPT
NKAIKEEIKKPIETFGILIWTGKPNQDSGSRTKIDKASVKKSERLVQTYTVSSLTEEEMDIF
RDYCGKPSPIGEDKYCAPSLESMMNFVISKLGKNIKAMSSSFSQNQEEYVIEEVKKLGEKTV
MCHRLNFKKVAFYCHQVNATSTYMVPLVASDGTKSNALTICHHDTRGMDPSIYEILKVKPG
TVPVCHFIGNKAIAWIPNEEDVTTSNGHPCVI >SheBURP1 (*Senna hebecarpa*) (SEQ ID NO: 246)
MKFPRLALLALFCVFVVGTDASPSDEDYWRSIWPNTPMPKNLQDLLKPANEITSTKVEDTQY
PSNFFLVKDIQGGRKMKLHFNKRSNAQPFGVFAWSKHKVNNDSDTSTEVEDTQYPSIFFFEN
DLHPGQQMNLKFNKRSNA >SheBURP2 (*Senna hebecarpa*) (SEQ ID NO: 247)
FLVKDIQGGRKMKLHFNKRSNAQPYGVFAWRKHKVNSDSDTSTEVERGHANSLEKFTLEEEL
CEKRPLAVGEDKICAKSLESLVDFIISKLGKDVEPLSSSFVPHQNQYNILDGVQKVAEDGVM
CHRLNFRNVVFYCHQVNATSAYTVPLAAPDGTETKALVVCHHDTRGINEHILFHQLKIKPGT
VPVCHFLGTKALLWVPNNKPIQAI

FIG. 43H

\>AamBURP (*Apios americana*) (SEQ ID NO: 248)
MEFHHLLISTCVIFSLAIVGETHAHASLLDEDYWQAVWPNTAIPNALRELLKPGPAGVEIND
LPMKIDDTQYPKTFFLSRDLYPGKTMNMEFSKIPYAQPYGVYAWSPKIKDIEKEGYTFNDVC
VDSAPAKGEDKYCAKSLGTLIGFSISKLGKNIQVLSSSFVKKQEQYTVEGVQNLGDKAVMCH
RLNFQKVVFYCHEIKETNAYMVALVAGDGTKTQAVAVCHADTSGMNHDFVHKMLKYDPGTNP
LCHFLGNKAVLWVPNLAVNNAYRTNVAT \>AbiBURP (*Achyranthes bidentata*) (SEQ ID NO: 249)
MALHSKLQLSTFFLLVFLVYYVSSCEQEKYWQMKLPNVPMPQAIRDNLFHSSGKYEADNNPK
VKAEDGVEPFTLHSNKKSSTNQPFTVFAWKYYVDNKLKDKAEDVVKPFILGSETKVGTNQPF
TVFGWGYDVGNKPKDKAEDVVESLTLNSNKKAGTNQPFTVFGWNYDANHKLKEKSQDVVERF
TLDSNTKVGTNQPFTVFGWGYDAGNKPKDKVENVLESLTLDSNKKAGTNQPFTVFGWNYDAN
HKLKEKSQDVVEPFTFDSNTKVGTNQPFTVFGWGYDAGNKPKDKVENVLESLTLDSNKKAGT
NQPFTVFGWKYDANHKLKEKSQDVVEPFIHDLNTKVGTNQPYTVFGWGYEVGNNPKGKDEDV
VESLSLDSNKKARTNQPFTVFGWKYDANHKLKDKSQSLESNTKVGTNQPFTVFGWNYAFENL
KSKAGDVVKAPDMKETSHDYHHFLNKNKNSNEEDPNGGSLFFVEKSLRLGMILKHDFQKTP
KIPFLPKKIAQTIPFKVEKVTDILNFSLDSESTEGIAIKETLDVCLQRPKVKKENRTCAQS
MEDVVDFVVGELGTNDVKVRMMNNNIEVPNGIQDYLITKVKKLEVTNMNGVACHRMSYPYVV
YYCHHQKDIGHYDVTLVSPTSGSRPIQTTAVCHYDTYAWQPDVPALQHLGIRPGDAPVCHFS
AINDMFWSVKVGSKSLDMVQ

FIG. 43I

```
>Sali3-2-[QPFGVFGW]
MEFRCSVISFTILFSLALAGESHVHASLPEED
YWEAVWPNTPIPTALRELLKPLPAGVEIDELP
KQIDDTQYPKTFFYKEDLHPGKTMKVQFTKRP
YAQPFGVFGWLTDIKDTSKEGYSFEEICIKKE
AFEGEEKFCAKSLGTVIGFAISKLGKNIQVLS
SSFVNKQEQYTVEGVQNLGDKAVMCHGLNFRT
AVFYCHKVRETTAFMVPLVAGDGTKTQALAVC
HSDTSGMNHHMLHELMGVDPGTNPVCHFLGSK
AILWVPNLSMDTAYQTNVVV
```

(SEQ ID NO: 249)

FIG. 44A

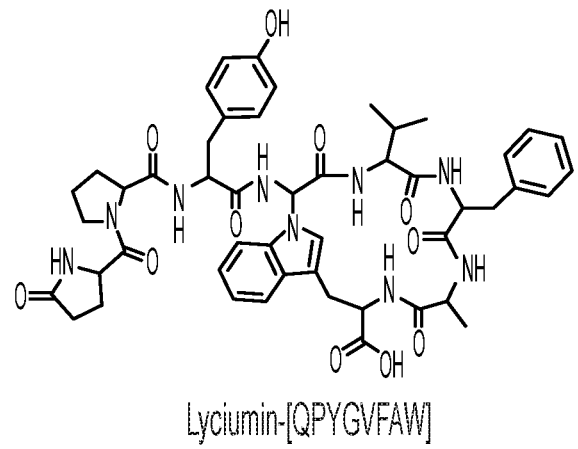

Lyciumin-[QPYGVFAW]

(SEQ ID NO: 78)

FIG. 44B

Closest Blastp hit to CocDUF2775 (Celtis occidentalis, 63% similarity, 51% identity):

>PON47930.1 Organ specific protein [Parasponia andersonii]
MKSRCAVIVALLSLLLYSVGTTESRKYPAEYWTTVMNDQPMPEAIQEL
IREASPHQEHLGHYDRGVDTKSEKSFTKELETNTEKGVDSSKGETPFT
KDFEPHSNSIPFELIWSKNSKKFANDFQPQNPLPFGVLWSKESQNFA
KDFEPRLNPIPFELIWVKNSKNSAEDFEPHPNPLPFELIWSKDSKTFS
KDFEPHQNPIPFELIWAKNSPKFGEKFYPNRNPVPFELIWAKDSKKFA
NGFRPQPNLIPSELIWSKDSEANSQPKIELEAKV (SEQ ID NO: 278)

FIG. 45A

```
CocDUF2775    1 MAEMKSSRSVIVALLSLLLYSVSTAESRKNPAEYWKTVMKIQPMPELIRE    50
                | ||..:|||||||||||||.|.||||.|||||.|||.|||||||.|:|
PON47930.1    1 ---MKSRCAVIVALLSLLLYSVGTTESRKYPAEYWTTVMNDQPMPEAIQE    47

CocDUF2775   51 LVHPELFEQEHFDHNEGRVDKKSDKSFTKESESSISNLD-NIKDSQKIAK    99
                |:......|||..|.:..||.||:|||||||.|::....|  :..|....|
PON47930.1   48 LIREASPHQEHLGHYDRGVDTKSEKSFTKELETNTEKGDVSSKGETPFTK   97

CocDUF2775  100 DFELDTDSQPFGVFGWVKDSQKFAKDFELDKPSQPFGVFGWAKDSQKFVN  149
                |||...:.:|.||.:.  |.|:|:|||.|.:......||||. |::|..|..
PON47930.1   98 DFEPHSNSIPFELI-WSKNSKKFANDFQPQNPLPFGVL-WSKESQNFAK   145

CocDUF2775  150 DFELDTNSQPFGVFGWAKDSQKFNNDFGPNPHQRIEGNAKA--------  190
                |||...|..||.:. |.|:|:....||.|:|       |...
PON47930.1  146 DFEPRLNPIPFELI-WVKNSKNSAEDFEPHP------NPLPFELIWSKDS 188

CocDUF2775  191 --------------------------------------------------  190

PON47930.1  189 KTFSKDFEPHQNPIPFELIWAKNSPKFGEKFYPNRNPVPFELIWAKDSKK  238

CocDUF2775  191 --------------------------------------  190

PON47930.1  239 FANGFRPQPNLIPSELIWSKDSEANSQPKIELEAKV    274
```

FIG. 45B (SEQ ID NO: 277)
```
>Sal13-2-[QPFGVFGW]
MEFRCSVISFTILFSLALAGESHVHASLPEEDYWEAV
WPNTPIPTALRELLKPLPAGVEIDELPKQIDLTQYPK
TFEYKEDLEPGKTMKVQPTNKPYA[QPFGVFGW]LTDIK
DTSKEGYSFEEICIPKEAFESEERKCAKSLGTVIGFA
ISKLSKNIQVLSSSFVNKQEQYTVESVQNLGDKAVMC
HGLNFRTAVFICHKVREPTAFMVFLVAGLGTKTQALA
VCHSDTSGNNHEMLSELMGVDPSTNEVCFLSSKAIL
KVPNLSMDTAIQTNVVV
```
FIG. 46C
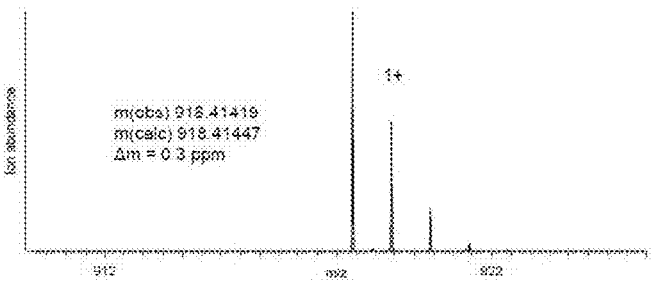
FIG. 46D
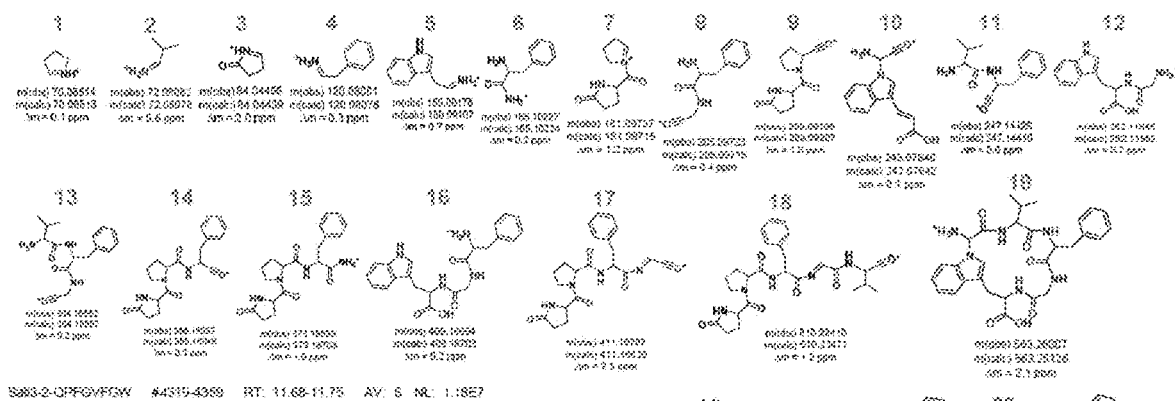
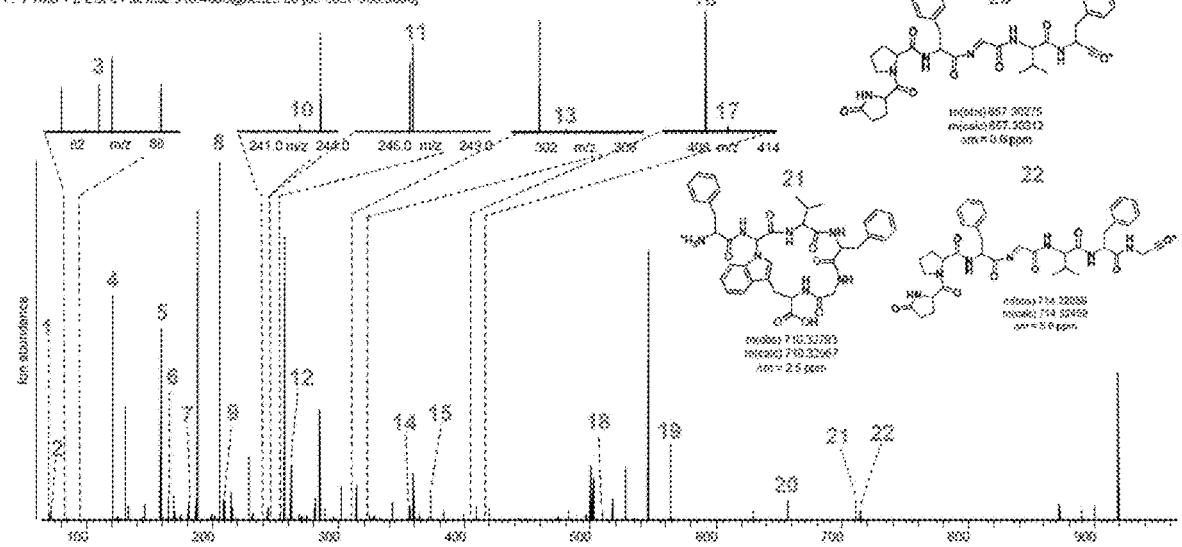
FIG. 46E

SEQUENCE LISTING

<160> NUMBER OF SEQ ID NOS: 299

<210> SEQ ID NO 1
<211> LENGTH: 543
<212> TYPE: PRT
<213> ORGANISM: Lycium barbarum

<400> SEQUENCE: 1

```
Met Glu Leu His His His Tyr Phe Phe Ile Leu Leu Ser Leu Ala Phe
1               5                   10                  15

Ile Ala Ser His Ala Ala Asn Leu Ser Pro Glu Val Tyr Trp Lys Val
            20                  25                  30

Lys Leu Pro Asn Thr Pro Met Pro Arg Pro Ile Lys Asp Ala Leu His
            35                  40                  45

Tyr Ser Glu Ala Ser Glu Gly Asp Val His Lys Leu Arg Gln Pro Trp
50                  55                  60

Gly Val Gly Ser Trp Tyr Gln Ala Ala Asn Glu Gly Asp Ile Lys Lys
65                  70                  75                  80

Leu Arg Gln Pro Tyr Gly Val Gly Ile Trp Tyr Gln Ala Ala Asn Glu
                85                  90                  95

Gly Asp Val Lys Lys Leu Arg Gln Pro Trp Gly Val Gly Ser Trp Tyr
            100                 105                 110

Gln Ala Ala Asn Glu Gly Asp Val Lys Lys Leu Arg Gln Pro Trp Gly
            115                 120                 125

Val Gly Ser Trp Tyr Gln Ala Ala Asn Glu Gly Asp Val Lys Lys Leu
        130                 135                 140

Arg Gln Pro Trp Gly Val Gly Ser Trp Tyr Gln Ala Ala Asn Glu Gly
145                 150                 155                 160

Asp Ala Asn Glu Gly Asp Val Lys Lys Leu Arg Gln Pro Tyr Gly Val
                165                 170                 175

Gly Ile Trp Tyr Gln Ala Ala Asn Glu Gly Asp Val Lys Lys Leu Arg
            180                 185                 190

Gln Pro Trp Gly Val Gly Ser Trp Tyr Gln Ala Ala Asn Glu Gly Asp
        195                 200                 205

Val Lys Lys Leu Arg Gln Pro Trp Gly Val Gly Ser Trp Tyr Gln Ala
    210                 215                 220

Ala Asn Glu Gly Asp Val Lys Lys Leu His Gln Pro Trp Gly Val Gly
225                 230                 235                 240

Ser Trp Tyr Gln Ala Ala Asn Glu Gly Asp Val Lys Lys Leu Pro Gln
                245                 250                 255

Pro Trp Gly Val Gly Ser Trp Tyr Gln Ala Ala Asn Glu Gly Asp Val
            260                 265                 270

Lys Lys Leu Arg Gln Pro Tyr Gly Val Gly Ile Trp Tyr Glu Ala Ala
        275                 280                 285

Asn Glu Gly Gln Val Lys Lys Leu Arg Gln Pro Tyr Gly Val Gly Ser
    290                 295                 300

Trp Tyr Asn Thr Ala Thr Lys Lys Asp Val Asn Glu Asn Leu Pro Val
305                 310                 315                 320

Thr Pro Tyr Phe Phe Glu Thr Asp Leu His Gln Gly Lys Lys Met Asn
                325                 330                 335

Leu Pro Ser Leu Lys Asn Tyr Asn Pro Ala Pro Ile Leu Pro Arg Lys
            340                 345                 350

Val Ala Asp Ser Ile Pro Phe Ser Asp Lys Ile Glu Glu Ile Leu
        355                 360                 365
```

```
Lys His Phe Ser Ile Asp Lys Asp Ser Glu Gly Ala Lys Met Ile Lys
    370                 375                 380
Lys Thr Ile Lys Met Cys Glu Glu Gln Ala Gly Asn Gly Glu Lys Lys
385                 390                 395                 400
Tyr Cys Ala Thr Ser Leu Glu Ser Met Val Asp Phe Thr Ser Ser Tyr
                405                 410                 415
Leu Gly Thr Asn Asn Ile Ile Ala Leu Ser Thr Leu Val Glu Lys Glu
                420                 425                 430
Thr Pro Glu Val Gln Ile Tyr Thr Ile Glu Gly Val Lys Glu Lys Ala
                435                 440                 445
Asn Gly Lys Gly Val Ile Cys His Lys Val Ala Tyr Pro Tyr Ala Ile
    450                 455                 460
His Tyr Cys His Ser Val Gly Ser Thr Arg Thr Phe Met Val Ser Met
465                 470                 475                 480
Val Gly Ser Asp Gly Thr Lys Val Asn Ala Val Ser Glu Cys His Glu
                485                 490                 495
Asp Thr Ala Pro Met Asn Pro Lys Ala Leu Pro Phe Gln Leu Leu Asn
                500                 505                 510
Val Lys Pro Gly Asp Lys Pro Ile Cys His Phe Ile Leu Asp Asp Gln
            515                 520                 525
Ile Ala Leu Val Pro Ser Gln Asp Ala Thr Gln Val Ser Glu Asn
    530                 535                 540

<210> SEQ ID NO 2
<211> LENGTH: 276
<212> TYPE: PRT
<213> ORGANISM: Glycine max

<400> SEQUENCE: 2

Met Glu Phe Arg Cys Ser Val Ile Ser Phe Thr Ile Leu Phe Ser Leu
1               5                   10                  15
Ala Leu Ala Gly Glu Ser His Val His Ala Ser Leu Pro Glu Glu Asp
                20                  25                  30
Tyr Trp Glu Ala Val Trp Pro Asn Thr Pro Ile Pro Thr Ala Leu Arg
            35                  40                  45
Glu Leu Leu Lys Pro Leu Pro Ala Gly Val Glu Ile Asp Glu Leu Pro
    50                  55                  60
Lys Gln Ile Asp Asp Thr Gln Tyr Pro Lys Thr Phe Tyr Lys Glu
65                  70                  75                  80
Asp Leu His Pro Gly Lys Thr Met Lys Val Gln Phe Thr Lys Arg Pro
                85                  90                  95
Tyr Ala Gln Pro Tyr Gly Val Tyr Thr Trp Leu Thr Asp Ile Lys Asp
                100                 105                 110
Thr Ser Lys Glu Gly Tyr Ser Phe Glu Glu Ile Cys Ile Lys Lys Glu
            115                 120                 125
Ala Phe Glu Gly Glu Lys Phe Cys Ala Lys Ser Leu Gly Thr Val
    130                 135                 140
Ile Gly Phe Ala Ile Ser Lys Leu Gly Lys Asn Ile Gln Val Leu Ser
145                 150                 155                 160
Ser Ser Phe Val Asn Lys Gln Glu Gln Tyr Thr Val Glu Gly Val Gln
                165                 170                 175
Asn Leu Gly Asp Lys Ala Val Met Cys His Gly Leu Asn Phe Arg Thr
                180                 185                 190
Ala Val Phe Tyr Cys His Lys Val Arg Glu Thr Thr Ala Phe Met Val
            195                 200                 205
```

```
Pro Leu Val Ala Gly Asp Gly Thr Lys Thr Gln Ala Leu Ala Val Cys
    210                 215                 220
His Ser Asp Thr Ser Gly Met Asn His His Met Leu His Glu Leu Met
225                 230                 235                 240
Gly Val Asp Pro Gly Thr Asn Pro Val Cys His Phe Leu Gly Ser Lys
                245                 250                 255
Ala Ile Leu Trp Val Pro Asn Leu Ser Met Asp Thr Ala Tyr Gln Thr
            260                 265                 270
Asn Val Val Val
            275

<210> SEQ ID NO 3
<211> LENGTH: 327
<212> TYPE: PRT
<213> ORGANISM: Capsicum annuum

<400> SEQUENCE: 3

Met Ala Met Leu Tyr Gln Tyr Tyr Phe Phe Thr Leu Leu Ser Leu Val
1               5                   10                  15
Phe Val Val Ile Ser His Ala Ala Asn Leu Ser Pro Glu Val Tyr Trp
                20                  25                  30
Lys Ile Lys Leu Pro Asn Thr Pro Met Pro Lys Pro Ile Lys Asp Ala
            35                  40                  45
Leu His Ile Ser Glu Lys Thr Ser Gln Pro Tyr Gly Gly Leu Thr Trp
        50                  55                  60
Asp Trp Phe His Val Phe Ser Lys Asn Glu Leu His Lys Leu His Gln
65                  70                  75                  80
Leu Ser Gln Pro Tyr Gly Val Tyr Phe Tyr Gly Val Ser Leu Lys Asn
                85                  90                  95
Leu Asn Glu Asp His Leu Val Thr Arg Phe Phe Glu Thr Asp Leu
                100                 105                 110
His Gln Gly Lys Lys Val Asn Leu Lys Ser Leu Lys Asn Asn Asn Pro
            115                 120                 125
Ala Pro Leu Leu Pro Arg Lys Val Val Asp Ser Ile Ser Phe Ser Ser
        130                 135                 140
Asn Arg Ile Glu Glu Ile Leu Asp His Phe Ser Val Asp Asn Asn Ser
145                 150                 155                 160
Glu Asp Ala Lys Val Ile Lys Arg Thr Val Glu Leu Cys Glu Gln Pro
                165                 170                 175
Ala Ala Asp Gly Glu Ile Lys Tyr Cys Ala Thr Ser Leu Glu Ser Ile
            180                 185                 190
Ile Asp Phe Ala Ser Ser Arg Leu Glu Thr Asn Asn Ile Leu Ala Ile
        195                 200                 205
His Thr Glu Val Glu Lys Glu Thr Pro Val Leu Gln Thr Tyr Thr Ile
    210                 215                 220
Lys Glu Val Lys Glu Lys Ala Asn Gly Lys Cys Val Ile Cys His Lys
225                 230                 235                 240
Val Pro Tyr Pro Tyr Ala Val His Phe Cys His Asp Val Gly Ser Thr
                245                 250                 255
Arg Ala Phe Arg Val Thr Met Val Gly Ala Asp Gly Thr Lys Val Asn
            260                 265                 270
Ala Val Ser Val Cys His Glu Asp Thr Ala Ser Met Asn Pro Lys Ala
        275                 280                 285
Leu Val Phe Gln Leu Leu Asn Ile Lys Pro Gly Asp Lys Pro Ile Cys
```

```
                290                 295                 300
His Phe Ile Met Asp Asp Gln Ile Ala Leu Phe Pro Ser Gln Asn Ala
305                 310                 315                 320

Val Leu Gln Met Ala Glu Gly
                325

<210> SEQ ID NO 4
<211> LENGTH: 236
<212> TYPE: PRT
<213> ORGANISM: Chenopodium quinoa

<400> SEQUENCE: 4

Met Leu Lys Phe Leu Tyr Phe Pro Phe Ala Tyr Tyr Leu His Ser Leu
1               5                   10                  15

Ala Glu Val Glu Ala Phe Leu Val Met Ser Ser Ser Tyr Phe Gly Glu
                20                  25                  30

Gly Leu Thr Leu Val Gly Glu Arg Leu Tyr Gln Leu Thr Tyr Asp Gln
            35                  40                  45

Asn Thr Gly Phe Ile Tyr Asp Arg Thr Thr Leu Ser Lys Val Ser Asn
    50                  55                  60

Ser Gly Val Pro Leu Leu Thr Ile Gly Ile Phe Asn His Gln Met
65                  70                  75                  80

Lys Asp Gly Trp Gly Leu Thr Thr Asp Gly Lys Ile Met Phe Gly Ser
                85                  90                  95

Asp Gly Ser Ser Thr Leu Tyr His Ile Asp Pro Arg Thr Met Lys Val
            100                 105                 110

Ile Lys Arg Gln Asn Val Arg Tyr Lys Asp Leu Asp Val His Tyr Leu
        115                 120                 125

Asn Glu Leu Glu Tyr Val His Gly Glu Val Trp Ala Asn Val Phe Arg
    130                 135                 140

Thr Asp Cys Ile Ile Arg Ile Ser Pro Glu Asp Gly Thr Val Leu Gly
145                 150                 155                 160

Trp Ile Leu Leu Pro Met Leu Arg Glu Arg Leu Glu Ala Ala Gly Glu
                165                 170                 175

Ile Glu Ser Glu Asp Val Leu Asn Gly Ile Ala Trp Asp Ser Asp Gly
            180                 185                 190

Lys Arg Ile Phe Val Thr Gly Lys Leu Trp Pro Lys Leu Phe Glu Ile
        195                 200                 205

Lys Val His Ser Ser Asn Asp His Ser Gln Val Asp Ile Glu Arg Met
    210                 215                 220

Cys Ile Gln Met Leu Thr Arg Leu Glu Gly Met Lys
225                 230                 235

<210> SEQ ID NO 5
<211> LENGTH: 201
<212> TYPE: PRT
<213> ORGANISM: Beta vulgaris subsp. vulgaris

<400> SEQUENCE: 5

Met Ala Ser Glu Cys Ile Leu Val Pro Cys Tyr Lys Arg Leu Ser Arg
1               5                   10                  15

Ala Val Ser Ile Ala Cys Leu Leu Gly Phe Leu Val Pro Leu Ser Ile
                20                  25                  30

Leu Ser Asn Thr Leu Ser Ala Leu Pro Leu Asp Ser Gln Lys Asn Ile
            35                  40                  45

Gln Leu Pro Gln Ile Tyr Thr Ile Glu Val Val Asn Val Tyr Pro His
```

```
            50                  55                  60
Asp Pro Arg Ala Phe Thr Glu Gly Leu Leu Tyr Gly Gly Asn Asn Thr
 65                  70                  75                  80

Leu Tyr Glu Ser Thr Gly Leu Tyr Gly Met Ser Thr Val Arg Arg Val
                 85                  90                  95

Thr Leu Gln Thr Gly Lys Val Glu Ala Leu Gln Thr Met Asp Leu Ser
                100                 105                 110

Tyr Phe Gly Glu Gly Leu Thr Leu Val Asp Glu Arg Leu Tyr Gln Leu
            115                 120                 125

Thr Tyr Glu His Asn Thr Gly Phe Ile His Asp Arg Ser Asn Leu Ser
            130                 135                 140

Lys Val Arg Asn Ser Gly Asn Pro Phe Leu Phe Cys Trp Asn Leu Ser
145                 150                 155                 160

Phe Glu His Ser Cys Ser Pro Thr Gly His Phe Cys Leu Asp Leu Asp
                165                 170                 175

Leu Ser Arg Val Gly Met Leu Gln Glu Asp Glu Leu Ile Asp Phe Tyr
            180                 185                 190

Thr Leu Gln Ser Pro Cys Tyr Ser Arg
            195                 200

<210> SEQ ID NO 6
<211> LENGTH: 309
<212> TYPE: PRT
<213> ORGANISM: Beta vulgaris subsp. vulgaris

<400> SEQUENCE: 6

Met Ala Ser Glu Cys Ile Leu Ala Pro Cys Tyr Lys Arg Leu Ser Arg
 1               5                  10                  15

Ala Val Ser Ile Ala Cys Leu Leu Gly Phe Leu Val Pro Leu Ser Ile
                 20                  25                  30

Leu Ser Asn Thr Leu Ser Ala Leu Pro Leu Asp Ser Gln Lys Asn Ile
             35                  40                  45

Gln Leu Pro Gln Ile Tyr Thr Ile Glu Val Val Asn Val Tyr Pro His
 50                  55                  60

Asp Pro Arg Ala Phe Thr Glu Gly Leu Leu Tyr Gly Gly Asn Asn Thr
 65                  70                  75                  80

Leu Tyr Glu Ser Thr Gly Leu Tyr Gly Met Ser Thr Val Arg Arg Val
                 85                  90                  95

Thr Leu Gln Thr Gly Lys Val Glu Ala Phe Gln Thr Met Asp Leu Ser
                100                 105                 110

Tyr Phe Gly Glu Gly Leu Thr Leu Val Asp Glu Arg Leu Tyr Gln Leu
            115                 120                 125

Thr Tyr Glu His Asn Thr Gly Phe Ile Tyr Asp Arg Ser Asn Leu Ser
            130                 135                 140

Lys Ile Gly Gln Phe Thr His Gln Met Ala Asp Gly Trp Gly Leu Ala
145                 150                 155                 160

Ser Asp Gly Lys Val Leu Phe Gly Ser Asp Gly Ser Ser Thr Leu Tyr
                165                 170                 175

Gln Ile Asp Pro Lys Thr Met Lys Glu Ile Gln Arg Gln Thr Val Arg
            180                 185                 190

Tyr Met Asp Leu Asp Val Pro Tyr Leu Asn Glu Leu Glu Tyr Val Asn
            195                 200                 205

Gly Glu Val Trp Ala Asn Val Ala Thr Thr Asp Cys Ile Val Arg Ile
210                 215                 220
```

```
Ser Pro Glu Asp Gly Thr Val Leu Gly Trp Ile Leu Leu Pro Ile Leu
225                 230                 235                 240

Arg Glu Arg Met Met Ala Asp Gly Glu Leu Asp Val Phe Asp Ile Leu
            245                 250                 255

Asn Gly Ile Ala Trp Asp Lys Asp Glu Gln Arg Val Phe Val Thr Gly
            260                 265                 270

Lys Cys Trp Pro Lys Val Phe Glu Ile Lys Val Asn Gln Ser Lys Asp
            275                 280                 285

His Ser Asp Ala Asp Val Arg Arg Leu Cys Ile Pro Val Pro Ala Ser
            290                 295                 300

Val Glu Ala Met Lys
305

<210> SEQ ID NO 7
<211> LENGTH: 287
<212> TYPE: PRT
<213> ORGANISM: Lycium barbarum

<400> SEQUENCE: 7

Met Pro Leu Leu Asn Pro Arg Phe Leu Val Ile Ser Leu Ile Val Leu
1               5                   10                  15

Leu Ser Ile Thr Val Phe Arg Glu Ala Glu Ala Ser Tyr Arg Val Tyr
                20                  25                  30

Lys Val Lys Val Val Asn Glu Phe Pro His Asp Pro Gln Ala Tyr Thr
            35                  40                  45

Gln Gly Leu Leu Tyr Ala Glu Asn Asn Thr Leu Phe Glu Ser Thr Gly
        50                  55                  60

Leu Tyr Gly Arg Ser Ser Val Arg Lys Val Ala Leu Leu Asp Gly Lys
65                  70                  75                  80

Val Glu Arg Leu His Glu Met Glu Ser Ser Tyr Phe Gly Glu Gly Leu
                85                  90                  95

Thr Leu Leu Gly Glu Arg Leu Phe Gln Leu Thr Trp Leu Leu Asp Thr
            100                 105                 110

Gly Phe Ile Tyr Asp Arg Tyr Asn Phe Ser Lys Phe Lys Lys Phe Thr
        115                 120                 125

His His Met Gln Asp Gly Trp Gly Leu Ala Thr Asp Gly Lys Val Leu
130                 135                 140

Phe Gly Ser Asp Gly Thr Ser Thr Leu Tyr Lys Ile Asp Pro Lys Thr
145                 150                 155                 160

Met Lys Val Ile Arg Lys Gln Val Val Lys Ser Gln Gly His Glu Val
                165                 170                 175

Arg Tyr Leu Asn Glu Leu Glu Tyr Val Lys Ala Glu Val Trp Ala Asn
            180                 185                 190

Val Tyr Val Thr Asp Cys Ile Ala Arg Ile Ser Pro Lys Asp Gly Thr
        195                 200                 205

Val Ile Gly Trp Ile Leu Leu Gln Ser Leu Arg Glu Glu Leu Ile Ser
        210                 215                 220

Arg Gly Tyr Lys Asp Phe Glu Val Leu Asn Gly Ile Ala Trp Asp Arg
225                 230                 235                 240

Asp Gly Asp Arg Ile Phe Val Thr Gly Lys Leu Trp Pro Lys Leu Phe
            245                 250                 255

Glu Ile Lys Leu Leu Pro Leu Thr Pro Asn Asp Pro Leu Ala Gly Glu
            260                 265                 270

Ile Asn Asn Leu Cys Ile Pro Lys Thr Ser Phe Leu Leu Glu Ile
        275                 280                 285
```

<210> SEQ ID NO 8
<211> LENGTH: 831
<212> TYPE: DNA
<213> ORGANISM: Glycine max

<400> SEQUENCE: 8

| | | |
|---|---|---|
| atggaatttc gatgctcagt catctctttt accattctct tctctcttgc tcttgcagga | 60 |
| gagagccatg tccatgcatc gctacctgag gaagattatt gggaagctgt ttggccaaac | 120 |
| actcccattc ccactgcact gcgagagctt ctaaagcctc tccctgcagg tgttgaaatc | 180 |
| gatgaactcc ctaagcaaat tgatgataca cagtacccaa aaacattctt ctataaagaa | 240 |
| gaccttcatc caggcaaaac aatgaaagta caattcacca agcgtcccta tgcacaacct | 300 |
| tatggtgtat atacatggtt aacgatatt aagacacct ctaaagaagg atatagtttt | 360 |
| gaagagatat gcatcaagaa agaagcgttt gagggagaag agaagttttg tgcaaaatcc | 420 |
| ttgggaacag taattggttt tgccatttca agctgggaa agaacattca agtactttca | 480 |
| agttcctttg tcaataagca agagcaatac actgtggaag gagtgcagaa tcttggagac | 540 |
| aaaagcagtga tgtgtcatgg gctaaatttc agaactgcag tattttactg ccataaagtc | 600 |
| cgtgaaacaa cagctttcat ggttccattg gtggctggtg atggaaccaa aactcaggca | 660 |
| cttgctgttt gccactcaga tacttctgga atgaatcatc acatgcttca tgaactcatg | 720 |
| ggagttgatc ctggaactaa ccctgtttgc catttccttg gaagcaaggc cattttatgg | 780 |
| gtacccaatt tatctatgga cactgcctat cagactaacg ttgttgttta a | 831 |

<210> SEQ ID NO 9
<211> LENGTH: 831
<212> TYPE: DNA
<213> ORGANISM: Artificial Sequence
<220> FEATURE:
<223> OTHER INFORMATION: Sali3-2-[QPWGVYTW]

<400> SEQUENCE: 9

| | | |
|---|---|---|
| atggaatttc gatgctcagt catctctttt accattctct tctctcttgc tcttgcagga | 60 |
| gagagccatg tccatgcatc gctacctgag gaagattatt gggaagctgt ttggccaaac | 120 |
| actcccattc ccactgcact gcgagagctt ctaaagcctc tccctgcagg tgttgaaatc | 180 |
| gatgaactcc ctaagcaaat tgatgataca cagtacccaa aaacattctt ctataaagaa | 240 |
| gaccttcatc caggcaaaac aatgaaagta caattcacca agcgtcccta tgcacaacct | 300 |
| tggggtgtat atacatggtt aacgatatt aagacacct ctaaagaagg atatagtttt | 360 |
| gaagagatat gcatcaagaa agaagcgttt gagggagaag agaagttttg tgcaaaatcc | 420 |
| ttgggaacag taattggttt tgccatttca agctgggaa agaacattca agtactttca | 480 |
| agttcctttg tcaataagca agagcaatac actgtggaag gagtgcagaa tcttggagac | 540 |
| aaaagcagtga tgtgtcatgg gctaaatttc agaactgcag tattttactg ccataaagtc | 600 |
| cgtgaaacaa cagctttcat ggttccattg gtggctggtg atggaaccaa aactcaggca | 660 |
| cttgctgttt gccactcaga tacttctgga atgaatcatc acatgcttca tgaactcatg | 720 |
| ggagttgatc ctggaactaa ccctgtttgc catttccttg gaagcaaggc cattttatgg | 780 |
| gtacccaatt tatctatgga cactgcctat cagactaacg ttgttgttta a | 831 |

<210> SEQ ID NO 10
<211> LENGTH: 831
<212> TYPE: DNA

<213> ORGANISM: Artificial Sequence
<220> FEATURE:
<223> OTHER INFORMATION: Sali3-2-[QPYGVYFW]

<400> SEQUENCE: 10

```
atggaatttc gatgctcagt catctctttt accattctct ctctcttgc tcttgcagga      60
gagagccatg tccatgcatc gctacctgag gaagattatt gggaagctgt ttggccaaac    120
actcccattc ccactgcact gcgagagctt ctaaagcctc tccctgcagg tgttgaaatc    180
gatgaactcc ctaagcaaat tgatgataca cagtacccaa aaacattctt ctataaagaa    240
gaccttcatc caggcaaaac aatgaaagta caattcacca agcgtcccta tgcacaacct    300
tatggtgtat atttctggtt aacggatatt aaagacacct ctaaagaagg atatagtttt    360
gaagagatat gcatcaagaa agaagcgttt gagggagaag agaagttttg tgcaaaatcc    420
ttgggaacag taattggttt tgccatttca agctgggaa agaacattca agtactttca    480
agttcctttg tcaataagca agagcaatac actgtggaag gagtgcagaa tcttggagac    540
aaagcagtga tgtgtcatgg gctaaatttc agaactgcag tattttactg ccataaagtc    600
cgtgaaacaa cagctttcat ggttccattg gtggctggtg atggaaccaa aactcaggca    660
cttgctgttt gccactcaga tacttctgga atgaatcatc acatgcttca tgaactcatg    720
ggagttgatc ctggaactaa ccctgtttgc catttccttg aagcaaggc catttttatgg    780
gtacccaatt tatctatgga cactgcctat cagactaacg ttgttgttta a             831
```

<210> SEQ ID NO 11
<211> LENGTH: 831
<212> TYPE: DNA
<213> ORGANISM: Artificial Sequence
<220> FEATURE:
<223> OTHER INFORMATION: Sali3-2-[QPWGVGAW]

<400> SEQUENCE: 11

```
atggaatttc gatgctcagt catctctttt accattctct ctctcttgc tcttgcagga      60
gagagccatg tccatgcatc gctacctgag gaagattatt gggaagctgt ttggccaaac    120
actcccattc ccactgcact gcgagagctt ctaaagcctc tccctgcagg tgttgaaatc    180
gatgaactcc ctaagcaaat tgatgataca cagtacccaa aaacattctt ctataaagaa    240
gaccttcatc caggcaaaac aatgaaagta caattcacca agcgtcccta tgcacaacct    300
tggggtgtag gtgcatggtt aacggatatt aaagacacct ctaaagaagg atatagtttt    360
gaagagatat gcatcaagaa agaagcgttt gagggagaag agaagttttg tgcaaaatcc    420
ttgggaacag taattggttt tgccatttca agctgggaa agaacattca agtactttca    480
agttcctttg tcaataagca agagcaatac actgtggaag gagtgcagaa tcttggagac    540
aaagcagtga tgtgtcatgg gctaaatttc agaactgcag tattttactg ccataaagtc    600
cgtgaaacaa cagctttcat ggttccattg gtggctggtg atggaaccaa aactcaggca    660
cttgctgttt gccactcaga tacttctgga atgaatcatc acatgcttca tgaactcatg    720
ggagttgatc ctggaactaa ccctgtttgc catttccttg aagcaaggc catttttatgg    780
gtacccaatt tatctatgga cactgcctat cagactaacg ttgttgttta a             831
```

<210> SEQ ID NO 12
<211> LENGTH: 831
<212> TYPE: DNA
<213> ORGANISM: Artificial Sequence
<220> FEATURE:
<223> OTHER INFORMATION: Sali3-2-[QPFGVYTW]

<400> SEQUENCE: 12

```
atggaatttc gatgctcagt catctctttt accattctct tctctcttgc tcttgcagga      60
gagagccatg tccatgcatc gctacctgag gaagattatt gggaagctgt ttggccaaac     120
actcccattc ccactgcact gcgagagctt ctaaagcctc tccctgcagg tgttgaaatc     180
gatgaactcc ctaagcaaat tgatgataca cagtacccaa aaacattctt ctataaagaa     240
gaccttcatc caggcaaaac aatgaaagta caattcacca gcgtcccta tgcacaacct      300
tttggtgtat atacatggtt aacggatatt aaagacacct ctaaagaagg atatagtttt     360
gaaagagatat gcatcaagaa agaagcgttt gagggagaag agaagttttg tgcaaaatcc    420
ttgggaacag taattggttt tgccatttca agctgggaa agaacattca agtactttca      480
agttcctttg tcaataagca agagcaatac actgtggaag gagtgcagaa tcttggagac     540
aaagcagtga tgtgtcatgg gctaaatttc agaactgcag tattttactg ccataaagtc     600
cgtgaaacaa cagctttcat ggttccattg gtggctggtg atggaaccaa aactcaggca     660
cttgctgttt gccactcaga tacttctgga atgaatcatc acatgcttca tgaactcatg     720
ggagttgatc ctggaactaa ccctgtttgc catttccttg gaagcaaggc catttttatgg   780
gtacccaatt tatctatgga cactgcctat cagactaacg ttgttgttta a              831
```

<210> SEQ ID NO 13
<211> LENGTH: 831
<212> TYPE: DNA
<213> ORGANISM: Artificial Sequence
<220> FEATURE:
<223> OTHER INFORMATION: Sali3-2-[QPWGVGTW]

<400> SEQUENCE: 13

```
atggaatttc gatgctcagt catctctttt accattctct tctctcttgc tcttgcagga      60
gagagccatg tccatgcatc gctacctgag gaagattatt gggaagctgt ttggccaaac     120
actcccattc ccactgcact gcgagagctt ctaaagcctc tccctgcagg tgttgaaatc     180
gatgaactcc ctaagcaaat tgatgataca cagtacccaa aaacattctt ctataaagaa     240
gaccttcatc caggcaaaac aatgaaagta caattcacca gcgtcccta tgcacaacct      300
tggggtgtag gtacatggtt aacggatatt aaagacacct ctaaagaagg atatagtttt     360
gaaagagatat gcatcaagaa agaagcgttt gagggagaag agaagttttg tgcaaaatcc    420
ttgggaacag taattggttt tgccatttca agctgggaa agaacattca agtactttca      480
agttcctttg tcaataagca agagcaatac actgtggaag gagtgcagaa tcttggagac     540
aaagcagtga tgtgtcatgg gctaaatttc agaactgcag tattttactg ccataaagtc     600
cgtgaaacaa cagctttcat ggttccattg gtggctggtg atggaaccaa aactcaggca     660
cttgctgttt gccactcaga tacttctgga atgaatcatc acatgcttca tgaactcatg     720
ggagttgatc ctggaactaa ccctgtttgc catttccttg gaagcaaggc catttttatgg   780
gtacccaatt tatctatgga cactgcctat cagactaacg ttgttgttta a              831
```

<210> SEQ ID NO 14
<211> LENGTH: 831
<212> TYPE: DNA
<213> ORGANISM: Artificial Sequence
<220> FEATURE:
<223> OTHER INFORMATION: Sali3-2-[EPYGVYTW]

<400> SEQUENCE: 14

```
atggaatttc gatgctcagt catctctttt accattctct tctctcttgc tcttgcagga    60
gagagccatg tccatgcatc gctacctgag gaagattatt gggaagctgt ttggccaaac   120
actcccattc ccactgcact gcgagagctt ctaaagcctc tccctgcagg tgttgaaatc   180
gatgaactcc ctaagcaaat tgatgataca cagtacccaa aaacattctt ctataaagaa   240
gaccttcatc caggcaaaac aatgaaagta caattcacca agcgtcccta tgcagaacct   300
tatggtgtat atacatggtt aacggatatt aagacacctc taaagaagg atatagtttt   360
gaagagatat gcatcaagaa agaagcgttt gagggagaag agaagttttg tgcaaaatcc   420
ttgggaacag taattggttt tgccatttca aagctgggaa agaacattca agtactttca   480
agttcctttg tcaataagca agagcaatac actgtggaag gagtgcagaa tcttggagac   540
aaagcagtga tgtgtcatgg gctaaatttc agaactgcag tatttactg ccataaagtc   600
cgtgaaacaa cagctttcat ggttccattg gtggctggtg atggaaccaa aactcaggca   660
cttgctgttt gccactcaga tacttctgga atgaatcatc acatgcttca tgaactcatg   720
ggagttgatc ctggaactaa ccctgtttgc catttccttg gaagcaaggc catttatgg   780
gtacccaatt tatctatgga cactgcctat cagactaacg ttgttgttta a            831
```

<210> SEQ ID NO 15
<211> LENGTH: 831
<212> TYPE: DNA
<213> ORGANISM: Artificial Sequence
<220> FEATURE:
<223> OTHER INFORMATION: Sali3-2-[QAYGVYTW]

<400> SEQUENCE: 15

```
atggaatttc gatgctcagt catctctttt accattctct tctctcttgc tcttgcagga    60
gagagccatg tccatgcatc gctacctgag gaagattatt gggaagctgt ttggccaaac   120
actcccattc ccactgcact gcgagagctt ctaaagcctc tccctgcagg tgttgaaatc   180
gatgaactcc ctaagcaaat tgatgataca cagtacccaa aaacattctt ctataaagaa   240
gaccttcatc caggcaaaac aatgaaagta caattcacca agcgtcccta tgcacaagct   300
tatggtgtat atacatggtt aacggatatt aagacacctc taaagaagg atatagtttt   360
gaagagatat gcatcaagaa agaagcgttt gagggagaag agaagttttg tgcaaaatcc   420
ttgggaacag taattggttt tgccatttca aagctgggaa agaacattca agtactttca   480
agttcctttg tcaataagca agagcaatac actgtggaag gagtgcagaa tcttggagac   540
aaagcagtga tgtgtcatgg gctaaatttc agaactgcag tatttactg ccataaagtc   600
cgtgaaacaa cagctttcat ggttccattg gtggctggtg atggaaccaa aactcaggca   660
cttgctgttt gccactcaga tacttctgga atgaatcatc acatgcttca tgaactcatg   720
ggagttgatc ctggaactaa ccctgtttgc catttccttg gaagcaaggc catttatgg   780
gtacccaatt tatctatgga cactgcctat cagactaacg ttgttgttta a            831
```

<210> SEQ ID NO 16
<211> LENGTH: 831
<212> TYPE: DNA
<213> ORGANISM: Artificial Sequence
<220> FEATURE:
<223> OTHER INFORMATION: Sali3-2-[QPAGVYTW]

<400> SEQUENCE: 16

```
atggaatttc gatgctcagt catctctttt accattctct tctctcttgc tcttgcagga    60
gagagccatg tccatgcatc gctacctgag gaagattatt gggaagctgt ttggccaaac   120
```

```
actcccattc ccactgcact gcgagagctt ctaaagcctc tccctgcagg tgttgaaatc    180
gatgaactcc ctaagcaaat tgatgataca cagtacccaa aaacattctt ctataaagaa    240
gaccttcatc caggcaaaac aatgaaagta caattcacca agcgtccta tgcacaacct     300 gctggtgtat atacatggtt aacgatatt aaagacacct ctaaagaagg atatagtttt     360
gaagagatat gcatcaagaa agaagcgttt gagggagaag agaagttttg tgcaaaatcc    420
ttgggaacag taattggttt tgccatttca agctgggaa agaacattca agtactttca     480
agttcctttg tcaataagca agagcaatac actgtggaag gagtgcagaa tcttggagac    540
aaagcagtga tgtgtcatgg gctaaatttc agaactgcag tattttactg ccataaagtc    600
cgtgaaacaa cagctttcat ggttccattg gtggctggtg atggaaccaa aactcaggca    660
cttgctgttt gccactcaga tacttctgga atgaatcatc acatgcttca tgaactcatg    720
ggagttgatc ctggaactaa ccctgtttgc catttccttg aagcaaggc cattttatgg     780 gtacccaatt tatctatgga cactgcctat cagactaacg ttgttgttta a             831
```

```
<210> SEQ ID NO 17
<211> LENGTH: 831
<212> TYPE: DNA
<213> ORGANISM: Artificial Sequence
<220> FEATURE:
<223> OTHER INFORMATION: Sali3-2-[QPFGFFSW]

<400> SEQUENCE: 17
```

```
atggaatttc gatgctcagt catctctttt accattctct ctctcttgc tcttgcagga     60 gagagccatg tccatgcatc gctacctgag gaagattatt gggaagctgt ttggccaaac    120
actcccattc ccactgcact gcgagagctt ctaaagcctc tccctgcagg tgttgaaatc    180
gatgaactcc ctaagcaaat tgatgataca cagtacccaa aaacattctt ctataaagaa    240
gaccttcatc caggcaaaac aatgaaagta caattcacca agcgtccta tgcacaacct     300 tttggtttct tctcatggtt aacgatatt aaagacacct ctaaagaagg atatagtttt     360
gaagagatat gcatcaagaa agaagcgttt gagggagaag agaagttttg tgcaaaatcc    420
ttgggaacag taattggttt tgccatttca agctgggaa agaacattca agtactttca     480
agttcctttg tcaataagca agagcaatac actgtggaag gagtgcagaa tcttggagac    540
aaagcagtga tgtgtcatgg gctaaatttc agaactgcag tattttactg ccataaagtc    600
cgtgaaacaa cagctttcat ggttccattg gtggctggtg atggaaccaa aactcaggca    660
cttgctgttt gccactcaga tacttctgga atgaatcatc acatgcttca tgaactcatg    720
ggagttgatc ctggaactaa ccctgtttgc catttccttg aagcaaggc cattttatgg     780 gtacccaatt tatctatgga cactgcctat cagactaacg ttgttgttta a             831
```

```
<210> SEQ ID NO 18
<211> LENGTH: 828
<212> TYPE: DNA
<213> ORGANISM: Artificial Sequence
<220> FEATURE:
<223> OTHER INFORMATION: Sali3-2-[QPYGVYW]

<400> SEQUENCE: 18
```

```
atggaatttc gatgctcagt catctctttt accattctct ctctcttgc tcttgcagga     60 gagagccatg tccatgcatc gctacctgag gaagattatt gggaagctgt ttggccaaac    120
actcccattc ccactgcact gcgagagctt ctaaagcctc tccctgcagg tgttgaaatc    180
```

| | |
|---|---|
| gatgaactcc ctaagcaaat tgatgataca cagtacccaa aaacattctt ctataaagaa | 240 |
| gaccttcatc caggcaaaac aatgaaagta caattcacca agcgtccta tgcacaacct | 300 |
| tatggtgtat attggttaac ggatattaaa gacacctcta agaaggata tagttttgaa | 360 |
| gagatatgca tcaagaaaga agcgtttgag ggagaagaga agttttgtgc aaaatccttg | 420 |
| ggaacagtaa ttggttttgc catttcaaag ctgggaaaga acattcaagt actttcaagt | 480 |
| tcctttgtca ataagcaaga gcaatacact gtggaaggag tgcagaatct tggagacaaa | 540 |
| gcagtgatgt gtcatgggct aaatttcaga actgcagtat tttactgcca taaagtccgt | 600 |
| gaaacaacag ctttcatggt tccattggtg ctggtgatg gaaccaaaac tcaggcactt | 660 |
| gctgtttgcc actcagatac ttctggaatg aatcatcaca tgcttcatga actcatggga | 720 |
| gttgatcctg gaactaaccc tgtttgccat ttccttggaa gcaaggccat tttatgggta | 780 |
| cccaatttat ctatggacac tgcctatcag actaacgttg ttgttttaa | 828 |

<210> SEQ ID NO 19
<211> LENGTH: 834
<212> TYPE: DNA
<213> ORGANISM: Artificial Sequence
<220> FEATURE:
<223> OTHER INFORMATION: Sali3-2-[QPYGVYTAW]

<400> SEQUENCE: 19

| | |
|---|---|
| atggaatttc gatgctcagt catctctttt accattctct ctctcttgc tcttgcagga | 60 |
| gagagccatg tccatgcatc gctacctgag gaagattatt gggaagctgt ttggccaaac | 120 |
| actcccattc ccactgcact gcgagagctt ctaaagcctc tccctgcagg tgttgaaatc | 180 |
| gatgaactcc ctaagcaaat tgatgataca cagtacccaa aaacattctt ctataaagaa | 240 |
| gaccttcatc caggcaaaac aatgaaagta caattcacca agcgtccta tgcacaacct | 300 |
| tatggtgtat atacagcatg gttaacggat attaaagaca cctctaaaga aggatatagt | 360 |
| tttgaagaga tatgcatcaa gaagaagcg tttgagggag aagagaagtt ttgtgcaaaa | 420 |
| tccttgggaa cagtaattgg ttttgccatt caaagctgg gaagaacat tcaagtactt | 480 |
| tcaagttcct ttgtcaataa gcaagagcaa tacactgtgg aaggagtgca gaatcttgga | 540 |
| gacaaagcag tgatgtgtca tgggctaaat ttcagaactg cagtatttta ctgccataaa | 600 |
| gtccgtgaaa caacagcttt catggttcca ttggtggctg gtgatggaac caaaactcag | 660 |
| gcacttgctg tttgccactc agatacttct ggaatgaatc atcacatgct tcatgaactc | 720 |
| atgggagttg atcctggaac taaccctgtt gccatttcc ttggaagcaa ggccattta | 780 |
| tgggtaccca atttatctat ggacactgcc tatcagacta acgttgttgt ttaa | 834 |

<210> SEQ ID NO 20
<211> LENGTH: 831
<212> TYPE: DNA
<213> ORGANISM: Artificial Sequence
<220> FEATURE:
<223> OTHER INFORMATION: Sali3-2-[QPWGVYSW]

<400> SEQUENCE: 20

| | |
|---|---|
| atggaatttc gatgctcagt catctctttt accattctct ctctcttgc tcttgcagga | 60 |
| gagagccatg tccatgcatc gctacctgag gaagattatt gggaagctgt ttggccaaac | 120 |
| actcccattc ccactgcact gcgagagctt ctaaagcctc tccctgcagg tgttgaaatc | 180 |
| gatgaactcc ctaagcaaat tgatgataca cagtacccaa aaacattctt ctataaagaa | 240 |
| gaccttcatc caggcaaaac aatgaaagta caattcacca agcgtccta tgcacaacct | 300 |

```
tggggtgtat attcatggtt aacggatatt aaagacacct ctaaagaagg atatagtttt    360
gaagagatat gcatcaagaa agaagcgttt gagggagaag agaagttttg tgcaaaatcc    420
ttgggaacag taattggttt tgccatttca aagctgggaa agaacattca agtactttca    480
agttcctttg tcaataagca agagcaatac actgtggaag gagtgcagaa tcttggagac    540
aaagcagtga tgtgtcatgg gctaaatttc agaactgcag tattttactg ccataaagtc    600
cgtgaaacaa cagctttcat ggttccattg gtggctggtg atggaaccaa aactcaggca    660
cttgctgttt gccactcaga tacttctgga atgaatcatc acatgcttca tgaactcatg    720
ggagttgatc ctggaactaa ccctgtttgc catttccttg gaagcaaggc cattttatgg    780
gtacccaatt tatctatgga cactgcctat cagactaacg ttgttgttta a             831
```

<210> SEQ ID NO 21
<211> LENGTH: 831
<212> TYPE: DNA
<213> ORGANISM: Artificial Sequence
<220> FEATURE:
<223> OTHER INFORMATION: Sali3-2-[QPYAVYTW]

<400> SEQUENCE: 21

```
atggaatttc gatgctcagt catctctttt accattctct ctctcttgc tcttgcagga    60 gagagccatg tccatgcatc gctacctgag gaagattatt gggaagctgt ttggccaaac   120
actcccattc ccactgcact gcgagagctt ctaaagcctc tccctgcagg tgttgaaatc   180
gatgaactcc ctaagcaaat tgatgataca cagtacccaa aacattctt ctataaagaa    240 gaccttcatc caggcaaaac aatgaaagta caattcacca agcgtcccta tgcacaacct   300
tatgctgtat atacatggtt aacggatatt aaagacacct ctaaagaagg atatagtttt   360
gaagagatat gcatcaagaa agaagcgttt gagggagaag agaagttttg tgcaaaatcc   420
ttgggaacag taattggttt tgccatttca aagctgggaa agaacattca agtactttca   480
agttcctttg tcaataagca agagcaatac actgtggaag gagtgcagaa tcttggagac   540
aaagcagtga tgtgtcatgg gctaaatttc agaactgcag tattttactg ccataaagtc   600
cgtgaaacaa cagctttcat ggttccattg gtggctggtg atggaaccaa aactcaggca   660
cttgctgttt gccactcaga tacttctgga atgaatcatc acatgcttca tgaactcatg   720
ggagttgatc ctggaactaa ccctgtttgc catttccttg gaagcaaggc cattttatgg   780
gtacccaatt tatctatgga cactgcctat cagactaacg ttgttgttta a             831
```

<210> SEQ ID NO 22
<211> LENGTH: 831
<212> TYPE: DNA
<213> ORGANISM: Artificial Sequence
<220> FEATURE:
<223> OTHER INFORMATION: Sali3-2-[QPYTVYTW]

<400> SEQUENCE: 22

```
atggaatttc gatgctcagt catctctttt accattctct ctctcttgc tcttgcagga    60 gagagccatg tccatgcatc gctacctgag gaagattatt gggaagctgt ttggccaaac   120
actcccattc ccactgcact gcgagagctt ctaaagcctc tccctgcagg tgttgaaatc   180
gatgaactcc ctaagcaaat tgatgataca cagtacccaa aacattctt ctataaagaa    240 gaccttcatc caggcaaaac aatgaaagta caattcacca agcgtcccta tgcacaacct   300
tatactgtat atacatggtt aacggatatt aaagacacct ctaaagaagg atatagtttt   360
```

| | | |
|---|---|---|
| gaagagatat gcatcaagaa agaagcgttt gagggagaag agaagttttg tgcaaaatcc | 420 | |
| ttgggaacag taattggttt tgccatttca aagctgggaa agaacattca agtactttca | 480 | |
| agttcctttg tcaataagca agagcaatac actgtggaag gagtgcagaa tcttggagac | 540 | |
| aaagcagtga tgtgtcatgg gctaaatttc agaactgcag tatttactg ccataaagtc | 600 | |
| cgtgaaacaa cagctttcat ggttccattg gtggctggtg atggaaccaa aactcaggca | 660 | |
| cttgctgttt gccactcaga tacttctgga atgaatcatc acatgcttca tgaactcatg | 720 | |
| ggagttgatc ctggaactaa ccctgtttgc catttccttg aagcaaggc catttatgg | 780 | |
| gtacccaatt tatctatgga cactgcctat cagactaacg ttgttgttta a | 831 | |

```
<210> SEQ ID NO 23
<211> LENGTH: 831
<212> TYPE: DNA
<213> ORGANISM: Artificial Sequence
<220> FEATURE:
<223> OTHER INFORMATION: Sali3-2-[QPYGAYTW]

<400> SEQUENCE: 23
```

| | | |
|---|---|---|
| atggaatttc gatgctcagt catctctttt accattctct ctctcttgc tcttgcagga | 60 | |
| gagagccatg tccatgcatc gctacctgag gaagattatt gggaagctgt ttggccaaac | 120 | |
| actcccattc ccactgcact gcgagagctt ctaaagcctc tccctgcagg tgttgaaatc | 180 | |
| gatgaactcc ctaagcaaat tgatgataca cagtacccaa aaacattctt ctataaagaa | 240 | |
| gaccttcatc caggcaaaac aatgaaagta caattcacca agcgtcccta tgcacaacct | 300 | |
| tatggtgcat acacatggtt aacggatatt aaagacacct ctaaagaagg atatagtttt | 360 | |
| gaagagatat gcatcaagaa agaagcgttt gagggagaag agaagttttg tgcaaaatcc | 420 | |
| ttgggaacag taattggttt tgccatttca aagctgggaa agaacattca agtactttca | 480 | |
| agttcctttg tcaataagca agagcaatac actgtggaag gagtgcagaa tcttggagac | 540 | |
| aaagcagtga tgtgtcatgg gctaaatttc agaactgcag tatttactg ccataaagtc | 600 | |
| cgtgaaacaa cagctttcat ggttccattg gtggctggtg atggaaccaa aactcaggca | 660 | |
| cttgctgttt gccactcaga tacttctgga atgaatcatc acatgcttca tgaactcatg | 720 | |
| ggagttgatc ctggaactaa ccctgtttgc catttccttg aagcaaggc catttatgg | 780 | |
| gtacccaatt tatctatgga cactgcctat cagactaacg ttgttgttta a | 831 | |

```
<210> SEQ ID NO 24
<211> LENGTH: 831
<212> TYPE: DNA
<213> ORGANISM: Artificial Sequence
<220> FEATURE:
<223> OTHER INFORMATION: Sali3-2-[QPYGVATW]

<400> SEQUENCE: 24
```

| | | |
|---|---|---|
| atggaatttc gatgctcagt catctctttt accattctct ctctcttgc tcttgcagga | 60 | |
| gagagccatg tccatgcatc gctacctgag gaagattatt gggaagctgt ttggccaaac | 120 | |
| actcccattc ccactgcact gcgagagctt ctaaagcctc tccctgcagg tgttgaaatc | 180 | |
| gatgaactcc ctaagcaaat tgatgataca cagtacccaa aaacattctt ctataaagaa | 240 | |
| gaccttcatc caggcaaaac aatgaaagta caattcacca agcgtcccta tgcacaacct | 300 | |
| tatggtgtag ctacatggtt aacggatatt aaagacacct ctaaagaagg atatagtttt | 360 | |
| gaagagatat gcatcaagaa agaagcgttt gagggagaag agaagttttg tgcaaaatcc | 420 | |
| ttgggaacag taattggttt tgccatttca aagctgggaa agaacattca agtactttca | 480 | |

```
agttcctttg tcaataagca agagcaatac actgtggaag gagtgcagaa tcttggagac    540
aaagcagtga tgtgtcatgg gctaaatttc agaactgcag tattttactg ccataaagtc    600
cgtgaaacaa cagctttcat ggttccattg gtggctggtg atggaaccaa aactcaggca    660
cttgctgttt gccactcaga tacttctgga atgaatcatc acatgcttca tgaactcatg    720
ggagttgatc ctggaactaa ccctgtttgc catttccttg gaagcaaggc cattttatgg    780
gtacccaatt tatctatgga cactgcctat cagactaacg ttgttgttta a             831
```

<210> SEQ ID NO 25
<211> LENGTH: 831
<212> TYPE: DNA
<213> ORGANISM: Artificial Sequence
<220> FEATURE:
<223> OTHER INFORMATION: Sali3-2-[QPYGVYAW]

<400> SEQUENCE: 25

```
atggaatttc gatgctcagt catctctttt accattctct tctctcttgc tcttgcagga     60
gagagccatg tccatgcatc gctacctgag gaagattatt gggaagctgt ttggccaaac    120
actcccattc ccactgcact gcgagagctt ctaaagcctc tccctgcagg tgttgaaatc    180
gatgaactcc ctaagcaaat tgatgataca cagtacccaa aaacattctt ctataaagaa    240
gaccttcatc caggcaaaac aatgaaagta caattcacca agcgtcccta tgcacaacct    300
tatggtgtat atgcatggtt aacggatatt aaagacacct ctaaagaagg atatagtttt    360
gaagagatat gcatcaagaa agaagcgttt gagggagaag agaagttttg tgcaaaatcc    420
ttgggaacag taattggttt tgccatttca agctgggaa agaacattca agtactttca    480
agttcctttg tcaataagca agagcaatac actgtggaag gagtgcagaa tcttggagac    540
aaagcagtga tgtgtcatgg gctaaatttc agaactgcag tattttactg ccataaagtc    600
cgtgaaacaa cagctttcat ggttccattg gtggctggtg atggaaccaa aactcaggca    660
cttgctgttt gccactcaga tacttctgga atgaatcatc acatgcttca tgaactcatg    720
ggagttgatc ctggaactaa ccctgtttgc catttccttg gaagcaaggc cattttatgg    780
gtacccaatt tatctatgga cactgcctat cagactaacg ttgttgttta a             831
```

<210> SEQ ID NO 26
<211> LENGTH: 831
<212> TYPE: DNA
<213> ORGANISM: Artificial Sequence
<220> FEATURE:
<223> OTHER INFORMATION: Sali3-2-[QPYGVYTA]

<400> SEQUENCE: 26

```
atggaatttc gatgctcagt catctctttt accattctct tctctcttgc tcttgcagga     60
gagagccatg tccatgcatc gctacctgag gaagattatt gggaagctgt ttggccaaac    120
actcccattc ccactgcact gcgagagctt ctaaagcctc tccctgcagg tgttgaaatc    180
gatgaactcc ctaagcaaat tgatgataca cagtacccaa aaacattctt ctataaagaa    240
gaccttcatc caggcaaaac aatgaaagta caattcacca agcgtcccta tgcacaacct    300
tatggtgtat atacagcgtt aacggatatt aaagacacct ctaaagaagg atatagtttt    360
gaagagatat gcatcaagaa agaagcgttt gagggagaag agaagttttg tgcaaaatcc    420
ttgggaacag taattggttt tgccatttca agctgggaa agaacattca agtactttca    480
agttcctttg tcaataagca agagcaatac actgtggaag gagtgcagaa tcttggagac    540
```

| | |
|---|---|
| aaagcagtga tgtgtcatgg gctaaatttc agaactgcag tattttactg ccataaagtc | 600 |
| cgtgaaacaa cagcttcat ggttccattg gtggctggtg atggaaccaa aactcaggca | 660 |
| cttgctgttt gccactcaga tacttctgga atgaatcatc acatgcttca tgaactcatg | 720 |
| ggagttgatc ctggaactaa ccctgtttgc catttccttg gaagcaaggc cattttatgg | 780 |
| gtacccaatt tatctatgga cactgcctat cagactaacg ttgttgttta a | 831 |

<210> SEQ ID NO 27
<211> LENGTH: 831
<212> TYPE: DNA
<213> ORGANISM: Artificial Sequence
<220> FEATURE:
<223> OTHER INFORMATION: Sali3-2-[QPYGVYTY]

<400> SEQUENCE: 27

| | |
|---|---|
| atggaatttc gatgctcagt catctctttt accattctct ctctcttgc tcttgcagga | 60 |
| gagagccatg tccatgcatc gctacctgag aagattatt gggaagctgt ttggccaaac | 120 |
| actcccattc ccactgcact gcgagagctt ctaaagcctc tccctgcagg tgttgaaatc | 180 |
| gatgaactcc ctaagcaaat tgatgataca cagtacccaa aaacattctt ctataaagaa | 240 |
| gaccttcatc caggcaaaac aatgaaagta caattcacca gcgtcccta tgcacaacct | 300 |
| tatggtgtat atacatactt aacggatatt aagacacct aaagaagg atatagtttt | 360 |
| gaagagatat gcatcaagaa agaagcgttt gagggagaag agaagttttg tgcaaaatcc | 420 |
| ttgggaacag taattggttt tgccatttca agctgggaa agaacattca agtactttca | 480 |
| agttccttg tcaataagca agagcaatac actgtggaag gagtgcagaa tcttggagac | 540 |
| aaagcagtga tgtgtcatgg gctaaatttc agaactgcag tattttactg ccataaagtc | 600 |
| cgtgaaacaa cagcttcat ggttccattg gtggctggtg atggaaccaa aactcaggca | 660 |
| cttgctgttt gccactcaga tacttctgga atgaatcatc acatgcttca tgaactcatg | 720 |
| ggagttgatc ctggaactaa ccctgtttgc catttccttg gaagcaaggc cattttatgg | 780 |
| gtacccaatt tatctatgga cactgcctat cagactaacg ttgttgttta a | 831 |

<210> SEQ ID NO 28
<211> LENGTH: 828
<212> TYPE: DNA
<213> ORGANISM: Artificial Sequence
<220> FEATURE:
<223> OTHER INFORMATION: Sali3-2-[QYGVYTW]

<400> SEQUENCE: 28

| | |
|---|---|
| atggaatttc gatgctcagt catctctttt accattctct ctctcttgc tcttgcagga | 60 |
| gagagccatg tccatgcatc gctacctgag aagattatt gggaagctgt ttggccaaac | 120 |
| actcccattc ccactgcact gcgagagctt ctaaagcctc tccctgcagg tgttgaaatc | 180 |
| gatgaactcc ctaagcaaat tgatgataca cagtacccaa aaacattctt ctataaagaa | 240 |
| gaccttcatc caggcaaaac aatgaaagta caattcacca gcgtcccta tgcacaatat | 300 |
| ggtgtatata catggttaac ggatattaaa gacacctcta agaaggata tagttttgaa | 360 |
| gagatatgca tcaagaaaga agcgtttgag ggagaagaga gttttgtgc aaaatccttg | 420 |
| ggaacagtaa ttggttttgc catttcaaag ctgggaaga acattcaagt actttcaagt | 480 |
| tcctttgtca ataagcaaga gcaatacact gtgaaggag tgcagaatct tggagacaaa | 540 |
| gcagtgatgt gtcatgggct aaatttcaga actgcagtat tttactgcca taaagtccgt | 600 |
| gaaacaacag ctttcatggt tccattggtg gctggtgatg gaaccaaaac tcaggcactt | 660 |

```
gctgtttgcc actcagatac ttctggaatg aatcatcaca tgcttcatga actcatggga    720
gttgatcctg gaactaaccc tgtttgccat tccttggaa gcaaggccat tttatgggta     780
cccaatttat ctatggacac tgcctatcag actaacgttg ttgtttaa                 828

<210> SEQ ID NO 29
<211> LENGTH: 825
<212> TYPE: DNA
<213> ORGANISM: Artificial Sequence
<220> FEATURE:
<223> OTHER INFORMATION: Sali3-2-[QGVYTW]

<400> SEQUENCE: 29
atggaatttc gatgctcagt catctctttt accattctct ctctcttgc tcttgcagga     60 gagagccatg tccatgcatc gctacctgag gaagattatt gggaagctgt ttggccaaac    120
actcccattc ccactgcact gcgagagctt ctaaagcctc tccctgcagg tgttgaaatc    180
gatgaactcc ctaagcaaat tgatgataca cagtacccaa aaacattctt ctataaagaa    240
gaccttcatc caggcaaaac aatgaaagta caattcacca agcgtcccta tgcacaaggt    300
gtatatacat ggttaacgga tattaaagac acctctaaag aaggatatag ttttgaagag    360
atatgcatca agaaagaagc gtttgagggga agagaagt tttgtgcaaa atccttggga    420
acagtaattg gttttgccat tcaaagctgg gaaagaaca ttcaagtact ttcaagttcc    480
tttgtcaata agcaagagca atacactgtg gaaggagtgc agaatcttgg agacaaagca    540
gtgatgtgtc atgggctaaa tttcagaact gcagtatttt actgccataa agtccgtgaa    600
acaacagctt tcatggttcc attggtggct ggtgatggaa ccaaaactca ggcacttgct    660
gtttgccact cagatacttc tggaatgaat catcacatgc ttcatgaact catgggagtt    720
gatcctggaa ctaaccctgt ttgccatttc cttggaagca aggccatttt atgggtaccc    780
aatttatcta tggacactgc ctatcagact aacgttgttg tttaa                    825

<210> SEQ ID NO 30
<211> LENGTH: 834
<212> TYPE: DNA
<213> ORGANISM: Artificial Sequence
<220> FEATURE:
<223> OTHER INFORMATION: Sali3-2-[QAPYGVYTW]

<400> SEQUENCE: 30
atggaatttc gatgctcagt catctctttt accattctct ctctcttgc tcttgcagga     60 gagagccatg tccatgcatc gctacctgag gaagattatt gggaagctgt ttggccaaac    120
actcccattc ccactgcact gcgagagctt ctaaagcctc tccctgcagg tgttgaaatc    180
gatgaactcc ctaagcaaat tgatgataca cagtacccaa aaacattctt ctataaagaa    240
gaccttcatc caggcaaaac aatgaaagta caattcacca agcgtcccta tgcacaagca    300
ccttatggtg tatatacatg gttaacggat attaaagaca cctctaaaga aggatatagt    360
tttgaagaga tatgcatcaa gaaagaagcg tttgagggag aagagaagtt ttgtgcaaaa    420
tccttgggaa cagtaattgg ttttgccatt caaagctgg gaaagaacat tcaagtactt    480
tcaagttcct ttgtcaataa gcaagagcaa tacactgtgg aaggagtgca gaatcttgga    540
gacaaagcag tgatgtgtca tgggctaaat ttcagaactg cagtatttta ctgccataaa    600
gtccgtgaaa caacagcttt catggttcca ttggtggctg gtgatggaac caaaactcag    660
gcacttgctg tttgccactc agatacttct ggaatgaatc atcacatgct tcatgaactc    720
```
atgggagttg atcctggaac taaccctgtt tgccatttcc ttggaagcaa ggccatttta    780
tgggtaccca atttatctat ggacactgcc tatcagacta acgttgttgt ttaa          834

<210> SEQ ID NO 31
<211> LENGTH: 831
<212> TYPE: DNA
<213> ORGANISM: Artificial Sequence
<220> FEATURE:
<223> OTHER INFORMATION: Sali3-2-[QPYGVYTF]

<400> SEQUENCE: 31
atggaatttc gatgctcagt catctctttt accattctct tctctcttgc tcttgcagga     60
gagagccatg tccatgcatc gctacctgag gaagattatt gggaagctgt ttggccaaac    120
actcccattc ccactgcact gcgagagctt ctaaagcctc tccctgcagg tgttgaaatc    180
gatgaactcc ctaagcaaat tgatgataca cagtacccaa aaacattctt ctataaagaa    240
gaccttcatc caggcaaaac aatgaaagta caattcacca agcgtcccta tgcacaacct    300
tatggtgtat atacattctt aacgatatt aaagacacct ctaaagaagg atatagtttt    360
gaagagatat gcatcaagaa agaagcgttt gagggagaag agaagttttg tgcaaaatcc    420
ttgggaacag taattggttt tgccatttca agctgggaa agaacattca agtactttca    480
agttcctttg tcaataagca agagcaatac actgtggaag gagtgcagaa tcttggagac    540
aaagcagtga tgtgtcatgg gctaaatttc agaactgcag tattttactg ccataaagtc    600
cgtgaaacaa cagctttcat ggttccattg gtggctggtg atggaaccaa aactcaggca    660
cttgctgttt gccactcaga tacttctgga atgaatcatc acatgcttca tgaactcatg    720
ggagttgatc ctggaactaa ccctgtttgc catttccttg gaagcaaggc catttatgg    780 gtacccaatt tatctatgga cactgcctat cagactaacg ttgttgttta a             831

<210> SEQ ID NO 32
<211> LENGTH: 831
<212> TYPE: DNA
<213> ORGANISM: Artificial Sequence
<220> FEATURE:
<223> OTHER INFORMATION: Sali3-2-[QPYGVYTH]

<400> SEQUENCE: 32
atggaatttc gatgctcagt catctctttt accattctct tctctcttgc tcttgcagga     60
gagagccatg tccatgcatc gctacctgag gaagattatt gggaagctgt ttggccaaac    120
actcccattc ccactgcact gcgagagctt ctaaagcctc tccctgcagg tgttgaaatc    180
gatgaactcc ctaagcaaat tgatgataca cagtacccaa aaacattctt ctataaagaa    240
gaccttcatc caggcaaaac aatgaaagta caattcacca agcgtcccta tgcacaacct    300
tatggtgtat atacacactt aacgatatt aaagacacct ctaaagaagg atatagtttt    360
gaagagatat gcatcaagaa agaagcgttt gagggagaag agaagttttg tgcaaaatcc    420
ttgggaacag taattggttt tgccatttca agctgggaa agaacattca agtactttca    480
agttcctttg tcaataagca agagcaatac actgtggaag gagtgcagaa tcttggagac    540
aaagcagtga tgtgtcatgg gctaaatttc agaactgcag tattttactg ccataaagtc    600
cgtgaaacaa cagctttcat ggttccattg gtggctggtg atggaaccaa aactcaggca    660
cttgctgttt gccactcaga tacttctgga atgaatcatc acatgcttca tgaactcatg    720
ggagttgatc ctggaactaa ccctgtttgc catttccttg gaagcaaggc catttatgg    780 gtacccaatt tatctatgga cactgcctat cagactaacg ttgttgttta a             831

<210> SEQ ID NO 33
<211> LENGTH: 831
<212> TYPE: DNA
<213> ORGANISM: Artificial Sequence
<220> FEATURE:
<223> OTHER INFORMATION: Sali3-2-[QPYGVYFY]

<400> SEQUENCE: 33

```
atggaatttc gatgctcagt catctctttt accattctct tctctcttgc tcttgcagga      60
gagagccatg tccatgcatc gctacctgag gaagattatt gggaagctgt tggccaaac     120
actcccattc ccactgcact gcgagagctt ctaaagcctc tccctgcagg tgttgaaatc    180
gatgaactcc ctaagcaaat tgatgataca cagtacccaa aacattctt ctataagaa      240
gaccttcatc caggcaaaac aatgaaagta caattcacca agcgtcccta tgcacaacct   300
tatggtgtat atttctactt aacggatatt aaagacacct ctaaagaagg atatagtttt    360
gaagagatat gcatcaagaa agaagcgttt gagggagaag agaagttttg tgcaaaatcc   420
ttgggaacag taattggttt tgccatttca agctgggaa agaacattca gtactttca     480
agttcctttg tcaataagca agagcaatac actgtggaag gagtgcagaa tcttggagac  540
aaagcagtga tgtgtcatgg gctaaatttc agaactgcag tattttactg ccataaagtc  600
cgtgaaacaa cagctttcat ggttccattg gtggctggtg atggaaccaa aactcaggca   660
cttgctgttt gccactcaga tacttctgga atgaatcatc acatgcttca tgaactcatg  720
ggagttgatc ctggaactaa ccctgtttgc catttccttg aagcaaggc cattttatgg   780
gtacccaatt tatctatgga cactgcctat cagactaacg ttgttgttta a            831
```

<210> SEQ ID NO 34
<211> LENGTH: 643
<212> TYPE: PRT
<213> ORGANISM: Amaranthus hypochondriacus

<400> SEQUENCE: 34

```
Met Ala Met Asp Leu Arg Leu Gln Phe Pro Ala Leu Phe Leu Leu Thr
1               5                   10                  15

Phe Leu Ala Leu His Ala Ser Ser Cys Lys Gln Glu Asp Tyr Trp Lys
                20                  25                  30

Met Lys Leu Pro Lys Val Pro Met Pro Glu Ala Ile Lys Gln Ser Leu
            35                  40                  45

Leu His Ser Gly Gly Glu Asn Lys Leu Lys Asp Asp Ser Ala Leu Lys
        50                  55                  60

Gln Pro Tyr Thr Val Gly Ser Trp Lys Tyr Asp Val Asp Thr Asn Lys
65                  70                  75                  80

Val Lys Asp Asp Ser Val Val Lys Gln Pro Tyr Thr Val Gly Ser Trp
                85                  90                  95

Lys Tyr Asp Ala Asp Lys Asn Lys Val Pro Asp Glu Ser Ala Leu Lys
                100                 105                 110

Gln Pro Tyr Thr Val Phe Ser Trp Lys Tyr Asp Ala Gly Glu Asn Lys
            115                 120                 125

Val Lys Asp Glu Ser Ala Leu Lys Gln Pro Tyr Thr Val Phe Ser Trp
        130                 135                 140

Lys Tyr Asp Ala Gly Glu Asn Lys Val Lys Asp Glu Ser Ala Leu Lys
145                 150                 155                 160

Gln Pro Tyr Thr Val Phe Ser Trp Lys Tyr Asp Ala Gly Glu Asn Lys
                165                 170                 175
```

```
Val Lys Asp Glu Ser Ala Leu Lys Gln Pro Tyr Thr Val Phe Ser Trp
            180                 185                 190

Lys Tyr Asp Ala Gly Glu Asn Lys Val Lys Asp Glu Ser Ala Leu Lys
                195                 200                 205

Gln Pro Tyr Thr Val Phe Ser Trp Lys Tyr Asp Ala Gly Glu Asn Lys
    210                 215                 220

Val Lys Asp Glu Ser Ala Leu Lys Gln Pro Tyr Thr Val Phe Ser Trp
225                 230                 235                 240

Lys Tyr Asp Ala Gly Glu Asn Lys Val Lys Asp Glu Ser Ala Leu Lys
                245                 250                 255

Gln Pro Tyr Thr Val Phe Ser Trp Lys Tyr Asp Ala Gly Glu Asn Lys
    260                 265                 270

Val Lys Asp Glu Ser Ala Leu Lys Gln Pro Tyr Thr Val Phe Ser Trp
            275                 280                 285

Lys Tyr Asp Ala Gly Glu Asn Lys Val Lys Asp Glu Ser Ala Leu Lys
            290                 295                 300

Gln Pro Tyr Thr Val Phe Ser Trp Lys Tyr Asp Ala Gly Glu Asn Lys
305                 310                 315                 320

Val Lys Asp Glu Ser Ala Leu Lys Gln Pro Tyr Thr Val Phe Ser Trp
                325                 330                 335

Lys Tyr Asp Ala Gly Glu Asn Lys Val Lys Asp Glu Ser Ala Leu Lys
            340                 345                 350

Gln Pro Tyr Thr Val Phe Ser Trp Lys Tyr Asp Ala Gly Glu Asn Lys
            355                 360                 365

Val Lys Asp Glu Ser Ala Leu Lys Gln Pro Tyr Thr Val Gly Ser Trp
            370                 375                 380

Lys Tyr Asp Ala Gly Glu Asn Lys Val Lys Asp Glu Ser Ala Leu Lys
385                 390                 395                 400

Gln Pro Tyr Thr Val Gly Ser Trp Lys Tyr Asn Glu Asn Asp Glu Ser
                405                 410                 415

Lys Gln Ala Ser Pro His His Leu His His Lys Leu Met His Asp
                420                 425                 430

Asn Val Asn Ser Lys Asp Gln Glu Asp Leu Thr Asp Gly Ser Val Phe
            435                 440                 445

Phe Val Glu Lys Ser Leu His Ile Gly Ser Lys Leu Lys His Asp Phe
450                 455                 460

Gln Lys Thr Pro Lys Thr Ser Phe Leu Ser Lys Gln Glu Ala Gln Ser
465                 470                 475                 480

Ile Pro Phe Ser Met Glu Lys Ile Gly Asp Ile Leu Asn Leu Thr Cys
                485                 490                 495

Ala Gln Ser Met Glu Asp Ile Val Asp Phe Val Val Gly Glu Leu Gly
            500                 505                 510

Thr Asn Glu Val Glu Ile Lys Met Met Asn Asn Ile Glu Val Pro
            515                 520                 525

Asn Gly Ile Gln Asp Tyr Val Leu Ser Lys Val Glu Lys Leu Val Val
            530                 535                 540

Pro Gly Asn Thr Ala Val Ala Cys His Arg Met Ser Tyr Pro Tyr Ile
545                 550                 555                 560

Val Tyr Tyr Cys His His Gln Asp Ile Gly Gln Tyr Asn Val Thr
                565                 570                 575

Leu Val Ser Pro Ser Thr Gly Ala Ala Phe Gln Thr Thr Ala Val Cys
            580                 585                 590
```

```
His Tyr Asp Thr Tyr Ala Trp Gln Pro Asp Val Val Ala Leu Lys Tyr
            595                 600                 605

Leu Gly Ile Arg Pro Gly Asp Ala Pro Val Cys His Phe Ser Ala Ile
610                 615                 620

Asn Asp Met Phe Trp Asn Arg Lys Asn Asn Asp Phe Lys Ser Leu Asp
625                 630                 635                 640

Met Val Gln

<210> SEQ ID NO 35
<211> LENGTH: 550
<212> TYPE: PRT
<213> ORGANISM: Chenopodium quinoa

<400> SEQUENCE: 35

Met Ser Leu Tyr Ser Asn Asp Ala Asp Lys Ala Lys Lys Ala Asn Thr
1               5                   10                  15

Asn Gln Pro Phe Thr Val Val Gly Trp Lys Tyr Asn Ala Asp Gly Ala
                20                  25                  30

Lys Glu Arg Val Gly Met Ser Gln Pro Tyr Thr Val Met Ala Trp Lys
            35                  40                  45

Tyr Asn Val Asp Asp Ala Lys Glu Arg Val Gly Ile Asp Gln Pro Tyr
50                  55                  60

Thr Val Trp Gly Trp Asn Tyr Asn Thr Asp Ser Ala Asn Lys Glu Lys
65                  70                  75                  80

Val Lys Glu Ala Tyr Lys Pro Leu Ser Ile Glu Thr Asn Thr Lys Lys
                85                  90                  95

Thr Gly Ile Asp Gln Pro Tyr Thr Val Trp Gly Trp Asn Tyr Asn Thr
            100                 105                 110

Asn Ser Ala Asn Lys Glu Lys Val Lys Glu Ala Glu Lys Pro Leu Ser
        115                 120                 125

Ile Glu Thr Asn Thr Lys Lys Thr Gly Val Asp Gln Pro Tyr Thr Val
    130                 135                 140

Trp Gly Trp Asn Tyr Asn Thr Asn Asn Ala Asn Lys Glu Lys Val Lys
145                 150                 155                 160

Glu Ala Glu Lys Pro Leu Ser Ile Glu Thr Asn Thr Lys Lys Thr Gly
                165                 170                 175

Ile Asp Gln Pro Tyr Thr Val Trp Gly Trp Asn Tyr Asn Thr Asp Ser
            180                 185                 190

Ala Asn Lys Glu Lys Val Lys Glu Ala Asn Lys Pro Leu Ser Ile Glu
        195                 200                 205

Thr Asp Thr Lys Lys Thr Gly Ile Asp Gln Pro Tyr Thr Val Trp Gly
    210                 215                 220

Trp Asn Tyr Asn Thr Asp Ser Ala Asn Lys Glu Lys Val Lys Glu Ala
225                 230                 235                 240

Glu Lys Ser Leu Ser Ile Glu Thr Asn Thr Lys Lys Thr Gly Ile Asp
                245                 250                 255

Gln Pro Tyr Thr Val Trp Gly Trp Asn Tyr Asn Thr Asn Ser Gly Asn
            260                 265                 270

Lys Glu Lys Val Lys Glu Ala Asp Lys Val Phe Thr Met Asp Thr Ser
        275                 280                 285

Thr Lys Lys Ala Gly Thr Lys Gln Pro Tyr Thr Val Met Gly Trp Lys
    290                 295                 300

Tyr Asn Ala Asp Asn Gly Lys Arg Glu Lys Val Gly His Glu Val Ser
305                 310                 315                 320
```

Val Gly Ser Val Phe Ile Glu Lys Ser Leu Arg Leu Gly Asp Lys
            325                 330                 335

Leu Lys His Asp Phe Gln Lys Thr Pro Ser Val Pro Phe Leu Pro Lys
        340                 345                 350

His Ile Ala Lys Ser Ile Pro Phe Ser Glu Asp Lys Phe Thr Glu Ile
            355                 360                 365

Leu Asn Leu Phe Ser Ile Lys Pro Gly Ser Val Glu Ala Thr Gly Ile
        370                 375                 380

Lys Gly Thr Leu Asp Val Cys Leu His Arg Pro Lys Val Glu Lys Glu
385                 390                 395                 400

Asn Arg Thr Cys Ala Gln Ser Met Glu Asp Val Val Asp Phe Val Val
            405                 410                 415

Arg Glu Leu Gly Ser Asn Asp Val Glu Leu Arg Met Met Lys Asn Asp
        420                 425                 430

Ile Glu Val Pro Lys Gly Ile Gln Asp Tyr Val Ile Thr Lys Val Lys
            435                 440                 445

Lys Leu Val Val Pro Gly Asn Thr Ala Ala Cys His Arg Met Ser
        450                 455                 460

Tyr Pro Tyr Val Val Tyr Tyr Cys His His Gln Gln Asp Ile Gly His
465                 470                 475                 480

Tyr Asp Val Thr Leu Val Ser Pro Thr Thr Gly Asn Ala Ile Gln Thr
            485                 490                 495

Thr Ala Val Cys His Tyr Asp Thr Tyr Ala Trp Lys Pro Asn Val Pro
        500                 505                 510

Ala Leu Gln Tyr Leu Gly Ile Arg Pro Gly Asp Ala Pro Val Cys His
            515                 520                 525

Phe Ser Ala Ile Asn Asp Met Phe Trp Ser Leu Lys Ala Asn Ser Lys
530                 535                 540

Ser Leu Asp Met Val Val
545                 550

<210> SEQ ID NO 36
<211> LENGTH: 272
<212> TYPE: PRT
<213> ORGANISM: Glycine max

<400> SEQUENCE: 36

Met Ala Leu Arg Cys Leu Val Met Ser Leu Ser Val Leu Phe Thr Leu
1               5                   10                  15

Gly Leu Ala Arg Glu Ser His Ala Arg Asp Glu Asp Phe Trp His Ala
            20                  25                  30

Val Trp Pro Asn Thr Pro Ile Pro Ser Ser Leu Arg Asp Leu Leu Lys
        35                  40                  45

Pro Gly Pro Ala Ser Val Glu Ile Asp Asp His Pro Met Gln Ile Glu
    50                  55                  60

Glu Thr Gln Tyr Pro Lys Thr Phe Phe Tyr Lys Glu Asp Leu His Pro
65                  70                  75                  80

Gly Lys Thr Met Lys Val Gln Phe Ser Lys Pro Pro Phe Gln Gln Pro
                85                  90                  95

Trp Gly Val Gly Thr Trp Leu Lys Glu Ile Lys Asp Thr Thr Lys Glu
            100                 105                 110

Gly Tyr Ser Phe Glu Glu Leu Cys Ile Lys Lys Glu Ala Ile Glu Gly
        115                 120                 125

Glu Glu Lys Phe Cys Ala Lys Ser Leu Gly Thr Val Ile Gly Phe Ala
    130                 135                 140

Ile Ser Lys Leu Gly Lys Asn Ile Gln Val Leu Ser Ser Phe Val
145                 150                 155                 160

Asn Lys Gln Asp Gln Tyr Thr Val Glu Gly Val Gln Asn Leu Gly Asp
                165                 170                 175

Lys Ala Val Met Cys His Arg Leu Asn Phe Arg Thr Val Phe Tyr
            180                 185                 190

Cys His Glu Val Arg Glu Thr Thr Ala Phe Met Val Pro Leu Val Ala
        195                 200                 205

Gly Asp Gly Thr Lys Thr Gln Ala Leu Ala Ile Cys His Ser Asn Thr
        210                 215                 220

Ser Gly Met Asn His Gln Met Leu His Gln Leu Met Gly Val Asp Pro
225                 230                 235                 240

Gly Thr Asn Pro Val Cys His Phe Leu Gly Ser Lys Ala Ile Leu Trp
                245                 250                 255

Val Pro Asn Leu Ser Val Asp Thr Ala Tyr Gln Thr Asn Ile Val Ala
            260                 265                 270

<210> SEQ ID NO 37
<211> LENGTH: 984
<212> TYPE: DNA
<213> ORGANISM: Capsicum annuum

<400> SEQUENCE: 37
atggcgatgc tttaccaata ttacttcttc acacttcttt ctcttgtttt tgtcgtaatt      60
agtcatgcag caaatttatc tcctgaggtg tattggaaaa tcaaactacc caatactcct     120
atgcccaaac ctatcaagga tgccctacac atttctgaga aacgtcccca accatatgga     180
ggtcttactt gggattggtt tcacgttttc tccaagaacg agctacacaa attacaccaa     240
ttaagccaac catatggagt gtactttat ggtgtttctt tgaaaaacct taatgaagat      300
cacctagtta cacgtttctt ttttgaaacc gatttacatc aagggaaaaa agtgaatctt     360
aagtcgctca aaaacaacaa tccagctccc cttttgcctc gcaaagttgt agattccatc     420
tctttctcat cgaacagaat tgaggaaatt cttgatcact tttctgttga caacaattca     480
gaagatgcta aagtgatcaa gagaacagtc gaactctgtg aacagcccgc agctgatgga     540
gagataaaat attgtgccac ttccttggaa tctataattg atttcgcctc atctcgcttg     600
gaaacaaaca atattttggc aattcacacc gaggtagaga aggaaactcc agtgctgcaa     660
acatatacta tcaaagaagt gaaagagaaa gcaaacggta aatgtgtcat atgccacaaa     720
gtaccttacc catatgcagt acacttttgc catgatgtag aagcaccagg gcttttaggg     780
gtcactatgg tgggtgctga tggaacaaaa gttaatgcag tatcagtctg ccatgaggat     840
actgcatcca tgaatcctaa ggcattggtt tttcagttgc tcaatattaa gcccggagat     900
aagcctattt gccatttat tatggatgat caaattgccc tgtttccttc acaaaacgca     960
gttcttcaaa tggctgaagg ctaa                                           984

<210> SEQ ID NO 38
<211> LENGTH: 355
<212> TYPE: PRT
<213> ORGANISM: Solanum tuberosum

<400> SEQUENCE: 38

Met Glu Leu His His Gln Tyr Tyr Phe Phe Thr Phe Phe Ser Val Ile
1               5                   10                  15

Phe Val Val Ser His Ala Ala Asn Leu Ser Pro Glu Val Tyr Trp Arg

```
            20                  25                  30
Val Lys Leu Pro Asn Thr Pro Met Pro Thr Pro Ile Lys Asp Ala Leu
        35                  40                  45

His Ile Ser Asp Gly Ile Arg Leu Pro Leu Arg Thr Ser Phe Thr Lys
    50                  55                  60

Tyr Ala Asn His Gly Glu Trp Val Asp Gly Ile Arg Leu Pro Phe Glu
65                  70                  75                  80

Asn Glu Leu His Lys Val Arg Gln Pro Trp Gly Val Asp Ser Trp Tyr
                85                  90                  95

Gln Ala Ala Pro Glu Asn Glu Leu His Lys Val Arg Gln Pro Tyr Gly
            100                 105                 110

Val Gly Val Trp Tyr Asn Asp Ala Ala Lys Lys Asp Leu Asn Asp Asn
        115                 120                 125

His Pro Val Thr Pro Tyr Phe Phe Glu Thr Asp Leu His Gln Gly Lys
    130                 135                 140

Lys Met Asn Leu Gln Ser Leu Lys Asn Tyr Asn Pro Ala Pro Ile Leu
145                 150                 155                 160

Pro Arg Lys Val Val Asp Ser Ile Ala Phe Ser Ser Asp Lys Ile Glu
                165                 170                 175

Glu Ile Leu Asn His Phe Ser Val Asp Lys Asp Ser Glu Arg Ala Lys
            180                 185                 190

Asp Ile Lys Lys Thr Ile Lys Thr Cys Glu Glu Pro Ala Gly Asn Gly
        195                 200                 205

Glu Val Lys His Cys Ala Thr Ser Leu Glu Ser Met Ile Asp Phe Thr
    210                 215                 220

Leu Ser His Leu Gly Thr Asn Asn Ile Ile Ala Met Ser Thr Glu Val
225                 230                 235                 240

Glu Lys Glu Thr Pro Glu Val Gln Ala Tyr Thr Ile Glu Lys Val Glu
                245                 250                 255

Glu Lys Ala Asn Gly Lys Gly Val Val Cys His Lys Val Ala Tyr Pro
            260                 265                 270

Tyr Ala Val His Phe Cys His Asp Val Gly Ser Thr Arg Thr Phe Met
        275                 280                 285

Val Ser Met Val Gly Ala Asp Gly Thr Lys Val Asn Ala Val Ser Val
    290                 295                 300

Cys His Glu Asp Thr Ala Ser Met Asn Pro Lys Ala Leu Pro Phe Gln
305                 310                 315                 320

Leu Leu Asn Val Lys Pro Gly Asp Lys Pro Ile Cys His Phe Thr Leu
                325                 330                 335

Asp Asp Gln Ile Ala Leu Phe Pro Ser Gln Asn Ala Val Leu Gln Val
            340                 345                 350

Ala Glu Asn
        355

<210> SEQ ID NO 39
<211> LENGTH: 273
<212> TYPE: PRT
<213> ORGANISM: Medicago truncatula

<400> SEQUENCE: 39

Met Gly Phe Gln His Leu Leu Ile Phe Ile Ser Val Leu Ser Leu Ala
1               5                   10                  15

Leu Ala Gly Gly Ser His Ala Ser Val Pro Glu Glu Glu Tyr Trp Glu
            20                  25                  30
```

```
Ala Val Trp Pro Asn Thr Pro Ile Pro Thr Ser Leu Leu Glu Leu Leu
        35                  40                  45

Lys Pro Gly Pro Lys Gly Val Glu Ile Asp Asp Leu Pro Thr Glu Ile
 50                  55                  60

Asp Asp Thr Gln Phe Pro Thr Asn Phe Phe Tyr Glu His Glu Leu Tyr
 65                  70                  75                  80

Pro Gly Lys Thr Met Asn Met Gln Phe Ser Lys Arg Pro Leu Ala Gln
                 85                  90                  95

Pro Tyr Gly Val Tyr Phe Trp Met His Asp Ile Lys Asp Leu Gln Lys
            100                 105                 110

Glu Gly Tyr Thr Ile Asp Glu Met Cys Val Lys Asn Lys Pro Lys Lys
            115                 120                 125

Val Glu Glu Lys Phe Cys Ala Lys Ser Leu Gly Thr Leu Ile Gly Phe
130                 135                 140

Ala Ile Ser Lys Leu Gly Lys Asn Ile Gln Ser Leu Ser Ser Ser Phe
145                 150                 155                 160

Ile Asp Lys His Glu Gln Tyr Lys Ile Glu Ser Val Gln Asn Leu Gly
                165                 170                 175

Asp Lys Ala Val Met Cys His Arg Leu Asn Phe Gln Lys Val Val Phe
            180                 185                 190

Tyr Cys His Glu Val His Gly Thr Thr Ala Phe Lys Val Pro Leu Val
            195                 200                 205

Ala Asn Asp Gly Thr Lys Thr His Ala Ile Ala Thr Cys His Ala Asp
        210                 215                 220

Ile Ser Gly Met Asn Gln His Met Leu His Gln Ile Met Lys Gly Asp
225                 230                 235                 240

Pro Gly Ser Asn His Val Cys His Phe Leu Gly Asn Lys Ala Ile Leu
                245                 250                 255

Trp Val Pro Asn Leu Gly Leu Asp Asn Ala Tyr Gly Ala Asn Ala Ala
            260                 265                 270

Leu

<210> SEQ ID NO 40
<211> LENGTH: 273
<212> TYPE: PRT
<213> ORGANISM: Medicago truncatula

<400> SEQUENCE: 40

Met Glu Leu Lys His Ile Leu Ile Phe Ile Ser Val Leu Ser Leu Ala
 1               5                  10                  15

Leu Ala Gly Gly Ser His Ala Ser Leu Pro Glu Glu Glu Tyr Trp Glu
                20                  25                  30

Ala Val Trp Pro Asn Thr Pro Ile Pro Ser Ser Leu Arg Glu Leu Leu
        35                  40                  45

Lys Pro Gly Pro Glu Gly Val Glu Ile Asp Asp Leu Pro Met Glu Val
 50                  55                  60

Asp Asp Thr Gln Tyr Pro Lys Thr Phe Phe Tyr Glu His Glu Leu Tyr
 65                  70                  75                  80

Pro Gly Lys Thr Met Lys Val Gln Phe Ser Lys Arg Pro Phe Ala Gln
                 85                  90                  95

Pro Tyr Gly Val Tyr Thr Trp Met Arg Glu Ile Lys Asp Ile Glu Lys
            100                 105                 110

Glu Gly Tyr Thr Phe Asn Glu Val Cys Val Lys Lys Ala Ala Ala Glu
            115                 120                 125
```

```
                                              -continued

Gly Glu Gln Lys Phe Cys Ala Lys Ser Leu Gly Thr Leu Ile Gly Phe
    130                 135                 140

Ser Ile Ser Lys Leu Gly Lys Asn Ile Gln Ala Leu Ser Ser Ser Phe
145                 150                 155                 160

Ile Asp Lys His Glu Gln Tyr Lys Ile Glu Ser Val Gln Asn Leu Gly
                165                 170                 175

Glu Lys Ala Val Met Cys His Arg Leu Asn Phe Gln Lys Val Val Phe
            180                 185                 190

Tyr Cys His Glu Ile His Gly Thr Thr Ala Phe Met Val Pro Leu Val
        195                 200                 205

Ala Asn Asp Gly Arg Lys Thr Gln Ala Leu Ala Val Cys His Thr Asp
    210                 215                 220

Thr Ser Gly Met Asn His Glu Met Leu Gln Gln Ile Met Lys Ala Asp
225                 230                 235                 240

Pro Gly Ser Lys Pro Val Cys His Phe Leu Gly Asn Lys Ala Ile Leu
                245                 250                 255

Trp Val Pro Asn Leu Gly Leu Asp Asn Ala Tyr Gly Ala Asn Ala Ala
                260                 265                 270

Val

<210> SEQ ID NO 41
<211> LENGTH: 8
<212> TYPE: PRT
<213> ORGANISM: Amaranthus hypochondriacus

<400> SEQUENCE: 41

Gln Pro Tyr Thr Val Gly Ser Trp
1               5

<210> SEQ ID NO 42
<211> LENGTH: 8
<212> TYPE: PRT
<213> ORGANISM: Amaranthus hypochondriacus

<400> SEQUENCE: 42

Gln Pro Tyr Thr Val Phe Ser Trp
1               5

<210> SEQ ID NO 43
<211> LENGTH: 8
<212> TYPE: PRT
<213> ORGANISM: Arachis duranensis

<400> SEQUENCE: 43

Gln Pro Tyr Gly Val Tyr Thr Trp
1               5

<210> SEQ ID NO 44
<211> LENGTH: 8
<212> TYPE: PRT
<213> ORGANISM: Beta vulgaris

<400> SEQUENCE: 44

Gln Pro Trp Thr Val Tyr Gly Trp
1               5

<210> SEQ ID NO 45
<211> LENGTH: 8
<212> TYPE: PRT
<213> ORGANISM: Beta vulgaris
```

```
<400> SEQUENCE: 45

Gln Pro Trp Thr Val Ala Gly Trp
1               5

<210> SEQ ID NO 46
<211> LENGTH: 8
<212> TYPE: PRT
<213> ORGANISM: Beta vulgaris

<400> SEQUENCE: 46

Gln Pro Phe Thr Ile Ser Ala Trp
1               5

<210> SEQ ID NO 47
<211> LENGTH: 8
<212> TYPE: PRT
<213> ORGANISM: Beta vulgaris

<400> SEQUENCE: 47

Gln Pro Trp Thr Val Ala Ala Trp
1               5

<210> SEQ ID NO 48
<211> LENGTH: 8
<212> TYPE: PRT
<213> ORGANISM: Capsicum annuum

<400> SEQUENCE: 48

Gln Pro Tyr Gly Gly Leu Thr Trp
1               5

<210> SEQ ID NO 49
<211> LENGTH: 8
<212> TYPE: PRT
<213> ORGANISM: Capsicum annuum

<400> SEQUENCE: 49

Gln Pro Trp Gly Val Cys Leu Trp
1               5

<210> SEQ ID NO 50
<211> LENGTH: 8
<212> TYPE: PRT
<213> ORGANISM: Capsicum annuum

<400> SEQUENCE: 50

Gln Pro Trp Gly Val Gly Ser Trp
1               5

<210> SEQ ID NO 51
<211> LENGTH: 8
<212> TYPE: PRT
<213> ORGANISM: Capsicum annuum

<400> SEQUENCE: 51

Gln Pro Trp Gly Val Gly Phe Trp
1               5

<210> SEQ ID NO 52
<211> LENGTH: 8
<212> TYPE: PRT
<213> ORGANISM: Capsicum chinense

<400> SEQUENCE: 52
```

```
Gln Pro Trp Gly Val Cys Phe Trp
1               5

<210> SEQ ID NO 53
<211> LENGTH: 8
<212> TYPE: PRT
<213> ORGANISM: Chenopodium quinoa

<400> SEQUENCE: 53

Gln Pro Phe Thr Val Val Gly Trp
1               5

<210> SEQ ID NO 54
<211> LENGTH: 8
<212> TYPE: PRT
<213> ORGANISM: Chenopodium quinoa

<400> SEQUENCE: 54

Gln Pro Tyr Thr Val Met Ala Trp
1               5

<210> SEQ ID NO 55
<211> LENGTH: 8
<212> TYPE: PRT
<213> ORGANISM: Chenopodium quinoa

<400> SEQUENCE: 55

Gln Pro Tyr Thr Val Trp Gly Trp
1               5

<210> SEQ ID NO 56
<211> LENGTH: 8
<212> TYPE: PRT
<213> ORGANISM: Chenopodium quinoa

<400> SEQUENCE: 56

Gln Pro Tyr Thr Val Met Gly Trp
1               5

<210> SEQ ID NO 57
<211> LENGTH: 8
<212> TYPE: PRT
<213> ORGANISM: Chenopodium quinoa

<400> SEQUENCE: 57

Gln Pro Tyr Thr Val Tyr Gly Trp
1               5

<210> SEQ ID NO 58
<211> LENGTH: 8
<212> TYPE: PRT
<213> ORGANISM: Chenopodium quinoa

<400> SEQUENCE: 58

Gln Pro Phe Thr Val Phe Gly Trp
1               5

<210> SEQ ID NO 59
<211> LENGTH: 8
<212> TYPE: PRT
<213> ORGANISM: Chenopodium quinoa

<400> SEQUENCE: 59

Gln Pro Tyr Thr Val Asp Gly Trp
1               5
```

```
<210> SEQ ID NO 60
<211> LENGTH: 8
<212> TYPE: PRT
<213> ORGANISM: Glycine max

<400> SEQUENCE: 60

Gln Pro Phe Thr Val Phe Ala Trp
1               5

<210> SEQ ID NO 61
<211> LENGTH: 8
<212> TYPE: PRT
<213> ORGANISM: Glycine max

<400> SEQUENCE: 61

Gln Pro Trp Gly Val Gly Thr Trp
1               5

<210> SEQ ID NO 62
<211> LENGTH: 8
<212> TYPE: PRT
<213> ORGANISM: Medicago truncatula

<400> SEQUENCE: 62

Gln Pro Leu Leu Phe Ile Tyr Trp
1               5

<210> SEQ ID NO 63
<211> LENGTH: 8
<212> TYPE: PRT
<213> ORGANISM: Medicago truncatula

<400> SEQUENCE: 63

Gln Pro Tyr Gly Val Tyr Phe Trp
1               5

<210> SEQ ID NO 64
<211> LENGTH: 8
<212> TYPE: PRT
<213> ORGANISM: Medicago truncatula

<400> SEQUENCE: 64

Gln Pro Leu Thr Thr Arg Met Trp
1               5

<210> SEQ ID NO 65
<211> LENGTH: 8
<212> TYPE: PRT
<213> ORGANISM: Medicago truncatula

<400> SEQUENCE: 65

Gln Pro Leu Thr Thr Ser Met Trp
1               5

<210> SEQ ID NO 66
<211> LENGTH: 8
<212> TYPE: PRT
<213> ORGANISM: Medicago truncatula

<400> SEQUENCE: 66

Gln Pro Ile Thr Thr His Met Trp
1               5
```

```
<210> SEQ ID NO 67
<211> LENGTH: 8
<212> TYPE: PRT
<213> ORGANISM: Medicago truncatula

<400> SEQUENCE: 67

Gln Pro Phe Gly Ile Asn Ile Trp
1               5

<210> SEQ ID NO 68
<211> LENGTH: 8
<212> TYPE: PRT
<213> ORGANISM: Medicago truncatula

<400> SEQUENCE: 68

Gln Pro Phe Gly Val Leu Thr Trp
1               5

<210> SEQ ID NO 69
<211> LENGTH: 8
<212> TYPE: PRT
<213> ORGANISM: Medicago truncatula

<400> SEQUENCE: 69

Gln Pro Phe Gly Phe Phe Ser Trp
1               5

<210> SEQ ID NO 70
<211> LENGTH: 8
<212> TYPE: PRT
<213> ORGANISM: Medicago truncatula

<400> SEQUENCE: 70

Gln Pro Leu Pro Ala His Lys Trp
1               5

<210> SEQ ID NO 71
<211> LENGTH: 8
<212> TYPE: PRT
<213> ORGANISM: Medicago truncatula

<400> SEQUENCE: 71

Gln Pro Phe Arg Thr Ile Gly Trp
1               5

<210> SEQ ID NO 72
<211> LENGTH: 8
<212> TYPE: PRT
<213> ORGANISM: Medicago truncatula

<400> SEQUENCE: 72

Gln Pro Leu Gly Ala Val Lys Trp
1               5

<210> SEQ ID NO 73
<211> LENGTH: 8
<212> TYPE: PRT
<213> ORGANISM: Medicago truncatula

<400> SEQUENCE: 73

Gln Pro Phe Gly Ser Leu Thr Trp
1               5

<210> SEQ ID NO 74
<211> LENGTH: 8
```

```
<212> TYPE: PRT
<213> ORGANISM: Medicago truncatula

<400> SEQUENCE: 74

Gln Pro Phe Gly Val Ala Ala Trp
1               5

<210> SEQ ID NO 75
<211> LENGTH: 8
<212> TYPE: PRT
<213> ORGANISM: Medicago truncatula

<400> SEQUENCE: 75

Gln Pro Phe Gly Phe Arg Ala Trp
1               5

<210> SEQ ID NO 76
<211> LENGTH: 8
<212> TYPE: PRT
<213> ORGANISM: Medicago truncatula

<400> SEQUENCE: 76

Gln Pro Phe Glu Ala His Thr Trp
1               5

<210> SEQ ID NO 77
<211> LENGTH: 8
<212> TYPE: PRT
<213> ORGANISM: Nicotiana attenuata

<400> SEQUENCE: 77

Gln Pro Trp Gly Val Tyr Ser Trp
1               5

<210> SEQ ID NO 78
<211> LENGTH: 8
<212> TYPE: PRT
<213> ORGANISM: Petunia axillaris

<400> SEQUENCE: 78

Gln Pro Tyr Gly Val Phe Ala Trp
1               5

<210> SEQ ID NO 79
<211> LENGTH: 8
<212> TYPE: PRT
<213> ORGANISM: Petunia axillaris

<400> SEQUENCE: 79

Gln Pro Phe Gly Val Phe Ala Trp
1               5

<210> SEQ ID NO 80
<211> LENGTH: 8
<212> TYPE: PRT
<213> ORGANISM: Petunia inflata

<400> SEQUENCE: 80

Gln Pro Tyr Gly Pro Phe Gly Trp
1               5

<210> SEQ ID NO 81
<211> LENGTH: 8
<212> TYPE: PRT
<213> ORGANISM: Petunia inflata
```

<400> SEQUENCE: 81

Gln Pro Phe Gly Asp Tyr Val Trp
1               5

<210> SEQ ID NO 82
<211> LENGTH: 8
<212> TYPE: PRT
<213> ORGANISM: Petunia inflata

<400> SEQUENCE: 82

Gln Pro Tyr Gly Val Phe Gly Trp
1               5

<210> SEQ ID NO 83
<211> LENGTH: 8
<212> TYPE: PRT
<213> ORGANISM: Petunia inflata

<400> SEQUENCE: 83

Gln Pro Phe Gly Val Phe Gly Trp
1               5

<210> SEQ ID NO 84
<211> LENGTH: 8
<212> TYPE: PRT
<213> ORGANISM: Petunia inflata

<400> SEQUENCE: 84

Gln Pro Phe Gly Val Phe Val Trp
1               5

<210> SEQ ID NO 85
<211> LENGTH: 8
<212> TYPE: PRT
<213> ORGANISM: Prunus avium

<400> SEQUENCE: 85

Gln Pro Ala Pro Gln Leu Tyr Trp
1               5

<210> SEQ ID NO 86
<211> LENGTH: 8
<212> TYPE: PRT
<213> ORGANISM: Prunus persica

<400> SEQUENCE: 86

Gln Pro Ala Ala Gln Leu Tyr Trp
1               5

<210> SEQ ID NO 87
<211> LENGTH: 8
<212> TYPE: PRT
<213> ORGANISM: Solanum lycopersicum

<400> SEQUENCE: 87

Gln Pro Trp Gly Val Gly Ala Trp
1               5

<210> SEQ ID NO 88
<211> LENGTH: 8
<212> TYPE: PRT
<213> ORGANISM: Solanum lycopersicum

<400> SEQUENCE: 88

Gln Pro Trp Gly Val Tyr Arg Trp
1               5

<210> SEQ ID NO 89
<211> LENGTH: 8
<212> TYPE: PRT
<213> ORGANISM: Solanum lycopersicum

<400> SEQUENCE: 89

Gln Pro Tyr Gly Val Tyr Arg Trp
1               5

<210> SEQ ID NO 90
<211> LENGTH: 8
<212> TYPE: PRT
<213> ORGANISM: Solanum lycopersicum

<400> SEQUENCE: 90

Gln Pro Tyr Gly Val Tyr Ser Trp
1               5

<210> SEQ ID NO 91
<211> LENGTH: 8
<212> TYPE: PRT
<213> ORGANISM: Solanum melongena

<400> SEQUENCE: 91

Gln Pro Trp Gly Val Asn Ser Trp
1               5

<210> SEQ ID NO 92
<211> LENGTH: 8
<212> TYPE: PRT
<213> ORGANISM: Solanum melongena

<400> SEQUENCE: 92

Gln Pro Trp Gly Val Leu Arg Trp
1               5

<210> SEQ ID NO 93
<211> LENGTH: 8
<212> TYPE: PRT
<213> ORGANISM: Solanum melongena

<400> SEQUENCE: 93

Gln Pro Trp Gly Val Leu Gly Trp
1               5

<210> SEQ ID NO 94
<211> LENGTH: 8
<212> TYPE: PRT
<213> ORGANISM: Solanum pennellii

<400> SEQUENCE: 94

Gln Pro Phe Gly Val Tyr Arg Trp
1               5

<210> SEQ ID NO 95
<211> LENGTH: 8
<212> TYPE: PRT
<213> ORGANISM: Solanum pennellii

<400> SEQUENCE: 95

Gln Pro Trp Gly Val Phe Arg Trp

<210> SEQ ID NO 96
<211> LENGTH: 276
<212> TYPE: PRT
<213> ORGANISM: Artificial Sequence
<220> FEATURE:
<223> OTHER INFORMATION: Glyma.12G217400-[QAYGVYTW]

<400> SEQUENCE: 96

```
Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
            20                  25                  30

Tyr Trp Glu Ala Val Trp Pro Asn Thr Pro Ile Pro Thr Ala Leu Arg
        35                  40                  45

Glu Leu Leu Lys Pro Leu Pro Ala Gly Val Glu Ile Asp Glu Leu Pro
    50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Ala Tyr Gly Val Tyr Thr Trp Leu Thr Asp Ile Lys Asp
            100                 105                 110

Thr Ser Lys Glu Gly Tyr Ser Phe Glu Glu Ile Cys Ile Lys Lys Glu
        115                 120                 125

Ala Phe Glu Gly Glu Lys Phe Cys Ala Lys Ser Leu Gly Thr Val
    130                 135                 140

Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
            180                 185                 190

Ala Val Phe Tyr Cys His Lys Val Arg Glu Thr Thr Ala Phe Met Val
        195                 200                 205

Pro Leu Val Ala Gly Asp Gly Thr Lys Thr Gln Ala Leu Ala Val Cys
    210                 215                 220

His Ser Asp Thr Ser Gly Met Asn His His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Asp Thr Ala Tyr Gln Thr
            260                 265                 270

Asn Val Val Val
        275
```

<210> SEQ ID NO 97
<211> LENGTH: 8
<212> TYPE: PRT
<213> ORGANISM: Solanum tuberosum

<400> SEQUENCE: 97

```
Gln Pro Trp Gly Val Asp Ser Trp
1               5
```

<210> SEQ ID NO 98

```
<211> LENGTH: 8
<212> TYPE: PRT
<213> ORGANISM: Solanum tuberosum

<400> SEQUENCE: 98

Gln Pro Tyr Gly Val Gly Val Trp
1               5

<210> SEQ ID NO 99
<211> LENGTH: 8
<212> TYPE: PRT
<213> ORGANISM: Solanum tuberosum

<400> SEQUENCE: 99

Gln Pro Phe Gly Val Gly Arg Trp
1               5

<210> SEQ ID NO 100
<211> LENGTH: 8
<212> TYPE: PRT
<213> ORGANISM: Solanum tuberosum

<400> SEQUENCE: 100

Gln Pro Trp Gly Val Gly Arg Trp
1               5

<210> SEQ ID NO 101
<211> LENGTH: 8
<212> TYPE: PRT
<213> ORGANISM: Solanum tuberosum

<400> SEQUENCE: 101

Gln Pro Phe Gly Val Val Ala Trp
1               5

<210> SEQ ID NO 102
<211> LENGTH: 8
<212> TYPE: PRT
<213> ORGANISM: Solanum tuberosum

<400> SEQUENCE: 102

Gln Pro Tyr Gly Val Leu Ala Trp
1               5

<210> SEQ ID NO 103
<211> LENGTH: 8
<212> TYPE: PRT
<213> ORGANISM: Solanum tuberosum

<400> SEQUENCE: 103

Gln Pro Tyr Gly Val Ser Arg Trp
1               5

<210> SEQ ID NO 104
<211> LENGTH: 8
<212> TYPE: PRT
<213> ORGANISM: Solanum tuberosum

<400> SEQUENCE: 104

Gln Pro Trp Gly Val Val Ala Trp
1               5

<210> SEQ ID NO 105
<211> LENGTH: 8
<212> TYPE: PRT
```

<213> ORGANISM: Solanum tuberosum

<400> SEQUENCE: 105

Gln Pro Tyr Gly Val Phe Arg Trp
1               5

<210> SEQ ID NO 106
<211> LENGTH: 286
<212> TYPE: PRT
<213> ORGANISM: Selaginella uncinata

<400> SEQUENCE: 106

Thr Leu Phe Leu Ser Pro Ser Pro Thr Ser Asn Trp Val Asn Lys Gln
1               5                   10                  15

Pro Tyr Ser Val Phe Ala Trp Thr Asn Glu Asp Gln Pro Ser Lys Trp
            20                  25                  30

Phe Asn Lys Gln Pro Tyr Ser Val Phe Ala Trp Thr Asn Glu Asp Gln
        35                  40                  45

Pro Ser Lys Trp Phe Asn Lys Gln Pro Phe Gly Glu His Pro Lys Gln
    50                  55                  60

Lys Leu Glu Ser Leu Pro Thr Lys Gly Arg Ala Phe Arg Phe Ala Ser
65                  70                  75                  80

Ala Gln Ala Gly Lys Ser Ile Leu Pro Pro Ile Thr Pro Leu Leu
                85                  90                  95

Ser Asn Lys Leu Ile His Pro His Leu Glu Asp Val Leu Pro Phe Asn
            100                 105                 110

Lys Glu Ser Leu Ser Gln Val Leu Arg Ser Phe Asn Leu Ser Ala Asn
        115                 120                 125

Ser Gly Met Gly Gln Ser Met Glu Phe Ala Leu Asp Met Gly Lys Ser
    130                 135                 140

Thr Asn Asn Gly Val Glu Phe Arg Lys Ser Val Ala Thr Thr Lys Glu
145                 150                 155                 160

Met Val Asp Phe Val Gly Gly Val Leu Cys Lys Glu Lys Gly Asp Cys
                165                 170                 175

His Val Lys Ser Ile Ala Gln Ser Phe Glu Asn Lys Glu Ser Lys Met
            180                 185                 190

Val Lys Val Val Asp Val Glu Leu Val Ser Lys Asp Pro Val Ala Cys
        195                 200                 205

His Thr Val Pro Phe Pro Tyr Lys Val Tyr Val Cys His Lys Ile Lys
    210                 215                 220

Asp Ser Pro Val Tyr Lys Val Asn Met Met Val Glu Gly Gly Lys Thr
225                 230                 235                 240

Leu Ser Thr Pro Phe Ile Cys His Trp Asp Thr Ser Lys Phe Arg Thr
                245                 250                 255

Asn His Gln Ala Phe Glu Asp Leu Asn Ile Lys Pro Gly Gln Gly Glu
            260                 265                 270

Ile Cys His Trp Leu Gly Tyr Glu Thr Ile Val Trp Tyr Val
        275                 280                 285

<210> SEQ ID NO 107
<211> LENGTH: 8
<212> TYPE: PRT
<213> ORGANISM: Solanum tuberosum

<400> SEQUENCE: 107

Gln Pro Tyr Gly Val Asp Gly Trp
1               5

<210> SEQ ID NO 108
<211> LENGTH: 8
<212> TYPE: PRT
<213> ORGANISM: Trifolium pratense

<400> SEQUENCE: 108

Gln Pro Leu Gly Thr Trp Ile Trp
1               5

<210> SEQ ID NO 109
<211> LENGTH: 8
<212> TYPE: PRT
<213> ORGANISM: Trifolium pratense

<400> SEQUENCE: 109

Gln Pro Phe Gly Ile Ala Ala Trp
1               5

<210> SEQ ID NO 110
<211> LENGTH: 8
<212> TYPE: PRT
<213> ORGANISM: Trifolium pratense

<400> SEQUENCE: 110

Gln Pro Ser Gly Val Tyr Ile Trp
1               5

<210> SEQ ID NO 111
<211> LENGTH: 8
<212> TYPE: PRT
<213> ORGANISM: Vigna unguiculata

<400> SEQUENCE: 111

Gln Pro Ala Thr Leu Leu Ala Trp
1               5

<210> SEQ ID NO 112
<211> LENGTH: 924
<212> TYPE: DNA
<213> ORGANISM: Artificial Sequence
<220> FEATURE:
<223> OTHER INFORMATION: LycA-1x-QPWGVGSW

<400> SEQUENCE: 112
atggagttgc atcaccatta cttcttcata cttctttctc ttgcttttat agcaagtcat      60
gcagctaatt tatctcctga ggtgtattgg aaagtcaagc tgcccaacac tcctatgccc     120
agacccatta aggatgctct acactattct gaagcctccg agggtgacgt tcacaagttg     180
cgccaaccat ggggagtggg ttcgtggtat aatactgcta caagaaaga tgttaatgaa      240 aacctcccag tcaccccta cttttttgaa acagattac atcaagggaa aagatgaat       300 cttccatctc tcaaaaatta taatccagct cccattttgc ctcgcaaagt tgcagattcc    360
atccccttct catcagacaa gattgaagaa attctaaagc acttttccat tgataaggac    420 tcagagggg ctaaaatgat caagaaaact atcaaaatgt gtgaggagca agcgggtaat    480
ggcgagaaga aatattgtgc cacttcctta gaatcaatgg ttgatttcac ctcatcttat    540
ctgggaacaa ataatattat agcactttcc actttagtag agaaggaaac tccagaggtg    600
caaatatata ccatcgaaga agtgaaagag aaagcaaatg gcaaaggcgt gatatgccac    660
aaagtggctt acccgtatgc gatacattat tgccatagtg taggaagcac aaggaccttt    720

```
atggtctcaa tggtgggttc tgatggaaca aaagttaatg cagtatcaga gtgtcatgag    780
gatactgcac ccatgaaccc taaggcattg ccttttcaat tgctcaacgt taagccagga    840
gataaaccta tttgccattt catattggat gatcagattg ccttagttcc ttctcaagac    900
gcaactcaag tgtctgaaaa ctaa                                           924
```

<210> SEQ ID NO 113
<211> LENGTH: 307
<212> TYPE: PRT
<213> ORGANISM: Artificial Sequence
<220> FEATURE:
<223> OTHER INFORMATION: LycA-1x-QPWGVGSW

<400> SEQUENCE: 113

```
Met Glu Leu His His His Tyr Phe Phe Ile Leu Leu Ser Leu Ala Phe
1               5                   10                  15

Ile Ala Ser His Ala Ala Asn Leu Ser Pro Glu Val Tyr Trp Lys Val
                20                  25                  30

Lys Leu Pro Asn Thr Pro Met Pro Arg Pro Ile Lys Asp Ala Leu His
            35                  40                  45

Tyr Ser Glu Ala Ser Glu Gly Asp Val His Lys Leu Arg Gln Pro Trp
        50                  55                  60

Gly Val Gly Ser Trp Tyr Asn Thr Ala Thr Lys Lys Asp Val Asn Glu
65                  70                  75                  80

Asn Leu Pro Val Thr Pro Tyr Phe Phe Glu Thr Asp Leu His Gln Gly
                85                  90                  95

Lys Lys Met Asn Leu Pro Ser Leu Lys Asn Tyr Asn Pro Ala Pro Ile
            100                 105                 110

Leu Pro Arg Lys Val Ala Asp Ser Ile Pro Phe Ser Ser Asp Lys Ile
        115                 120                 125

Glu Glu Ile Leu Lys His Phe Ser Ile Asp Lys Asp Ser Glu Gly Ala
    130                 135                 140

Lys Met Ile Lys Lys Thr Ile Lys Met Cys Glu Glu Gln Ala Gly Asn
145                 150                 155                 160

Gly Glu Lys Lys Tyr Cys Ala Thr Ser Leu Glu Ser Met Val Asp Phe
                165                 170                 175

Thr Ser Ser Tyr Leu Gly Thr Asn Asn Ile Ile Ala Leu Ser Thr Leu
            180                 185                 190

Val Glu Lys Glu Thr Pro Glu Val Gln Ile Tyr Thr Ile Glu Glu Val
        195                 200                 205

Lys Glu Lys Ala Asn Gly Lys Gly Val Ile Cys His Lys Val Ala Tyr
    210                 215                 220

Pro Tyr Ala Ile His Tyr Cys His Ser Val Gly Ser Thr Arg Thr Phe
225                 230                 235                 240

Met Val Ser Met Val Gly Ser Asp Gly Thr Lys Val Asn Ala Val Ser
                245                 250                 255

Glu Cys His Glu Asp Thr Ala Pro Met Asn Pro Lys Ala Leu Pro Phe
            260                 265                 270

Gln Leu Leu Asn Val Lys Pro Gly Asp Lys Pro Ile Cys His Phe Ile
        275                 280                 285

Leu Asp Asp Gln Ile Ala Leu Val Pro Ser Gln Asp Ala Thr Gln Val
    290                 295                 300

Ser Glu Asn
305
```

<210> SEQ ID NO 114
<211> LENGTH: 1215
<212> TYPE: DNA
<213> ORGANISM: Artificial Sequence
<220> FEATURE:
<223> OTHER INFORMATION: LycA-5x-QPWGVGSW

<400> SEQUENCE: 114

```
atggagttgc atcaccatta cttcttcata cttctttctc ttgcttttat agcaagtcat      60
gcagctaatt tatctcctga ggtgtattgg aaagtcaagc tgcccaacac tcctatgccc     120
agacccatta aggatgctct acactattct gaagcctccg agggtgacgt tcacaagttg     180
cgccaaccat ggggagtggg ttcgtggtat caagcagcaa acgagggtga tgttaaaaaa     240
ttacgccagc cttggggtgt tggctcttgg tataaggctg ccccagagga cgagcttcac     300
aaaatacgcc agccctgggg cgtcggatcc tggtatcaag ctgccaaaga gaatgaccta     360
cccagaatgt cccagccgtg gggggtaggg agttggtatc aggctgcccc cgagaacgag     420
cttcacaaag tacggcagcc atggggcgtc ggaagctggt accaacccgc agcagaaggg     480
gatttacaca agctccgata taatactgct acaagaaaag atgttaatga aacctccca     540
gtcacccctt acttttttga aacagattta catcaaggga aaaagatgaa tcttccatct     600
ctcaaaaatt ataatccagc tcccattttg cctcgcaaag ttgcagattc catcccttc     660
tcatcagaca agattgaaga aattctaaag cacttttcca ttgataagga ctcagagggg     720
gctaaaatga tcaagaaaac tatcaaaatg tgtgaggagc aagcgggtaa tggcgagaag     780
aaatattgtg ccacttcctt agaatcaatg gttgatttca cctcatctta tctgggaaca     840
aataatatta tagcactttc cactttagta gagaaggaaa ctccagaggt gcaaatatat     900
accatcgaag aagtgaaaga gaaagcaaat ggcaaaggcg tgatatgcca caaagtggct     960
tacccgtatg cgatacatta ttgccatagt gtaggaagca caaggacctt tatggtctca    1020
atggtgggtt ctgatggaac aaaagttaat gcagtatcag agtgtcatga ggatactgca    1080
cccatgaacc ctaaggcatt gcctttcaa ttgctcaacg ttaagccagg agataaacct    1140
atttgccatt tcatattgga tgatcagatt gccttagttc cttctcaaga cgcaactcaa    1200
gtgtctgaaa actaa                                                    1215
```

<210> SEQ ID NO 115
<211> LENGTH: 404
<212> TYPE: PRT
<213> ORGANISM: Artificial Sequence
<220> FEATURE:
<223> OTHER INFORMATION: LycA-5x-QPWGVGSW

<400> SEQUENCE: 115

```
Met Glu Leu His His His Tyr Phe Phe Ile Leu Leu Ser Leu Ala Phe
1               5                   10                  15

Ile Ala Ser His Ala Ala Asn Leu Ser Pro Glu Val Tyr Trp Lys Val
            20                  25                  30

Lys Leu Pro Asn Thr Pro Met Pro Arg Pro Ile Lys Asp Ala Leu His
        35                  40                  45

Tyr Ser Glu Ala Ser Glu Gly Asp Val His Lys Leu Arg Gln Pro Trp
    50                  55                  60

Gly Val Gly Ser Trp Tyr Gln Ala Ala Asn Glu Gly Asp Val Lys Lys
65                  70                  75                  80

Leu Arg Gln Pro Trp Gly Val Gly Ser Trp Tyr Lys Ala Ala Pro Glu
                85                  90                  95
```

Asp Glu Leu His Lys Ile Arg Gln Pro Trp Gly Val Gly Ser Trp Tyr
            100                 105                 110

Gln Ala Ala Lys Glu Asn Asp Leu Pro Arg Met Ser Gln Pro Trp Gly
        115                 120                 125

Val Gly Ser Trp Tyr Gln Ala Ala Pro Glu Asn Glu Leu His Lys Val
    130                 135                 140

Arg Gln Pro Trp Gly Val Gly Ser Trp Tyr Gln Pro Ala Ala Glu Gly
145                 150                 155                 160

Asp Leu His Lys Leu Arg Tyr Asn Thr Ala Thr Lys Lys Asp Val Asn
                165                 170                 175

Glu Asn Leu Pro Val Thr Pro Tyr Phe Phe Glu Thr Asp Leu His Gln
            180                 185                 190

Gly Lys Lys Met Asn Leu Pro Ser Leu Lys Asn Tyr Asn Pro Ala Pro
        195                 200                 205

Ile Leu Pro Arg Lys Val Ala Asp Ser Ile Pro Phe Ser Ser Asp Lys
    210                 215                 220

Ile Glu Glu Ile Leu Lys His Phe Ser Ile Asp Lys Asp Ser Glu Gly
225                 230                 235                 240

Ala Lys Met Ile Lys Lys Thr Ile Lys Met Cys Glu Glu Gln Ala Gly
                245                 250                 255

Asn Gly Glu Lys Lys Tyr Cys Ala Thr Ser Leu Glu Ser Met Val Asp
            260                 265                 270

Phe Thr Ser Ser Tyr Leu Gly Thr Asn Asn Ile Ile Ala Leu Ser Thr
        275                 280                 285

Leu Val Glu Lys Glu Thr Pro Glu Val Gln Ile Tyr Thr Ile Glu Glu
    290                 295                 300

Val Lys Glu Lys Ala Asn Gly Lys Gly Val Ile Cys His Lys Val Ala
305                 310                 315                 320

Tyr Pro Tyr Ala Ile His Tyr Cys His Ser Val Gly Ser Thr Arg Thr
                325                 330                 335

Phe Met Val Ser Met Val Gly Ser Asp Gly Thr Lys Val Asn Ala Val
            340                 345                 350

Ser Glu Cys His Glu Asp Thr Ala Pro Met Asn Pro Lys Ala Leu Pro
        355                 360                 365

Phe Gln Leu Leu Asn Val Lys Pro Gly Asp Lys Pro Ile Cys His Phe
    370                 375                 380

Ile Leu Asp Asp Gln Ile Ala Leu Val Pro Ser Gln Asp Ala Thr Gln
385                 390                 395                 400

Val Ser Glu Asn

<210> SEQ ID NO 116
<211> LENGTH: 1491
<212> TYPE: DNA
<213> ORGANISM: Artificial Sequence
<220> FEATURE:
<223> OTHER INFORMATION: LycA-10x-QPWGVGSW

<400> SEQUENCE: 116
atggagttgc atcaccatta cttcttcata cttctttctc ttgcttttat agcaagtcat     60
gcagctaatt tatctcctga ggtgtattgg aaagtcaagc tgcccaacac tcctatgccc    120
agacccatta aggatgctct acactattct gaagcctccg agggtgacgt tcacaagttg    180
cgccaaccat ggggagtggg ttcgtggtat caagcagcaa acgagggtga tgttaaaaaa    240
ttacgccagc cttggggtgt tggctcttgg tataaggctg ccccagagga cgagcttcac    300

```
aaaatacgcc aaccctgggg cgtcggatcc tggtatcaag ctgccaaaga gaatgaccta    360
cccagaatgt cccagccgtg gggggtaggg agttggtatc aggctgcccc cgagaacgag    420
cttcacaaag tacggcaacc atggggcgtc ggaagctggt accaacccgc agcagaaggg    480
gatttacaca agctccgaca gccttgggc gtggggagtt ggtacaacga cgcaccagag     540
aatgaactcc ataagttccg tcaaccctgg ggagttggat cgtggtacag ggcagctact    600
gaaggggacg ttcaaaagct gcgtcagccg tggggcgtcg gctcatggta ccaagcagca    660
aacgagggag acattaagaa gctacggcag ccatggggag tcggctcttg gtacagagcc    720
gctactgagg gtgacgttca gaagctaaga cagccctggg gggtcggtag ttggtataat    780
actgctacaa agaaagatgt taatgaaaac ctcccagtca ccccttactt ttttgaaaca    840
gatttacatc aagggaaaaa gatgaatctt ccatctctca aaattataa tccagctccc     900
attttgcctc gcaaagttgc agattccatc cccttctcat cagacaagat tgaagaaatt    960
ctaaagcact tttccattga taaggactca gagggggcta aatgatcaa gaaaactatc    1020
aaaatgtgtg aggagcaagc gggtaatggc gagaagaaat attgtgccac ttccttagaa    1080
tcaatggttg atttcacctc atcttatctg gaacaaata atattatagc actttccact    1140
ttagtagaga aggaaactcc agaggtgcaa atatatacca tcgaagaagt gaaagagaaa    1200
gcaaatggca aggcgtgat atgccacaaa gtggcttacc cgtatgcgat acattattgc    1260
catagtgtag aagcacaag gacctttatg gtctcaatgg tgggttctga tggaacaaaa    1320
gttaatgcag tatcagagtg tcatgaggat actgcaccca tgaaccctaa ggcattgcct    1380
tttcaattgc tcaacgttaa gccaggagat aaacctattt gccatttcat attggatgat    1440
cagattgcct tagttccttc tcaagacgca actcaagtgt ctgaaaacta a             1491
```

<210> SEQ ID NO 117
<211> LENGTH: 496
<212> TYPE: PRT
<213> ORGANISM: Artificial Sequence
<220> FEATURE:
<223> OTHER INFORMATION: LycA-10x-QPWGVGSW

<400> SEQUENCE: 117

```
Met Glu Leu His His His Tyr Phe Phe Ile Leu Leu Ser Leu Ala Phe
1               5                   10                  15

Ile Ala Ser His Ala Ala Asn Leu Ser Pro Glu Val Tyr Trp Lys Val
            20                  25                  30

Lys Leu Pro Asn Thr Pro Met Pro Arg Pro Ile Lys Asp Ala Leu His
        35                  40                  45

Tyr Ser Glu Ala Ser Glu Gly Asp Val His Lys Leu Arg Gln Pro Trp
    50                  55                  60

Gly Val Gly Ser Trp Tyr Gln Ala Ala Asn Glu Gly Asp Val Lys Lys
65                  70                  75                  80

Leu Arg Gln Pro Trp Gly Val Gly Ser Trp Tyr Lys Ala Ala Pro Glu
                85                  90                  95

Asp Glu Leu His Lys Ile Arg Gln Pro Trp Gly Val Gly Ser Trp Tyr
            100                 105                 110

Gln Ala Ala Lys Glu Asn Asp Leu Pro Arg Met Ser Gln Pro Trp Gly
        115                 120                 125

Val Gly Ser Trp Tyr Gln Ala Ala Pro Glu Asn Glu Leu His Lys Val
    130                 135                 140

Arg Gln Pro Trp Gly Val Gly Ser Trp Tyr Gln Pro Ala Ala Glu Gly
145                 150                 155                 160
```

Asp Leu His Lys Leu Arg Gln Pro Trp Gly Val Gly Ser Trp Tyr Asn
                165                 170                 175

Asp Ala Pro Glu Asn Glu Leu His Lys Phe Arg Gln Pro Trp Gly Val
            180                 185                 190

Gly Ser Trp Tyr Arg Ala Ala Thr Glu Gly Asp Val Gln Lys Leu Arg
        195                 200                 205

Gln Pro Trp Gly Val Gly Ser Trp Tyr Gln Ala Ala Asn Glu Gly Asp
    210                 215                 220

Ile Lys Lys Leu Arg Gln Pro Trp Gly Val Gly Ser Trp Tyr Arg Ala
225                 230                 235                 240

Ala Thr Glu Gly Asp Val Gln Lys Leu Arg Gln Pro Trp Gly Val Gly
                245                 250                 255

Ser Trp Tyr Asn Thr Ala Thr Lys Lys Asp Val Asn Glu Asn Leu Pro
            260                 265                 270

Val Thr Pro Tyr Phe Phe Glu Thr Asp Leu His Gln Gly Lys Lys Met
        275                 280                 285

Asn Leu Pro Ser Leu Lys Asn Tyr Asn Pro Ala Pro Ile Leu Pro Arg
    290                 295                 300

Lys Val Ala Asp Ser Ile Pro Phe Ser Ser Asp Lys Ile Glu Glu Ile
305                 310                 315                 320

Leu Lys His Phe Ser Ile Asp Lys Asp Ser Glu Gly Ala Lys Met Ile
                325                 330                 335

Lys Lys Thr Ile Lys Met Cys Glu Glu Gln Ala Gly Asn Gly Glu Lys
            340                 345                 350

Lys Tyr Cys Ala Thr Ser Leu Glu Ser Met Val Asp Phe Thr Ser Ser
        355                 360                 365

Tyr Leu Gly Thr Asn Asn Ile Ile Ala Leu Ser Thr Leu Val Glu Lys
    370                 375                 380

Glu Thr Pro Glu Val Gln Ile Tyr Thr Ile Glu Val Lys Glu Lys
385                 390                 395                 400

Ala Asn Gly Lys Gly Val Ile Cys His Lys Val Ala Tyr Pro Tyr Ala
                405                 410                 415

Ile His Tyr Cys His Ser Val Gly Ser Thr Arg Thr Phe Met Val Ser
        420                 425                 430

Met Val Gly Ser Asp Gly Thr Lys Val Asn Ala Val Ser Glu Cys His
    435                 440                 445

Glu Asp Thr Ala Pro Met Asn Pro Lys Ala Leu Pro Phe Gln Leu Leu
450                 455                 460

Asn Val Lys Pro Gly Asp Lys Pro Ile Cys His Phe Ile Leu Asp Asp
465                 470                 475                 480

Gln Ile Ala Leu Val Pro Ser Gln Asp Ala Thr Gln Val Ser Glu Asn
                485                 490                 495

<210> SEQ ID NO 118
<211> LENGTH: 29
<212> TYPE: DNA
<213> ORGANISM: Artificial Sequence
<220> FEATURE:
<223> OTHER INFORMATION: LbaLycA-pEAQ-AgeI

<400> SEQUENCE: 118
agaccggtat ggagttgcat caccattac                                    29

<210> SEQ ID NO 119
<211> LENGTH: 33

<212> TYPE: DNA
<213> ORGANISM: Artificial Sequence
<220> FEATURE:
<223> OTHER INFORMATION: LbaLycA-pEAQ-XhoI

<400> SEQUENCE: 119
agctcgagtt agttttcaga cacttgagtt gcg         33

<210> SEQ ID NO 120
<211> LENGTH: 40
<212> TYPE: DNA
<213> ORGANISM: Artificial Sequence
<220> FEATURE:
<223> OTHER INFORMATION: StuBURP-pEAQ-fwd

<400> SEQUENCE: 120
tgcccaaatt cgcgaccggt atggagttgc atcaccaata         40

<210> SEQ ID NO 121
<211> LENGTH: 46
<212> TYPE: DNA
<213> ORGANISM: Artificial Sequence
<220> FEATURE:
<223> OTHER INFORMATION: StuBURP-pEAQ-rev

<400> SEQUENCE: 121
ccagagttaa aggcctcgag ttagttttca gccacttgaa gaactg         46

<210> SEQ ID NO 122
<211> LENGTH: 906
<212> TYPE: DNA
<213> ORGANISM: Lycium barbarum

<400> SEQUENCE: 122
atggtttctt ctacttcata tctacctacc aatcacacaa aaatgcctct gctaaatcca         60
aggtttctag tcataagctt gattgttcta ctgagcatca ccgtattcag agaagctgaa        120
gcatcatata gagtttacaa agtcaaagta gtcaatgaat tccctcacga cccccaagcc        180
tacactcagg ggcttctcta tgcagaaaat aatacactct ttgaatcaac tggactttac        240
ggacgttcat ctgttcgaaa agttgcattg ctggacggta aggttgagag acttcatgaa        300
atggagtctt cttactttgg agagggtcta actcttcttg gtgagaggtt gttccaacta        360
acatggttgc tggatacagg tttcatatat gatcgataca acttcagcaa attcaaaaag        420
tttactcatc acatgcaaga tggttgggga ttggcaaccg atgggaaagt acttttttgga       480
agtgatggaa catcaacatt atataagatt gaccctaaaa caatgaaagt catcagaaaa        540
caagttgtca agtctcaagg gcatgaagtg cgctacctga tgagctgga gtatgtgaaa         600
gctgaagtct gggcaaatgt ttatgtgact gattgcattg ctagaatttc accaaaagat        660
ggcactgtga tcgggtggat tctccttcaa tctctaagag aagagttaat atcaagagga        720
tataaggact tcgaggtcct gaatggaatc gcatgggaca gagatggtga ccgtattttt        780
gtgacaggga aactatggcc aaagctcttt gagatcaagt tgctccccct cacaccgaat        840
gatccattgg ctggagaaat caataacttg tgcatcccga aaccagtttt tctcttggaa        900
atttag                                                                     906

<210> SEQ ID NO 123
<211> LENGTH: 20
<212> TYPE: DNA
<213> ORGANISM: Artificial Sequence
<220> FEATURE:

<223> OTHER INFORMATION: 5'-adapter for LbaQC Gibson assembly

<400> SEQUENCE: 123
tgcccaaatt cgcgaccggt					20

<210> SEQ ID NO 124
<211> LENGTH: 20
<212> TYPE: DNA
<213> ORGANISM: Artificial Sequence
<220> FEATURE:
<223> OTHER INFORMATION: 3'-adapter for LbaQC Gibson assembly

<400> SEQUENCE: 124
ctcgaggcct ttaactctgg					20

<210> SEQ ID NO 125
<211> LENGTH: 1632
<212> TYPE: DNA
<213> ORGANISM: Lycium barbarum

<400> SEQUENCE: 125

| | | |
|---|---|---|
| atggagttgc atcaccatta cttcttcata cttctttctc ttgcttttat agcaagtcat | 60 |
| gcagctaatt tatctcctga ggtgtattgg aaagtcaagc tgcccaacac tcctatgccc | 120 |
| agacccatta aggatgctct acactattct gaagcctccg agggtgacgt tcacaagttg | 180 |
| cgccaaccat ggggagtggg ttcgtggtat caagcagcaa acgagggtga tattaaaaaa | 240 |
| ttacgccaac catatggagt tggtatatgg tatcaagcag caaacgaggg tgatgttaaa | 300 |
| aaattacgcc aaccatgggg agttggttcc tggtatcaag cagcaaacga gggtgatgtt | 360 |
| aaaaaattac gccaaccatg gggagtgggt tcctggtatc aagcagcaaa cgagggtgat | 420 |
| gttaaaaaat acgccaacc atggggagtg ggttcctggt atcaagcagc aaacgagggt | 480 |
| gatgcaaatg agggtgatgt taaaaaatta cgccaaccat atggagttgg tatatggtat | 540 |
| caagcagcaa acgagggtga tgttaaaaaa ttacgccaac catggggagt gggttcttgg | 600 |
| tatcaagcag caaacgaggg tgatgttaaa aaattacgcc aaccatgggg agtgggttcc | 660 |
| tggtatcaag cagcaaacga gggtgatgtt aaaaaattac accaaccatg gggagtgggt | 720 |
| tcctggtatc aagcagcaaa cgagggtgat gttaaaaaat accccaacc atggggagtg | 780 |
| ggttcctggt atcaagcagc aaacgagggt gatgttaaaa aattacgcca accatatgga | 840 |
| gttggtatat ggtatgaagc agcaaacgag gtcaagtta aaaaattacg ccaaccctat | 900 |
| ggagtgggtt cgtggtataa tactgctaca aagaaagatg ttaatgaaaa cctcccagtc | 960 |
| acccccttact tttttgaaac agatttacat caagggaaaa agatgaatct tccatctctc | 1020 |
| aaaaattata atccagctcc cattttgcct cgcaaagttg cagattccat cccttctca | 1080 |
| tcagacaaga ttgaagaaat ctaaagcac ttttccattg ataaggactc agaggggct | 1140 |
| aaaatgatca agaaaactat caaaatgtgt gaggagcaag cgggtaatgg cgagaagaaa | 1200 |
| tattgtgcca cttccttaga atcaatggtt gatttcacct catcttatct gggaacaaat | 1260 |
| aatattatag cactttccac tttagtagag aaggaaactc cagaggtgca aatatatacc | 1320 |
| atcgaagaag tgaaagagaa agcaaatggc aaaggcgtga tatgccacaa agtggcttac | 1380 |
| ccgtatgcga tacattattg ccatagtgta ggaagcacaa ggaccttttat ggtctcaatg | 1440 |
| gtgggttctg atggaacaaa agttaatgca gtatcagagt gtcatgagga tactgcaccc | 1500 |
| atgaacccta aggcattgcc ttttcaattg ctcaacgtta gccaggaga taaacctatt | 1560 |
| tgccatttca tattggatga tcagattgcc ttagttcctt ctcaagacgc aactcaagtg | 1620 | tctgaaaact aa                                                          1632

<210> SEQ ID NO 126
<211> LENGTH: 1254
<212> TYPE: DNA
<213> ORGANISM: Solanum tuberosum

<400> SEQUENCE: 126
atggagttgc ttcaccaata ttatttcttc acattttttt ctgtaatttt tgtggtaagt      60
catgcagcaa atttatctcc tgaggtgtat tggagagtca aattgcctaa tactcccatg     120
cccacaccta tcaaagatgc actacacatt tctgagaaaa ctgcatataa tggagatgga     180
aacaccaaaa tatcccaacc atatggagtg tttgcatggt atcaggctgc ctccgagaat     240
gagcttcaca agtacgcca accatatgga gtggatgga ggtacaaggc tgcctccgag       300
aatgagcttc acaaagtacg ccaaccatat ggagtgtttg catggtacaa ggctatcacc     360
gagaatgagc ttcacaaagt acgccaacca tatggagtgt ttgcatggta caaggctgcc     420
accgagaatg agcttcacaa agtacgccaa ccatatggag tgtttgcatg gtacaaggct     480
gcctccgaga atgtgcttca caaagtacgc caaccatatg gagtgtttgc atggtacaat     540
gatgctgcta agaaagatct taatgacaat cacccagtga cgccatactt ctttgaaaca     600
gatttacatc aagggaaaaa aatgaatctt cagtctctca aaactacaa tccagcaccc      660 attttgccac gcaaagttgt agattcaatt gctttctcat cggacaaaat tgaggaaatt     720
cttaatcact tctctgttga taaggactcg gaacgtgcta agacatcaa gaaacaatc      780 aaaatgtgtg aagagcctgc gggtaacgga gaggtaaaac attgtgccac ttctttggaa     840
tctatgattg atttcacctt atctcacctg gaacaaaca atattgtagc aatttccact     900
gaagtagaca aggaaactcc agaggtgcaa acatatacca tcgaaaaagt ggaagagaaa     960
gcaaatggca aggtgttgt atgtcacaaa gtagcttacc catatgcagt acacttttgc    1020
catgatgtag aagcactag gacatttgtg gtgtctatgg tgggtgctga cggaacaaaa    1080
gttaatgcag tatcagtctg ccatgaggat actgcatcca tgaaccctaa ggcattgcct    1140
tttcagttgc tcaacgttaa gcctggagac aagcctattt gccatttcac tttggacgat    1200
caaattgccc tgtttccttc tcaaaacgca cttcttcaag tggctgaaaa ctaa          1254

<210> SEQ ID NO 127
<211> LENGTH: 417
<212> TYPE: PRT
<213> ORGANISM: Solanum tuberosum

<400> SEQUENCE: 127

Met Glu Leu Leu His Gln Tyr Tyr Phe Phe Thr Phe Phe Ser Val Ile
1               5                   10                  15

Phe Val Val Ser His Ala Ala Asn Leu Ser Pro Glu Val Tyr Trp Arg
            20                  25                  30

Val Lys Leu Pro Asn Thr Pro Met Pro Thr Pro Ile Lys Asp Ala Leu
        35                  40                  45

His Ile Ser Glu Lys Thr Ala Tyr Asn Gly Asp Gly Asn Thr Lys Ile
    50                  55                  60

Ser Gln Pro Tyr Gly Val Phe Ala Trp Tyr Gln Ala Ala Ser Glu Asn
65                  70                  75                  80

Glu Leu His Lys Val Arg Gln Pro Tyr Gly Val Asp Gly Trp Tyr Lys
                85                  90                  95

```
Ala Ala Ser Glu Asn Glu Leu His Lys Val Arg Gln Pro Tyr Gly Val
            100                 105                 110
Phe Ala Trp Tyr Lys Ala Ile Thr Glu Asn Glu Leu His Lys Val Arg
        115                 120                 125
Gln Pro Tyr Gly Val Phe Ala Trp Tyr Lys Ala Ala Thr Glu Asn Glu
    130                 135                 140
Leu His Lys Val Arg Gln Pro Tyr Gly Val Phe Ala Trp Tyr Lys Ala
145                 150                 155                 160
Ala Ser Glu Asn Val Leu His Lys Val Arg Gln Pro Tyr Gly Val Phe
                165                 170                 175
Ala Trp Tyr Asn Asp Ala Ala Lys Lys Asp Leu Asn Asp Asn His Pro
            180                 185                 190
Val Thr Pro Tyr Phe Phe Glu Thr Asp Leu His Gln Gly Lys Lys Met
        195                 200                 205
Asn Leu Gln Ser Leu Lys Asn Tyr Asn Pro Ala Pro Ile Leu Pro Arg
    210                 215                 220
Lys Val Val Asp Ser Ile Ala Phe Ser Ser Asp Lys Ile Glu Glu Ile
225                 230                 235                 240
Leu Asn His Phe Ser Val Asp Lys Asp Ser Glu Arg Ala Lys Asp Ile
                245                 250                 255
Lys Lys Thr Ile Lys Met Cys Glu Glu Pro Ala Gly Asn Gly Glu Val
            260                 265                 270
Lys His Cys Ala Thr Ser Leu Glu Ser Met Ile Asp Phe Thr Leu Ser
        275                 280                 285
His Leu Gly Thr Asn Asn Ile Val Ala Ile Ser Thr Glu Val Asp Lys
    290                 295                 300
Glu Thr Pro Glu Val Gln Thr Tyr Thr Ile Glu Lys Val Glu Lys
305                 310                 315                 320
Ala Asn Gly Lys Gly Val Val Cys His Lys Val Ala Tyr Pro Tyr Ala
                325                 330                 335
Val His Phe Cys His Asp Val Gly Ser Thr Arg Thr Phe Val Val Ser
            340                 345                 350
Met Val Gly Ala Asp Gly Thr Lys Val Asn Ala Val Ser Val Cys His
        355                 360                 365
Glu Asp Thr Ala Ser Met Asn Pro Lys Ala Leu Pro Phe Gln Leu Leu
    370                 375                 380
Asn Val Lys Pro Gly Asp Lys Pro Ile Cys His Phe Thr Leu Asp Asp
385                 390                 395                 400
Gln Ile Ala Leu Phe Pro Ser Gln Asn Ala Leu Leu Gln Val Ala Glu
                405                 410                 415
Asn

<210> SEQ ID NO 128
<211> LENGTH: 45
<212> TYPE: DNA
<213> ORGANISM: Artificial Sequence
<220> FEATURE:
<223> OTHER INFORMATION: SunBURP-pEAQ-fwd cloning primer

<400> SEQUENCE: 128
tgcccaaatt cgcgaccggt atggcatcta atctccttta cttgc                45

<210> SEQ ID NO 129
<211> LENGTH: 43
<212> TYPE: DNA
<213> ORGANISM: Artificial Sequence
```

```
<220> FEATURE:
<223> OTHER INFORMATION: SunBURP-pEAQ-rev cloning primer

<400> SEQUENCE: 129
ccagagttaa aggcctcgag ttaccacaca atggtttcgt acc                              43

<210> SEQ ID NO 130
<211> LENGTH: 296
<212> TYPE: PRT
<213> ORGANISM: Lycium barbarum

<400> SEQUENCE: 130
```

| | | | | | | | | | | | | | | | |
|---|---|---|---|---|---|---|---|---|---|---|---|---|---|---|---|
| Glu | Gly | Asp | Val | Lys | Lys | Leu | Pro | Gln | Pro | Trp | Gly | Val | Gly | Ser | Trp |
| 1 | | | | 5 | | | | | 10 | | | | | 15 | |
| Tyr | Gln | Ala | Ala | Asn | Glu | Gly | Asp | Val | Lys | Lys | Leu | Arg | Gln | Pro | Tyr |
| | | | 20 | | | | | 25 | | | | | 30 | | |
| Gly | Val | Gly | Ile | Trp | Tyr | Glu | Ala | Ala | Asn | Glu | Gly | Gln | Val | Lys | Lys |
| | | 35 | | | | | 40 | | | | | 45 | | | |
| Leu | Arg | Gln | Pro | Tyr | Gly | Val | Gly | Ser | Trp | Tyr | Asn | Thr | Ala | Thr | Lys |
| 50 | | | | | 55 | | | | | 60 | | | | | |
| Lys | Asp | Val | Asn | Glu | Asn | Leu | Pro | Val | Thr | Pro | Tyr | Phe | Phe | Glu | Thr |
| 65 | | | | | 70 | | | | | 75 | | | | | 80 |
| Asp | Leu | His | Gln | Gly | Lys | Lys | Met | Asn | Leu | Pro | Ser | Leu | Lys | Asn | Tyr |
| | | | | 85 | | | | | 90 | | | | | 95 | |
| Asn | Pro | Ala | Pro | Ile | Leu | Pro | Arg | Lys | Val | Ala | Asp | Ser | Ile | Pro | Phe |
| | | | 100 | | | | | 105 | | | | | 110 | | |
| Ser | Ser | Asp | Lys | Ile | Glu | Glu | Ile | Leu | Lys | His | Phe | Ser | Ile | Asp | Lys |
| | | | 115 | | | | | 120 | | | | | 125 | | |
| Asp | Ser | Glu | Gly | Ala | Lys | Met | Ile | Lys | Lys | Thr | Ile | Lys | Met | Cys | Glu |
| | 130 | | | | | 135 | | | | | 140 | | | | |
| Glu | Gln | Ala | Gly | Asn | Gly | Glu | Lys | Lys | Tyr | Cys | Ala | Thr | Ser | Leu | Glu |
| 145 | | | | | 150 | | | | | 155 | | | | | 160 |
| Ser | Met | Val | Asp | Phe | Thr | Ser | Ser | Tyr | Leu | Gly | Thr | Asn | Asn | Ile | Ile |
| | | | | 165 | | | | | 170 | | | | | 175 | |
| Ala | Leu | Ser | Thr | Leu | Val | Glu | Lys | Glu | Thr | Pro | Glu | Val | Gln | Ile | Tyr |
| | | | 180 | | | | | 185 | | | | | 190 | | |
| Thr | Ile | Glu | Glu | Val | Lys | Glu | Lys | Ala | Asn | Gly | Lys | Gly | Val | Ile | Cys |
| | | 195 | | | | | 200 | | | | | 205 | | | |
| His | Lys | Val | Ala | Tyr | Pro | Tyr | Ala | Ile | His | Tyr | Cys | His | Ser | Val | Gly |
| | 210 | | | | | 215 | | | | | 220 | | | | |
| Ser | Thr | Arg | Thr | Phe | Met | Val | Ser | Met | Val | Gly | Ser | Asp | Gly | Thr | Lys |
| 225 | | | | | 230 | | | | | 235 | | | | | 240 |
| Val | Asn | Ala | Val | Ser | Glu | Cys | His | Glu | Asp | Thr | Ala | Pro | Met | Asn | Pro |
| | | | | 245 | | | | | 250 | | | | | 255 | |
| Lys | Ala | Leu | Pro | Phe | Gln | Leu | Leu | Asn | Val | Lys | Pro | Gly | Asp | Lys | Pro |
| | | | 260 | | | | | 265 | | | | | 270 | | |
| Ile | Cys | His | Phe | Ile | Leu | Asp | Asp | Gln | Ile | Ala | Leu | Val | Pro | Ser | Gln |
| | | 275 | | | | | 280 | | | | | 285 | | | |
| Asp | Ala | Thr | Gln | Val | Ser | Glu | Asn | | | | | | | | |
| | 290 | | | | | 295 | | | | | | | | | |

```
<210> SEQ ID NO 131
<211> LENGTH: 129
<212> TYPE: PRT
<213> ORGANISM: Lycium barbarum

<400> SEQUENCE: 131
```

```
Gly Ile Lys Gln Gln Thr Arg Val Met Leu Lys Asn Tyr Ala Asn His
1               5                   10                  15

Gly Glu Trp Val Pro Gly Ile Lys Gln Gln Thr Arg Val Met Leu Lys
                20                  25                  30

Asn Tyr Thr Asn His Gly Glu Trp Val Pro Gly Ile Lys Gln Gln Thr
            35                  40                  45

Arg Val Met Leu Lys Asn Tyr Pro Asn His Gly Glu Trp Val Pro Gly
        50                  55                  60

Ile Lys Gln Gln Thr Arg Val Met Leu Lys Asn Tyr Ala Asn His Met
65                  70                  75                  80

Glu Leu Val Tyr Gly Met Lys Gln Gln Thr Arg Val Lys Leu Lys Lys
                85                  90                  95

Leu Arg Gln Pro Tyr Gly Val Gly Ser Trp Tyr Gln Ala Ala Asn Glu
                100                 105                 110

Gly Asp Val Lys Lys Ile Arg Gln Pro Trp Gly Val Gly Ser Trp Tyr
            115                 120                 125

Gln

<210> SEQ ID NO 132
<211> LENGTH: 344
<212> TYPE: PRT
<213> ORGANISM: Lycium barbarum

<400> SEQUENCE: 132

Trp Tyr Gln Ala Ala Asn Glu Gly Asp Val Lys Lys Leu Arg Gln Pro
1               5                   10                  15

Trp Gly Val Gly Ser Trp Tyr Gln Ala Ala Asn Glu Gly Asp Val Lys
                20                  25                  30

Lys Leu His Gln Pro Trp Gly Val Gly Ser Trp Tyr Gln Ala Ala Asn
            35                  40                  45

Glu Gly Asp Val Lys Lys Leu Pro Gln Pro Trp Gly Val Gly Ser Trp
        50                  55                  60

Tyr Gln Ala Ala Asn Glu Gly Asp Val Lys Lys Leu Arg Gln Pro Tyr
65                  70                  75                  80

Gly Val Gly Ile Trp Tyr Glu Ala Ala Asn Glu Gly Gln Val Lys Lys
                85                  90                  95

Leu Arg Gln Pro Tyr Gly Val Gly Ser Trp Tyr Asn Thr Ala Thr Lys
                100                 105                 110

Lys Asp Val Asn Glu Asn Leu Pro Val Thr Pro Tyr Phe Phe Glu Thr
            115                 120                 125

Asp Leu Arg Gln Gly Lys Lys Met Asn Leu Pro Ser Leu Lys Asn Tyr
        130                 135                 140

Asn Pro Ala Pro Ile Leu Pro Arg Lys Val Ala Asp Ser Ile Pro Phe
145                 150                 155                 160

Ser Ser Asp Lys Ile Glu Glu Ile Leu Lys His Phe Ser Ile Asp Lys
                165                 170                 175

Asp Ser Glu Gly Ala Lys Met Ile Lys Lys Thr Ile Lys Met Cys Glu
            180                 185                 190

Glu Gln Ala Gly Asn Gly Glu Lys Lys Tyr Cys Ala Thr Ser Leu Glu
        195                 200                 205

Ser Met Val Asp Phe Thr Ser Ser Tyr Leu Gly Thr Asn Asn Ile Ile
210                 215                 220

Ala Leu Ser Thr Leu Val Glu Lys Glu Thr Pro Glu Val Gln Ile Tyr
225                 230                 235                 240
```

-continued

```
Thr Ile Glu Glu Val Lys Glu Lys Ala Asn Gly Lys Val Ile Cys
                245                 250                 255

His Lys Val Ala Tyr Pro Tyr Ala Ile His Tyr Cys His Ser Val Gly
            260                 265                 270

Ser Thr Arg Thr Phe Met Val Ser Met Val Gly Ser Asp Gly Thr Lys
        275                 280                 285

Val Asn Ala Val Ser Glu Cys His Glu Asp Thr Ala Pro Met Asn Pro
    290                 295                 300

Lys Ala Leu Pro Phe Gln Leu Leu Asn Val Lys Pro Gly Asp Lys Pro
305                 310                 315                 320

Ile Cys His Phe Ile Leu Asp Asp Gln Ile Ala Leu Val Pro Ser Gln
                325                 330                 335

Asp Ala Thr Gln Val Ser Glu Asn
                340
```

<210> SEQ ID NO 133
<211> LENGTH: 404
<212> TYPE: PRT
<213> ORGANISM: Beta vulgaris subsp. vulgaris

<400> SEQUENCE: 133

```
Met Gly Lys Gln Leu Trp Gly Gln Leu Gln Tyr Ile Glu Thr Lys Glu
1               5                   10                  15

Lys Leu Ala Asn Phe Asp Lys Pro Tyr Thr Ala Lys Lys Asp Lys Ile
            20                  25                  30

Val Ala Ser Glu Asn Gln Pro Phe Thr Ile Ser Ala Trp His Tyr Asn
        35                  40                  45

Pro Glu Thr Gly Ala Asn Val Val Glu Pro Val Ser His Asp Val Ala
    50                  55                  60

Thr Thr Lys Lys Asp Lys Thr Val Ala Ser Glu Asn Gln Pro Phe Thr
65                  70                  75                  80

Ile Ser Ala Trp Arg Tyr Asn Ser Asp Thr Asn Ala Asn Ala Val Glu
                85                  90                  95

Pro Val Ser Asp Gly Ala Thr Thr Asp Thr Val Thr Thr Lys Lys Asp
            100                 105                 110

Lys Thr Val Ala Ser Glu Asn Gln Pro Trp Thr Val Ala Ala Trp Arg
        115                 120                 125

Tyr Asn Pro Asp Asn Ile Asn Glu Lys Tyr Ser Ile Lys Ala Ser His
    130                 135                 140

Asn His His Phe Met His Asn Ala Asn Ser Lys Asp Ser Glu Val
145                 150                 155                 160

Lys Glu Glu Asn Leu Asn Gly Gly Ser Val Phe Phe Val Glu Ser
                165                 170                 175

Leu Arg Leu Gly Met Lys Leu Lys His Asp Phe Gln Lys Thr Lys Lys
            180                 185                 190

Arg Pro Tyr Leu Pro Lys Lys Ile Ala Gln Ser Ile Pro Phe Ser Val
        195                 200                 205

Asp Lys Val Ala Glu Ile Val Asn Leu Phe Ser Ile Lys Ser Glu Ser
    210                 215                 220

Ala Glu Ala Thr Ala Ile Lys Glu Thr Leu Gly Ile Cys Leu Gln Arg
225                 230                 235                 240

Pro Lys Val Lys Lys Glu Asn Arg Thr Cys Ala Gln Ser Met Glu Asp
                245                 250                 255

Ile Val Asp Phe Val Val Lys Glu Leu Gly Thr Asn Asp Val Glu Leu
```

```
            260                 265                 270
Arg Met Met Arg Asn Asn Ile Glu Val Pro His Gly Ile Gln Asp Tyr
        275                 280                 285
Val Val Thr Lys Val Lys Lys Leu Val Val Pro Gly Asn Thr Ala Ala
        290                 295                 300
Ala Cys His Arg Met Val Tyr Pro Tyr Val Val Tyr Tyr Cys His His
305                 310                 315                 320
Gln Gln Asp Ile Gly His Tyr Asp Val Thr Leu Val Ser Pro Thr Phe
                325                 330                 335
Gly Asn Ala Ile Gln Thr Thr Ala Val Cys His Tyr Asp Thr Tyr Ala
                340                 345                 350
Trp Gln Pro Asp Val Leu Ala Leu Arg Tyr Leu Gly Ile Arg Pro Gly
        355                 360                 365
Asp Ala Pro Val Cys His Phe Ser Ala Ile Asn Asp Met Phe Trp Ser
        370                 375                 380
Ile Lys Pro Asn Ser Lys Tyr Ile Ser Arg His Gly Ser Val Lys Arg
385                 390                 395                 400
Val Ile Glu Ser
```

<210> SEQ ID NO 134
<211> LENGTH: 351
<212> TYPE: PRT
<213> ORGANISM: Solanum melongena

<400> SEQUENCE: 134

```
Met Glu Leu Tyr Phe Phe Thr Leu Phe Ser Val Ile Phe Val Val Ser
1               5                   10                  15
His Ala Ala Asn Leu Ser Pro Glu Val Tyr Trp Lys Val Thr Leu Pro
                20                  25                  30
Asn Thr Pro Met Pro Lys Pro Ile Lys Asp Ala Leu His Ile Ser Glu
            35                  40                  45
Glu Lys Leu Lys Pro Glu Asp Glu Leu Asp Lys Leu Arg Gln Trp Gly
        50                  55                  60
Val Tyr Ala Arg Tyr Asp Gly Val Pro Lys Ser Glu Leu Arg Lys Leu
65                  70                  75                  80
His Gln Pro Tyr Gly Val Tyr Thr Trp Tyr Arg Gly Ala Ala Glu Asp
                85                  90                  95
Pro Val Tyr Ala Arg Tyr His Asp Ala Ser Glu Asn Glu Leu His Lys
                100                 105                 110
Val His Gln Pro Ser Leu Lys Asp His Lys Glu Asn His Leu Val Met
            115                 120                 125
Pro Tyr Phe Phe Glu Thr His Leu His Gln Gly Lys Gln Leu Asn Leu
        130                 135                 140
Leu Ser Leu Lys Asn Asn Asn Pro Ala Pro Phe Leu Pro Arg Lys Ile
145                 150                 155                 160
Val Asp Ser Ile Pro Phe Ser Ser Asp Lys Ile Glu Glu Ile Phe Ser
                165                 170                 175
Tyr Phe Ser Val Asp Lys Asp Ser Lys Pro Ala Glu Met Ile Gly Lys
                180                 185                 190
Thr Ile Lys Leu Cys Glu Gly Pro Ala Gly Asn Gly Val Lys Tyr
            195                 200                 205
Cys Ala Thr Ser Leu Glu Ser Met Ile Glu Phe Thr Leu Ser His Val
        210                 215                 220
Gly Thr Asn Asn Ile Ile Ala Ile Ser Thr Glu Val Glu Lys Glu Thr
```

```
                225                 230                 235                 240
Pro Glu Val Gln Thr Tyr Thr Ile Glu Lys Val Glu Lys Ala Asn
                    245                 250                 255

Gly Lys Gly Val Ile Cys His Lys Val Ala Tyr Pro Tyr Ala Val His
                260                 265                 270

Tyr Cys His Asp Val Gly Ser Thr Arg Val Phe Met Val Ser Met Val
            275                 280                 285

Gly Ala Asp Gly Thr Lys Val Asn Gly Val Ser Val Cys His Glu Asp
290                 295                 300

Thr Thr Pro Met Asn Pro Glu Ala Leu Pro Phe Gln Leu Leu Asn Val
305                 310                 315                 320

Lys Pro Gly Glu Lys Pro Ile Cys His Phe Thr Leu Asp Asp Gln Ile
                325                 330                 335

Val Leu Phe Pro Ser Pro Asn Val Leu Leu Gln Val Thr Asp Asn
            340                 345                 350

<210> SEQ ID NO 135
<211> LENGTH: 409
<212> TYPE: PRT
<213> ORGANISM: Solanum melongena

<400> SEQUENCE: 135

Met Cys Asp Val Tyr Thr Ser Gln Leu Val Leu Val Ala Ser Gln Ala
1               5                   10                  15

Ala Asn Leu Ser Pro Glu Val Tyr Trp Lys Val Lys Leu Pro Asn Thr
                20                  25                  30

Pro Met Pro Lys Pro Ile Lys Asp Ala Leu His Ile Ser Glu Lys Thr
            35                  40                  45

Ala Tyr Asn Gly Asp Lys Ser Thr Lys Ile Ser Gln Pro Trp Gly Val
        50                  55                  60

Gly Ser Trp Tyr Gln Ala Ala Pro Glu Asn Asp Leu His Lys Val Arg
65                  70                  75                  80

Gln Pro Trp Gly Val Leu Gly Trp Tyr His Asp Ala Pro Glu Asn Glu
                85                  90                  95

Leu His Lys Leu Arg Gln Pro Trp Gly Val Gly Ser Trp Tyr Gln Ala
                100                 105                 110

Ala Leu Gly Asn Glu Leu His Lys Leu Arg Gln Pro Trp Gly Val Gly
            115                 120                 125

Ser Trp Tyr His Asp Ala Pro Glu Asn Glu Leu His Lys Leu Arg Gln
        130                 135                 140

Pro Trp Gly Val Gly Ser Trp Tyr Gln Ala Ala Pro Glu Asn Glu Leu
145                 150                 155                 160

Tyr Lys Val Arg Gln Pro Trp Gly Val Leu Gly Trp Ser His Val Pro
                165                 170                 175

Leu Arg Met Ser Phe Thr Asn Cys Ala Asn Arg Gly Glu Trp Ala His
            180                 185                 190

Asp Leu His Gln Gly Lys Ala Met Asn Leu Leu Ser Leu Lys Asn Tyr
        195                 200                 205

Asn Pro Ala Pro Ile Leu Pro Arg Lys Val Val Asp Ser Ile Phe Phe
    210                 215                 220

Ser Ser Asp Lys Ile Glu Glu Ile Leu Ser His Phe Ser Ala Asp Lys
225                 230                 235                 240

Asp Ser Glu Arg Ala Glu Met Ile Lys Lys Thr Ile Lys Met Cys Glu
                245                 250                 255
```

Asp Pro Ala Gly Asn Gly Glu Val Lys His Cys Ala Thr Ser Leu Glu
            260                 265                 270

Ser Met Leu Asp Phe Thr Val Ser His Leu Gly Thr Asn Asn Ile Ile
            275                 280                 285

Ala Ile Ser Thr Glu Val Glu Lys Glu Thr Pro Glu Val Gln Thr Tyr
        290                 295                 300

Thr Ile Glu Lys Val Glu Lys Ala Asn Gly Lys Gly Val Val Cys
305                 310                 315                 320

His Lys Val Ala Tyr Pro Tyr Ser Val His Phe Cys His Asp Val Gly
                    325                 330                 335

Ser Thr Arg Thr Phe Met Val Ser Met Val Gly Ala Asp Gly Thr Lys
            340                 345                 350

Val Asn Ala Val Ser Val Cys His Glu Asp Thr Ala Pro Met Asn Pro
        355                 360                 365

Lys Ala Leu Pro Phe Gln Leu Leu Asn Val Lys Pro Gly Asp Lys Pro
    370                 375                 380

Ile Cys His Phe Thr Leu Asp Asp Gln Ile Ala Leu Phe Pro Ser Pro
385                 390                 395                 400

Asn Val Pro Leu Gln Val Thr Lys Asn
            405

<210> SEQ ID NO 136
<211> LENGTH: 288
<212> TYPE: PRT
<213> ORGANISM: Solanum tuberosum

<400> SEQUENCE: 136

Val Arg Gln Pro Phe Gly Val Gly Arg Trp Tyr Asn Asp Ala Ser Glu
1               5                   10                  15

Asn Glu Leu His Lys Val Arg Gln Pro Phe Gly Val Phe Gly Trp Tyr
            20                  25                  30

Gln Ala Ala Ser Glu Asn Glu Leu His Lys Val Arg Gln Pro Tyr Gly
        35                  40                  45

Val Phe Gly Trp Tyr Asn Asp Ala Ala Lys Lys Asp Leu Asn Asp Asn
    50                  55                  60

His Pro Val Thr Pro Tyr Phe Phe Glu Thr Asp Leu His Gln Gly Lys
65                  70                  75                  80

Lys Met Asn Leu Glu Ser Leu Lys Asn Tyr Asn Pro Ala Pro Ile Leu
            85                  90                  95

Pro Arg Lys Val Val Asp Ser Ile Ala Phe Ser Ser Asp Lys Ile Glu
        100                 105                 110

Glu Ile Leu Asn His Phe Ser Val Asp Lys Asp Ser Glu Arg Ala Lys
    115                 120                 125

Asp Ile Lys Lys Thr Ile Lys Met Cys Glu Asp Pro Ala Gly Asn Gly
130                 135                 140

Glu Val Lys His Cys Ala Thr Ser Leu Glu Ser Met Ile Asp Phe Thr
145                 150                 155                 160

Leu Ser His Leu Gly Thr Asn Asn Ile Ile Ala Ile Ser Thr Glu Val
            165                 170                 175

Glu Lys Glu Thr Pro Glu Val Gln Thr Tyr Thr Ile Glu Lys Val Glu
        180                 185                 190

Glu Lys Ala Asn Gly Lys Gly Val Val Cys His Lys Val Ala Tyr Pro
    195                 200                 205

Tyr Ala Val His Phe Cys His Asp Val Gly Ser Thr Arg Thr Phe Met
210                 215                 220

```
Val Ser Met Val Gly Ala Asp Gly Thr Lys Val Asn Ala Val Ser Val
225                 230                 235                 240

Cys His Glu Asp Thr Ala Ser Met Asn Pro Lys Ala Leu Pro Phe Gln
            245                 250                 255

Leu Leu Asn Val Lys Pro Gly Asp Lys Pro Ile Cys His Phe Thr Leu
            260                 265                 270

Asp Asp Gln Ile Ala Leu Phe Pro Ser Gln Asn Ala Leu Ala Glu Asn
            275                 280                 285

<210> SEQ ID NO 137
<211> LENGTH: 296
<212> TYPE: PRT
<213> ORGANISM: Solanum tuberosum

<400> SEQUENCE: 137

Ala Pro Glu Asn Glu Leu Gln Lys Val Arg Gln Pro Trp Gly Val Gly
1               5                   10                  15

Arg Trp Tyr Asn Asp Ala Pro Glu Asn Glu Leu Gln Lys Val Arg Gln
            20                  25                  30

Pro Trp Gly Val Gly Arg Trp Tyr Asn Asp Ala Pro Glu Asn Glu Leu
            35                  40                  45

Tyr Lys Val Arg Gln Pro Trp Gly Val Gly Arg Trp Tyr Asn Asp Ala
50                  55                  60

Ala Lys Lys Asp Leu Asn Asp Asn His Pro Val Thr Pro Tyr Phe Phe
65                  70                  75                  80

Glu Thr Asp Leu His Gln Gly Lys Gln Met Asn Leu Gln Ser Leu Lys
                85                  90                  95

Asn Tyr Asn Pro Ala Pro Ile Leu Pro Arg Lys Val Val Asp Ser Ile
            100                 105                 110

Ala Phe Ser Ser Asp Lys Ile Glu Glu Ile Leu Asn His Phe Ser Val
            115                 120                 125

Asp Lys Asp Ser Glu Arg Ala Lys Asp Ile Lys Lys Thr Ile Lys Met
            130                 135                 140

Cys Glu Asp Pro Ala Gly Asn Gly Glu Val Lys His Cys Ala Thr Ser
145                 150                 155                 160

Leu Glu Ser Met Ile Asp Phe Thr Leu Ser His Leu Gly Thr Asn Asn
                165                 170                 175

Ile Ile Ala Met Ser Thr Glu Val Glu Lys Glu Thr Pro Glu Val Gln
            180                 185                 190

Thr Tyr Thr Ile Glu Lys Val Glu Lys Ala Asn Gly Lys Gly Val
            195                 200                 205

Val Cys His Lys Val Ala Tyr Pro Tyr Ala Val His Phe Cys His Asp
210                 215                 220

Val Gly Ser Thr Arg Thr Phe Met Val Ser Met Val Gly Ala Asp Gly
225                 230                 235                 240

Thr Lys Val Asn Ala Val Ser Val Cys His Glu Asp Thr Ala Ser Met
            245                 250                 255

Asn Pro Lys Ala Leu Pro Phe Gln Leu Leu Asn Val Lys Pro Gly Asp
            260                 265                 270

Lys Pro Ile Cys His Phe Thr Leu Asp Asp Gln Ile Ala Leu Phe Pro
            275                 280                 285

Ser Gln Asn Ala Leu Ala Glu Asn
            290                 295
```

<210> SEQ ID NO 138
<211> LENGTH: 261
<212> TYPE: PRT
<213> ORGANISM: Solanum tuberosum

<400> SEQUENCE: 138

Met Gly Ser Trp Tyr Gln Ala Ala Pro Glu Asn Glu Leu His Lys Val
1               5                   10                  15

His Gln Pro Phe Gly Val Val Ala Trp Tyr Asn Asp Ala Ala Lys Lys
            20                  25                  30

Asp Leu Asn Asp Asn His Pro Val Thr Pro Tyr Phe Glu Thr Asp
        35                  40                  45

Leu His Gln Gly Lys Lys Met Asn Leu Gln Ser Leu Lys Asn Tyr Asn
    50                  55                  60

Pro Ala Pro Ile Leu Pro Arg Lys Val Val Asp Ser Ile Ala Phe Ser
65                  70                  75                  80

Ser Asp Lys Ile Glu Glu Ile Leu Asn His Phe Ser Val Asp Lys Asp
                85                  90                  95

Ser Glu Arg Ala Lys Asp Ile Lys Lys Thr Ile Lys Met Cys Glu Asp
            100                 105                 110

Pro Ala Gly Asn Gly Glu Val Lys His Cys Ala Thr Ser Leu Glu Ser
        115                 120                 125

Met Ile Asp Phe Thr Leu Ser His Leu Gly Thr Asn Asn Ile Ile Ala
    130                 135                 140

Met Ser Thr Glu Val Glu Lys Glu Thr Pro Glu Val Gln Thr Tyr Thr
145                 150                 155                 160

Ile Glu Lys Val Glu Glu Lys Ala Asn Gly Lys Gly Val Cys His
                165                 170                 175

Lys Val Ala Tyr Pro Tyr Ala Val His Phe Cys His Asp Val Gly Ser
            180                 185                 190

Thr Arg Thr Phe Met Val Ser Met Val Gly Ala Asp Gly Thr Lys Val
        195                 200                 205

Asn Ala Val Ser Val Cys His Glu Asp Thr Ala Ser Met Asn Pro Lys
210                 215                 220

Ala Leu Pro Phe Gln Leu Leu Asn Val Lys Pro Gly Asp Lys Pro Ile
225                 230                 235                 240

Cys His Phe Thr Leu Asp Asp Gln Ile Ala Leu Phe Pro Ser Gln Asn
                245                 250                 255

Ala Leu Ala Glu Asn
            260

<210> SEQ ID NO 139
<211> LENGTH: 111
<212> TYPE: PRT
<213> ORGANISM: Solanum tuberosum

<400> SEQUENCE: 139

Met Glu Leu His His Gln Tyr Tyr Phe Phe Thr Phe Phe Ser Val Ile
1               5                   10                  15

Phe Val Val Ser His Ala Ala Asn Leu Ser Pro Glu Val Tyr Trp Arg
            20                  25                  30

Val Lys Leu Pro Asn Thr Pro Met Pro Thr Pro Ile Lys Asp Ala Leu
        35                  40                  45

His Ile Ser Glu Lys Thr Ala Tyr Asn Gly Asp Gly Asn Thr Lys Ile
    50                  55                  60

Ser Gln Pro Tyr Gly Val Phe Ala Trp Tyr Lys Ala Ala Thr Glu Asn

```
            65                   70                  75                  80
Glu Leu His Lys Val Arg Gln Pro Tyr Gly Val Phe Ala Trp Tyr Lys
                    85                  90                  95

Ala Ala Ser Glu Asn Val Leu His Lys Val Arg Gln Pro Tyr Gly
                100                 105                 110

<210> SEQ ID NO 140
<211> LENGTH: 429
<212> TYPE: PRT
<213> ORGANISM: Solanum tuberosum

<400> SEQUENCE: 140

Met Glu Leu His His Gln Tyr Tyr Phe Phe Thr Leu Phe Ser Val Ile
1               5                   10                  15

Phe Leu Val Ser His Ala Ala Asn Leu Ser Pro Glu Val Tyr Trp Arg
                20                  25                  30

Val Lys Leu Pro Asn Thr Pro Met Pro Thr Pro Ile Lys Asp Ala Leu
            35                  40                  45

His Ile Ser Glu Asn Glu Leu His Lys Val Arg Gln Pro Tyr Gly Val
        50                  55                  60

Leu Ala Trp Tyr Gln Ala Ala Ser Glu Asn Glu Leu His Lys Val Arg
65                  70                  75                  80

Gln Pro Tyr Gly Val Leu Ala Leu His Gln Ala Ala Ser Glu Asn Glu
                85                  90                  95

Leu His Lys Val Arg Gln Pro Tyr Gly Val Leu Ala Leu His Gln Ala
                100                 105                 110

Ala Pro Glu Asn Glu Leu His Lys Val Arg Gln Pro Tyr Gly Val Tyr
                115                 120                 125

Arg Trp Tyr Gln Ala Ala Ser Glu Asn Glu Leu His Lys Val Arg Gln
            130                 135                 140

Pro Tyr Gly Val Tyr Arg Trp Tyr Gln Ala Ala Ser Glu Asn Glu Leu
145                 150                 155                 160

His Lys Val Arg Gln Pro Tyr Gly Val Tyr Arg Trp Tyr Gln Ala Ala
                165                 170                 175

Pro Glu Asn Lys Leu His Lys Val Arg Gln Pro Tyr Gly Val Ser Arg
                180                 185                 190

Trp Tyr Asn Asp Ala Ala Thr Lys Asp Leu Asn Asp Asn His Pro Val
            195                 200                 205

Thr Pro Tyr Phe Phe Glu Thr Asp Leu His Gln Gly Lys Lys Met Asn
        210                 215                 220

Leu Gln Ser Leu Lys Asn Tyr Asn Pro Ala Pro Ile Leu Pro Arg Lys
225                 230                 235                 240

Val Val Asp Ser Ile Ala Phe Ser Ser Asp Lys Ile Glu Glu Ile Leu
                245                 250                 255

Asn His Phe Ser Val Asp Lys Asp Ser Glu Arg Ala Lys Asp Ile Lys
                260                 265                 270

Lys Thr Ile Lys Met Cys Glu Asp Pro Ala Gly Asn Gly Glu Val Lys
            275                 280                 285

His Cys Ala Thr Ser Leu Glu Ser Met Ile Asp Phe Thr Leu Ser His
        290                 295                 300

Leu Gly Thr Asn Asn Ile Ile Ala Ile Ser Thr Glu Val Glu Lys Glu
305                 310                 315                 320

Thr Pro Glu Val Gln Thr Tyr Thr Ile Glu Lys Val Glu Glu Lys Ala
                325                 330                 335
```

```
Asn Gly Lys Gly Val Val Cys His Lys Val Ala Tyr Pro Tyr Ala Val
            340                 345                 350

His Phe Cys His Asp Val Gly Ser Thr Arg Thr Phe Met Val Ser Met
        355                 360                 365

Val Gly Ala Asp Gly Thr Lys Val Asn Ala Val Ser Val Cys His Glu
    370                 375                 380

Asp Thr Ala Ser Met Asn Pro Lys Ala Leu Pro Phe Gln Leu Leu Asn
385                 390                 395                 400

Val Lys Pro Gly Asp Lys Pro Ile Cys His Phe Thr Leu Asp Asp Gln
                405                 410                 415

Ile Ala Leu Phe Pro Ser Gln Asn Ala Leu Ala Glu Asn
            420                 425

<210> SEQ ID NO 141
<211> LENGTH: 195
<212> TYPE: PRT
<213> ORGANISM: Solanum tuberosum

<400> SEQUENCE: 141

Met Glu Leu Leu His Gln Tyr Tyr Phe Phe Thr Leu Phe Ser Val Ile
1               5                   10                  15

Phe Val Val Ser His Ala Ala Asn Leu Ser Pro Glu Val Tyr Trp Arg
            20                  25                  30

Val Lys Leu Pro Asn Thr Pro Met Pro Thr Pro Ile Lys Asp Ala Leu
        35                  40                  45

His Ile Ser Glu Lys Thr Ala Tyr Asn Gly Asp Gly Asn Thr Lys Ile
    50                  55                  60

Ser Gln Pro Trp Gly Val Gly Ala Trp Tyr Gln Asp Ala Pro Glu Asn
65                  70                  75                  80

Glu Leu His Lys Val Arg Gln Pro Trp Gly Val Gly Ser Trp Tyr Gln
                85                  90                  95

Ala Ser Pro Glu Asn Lys Leu His Lys Val Arg Gln Pro Trp Gly Val
            100                 105                 110

Val Ala Trp Tyr Gln Ala Ala Ser Glu Asn Lys Leu His Lys Val Arg
        115                 120                 125

Gln Pro Trp Gly Val Gly Ser Trp Tyr Gln Ala Ala Pro Glu Asn Glu
    130                 135                 140

Leu His Lys Val Arg Gln Pro Tyr Gly Val Phe Arg Trp Tyr Gln Ala
145                 150                 155                 160

Ala Ser Glu Asn Glu Leu His Lys Val Arg Gln Pro Trp Gly Val Gly
                165                 170                 175

Ser Trp Tyr Gln Asp Ala Ser Glu Asn Glu Leu His Lys Val Arg Gln
            180                 185                 190

Pro Trp Gly
        195

<210> SEQ ID NO 142
<211> LENGTH: 208
<212> TYPE: PRT
<213> ORGANISM: Solanum tuberosum

<400> SEQUENCE: 142

Met Glu Leu His His Gln Tyr Tyr Phe Phe Thr Phe Ser Val Ile
1               5                   10                  15

Phe Val Val Ser His Ala Ala Asn Leu Ser Pro Glu Val Tyr Trp Arg
            20                  25                  30
```

```
Val Lys Leu Pro Asn Thr Pro Met Pro Thr Pro Ile Lys Asp Ala Leu
         35                  40                  45

His Ile Ser Glu Lys Thr Ala Tyr Asn Gly Asp Gly Asn Thr Lys Ile
 50                  55                  60

Ser Gln Pro Tyr Gly Val Phe Ala Trp Tyr Gln Ala Ala Ser Glu Asn
 65                  70                  75                  80

Glu Leu His Lys Val Arg Gln Pro Tyr Gly Val Asp Gly Trp Tyr Gln
                 85                  90                  95

Ala Ala Ser Glu Asn Glu Leu His Lys Val Arg Gln Pro Tyr Gly Val
                100                 105                 110

Phe Ala Trp Tyr Lys Ala Ile Thr Glu Asn Glu Leu His Lys Val Arg
            115                 120                 125

Gln Pro Tyr Gly Val Phe Ala Trp Tyr Lys Ala Ala Thr Glu Asn Glu
        130                 135                 140

Leu His Lys Val Arg Gln Pro Tyr Gly Val Phe Ala Trp Tyr Lys Ala
145                 150                 155                 160

Ala Ser Glu Asn Glu Leu His Lys Val Arg Gln Pro Tyr Gly Val Phe
                165                 170                 175

Ala Trp Tyr Asn Asp Ala Ala Lys Lys Asp Leu Asn Asp Asn His Pro
            180                 185                 190

Val Thr Pro Tyr Phe Phe Glu Thr Asp Leu His Gln Gly Lys Lys Met
        195                 200                 205
```

<210> SEQ ID NO 143
<211> LENGTH: 152
<212> TYPE: PRT
<213> ORGANISM: Solanum tuberosum

<400> SEQUENCE: 143

```
Ile Lys Asp Ala Leu His Ile Ser Glu Lys Thr Ala Tyr Asn Gly Asp
 1               5                  10                  15

Gly Asn Thr Lys Ile Ser Gln Pro Trp Gly Val Gly Ala Trp Tyr Gln
                 20                  25                  30

Asp Ala Pro Glu Asn Glu Leu His Lys Val Arg Gln Pro Trp Gly Val
             35                  40                  45

Gly Ser Trp Tyr Gln Ala Ser Pro Glu Asn Lys Leu His Lys Val Arg
 50                  55                  60

Gln Pro Trp Gly Val Gly Ala Trp Tyr Gln Ala Ala Pro Glu Asn Glu
 65                  70                  75                  80

Leu His Lys Val Arg Gln Pro Trp Gly Val Gly Ser Trp Tyr Gln Ala
                 85                  90                  95

Ala Pro Glu Asn Glu Leu His Lys Val Arg Gln Pro Tyr Gly Val Phe
                100                 105                 110

Arg Trp Tyr Gln Ala Ala Ser Glu Asn Glu Leu His Lys Val Arg Gln
            115                 120                 125

Pro Trp Gly Val Gly Ser Trp Tyr Gln Asp Ala Ser Glu Asn Glu Leu
        130                 135                 140

His Lys Val Arg Gln Pro Trp Gly
145                 150
```

<210> SEQ ID NO 144
<211> LENGTH: 195
<212> TYPE: PRT
<213> ORGANISM: Solanum tuberosum

<400> SEQUENCE: 144

```
Met Glu Leu Leu His Gln Tyr Tyr Phe Phe Thr Leu Phe Ser Val Ile
1               5                   10                  15

Phe Val Val Ser His Ala Ala Asn Leu Ser Pro Glu Val Tyr Trp Arg
            20                  25                  30

Val Lys Leu Pro Asn Thr Pro Met Pro Thr Pro Ile Lys Asp Ala Leu
        35                  40                  45

His Ile Ser Glu Lys Thr Ala Tyr Asn Gly Asp Gly Asn Thr Lys Ile
    50                  55                  60

Ser Gln Pro Trp Gly Val Gly Ala Trp Tyr Gln Asp Ala Pro Glu Asn
65                  70                  75                  80

Glu Leu His Lys Val Arg Gln Pro Trp Gly Val Gly Ser Trp Tyr Gln
                85                  90                  95

Ala Ser Pro Glu Asn Lys Leu His Lys Val Arg Gln Pro Trp Gly Val
            100                 105                 110

Val Ala Trp Tyr Gln Ala Ala Ser Glu Asn Lys Leu His Lys Val Arg
            115                 120                 125

Gln Pro Trp Gly Val Gly Ser Trp Tyr Gln Ala Ala Pro Glu Asn Glu
            130                 135                 140

Leu His Lys Val Arg Gln Pro Tyr Gly Val Phe Arg Trp Tyr Gln Ala
145                 150                 155                 160

Ala Ser Glu Asn Glu Leu His Lys Val Arg Gln Pro Trp Gly Val Gly
            165                 170                 175

Ser Trp Tyr Gln Asp Ala Ser Glu Asn Glu Leu His Lys Val Arg Gln
            180                 185                 190

Pro Trp Gly
        195

<210> SEQ ID NO 145
<211> LENGTH: 429
<212> TYPE: PRT
<213> ORGANISM: Solanum tuberosum

<400> SEQUENCE: 145

Met Glu Leu His His Gln Tyr Tyr Phe Phe Thr Leu Phe Ser Val Ile
1               5                   10                  15

Phe Leu Val Ser His Ala Ala Asn Leu Ser Pro Glu Val Tyr Trp Arg
            20                  25                  30

Val Lys Leu Pro Asn Thr Pro Met Pro Thr Pro Ile Lys Asp Ala Leu
        35                  40                  45

His Ile Ser Glu Asn Glu Leu His Lys Val Arg Gln Pro Tyr Gly Val
    50                  55                  60

Leu Ala Trp Tyr Gln Ala Ala Ser Glu Asn Glu Leu His Lys Val Arg
65                  70                  75                  80

Gln Pro Tyr Gly Val Leu Ala Leu His Gln Ala Ala Ser Glu Asn Glu
            85                  90                  95

Leu His Lys Val Arg Gln Pro Tyr Gly Val Leu Ala Leu His Gln Ala
            100                 105                 110

Ala Pro Glu Asn Glu Leu His Lys Val Arg Gln Pro Tyr Gly Val Tyr
            115                 120                 125

Arg Trp Tyr Gln Ala Ala Ser Glu Asn Glu Leu His Lys Val Arg Gln
            130                 135                 140

Pro Tyr Gly Val Tyr Arg Trp Tyr Gln Ala Ala Ser Glu Asn Glu Leu
145                 150                 155                 160

His Lys Val Arg Gln Pro Tyr Gly Val Tyr Arg Trp Tyr Gln Ala Ala
            165                 170                 175
```

```
Pro Glu Asn Lys Leu His Lys Val Arg Gln Pro Tyr Gly Val Ser Arg
                180                 185                 190

Trp Tyr Asn Asp Ala Ala Thr Lys Asp Leu Asn Asp Asn His Pro Val
            195                 200                 205

Thr Pro Tyr Phe Phe Glu Thr Asp Leu His Gln Gly Lys Lys Met Asn
        210                 215                 220

Leu Gln Ser Leu Lys Asn Tyr Asn Pro Ala Pro Ile Leu Pro Arg Lys
225                 230                 235                 240

Val Val Asp Ser Ile Ala Phe Ser Ser Asp Lys Ile Glu Glu Ile Leu
                245                 250                 255

Asn His Phe Ser Val Asp Lys Asp Ser Glu Arg Ala Lys Asp Ile Lys
            260                 265                 270

Lys Thr Ile Lys Met Cys Glu Asp Pro Ala Gly Asn Gly Glu Val Lys
        275                 280                 285

His Cys Ala Thr Ser Leu Glu Ser Met Ile Asp Phe Thr Leu Ser His
290                 295                 300

Leu Gly Thr Asn Asn Ile Ile Ala Ile Ser Thr Glu Val Glu Lys Glu
305                 310                 315                 320

Thr Pro Glu Val Gln Thr Tyr Thr Ile Glu Lys Val Glu Glu Lys Ala
                325                 330                 335

Asn Gly Lys Gly Val Val Cys His Lys Val Ala Tyr Pro Tyr Ala Val
            340                 345                 350

His Phe Cys His Asp Val Gly Ser Thr Arg Thr Phe Met Val Ser Met
        355                 360                 365

Val Gly Ala Asp Gly Thr Lys Val Asn Ala Val Ser Val Cys His Glu
370                 375                 380

Asp Thr Ala Ser Met Asn Pro Lys Ala Leu Pro Phe Gln Leu Leu Asn
385                 390                 395                 400

Val Lys Pro Gly Asp Lys Pro Ile Cys His Phe Thr Leu Asp Asp Gln
                405                 410                 415

Ile Ala Leu Phe Pro Ser Gln Asn Ala Leu Ala Glu Asn
            420                 425

<210> SEQ ID NO 146
<211> LENGTH: 8
<212> TYPE: PRT
<213> ORGANISM: Medicago truncatula

<400> SEQUENCE: 146

Gln Pro Leu Ile Thr Arg Met Trp
1               5

<210> SEQ ID NO 147
<211> LENGTH: 8
<212> TYPE: PRT
<213> ORGANISM: Selaginella willdenowii

<400> SEQUENCE: 147

Gln Pro Tyr Ser Val Phe Ala Trp
1               5

<210> SEQ ID NO 148
<211> LENGTH: 8
<212> TYPE: PRT
<213> ORGANISM: Selaginella bryopteris

<400> SEQUENCE: 148
```

Gln Pro Tyr Gly Val Gly Ser Trp
1               5

<210> SEQ ID NO 149
<211> LENGTH: 8
<212> TYPE: PRT
<213> ORGANISM: Selaginella bryopteris

<400> SEQUENCE: 149

Gln Pro Tyr Gly Val Ile Arg Trp
1               5

<210> SEQ ID NO 150
<211> LENGTH: 8
<212> TYPE: PRT
<213> ORGANISM: Selaginella moellendorffii

<400> SEQUENCE: 150

Gln Pro Tyr Gly Val Gly Ala Trp
1               5

<210> SEQ ID NO 151
<211> LENGTH: 8
<212> TYPE: PRT
<213> ORGANISM: Apios americana

<400> SEQUENCE: 151

Gln Pro Tyr Gly Val Tyr Ala Trp
1               5

<210> SEQ ID NO 152
<211> LENGTH: 8
<212> TYPE: PRT
<213> ORGANISM: Astragalus membranaceus

<400> SEQUENCE: 152

Gln Pro Phe Gly Ala Arg Thr Trp
1               5

<210> SEQ ID NO 153
<211> LENGTH: 8
<212> TYPE: PRT
<213> ORGANISM: Astragalus membranaceus

<400> SEQUENCE: 153

Gln Pro Phe Gly Ala Leu Val Trp
1               5

<210> SEQ ID NO 154
<211> LENGTH: 8
<212> TYPE: PRT
<213> ORGANISM: Astragalus membranaceus

<400> SEQUENCE: 154

Gln Pro Phe Gly Gly Phe Ala Trp
1               5

<210> SEQ ID NO 155
<211> LENGTH: 8
<212> TYPE: PRT
<213> ORGANISM: Astragalus membranaceus

<400> SEQUENCE: 155

Gln Pro Phe Gly Phe Leu Ile Trp
1               5

<210> SEQ ID NO 156
<211> LENGTH: 8
<212> TYPE: PRT
<213> ORGANISM: Bituminaria bituminosa

<400> SEQUENCE: 156

Gln Pro Tyr Gly Val Leu Tyr Trp
1               5

<210> SEQ ID NO 157
<211> LENGTH: 8
<212> TYPE: PRT
<213> ORGANISM: Lathyrus sativus

<400> SEQUENCE: 157

Gln Pro Phe Gly Ile Asn Ser Trp
1               5

<210> SEQ ID NO 158
<211> LENGTH: 8
<212> TYPE: PRT
<213> ORGANISM: Delosperma echinatum

<400> SEQUENCE: 158

Gln Pro Trp Thr Val Ser Leu Trp
1               5

<210> SEQ ID NO 159
<211> LENGTH: 8
<212> TYPE: PRT
<213> ORGANISM: Delosperma echinatum

<400> SEQUENCE: 159

Gln Pro Trp Gly Val Ser Leu Trp
1               5

<210> SEQ ID NO 160
<211> LENGTH: 8
<212> TYPE: PRT
<213> ORGANISM: Delosperma echinatum

<400> SEQUENCE: 160

Gln Pro Trp Thr Val Ser Ser Trp
1               5

<210> SEQ ID NO 161
<211> LENGTH: 8
<212> TYPE: PRT
<213> ORGANISM: Delosperma echinatum

<400> SEQUENCE: 161

Gln Pro Trp Gly Val Ser Ser Trp
1               5

<210> SEQ ID NO 162
<211> LENGTH: 8
<212> TYPE: PRT
<213> ORGANISM: Alternanthera brasiliana

<400> SEQUENCE: 162

Gln Pro Tyr Thr Val Gly Ala Trp
1               5

```
<210> SEQ ID NO 163
<211> LENGTH: 8
<212> TYPE: PRT
<213> ORGANISM: Alternanthera sessilis

<400> SEQUENCE: 163

Gln Pro Phe Thr Val Gly Ala Trp
1               5

<210> SEQ ID NO 164
<211> LENGTH: 8
<212> TYPE: PRT
<213> ORGANISM: Alternanthera sessilis

<400> SEQUENCE: 164

Gln Pro Phe Gly Val Gly Ala Trp
1               5

<210> SEQ ID NO 165
<211> LENGTH: 8
<212> TYPE: PRT
<213> ORGANISM: Bougainvillea spectabilis

<400> SEQUENCE: 165

Gln Pro Phe Thr Val Gly Ser Trp
1               5

<210> SEQ ID NO 166
<211> LENGTH: 8
<212> TYPE: PRT
<213> ORGANISM: Amaranthus tricolor

<400> SEQUENCE: 166

Gln Pro Phe Gly Val Gly Ser Trp
1               5

<210> SEQ ID NO 167
<211> LENGTH: 8
<212> TYPE: PRT
<213> ORGANISM: Atriplex prostrata

<400> SEQUENCE: 167

Gln Pro Phe Thr Phe Arg Ala Trp
1               5

<210> SEQ ID NO 168
<211> LENGTH: 8
<212> TYPE: PRT
<213> ORGANISM: Chenopodium quinoa

<400> SEQUENCE: 168

Gln Pro Phe Gly Val Val Gly Trp
1               5

<210> SEQ ID NO 169
<211> LENGTH: 8
<212> TYPE: PRT
<213> ORGANISM: Chenopodium quinoa

<400> SEQUENCE: 169

Gln Pro Tyr Gly Val Met Ala Trp
1               5

<210> SEQ ID NO 170
<211> LENGTH: 8
```

```
<212> TYPE: PRT
<213> ORGANISM: Chenopodium quinoa

<400> SEQUENCE: 170

Gln Pro Tyr Gly Val Trp Gly Trp
1               5

<210> SEQ ID NO 171
<211> LENGTH: 8
<212> TYPE: PRT
<213> ORGANISM: Chenopodium quinoa

<400> SEQUENCE: 171

Gln Pro Tyr Gly Val Met Gly Trp
1               5

<210> SEQ ID NO 172
<211> LENGTH: 8
<212> TYPE: PRT
<213> ORGANISM: Solanum virginianum

<400> SEQUENCE: 172

Gln Pro Tyr Gly Val Tyr Gly Trp
1               5

<210> SEQ ID NO 173
<211> LENGTH: 8
<212> TYPE: PRT
<213> ORGANISM: Solanum dulcamara

<400> SEQUENCE: 173

Gln Pro Tyr Gly Val Ser Ile Trp
1               5

<210> SEQ ID NO 174
<211> LENGTH: 8
<212> TYPE: PRT
<213> ORGANISM: Solanum dulcamara

<400> SEQUENCE: 174

Gln Pro Tyr Gly Val Gly Ile Trp
1               5

<210> SEQ ID NO 175
<211> LENGTH: 8
<212> TYPE: PRT
<213> ORGANISM: Atropa belladonna

<400> SEQUENCE: 175

Gln Pro Tyr Gly Val Phe Ser Trp
1               5

<210> SEQ ID NO 176
<211> LENGTH: 8
<212> TYPE: PRT
<213> ORGANISM: Atropa belladonna

<400> SEQUENCE: 176

Gln Pro Tyr Gly Val Gly Phe Trp
1               5

<210> SEQ ID NO 177
<211> LENGTH: 8
<212> TYPE: PRT
<213> ORGANISM: Atropa belladonna
```

```
<400> SEQUENCE: 177

Gln Pro Trp Glu Val Phe Ser Trp
1               5

<210> SEQ ID NO 178
<211> LENGTH: 8
<212> TYPE: PRT
<213> ORGANISM: Solanum sisymbriifolium

<400> SEQUENCE: 178

Gln Pro Tyr Asp Ala Tyr Ser Trp
1               5

<210> SEQ ID NO 179
<211> LENGTH: 8
<212> TYPE: PRT
<213> ORGANISM: Hypertelis cerviana

<400> SEQUENCE: 179

Gln Pro Phe Thr Val Leu Gly Trp
1               5

<210> SEQ ID NO 180
<211> LENGTH: 8
<212> TYPE: PRT
<213> ORGANISM: Hypertelis cerviana

<400> SEQUENCE: 180

Gln Pro Phe Gly Val Leu Gly Trp
1               5

<210> SEQ ID NO 181
<211> LENGTH: 8
<212> TYPE: PRT
<213> ORGANISM: Bougainvillea spectabilis

<400> SEQUENCE: 181

Gln Pro Tyr Thr Val Gly Gly Trp
1               5

<210> SEQ ID NO 182
<211> LENGTH: 8
<212> TYPE: PRT
<213> ORGANISM: Bougainvillea spectabilis

<400> SEQUENCE: 182

Gln Pro Tyr Gly Val Gly Gly Trp
1               5

<210> SEQ ID NO 183
<211> LENGTH: 8
<212> TYPE: PRT
<213> ORGANISM: Bougainvillea spectabilis

<400> SEQUENCE: 183

Gln Pro Cys Thr Val Gly Ala Trp
1               5

<210> SEQ ID NO 184
<211> LENGTH: 8
<212> TYPE: PRT
<213> ORGANISM: Bougainvillea spectabilis

<400> SEQUENCE: 184
```

Gln Pro Cys Gly Val Gly Ala Trp
1               5

<210> SEQ ID NO 185
<211> LENGTH: 8
<212> TYPE: PRT
<213> ORGANISM: Phytolacca bogotensis

<400> SEQUENCE: 185

Gln Pro Tyr Thr Val Phe Ala Trp
1               5

<210> SEQ ID NO 186
<211> LENGTH: 8
<212> TYPE: PRT
<213> ORGANISM: Hilleria latifolia

<400> SEQUENCE: 186

Gln Pro Tyr Ile Ala Ile Leu Trp
1               5

<210> SEQ ID NO 187
<211> LENGTH: 8
<212> TYPE: PRT
<213> ORGANISM: Beta vulgaris

<400> SEQUENCE: 187

Gln Pro Trp Gly Val Tyr Gly Trp
1               5

<210> SEQ ID NO 188
<211> LENGTH: 8
<212> TYPE: PRT
<213> ORGANISM: Beta vulgaris

<400> SEQUENCE: 188

Gln Pro Trp Gly Val Ala Gly Trp
1               5

<210> SEQ ID NO 189
<211> LENGTH: 8
<212> TYPE: PRT
<213> ORGANISM: Beta vulgaris

<400> SEQUENCE: 189

Gln Pro Phe Gly Ile Ser Ala Trp
1               5

<210> SEQ ID NO 190
<211> LENGTH: 8
<212> TYPE: PRT
<213> ORGANISM: Beta vulgaris

<400> SEQUENCE: 190

Gln Pro Trp Gly Val Ala Ala Trp
1               5

<210> SEQ ID NO 191
<211> LENGTH: 8
<212> TYPE: PRT
<213> ORGANISM: Medicago truncatula

<400> SEQUENCE: 191

Gln Pro Leu Gly Thr Arg Met Trp
1               5

<210> SEQ ID NO 192
<211> LENGTH: 8
<212> TYPE: PRT
<213> ORGANISM: Medicago truncatula

<400> SEQUENCE: 192

Gln Pro Leu Gly Thr Ser Met Trp
1               5

<210> SEQ ID NO 193
<211> LENGTH: 8
<212> TYPE: PRT
<213> ORGANISM: Medicago truncatula

<400> SEQUENCE: 193

Gln Pro Ile Gly Thr His Met Trp
1               5

<210> SEQ ID NO 194
<211> LENGTH: 8
<212> TYPE: PRT
<213> ORGANISM: Vigna unguiculata

<400> SEQUENCE: 194

Gln Pro Ala Gly Leu Leu Ala Trp
1               5

<210> SEQ ID NO 195
<211> LENGTH: 8
<212> TYPE: PRT
<213> ORGANISM: Hypertelis cerviana

<400> SEQUENCE: 195

Gln Pro Phe Gly Val Leu Gly Trp
1               5

<210> SEQ ID NO 196
<211> LENGTH: 831
<212> TYPE: DNA
<213> ORGANISM: Artificial Sequence
<220> FEATURE:
<223> OTHER INFORMATION: Sali3-2-[QPFGVFGW]

<400> SEQUENCE: 196
atggaatttc gatgctcagt catctctttt accattctct tctctcttgc tcttgcagga      60
gagagccatg tccatgcatc gctacctgag gaagattatt gggaagctgt tggccaaac     120 actcccattc ccactgcact gcgagagctt ctaaagcctc tccctgcagg tgttgaaatc     180
gatgaactcc ctaagcaaat tgatgataca cagtacccaa aaacattctt ctataaagaa    240
gaccttcatc caggcaaaac aatgaaagta caattcacca gcgtccccta tgcacaaccg    300
tttggagtat ttggttggtt aacgatatt aaagacacct ctaaagaagg atatagtttt     360
gaagagatat gcatcaagaa agaagcgttt gagggagaag agaagttttg tgcaaaatcc    420
ttgggaacag taattggttt tgccatttca agctgggaa agaacattca agtactttca     480
agttcctttg tcaataagca agagcaatac actgtggaag gagtgcagaa tcttggagac    540
aaagcagtga tgtgtcatgg gctaaatttc agaactgcag tattttactg ccataaagtc    600
cgtgaaacaa cagcttttcat ggttccattg gtggctggtg atggaaccaa aactcaggca    660
cttgctgttt gccactcaga tacttctgga atgaatcatc acatgcttca tgaactcatg   720

```
ggagttgatc ctggaactaa ccctgtttgc catttccttg gaagcaaggc cattttatgg      780
gtacccaatt tatctatgga cactgcctat cagactaacg ttgttgttta a              831
```

<210> SEQ ID NO 197
<211> LENGTH: 831
<212> TYPE: DNA
<213> ORGANISM: Artificial Sequence
<220> FEATURE:
<223> OTHER INFORMATION: Sali3-2-[QPYGVFAW]

<400> SEQUENCE: 197

```
atggaatttc gatgctcagt catctctttt accattctct tctctcttgc tcttgcagga       60
gagagccatg tccatgcatc gctacctgag gaagattatt gggaagctgt tggccaaac      120 actcccattc ccactgcact gcgagagctt ctaaagcctc tccctgcagg tgttgaaatc      180
gatgaactcc ctaagcaaat tgatgataca cagtacccaa aacattctt ctataagaa       240 gaccttcatc caggcaaaac aatgaaagta caattcacca gcgtccccta tgcacaacct      300
tatggtgtat cgcctggtt aacggatatt aaagacacct ctaaagaagg atatagtttt      360
gaagagatat gcatcaagaa agaagcgttt gagggagaag agaagttttg tgcaaaatcc      420
ttgggaacag taattggttt tgccatttca agctgggaa agaacattca agtactttca      480
agttcctttg tcaataagca agagcaatac actgtggaag gagtgcagaa tcttggagac      540
aaagcagtga tgtgtcatgg gctaaatttc agaactgcag tatttactg ccataaagtc      600 cgtgaaacaa cagctttcat ggttccattg gtggctggtg atggaaccaa aactcaggca      660
cttgctgttt gccactcaga tacttctgga atgaatcatc acatgcttca tgaactcatg      720
ggagttgatc ctggaactaa ccctgtttgc catttccttg gaagcaaggc cattttatgg      780
gtacccaatt tatctatgga cactgcctat cagactaacg ttgttgttta a              831
```

<210> SEQ ID NO 198
<211> LENGTH: 8
<212> TYPE: PRT
<213> ORGANISM: Artificial Sequence
<220> FEATURE:
<223> OTHER INFORMATION: QAYGVYTW

<400> SEQUENCE: 198

Gln Ala Tyr Gly Val Tyr Thr Trp
1               5

<210> SEQ ID NO 199
<211> LENGTH: 454
<212> TYPE: PRT
<213> ORGANISM: Selaginella willdenowii

<400> SEQUENCE: 199

Met Ala Ala His Leu Leu Tyr Leu Leu Phe Leu Val Ala Gly Ser Ala
1               5                  10                  15

Ala Gly Ala Leu Gly Tyr Gln Phe Asp Ile Pro Asp Thr Leu Thr Asn
            20                  25                  30

Ala Lys Ser Pro Leu Asp Glu Ser Thr Ala Lys Ser Leu Lys Gly Leu
        35                  40                  45

Leu Glu Arg Gly Leu Val Leu Asn Thr Pro Asp Val Cys His Ser Leu
    50                  55                  60

Gly Phe Phe Cys Glu His Glu Ile Ser Ser Ser Glu Pro Glu Val
65                  70                  75                  80

```
Pro Lys Gln Ser Leu Gly Thr Arg Lys Leu Asp Ala Ala Leu Glu
            85                  90                  95

Ser His Leu Gly His Pro Glu Ser Ala Asn Gln Pro Ser Pro Ser Lys
        100                 105                 110

Trp Met Asn Lys Gln Pro Tyr Ser Val Phe Ala Trp Thr Asn Glu Asn
        115                 120                 125

Gln Pro Ser Lys Trp Phe Asn Lys Gln Pro Tyr Ser Val Phe Ala Trp
130                 135                 140

Thr Asn Glu Asp Gln Ala Pro Ser Lys Trp Phe Asn Lys Gln Pro Tyr
145                 150                 155                 160

Ser Val Phe Ala Trp Thr Asn Lys Asp Gln Ser Pro Ser Lys Trp Phe
                165                 170                 175

Asn Lys Gln Pro Tyr Ser Val Phe Ala Trp Thr Asn Glu Asp Gln Ala
            180                 185                 190

Pro Ser Lys Trp Phe Asn Lys Gln Pro Tyr Ser Val Phe Ala Trp Thr
        195                 200                 205

Asn Glu Asp Gln Ser Pro Lys Trp Phe Asn Lys Gln Arg Phe Ala Arg
210                 215                 220

Ala Asn Gly Glu His Pro Lys Gln Lys Ser Glu Ser Leu Pro Thr Lys
225                 230                 235                 240

Gly Arg Ala Phe Arg Phe Ala Ser Ala Gln Ala Gly Lys Ser Ile Leu
                245                 250                 255

Leu Pro Pro Ile Thr Ser Leu Leu Ser Asn Lys Leu Ile His Pro His
            260                 265                 270

Leu Glu Asp Val Leu Thr Phe Asn Lys Glu Ser Leu Ser Gln Val Leu
        275                 280                 285

Arg Ala Phe Asn Ile Pro Ala Asn Ser Gly Met Gly Gln Ser Met Glu
290                 295                 300

Phe Ala Leu Asp Met Gly Lys Pro Thr Asn Asn Gly Val Glu Leu Arg
305                 310                 315                 320

Lys Ala Val Thr Thr Thr Lys Glu Met Val Asp Phe Val Gly Gly Val
                325                 330                 335

Leu Cys Lys Glu Lys Glu Asp Cys His Val Lys Ser Ile Ser Gln Ser
            340                 345                 350

Phe Glu Asn Lys Glu Ser Lys Met Val Lys Val Asp Leu Glu Leu
        355                 360                 365

Val Ser Lys Asp Pro Val Ala Cys His Thr Val Pro Phe Pro Tyr Lys
370                 375                 380

Val Tyr Val Cys His Lys Ile Lys Asp Ser Pro Val Tyr Lys Val Asn
385                 390                 395                 400

Met Met Leu Glu Gly Gly Lys Thr Leu Ser Thr Pro Phe Ile Cys His
                405                 410                 415

Trp Asp Thr Ser Lys Phe Arg Thr Asn His Gln Ser Phe Glu Asp Leu
            420                 425                 430

Asn Met Lys Pro Gly Glu Gly Glu Ile Cys His Trp Leu Gly Tyr Glu
        435                 440                 445

Thr Ile Val Trp Tyr Val
    450

<210> SEQ ID NO 200
<211> LENGTH: 287
<212> TYPE: PRT
<213> ORGANISM: Selaginella bryopteris

<400> SEQUENCE: 200
```

```
Pro Tyr Gly Val Gly Ser Trp Val Ser Lys Gln Pro Tyr Gly Val
  1               5                  10                  15

Ser Trp Val Ser Lys Gln Pro Tyr Gly Val Gly Ser Trp Val Asn Lys
             20                  25                  30

Gln Pro Tyr Gly Val Gly Ser Trp Val His Lys Gln Pro Tyr Gly Val
             35                  40                  45

Gly Ser Trp Val Asp Lys Gln Pro Tyr Gly Val Ile Arg Trp Val Ser
     50                  55                  60

Lys Lys Ser Glu Glu Glu Gly Leu Pro Lys Gly Arg Ala Phe Arg Phe
 65              70                  75                  80

Ala Ser Leu Gln Ser Gly Lys Ser Ile Leu Leu Pro Ser Ile Ile Pro
                 85                  90                  95

Leu Val Ser Asn Lys Phe Ile His Gln Leu Leu Arg Asp Val Met Pro
                100                 105                 110

Phe Thr Ala Glu Ser Leu Pro Gln Val Leu Thr Thr Leu Asn Leu Pro
            115                 120                 125

Val Asp Ser Glu Met Ala Trp Ser Met His Leu Ala Leu Glu Met Gly
            130                 135                 140

Glu Asp Cys Asn Asn Glu Val Glu Val Lys Lys Ser Ile Leu Ser Thr
145                 150                 155                 160

Glu Glu Met Val Asp Phe Val Gly Gly Leu Val Cys Lys Gly Ser Ser
                165                 170                 175

Glu Cys His Leu Lys Ser Ile Ser Gln Ser Phe Asp Asn Lys Asp Pro
            180                 185                 190

Lys Met Val Glu Ile Val Asp Val Gln Gln Leu Ser Lys His Pro Val
            195                 200                 205

Ala Cys His Thr Val Pro Phe Ala Tyr Lys Val Tyr Val Cys His Thr
            210                 215                 220

Ile Lys Asp Ser Pro Ile Tyr Lys Val Thr Met Leu Glu Asp Gly Lys
225                 230                 235                 240

Glu Thr Thr Val Pro Val Met Cys His Trp Asp Thr Ser Asn Phe Arg
                245                 250                 255

Pro Asp His Gln Ala Phe Lys Asp Leu Asn Met Lys Pro Gly Asp Gly
            260                 265                 270

Glu Ile Cys His Trp Met Ala Tyr Glu Thr Ile Val Trp Tyr Ala
            275                 280                 285

<210> SEQ ID NO 201
<211> LENGTH: 262
<212> TYPE: PRT
<213> ORGANISM: Selaginella moellendorffii

<400> SEQUENCE: 201

Val Lys Glu Pro Phe Gly Val Gly Thr Trp Val Lys Glu Pro Phe Gly
  1               5                  10                  15

Val Gly Thr Trp Val Lys Glu Gln Pro Tyr Gly Val Gly Ala Trp Val
             20                  25                  30

Lys Glu Gln Pro Ala Pro Gln Gln Glu Glu Lys Asn Met Leu Gly Arg
             35                  40                  45

Ala Phe Arg Phe Ala Ser Ala Gln Ala Gly Glu Ile Leu Leu Pro Pro
     50                  55                  60

Ile Thr Ala Leu Leu Ser Asn Lys Leu Met His Pro His Leu Glu Asp
 65              70                  75                  80

Ala Leu Pro Phe Ser Met Lys Ser Leu Pro Gln Val Leu Arg Ala Phe
```

```
                85                  90                  95
Asn Leu Ser Ser Asp Ser Glu Met Ala Gln Ser Met Met Gln Ser Leu
            100                 105                 110

His Met Gly Arg Pro Thr Lys Asn Asp Val Glu Ile Arg Lys Ser Val
            115                 120                 125

Val Thr Ala Glu Gln Met Val Glu Leu Ala Gly Glu Leu Leu Cys Glu
130                 135                 140

Gly Lys Gly Glu Asp Cys His Leu Lys Ser Val Ala Gln Ser Phe Glu
145                 150                 155                 160

Asn Lys Glu Pro Thr Ala Lys Met Val Lys Val Ala Asn Ile Glu Leu
                165                 170                 175

Val Ser Lys Asp Pro Leu Ala Cys His Thr Val Pro Phe Pro Tyr Lys
            180                 185                 190

Val Tyr Val Cys His Lys Ile Lys Asp Ser Pro Val Tyr Lys Val Thr
            195                 200                 205

Met Thr Leu Glu Ser Gly Glu Thr Val Thr Pro Val Val Cys His
210                 215                 220

Trp Asp Thr Thr Lys Phe Arg Pro Asn His Pro Ala Phe Glu Glu Leu
225                 230                 235                 240

Asn Met Lys Pro Gly Glu Gly Glu Ile Cys His Trp Leu Ala Tyr Glu
                245                 250                 255

Thr Val Val Trp Tyr Ala
            260

<210> SEQ ID NO 202
<211> LENGTH: 286
<212> TYPE: PRT
<213> ORGANISM: Selaginella uncinata

<400> SEQUENCE: 202

Thr Leu Phe Leu Ser Pro Ser Thr Ser Asn Trp Val Asn Lys Gln
1               5                   10                  15

Pro Tyr Ser Val Phe Ala Trp Thr Asn Glu Asp Gln Pro Ser Lys Trp
            20                  25                  30

Phe Asn Lys Gln Pro Tyr Ser Val Phe Ala Trp Thr Asn Glu Asp Gln
        35                  40                  45

Pro Ser Lys Trp Phe Asn Lys Gln Pro Phe Gly Glu His Pro Lys Gln
    50                  55                  60

Lys Leu Glu Ser Leu Pro Thr Lys Gly Arg Ala Phe Arg Phe Ala Ser
65                  70                  75                  80

Ala Gln Ala Gly Lys Ser Ile Leu Leu Pro Ile Thr Pro Leu Leu
                85                  90                  95

Ser Asn Lys Leu Ile His Pro His Leu Glu Asp Val Leu Pro Phe Asn
            100                 105                 110

Lys Glu Ser Leu Ser Gln Val Leu Arg Ser Phe Asn Leu Ser Ala Asn
            115                 120                 125

Ser Gly Met Gly Gln Ser Met Glu Phe Ala Leu Asp Met Gly Lys Ser
130                 135                 140

Thr Asn Asn Gly Val Glu Phe Arg Lys Ser Val Ala Thr Thr Lys Glu
145                 150                 155                 160

Met Val Asp Phe Val Gly Gly Val Leu Cys Lys Glu Lys Gly Asp Cys
                165                 170                 175

His Val Lys Ser Ile Ala Gln Ser Phe Glu Asn Lys Glu Ser Lys Met
            180                 185                 190
```

```
Val Lys Val Val Asp Val Glu Leu Val Ser Lys Asp Pro Val Ala Cys
            195                 200                 205

His Thr Val Pro Phe Pro Tyr Lys Val Tyr Val Cys His Lys Ile Lys
210                 215                 220

Asp Ser Pro Val Tyr Lys Val Asn Met Met Val Glu Gly Gly Lys Thr
225                 230                 235                 240

Leu Ser Thr Pro Phe Ile Cys His Trp Asp Thr Ser Lys Phe Arg Thr
                245                 250                 255

Asn His Gln Ala Phe Glu Asp Leu Asn Ile Lys Pro Gly Gln Gly Glu
                260                 265                 270

Ile Cys His Trp Leu Gly Tyr Glu Thr Ile Val Trp Tyr Val
            275                 280                 285

<210> SEQ ID NO 203
<211> LENGTH: 349
<212> TYPE: PRT
<213> ORGANISM: Atropa belladonna

<400> SEQUENCE: 203

Met Glu Leu His His His Cys Phe Phe Ile Leu Leu Ser Leu Ala Phe
1               5                   10                  15

Val Ser Ser His Ala Ala Asn Leu Ser Pro Glu Val Tyr Trp Lys Val
                20                  25                  30

Lys Leu Pro Asn Thr Pro Met Pro Arg Pro Ile Lys Asp Ala Leu His
            35                  40                  45

Tyr Ser Glu Ala Ser Glu Gly Asp Ile His Lys Leu Ser Gln Pro Tyr
        50                  55                  60

Gly Val Phe Ser Trp Tyr Arg Ala Ala Thr Glu Gly Asp Val Gln Lys
65                  70                  75                  80

Leu Cys Gln Pro Tyr Gly Val Gly Phe Trp Tyr Gln Ala Ala Thr Glu
                85                  90                  95

Gly Asp Val Gln Lys Leu Arg Gln Pro Tyr Gly Val Gly Ser Trp Tyr
            100                 105                 110

Asn Ser Ala Pro Asn Lys Asp Leu Asn Glu Asn Ser Pro Val Thr Pro
        115                 120                 125

Tyr Phe Phe Glu Thr Asp Leu His Lys Gly Lys Lys Met Asn Leu Pro
    130                 135                 140

Ser Leu Lys Asn Tyr Asn Pro Ala Pro Ile Leu Pro Arg Lys Val Ala
145                 150                 155                 160

Asp Ser Ile Pro Phe Ser Ser Asp Lys Ile Glu Glu Ile Leu Asp His
                165                 170                 175

Phe Ser Ile Asp Lys Asp Ser Glu Gly Ala Lys Met Phe Lys Lys Thr
            180                 185                 190

Ile Lys Met Cys Glu Glu Pro Ala Gly Asn Gly Glu Lys Tyr Cys
        195                 200                 205

Ala Thr Ser Leu Glu Ser Met Ile Asp Phe Thr Ser Ser Tyr Leu Gly
    210                 215                 220

Thr Asn Asn Ile Leu Ala Ile Ser Thr Glu Val Glu Lys Glu Thr Pro
225                 230                 235                 240

Glu Val Gln Thr Tyr Ile Ile Glu Glu Val Lys Glu Lys Ala Asn Gly
                245                 250                 255

Lys Gly Val Ile Cys His Lys Val Ala Tyr Pro Tyr Ala Val His Tyr
            260                 265                 270

Cys His Ser Val Gly Arg Thr Arg Thr Phe Met Val Ser Met Val Gly
        275                 280                 285
```

Ala Asp Gly Thr Lys Val Asn Ala Val Ser Glu Cys His Glu Asp Thr
            290                 295                 300

Ala Pro Met Asn Pro Lys Ala Leu Pro Phe Gln Leu Leu Asn Val Lys
305                 310                 315                 320

Pro Gly Asp Lys Pro Ile Cys His Phe Ile Leu Asp Asp Gln Ile Ala
                325                 330                 335

Leu Val Pro Ser His Gly Ala Thr Gln Val Ala Gln Asn
            340                 345

<210> SEQ ID NO 204
<211> LENGTH: 332
<212> TYPE: PRT
<213> ORGANISM: Atropa belladonna

<400> SEQUENCE: 204

Met Glu Leu His His Gln Tyr Tyr Phe Phe Ala Leu Leu Ser Leu Val
1               5                   10                  15

Phe Val Val Ser His Ala Ala Asn Leu Ser Pro Glu Val Tyr Trp Lys
            20                  25                  30

Val Lys Leu Pro Asn Thr Pro Met Pro Thr Pro Ile Lys Asp Ala Leu
        35                  40                  45

His Ile Ser Glu Lys Pro Ala Ala His Asn Gly Asp Gly Asn Ile Lys
    50                  55                  60

Met Ser Gln Pro Trp Glu Val Phe Ser Trp Tyr His Ala Ala Thr Glu
65                  70                  75                  80

Asn Glu Leu Ser Thr Phe His Gln Pro Trp Gly Val Phe Ser Arg Tyr
                85                  90                  95

Asn Gly Val Gly Lys Lys Asp Leu Asn Glu Asn His Arg Val Thr Gln
            100                 105                 110

Tyr Phe Phe Glu Thr Asp Leu His Lys Gly Lys Lys Met Asn Leu Pro
        115                 120                 125

Ser Leu Lys Asn Tyr Asn Pro Ala Pro Ile Leu Ser Arg Lys Val Ile
    130                 135                 140

Asp Ser Ile Pro Phe Ser Ser Asp Lys Ile Glu Glu Ile Leu Asp His
145                 150                 155                 160

Phe Ser Ile Asp Lys Asp Ser Glu Ser Ala Gln Thr Ile Met Lys Thr
                165                 170                 175

Ile Lys Met Cys Glu Glu Pro Ala Gly Asn Gly Glu Val Lys Tyr Cys
            180                 185                 190

Ala Thr Ser Leu Glu Ser Met Val Asp Phe Thr Ser Ser Gln Leu Gly
        195                 200                 205

Thr Asn Ser Ile Leu Ala Ile Phe Thr Glu Val Glu Lys Glu Thr Pro
    210                 215                 220

Glu Val Gln Thr Tyr Ile Ile Gln Gln Val Lys Glu Lys Thr Asn Gly
225                 230                 235                 240

Asn Gly Ile Val Cys His Lys Met Ala Tyr Pro Tyr Gly Val His Phe
                245                 250                 255

Cys His Asn Val Gly Ser Thr Arg Thr Phe Met Val Ser Met Val Gly
            260                 265                 270

Ala Asp Gly Thr Ile Val Asn Ala Val Ser Ile Cys His Glu Asp Thr
        275                 280                 285

Ala Tyr Met Asn Pro Lys Ser Leu Pro Phe Gln Leu Leu His Val Lys
    290                 295                 300

Pro Gly Asp Lys Pro Ile Cys His Phe Ile Leu Asp Asp Glu Ile Ala

```
                305                 310                 315                 320
Met Phe Pro Ser Gln Asn Lys Thr Leu Leu Ser Asp
                325                 330

<210> SEQ ID NO 205
<211> LENGTH: 108
<212> TYPE: PRT
<213> ORGANISM: Solanum ptychanthum

<400> SEQUENCE: 205

Met Glu Leu His His Gln Tyr Tyr Phe Phe Thr Leu Phe Ser Leu Val
1               5                   10                  15

Phe Val Ala Ser His Ala Ala Asn Leu Ser Pro Glu Val Tyr Trp Arg
            20                  25                  30

Val Lys Phe Pro Asn Thr Pro Met Pro Thr Pro Ile Lys Asp Ala Leu
        35                  40                  45

His Ile Ser Glu Lys Thr Ala Asn Asn Gly Asp Gly Asn Thr Lys Ile
    50                  55                  60

Arg Gln Pro Tyr Gly Val Phe Ala Trp Tyr His Asp Ala Pro Lys Asn
65                  70                  75                  80

Glu Leu His Lys Leu His Gln Pro Tyr Gly Val Phe Ala Trp Tyr His
                85                  90                  95

Asp Ala Pro Glu Asn Glu Leu His Lys Leu Arg Gln
                100                 105

<210> SEQ ID NO 206
<211> LENGTH: 396
<212> TYPE: PRT
<213> ORGANISM: Solanum dulcamara

<400> SEQUENCE: 206

Met Glu Leu Tyr His Gln Tyr Tyr Phe Phe Thr Leu Phe Ser Ile Val
1               5                   10                  15

Phe Val Val Ser His Ala Ala Asn Leu Ser Pro Glu Val Tyr Trp Lys
            20                  25                  30

Val Lys Leu Pro Asn Thr Pro Met Pro Thr Pro Ile Lys Asp Cys Leu
        35                  40                  45

Tyr Ile Ser Glu Lys Thr Thr Ser Asn Gly Asp Gly Ser Thr Lys Val
    50                  55                  60

Arg Gln Pro Tyr Gly Val Ser Ile Trp Tyr Lys Ala Ala Ser Glu Asn
65                  70                  75                  80

Glu Leu His Lys Val Arg Gln Pro Trp Gly Val Gly Ser Trp Tyr Lys
                85                  90                  95

Ala Ala Ser Glu Asn Glu Leu His Lys Val Arg Gln Pro Tyr Gly Val
                100                 105                 110

Phe Ser Trp Tyr Lys Ala Ala Ser Glu Asn Glu Leu His Lys Val Arg
            115                 120                 125

Gln Pro Tyr Gly Val Gly Ile Trp Tyr Lys Ala Ala Ser Glu Asn Glu
        130                 135                 140

Leu His Lys Val Arg Gln Pro Tyr Gly Val Phe Ser Trp Tyr Asn Gly
145                 150                 155                 160

Ala Asn Lys Lys Asp Leu Asn Glu Asn His Gln Val Thr Pro Tyr Phe
                165                 170                 175

Phe Glu Thr Asp Leu His Gln Gly Lys Lys Met Asn Leu Gln Ser Leu
                180                 185                 190

Lys Asn Tyr Asn Pro Ala Pro Ile Leu Pro Arg Lys Val Val Asp Ser
```

-continued

```
                195                 200                 205
Ile Pro Phe Ser Ser Asp Lys Ile Glu Glu Ile Leu Asn Asn Phe Ser
210                 215                 220

Val Asp Lys Asp Ser Glu Arg Ala Lys Val Ile Lys Lys Thr Ile Lys
225                 230                 235                 240

Met Cys Glu Glu Pro Ala Gly Asn Gly Glu Val Lys His Cys Ala Thr
                245                 250                 255

Ser Leu Glu Ser Met Val Glu Phe Thr Leu Ser His Leu Gly Thr Asn
                260                 265                 270

Asn Ile Ile Ala Ile Ser Thr Glu Val Glu Lys Glu Thr Pro Glu Val
                275                 280                 285

Gln Thr Tyr Thr Ile Glu Lys Val Glu Glu Lys Ala Asn Gly Lys Gly
                290                 295                 300

Val Val Cys His Lys Val Ala Tyr Pro Tyr Ala Val His Phe Cys His
305                 310                 315                 320

Asp Val Gly Ser Thr Arg Thr Phe Met Val Ser Met Val Gly Ala Asp
                325                 330                 335

Gly Thr Lys Val Asn Ala Val Ser Val Cys His Glu Asp Thr Ala Ser
                340                 345                 350

Met Asn Pro Lys Ala Leu Pro Phe Gln Leu Leu Asn Val Lys Pro Gly
                355                 360                 365

Asp Lys Pro Ile Cys His Phe Ile Leu Asp Asp Gln Ile Ala Leu Phe
370                 375                 380

Pro Ser Gln Asn Ala Val Leu Gln Val Ala Glu Asn
385                 390                 395

<210> SEQ ID NO 207
<211> LENGTH: 225
<212> TYPE: PRT
<213> ORGANISM: Solanum sisymbriifolium

<400> SEQUENCE: 207

Met Glu Leu His His Gln Tyr Tyr Phe Leu Thr Leu Phe Ser Val Val
1               5                   10                  15

Phe Val Val Ser His Ala Ala Asn Leu Ser Pro Glu Val Tyr Trp Lys
                20                  25                  30

Val Thr Met Pro Asn Thr Pro Met Pro Lys Pro Ile Lys Asp Ala Leu
                35                  40                  45

His Ile Ser Glu Lys Thr Ala Tyr Asn Gly Asp Gly Asn Thr Lys Ile
                50                  55                  60

Ser Gln Pro Tyr Asp Ala Tyr Ser Trp Tyr His Ala Ser Leu Glu Ser
65                  70                  75                  80

Glu Leu His Lys Ile Arg Val Pro Phe Gly Val Gly Ser Trp Tyr Asn
                85                  90                  95

Gly Ala Ala Thr Lys Asp Leu Asn Glu Asn His Leu Val Thr Pro Tyr
                100                 105                 110

Phe Phe Glu Thr Asp Leu His Lys Gly Lys Gln Met Asn Leu Pro Ser
                115                 120                 125

Leu Lys Asn Tyr Asn Pro Ala Pro Ile Leu Pro Arg Lys Val Val Asp
                130                 135                 140

Ser Ile Pro Phe Ser Ser Asn Lys Ile Glu Glu Ile Leu Ser His Phe
145                 150                 155                 160

Ser Val Asp Lys Asp Ser Glu Arg Ala Glu Ala Ile Lys Lys Thr Ile
                165                 170                 175
```

Lys Met Cys Glu Asp Pro Ala Gly Lys Gly Glu Val Lys His Cys Ala
            180                 185                 190

Thr Ser Leu Glu Ser Met Val Asp Phe Thr Leu Ser His Leu Gly Thr
        195                 200                 205

Asn Asn Ile Ile Ala Met Ser Thr Glu Val Glu Lys Glu Thr Pro Glu
    210                 215                 220

Val
225

<210> SEQ ID NO 208
<211> LENGTH: 148
<212> TYPE: PRT
<213> ORGANISM: Solanum virginianum

<400> SEQUENCE: 208

Met Glu Leu Tyr His Gln Tyr Tyr Phe Phe Thr Leu Phe Ser Val Ile
1               5                   10                  15

Phe Val Val Ser Asp Ala Ala Asn Leu Ser Pro Glu Val Tyr Trp Lys
            20                  25                  30

Val Lys Leu Pro Asn Thr Pro Met Pro Thr Pro Ile Lys Asp Ala Leu
        35                  40                  45

His Ile Ser Glu Lys Asn Leu Lys Pro Lys Asp Glu Leu His Glu Leu
    50                  55                  60

Arg Gln Trp Gly Val Tyr Ala Leu His His Tyr Ala Pro Lys Ala Glu
65                  70                  75                  80

Leu Arg Lys Leu Pro Gln Pro Tyr Gly Val Tyr Ser Trp Phe His Gly
                85                  90                  95

Ala Pro Glu Asp Pro Val Tyr Ala Arg Tyr Leu Glu Ala Glu Asn Glu
            100                 105                 110

Leu His Lys Val His Gln Pro Ser Gln Tyr Asp Gly Ala Ala Lys Lys
        115                 120                 125

Asp Val Asn Glu Asn His Leu Val Thr Pro Tyr Phe Phe Glu Thr Asn
    130                 135                 140

Leu His Gln Gly
145

<210> SEQ ID NO 209
<211> LENGTH: 116
<212> TYPE: PRT
<213> ORGANISM: Solanum virginianum
<220> FEATURE:
<221> NAME/KEY: VARIANT
<222> LOCATION: 116
<223> OTHER INFORMATION: Any amino acid

<400> SEQUENCE: 209

Ser Pro Glu Val Tyr Trp Lys Val Lys Leu Pro Asn Thr Leu Met Pro
1               5                   10                  15

Lys Pro Ile Lys Asp Ala Leu His Ile Ser Glu Lys Thr Ala Tyr Asn
            20                  25                  30

Gly Asp Lys Asn Thr Lys Ile Ser Gln Pro Tyr Gly Val Tyr Gly Trp
        35                  40                  45

Tyr His Asp Ala Pro Glu Asp Lys Leu His Lys Leu Arg Gln Pro Tyr
    50                  55                  60

Gly Val Tyr Val Trp Tyr Gln Asp Ala Pro Asp Glu Leu His Asn
65                  70                  75                  80

Leu Arg Gln Pro Trp Gly Val Gly Ser Gln Tyr Ser Gly Ala Ala Lys
                85                  90                  95

Lys Asp Leu Asn Glu Asn His Gln Val Thr Pro Tyr Phe Phe Glu Thr
                100                 105                 110

Asn Leu His Xaa
        115

<210> SEQ ID NO 210
<211> LENGTH: 269
<212> TYPE: PRT
<213> ORGANISM: Lycium barbarum

<400> SEQUENCE: 210

Leu Arg Gln Pro Tyr Gly Val Gly Ser Trp Tyr Gln Ala Ala Thr Glu
1               5                   10                  15

Gly Glu Val Lys Lys Leu Arg Gln Pro Tyr Gly Val Gly Ser Trp Tyr
            20                  25                  30

Asn Thr Ala Thr Lys Lys Asp Val Asn Glu Asn Leu Pro Val Thr Pro
        35                  40                  45

Tyr Phe Phe Glu Thr Asp Leu His Gln Gly Lys Lys Met Asn Leu Pro
    50                  55                  60

Ser Leu Lys Asn Tyr Asn Pro Ala Pro Ile Leu Pro Arg Lys Val Ala
65                  70                  75                  80

Asp Ser Thr Pro Phe Ser Ser Asp Lys Ile Glu Glu Ile Leu Asn His
                85                  90                  95

Phe Ser Ile Asp Lys Asp Ser Glu Gly Ala Lys Met Ile Lys Lys Thr
                100                 105                 110

Ile Lys Met Cys Glu Glu Pro Ala Gly Asn Gly Glu Lys Lys Tyr Cys
            115                 120                 125

Ala Thr Ser Leu Glu Ser Met Val Asp Phe Thr Ser Ser Tyr Leu Gly
        130                 135                 140

Thr Asn Asn Ile Ile Ala Leu Ser Thr Leu Val Glu Lys Glu Thr Pro
145                 150                 155                 160

Glu Val Gln Ile Tyr Thr Ile Glu Glu Val Lys Glu Lys Ala Asn Gly
                165                 170                 175

Lys Gly Val Ile Cys His Lys Val Ala Tyr Pro Tyr Ala Ile His Tyr
            180                 185                 190

Cys His Ser Val Gly Ser Thr Arg Thr Phe Met Val Ser Met Val Gly
        195                 200                 205

Ser Asp Gly Thr Lys Val Asn Ala Val Ser Glu Cys His Glu Asp Thr
    210                 215                 220

Ala Pro Met Asn Pro Lys Ala Leu Pro Phe Gln Leu Leu Asn Val Lys
225                 230                 235                 240

Pro Gly Asp Lys Pro Ile Cys His Phe Ile Leu Asp Asp Gln Ile Ala
                245                 250                 255

Leu Val Pro Ser Gln Asp Ala Thr Gln Val Ser Glu Asn
            260                 265

<210> SEQ ID NO 211
<211> LENGTH: 175
<212> TYPE: PRT
<213> ORGANISM: Lycium barbarum

<400> SEQUENCE: 211

Met Glu Leu His His His Tyr Phe Phe Ile Leu Leu Ser Leu Ala Phe
1               5                   10                  15

Ile Ala Ser His Ala Ala Asn Leu Ser Pro Glu Val Tyr Trp Lys Val
            20                  25                  30

Lys Leu Pro Asn Thr Pro Met Pro Arg Pro Ile Lys Asp Ala Leu His
            35                  40                  45

Tyr Ser Glu Ala Ser Glu Gly Asp Val His Lys Leu Arg Gln Pro Tyr
        50                  55                  60

Gly Val Gly Ser Trp Tyr Gln Ala Ala Thr Glu Gly Asp Val Gln Lys
 65                  70                  75                  80

Leu Arg Gln Pro Tyr Gly Val Gly Ser Trp Tyr Gln Ala Ala Thr Glu
                85                  90                  95

Gly Glu Val Lys Lys Leu Arg Gln Pro Tyr Gly Val Phe Ser Trp Tyr
            100                 105                 110

Gln Ala Ala Asn Glu Gly Asp Val Lys Lys Leu Arg Gln Pro Trp Gly
            115                 120                 125

Val Gly Ser Trp Tyr Gln Ala Ala Ile Glu Gly Asp Val Gln Lys Leu
            130                 135                 140

Gln Pro Phe Gly Val Gly Ser Trp Gln Ala Ala Thr Glu Gly Asp Val
145                 150                 155                 160

Gln Lys Leu Arg Gln Pro Tyr Gly Val Gly Ser Trp Tyr Gln Ala
                165                 170                 175

<210> SEQ ID NO 212
<211> LENGTH: 347
<212> TYPE: PRT
<213> ORGANISM: Solanum cheesmaniae

<400> SEQUENCE: 212

Val Ile Phe Val Val Ser His Ala Ala Asn Leu Ser Pro Glu Val Tyr
 1               5                  10                  15

Trp Lys Val Thr Leu Pro Asn Thr Pro Met Pro Lys Pro Ile Lys Asp
                20                  25                  30

Ala Leu His Ile Ser Glu Glu Lys Leu Lys Pro Glu Asp Glu Leu Asp
            35                  40                  45

Lys Leu Arg Gln Trp Gly Val Tyr Ala Arg Tyr Asp Gly Val Pro Lys
 50                  55                  60

Ser Glu Leu Arg Lys Leu His Gln Pro Tyr Gly Val Tyr Thr Trp Tyr
 65                  70                  75                  80

Arg Gly Ala Ala Glu Asp Pro Val Tyr Ala Arg Tyr Leu Asp Ala Ser
                85                  90                  95

Arg Tyr Leu Asp Ala Ser Glu Lys Glu Leu His Lys Val His Pro Pro
            100                 105                 110

Ser Leu Lys Asp Asp Asn Glu Asn His Leu Val Met Pro Tyr Phe Phe
            115                 120                 125

Glu Thr His Leu His Gln Gly Gln Gln Leu Asn Leu Leu Ser Leu Lys
            130                 135                 140

Asn Asn Asn Pro Ala Pro Phe Leu Pro Arg Lys Ile Val Asp Ser Ile
145                 150                 155                 160

Pro Phe Ser Leu Asp Lys Ile Glu Glu Ile Phe Ser Tyr Phe Ser Val
                165                 170                 175

Asp Lys Asp Ser Lys Pro Ala Glu Met Ile Ser Lys Thr Ile Lys Leu
            180                 185                 190

Cys Glu Gly Pro Ala Gly Asn Gly Glu Val Lys Tyr Cys Ala Thr Ser
            195                 200                 205

Leu Glu Ser Met Ile Glu Phe Thr Leu Ser His Val Gly Thr Asn Asn
            210                 215                 220

Ile Ile Ala Ile Ser Ser Glu Val Glu Lys Glu Thr Pro Glu Val Gln

```
              225                 230                 235                 240
Thr Tyr Thr Ile Glu Arg Val Glu Glu Lys Ala Asn Gly Lys Gly Val
                245                 250                 255

Ile Cys His Lys Val Ala Tyr Pro Tyr Ala Val His Tyr Cys His Asp
            260                 265                 270

Val Gly Ser Thr Arg Val Phe Met Val Ser Met Val Gly Ala Asp Gly
        275                 280                 285

Thr Lys Val Asn Gly Val Ser Val Cys His Glu Asp Thr Ala Pro Met
    290                 295                 300

Asn Pro Glu Ala Leu Pro Phe Gln Leu Leu Asn Val Lys Pro Gly Glu
305                 310                 315                 320

Lys Pro Ile Cys His Phe Thr Leu Asp Asp Gln Ile Val Leu Phe Pro
                325                 330                 335

Ser Pro Asn Val Leu Leu Gln Val Thr Asp Asn
            340                 345

<210> SEQ ID NO 213
<211> LENGTH: 198
<212> TYPE: PRT
<213> ORGANISM: Solanum cheesmaniae

<400> SEQUENCE: 213

Pro Tyr Gly Val Tyr Ser Trp Tyr Gln Ala Ala Pro Glu Asn Glu Leu
1               5                   10                  15

His Lys Val His Gln Pro Trp Gly Val Gly Ser Trp Tyr Asn His Ala
            20                  25                  30

Ala Lys Lys Asp Leu Asn Asp Asn His Pro Val Thr Pro Tyr Phe Phe
        35                  40                  45

Glu Thr Asp Leu His Gln Gly Lys Lys Met Asn Leu Glu Ser Leu Lys
    50                  55                  60

Asn Tyr Asn Pro Ala Pro Ile Leu Pro Arg Lys Val Val Asp Ser Ile
65                  70                  75                  80

Ala Phe Ser Ser Asp Lys Ile Glu Glu Ile Leu Asn His Phe Ser Ala
                85                  90                  95

Asp Lys Asp Ser Glu Arg Ala Lys Asp Ile Lys Lys Thr Ile Lys Met
            100                 105                 110

Cys Glu Glu Pro Ala Gly Asn Gly Glu Val Lys His Cys Ala Thr Ser
        115                 120                 125

Leu Glu Ser Met Ile Asp Phe Thr Leu Ser His Leu Gly Thr Asn Lys
    130                 135                 140

Ile Ile Ala Ile Ser Thr Glu Val Glu Lys Glu Thr Pro Glu Val Gln
145                 150                 155                 160

Thr Tyr Thr Ile Glu Lys Val Glu Glu Lys Ala Asn Gly Lys Gly Val
                165                 170                 175

Val Cys His Lys Val Ala Tyr Pro Tyr Ala Val His Phe Cys His Asp
            180                 185                 190

Val Gly Ser Thr Arg Thr
        195

<210> SEQ ID NO 214
<211> LENGTH: 230
<212> TYPE: PRT
<213> ORGANISM: Solanum lasiophyllum

<400> SEQUENCE: 214

Lys Pro Ala Tyr Asn Gly Asp Gly Asn Thr Lys Ile Ser Gln Pro Trp
```

```
    1               5                   10                  15
Gly Val Gly Ala Trp Tyr Lys Ala Ala Pro Glu Asp Glu Leu His Lys
                20                  25                  30

Ile Arg Gln Pro Tyr Gly Val Tyr Ser Trp Tyr Gln Ala Ala Pro Glu
                35                  40                  45

Asn Glu Leu His Lys Val His Gln Pro Trp Gly Val Gly Ser Trp Tyr
 50                      55                  60

Asn His Ala Ala Lys Lys Asp Leu Asn Asp Asn His Pro Val Thr Pro
 65                  70                  75                  80

Tyr Phe Phe Glu Thr Asp Leu His Gln Gly Lys Lys Met Asn Leu Glu
                    85                  90                  95

Ser Leu Lys Asn Tyr Asn Pro Ala Pro Ile Leu Pro Arg Lys Val Val
                100                 105                 110

Asp Ser Ile Ala Phe Ser Asp Lys Ile Glu Glu Ile Leu Asn His
                115                 120                 125

Phe Ser Ala Asp Lys Asp Ser Glu Arg Ala Lys Asp Ile Lys Lys Thr
 130                 135                 140

Ile Lys Met Cys Glu Glu Pro Ala Gly Asn Gly Glu Val Lys His Cys
145                 150                 155                 160

Ala Thr Ser Leu Glu Ser Met Ile Asp Phe Thr Leu Ser His Leu Gly
                165                 170                 175

Thr Asn Lys Ile Ile Ala Ile Ser Thr Glu Val Glu Lys Glu Thr Pro
                180                 185                 190

Glu Val Gln Thr Tyr Thr Ile Glu Lys Val Glu Glu Lys Ala Asn Gly
                195                 200                 205

Lys Gly Val Val Cys His Lys Val Ala Tyr Pro Tyr Ala Val His Phe
 210                 215                 220

Cys His Asp Val Gly Ser
225                 230

<210> SEQ ID NO 215
<211> LENGTH: 96
<212> TYPE: PRT
<213> ORGANISM: Solanum lasiophyllum

<400> SEQUENCE: 215

Leu Leu Arg Asn Leu Pro Leu Ala Glu Lys Pro Ala Tyr Asn Gly Asp
 1               5                   10                  15

Gly Asn Thr Lys Ile Ser Gln Pro Trp Gly Val Gly Ala Trp Tyr Lys
                20                  25                  30

Ala Asp Pro Glu Asp Glu Leu His Lys Ile Arg Gln Pro Trp Gly Val
                35                  40                  45

Tyr Arg Trp Tyr Gln Ala Ala Pro Glu Asp Glu Leu His Lys Ile Arg
 50                  55                  60

Gln Pro Tyr Gly Val Tyr Arg Trp Tyr Gln Ala Ala Pro Glu Asp Glu
 65                  70                  75                  80

Leu His Lys Ile Arg Gln Pro Tyr Gly Val Tyr Ser Trp Tyr Gln Ala
                    85                  90                  95

<210> SEQ ID NO 216
<211> LENGTH: 265
<212> TYPE: PRT
<213> ORGANISM: Bituminaria bituminosa

<400> SEQUENCE: 216

Met Glu Ser Trp Asn Leu Gly Phe Cys Ile Leu Val Leu Phe Ser Leu
```

```
                1               5                   10                  15
            Ala Leu Ala Gly Glu Ser His Gly Arg Asn Trp Gln Ala Val Trp Pro
                            20                  25                  30
            Asn Thr Pro Ile Pro Asp Ser Leu Lys Asp Leu Leu Glu Pro Gly Gln
                            35                  40                  45
            Ser Gly Val Glu Asn Glu Asp Val Pro Met Lys Val Asp Asp Thr Gln
                50                  55                  60
            Tyr Pro Thr Asp Phe Phe Phe Asn Lys Glu Leu Tyr Pro Gly Lys Thr
             65                 70                  75                  80
            Met Asn Ile Glu Phe Ser Thr His His Leu Thr Gln Pro Tyr Gly Val
                            85                  90                  95
            Leu Tyr Trp Val His Gly Ser Asp Val Lys Asp Ile Glu Lys Glu Gly
                            100                 105                 110
            Tyr Thr Pro Glu Gln Leu Cys Leu Arg Lys Gly Pro Lys Gly Glu Asp
                            115                 120                 125
            Lys Tyr Cys Ala Lys Ser Leu Asp Thr Leu Met Glu Phe Val Thr Ser
                130                 135                 140
            Lys Leu Gly Lys Asn Val Gln Pro Phe Thr Ser Ser Phe Val Ser Lys
            145                 150                 155                 160
            Gln Gly Gln Tyr Thr Val Lys Gly Ala Gln Asn Leu Gly Asp Lys Ala
                            165                 170                 175
            Val Met Cys His Arg Leu Asn Phe Gln Lys Pro Met Phe Tyr Cys His
                            180                 185                 190
            Glu Ile His Ala Thr Thr Ala Phe Leu Val Pro Leu Val Ala Gly Asp
                            195                 200                 205
            Gly Thr Lys Thr His Ala Val Ala Val Cys His Phe Asp Thr Ser Val
                            210                 215                 220
            Leu Asn Phe Gln Leu Phe Arg Gln Ile Thr Lys Val Asp Pro Gly Thr
            225                 230                 235                 240
            Asn Pro Leu Cys His Phe Leu Gly Asn Lys Ser Ile Leu Trp Val Pro
                            245                 250                 255
            Asn Ser Ala Met Pro Tyr Gln Thr Asn
                            260                 265

<210> SEQ ID NO 217
<211> LENGTH: 276
<212> TYPE: PRT
<213> ORGANISM: Glycyrrhiza lepidota

<400> SEQUENCE: 217

Met Asp Phe Arg His Pro Leu Ile Ser Ile Leu Val Leu Phe Ser Leu
             1               5                   10                  15
            Ala Leu Ala Gly Glu Ser His Ala Arg Ala Ser Leu Pro Glu Glu Glu
                            20                  25                  30
            Tyr Trp Asp Ala Val Trp Pro Asn Thr Pro Ile Pro Thr Ala Leu Arg
                            35                  40                  45
            Glu Leu Leu Lys Pro Gly Pro Gln Gly Val Asp Ile Asp Asn Leu Pro
                50                  55                  60
            Met Glu Ile Asp Asp Thr Gln Tyr Pro Lys Thr Phe Phe Tyr Glu His
             65                 70                  75                  80
            Asp Leu Tyr Pro Gly Lys Arg Met Asn Val Gln Phe Ser Lys Arg Pro
                            85                  90                  95
            Phe Ala Gln Pro Tyr Gly Val Tyr Thr Trp Met Arg Glu Ile Lys Asp
                            100                 105                 110
```

```
Ile Asp Lys Glu Gly Tyr Thr Phe Asn Glu Val Cys Val Lys Lys Gly
            115                 120                 125

Ala Ala Lys Gly Glu His Lys Tyr Cys Ala Lys Ser Leu Gly Thr Leu
        130                 135                 140

Ile Gly Phe Ala Ile Ser Lys Leu Gly Lys Asn Ile Gln Ser Leu Ser
145                 150                 155                 160

Ser Ser Phe Pro Asp Ala Gln Glu Gln Tyr Thr Val Glu Ser Val Gln
                165                 170                 175

Asn Leu Gly Asp Lys Ala Val Met Cys His Arg Leu Asn Phe Gln Lys
            180                 185                 190

Val Val Phe Tyr Cys His Glu Ile Asn Ala Thr Thr Ala Phe Met Val
        195                 200                 205

Pro Leu Val Ala Ser Asp Gly Thr Lys Thr Gln Ala Leu Ala Val Cys
    210                 215                 220

His Lys Asp Thr Ser Gly Met Asn His Asp Met Leu His Gln Ile Leu
225                 230                 235                 240

Lys Ala Asp Pro Gly Thr Asn Pro Val Cys His Phe Leu Gly Asn Lys
                245                 250                 255

Ala Ile Leu Trp Val Pro Asn Leu Ala Leu Asp Ser Gly Tyr Gln Thr
            260                 265                 270

Asn Val Val Val
        275

<210> SEQ ID NO 218
<211> LENGTH: 272
<212> TYPE: PRT
<213> ORGANISM: Glycine soja

<400> SEQUENCE: 218

Met Ala Leu Arg Cys Leu Val Met Ser Leu Ser Val Leu Phe Thr Leu
1               5                   10                  15

Gly Leu Ala Arg Glu Ser His Ala Arg Asp Glu Asp Phe Trp His Ala
            20                  25                  30

Val Trp Pro Asn Thr Pro Ile Pro Ser Ser Leu Arg Asp Leu Leu Lys
        35                  40                  45

Pro Gly Pro Ala Ser Val Glu Ile Asp Asp His Pro Met Gln Ile Glu
    50                  55                  60

Glu Thr Gln Tyr Pro Lys Thr Phe Phe Tyr Lys Glu Asp Leu His Pro
65                  70                  75                  80

Gly Lys Thr Met Lys Val Gln Phe Ser Lys Pro Pro Phe Pro Gln Pro
                85                  90                  95

Trp Gly Val Gly Thr Trp Leu Lys Glu Ile Lys Asp Thr Ser Lys Glu
            100                 105                 110

Gly Tyr Ser Phe Glu Glu Ile Cys Ile Lys Lys Glu Ala Phe Glu Gly
        115                 120                 125

Glu Glu Lys Phe Cys Ala Lys Ser Leu Gly Thr Val Ile Gly Phe Ala
    130                 135                 140

Ile Ser Lys Leu Gly Lys Asn Ile Gln Val Leu Ser Ser Phe Pro Val
145                 150                 155                 160

Asn Lys Gln Glu Gln Tyr Thr Val Glu Gly Val Gln Asn Leu Gly Asp
                165                 170                 175

Lys Ala Val Met Cys His Gly Leu Asn Phe Arg Thr Ala Val Phe Tyr
            180                 185                 190

Cys His Lys Val Arg Glu Thr Thr Ala Phe Met Val Pro Leu Val Ala
        195                 200                 205
```

```
Gly Asp Gly Thr Lys Thr Gln Ala Leu Ala Val Cys His Ser Asp Thr
    210                 215                 220

Ser Gly Met Asn His Met Leu His Glu Leu Met Gly Val Asp Pro
225                 230                 235                 240

Gly Thr Asn Pro Val Cys His Phe Leu Gly Ser Lys Ala Ile Leu Trp
                245                 250                 255

Val Pro Asn Leu Ser Met Asp Thr Ala Tyr Gln Thr Asn Val Val Val
            260                 265                 270
```

<210> SEQ ID NO 219
<211> LENGTH: 154
<212> TYPE: PRT
<213> ORGANISM: Glycine soja

<400> SEQUENCE: 219

```
Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
            20                  25                  30

Tyr Trp Glu Ala Val Trp Pro Asn Thr Pro Ile Pro Thr Ala Leu Arg
        35                  40                  45

Glu Leu Leu Lys Pro Leu Pro Ala Gly Val Glu Ile Asp Glu Leu Pro
50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Pro Tyr Gly Val Tyr Thr Trp Leu Thr Asp Ile Lys Asp
            100                 105                 110

Thr Ser Lys Glu Gly Tyr Ser Phe Glu Glu Ile Cys Ile Lys Lys Glu
        115                 120                 125

Ala Phe Glu Gly Glu Glu Lys Cys Ala Lys Ser Leu Gly Thr Val
    130                 135                 140

Ile Gly Phe Ala Ile Ser Lys Leu Gly Lys
145                 150
```

<210> SEQ ID NO 220
<211> LENGTH: 571
<212> TYPE: PRT
<213> ORGANISM: Acacia pycnantha

<400> SEQUENCE: 220

```
Met Asp Leu Arg Arg Arg Phe Gly Val Leu Ala Leu Leu Leu Cys Leu
1               5                   10                  15

Ala Leu Ala Glu Ser Asp Val Thr Ser Ser Arg Ser Ala Glu Glu Tyr
            20                  25                  30

Trp Arg Ser Ile Trp Pro Asp Thr Ser Met Pro Lys Asn Leu Glu Tyr
        35                  40                  45

Leu Leu Gly Ser Ser Val Ser Asp Ala Glu Asn Thr Asp Asn Thr Gln
50                  55                  60

Tyr Pro Tyr Thr Ser Phe Phe Glu Gln Asp Leu His Ala Gly Lys Lys
65                  70                  75                  80

Met Asp Ile Ile Phe Asn Ser Pro Tyr Ala Asp Lys Glu Gln Lys Ser
                85                  90                  95

Asn Pro Thr Glu Lys Tyr Pro Lys Lys Ser Ser Trp Lys Arg Asn Thr
            100                 105                 110
```

```
Lys Asn Glu Asp Ser Glu Lys Ser Ala Ser Pro Gln Pro Trp Gly Val
            115                 120                 125

Gly Thr Trp Arg Arg Asn Thr Met Asn Glu Asp Ser Lys Lys Ser Ala
        130                 135                 140

Ser Pro Gln Pro Trp Gly Val Gly Thr Trp Arg Arg Asn Ala Met Asn
145                 150                 155                 160

Glu Asp Ser Glu Lys Ser Ala Ser Pro Gln Pro Trp Gly Val Gly Thr
                165                 170                 175

Trp Arg Arg Asn Thr Met Asn Glu Asp Ser Glu Lys Ser Gly Ser Pro
            180                 185                 190

Gln Pro Trp Gly Val Gly Thr Trp Arg Arg Asn Glu Met Asn Glu Asp
            195                 200                 205

Ser Glu Lys Ser Thr Tyr Pro Gln Pro Trp Gly Val Gly Thr Trp Arg
            210                 215                 220

Arg Asn Ala Met Asn Glu Glu Ser Glu Lys Ser Ala Ser Pro Gln Pro
225                 230                 235                 240

Trp Gly Val Gly Thr Trp Arg Arg Asn Thr Met Asn Glu Asp Ser Lys
                245                 250                 255

Lys Ser Ala Ser Pro Gln Pro Trp Gly Val Gly Thr Trp Arg Arg Asn
            260                 265                 270

Ala Met Asn Glu Asp Ser Glu Lys Ser Gly Ser Pro Gln Pro Trp Gly
            275                 280                 285

Val Gly Thr Trp Arg Arg Asn Thr Met Asn Glu Tyr Ser Glu Lys Ser
            290                 295                 300

Gly Ser Pro Gln Pro Trp Gly Val Gly Thr Leu Arg Arg Asn Ala Met
305                 310                 315                 320

Asn Glu Asp Ser Glu Lys Ser Thr Tyr Pro Gln Pro Trp Gly Val Gly
                325                 330                 335

Thr Trp Arg Arg Asp Ala Met Asn Glu Glu Ser Glu Lys Ser Ala Ser
            340                 345                 350

Pro Gln Pro Trp Gly Val Gly Thr Trp Arg Arg Asn Thr Met Asn Glu
            355                 360                 365

Asp Ser Glu Arg Ser Ala Ser Pro Leu Pro Trp Gly Val Gly Thr Trp
            370                 375                 380

Arg Arg Asn Ala Asp Ser Glu Lys Ser Ala Phe Pro Gln Pro Trp Gly
385                 390                 395                 400

Val Gly Thr Trp Lys Arg Asn Thr Met Lys Asn Val His Glu His Leu
                405                 410                 415

Ser Met Glu Ala Ile Cys Asn Thr Lys Glu Arg Phe Val Gly Glu Asp
                420                 425                 430

Asp Lys Phe Cys Ala Glu Ser Val Glu Ser Leu Ile Asp Phe Val Ile
            435                 440                 445

Ser Lys Leu Gly Lys Asp Ile Glu Ala Leu Thr Ser Ser Phe Val Pro
            450                 455                 460

His Gln Thr Gln Tyr Lys Ile Leu Glu Gly Ile Gln Arg Val Ser Ser
465                 470                 475                 480

Glu Gly Val Met Cys His Lys Leu Asn Phe Glu Lys Pro Leu Phe Tyr
                485                 490                 495

Cys His Gln Val Asn Ala Thr Ile Thr Tyr Ile Val Pro Met Glu Ala
                500                 505                 510

Ser Asp Gly Thr Arg Thr Ser Ile Val Ala Leu Cys His Arg Asp Thr
            515                 520                 525
```

```
Arg Gly Leu Asp Pro His Lys Leu Phe His Gln Leu Lys Val Lys Pro
            530                 535                 540

Gly Thr Val Pro Val Cys His Leu Leu Gly Ser Gly Ala Ile Ser Trp
545                 550                 555                 560

Val Pro Lys Asn Asn Glu Leu Lys Ala Ala Phe
                565                 570
```

<210> SEQ ID NO 221
<211> LENGTH: 186
<212> TYPE: PRT
<213> ORGANISM: Acacia argyrophylla

<400> SEQUENCE: 221

```
Arg Asn Ala Asp Ser Glu Lys Ser Ala Phe Pro Gln Pro Trp Gly Val
1               5                   10                  15

Gly Thr Trp Lys Arg Asn Thr Met Lys Asn Val His Glu His Leu Ser
                20                  25                  30

Met Glu Ala Ile Cys Asn Thr Lys Glu Arg Phe Val Gly Glu Asp Asp
            35                  40                  45

Lys Phe Cys Ala Glu Ser Val Glu Ser Leu Ile Asp Phe Val Ile Ser
    50                  55                  60

Lys Leu Gly Lys Asp Ile Glu Ala Leu Thr Ser Ser Phe Val Pro His
65                  70                  75                  80

Gln Thr Gln Tyr Lys Ile Leu Glu Gly Ile Gln Arg Val Ser Ser Glu
                85                  90                  95

Gly Val Met Cys His Lys Leu Asn Phe Glu Lys Pro Leu Phe Tyr Cys
            100                 105                 110

His Gln Val Asn Ala Thr Ile Thr Tyr Ile Val Pro Met Glu Ala Ser
        115                 120                 125

Asp Gly Thr Arg Thr Ser Ile Val Ala Leu Cys His Arg Asp Thr Arg
    130                 135                 140

Gly Leu Asp Pro His Lys Leu Phe His Gln Leu Lys Val Lys Pro Gly
145                 150                 155                 160

Thr Val Pro Val Cys His Phe Leu Gly Ser Gly Ala Ile Ser Trp Val
                165                 170                 175

Pro Arg Asn Asn Glu Leu Lys Ala Ala Phe
            180                 185
```

<210> SEQ ID NO 222
<211> LENGTH: 167
<212> TYPE: PRT
<213> ORGANISM: Amaranthus tricolor

<400> SEQUENCE: 222

```
Met Leu Ser Leu Leu Ala His Ile Asn Arg Ile Pro Asn Ser Arg Ser
1               5                   10                  15

Leu His Tyr Leu Asn Ser Tyr Phe Leu Pro Asn Met Ala Met Asp Leu
                20                  25                  30

Arg Leu Gln Val Pro Ala Leu Phe Leu Leu Thr Phe Leu Ala Ile His
            35                  40                  45

Val Ser Ser Cys Lys Gln Glu Asp Tyr Trp Lys Met Lys Leu Pro Lys
    50                  55                  60

Val Pro Met Pro Glu Ala Ile Lys His Ser Leu Leu His Ser Gly Gly
65                  70                  75                  80

Glu Asn Lys Leu Lys Asp Glu Tyr Thr Ile Lys Gln Pro Tyr Thr Val
                85                  90                  95
```

-continued

```
Gly Ser Trp Lys Tyr Asp Val Asp Lys Asn Lys Val Val Asp Glu Ser
            100                 105                 110

Ala Leu Lys Gln Pro Phe Thr Val Gly Ser Trp Lys Tyr Asp Ala Asp
        115                 120                 125

Lys Asn Lys Val Lys Asp Asp Ser Ala Leu Lys Gln Pro Phe Thr Val
    130                 135                 140

Gly Ser Trp Lys Tyr Asp Val Asp Lys Asn Lys Val Lys Asp Asp Ser
145                 150                 155                 160

Ala Leu Lys Gln Pro Tyr Thr
                165

<210> SEQ ID NO 223
<211> LENGTH: 358
<212> TYPE: PRT
<213> ORGANISM: Amaranthus tricolor

<400> SEQUENCE: 223

Ala Asp Lys Asn Lys Val Asp Glu Ser Ala Leu Lys Gln Pro Tyr
1               5                   10                  15

Thr Val Gly Ser Trp Lys Tyr Asp Val Asp Lys Asn Lys Val Lys Asp
            20                  25                  30

Asp Ser Ala Leu Lys Gln Pro Phe Thr Val Gly Ser Trp Lys Tyr Asp
        35                  40                  45

Ala Asp Lys Asn Lys Val Lys Asp Asp Ser Ala Leu Arg Gln Pro Tyr
    50                  55                  60

Thr Val Gly Ser Trp Lys Tyr Asp Val Asp Lys Asn Glu Val Lys Asp
65                  70                  75                  80

Asp Ser Ala Leu Lys Gln Pro Tyr Thr Val Gly Ser Trp Lys Tyr Asn
                85                  90                  95

Glu Asn Asp Glu Ser Lys Gln Ala Ser Pro His His Leu His His Gln
            100                 105                 110

Lys Leu Met His Glu Asn Val Asn Ser Asn Asp Lys Glu Asp Leu Thr
        115                 120                 125

Asp Gly Ser Val Phe Phe Val Glu Lys Ser Leu His Ile Gly Ser Lys
    130                 135                 140

Leu Lys His Asp Phe Gln Lys Thr Pro Glu Met Ser Phe Leu Ser Lys
145                 150                 155                 160

Gln Glu Ala Gln Ser Ile Pro Phe Ser Met Glu Lys Ile Gly Asp Ile
                165                 170                 175

Leu Asn Leu Phe Ser Leu Lys Ser Asn Ser Ala Glu Ala Asn Ala Ile
            180                 185                 190

Lys Gly Thr Leu Asp Ile Cys Leu Tyr Arg Pro Lys Val Ser Lys Glu
        195                 200                 205

Asn Arg Thr Cys Ala Gln Ser Met Glu Asp Ile Val Asp Phe Val Val
    210                 215                 220

Gly Glu Leu Gly Thr Asn Glu Val Glu Ile Lys Met Met Asn Asn Asn
225                 230                 235                 240

Ile Glu Val Pro Asn Gly Ile Gln Asp Tyr Leu Leu Ser Lys Val Glu
                245                 250                 255

Lys Leu Phe Val Pro Gly Asn Thr Ala Val Ala Cys His Arg Met Ser
            260                 265                 270

Tyr Pro Tyr Ile Val Tyr Tyr Cys His His Gln Gln Asp Ile Gly Gln
        275                 280                 285

Tyr Asn Val Thr Leu Val Ser Pro Ser Thr Gly Ala Ala Phe Gln Thr
    290                 295                 300
```

```
Thr Ala Val Cys His Tyr Asp Thr Tyr Ala Trp Gln Pro Asp Val Val
305                 310                 315                 320

Ala Leu Lys Tyr Leu Gly Ile Arg Pro Gly Asp Ala Pro Val Cys His
                325                 330                 335

Phe Ser Ala Ile Asn Asp Met Phe Trp Thr Leu Lys Asp Glu Pro Lys
            340                 345                 350

Ser Leu Asp Met Val Gln
        355

<210> SEQ ID NO 224
<211> LENGTH: 109
<212> TYPE: PRT
<213> ORGANISM: Atriplex hortensis

<400> SEQUENCE: 224

Ser Glu Asn Gly Lys Glu Arg Val Gly Ile Asp Gln Pro Phe Thr Val
1               5                   10                  15

Gly Ala Trp Lys Tyr Asn Ser Lys Asn Ala Lys Glu Arg Val Gly Ile
            20                  25                  30

Asn Gln Pro Phe Thr Val Gly Ala Trp Lys Tyr Asn Ser Glu Asn Arg
        35                  40                  45

Lys Glu Arg Val Gly Ile Asn Gln Pro Phe Thr Val Gly Ala Trp Lys
    50                  55                  60

Tyr Asn Ser Glu Asn Gly Lys Glu Arg Val Gly Ile Asp Gln Pro Phe
65                  70                  75                  80

Thr Val Gly Ala Trp Lys Tyr Asn Ser Glu Asn Ala Asn Asn Lys Asn
                85                  90                  95

Asn Gly Asp Lys Glu Lys Asp Asn Asp Val Arg Met Gly
            100                 105

<210> SEQ ID NO 225
<211> LENGTH: 297
<212> TYPE: PRT
<213> ORGANISM: Atriplex prostrata

<400> SEQUENCE: 225

Trp Lys Tyr Asn Ser Glu Asn Gly Lys Glu Arg Val Gly Met Asp Gln
1               5                   10                  15

Pro Phe Thr Val Gly Ala Trp Lys Tyr Asn Ser Lys Asn Gly Lys Glu
            20                  25                  30

Arg Val Ala Ile Asp Gln Pro Phe Thr Val Gly Ala Trp Lys Tyr Asn
        35                  40                  45

Ser Lys Asn Ala Asn Asn Lys Asp Asn Gly Asp Lys Glu Lys Asp Asn
    50                  55                  60

Asp Leu Arg Met Gly Ser Val Phe Phe Ile Glu Lys Ser Leu Arg Leu
65                  70                  75                  80

Gly Ala Lys Leu Lys His Asp Phe Gln Lys Thr Pro Ser Val Pro Phe
                85                  90                  95

Leu Pro Lys His Phe Val Gln Ser Ile Pro Phe Ser Asp Asn Lys Phe
            100                 105                 110

Thr Glu Ile Leu Asp Leu Phe Ser Ile Lys Pro Gly Ser Pro Glu Ala
        115                 120                 125

Thr Gly Ile Lys Gly Thr Leu Asn Ile Cys Leu His Arg Pro Lys Val
    130                 135                 140

Glu Lys Glu Asn Arg Thr Cys Ala Gln Ser Met Glu Asp Val Val Asp
145                 150                 155                 160
```

-continued

```
Phe Val Val Arg Glu Leu Gly Ser Asn Asp Val Glu Leu Arg Met Met
                165                 170                 175

Arg Asn Asp Ile Glu Val Pro Lys Gly Ile Gln Asp Tyr Val Val Thr
            180                 185                 190

Lys Val Lys Lys Leu Ser Val Pro Ser Asn Thr Ala Ala Ala Cys His
        195                 200                 205

Arg Met Val Tyr Pro Tyr Val Val Tyr Cys His His Gln Lys Asp
    210                 215                 220

Ile Gly His Tyr Asp Val Thr Leu Val Asn Pro Thr Thr Asn Thr Ala
225                 230                 235                 240

Phe Gln Thr Thr Ala Val Cys His Tyr Asp Thr Tyr Ala Trp Lys Pro
                245                 250                 255

Asn Val Pro Ala Leu Arg Tyr Leu Glu Ile Arg Pro Gly Asp Ala Pro
            260                 265                 270

Val Cys His Phe Ser Ala Ile Asn Asp Met Trp Trp Asn Leu Lys Pro
        275                 280                 285

Asn Ser Lys Ser Leu Asp Met Val Val
    290                 295

<210> SEQ ID NO 226
<211> LENGTH: 182
<212> TYPE: PRT
<213> ORGANISM: Atriplex prostrata

<400> SEQUENCE: 226

Met Ala Met His Phe Gly Leu Gly Leu Gln Val His Ala Ile
1               5                   10                  15

Phe Leu Leu Val Phe Leu Ala Phe His Ala Ser Ser Cys Glu Gln Glu
                20                  25                  30

Asp Tyr Trp Gln Met Lys Leu Pro Lys Val Pro Met Pro Gln Ala Ile
            35                  40                  45

Lys Asp Asn Leu Phe His Pro Lys Gly Ser Tyr Val Asp Ala Lys
50                  55                  60

Lys Asn Val Asp Val Asp Gln Pro Phe Thr Val Gly Ala Trp Lys Tyr
65                  70                  75                  80

Asn Ser Asp Asn Gly Lys Glu Arg Val Gly Ile Asp Gln Pro Phe Thr
                85                  90                  95

Val Gly Ala Trp Lys Tyr Asn Ser Lys Asn Gly Lys Glu Arg Val Ala
            100                 105                 110

Ile Asp Gln Pro Phe Thr Val Gly Ala Trp Lys Tyr Asn Ser Lys Asn
        115                 120                 125

Gly Lys Glu Arg Val Gly Ile Asp Gln Pro Phe Thr Val Gly Ala Trp
    130                 135                 140

Lys Tyr Asn Ser Glu Asn Gly Lys Glu Arg Val Asp Ile Asp Gln Pro
145                 150                 155                 160

Phe Thr Val Gly Ala Trp Lys Tyr Asn Ser Asp Asn Gly Lys Glu Arg
                165                 170                 175

Leu Val Asn Thr Asn Ser
            180

<210> SEQ ID NO 227
<211> LENGTH: 238
<212> TYPE: PRT
<213> ORGANISM: Atriplex prostrata

<400> SEQUENCE: 227
```

Ser Glu Asn Gly Lys Glu Arg Val Gly Ile Asp Gln Pro Phe Thr Val
1               5                   10                  15

Gly Ala Trp Lys Tyr Asn Ser Glu Asn Gly Lys Glu Arg Val Gly Ile
            20                  25                  30

Asp Gln Pro Phe Thr Val Gly Ala Trp Lys Tyr Asn Ser Asp Asn Gly
        35                  40                  45

Lys Glu Arg Val Gly Val Asp Gln Pro Phe Thr Val Gly Ala Trp Lys
50                  55                  60

Tyr Asn Ser Glu Asn Gly Lys Glu Arg Val Gly Ile Asp Gln Pro Phe
65                  70                  75                  80

Thr Val Gly Ala Trp Lys Tyr Asn Ser Glu Asn Gly Lys Glu Arg Val
                85                  90                  95

Gly Val Asp Gln Pro Phe Thr Val Gly Ala Trp Lys Tyr Asn Ser Glu
            100                 105                 110

Asn Gly Lys Glu Arg Val Gly Ile Asp Gln Pro Phe Thr Val Gly Ala
        115                 120                 125

Trp Lys Tyr Asn Ser Glu Asn Gly Lys Glu Arg Val Gly Ile Asp Gln
130                 135                 140

Pro Phe Thr Val Gly Ala Trp Lys Tyr Asn Ser Glu Asn Gly Lys Glu
145                 150                 155                 160

Arg Val Gly Ile Asp Gln Pro Phe Thr Phe Arg Ala Trp Lys Tyr Asn
            165                 170                 175

Ser Asn Asn Gly Lys Glu Arg Val Gly Ile Asp Gln Pro Phe Thr Val
        180                 185                 190

Gly Ala Trp Lys Tyr Asn Ser Glu Asn Gly Lys Glu Arg Val Gly Ile
195                 200                 205

Asp Gln Pro Phe Thr Val Gly Ala Trp Lys Tyr Asn Ser Glu Asn Gly
            210                 215                 220

Lys Glu Arg Val Gly Ile Asp Gln Pro Phe Thr Val Gly Ala
225                 230                 235

<210> SEQ ID NO 228
<211> LENGTH: 619
<212> TYPE: PRT
<213> ORGANISM: Chenopodium quinoa

<400> SEQUENCE: 228

Met Ala Met His Phe Gly Leu Pro Arg Leu Leu His Ala Ile Phe
1               5                   10                  15

Leu Leu Val Phe Leu Ala Phe His Ala Ser Ser Cys Glu Gln Glu Asp
            20                  25                  30

Tyr Trp Gln Met Lys Leu Pro Lys Val Pro Met Pro Gln Ala Ile Lys
        35                  40                  45

Asp Asn Leu Phe His Pro Lys Asp Lys Met Ser Met Met Thr Pro Ser
50                  55                  60

Ile Glu Thr Lys Asp Lys Ala Ala His Gly Asn Asp Ala Asp Lys Ala
65                  70                  75                  80

Lys Lys Ala Asn Thr Asn Gln Pro Phe Thr Val Val Gly Trp Lys Tyr
                85                  90                  95

Asn Ala Asp Gly Ala Lys Glu Arg Val Gly Met Ser Gln Pro Tyr Thr
            100                 105                 110

Val Met Ala Trp Lys Tyr Asn Val Asp Ala Lys Glu Arg Val Gly
        115                 120                 125

Ile Asp Gln Pro Tyr Thr Val Trp Gly Trp Asn Tyr Asn Thr Asp Ser

```
                  130                 135                 140
Ala Asn Lys Glu Lys Val Lys Glu Ala Tyr Lys Pro Leu Ser Ile Glu
145                 150                 155                 160

Thr Asn Thr Lys Lys Thr Gly Ile Asp Gln Pro Tyr Thr Val Trp Gly
                    165                 170                 175

Trp Asn Tyr Asn Thr Asn Ser Ala Asn Lys Glu Lys Val Lys Glu Ala
                180                 185                 190

Glu Lys Pro Leu Ser Ile Glu Thr Asn Thr Lys Lys Thr Gly Val Asp
            195                 200                 205

Gln Pro Tyr Thr Val Trp Gly Trp Asn Tyr Asn Thr Asn Asn Ala Asn
        210                 215                 220

Lys Glu Lys Val Lys Glu Ala Glu Lys Pro Leu Ser Ile Glu Thr Asn
225                 230                 235                 240

Thr Lys Lys Thr Gly Ile Asp Gln Pro Tyr Thr Val Trp Gly Trp Asn
                    245                 250                 255

Tyr Asn Thr Asp Ser Ala Asn Lys Glu Lys Val Lys Glu Ala Glu Lys
                260                 265                 270

Ser Leu Ser Ile Glu Thr Asp Thr Lys Lys Thr Gly Ile Asp Gln Pro
            275                 280                 285

Tyr Thr Val Trp Gly Trp Asn Tyr Asn Thr Asp Ser Ala Asn Lys Glu
        290                 295                 300

Lys Val Lys Glu Ala Glu Lys Ser Leu Ser Ile Glu Thr Asn Thr Lys
305                 310                 315                 320

Lys Thr Gly Ile Asp Gln Pro Tyr Thr Val Trp Gly Trp Asn Tyr Asn
                    325                 330                 335

Thr Asn Ser Gly Asn Lys Glu Lys Val Lys Glu Ala Asp Lys Val Phe
                340                 345                 350

Thr Met Asp Thr Ser Thr Lys Lys Ala Gly Thr Lys Gln Pro Tyr Thr
            355                 360                 365

Val Met Gly Trp Lys Tyr Asn Ala Asp Asn Gly Lys Arg Glu Lys Val
        370                 375                 380

Gly His Glu Val Ser Val Gly Ser Val Phe Ile Glu Lys Ser Leu
385                 390                 395                 400

Arg Leu Gly Asp Lys Leu Lys His Asp Phe Gln Lys Thr Pro Ser Val
                    405                 410                 415

Pro Phe Leu Pro Lys His Ile Ala Lys Ser Ile Pro Phe Ser Glu Asp
                420                 425                 430

Lys Phe Thr Glu Ile Leu Asn Leu Phe Ser Ile Lys Pro Gly Ser Val
            435                 440                 445

Glu Ala Thr Gly Ile Lys Gly Thr Leu Asp Val Cys Leu His Arg Pro
        450                 455                 460

Lys Val Glu Lys Glu Asn Arg Thr Cys Ala Gln Ser Met Glu Asp Val
465                 470                 475                 480

Val Asp Phe Val Val Arg Glu Leu Gly Ser Asn Asp Val Glu Leu Arg
                    485                 490                 495

Met Met Lys Asn Asp Ile Glu Val Pro Lys Gly Ile Gln Asp Tyr Val
                500                 505                 510

Ile Thr Lys Val Lys Lys Leu Val Val Pro Gly Asn Thr Ala Ala Ala
            515                 520                 525

Cys His Arg Met Ser Tyr Pro Tyr Val Val Tyr Tyr Cys His His Gln
        530                 535                 540

Gln Asp Ile Gly His Tyr Asp Val Thr Leu Val Ser Pro Thr Thr Gly
545                 550                 555                 560
```

-continued

```
Asn Ala Ile Gln Thr Thr Ala Val Cys His Tyr Asp Thr Tyr Ala Trp
                565                 570                 575

Lys Pro Asn Val Pro Ala Leu Gln Tyr Leu Gly Ile Arg Pro Gly Asp
            580                 585                 590

Ala Pro Val Cys His Phe Ser Ala Ile Asn Asp Met Phe Trp Ser Leu
        595                 600                 605

Lys Ala Asn Ser Lys Ser Leu Asp Met Val Val
    610                 615

<210> SEQ ID NO 229
<211> LENGTH: 414
<212> TYPE: PRT
<213> ORGANISM: Alternanthera brasiliana

<400> SEQUENCE: 229

Ala Gln Asp Ala Glu Pro Gln Glu Met Glu Ser Leu Ser Leu Asp Asp
1               5                   10                  15

Asn Lys Lys Met Ser Ser Arg Thr Asn Gln Pro Tyr Thr Val Gly Ala
            20                  25                  30

Trp Lys Tyr Asp Asp Ala Gly Lys Ser Lys Val Glu Gln Ile Val
        35                  40                  45

Asp Pro Phe Ser Ser Asp Lys Thr Lys Lys Met Ser Ser Arg Thr Asn
    50                  55                  60

Gln Pro Tyr Thr Val Gly Ala Trp Lys Tyr Val Gln Asp Val Glu Pro
65                  70                  75                  80

Gln Glu Lys Val Lys Gln Val Gly Asn Leu Leu Ser Leu Asp Asn Ser
                85                  90                  95

Lys Lys Thr Ile Ser His Thr Asn Gln Pro Tyr Thr Val Gly Ala Trp
            100                 105                 110

Lys Tyr Asp Glu Ala Gly Lys Pro Gln Glu Lys Val Glu Gln Val Val
        115                 120                 125

Asp Pro Leu Ser Leu Asp Lys Asn Lys Lys Met Thr Ser Tyr Thr Asn
    130                 135                 140

Gln Pro Tyr Thr Val Gly Ala Trp Lys Tyr Asp Ser Asp Lys Pro Lys
145                 150                 155                 160

Ile Lys Ser Glu Asp Thr Ser His His His Asp Leu Met His Asn Asn
                165                 170                 175

Ile Lys Ser Asp Gln Glu Asp Gly Gly Ser Val Phe Phe Ile Glu Lys
            180                 185                 190

Ser Leu Ser Pro Gly Met Ile Leu Lys His Asp Phe Gln Lys Thr Pro
        195                 200                 205

Tyr Val Pro Phe Leu Pro Lys His Ile Ser Gln Asn Val Pro Phe Glu
    210                 215                 220

Val Glu Asn Phe Ser Glu Ile Leu Asn Leu Phe Ser Leu Asp Pro Lys
225                 230                 235                 240

Ser Thr Glu Ala Thr Ala Ile Lys Glu Thr Leu Glu Ile Cys Leu Gln
                245                 250                 255

Arg Pro Lys Val Lys Lys Glu Asn Arg Thr Cys Ala Gln Ser Val Glu
            260                 265                 270

Asp Val Asp Phe Val Ile Gly Glu Leu Gly Thr Asn Asp Val Lys
        275                 280                 285

Leu Arg Met Met Asn Asn Asn Ile Glu Val Arg Asn Gly Ile Gln Asp
    290                 295                 300

Tyr Val Leu Thr Lys Val Lys Lys Leu Glu Val Pro Gly Tyr Asn Ala
```

```
                305                 310                 315                 320
Val Ala Cys His Arg Met Ser Tyr Pro Tyr Val Val Tyr Cys His
                    325                 330                 335

His Gln Gln Asp Ile Gly His Phe Asp Val Thr Leu Val Asp Pro Thr
                    340                 345                 350

Ser Gly Ser Ala Ile Gln Thr Thr Ala Val Cys His Tyr Asp Thr Tyr
                    355                 360                 365

Ala Trp Lys Pro Asn Val Pro Ala Leu Arg Tyr Leu Lys Ile Asn Pro
                    370                 375                 380

Gly Asp Ala Pro Val Cys His Phe Ser Ala Ile Asn Asp Met Phe Trp
385                 390                 395                 400

Ser Leu Lys Asp Asp Thr Asn Lys Ser Leu Leu Lys Val Gln
                    405                 410

<210> SEQ ID NO 230
<211> LENGTH: 105
<212> TYPE: PRT
<213> ORGANISM: Alternanthera sessilis

<400> SEQUENCE: 230

Met Ala Met His Phe Gly Leu Gly Leu Gly Leu Gln Val His Ala Ile
1               5                   10                  15

Phe Leu Leu Val Phe Leu Ala Phe His Ala Ser Ser Cys Glu Gln Glu
                20                  25                  30

Asp Tyr Trp Gln Met Lys Leu Pro Lys Val Pro Met Pro Gln Ala Ile
                35                  40                  45

Lys Asp Asn Leu Phe His Pro Lys Gly Ser Tyr Val Asp Ala Lys
    50                  55                  60

Lys Asn Val Asp Val Asp Gln Pro Phe Thr Val Gly Ala Trp Lys Tyr
65                  70                  75                  80

Asn Ser Asp Asn Gly Lys Glu Arg Val Gly Ile Asp Gln Pro Phe Thr
                85                  90                  95

Val Gly Ala Trp Lys Tyr Asn Ser Glu
                100                 105

<210> SEQ ID NO 231
<211> LENGTH: 502
<212> TYPE: PRT
<213> ORGANISM: Hypertelis cerviana

<400> SEQUENCE: 231

Met Ala Thr Pro Val Ile Ile Leu Arg Ala Phe Leu Ile Val Ala Leu
1               5                   10                  15

Met Val Phe His Gly Ser Ser Cys Ser Gln Glu Asp Tyr Trp Lys Met
                20                  25                  30

Lys Leu Pro Glu Val Thr Met Pro Gln Ala Leu Lys Asp Asn Leu Leu
                35                  40                  45

His Glu Ile Ser Asn Ser Gln Lys Glu Pro Ile Ile Thr Gln Ala Ser
    50                  55                  60

Ser Leu His Asp Val Lys Asp Lys Val Asp Ile Asn Asp Met Thr Ser
65                  70                  75                  80

Thr Thr Gln Pro Phe Thr Val Leu Gly Trp Lys Tyr Asn Arg Asp Ala
                85                  90                  95

Ser Glu Lys Glu Asp Val Thr Met Gln Pro Ser Leu His Asp Phe Lys
                100                 105                 110

Glu Asn Val Asp Val Lys Asp Met Thr Ala Thr Lys Gln Pro Phe Thr
```

```
                115                 120                 125
Val Phe Gly Trp Lys Tyr Asn Lys Asp Ala Ser Glu Lys Gln Asn Val
            130                 135                 140

Asp Val Lys Asp Met Thr Ala Thr Lys Gln Pro Phe Thr Val Phe Gly
145                 150                 155                 160

Trp Lys Tyr Asn Lys Asp Ala Ser Glu Lys Gln Asn Val Asp Val Lys
                165                 170                 175

Asp Met Thr Thr Thr Lys Gln Pro Phe Thr Val Phe Gly Trp Lys Tyr
            180                 185                 190

Asn Gly Asp Ser Ile Glu Lys Glu Asn Val Asp Val Lys Asp Met Thr
        195                 200                 205

Ala Thr Lys Gln Pro Phe Thr Val Phe Gly Trp Lys Tyr Asn Lys Asp
    210                 215                 220

Asp Ser Glu Lys Ala Glu Val Asp Arg Pro Lys Lys His Thr Lys
225                 230                 235                 240

Asp Val Thr Thr Met Glu Asn His Lys Ser His His Val Met His
                245                 250                 255

His His Val His Asn Ser Gly Glu Asp Asn Asn Val Ala Gly Ser Val
            260                 265                 270

Phe Phe Lys Glu Gly Ser Leu Tyr Leu Arg Ala Lys Leu Lys His Asp
        275                 280                 285

Phe Gln Asn Thr Ser Lys Val Val Phe Leu Pro Arg Asn Glu Val Glu
    290                 295                 300

Leu Ile Pro Phe Ser Met Asp Lys Tyr Met Glu Ile Leu Asn Arg Leu
305                 310                 315                 320

Ser Ile Lys Pro Gly Ser Leu Glu Ala Ile Gly Val Lys Gly Thr Leu
                325                 330                 335

Ala Ile Cys Leu Glu Lys Pro Asn Val His Lys Glu Asn Arg Thr Cys
            340                 345                 350

Ala Arg Ser Leu Glu Glu Met Val Asp Phe Val Thr Lys Glu Leu Gly
        355                 360                 365

Thr Asn Lys Val His Val Thr Met Met Arg Asn Thr Asp Asn Thr Glu
    370                 375                 380

Ile Pro Asn Gly Ile Gln Glu Tyr Glu Val Ile Ser Leu Lys Lys Leu
385                 390                 395                 400

Val Ile Pro Asp Asn Thr Ala Val Ala Cys His Lys Met Ser Tyr Pro
                405                 410                 415

Tyr Ala Val Tyr Tyr Cys His His Gln Gln Asp Ile Gly His Tyr Ser
            420                 425                 430

Val Thr Val Arg Asn Ser Asp Gly Val Leu Val Asp Thr Thr Ala Val
        435                 440                 445

Cys His Tyr Asp Thr Tyr Ala Trp Glu Ala Asp Val Pro Ala Leu Lys
    450                 455                 460

Tyr Leu Lys Ile Ala Pro Gly Asp Ala Pro Val Cys His Phe Ser Ala
465                 470                 475                 480

Val Asn Asp Ile Phe Trp Thr Thr Lys Ala Asp Ser Tyr Ile Arg Lys
                485                 490                 495

Phe Leu Asp Lys Asp Gln
            500

<210> SEQ ID NO 232
<211> LENGTH: 327
<212> TYPE: PRT
<213> ORGANISM: Bougainvillea spectabilis
```

```
<220> FEATURE:
<221> NAME/KEY: VARIANT
<222> LOCATION: 327
<223> OTHER INFORMATION: Any amino acid

<400> SEQUENCE: 232

Met Ala Lys Asn Leu Leu Ile Leu Arg Ser Phe Leu Leu Val Cys Leu
1               5                   10                  15

Val Ala Tyr Ala Ser Ser Cys Lys Gln Ala Glu Tyr Trp Lys Met Lys
            20                  25                  30

Leu Pro Arg Val Pro Leu Pro Lys Ala Leu Glu Asn Asn Leu His Tyr
        35                  40                  45

Phe His His Asp Glu Lys Ala Thr Ile Ala Gln Pro Tyr Thr Val Gly
    50                  55                  60

Ser Trp Ser Tyr Lys Ser Asp Lys Pro Thr Ile Ala His Pro Tyr Thr
65                  70                  75                  80

Val Gly Ser Trp Ser Tyr Lys Gln Asn Asn Gln Asp Lys Ser Thr Ile
                85                  90                  95

Ser Gln Pro Phe Thr Val Gly Ser Trp Ser Tyr Lys Gln Asp Asn Gln
            100                 105                 110

Asp Lys Ser Thr Ile Ser Gln Thr Tyr Thr Val Gly Ser Arg Ser Tyr
            115                 120                 125

Lys Gln Asn Asp Gln Glu Lys Pro Thr Ile Ala Gln Pro Phe Thr Val
130                 135                 140

Gly Ser Trp Ser Tyr Lys Gln Asp Asn Gln Asp Lys Ser Thr Ile Ser
145                 150                 155                 160

Gln Thr Tyr Thr Val Gly Ser Arg Ser Tyr Lys Gln Asn Asp Gln Glu
                165                 170                 175

Lys Pro Thr Ile Ala Gln Pro Phe Thr Val Gly Ser Trp Ser Tyr Lys
            180                 185                 190

Gln Asp Asn Gln Asp Lys Ser Thr Ile Ser Gln Pro Phe Thr Val Gly
            195                 200                 205

Ser Trp Ser Tyr Lys Gln Ser Asn Gln Asp Lys Ser Thr Ile Ser Gln
        210                 215                 220

Pro Phe Thr Val Gly Ser Trp Ser Tyr Lys Gln Asn Asp Gln Glu Lys
225                 230                 235                 240

Pro Thr Ile Ala Gln Pro Phe Thr Val Gly Ser Trp Ser Tyr Lys Gln
                245                 250                 255

Asp Asn Gln Asp Lys Ser Thr Ile Ser Gln Pro Tyr Thr Val Gly Ser
            260                 265                 270

Trp Ser Tyr Lys Gln Ser Asn Gln Asp Lys Ser Thr Ile Ser Gln Pro
        275                 280                 285

Phe Thr Val Gly Ser Trp Ser Tyr Lys Gln Asn Asp Gln Glu Lys Pro
    290                 295                 300

Thr Ile Ala Gln Pro Tyr Thr Val Gly Ala Trp Trp Tyr Lys Ala Asp
305                 310                 315                 320

Lys Asn Gln Gln Asn His Xaa
                325

<210> SEQ ID NO 233
<211> LENGTH: 213
<212> TYPE: PRT
<213> ORGANISM: Bougainvillea spectabilis

<400> SEQUENCE: 233

Pro Tyr Thr Val Gly Ala Trp Trp Tyr Lys Ala Asp Lys Asn Gln Gln
```

-continued

```
  1               5                  10                 15
Asn His His His Phe Asp Ala Ser Asp Asn Asn Gly Ile Lys Ser
            20                 25                 30
Ser Asn Lys Gly Asn Gln Asp Asp Gln Asp Met Val Gly Gly Ser
            35                 40                 45
Val Phe Phe Thr Glu Glu His Leu Arg Val Gly Met Lys Gln Thr His
    50                 55                 60
Asp Phe Gln Lys Ser Gly Lys Val Lys Phe Leu Pro Arg Asp Val Val
65                  70                 75                  80
Gln Ser Ile Pro Phe Ala Val Asp Lys Leu Pro Glu Ile Leu Asn Ile
                85                 90                 95
Leu Ser Val Asn Pro Lys Ser Ala Gln Ala Met Ala Ile Lys Asp Thr
               100                105                110
Leu Thr Thr Cys Leu Asp Arg Pro Arg Val Lys Lys Glu Asn Arg Thr
               115                120                125
Cys Thr Gln Ser Leu Glu Ser Ile Val Asp Phe Val Ile Asn Glu Leu
               130                135                140
Gly Thr Asn Asn Val Lys Leu Lys Met Met Gly Gln Pro Glu Glu Lys
145                150                155                160
Val Pro Thr Gly Met Gln Glu Tyr Leu Ile Thr Lys Val Thr Lys Leu
               165                170                175
Asp Val Pro Gly Asn Asn Gly Val Ala Cys His Arg Met Ile Tyr Pro
               180                185                190
Tyr Ala Val Tyr Trp Cys His His Gln Lys Asp Ile Gly Gln Tyr Ser
               195                200                205
Val Thr Leu Val Asp
               210
```

<210> SEQ ID NO 234
<211> LENGTH: 129
<212> TYPE: PRT
<213> ORGANISM: Bougainvillea spectabilis

<400> SEQUENCE: 234

```
Leu Pro Tyr Leu Phe His Arg Ser Thr His Ser Pro Lys Met Ala Lys
1               5                  10                 15
Asn Leu Leu Ile Leu Arg Leu Phe Phe Leu Val Cys Leu Val Ala Tyr
            20                 25                 30
Ala Ser Ser Cys Lys Gln Ala Glu Tyr Trp Lys Met Lys Leu Pro Lys
            35                 40                 45
Val Pro Leu Pro Lys Ala Leu Glu Asn Asn Leu Gln Tyr Ser His Pro
    50                 55                 60
Asp Glu Lys Ala Thr Ile Ala Gln Pro Cys Thr Val Gly Ala Trp Leu
65                  70                 75                  80
Tyr Lys Gln Thr Asp Gln Asp Lys Pro Ser Ile Ala Gln Pro Tyr Thr
            85                 90                 95
Val Gly Gly Trp Ser Tyr Lys Lys Asp Lys Ser Thr Ile Ala Gln Pro
               100                105                110
Tyr Thr Val Gly Ala Trp Ser Tyr Lys Gln Asn Asn Gln Asp Lys Ser
               115                120                125
Thr
```

<210> SEQ ID NO 235
<211> LENGTH: 374
<212> TYPE: PRT

<213> ORGANISM: Petiveria alliacea

<400> SEQUENCE: 235

```
Pro Lys Ser His Phe Leu Ser Leu His Gly Asn Lys Glu Asp Asn Glu
1               5                   10                  15

Gly Lys Ser Thr Ile Ala Gln Pro Tyr Thr Val Gly Ala Trp Lys Tyr
            20                  25                  30

Val Val Glu Lys Glu Lys Asp Lys Leu Thr Met Pro Gln Gln Pro Tyr
        35                  40                  45

Thr Val Gly Ala Trp Lys Tyr Asp Val Glu Lys Glu Lys Asp Lys Leu
    50                  55                  60

Thr Met Pro Gln Glu Ser Phe Leu Val Thr Ser Arg Lys Tyr Lys Glu
65                  70                  75                  80

Asp Asn Glu Gly Lys Ser Thr Ile Ala Gln Pro Tyr Thr Val Gly Ala
                85                  90                  95

Trp Arg Tyr Lys Met Asn Asp Ala Asn Asn His Lys Phe His Asn His
            100                 105                 110

Phe Met Asn Gln Phe His Thr Val Asp Gly Asp Lys Leu Leu Gly Ser
        115                 120                 125

Ser Lys Gln Gly Asn Gln Asp Gln Asp Leu Asp Gly Gly Ser Ile Phe
    130                 135                 140

Phe Thr Lys Gln Asn Leu Cys Val Gly Met Lys Gln Arg His Asp Phe
145                 150                 155                 160

Gln Lys Ser Gly Lys Val Lys Phe Trp Pro Lys Asn Met Val Glu Ser
                165                 170                 175

Ile Pro Phe Ala Leu Asp Lys Val Phe Glu Ile Leu Gly His Leu Ser
            180                 185                 190

Ile Asn Thr Asn Ser Phe Glu Ala Lys Thr Ile Lys Glu Thr Leu Ile
        195                 200                 205

Thr Cys Leu Glu Arg Pro Leu Val Lys Glu Asn Arg Thr Cys Ala
    210                 215                 220

Gln Ser Leu Glu Ser Ile Val Asp Phe Val Val Gln Glu Leu Gly Thr
225                 230                 235                 240

Asp Asn Val Lys Val Arg Met Met Ser Gln Thr Glu Asn Glu Val Pro
                245                 250                 255

Asn Gly Met Gln Val Tyr Glu Val Thr Lys Val Glu Lys Leu Asp Ile
            260                 265                 270

Pro Gly Asn Asn Gly Val Ala Cys His Lys Met Leu Tyr Pro Tyr Ala
        275                 280                 285

Val Tyr Trp Cys His His Gln Gln Asp Ile Gly Gln Tyr Ala Val Thr
    290                 295                 300

Leu Lys Thr Ser Gln Gly Asn Leu Val Asp Thr Thr Ala Val Cys His
305                 310                 315                 320

Tyr Asp Thr Tyr Ala Trp Asp Pro Asn Val Pro Ala Leu Lys Tyr Leu
                325                 330                 335

Lys Leu Asn Pro Gly Asp Ala His Val Cys His Phe Ser Gly Ile Asn
            340                 345                 350

Asp Met Phe Trp Ser Leu Asn Thr Pro Lys Ile Thr Asn Arg Lys Val
        355                 360                 365

Thr Leu Asp Ala Thr Ala
    370
```

<210> SEQ ID NO 236
<211> LENGTH: 395

<212> TYPE: PRT
<213> ORGANISM: Phytolacca bogotensis

<400> SEQUENCE: 236

```
Asp Lys Glu Lys Pro Met Ile Asn His Lys Glu Asp Asn Glu Lys Glu
1               5                   10                  15

Met Pro Met Thr Asn Gln Pro Tyr Thr Val Phe Ala Trp Lys Tyr Lys
            20                  25                  30

Gln Asp Asp Gln Glu Lys Pro Met Ile Asn Tyr Lys Glu Asp Asn Glu
        35                  40                  45

Lys Glu Met Pro Met Thr Asn Gln Pro Tyr Thr Val Phe Ser Trp Lys
    50                  55                  60

Tyr Lys Gln Asp Asp Gln Asp Lys Pro Met Ile Asn Tyr Lys Glu Asn
65                  70                  75                  80

Asn Glu Lys Glu Met Pro Met Thr Asn Gln Pro Tyr Thr Val Phe Ala
                85                  90                  95

Trp Lys Tyr Lys Gln Asp Asp Lys Glu Lys Pro Thr Ile Ala Gln Pro
            100                 105                 110

Tyr Thr Ser Ala Asp Asp Ser Asn Thr Asn Asn His Lys Leu His Asp
        115                 120                 125

His Leu Met His His Met Gly Ser Val Asp Asp Arg Asn Thr Leu Thr
    130                 135                 140

Pro Ser Asn Glu Glu Asn Gln Asp Lys Asp Leu Ile Gly Gly Ser Val
145                 150                 155                 160

Phe Phe Val Glu Glu Lys Leu Arg Val Gly Met Lys Gln Arg His Asp
                165                 170                 175

Phe Gln Lys Ile Glu Lys Val Ser Phe Leu Pro Lys Asp Met Val Asp
            180                 185                 190

Thr Ile Pro Phe Gly Val Asp Arg Leu Pro Glu Ala Leu Asn Arg Leu
        195                 200                 205

Ser Ile Asn Pro Asp Ser Val Glu Ala Thr Ser Met Lys Glu Thr Leu
    210                 215                 220

Thr Thr Cys Leu Glu Arg Pro Arg Val Lys Lys Glu Asn Arg Thr Cys
225                 230                 235                 240

Ala Gln Ser Leu Glu Asp Ile Val Asp Phe Val Ile Arg Glu Leu Gly
                245                 250                 255

Ser Asp Asn Val Lys Val Arg Met Met Ser Met Pro Glu Asp Glu Val
            260                 265                 270

Pro Ile Gly Met His Glu Phe Glu Ile Thr Lys Val Asp Lys Leu Glu
        275                 280                 285

Val Pro Gly Gln Asn Gly Val Gly Cys His Lys Met Val Tyr Pro Tyr
    290                 295                 300

Ala Val Tyr Trp Cys His His Gln Gln Asp Ile Gly Gln Tyr Ala Val
305                 310                 315                 320

Thr Leu Val Ser Pro Glu Gly Val Lys Val Glu Thr Thr Ala Val Cys
                325                 330                 335

His Tyr Asp Thr Tyr Ala Trp Asp Pro Asn Val Leu Ala Leu Arg Tyr
            340                 345                 350

Leu Lys Ile Arg Pro Gly Asp Ala Pro Ile Cys His Phe Ser Gly Phe
        355                 360                 365

Asn Asp Met Phe Trp Ser Leu Asn Thr Ala Leu Gln Gly Lys Val Gly
    370                 375                 380

Arg Ser Gly Asn Arg Lys Leu Asp Leu Leu Gln
385                 390                 395
```

<210> SEQ ID NO 237
<211> LENGTH: 335
<212> TYPE: PRT
<213> ORGANISM: Microtea debilis

<400> SEQUENCE: 237

Glu Asn Thr Ile Asp Thr Thr Lys Lys Pro Ser Thr Ser Gln Pro Tyr
1               5                   10                  15

Thr Val Phe Ala Trp Gly Tyr Gly Lys Glu Asn Ala Asn Glu Lys Thr
            20                  25                  30

Thr Asp Thr Thr Glu Lys Pro Ser Thr Ser Gln Pro Tyr Thr Val Phe
        35                  40                  45

Ala Trp Gly Tyr Gly Lys Glu Asn Ala Asn Glu Lys Thr Ile Asp Thr
    50                  55                  60

Thr Glu Lys Pro Ser Thr Ser Gln Pro Tyr Thr Val Phe Ala Trp Arg
65                  70                  75                  80

Tyr Lys Asp Lys Asn Ala Lys Glu Thr Ile Ile Asp Asn Thr Lys Gly
                85                  90                  95

Ser Val Gly Thr Ser His Glu Val Pro His Gln His Phe Met His Lys
            100                 105                 110

Met Ser Ser Ala Val Asp Ala Asn Glu Glu Asp Ala Ser Gly Gly Ser
        115                 120                 125

Phe Phe Phe Met Glu Lys Asp Leu Ser Leu Gly Asn Lys Leu Lys His
    130                 135                 140

Asp Phe Gln Lys Ser Glu Arg Val Ser Phe Leu Pro Arg Asp Val Ala
145                 150                 155                 160

Glu Ser Ile Pro Phe Ser Val Asp Lys Tyr Gly Glu Ile Leu Asn Ile
                165                 170                 175

Leu Ser Leu Lys Pro Glu Ser Ile Asp Ala Lys Ala Ile Arg Glu Thr
            180                 185                 190

Leu Gly Leu Cys Leu Glu Lys Pro Met Ala Lys Glu Glu Asn Arg Thr
        195                 200                 205

Cys Ala Thr Ser Leu Glu Ala Leu Val Asp Phe Val Ile Gly Glu Leu
    210                 215                 220

Gly Thr Asn Asp Val Lys Val Thr Thr Met Ser Lys Lys Phe Glu Glu
225                 230                 235                 240

Val Pro Asn Gly Pro Met Lys Tyr Lys Ile Thr Arg Leu Arg Lys Leu
                245                 250                 255

Glu Thr Pro Ser Asn Thr Ala Val Ala Cys His Lys Met Ser Tyr Pro
            260                 265                 270

Tyr Val Val Tyr Tyr Cys His His Gln Gln Asn Ile Gly Tyr Tyr Ala
        275                 280                 285

Ala Thr Leu Leu Ser Pro Gly Gly Val Ser Val Asp Thr Thr Ala Ile
    290                 295                 300

Cys His Tyr Asp Thr Tyr Ala Trp Asp Pro Glu Val Pro Ala Leu Arg
305                 310                 315                 320

Tyr Leu Asn Ile Lys Pro Gly Asp Ser Pro Val Cys His Phe Ser
                325                 330                 335

<210> SEQ ID NO 238
<211> LENGTH: 325
<212> TYPE: PRT
<213> ORGANISM: Hilleria latifolia

<400> SEQUENCE: 238

Met Gly Lys Asn Phe Ile Leu Leu Arg Ala Phe Phe Leu Leu Ser Ile
1               5                   10                  15

Val Ala Ile His Ala Ser Ser Cys Lys Gln Glu Glu Tyr Trp Lys Met
            20                  25                  30

Lys Leu Pro Asn Val Pro Ile Pro Asn Ala Val Lys Asn Asn Leu Leu
        35                  40                  45

His Ser Asp Lys Asn Glu Lys His Lys Pro Thr Ile Ser Gln Pro Tyr
    50                  55                  60

Thr Val Gly Ser Trp Lys Tyr Asn Glu Gly Glu Lys Lys Gln Asn Pro
65                  70                  75                  80

Ile Thr Asn Gln Pro Tyr Thr Val Gly Ser Trp Lys Tyr Gly Glu Lys
                85                  90                  95

Glu Glu Glu Lys Pro Ser Ile Asn Gln Pro Tyr Thr Val Gly Ser Trp
            100                 105                 110

Lys Tyr Asn Glu Asp Lys Glu Lys Pro Ser Ile Asn Gln Leu Tyr
        115                 120                 125

Thr Val Ser Ala Trp Lys Tyr Asn Glu Asp Lys Asp Arg Glu Lys Pro
    130                 135                 140

Thr Ile Asn Gln Pro Tyr Thr Val Gly Ser Trp Lys Tyr Asn Glu Glu
145                 150                 155                 160

Lys Glu Lys Lys Lys Leu Asn Ile Asn Gln Pro Tyr Thr Val Gly Ser
            165                 170                 175

Trp Lys Tyr Asn Glu Lys Asn Met Lys Val Lys Pro Thr Ile Asn Gln
            180                 185                 190

Pro Tyr Thr Val Gly Ser Trp Lys Tyr Asn Glu Asp Glu Glu Lys Glu
        195                 200                 205

Lys Phe Ile Ile Asn Gln Pro Tyr Thr Val Gly Ser Trp Lys Tyr Asn
    210                 215                 220

Glu Asn Glu Glu Lys Glu Lys Leu Ser Ile Asn Gln Pro Tyr Ile Ala
225                 230                 235                 240

Ile Leu Trp Lys Asn Asn Glu Asp Lys Glu Glu Lys Pro Ser Ile
            245                 250                 255

Asn Gln Pro Tyr Thr Val Gly Ser Trp Lys Tyr Lys Glu Asp Lys Glu
        260                 265                 270

Arg Asp Lys Pro Thr Ile Asp Gln Pro Tyr Thr Val Gly Ser Trp Lys
    275                 280                 285

Tyr Asn Glu Asp Lys Glu Lys Met Lys Leu Ile Ile Asn Gln Pro Tyr
    290                 295                 300

Thr Val Gly Ser Trp Lys Tyr Asn Glu Glu Asn Met Lys Val Lys Pro
305                 310                 315                 320

Thr Ile Asn Gln Pro
            325

<210> SEQ ID NO 239
<211> LENGTH: 274
<212> TYPE: PRT
<213> ORGANISM: Delosperma echinatum

<400> SEQUENCE: 239

Thr Thr Gln Pro Trp Thr Val Ser Leu Trp Lys Tyr Asn Ala Asp Glu
1               5                   10                  15

Lys Lys Tyr Asp Val Asn Asn Ala Lys Gln Asp Gly Ser Ile His His
            20                  25                  30

His Ile His Asn His Asp Gly Glu Met Ala Gly Ala Ser Val Phe Phe

```
                35                  40                  45
Ile Glu Lys Asp Phe His Val Gly Ala Lys Leu Lys His Asp Phe Gln
 50                  55                  60

Lys Arg Pro Lys Ala Pro Leu Leu Ser Ser Glu Ile Ala Arg Ser Ile
 65                  70                  75                  80

Pro Phe Ser Ile Asp Arg Ile Pro Glu Ile Leu Gln Arg Phe Ser Ile
                 85                  90                  95

Ser Pro Glu Ser Ser Glu Ala Thr Ile Ile Lys Glu Thr Leu Ser Leu
            100                 105                 110

Cys Leu Glu Arg Pro Ile Val Lys Ile Glu Asn Arg Thr Cys Ala Gln
        115                 120                 125

Ser Leu Glu Ser Leu Val Glu Phe Ala Val Gln Glu Leu Gly Thr Asn
    130                 135                 140

Asp Ile Lys Ala Thr Met Met Asn Asn Leu Asn His Ile Arg Ser Gly
145                 150                 155                 160

Leu Gln Glu Tyr Thr Val Thr Lys Ile Lys Lys Met Ser Thr Gly Leu
                165                 170                 175

Glu Gly Asn Ala Leu Val Thr Cys His Arg Met Asn Tyr Pro Tyr Val
            180                 185                 190

Ile Tyr Tyr Cys His His Gln Arg Ala Ile Gly Leu Phe Ser Val Thr
        195                 200                 205

Leu Val Asp Pro Lys Gly Val Ala Val Asp Thr Ser Ala Thr Cys His
    210                 215                 220

Tyr Asp Thr Tyr Ala Trp Gln Pro Asp Val Pro Ala Leu Arg Tyr Leu
225                 230                 235                 240

Asn Ile Lys Pro Gly Asp Ser Pro Val Cys His Phe Ala Gly Ala Thr
                245                 250                 255

Asp Ile Ser Trp Thr Ile Asn Lys Ser Asn His Leu Ile Met Ala Thr
            260                 265                 270

Glu Ala

<210> SEQ ID NO 240
<211> LENGTH: 104
<212> TYPE: PRT
<213> ORGANISM: Delosperma echinatum

<400> SEQUENCE: 240

Lys Glu Lys Thr Thr Pro Thr Thr Thr Thr Thr Thr Gln Pro Trp
 1               5                  10                  15

Thr Val Ser Ser Trp Lys Tyr Asn Ala Asp Glu Lys Glu Lys Ile Thr
                 20                  25                  30

Thr Pro Thr Thr Thr Thr Thr Thr Gln Pro Trp Thr Val Ser Ser
            35                  40                  45

Trp Lys Tyr Asn Ala Asp Glu Lys Glu Lys Thr Thr Pro Thr Thr Thr
 50                  55                  60

Thr Thr Gln Pro Trp Thr Val Ser Ser Trp Lys Tyr Asn Ala Asp Glu
 65                  70                  75                  80

Lys Glu Lys Thr Thr Pro Thr Thr Thr Thr Thr Thr Gln Pro Trp Thr
                 85                  90                  95

Val Ser Ser Trp Lys Tyr Asn Ala
            100

<210> SEQ ID NO 241
<211> LENGTH: 451
<212> TYPE: PRT
```

<213> ORGANISM: Astragalus membranaceus

<400> SEQUENCE: 241

```
Met Glu Phe Thr Arg Leu Ser Val Leu Ala Leu Leu Cys Leu Ala Leu
1               5                   10                  15

Val Gly Ser Asp Ala Ser Lys Ser Glu Glu Asp Tyr Trp His Ser Val
            20                  25                  30

Trp Pro Asn Thr Pro Leu Pro Lys Thr Leu Ser Asp Leu Leu Met Pro
        35                  40                  45

Tyr Ser Glu Ile Pro Ile Lys Ala Lys Glu Glu Lys Gln Tyr Trp Thr
    50                  55                  60

Val Phe Phe Glu His Asp Leu Tyr Pro Gly Lys Gln Met Ser Leu Gly
65                  70                  75                  80

Val Gln Lys His Ser Asp Ile His His Glu His Phe Gln Ser Arg Ile
                85                  90                  95

Thr Lys Ala Ser Gln Pro Phe Gly Ala Arg Thr Trp Glu Thr Arg Glu
            100                 105                 110

Lys Glu Ser Gln Pro Phe Gly Ala Arg Thr Trp Glu Ala Arg Lys Gln
        115                 120                 125

Val Ser Gln Pro Phe Gly Ala Arg Thr Trp Glu Thr Ser Glu Lys Val
    130                 135                 140

Ser Gln Pro Phe Gly Ala Arg Thr Trp Glu Thr Ser Glu Lys Ile Ser
145                 150                 155                 160

Gln Pro Phe Gly Ala Arg Thr Trp Glu Ala Arg Lys Asp Val Ile Gln
                165                 170                 175

Pro Phe Gly Ala Arg Thr Trp Glu Thr Asn Glu Lys Val Ser Gln Pro
            180                 185                 190

Phe Gly Ala Arg Thr Trp Glu Ala Arg Lys Glu Val Ser Gln Pro Phe
        195                 200                 205

Gly Ala Arg Thr Trp Glu Thr Ser Glu Lys Ala Ser Gln Pro Phe Gly
    210                 215                 220

Ala Arg Thr Trp Glu Thr His Lys Glu Val Ser Gln Pro Phe Gly Ala
225                 230                 235                 240

Arg Thr Trp Glu Thr Asn Gln Lys Val Ser Gln Pro Phe Gly Ala Arg
                245                 250                 255

Thr Trp Glu Thr Leu Glu Lys Leu Asn Gln Pro Phe Gly Ala Arg Thr
            260                 265                 270

Trp Glu Thr Arg Glu Lys Glu Asn Gln Pro Phe Gly Thr Ser Thr Leu
        275                 280                 285

Gly Pro Glu Lys Asp Ser Ile Asp Asp Tyr Cys Gly Lys Pro Ser Ala
    290                 295                 300

Ile Gly Glu Glu Lys His Cys Ala Leu Ser Leu Lys Ser Met Met Asp
305                 310                 315                 320

Phe Ala Ile Ser Lys Leu Gly Thr Asn Ile Lys Val Ile Ser Ser Ser
                325                 330                 335

Phe Ala Gln Asn Arg Asp Gln Tyr Val Val Glu Val Lys Lys Ile
            340                 345                 350

Gly Asp Lys Ala Val Met Cys His Arg Leu Asn Phe Glu Lys Val Val
        355                 360                 365

Phe Tyr Cys His Gln Val Asn Ala Thr Thr Ser Tyr Met Val Pro Leu
    370                 375                 380

Val Ala Phe Asp Gly Ile Lys Ala Glu Ala Leu Thr Ile Cys His His
385                 390                 395                 400
```

```
Asp Thr Arg Gly Met Asn Pro Asp Val Leu Tyr Asp Val Leu Lys Val
                405                 410                 415

Lys Pro Gly Thr Val Pro Val Cys His Phe Val Gly Asn Lys Ala Val
            420                 425                 430

Ala Trp Val Pro Asn Arg Asp Ala Ser Asn Glu Ser Asn Asp His Pro
        435                 440                 445

Cys Val Ile
    450

<210> SEQ ID NO 242
<211> LENGTH: 317
<212> TYPE: PRT
<213> ORGANISM: Astragalus membranaceus

<400> SEQUENCE: 242

Met Glu Leu Thr Arg Pro Ser Leu Leu Ala Leu Ile Cys Leu Val Val
1               5                   10                  15

Val Gly Ser Asp Ala Ser Lys Ser Gly Glu Asp Tyr Trp His Ser Val
            20                  25                  30

Trp Pro Asn Thr Pro Leu Pro Lys Ile Ile Ser Asp Leu Leu Leu Pro
        35                  40                  45

Tyr Ser Glu Met Pro Ile Lys Ala Lys Glu Lys Gln Tyr Trp Thr
    50                  55                  60

Leu Phe Phe Glu His Asp Leu Tyr Pro Gly Lys Gln Met Ser Leu Gly
65                  70                  75                  80

Ile His Gly His Ser Glu Ile Gln Pro Phe Gly Ala Leu Val Trp Arg
                85                  90                  95

Lys Arg Glu Glu Pro Ser Gln Pro Phe Gly Ala Leu Val Trp Arg Lys
            100                 105                 110

Arg Glu Glu Pro Ser Gln Pro Phe Gly Gly Phe Ala Trp Arg Lys Arg
            115                 120                 125

Glu Glu Pro Ser Gln Pro Phe Gly Ala Arg Asp Arg Trp Thr Arg Glu
            130                 135                 140

Glu Pro Ser Gln His Phe Arg Ala His Thr Gln Lys Leu Glu Lys Asp
145                 150                 155                 160

Ile Ile Asp Glu Phe Cys Gly Ala Ser Ala Ile Gly Glu Asp Lys Tyr
                165                 170                 175

Cys Ala Leu Ser Leu Glu Ala Met Met Asp Phe Ala Ile Ser Lys Leu
            180                 185                 190

Gly Thr Asn Ile Lys Val Ile Ser Ser Leu Ser Lys Asn Gln Asp
            195                 200                 205

Gln Tyr Val Val Gln Glu Val Lys Lys Ile Gly Asn Lys Ala Val Met
    210                 215                 220

Cys His Arg Met Asn Phe Glu Lys Val Leu Phe Tyr Cys His Glu Val
225                 230                 235                 240

Asn Ala Thr Thr Ala Tyr Met Val Gln Leu Val Ala Pro Asp Gly Thr
                245                 250                 255

Lys Ala Glu Ala Leu Thr Ile Cys His His Asp Thr Arg Gly Met Asp
            260                 265                 270

Pro Asn Val Leu Tyr Lys Val Leu Lys Val Lys Pro Gly Thr Ile Pro
    275                 280                 285

Val Cys His Phe Val Gly Asn Lys Ala Val Ala Trp Val Pro Asn Arg
    290                 295                 300

Asp Ala Ser His Glu Ser Ser Asp His Leu Cys Val Thr
305                 310                 315
```

<210> SEQ ID NO 243
<211> LENGTH: 284
<212> TYPE: PRT
<213> ORGANISM: Astragalus membranaceus

<400> SEQUENCE: 243

```
Met Glu Leu Thr Arg Leu Tyr Val Leu Ala Leu Ile Cys Leu Gly Leu
1               5                   10                  15

Val Gly Ser Asn Ala Ser Gln Gly Glu Asp Tyr Trp His Ser Val Trp
            20                  25                  30

Pro Asn Thr Pro Leu Pro Lys Ile Leu Ser Asp Leu Leu Leu Pro Tyr
        35                  40                  45

Ser Glu Met Pro Ile Lys Ala Lys Glu Glu Lys Gln Tyr Trp Thr Val
    50                  55                  60

Phe Phe Glu His Asp Leu Tyr Pro Gly Lys Gln Met Ser Leu Gly Ile
65                  70                  75                  80

His Glu His Ser Glu Ile Gln His Phe Gln Ser Arg Val Thr Lys Ala
                85                  90                  95

Lys His Pro Leu Gly Ile Leu Val Trp Gly Gly Thr Arg Glu Lys Glu
            100                 105                 110

Thr Gln Pro Phe Gly Val Pro Thr Gln Gly Ala Arg Glu Lys Ser Asn
        115                 120                 125

Gln Pro Phe Gly Phe Leu Ile Trp Glu Gln Arg Glu Lys Ala Ser Gln
    130                 135                 140

Pro Phe Arg Ala Arg Thr Leu Gly Thr His Lys Lys Glu Ser Lys Pro
145                 150                 155                 160

Leu Ala Ala Asp Thr Arg Arg Ile Glu Lys Asp Ile Asp Glu Phe
                165                 170                 175

Cys Val Asn Pro Ser Ala Ile Gly Glu Asp Lys Tyr Cys Ala Leu Ser
            180                 185                 190

Leu Glu Ser Met Met Glu Phe Ala Ile Ser Lys Leu Gly Thr Asn Ile
        195                 200                 205

Lys Val Ile Ser Ser Ser Phe Ala Lys Asn Gln Asp Gln Tyr Val Val
    210                 215                 220

Glu Glu Val Lys Lys Ile Gly Asp Lys Ala Val Met Cys His Arg Met
225                 230                 235                 240

Asn Phe Glu Lys Val Phe Phe Tyr Cys His Glu Val Asn Ala Thr Thr
                245                 250                 255

Ala Tyr Met Val Pro Leu Val Ala Pro Asp Gly Thr Lys Ala Glu Ala
            260                 265                 270

Leu Thr Ile Cys His His Asp Thr Arg Gly Met Asp
        275                 280
```

<210> SEQ ID NO 244
<211> LENGTH: 271
<212> TYPE: PRT
<213> ORGANISM: Xanthocercis zambesiaca

<400> SEQUENCE: 244

```
Met Arg Ile Tyr Ile Leu Leu Gln Leu Ala Leu Val Gly Gly Ser His
1               5                   10                  15

Ala His Glu Ser Ile Pro Asp Ala Asp Tyr Trp Gln Ala Ile Trp Pro
            20                  25                  30

Asn Ile Pro Ile Pro Ser Ala Leu Cys Glu Leu Leu Lys Pro Gly Ala
        35                  40                  45
```

Ala Asp Ala Glu Ile Ser Asn Leu Pro Met Lys Ile Asp Asp Thr Gln
 50                  55                  60

Tyr Pro Glu Thr Phe Phe Glu His Asp Leu Tyr Pro Gly Lys Ile
 65                  70                  75                  80

Met Asn Leu Gln Phe Ser Lys Arg Pro Tyr Ala Gln Pro Tyr Gly Val
                 85                  90                  95

Tyr Ser Trp Gly Arg Leu Thr Asn Leu Lys Asn Leu Glu Thr Glu Gly
                100                 105                 110

Phe Thr Tyr Glu Glu Val Cys Val Lys Asn Pro Asn Ala Lys Gly Glu
                115                 120                 125

His Asn Tyr Cys Ala Lys Ser Leu Gly Thr Leu Ile Gly Phe Ala Ile
                130                 135                 140

Ser Lys Leu Gly Lys Asn Ile Gln Val Leu Ser Ser Ser Phe Val Asp
145                 150                 155                 160

Lys Gln Asn Gln Tyr Thr Ile Glu Gly Val His Asn Leu Gly Asp Lys
                165                 170                 175

Ala Val Met Cys Arg Arg Leu Asn Phe Gln Lys Val Val Phe Tyr Cys
                180                 185                 190

Gln Glu Ile His Lys Thr Thr Ala Phe Met Val Pro Leu Val Ala Ala
                195                 200                 205

Asp Gly Thr Lys Thr Lys Ala Leu Ala Val Cys His Ser Asp Thr Ser
                210                 215                 220

Gly Met Asn Ala Glu Val Leu Tyr Glu Leu Leu Lys Ile Lys Pro Gly
225                 230                 235                 240

Thr Ala Ser Ala Cys His Phe Leu Gly Ser Lys Ala Ile Leu Trp Val
                245                 250                 255

Pro Asn Phe Val Val Asp Asn Phe Tyr Asn Asn Asn Glu Ala Ser
                260                 265                 270

<210> SEQ ID NO 245
<211> LENGTH: 342
<212> TYPE: PRT
<213> ORGANISM: Lathyrus sativus

<400> SEQUENCE: 245

Met Gly Phe Thr His Leu Ser Leu Leu Ala Leu Leu Cys Leu Val Phe
1               5                   10                  15

Val Gly Ile Asn Ala Ser Lys Ser Asp Glu Glu Tyr Trp Lys Ser Ile
                20                  25                  30

Trp Pro Asn Thr Pro Ile Pro Arg Pro Leu Leu Asp Leu Leu Leu Pro
                35                  40                  45

Asp Ser Lys Thr Ser Val Pro Ile Arg Asp Tyr Glu Glu Asn Gln Tyr
 50                  55                  60

Trp Thr Val Phe Phe Glu His Asp Leu His Pro Gly Lys Lys Met Ser
 65                  70                  75                  80

Leu Gly Ile His Lys His Ser Lys Thr His Val Ser Val Glu Thr Arg
                85                  90                  95

Asn Gln Pro Phe Gly Ile Asn Ser Trp Trp Asp Arg Lys Ser Ser Glu
                100                 105                 110

Lys Ala Ser Gln Gly Phe Glu Thr His Arg Pro Thr Asn Lys Ala Ile
                115                 120                 125

Lys Glu Glu Ile Lys Lys Pro Ile Glu Thr Phe Gly Ile Leu Ile Trp
                130                 135                 140

Thr Gly Lys Pro Asn Gln Asp Ser Gly Ser Arg Thr Lys Ile Asp Lys

```
            145                 150                 155                 160
Ala Ser Val Lys Lys Ser Glu Arg Leu Val Gln Thr Tyr Thr Val Ser
            165                 170                 175

Ser Leu Thr Glu Glu Met Asp Ile Phe Arg Asp Tyr Cys Gly Lys
        180                 185                 190

Pro Ser Pro Ile Gly Glu Asp Lys Tyr Cys Ala Pro Ser Leu Glu Ser
        195                 200                 205

Met Met Asn Phe Val Ile Ser Lys Leu Gly Lys Asn Ile Lys Ala Met
        210                 215                 220

Ser Ser Ser Phe Ser Gln Asn Gln Glu Glu Tyr Val Ile Glu Glu Val
225                 230                 235                 240

Lys Lys Leu Gly Glu Lys Thr Val Met Cys His Arg Leu Asn Phe Lys
                245                 250                 255

Lys Val Ala Phe Tyr Cys His Gln Val Asn Ala Thr Ser Thr Tyr Met
                260                 265                 270

Val Pro Leu Val Ala Ser Asp Gly Thr Lys Ser Asn Ala Leu Thr Ile
            275                 280                 285

Cys His His Asp Thr Arg Gly Met Asp Pro Ser Ile Ile Tyr Glu Ile
            290                 295                 300

Leu Lys Val Lys Pro Gly Thr Val Pro Val Cys His Phe Ile Gly Asn
305                 310                 315                 320

Lys Ala Ile Ala Trp Ile Pro Asn Glu Glu Asp Val Thr Thr Ser Asn
                325                 330                 335

Gly His Pro Cys Val Ile
                340

<210> SEQ ID NO 246
<211> LENGTH: 142
<212> TYPE: PRT
<213> ORGANISM: Senna hebecarpa

<400> SEQUENCE: 246

Met Lys Phe Pro Arg Leu Ala Leu Leu Ala Leu Phe Cys Val Phe Val
1               5                   10                  15

Val Gly Thr Asp Ala Ser Pro Ser Asp Glu Asp Tyr Trp Arg Ser Ile
            20                  25                  30

Trp Pro Asn Thr Pro Met Pro Lys Asn Leu Gln Asp Leu Leu Lys Pro
        35                  40                  45

Ala Asn Glu Ile Thr Ser Thr Lys Val Glu Asp Thr Gln Tyr Pro Ser
    50                  55                  60

Asn Phe Phe Leu Val Lys Asp Ile Gln Gly Gly Arg Lys Met Lys Leu
65                  70                  75                  80

His Phe Asn Lys Arg Ser Asn Ala Gln Pro Phe Gly Val Phe Ala Trp
                85                  90                  95

Ser Lys His Lys Val Asn Asn Asp Ser Asp Thr Ser Thr Glu Val Glu
            100                 105                 110

Asp Thr Gln Tyr Pro Ser Ile Phe Phe Glu Asn Asp Leu His Pro
        115                 120                 125

Gly Gln Gln Met Asn Leu Lys Phe Asn Lys Arg Ser Asn Ala
    130                 135                 140

<210> SEQ ID NO 247
<211> LENGTH: 210
<212> TYPE: PRT
<213> ORGANISM: Senna hebecarpa
```

<400> SEQUENCE: 247

Phe Leu Val Lys Asp Ile Gln Gly Gly Arg Lys Met Lys Leu His Phe
1               5                   10                  15

Asn Lys Arg Ser Asn Ala Gln Pro Tyr Gly Val Phe Ala Trp Arg Lys
            20                  25                  30

His Lys Val Asn Ser Asp Ser Asp Thr Ser Thr Glu Val Glu Arg Gly
        35                  40                  45

His Ala Asn Ser Leu Glu Lys Phe Thr Leu Glu Glu Glu Leu Cys Glu
    50                  55                  60

Lys Arg Pro Leu Ala Val Gly Glu Asp Lys Ile Cys Ala Lys Ser Leu
65                  70                  75                  80

Glu Ser Leu Val Asp Phe Ile Ile Ser Lys Leu Gly Lys Asp Val Glu
                85                  90                  95

Pro Leu Ser Ser Ser Phe Val Pro His Gln Asn Gln Tyr Asn Ile Leu
            100                 105                 110

Asp Gly Val Gln Lys Val Ala Glu Asp Gly Val Met Cys His Arg Leu
        115                 120                 125

Asn Phe Arg Asn Val Val Phe Tyr Cys His Gln Val Asn Ala Thr Ser
    130                 135                 140

Ala Tyr Thr Val Pro Leu Ala Ala Pro Asp Gly Thr Glu Thr Lys Ala
145                 150                 155                 160

Leu Val Val Cys His His Asp Thr Arg Gly Ile Asn Glu His Ile Leu
                165                 170                 175

Phe His Gln Leu Lys Ile Lys Pro Gly Thr Val Pro Val Cys His Phe
            180                 185                 190

Leu Gly Thr Lys Ala Leu Leu Trp Val Pro Asn Asn Lys Pro Ile Gln
        195                 200                 205

Ala Ile
210

<210> SEQ ID NO 248
<211> LENGTH: 276
<212> TYPE: PRT
<213> ORGANISM: Apios americana

<400> SEQUENCE: 248

Met Glu Phe His His Leu Leu Ile Ser Thr Cys Val Ile Phe Ser Leu
1               5                   10                  15

Ala Ile Val Gly Glu Thr His Ala His Ala Ser Leu Leu Asp Glu Asp
            20                  25                  30

Tyr Trp Gln Ala Val Trp Pro Asn Thr Ala Ile Pro Asn Ala Leu Arg
        35                  40                  45

Glu Leu Leu Lys Pro Gly Pro Ala Gly Val Gly Ile Asn Asp Leu Pro
    50                  55                  60

Met Lys Ile Asp Asp Thr Gln Tyr Pro Lys Thr Phe Phe Leu Ser Arg
65                  70                  75                  80

Asp Leu Tyr Pro Gly Lys Thr Met Asn Met Glu Phe Ser Lys Ile Pro
                85                  90                  95

Tyr Ala Gln Pro Tyr Gly Val Tyr Ala Trp Ser Pro Lys Ile Lys Asp
            100                 105                 110

Ile Glu Lys Glu Gly Tyr Thr Phe Asn Asp Val Cys Val Asp Ser Ala
        115                 120                 125

Pro Ala Lys Gly Glu Asp Lys Tyr Cys Ala Lys Ser Leu Gly Thr Leu
    130                 135                 140

```
Ile Gly Phe Ser Ile Ser Lys Leu Gly Lys Asn Ile Gln Val Leu Ser
145                 150                 155                 160

Ser Ser Phe Val Lys Lys Gln Glu Gln Tyr Thr Val Glu Gly Val Gln
                165                 170                 175

Asn Leu Gly Asp Lys Ala Val Met Cys His Arg Leu Asn Phe Gln Lys
            180                 185                 190

Val Val Phe Tyr Cys His Glu Ile Lys Glu Thr Asn Ala Tyr Met Val
        195                 200                 205

Ala Leu Val Ala Gly Asp Gly Thr Lys Thr Gln Ala Val Ala Val Cys
    210                 215                 220

His Ala Asp Thr Ser Gly Met Asn His Asp Phe Val His Lys Met Leu
225                 230                 235                 240

Lys Tyr Asp Pro Gly Thr Asn Pro Leu Cys His Phe Leu Gly Asn Lys
                245                 250                 255

Ala Val Leu Trp Val Pro Asn Leu Ala Val Asn Asn Ala Tyr Arg Thr
            260                 265                 270

Asn Val Ala Thr
            275

<210> SEQ ID NO 249
<211> LENGTH: 702
<212> TYPE: PRT
<213> ORGANISM: Achyranthes bidentata

<400> SEQUENCE: 249

Met Ala Leu His Ser Lys Leu Gln Leu Ser Thr Phe Phe Leu Leu Val
1               5                   10                  15

Phe Leu Val Tyr Tyr Val Ser Ser Cys Glu Gln Glu Lys Tyr Trp Gln
                20                  25                  30

Met Lys Leu Pro Asn Val Pro Met Pro Gln Ala Ile Arg Asp Asn Leu
            35                  40                  45

Phe His Ser Ser Gly Lys Tyr Glu Ala Asp Asn Asn Pro Lys Val Lys
        50                  55                  60

Ala Glu Asp Gly Val Glu Pro Phe Thr Leu His Ser Asn Lys Lys Ser
65                  70                  75                  80

Ser Thr Asn Gln Pro Phe Thr Val Phe Ala Trp Lys Tyr Tyr Val Asp
                85                  90                  95

Asn Lys Leu Lys Asp Lys Ala Glu Asp Val Val Lys Pro Phe Ile Leu
            100                 105                 110

Gly Ser Glu Thr Lys Val Gly Thr Asn Gln Pro Phe Thr Val Phe Gly
        115                 120                 125

Trp Gly Tyr Asp Val Gly Asn Lys Pro Lys Lys Ala Glu Asp Val
    130                 135                 140

Val Glu Ser Leu Thr Leu Asn Ser Asn Lys Lys Ala Gly Thr Asn Gln
145                 150                 155                 160

Pro Phe Thr Val Phe Gly Trp Asn Tyr Asp Ala Asn His Lys Leu Lys
                165                 170                 175

Glu Lys Ser Gln Asp Val Val Glu Arg Phe Thr Leu Asp Ser Asn Thr
            180                 185                 190

Lys Val Gly Thr Asn Gln Pro Phe Thr Val Phe Gly Trp Gly Tyr Asp
        195                 200                 205

Ala Gly Asn Lys Pro Lys Asp Lys Val Glu Asn Val Leu Glu Ser Leu
    210                 215                 220

Thr Leu Asp Ser Asn Lys Lys Ala Gly Thr Asn Gln Pro Phe Thr Val
225                 230                 235                 240
```

```
Phe Gly Trp Asn Tyr Asp Ala Asn His Lys Leu Lys Glu Lys Ser Gln
                245                 250                 255

Asp Val Val Glu Pro Phe Thr Phe Asp Ser Asn Thr Lys Val Gly Thr
            260                 265                 270

Asn Gln Pro Phe Thr Val Phe Gly Trp Gly Tyr Asp Ala Gly Asn Lys
        275                 280                 285

Pro Lys Asp Lys Val Glu Asn Val Leu Glu Ser Leu Thr Leu Asp Ser
    290                 295                 300

Asn Lys Lys Ala Gly Thr Asn Gln Pro Phe Thr Val Phe Gly Trp Lys
305                 310                 315                 320

Tyr Asp Ala Asn His Lys Leu Lys Glu Lys Ser Gln Asp Val Val Glu
                325                 330                 335

Pro Phe Ile His Asp Leu Asn Thr Lys Val Gly Thr Asn Gln Pro Tyr
            340                 345                 350

Thr Val Phe Gly Trp Gly Tyr Glu Val Gly Asn Asn Pro Lys Gly Lys
        355                 360                 365

Asp Glu Asp Val Val Glu Ser Leu Ser Leu Asp Ser Asn Lys Lys Ala
    370                 375                 380

Arg Thr Asn Gln Pro Phe Thr Val Phe Gly Trp Lys Tyr Asp Ala Asn
385                 390                 395                 400

His Lys Leu Lys Asp Lys Ser Gln Ser Leu Glu Ser Asn Thr Lys Val
                405                 410                 415

Gly Thr Asn Gln Pro Phe Thr Val Phe Gly Trp Asn Tyr Ala Phe Glu
            420                 425                 430

Asn Leu Lys Ser Lys Ala Gly Asp Val Val Lys Ala Pro Asp Met Lys
        435                 440                 445

Glu Thr Ser His Asp His Tyr His His Phe Leu Asn Lys Asn Lys Asn
    450                 455                 460

Ser Asn Glu Glu Asp Pro Asn Gly Gly Ser Leu Phe Phe Val Glu Lys
465                 470                 475                 480

Ser Leu Arg Leu Gly Met Ile Leu Lys His Asp Phe Gln Lys Thr Pro
                485                 490                 495

Lys Ile Pro Phe Leu Pro Lys Lys Ile Ala Gln Thr Ile Pro Phe Lys
            500                 505                 510

Val Glu Lys Val Thr Asp Ile Leu Asn Leu Phe Ser Leu Asp Ser Glu
        515                 520                 525

Ser Thr Glu Gly Ile Ala Ile Lys Glu Thr Leu Asp Val Cys Leu Gln
    530                 535                 540

Arg Pro Lys Val Lys Lys Glu Asn Arg Thr Cys Ala Gln Ser Met Glu
545                 550                 555                 560

Asp Val Val Asp Phe Val Val Gly Glu Leu Gly Thr Asn Asp Val Lys
                565                 570                 575

Val Arg Met Met Asn Asn Asn Ile Glu Val Pro Asn Gly Ile Gln Asp
            580                 585                 590

Tyr Leu Ile Thr Lys Val Lys Lys Leu Glu Val Thr Asn Met Asn Gly
        595                 600                 605

Val Ala Cys His Arg Met Ser Tyr Pro Tyr Val Tyr Tyr Cys His
    610                 615                 620

His Gln Lys Asp Ile Gly His Tyr Asp Val Thr Leu Val Ser Pro Thr
625                 630                 635                 640

Ser Gly Ser Arg Pro Ile Gln Thr Thr Ala Val Cys His Tyr Asp Thr
                645                 650                 655
```

```
Tyr Ala Trp Gln Pro Asp Val Pro Ala Leu Gln His Leu Gly Ile Arg
            660                 665                 670

Pro Gly Asp Ala Pro Val Cys His Phe Ser Ala Ile Asn Asp Met Phe
        675                 680                 685

Trp Ser Val Lys Val Gly Ser Lys Ser Leu Asp Met Val Gln
    690                 695                 700

<210> SEQ ID NO 250
<211> LENGTH: 190
<212> TYPE: PRT
<213> ORGANISM: Celtis occidentalis

<400> SEQUENCE: 250

Met Ala Glu Met Lys Ser Ser Arg Ser Val Ile Val Ala Leu Leu Ser
1               5                   10                  15

Leu Leu Leu Tyr Ser Val Ser Thr Ala Glu Ser Arg Lys Asn Pro Ala
            20                  25                  30

Glu Tyr Trp Lys Thr Val Met Lys Asp Gln Pro Met Pro Glu Leu Ile
        35                  40                  45

Arg Glu Leu Val His Pro Glu Leu Phe Glu Gln Glu His Phe Asp His
    50                  55                  60

Asn Glu Gly Arg Val Asp Lys Lys Ser Asp Lys Ser Phe Thr Lys Glu
65                  70                  75                  80

Ser Glu Ser Ser Ile Ser Asn Leu Asp Asn Ile Lys Asp Ser Gln Lys
                85                  90                  95

Ile Ala Lys Asp Phe Glu Leu Asp Thr Asp Ser Gln Pro Phe Gly Val
            100                 105                 110

Phe Gly Trp Val Lys Asp Ser Gln Lys Phe Ala Lys Asp Phe Glu Leu
        115                 120                 125

Asp Lys Arg Ser Gln Pro Phe Gly Val Phe Gly Trp Ala Lys Asp Ser
    130                 135                 140

Gln Lys Phe Val Asn Asp Phe Glu Leu Asp Thr Asn Ser Gln Pro Phe
145                 150                 155                 160

Gly Val Phe Gly Trp Ala Lys Asp Ser Gln Lys Phe Asn Asn Asp Phe
                165                 170                 175

Gly Pro Asn Pro His Gln Arg Ile Glu Gly Asn Ala Lys Ala
            180                 185                 190

<210> SEQ ID NO 251
<211> LENGTH: 8
<212> TYPE: PRT
<213> ORGANISM: Solanum virginianum

<400> SEQUENCE: 251

Gln Pro Tyr Gly Val Tyr Val Trp
1               5

<210> SEQ ID NO 252
<211> LENGTH: 20
<212> TYPE: DNA
<213> ORGANISM: Artificial Sequence
<220> FEATURE:
<223> OTHER INFORMATION: 5'-adapter for synthesis of Sali3-2 as an IDT
      gBlock

<400> SEQUENCE: 252
tgcccaaatt cgcgaccggt                                            20

<210> SEQ ID NO 253
```

-continued

```
<211> LENGTH: 20
<212> TYPE: DNA
<213> ORGANISM: Artificial Sequence
<220> FEATURE:
<223> OTHER INFORMATION: 3'-adapter for synthesis of Sali3-2 as an IDT
      gBlock

<400> SEQUENCE: 253
ctcgaggcct ttaactctgg                                               20

<210> SEQ ID NO 254
<211> LENGTH: 276
<212> TYPE: PRT
<213> ORGANISM: Artificial Sequence
<220> FEATURE:
<223> OTHER INFORMATION: Glyma.12G217400-[QPAGVYTW]

<400> SEQUENCE: 254
```

Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
            20                  25                  30

Tyr Trp Glu Ala Val Trp Pro Asn Thr Pro Ile Pro Thr Ala Leu Arg
        35                  40                  45

Glu Leu Leu Lys Pro Leu Pro Ala Gly Val Glu Ile Asp Glu Leu Pro
    50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Pro Ala Gly Val Tyr Thr Trp Leu Thr Asp Ile Lys Asp
            100                 105                 110

Thr Ser Lys Glu Gly Tyr Ser Phe Glu Glu Ile Cys Ile Lys Lys Glu
        115                 120                 125

Ala Phe Glu Gly Glu Glu Lys Phe Cys Ala Lys Ser Leu Gly Thr Val
    130                 135                 140

Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
            180                 185                 190

Ala Val Phe Tyr Cys His Lys Val Arg Glu Thr Thr Ala Phe Met Val
        195                 200                 205

Pro Leu Val Ala Gly Asp Gly Thr Lys Thr Gln Ala Leu Ala Val Cys
    210                 215                 220

His Ser Asp Thr Ser Gly Met Asn His His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Asp Thr Ala Tyr Gln Thr
            260                 265                 270

Asn Val Val Val
        275

```
<210> SEQ ID NO 255
<211> LENGTH: 8
<212> TYPE: PRT
```

<213> ORGANISM: Artificial Sequence
<220> FEATURE:
<223> OTHER INFORMATION: Lyciumin-QPAGVYTW

<400> SEQUENCE: 255

Gln Pro Ala Gly Val Tyr Thr Trp
1               5

<210> SEQ ID NO 256
<211> LENGTH: 276
<212> TYPE: PRT
<213> ORGANISM: Artificial Sequence
<220> FEATURE:
<223> OTHER INFORMATION: Glyma.12G217400-[QPYAVYTW]

<400> SEQUENCE: 256

Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
                20                  25                  30

Tyr Trp Glu Ala Val Trp Pro Asn Thr Pro Ile Pro Thr Ala Leu Arg
            35                  40                  45

Glu Leu Leu Lys Pro Leu Pro Ala Gly Val Glu Ile Asp Glu Leu Pro
        50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Pro Tyr Ala Val Tyr Thr Trp Leu Thr Asp Ile Lys Asp
                100                 105                 110

Thr Ser Lys Glu Gly Tyr Ser Phe Glu Glu Ile Cys Ile Lys Lys Glu
            115                 120                 125

Ala Phe Glu Gly Glu Glu Lys Phe Cys Ala Lys Ser Leu Gly Thr Val
        130                 135                 140

Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
                180                 185                 190

Ala Val Phe Tyr Cys His Lys Val Arg Glu Thr Thr Ala Phe Met Val
            195                 200                 205

Pro Leu Val Ala Gly Asp Gly Thr Lys Thr Gln Ala Leu Ala Val Cys
        210                 215                 220

His Ser Asp Thr Ser Gly Met Asn His His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Asp Thr Ala Tyr Gln Thr
            260                 265                 270

Asn Val Val Val
        275

<210> SEQ ID NO 257
<211> LENGTH: 8
<212> TYPE: PRT
<213> ORGANISM: Artificial Sequence
<220> FEATURE:

<223> OTHER INFORMATION: Lyciumin-QPYAVYTW

<400> SEQUENCE: 257

Gln Pro Tyr Ala Val Tyr Thr Trp
1               5

<210> SEQ ID NO 258
<211> LENGTH: 276
<212> TYPE: PRT
<213> ORGANISM: Artificial Sequence
<220> FEATURE:
<223> OTHER INFORMATION: Glyma.12G217400-[QPYGAYTW]

<400> SEQUENCE: 258

Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
            20                  25                  30

Tyr Trp Glu Ala Val Trp Pro Asn Thr Pro Ile Pro Thr Ala Leu Arg
        35                  40                  45

Glu Leu Leu Lys Pro Leu Pro Ala Gly Val Glu Ile Asp Glu Leu Pro
    50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Pro Tyr Gly Ala Tyr Thr Trp Leu Thr Asp Ile Lys Asp
            100                 105                 110

Thr Ser Lys Glu Gly Tyr Ser Phe Glu Glu Ile Cys Ile Lys Lys Glu
        115                 120                 125

Ala Phe Glu Gly Glu Glu Lys Phe Cys Ala Lys Ser Leu Gly Thr Val
    130                 135                 140

Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
            180                 185                 190

Ala Val Phe Tyr Cys His Lys Val Arg Glu Thr Thr Ala Phe Met Val
        195                 200                 205

Pro Leu Val Ala Gly Asp Gly Thr Lys Thr Gln Ala Leu Ala Val Cys
    210                 215                 220

His Ser Asp Thr Ser Gly Met Asn His His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Asp Thr Ala Tyr Gln Thr
            260                 265                 270

Asn Val Val Val
        275

<210> SEQ ID NO 259
<211> LENGTH: 8
<212> TYPE: PRT
<213> ORGANISM: Artificial Sequence
<220> FEATURE:
<223> OTHER INFORMATION: Lyciumin-QPYGAYTW

```
<400> SEQUENCE: 259

Gln Pro Tyr Gly Ala Tyr Thr Trp
1               5

<210> SEQ ID NO 260
<211> LENGTH: 276
<212> TYPE: PRT
<213> ORGANISM: Artificial Sequence
<220> FEATURE:
<223> OTHER INFORMATION: Glyma.12G217400-[QPYGVATW]

<400> SEQUENCE: 260

Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
            20                  25                  30

Tyr Trp Glu Ala Val Trp Pro Asn Thr Pro Ile Pro Thr Ala Leu Arg
        35                  40                  45

Glu Leu Leu Lys Pro Leu Pro Ala Gly Val Glu Ile Asp Glu Leu Pro
    50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Pro Tyr Gly Val Ala Thr Trp Leu Thr Asp Ile Lys Asp
            100                 105                 110

Thr Ser Lys Glu Gly Tyr Ser Phe Glu Glu Ile Cys Ile Lys Lys Glu
        115                 120                 125

Ala Phe Glu Gly Glu Glu Lys Phe Cys Ala Lys Ser Leu Gly Thr Val
    130                 135                 140

Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
            180                 185                 190

Ala Val Phe Tyr Cys His Lys Val Arg Glu Thr Thr Ala Phe Met Val
        195                 200                 205

Pro Leu Val Ala Gly Asp Gly Thr Lys Thr Gln Ala Leu Ala Val Cys
    210                 215                 220

His Ser Asp Thr Ser Gly Met Asn His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Asp Thr Ala Tyr Gln Thr
            260                 265                 270

Asn Val Val Val
        275

<210> SEQ ID NO 261
<211> LENGTH: 8
<212> TYPE: PRT
<213> ORGANISM: Artificial Sequence
<220> FEATURE:
<223> OTHER INFORMATION: Lyciumin-[QPYGVATW]

<400> SEQUENCE: 261
```

Gln Pro Tyr Gly Val Ala Thr Trp
1               5

<210> SEQ ID NO 262
<211> LENGTH: 276
<212> TYPE: PRT
<213> ORGANISM: Artificial Sequence
<220> FEATURE:
<223> OTHER INFORMATION: Glyma.12G217400-[QPYGVYAW]

<400> SEQUENCE: 262

Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
            20                  25                  30

Tyr Trp Glu Ala Val Trp Pro Asn Thr Pro Ile Pro Thr Ala Leu Arg
        35                  40                  45

Glu Leu Leu Lys Pro Leu Pro Ala Gly Val Glu Ile Asp Glu Leu Pro
    50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Pro Tyr Gly Val Tyr Ala Trp Leu Thr Asp Ile Lys Asp
            100                 105                 110

Thr Ser Lys Glu Gly Tyr Ser Phe Glu Glu Ile Cys Ile Lys Lys Glu
        115                 120                 125

Ala Phe Glu Gly Glu Glu Lys Phe Cys Ala Lys Ser Leu Gly Thr Val
    130                 135                 140

Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
            180                 185                 190

Ala Val Phe Tyr Cys His Lys Val Arg Glu Thr Thr Ala Phe Met Val
        195                 200                 205

Pro Leu Val Ala Gly Asp Gly Thr Lys Thr Gln Ala Leu Ala Val Cys
    210                 215                 220

His Ser Asp Thr Ser Gly Met Asn His His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Asp Thr Ala Tyr Gln Thr
            260                 265                 270

Asn Val Val Val
        275

<210> SEQ ID NO 263
<211> LENGTH: 8
<212> TYPE: PRT
<213> ORGANISM: Artificial Sequence
<220> FEATURE:
<223> OTHER INFORMATION: Lyciumin-[QPYGVYAW]

<400> SEQUENCE: 263

Gln Pro Tyr Gly Val Tyr Ala Trp
1               5

<210> SEQ ID NO 264
<211> LENGTH: 276
<212> TYPE: PRT
<213> ORGANISM: Artificial Sequence
<220> FEATURE:
<223> OTHER INFORMATION: Glyma.12G217400-[QPYTVYTW]

<400> SEQUENCE: 264

```
Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
            20                  25                  30

Tyr Trp Glu Ala Val Trp Pro Asn Thr Pro Ile Pro Thr Ala Leu Arg
        35                  40                  45

Glu Leu Leu Lys Pro Leu Pro Ala Gly Val Glu Ile Asp Glu Leu Pro
    50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Pro Tyr Thr Val Tyr Thr Trp Leu Thr Asp Ile Lys Asp
            100                 105                 110

Thr Ser Lys Glu Gly Tyr Ser Phe Glu Glu Ile Cys Ile Lys Lys Glu
        115                 120                 125

Ala Phe Glu Gly Glu Glu Lys Phe Cys Ala Lys Ser Leu Gly Thr Val
    130                 135                 140

Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
            180                 185                 190

Ala Val Phe Tyr Cys His Lys Val Arg Glu Thr Thr Ala Phe Met Val
        195                 200                 205

Pro Leu Val Ala Gly Asp Gly Thr Lys Thr Gln Ala Leu Ala Val Cys
    210                 215                 220

His Ser Asp Thr Ser Gly Met Asn His His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Asp Thr Ala Tyr Gln Thr
            260                 265                 270

Asn Val Val Val
        275
```

<210> SEQ ID NO 265
<211> LENGTH: 8
<212> TYPE: PRT
<213> ORGANISM: Artificial Sequence
<220> FEATURE:
<223> OTHER INFORMATION: Lyciumin-[QPYTVYTW]

<400> SEQUENCE: 265

```
Gln Pro Tyr Thr Val Tyr Thr Trp
1               5
```

```
<210> SEQ ID NO 266
<211> LENGTH: 276
<212> TYPE: PRT
<213> ORGANISM: Artificial Sequence
<220> FEATURE:
<223> OTHER INFORMATION: Glyma.12G217400-[QPYGVYTY]

<400> SEQUENCE: 266

Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
            20                  25                  30

Tyr Trp Glu Ala Val Trp Pro Asn Thr Pro Ile Pro Thr Ala Leu Arg
        35                  40                  45

Glu Leu Leu Lys Pro Leu Pro Ala Gly Val Glu Ile Asp Glu Leu Pro
    50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Pro Tyr Gly Val Tyr Thr Tyr Leu Thr Asp Ile Lys Asp
            100                 105                 110

Thr Ser Lys Glu Gly Tyr Ser Phe Glu Glu Ile Cys Ile Lys Lys Glu
        115                 120                 125

Ala Phe Glu Gly Glu Glu Lys Phe Cys Ala Lys Ser Leu Gly Thr Val
    130                 135                 140

Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
            180                 185                 190

Ala Val Phe Tyr Cys His Lys Val Arg Glu Thr Thr Ala Phe Met Val
        195                 200                 205

Pro Leu Val Ala Gly Asp Gly Thr Lys Thr Gln Ala Leu Ala Val Cys
    210                 215                 220

His Ser Asp Thr Ser Gly Met Asn His His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Asp Thr Ala Tyr Gln Thr
            260                 265                 270

Asn Val Val Val
        275

<210> SEQ ID NO 267
<211> LENGTH: 8
<212> TYPE: PRT
<213> ORGANISM: Artificial Sequence
<220> FEATURE:
<223> OTHER INFORMATION: Lyciumin-type peptide [QPYGVYTY]

<400> SEQUENCE: 267

Gln Pro Tyr Gly Val Tyr Thr Tyr
1               5

<210> SEQ ID NO 268
<211> LENGTH: 8
```

```
<212> TYPE: PRT
<213> ORGANISM: Artificial Sequence
<220> FEATURE:
<223> OTHER INFORMATION: Lyciumin-type peptide [QPYGVYFY]

<400> SEQUENCE: 268

Gln Pro Tyr Gly Val Tyr Phe Tyr
1               5

<210> SEQ ID NO 269
<211> LENGTH: 276
<212> TYPE: PRT
<213> ORGANISM: Artificial Sequence
<220> FEATURE:
<223> OTHER INFORMATION: Glyma.12G217400-[QPWGVGTW]

<400> SEQUENCE: 269

Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
            20                  25                  30

Tyr Trp Glu Ala Val Trp Pro Asn Thr Pro Ile Pro Thr Ala Leu Arg
        35                  40                  45

Glu Leu Leu Lys Pro Leu Pro Ala Gly Val Glu Ile Asp Glu Leu Pro
    50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Pro Trp Gly Val Gly Thr Trp Leu Thr Asp Ile Lys Asp
            100                 105                 110

Thr Ser Lys Glu Gly Tyr Ser Phe Glu Glu Ile Cys Ile Lys Lys Glu
        115                 120                 125

Ala Phe Glu Gly Glu Lys Phe Cys Ala Lys Ser Leu Gly Thr Val
    130                 135                 140

Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
            180                 185                 190

Ala Val Phe Tyr Cys His Lys Val Arg Glu Thr Thr Ala Phe Met Val
        195                 200                 205

Pro Leu Val Ala Gly Asp Gly Thr Lys Thr Gln Ala Leu Ala Val Cys
    210                 215                 220

His Ser Asp Thr Ser Gly Met Asn His His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Asp Thr Ala Tyr Gln Thr
            260                 265                 270

Asn Val Val Val
        275

<210> SEQ ID NO 270
<211> LENGTH: 276
<212> TYPE: PRT
<213> ORGANISM: Artificial Sequence
```

```
<220> FEATURE:
<223> OTHER INFORMATION: Glyma.12G217400-[QPWGVGAW]

<400> SEQUENCE: 270

Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
            20                  25                  30

Tyr Trp Glu Ala Val Trp Pro Asn Thr Pro Ile Pro Thr Ala Leu Arg
        35                  40                  45

Glu Leu Leu Lys Pro Leu Pro Ala Gly Val Glu Ile Asp Glu Leu Pro
50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Pro Trp Gly Val Gly Ala Trp Leu Thr Asp Ile Lys Asp
            100                 105                 110

Thr Ser Lys Glu Gly Tyr Ser Phe Glu Glu Ile Cys Ile Lys Lys Glu
        115                 120                 125

Ala Phe Glu Gly Glu Glu Lys Phe Cys Ala Lys Ser Leu Gly Thr Val
130                 135                 140

Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
            180                 185                 190

Ala Val Phe Tyr Cys His Lys Val Arg Glu Thr Thr Ala Phe Met Val
        195                 200                 205

Pro Leu Val Ala Gly Asp Gly Thr Lys Thr Gln Ala Leu Ala Val Cys
210                 215                 220

His Ser Asp Thr Ser Gly Met Asn His His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Asp Thr Ala Tyr Gln Thr
            260                 265                 270

Asn Val Val Val
        275

<210> SEQ ID NO 271
<211> LENGTH: 276
<212> TYPE: PRT
<213> ORGANISM: Artificial Sequence
<220> FEATURE:
<223> OTHER INFORMATION: Glyma.12G217400-[QPWGVYTW]

<400> SEQUENCE: 271

Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
            20                  25                  30

Tyr Trp Glu Ala Val Trp Pro Asn Thr Pro Ile Pro Thr Ala Leu Arg
        35                  40                  45

Glu Leu Leu Lys Pro Leu Pro Ala Gly Val Glu Ile Asp Glu Leu Pro
```

```
                  50                  55                  60

Lys Gln Ile Asp Asp Thr Gln Tyr Pro Lys Thr Phe Phe Tyr Lys Glu
 65                  70                  75                  80

Asp Leu His Pro Gly Lys Thr Met Lys Val Gln Phe Thr Lys Arg Pro
                     85                  90                  95

Tyr Ala Gln Pro Phe Gly Val Tyr Thr Trp Leu Thr Asp Ile Lys Asp
                    100                 105                 110

Thr Ser Lys Glu Gly Tyr Ser Phe Glu Glu Ile Cys Ile Lys Lys Glu
                115                 120                 125

Ala Phe Glu Gly Glu Glu Lys Phe Cys Ala Lys Ser Leu Gly Thr Val
            130                 135                 140

Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
                180                 185                 190

Ala Val Phe Tyr Cys His Lys Val Arg Glu Thr Thr Ala Phe Met Val
                195                 200                 205

Pro Leu Val Ala Gly Asp Gly Thr Lys Thr Gln Ala Leu Ala Val Cys
                210                 215                 220

His Ser Asp Thr Ser Gly Met Asn His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Asp Thr Ala Tyr Gln Thr
                260                 265                 270

Asn Val Val Val
            275

<210> SEQ ID NO 272
<211> LENGTH: 276
<212> TYPE: PRT
<213> ORGANISM: Artificial Sequence
<220> FEATURE:
<223> OTHER INFORMATION: Glyma.12G217400-[QPFGVYTW]

<400> SEQUENCE: 272

Met Glu Phe Arg Cys Ser Val Ile Ser Phe Thr Ile Leu Phe Ser Leu
 1               5                  10                  15

Ala Leu Ala Gly Glu Ser His Val His Ala Ser Leu Pro Glu Glu Asp
                 20                  25                  30

Tyr Trp Glu Ala Val Trp Pro Asn Thr Pro Ile Pro Thr Ala Leu Arg
             35                  40                  45

Glu Leu Leu Lys Pro Leu Pro Ala Gly Val Glu Ile Asp Glu Leu Pro
 50                  55                  60

Lys Gln Ile Asp Asp Thr Gln Tyr Pro Lys Thr Phe Phe Tyr Lys Glu
 65                  70                  75                  80

Asp Leu His Pro Gly Lys Thr Met Lys Val Gln Phe Thr Lys Arg Pro
                     85                  90                  95

Tyr Ala Gln Pro Phe Gly Val Tyr Thr Trp Leu Thr Asp Ile Lys Asp
                    100                 105                 110

Thr Ser Lys Glu Gly Tyr Ser Phe Glu Glu Ile Cys Ile Lys Lys Glu
                115                 120                 125

Ala Phe Glu Gly Glu Glu Lys Phe Cys Ala Lys Ser Leu Gly Thr Val
```

```
            130                 135                 140
Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
            180                 185                 190

Ala Val Phe Tyr Cys His Lys Val Arg Glu Thr Thr Ala Phe Met Val
                195                 200                 205

Pro Leu Val Ala Gly Asp Gly Thr Lys Thr Gln Ala Leu Ala Val Cys
            210                 215                 220

His Ser Asp Thr Ser Gly Met Asn His His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Asp Thr Ala Tyr Gln Thr
            260                 265                 270

Asn Val Val Val
            275

<210> SEQ ID NO 273
<211> LENGTH: 275
<212> TYPE: PRT
<213> ORGANISM: Artificial Sequence
<220> FEATURE:
<223> OTHER INFORMATION: Glyma.12G217400-[QPFGFFSW]

<400> SEQUENCE: 273

Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
                20                  25                  30

Tyr Trp Glu Ala Val Trp Pro Asn Thr Pro Ile Pro Thr Ala Leu Arg
            35                  40                  45

Glu Leu Leu Lys Pro Leu Pro Ala Gly Val Glu Ile Asp Glu Leu Pro
50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Pro Phe Gly Phe Ser Trp Leu Thr Asp Ile Lys Asp Thr
            100                 105                 110

Ser Lys Glu Gly Tyr Ser Phe Glu Glu Ile Cys Ile Lys Lys Glu Ala
                115                 120                 125

Phe Glu Gly Glu Glu Lys Phe Cys Ala Lys Ser Leu Gly Thr Val Ile
            130                 135                 140

Gly Phe Ala Ile Ser Lys Leu Gly Lys Asn Ile Gln Val Leu Ser Ser
145                 150                 155                 160

Ser Phe Val Asn Lys Gln Glu Gln Tyr Thr Val Glu Gly Val Gln Asn
                165                 170                 175

Leu Gly Asp Lys Ala Val Met Cys His Gly Leu Asn Phe Arg Thr Ala
            180                 185                 190

Val Phe Tyr Cys His Lys Val Arg Glu Thr Thr Ala Phe Met Val Pro
                195                 200                 205

Leu Val Ala Gly Asp Gly Thr Lys Thr Gln Ala Leu Ala Val Cys His
```

```
                210                 215                 220
Ser Asp Thr Ser Gly Met Asn His His Met Leu His Glu Leu Met Gly
225                 230                 235                 240

Val Asp Pro Gly Thr Asn Pro Val Cys His Phe Leu Gly Ser Lys Ala
                245                 250                 255

Ile Leu Trp Val Pro Asn Leu Ser Met Asp Thr Ala Tyr Gln Thr Asn
                260                 265                 270

Tyr Val Val
        275
```

<210> SEQ ID NO 274
<211> LENGTH: 276
<212> TYPE: PRT
<213> ORGANISM: Artificial Sequence
<220> FEATURE:
<223> OTHER INFORMATION: Glyma.12G217400-[QPWGVYSW]

<400> SEQUENCE: 274

```
Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
                20                  25                  30

Tyr Trp Glu Ala Val Trp Pro Asn Thr Pro Ile Pro Thr Ala Leu Arg
            35                  40                  45

Glu Leu Leu Lys Pro Leu Pro Ala Gly Val Glu Ile Asp Glu Leu Pro
        50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Pro Trp Gly Val Tyr Ser Trp Leu Thr Asp Ile Lys Asp
                100                 105                 110

Thr Ser Lys Glu Gly Tyr Ser Phe Glu Glu Ile Cys Ile Lys Lys Glu
            115                 120                 125

Ala Phe Glu Gly Glu Glu Lys Phe Cys Ala Lys Ser Leu Gly Thr Val
        130                 135                 140

Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
                180                 185                 190

Ala Val Phe Tyr Cys His Lys Val Arg Glu Thr Thr Ala Phe Met Val
            195                 200                 205

Pro Leu Val Ala Gly Asp Gly Thr Lys Thr Gln Ala Leu Ala Val Cys
        210                 215                 220

His Ser Asp Thr Ser Gly Met Asn His His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Asp Thr Ala Tyr Gln Thr
                260                 265                 270

Asn Val Val Val
            275
```

```
<210> SEQ ID NO 275
<211> LENGTH: 276
<212> TYPE: PRT
<213> ORGANISM: Artificial Sequence
<220> FEATURE:
<223> OTHER INFORMATION: Glyma.12G217400-[QPYGVYFW]

<400> SEQUENCE: 275
```

Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
            20                  25                  30

Tyr Trp Glu Ala Val Trp Pro Asn Thr Pro Ile Pro Thr Ala Leu Arg
        35                  40                  45

Glu Leu Leu Lys Pro Leu Pro Ala Gly Val Glu Ile Asp Glu Leu Pro
50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Pro Tyr Gly Val Tyr Phe Trp Leu Thr Asp Ile Lys Asp
            100                 105                 110

Thr Ser Lys Glu Gly Tyr Ser Phe Glu Glu Ile Cys Ile Lys Lys Glu
        115                 120                 125

Ala Phe Glu Gly Glu Glu Lys Phe Cys Ala Lys Ser Leu Gly Thr Val
    130                 135                 140

Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
            180                 185                 190

Ala Val Phe Tyr Cys His Lys Val Arg Glu Thr Thr Ala Phe Met Val
        195                 200                 205

Pro Leu Val Ala Gly Asp Gly Thr Lys Thr Gln Ala Leu Ala Val Cys
    210                 215                 220

His Ser Asp Thr Ser Gly Met Asn His His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Gln Thr Ala Tyr Gln Thr
            260                 265                 270

Asn Val Val Val
        275

```
<210> SEQ ID NO 276
<211> LENGTH: 456
<212> TYPE: PRT
<213> ORGANISM: Selaginella uncinata

<400> SEQUENCE: 276
```

Met Ala Ser Asn Leu Leu Tyr Leu Leu Phe Leu Val Ala Ser Ala Gly
1               5                   10                  15

Ser Ala Ile Gly Ala Leu Gly Tyr Gln Phe Asp Ile Pro Asp Thr Leu
            20                  25                  30

Thr Asn Ala Lys Ser Pro Leu Asp Asp Ser Thr Ala Lys Phe Leu Lys
        35                  40                  45

```
Ser Leu Leu Glu Gly Gly Leu Val Leu Asn Thr Pro Asp Val Cys His
    50              55                  60

Ser Leu Gly Phe Phe Cys Ala Asp Glu Ile Ser Ser Ser Ser Ser Glu
65              70                  75                      80

Ala Pro Glu Val Pro Lys Arg Ser Leu Gly Thr Arg Lys Leu Leu Asn
                85                  90                  95

Ala Ala Phe Glu Ser His Pro Asn Trp Val Ser Lys Gln Pro Tyr Ser
                100                 105                 110

Val Phe Ala Trp Thr Asn Glu Glu Gln Pro Ser Pro Thr Ser Asn Trp
            115                 120                 125

Val Asn Lys Gln Pro Tyr Ser Val Phe Ala Trp Thr Asn Glu Glu Gln
    130                 135                 140

Pro Ser Lys Trp Phe Asn Lys Pro Thr Ser Ser Trp Val Asn Lys Gln
145                 150                 155                 160

Pro Tyr Ser Val Phe Ala Trp Thr Asn Glu Glu Gln Pro Ser Lys Trp
                165                 170                 175

Phe Asn Lys Pro Thr Ser Asn Trp Val Asn Lys Gln Pro Tyr Ser Val
            180                 185                 190

Phe Ala Trp Thr Asn Glu Asp Gln Pro Ser Lys Trp Phe Asn Lys Gln
        195                 200                 205

Pro Tyr Ser Val Phe Ala Trp Thr Asn Glu Asp Gln Pro Ser Lys Trp
    210                 215                 220

Phe Asn Lys Gln Pro Phe Gly Glu His Pro Lys Gln Lys Leu Glu Ser
225                 230                 235                 240

Leu Pro Thr Lys Gly Arg Ala Phe Arg Phe Ala Ser Gln Ala Gly
                245                 250                 255

Lys Ser Ile Leu Leu Pro Pro Ile Thr Pro Leu Leu Ser Asn Lys Leu
                260                 265                 270

Ile His Pro His Leu Glu Asp Val Leu Pro Phe Asn Lys Glu Ser Leu
                275                 280                 285

Ser Gln Val Leu Arg Ala Phe Asn Leu Ser Ala Asn Ser Gly Met Gly
    290                 295                 300

Gln Ser Met Glu Phe Ala Leu Asp Met Gly Lys Ser Thr Asn Asn Gly
305                 310                 315                 320

Val Glu Phe Arg Lys Ser Val Ala Thr Thr Lys Glu Met Val Asp Phe
                325                 330                 335

Val Gly Gly Val Leu Cys Lys Glu Lys Gly Asp Cys His Val Lys Ser
                340                 345                 350

Ile Ala Gln Ser Phe Glu Asn Lys Glu Ser Lys Met Val Lys Val Val
            355                 360                 365

Asp Val Glu Leu Val Ser Lys Asp Pro Val Ala Cys His Thr Val Pro
    370                 375                 380

Phe Pro Tyr Lys Val Tyr Val Cys His Lys Ile Lys Asp Ser Pro Val
385                 390                 395                 400

Tyr Lys Val Asn Met Met Val Glu Gly Gly Lys Thr Leu Ser Thr Pro
                405                 410                 415

Phe Ile Cys His Trp Asp Thr Ser Lys Phe Arg Thr Asn His Gln Ala
            420                 425                 430

Phe Glu Asp Leu Asn Met Lys Pro Gly Gln Gly Glu Ile Cys His Trp
        435                 440                 445

Leu Gly Tyr Glu Thr Ile Val Trp
    450                 455
```

<210> SEQ ID NO 277
<211> LENGTH: 276
<212> TYPE: PRT
<213> ORGANISM: Artificial Sequence
<220> FEATURE:
<223> OTHER INFORMATION: Sali3-2-[QPFGVFGW]

<400> SEQUENCE: 277

Met Glu Phe Arg Cys Ser Val Ile Ser Phe Thr Ile Leu Phe Ser Leu
1               5                   10                  15

Ala Leu Ala Gly Glu Ser His Val His Ala Ser Leu Pro Glu Glu Asp
            20                  25                  30

Tyr Trp Glu Ala Val Trp Pro Asn Thr Pro Ile Pro Thr Ala Leu Arg
        35                  40                  45

Glu Leu Leu Lys Pro Leu Pro Ala Gly Val Glu Ile Asp Glu Leu Pro
    50                  55                  60

Lys Gln Ile Asp Asp Thr Gln Tyr Pro Lys Thr Phe Phe Tyr Lys Glu
65                  70                  75                  80

Asp Leu His Pro Gly Lys Thr Met Lys Val Gln Phe Thr Lys Arg Pro
                85                  90                  95

Tyr Ala Gln Pro Phe Gly Val Phe Gly Trp Leu Thr Asp Ile Lys Asp
            100                 105                 110

Thr Ser Lys Glu Gly Tyr Ser Phe Glu Glu Ile Cys Ile Lys Lys Glu
        115                 120                 125

Ala Phe Glu Gly Glu Glu Lys Phe Cys Ala Lys Ser Leu Gly Thr Val
    130                 135                 140

Ile Gly Phe Ala Ile Ser Lys Leu Gly Lys Asn Ile Gln Val Leu Ser
145                 150                 155                 160

Ser Ser Phe Val Asn Lys Gln Glu Gln Tyr Thr Val Glu Gly Val Gln
                165                 170                 175

Asn Leu Gly Asp Lys Ala Val Met Cys His Gly Leu Asn Phe Arg Thr
            180                 185                 190

Ala Val Phe Tyr Cys His Lys Val Arg Glu Thr Thr Ala Phe Met Val
        195                 200                 205

Pro Leu Val Ala Gly Asp Gly Thr Lys Thr Gln Ala Leu Ala Val Cys
    210                 215                 220

His Ser Asp Thr Ser Gly Met Asn His His Met Leu His Glu Leu Met
225                 230                 235                 240

Gly Val Asp Pro Gly Thr Asn Pro Val Cys His Phe Leu Gly Ser Lys
                245                 250                 255

Ala Ile Leu Trp Val Pro Asn Leu Ser Met Asp Thr Ala Tyr Gln Thr
            260                 265                 270

Asn Val Val Val
        275

<210> SEQ ID NO 278
<211> LENGTH: 274
<212> TYPE: PRT
<213> ORGANISM: Parasponia andersonii

<400> SEQUENCE: 278

Met Lys Ser Arg Cys Ala Val Ile Val Ala Leu Leu Ser Leu Leu Leu
1               5                   10                  15

Tyr Ser Val Gly Thr Thr Glu Ser Arg Lys Tyr Pro Ala Glu Tyr Trp
            20                  25                  30

Thr Thr Val Met Asn Asp Gln Pro Met Pro Glu Ala Ile Gln Glu Leu

```
              35                  40                  45
Ile Arg Glu Ala Ser Pro His Gln Glu His Leu Gly His Tyr Asp Arg
 50                  55                  60
Gly Val Asp Thr Lys Ser Glu Lys Ser Phe Thr Lys Glu Leu Glu Thr
 65                  70                  75                  80
Asn Thr Glu Lys Gly Val Asp Ser Ser Gly Glu Thr Pro Phe Thr
                 85                  90                  95
Lys Asp Phe Glu Pro His Ser Asn Ser Ile Pro Phe Glu Leu Ile Trp
                100                 105                 110
Ser Lys Asn Ser Lys Lys Phe Ala Asn Asp Phe Gln Pro Gln Pro Asn
                115                 120                 125
Pro Leu Pro Phe Gly Val Leu Trp Ser Lys Glu Ser Gln Asn Phe Ala
                130                 135                 140
Lys Asp Phe Glu Pro Arg Leu Asn Pro Ile Pro Phe Glu Leu Ile Trp
145                 150                 155                 160
Val Lys Asn Ser Lys Asn Ser Ala Glu Asp Phe Glu Pro His Pro Asn
                165                 170                 175
Pro Leu Pro Phe Glu Leu Ile Trp Ser Lys Asp Ser Lys Thr Phe Ser
                180                 185                 190
Lys Asp Phe Glu Pro His Gln Asn Pro Ile Pro Phe Glu Leu Ile Trp
                195                 200                 205
Ala Lys Asn Ser Pro Lys Phe Gly Glu Lys Phe Tyr Pro Asn Arg Asn
                210                 215                 220
Pro Val Pro Phe Glu Leu Ile Trp Ala Lys Asp Ser Lys Lys Phe Ala
225                 230                 235                 240
Asn Gly Phe Arg Pro Gln Pro Asn Leu Ile Pro Ser Glu Leu Ile Trp
                245                 250                 255
Ser Lys Asp Ser Glu Ala Asn Ser Gln Pro Lys Ile Glu Leu Glu Ala
                260                 265                 270
Lys Val

<210> SEQ ID NO 279
<211> LENGTH: 8
<212> TYPE: PRT
<213> ORGANISM: Artificial Sequence
<220> FEATURE:
<223> OTHER INFORMATION: Lyciumin-[QPWGVYTW]

<400> SEQUENCE: 279

Gln Pro Trp Gly Val Tyr Thr Trp
1               5

<210> SEQ ID NO 280
<211> LENGTH: 8
<212> TYPE: PRT
<213> ORGANISM: Artificial Sequence
<220> FEATURE:
<223> OTHER INFORMATION: Lyciumin-[QPFGVYTW]

<400> SEQUENCE: 280

Gln Pro Phe Gly Val Tyr Thr Trp
1               5

<210> SEQ ID NO 281
<211> LENGTH: 7
<212> TYPE: PRT
<213> ORGANISM: Artificial Sequence
<220> FEATURE:
<223> OTHER INFORMATION: Typical first seven amino acids of the DUF2775
```

```
                              domain
<220> FEATURE:
<221> NAME/KEY: VARIANT
<222> LOCATION: 3, 5
<223> OTHER INFORMATION: Any amino acid

<400> SEQUENCE: 281

Lys Asp Xaa Tyr Xaa Gly Trp
1               5

<210> SEQ ID NO 282
<211> LENGTH: 71
<212> TYPE: PRT
<213> ORGANISM: Unknown
<220> FEATURE:
<223> OTHER INFORMATION: Description of Unknown:
      cysteine-histidine motif
<220> FEATURE:
<221> NAME/KEY: MOD_RES
<222> LOCATION: (3)..(12)
<223> OTHER INFORMATION: Any amino acid
<220> FEATURE:
<221> NAME/KEY: MOD_RES
<222> LOCATION: (15)..(41)
<223> OTHER INFORMATION: Any amino acid
<220> FEATURE:
<221> NAME/KEY: SITE
<222> LOCATION: (15)..(41)
<223> OTHER INFORMATION: This region may encompass 25-27 residues
<220> FEATURE:
<221> NAME/KEY: MOD_RES
<222> LOCATION: (44)..(69)
<223> OTHER INFORMATION: Any amino acid
<220> FEATURE:
<221> NAME/KEY: SITE
<222> LOCATION: (44)..(69)
<223> OTHER INFORMATION: This region may encompass 25-26 residues

<400> SEQUENCE: 282

Cys His Xaa Xaa Xaa Xaa Xaa Xaa Xaa Xaa Xaa Xaa Cys His Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Cys His Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Cys His
65                  70

<210> SEQ ID NO 283
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Glu Pro Tyr Gly Val Tyr Thr Trp
1               5

<210> SEQ ID NO 284
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 284

Gln Pro Tyr Gly Val Tyr Trp
1               5

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Gln Pro Tyr Gly Val Tyr Thr Ala Trp
1               5

<210> SEQ ID NO 286
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Gln Pro Tyr Gly Val Tyr Thr Ala
1               5

<210> SEQ ID NO 287
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Gln Tyr Gly Val Tyr Thr Trp
1               5

<210> SEQ ID NO 288
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Gln Gly Val Tyr Thr Trp
1               5

<210> SEQ ID NO 289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Gln Ala Pro Tyr Gly Val Tyr Thr Trp
1               5

<210> SEQ ID NO 290
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gln Pro Tyr Gly Val Tyr Thr Phe
1               5

<210> SEQ ID NO 291
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Gln Pro Tyr Gly Val Tyr Thr His
1               5

<210> SEQ ID NO 292
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Ala Pro Tyr Gly Val Tyr Thr Trp
1               5

<210> SEQ ID NO 293
<211> LENGTH: 70
<212> TYPE: PRT
<213> ORGANISM: Unknown
<220> FEATURE:
<223> OTHER INFORMATION: Description of Unknown:
      signal peptide

<400> SEQUENCE: 293

Met Glu Leu His His His Tyr Phe Phe Ile Leu Leu Ser Leu Ala Phe
1               5                   10                  15

Ile Ala Ser His Ala Ala Asn Leu Ser Pro Glu Val Tyr Trp Lys Val
                20                  25                  30

Lys Leu Pro Asn Thr Pro Met Pro Arg Pro Ile Lys Asp Ala Leu His
            35                  40                  45

Tyr Ser Glu Ala Ser Glu Gly Asp Val His Lys Leu Arg Gln Pro Trp
        50                  55                  60

Gly Val Gly Ser Trp Tyr
65                  70

<210> SEQ ID NO 294
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
```

```
<222> LOCATION: (4)..(4)
<223> OTHER INFORMATION: G, A, T, S, P, E, F, L, or R
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (8)..(8)
<223> OTHER INFORMATION: Y or W

<400> SEQUENCE: 294

Gln Xaa Xaa Xaa Xaa Xaa Xaa Xaa
1               5

<210> SEQ ID NO 295
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: G, A, T, S, or P
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (8)..(8)
<223> OTHER INFORMATION: Y or W

<400> SEQUENCE: 295

Gln Xaa Xaa Xaa Xaa Xaa Xaa Xaa
1               5

<210> SEQ ID NO 296
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: G, A, T, or S
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (8)..(8)
<223> OTHER INFORMATION: Y or W

<400> SEQUENCE: 296

Gln Xaa Xaa Xaa Xaa Xaa Xaa Xaa
1               5

<210> SEQ ID NO 297
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: G, A, or T
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (8)..(8)
<223> OTHER INFORMATION: Y or W

<400> SEQUENCE: 297

Gln Xaa Xaa Xaa Xaa Xaa Xaa Xaa
1               5

<210> SEQ ID NO 298
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Any amino acid

<400> SEQUENCE: 298

Gln Pro Xaa Xaa Xaa Xaa Xaa Trp
1               5

<210> SEQ ID NO 299
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Any amino acid

<400> SEQUENCE: 299

Gln Pro Xaa Xaa Xaa Xaa Xaa Tyr
1               5
```

BIOSYNTHETIC APPROACH FOR HETEROLOGOUS PRODUCTION AND DIVERSIFICATION OF BIOACTIVE LYCIUMIN CYCLIC PEPTIDES

RELATED APPLICATIONS

This application is the U.S. National Stage of International Application No. PCT/US2019/014430, filed on Jan. 21, 2019, published in English, which claims the benefit of U.S. Provisional Application No. 62/619,905, filed on Jan. 21, 2018. This application claims the benefit of U.S. Provisional Application No. 62/620,420, filed on Jan. 22, 2018. This application claims the benefit of U.S. Provisional Application No. 62/732,957, filed on Sep. 18, 2018. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
 a) File name: 0399_2061-004_SL.txt; created Dec. 4, 2023; 330,482 bytes in size.

BACKGROUND

Cyclic peptides are an emerging source of pharmaceutical and agrochemical innovation in order to treat human and plant diseases, respectively [1]. Cyclic peptide natural products can be used in medicine as immunosuppressants, antibiotics and anti-cancer agents [2] and in agriculture for plant pathogen control [3]. The emergence of resistance against many current antibiotics and pest control agents in human pathogens and plant pathogens [5], respectively, demands new discovery and metabolic engineering platforms for peptide-based drug and agrochemical development. Additionally, plant peptides are important endogenous chemicals to modulate the rhizosphere during plant development [6] and under abiotic stresses [7], and, thus, they have potential in optimizing plant fitness in changing climates through rhizosphere engineering.

SUMMARY

Described herein is a method of producing one or more lyciumin cyclic peptides. In some embodiments, the method of producing one or more lyciumin cyclic peptides can include providing a host cell that includes a transgene encoding a lyciumin precursor peptide, or a biologically-active fragment thereof, and expressing the transgene in the host cell to thereby produce a lyciumin precursor peptide, or biologically-active fragment thereof. The lyciumin precursor peptide, or biologically-active fragment thereof, can include one or more core lyciumin peptide domains. In some embodiments, the lyciumin precursor peptide, or biologically-active fragment thereof, can be converted to one or more lyciumin cyclic peptides in the host cell.

In some embodiments, the transgene is operably linked to a heterologous promoter in the host cell. In some embodiments, the transgene is introduced in a vector. In some embodiments, the method includes introducing the transgene into the host cell. In some embodiments, the method includes introducing a vector that includes the transgene into the host cell. In some embodiments, the lyciumin precursor peptide includes a plurality of core lyciumin peptide domains. In some embodiments, the core lyciumin peptide domains can encode two or more different lyciumin cyclic peptides.

The host cell can express one or more of: an enzyme that cyclizes the lyciumin precursor peptide; an endopeptidase; a glutamine cyclotransferase; and/or an exopeptidase. In some embodiments, arginine is immediately N-terminal to the core lyciumin peptide domain. In some embodiments, the endopeptidase is an arginine endopeptidase. In some embodiments tyrosine is immediately C-terminal to the core lyciumin peptide domain.

In some embodiments, the host cell is a plant cell. In some embodiments, the plant cell is an Amaranthaceae family plant cell. In some embodiments, the plant cell is an *Amaranthus* genus plant cell, such as an *Amaranthus hypochondriacus* plant cell. In some embodiments, the plant cell is a Beta genus plant cell, such as a *Beta vulgaris* plant cell. In some embodiments, the plant cell is a *Chenopodium* genus plant cell, such as a *Chenopodium quinoa* plant cell. In some embodiments, the plant cell is a Fabaceae family plant cell. In some embodiments, the plant cell is a Glycine genus plant cell, such as a *Glycine max* plant cell. In some embodiments, the plant cell is a *Medicago* genus plant cell, such as a *Medicago truncatula* plant cell. In some embodiments, the plant cell is a Solanaceae family plant cell. In some embodiments, the plant cell is a *Solanum* genus plant cell, such as a *Solanum melongena* plant cell or a *Solanum tuberosum* plant cell. In some embodiments, the plant cell is a *Nicotiana* genus plant cell, such as a *Nicotiana benthamiana* plant cell. In some embodiments, the plant cell is a *Capsicum* genus plant cell, such as a *Capsicum annuum* plant cell.

In some embodiments, the lyciumin precursor peptide includes SEQ ID NO: 1. In some embodiments, the lyciumin precursor peptide consists of SEQ ID NO: 1. In some embodiments, the lyciumin precursor peptide consists essentially of SEQ ID NO: 1. In some embodiments, the lyciumin precursor peptide includes SEQ ID NO: 2. In some embodiments, the lyciumin precursor peptide consists of SEQ ID NO: 2. In some embodiments, the lyciumin precursor peptide consists essentially of SEQ ID NO: 2. In some embodiments, the lyciumin cyclic peptide is Lyciumin A, Lyciumin B, Lyciumin C, or Lyciumin D, or a combination thereof.

Described herein also is a method of generating a library of nucleic acids encoding lyciumin precursor peptides, or biologically-active fragments thereof. The method can include constructing a plurality of vectors, each vector comprising a nucleic acid encoding a different lyciumin precursor peptide, or biologically-active fragment thereof, operably linked to a heterologous promoter for expression in a host cell. In some embodiments, the library can include at least at least hundreds of nucleic acids, e.g., at least $10^3$ nucleic acids, at least $10^4$ nucleic acids, at least $10^5$ nucleic acids, at least $10^6$ nucleic acids, or at least $10^7$ nucleic acids.

In some embodiments, the method of generating a library of nucleic acids can include introducing the plurality of vectors into host cells. In certain embodiments, the lyciumin precursor peptide, or biologically-active fragments thereof, can be converted to one or more lyciumin cyclic peptides in the host cell. In some embodiments, the host cell is a plant cell. In some embodiments, the plant cell is a Solanaceae family plant cell. In some embodiments, the plant cell is a *Nicotiana* genus plant cell, such as a *Nicotiana benthamiana* plant cell.

In some embodiments, the method can include isolating a lyciumin cyclic peptide from the host cell. In some embodiments, the method can include assaying for an activity of interest either crude extract from the host cell or a lyciumin peptide isolated from the host cell.

In some embodiments, the method of generating a library of nucleic acids can include introducing a nucleic acid encoding a lyciumin peptide having an activity of interest into a second host cell. In some embodiments, the second host cell is a plant cell. In some embodiments, the plant cell is an Amaranthaceae family plant cell. In some embodiments, the plant cell is an *Amaranthus* genus plant cell, such as an *Amaranthus hypochondriacus* plant cell. In some embodiments, the plant cell is a Beta genus plant cell, such as a *Beta vulgaris* plant cell. In some embodiments, the plant cell is a *Chenopodium* genus plant cell, such as a *Chenopodium quinoa* plant cell. In some embodiments, the plant cell is a Fabaceae family plant cell. In some embodiments, the plant cell is a Glycine genus plant cell, such as a *Glycine max* plant cell. In some embodiments, the plant cell is a *Medicago* genus plant cell, such as a *Medicago truncatula* plant cell. In some embodiments, the plant cell is a Solanaceae family plant cell. In some embodiments, the plant cell is a *Solanum* genus plant cell, such as a *Solanum melongena* plant cell or a *Solanum tuberosum* plant cell. In some embodiments, the plant cell is a *Nicotiana* genus plant cell, such as a *Nicotiana benthamiana* plant cell. In some embodiments, the plant cell is a *Capsicum* genus plant cell, such as a *Capsicum annuum* plant cell.

Also described herein are isolated nucleic acids comprising a nucleotide sequence encoding a lyciumin precursor peptide, or a biologically-active fragment thereof, operably linked to a heterologous promoter. In some embodiments, the lyciumin precursor peptide includes a plurality of core lyciumin peptide domains. In some embodiments, the core lyciumin peptide domains encode two or more different lyciumin cyclic peptides. In some embodiments, the lyciumin precursor peptide comprises SEQ ID NO: 1. In some embodiments, the lyciumin precursor peptide comprises SEQ ID NO: 2. In some embodiments, the nucleic acid is a cDNA.

Described herein are vectors that include any of the nucleic acids described herein.

Described herein are host cells that include any of the nucleic acids or vectors described herein. In some embodiments, the host cell is a plant cell. In some embodiments, the plant cell is an Amaranthaceae family plant cell. In some embodiments, the plant cell is an *Amaranthus* genus plant cell, such as an *Amaranthus hypochondriacus* plant cell. In some embodiments, the plant cell is a Beta genus plant cell, such as a *Beta vulgaris* plant cell. In some embodiments, the plant cell is a *Chenopodium* genus plant cell, such as a *Chenopodium quinoa* plant cell. In some embodiments, the plant cell is a Fabaceae family plant cell. In some embodiments, the plant cell is a Glycine genus plant cell, such as a *Glycine max* plant cell. In some embodiments, the plant cell is a *Medicago* genus plant cell, such as a *Medicago truncatula* plant cell. In some embodiments, the plant cell is a Solanaceae family plant cell. In some embodiments, the plant cell is a *Solanum* genus plant cell, such as a *Solanum melongena* plant cell or a *Solanum tuberosum* plant cell. In some embodiments, the plant cell is a *Nicotiana* genus plant cell, such as a *Nicotiana benthamiana* plant cell. In some embodiments, the plant cell is a *Capsicum* genus plant cell, such as a *Capsicum annuum* plant cell.

Further described herein is a library that includes a plurality of nucleic acid molecules, each nucleic acid molecule including a nucleotide sequence encoding a lyciumin precursor peptide, or a biologically-active fragment thereof. In some embodiments, the nucleotide sequence encoding a lyciumin precursor peptide, or a biologically-active fragment thereof, is operably linked to a heterologous promoter in each nucleic acid molecule. In some embodiments, the nucleic acid molecules are complementary DNA (cDNA) molecules.

In addition, described herein are lyciumin cyclic peptides produced by a method described herein.

Described herein is a method of producing one or more lyciumin cyclic peptides. The method can include: a) providing a host cell that includes a transgene encoding a polypeptide that includes one or more core lyciumin peptide domains; and b) expressing the transgene in the host cell to thereby produce a polypeptide that comprises one or more core lyciumin peptide domains. In some embodiments, the polypeptide is converted to one or more lyciumin cyclic peptides in the host cell.

The methods and products described herein can be used to produce a platform for lyciumin expression and diversification, which can be used to create a library of lyciumin cyclic peptides. The lyciumins precursor peptides described herein can be expressed in planta. The lyciumin cyclic peptides described herein can be used in agrochemical and pharmaceutical applications that aim to increase plant fitness towards abiotic and biotic stresses and treat human diseases, respectively.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 1A-D show characterization of lyciumins as plant ribosomal peptides. FIG. 1A is an image of Lyciumin producing plant *Lycium barbarum*. FIG. 1B is lyciumin structures from *Lycium* plants. FIG. 1C is Lyciumin precursor peptide sequence from *Lycium barbarum* root transcriptome. FIG. 1D is chromatograms showing heterologous expression of lyciumin precursor peptide gene LbaLycA in *Nicotiana benthamiana* via *Agrobacterium tumefaciens* LBA4404 pEAQ-HT system results in lyciumin A, B and D formation after 6 days. Base peak chromatograms (BPC) of lyciumin A, B and D mass signals.

FIG. 2A is a schematic showing precursor gene-guided genome mining for lyciumin discovery from plant genomes by identification of lyciumin precursors (BURP domain proteins) in a plant genome by core peptide prediction, prediction of lyciumin chemotype from the core peptide sequence and lyciumin chemotyping by LC-MS and MS/MS analysis of plant extracts. FIG. 2B shows structural diversity of lyciumins characterized by genome mining from Amaranthaceae, Fabaceae, and Solanaceae plants with corresponding precursor gene accession numbers and core peptide sequences. The stereochemistry of lyciumin glycine α-carbon is inferred from lyciumin A and lyciumin I structure elucidation.

FIGS. 3A-E pertain to investigation of lyciumin biosynthesis in *Lycium barbarum*. FIG. 3A is a schematic showing an example biosynthetic pathway for lyciumin B formation in *Lycium barbarum* from precursor peptide LbaLycA. FIG. 3B shows detection of [Gln1]-lyciumin B mass signals in *L. barbarum* root extract and *Nicotiana benthamiana* leaf extracts after heterologous expression of lyciumin precursor LbaLycA for six days. FIG. 3C shows genomic co-localization of lyciumin precursor genes and glutamine cyclotransferase genes for putative N-terminal lyciumin protection in *Chenopodium quinoa* and *Beta vulgaris*. FIG. 3D shows detection of abolished mass signals for [Gln1]-lyciumin species in *N. benthamiana* leaf extracts after heterologous expression of lyciumin precursor LbaLycA and glutamine cyclotransferase LbaQC from *Lycium barbarum* root transcriptome. FIG. 3E shows detection of [Tyr9]-lyciumin B and [Tyr9-Gln10]-lyciumin B mass signals in *L. barbarum* root extract and *N. benthamiana* leaf extracts after heterologous expression of lyciumin precursor LbaLycA for six days. Abbreviations: LbaLycA (6d)—*Nicotiana benthamiana* infiltrated with *Agrobacterium tumefaciens* LBA4404 containing pEAQ-HT-LbaLycA (six days), pEAQ-HT (6d)—*Nicotiana benthamiana* infiltrated with *Agrobacterium tumefaciens* LBA4404 containing pEAQ-HT (six days), BPC—base peak chromatogram, PTM—post-translational modification.

FIGS. 4A-B show investigation of promiscuity of the lyciumin pathway by heterologous expression of lyciumin I precursor gene Sali3-2 from *Glycine max* and corresponding mutants in *Nicotiana benthamiana* via *Agrobacterium tumefaciens* LBA4404 pEAQ-HT system (6 days). FIG. 4A shows LC-MS detection of lyciumin I after heterologous expression of Sali3-2 in *N. benthamiana*. FIG. 4B is a table of core peptide mutants of Sali3-2 in the lyciumin pathway in *Nicotiana benthamiana*. Abbreviations: aa—amino acid, N.b.—*Nicotiana benthamiana*, A.t.—*Agrobacterium tumefaciens*. FIG. 4B discloses SEQ ID NOs: 43, 292, 198, 255, 257, 259, 261, 151, 286, 265, 285, 284, 289, 287, 288, 61, 87, 69, 63, 77, 280, 279, 290, 291, 267, and 268, respectively, in order of appearance.

FIG. 5 is candidate transcripts of lyciumin precursor from *Lycium barbarum* root transcriptome. Predicted lyciumin core peptides are highlighted in green (lyciumin A), blue (lyciumin B) and red (lyciumin D).

FIG. 6 is a signal peptide prediction of LbaLycA with SignalP-4.1. FIG. 6 discloses SEQ ID NO: 293.

FIGS. 7A-C are MS/MS analyses of lyciumin B exemplifying planar structure elucidation of lyciumin peptides by tandem mass spectrometry. FIG. 7A is the lyciumin B MS/MS spectrum with highlighted amino acid iminium ions. FIG. 7B is the lyciumin B spectrum with highlighted fragments of linear lyciumin N-terminus. FIG. 7C is the lyciumin MS/MS spectrum of fragments of C-terminal lyciumin macrocycle.

FIGS. 8A-E show lyciumin precursor gene expression. FIG. 8A shows lyciumin precursor gene expression in *Amaranthus hypochondriacus*. FIG. 8B shows lyciumin precursor gene expression in *Chenopodium quinoa*. FIG. 8C shows lyciumin precursor gene expression in *Glycine max*. FIG. 8D shows lyciumin precursor gene expression in *Medicago truncatula*. FIG. 8E shows lyciumin precursor gene expression in *Solanum tuberosum*.

FIGS. 9A-D show lyciumin chemotyping in source plant tissues. FIG. 9A shows lyciumin chemotyping in *Amaranthus hypochondriacus* tissues. FIG. 9B shows lyciumin chemotyping in *Beta vulgaris* tissues. FIG. 9C shows lyciumin chemotyping in *Glycine max* tissues. FIG. 9D shows lyciumin chemotyping in *Chenopodium quinoa* tissues.

FIGS. 10A-D show an investigation of sequences and distribution of lyciumin precursors in plants. FIG. 10A shows types of lyciumin precursors based on primary structure analysis (Abbreviation: Core—core peptide (core lyciumin peptide domain)). FIG. 10B shows a neighbor-joining phylogenetic tree of the BURP-domain sequences of lyciumin precursors predicted from plant genomes (denoted by "g" after species name) and plant transcriptomes (denoted by "t" after species name) and founding members of BURP domain protein family (BMN2A [*Brassica napus*], Polygalacturonase-1 non-catalytic subunit beta [*Solanum lycopersicum*], USP87/92 [*Vicia faba*], RD22 [*Arabidopsis thaliana*]) generated with 2000 bootstrap generations using the p-distance method. The scale measures evolutionary distances in substitutions per amino acid. Precursors with characterized chemotypes are noted with an asterisk. Predicted cyclization sites at the fourth core peptide position of precursor peptides are noted after species name as capital letter (Abbreviations: A—alanine, G—glycine, L—leucine, P—proline, R—arginine, T—threonine). FIG. 10C is a Venn diagram of core peptide sequences of predicted and characterized lyciumin chemotypes based on genome and transcriptome mining (Table 4). FIG. 10C discloses SEQ ID NOS 78 and 148, respectively, in order of appearance. FIG. 10D is a phylogenetic relationship of plant families with predicted and characterized (noted by asterisks) lyciumin chemotypes (both highlighted in red).

FIG. 10D is a phylogenetic relationship of plant families with predicted and characterized (noted by asterisks) lyciumin chemotypes (both highlighted in red).

FIG. 11 shows a precursor gene-guided genome mining workflow for lyciumin discovery.

FIGS. 12A-B pertain to genome mining of lyciumins from *Amaranthus hypochondriacus*. FIG. 12A is *Amaranthus hypochondriacus* lyciumin precursor peptide (BURP domain underlined, core peptides highlighted in blue and red). FIG. 12B is predicted lyciumin chemotypes.

FIGS. 13A-B pertain to genome mining of lyciumins from *Beta vulgaris*. FIG. 13A is *Beta vulgaris* lyciumin precursor peptide (BURP domain underlined, core peptides highlighted in blue and green). FIG. 13B is predicted lyciumin chemotype.

FIGS. 14A-B pertain to genome mining of lyciumins from *Chenopodium quinoa*. FIG. 14A is *Chenopodium quinoa* lyciumin precursor peptide (BURP domain underlined, core peptides highlighted in blue, red and purple). FIG. 14B is predicted lyciumin chemotypes.

FIGS. 15A-D pertain to genome mining of lyciumins from *Glycine max*. FIG. 15A is *Glycine max* lyciumin H precursor peptide (BURP domain underlined, core peptide highlighted in red). FIG. 15B is predicted lyciumin H chemotypeU (SEQ ID NO. 61). FIG. 15C is *Glycine max* lyciumin I precursor peptide (BURP domain underlined, core peptide highlighted in red). FIG. 15D is predicted lyciumin I chemotype.

FIGS. 16A-D pertain to genome mining of lyciumins from *Solanum melongena*. FIG. 16A is *Solanum melongena* lyciumin I precursor peptide (BURP domain underlined, core peptide highlighted in red). FIG. 16B is predicted lyciumin I chemotype. FIG. 16C is *Solanum melongena* lyciumin B precursor peptide (BURP domain underlined, core peptides highlighted in blue and red). FIG. 16D is predicted lyciumin B chemotype.

FIGS. 17A-B pertain to genome mining of lyciumins from *Medicago truncatula*. FIG. 17A is *Medicago truncatula* lyciumin I precursor peptide (BURP domain underlined, core peptide highlighted in red). FIG. 17B is predicted lyciumin I chemotype.

FIGS. 18A-D pertain to genome and transcriptome mining of lyciumins from *Solanum tuberosum*. FIG. 18A is lyciumin precursor peptide derived from *Solanum tuberosum* genome (BURP domain underlined, core peptides highlighted in red). FIG. 18B is lyciumin precursor peptide transcripts derived from *Solanum tuberosum* tuber transcriptome (SRR5970148) de novo assembled with Trinity (v2.4, BURP domain underlined, core peptides highlighted in red). FIG. 18C is lyciumin precursor peptide transcripts derived from *Solanum tuberosum* tuber transcriptome (SRR5970148) de novo assembled with rnaSPAdes (v1.0, BURP domain underlined, core peptides highlighted in red). FIG. 18D is predicted lyciumin core peptides derived from genome mining and transcriptome mining of *Solanum tuberosum*. Bold core peptides indicate detected lyciumin chemotypes.

FIGS. 19A-O pertain to genome and transcriptome mining of lyciumins from *Solanum tuberosum*. FIG. 19A is *Solanum tuberosum* lyciumin J precursor peptide (BURP domain underlined, core peptide highlighted in red). FIG. 19B is predicted lyciumin J chemotype. FIG. 19C is *Solanum tuberosum* lyciumin B precursor peptide transcript (BURP domain underlined, core peptides highlighted in red). FIG. 19D is predicted lyciumin B chemotype. FIG. 19E is *Solanum tuberosum* lyciumin K precursor peptide transcript (BURP domain underlined, core peptides highlighted in red). FIG. 19F is predicted lyciumin K chemotype. FIG. 19G is *Solanum tuberosum* lyciumin L precursor peptide transcript (BURP domain underlined, core peptides highlighted in red). FIG. 19H is predicted lyciumin L chemotype. FIG. 19I is *Solanum tuberosum* lyciumin M precursor peptide transcript (BURP domain underlined, core peptides highlighted in red). FIG. 19J is predicted lyciumin M chemotype. FIG. 19K is *Solanum tuberosum* lyciumin N precursor peptide transcript (BURP domain underlined, core peptides highlighted in red). FIG. 19L is predicted lyciumin N chemotype. FIG. 19M is *Solanum tuberosum* lyciumin O precursor peptide transcript (BURP domain underlined, core peptides highlighted in red). FIG. 19N is predicted lyciumin O chemotype. FIG. 19O shows lyciumin chemotyping in *Solanum tuberosum* tuber tissue and sprout tissue.

FIGS. 20A-B pertain to transcriptome mining of lyciumin peptide in *Selaginella uncinata*. FIG. 20A is predicted lyciumin precursor transcript (5'-partial, Table 4) from de novo rnaSPAdes assembly of *Selaginella uncinata* transcriptome (SRR7132763, BURP domain underlined, core peptide highlighted in red). FIG. 20B is predicted [QPYSVFAW (SEQ ID NO: 147)]-lyciumin chemotype.

FIGS. 21A-B pertain to characterization of *Lycium barbarum* glutamine cyclotransferase (LbaQC). FIG. 21A is LbaQC sequence with predicted secretory pathway signaling peptide underlined (SignalP v4.1). FIG. 21B is bioinformatic analysis of candidate lyciumin-glutamine cyclotransferase LbaQC from root transcriptome of *Lycium barbarum*.

FIGS. 22A-E pertain to heterologous expression of Sali3-2-[QAYGVYTW (SEQ ID NO: 198)] in *Nicotiana benthamiana*. FIG. 22A is Sali3-2-[QAYGVYTW (SEQ ID NO: 198)] lyciumin precursor peptide (BURP domain underlined, core peptide highlighted in red). FIG. 22B is predicted [QAYGVYTW (SEQ ID NO: 198)]-lyciumin chemotype. FIG. 22C is LC-MS chemotyping of predicted [QAYGVYTW (SEQ ID NO: 198)]-lyciumin in peptide extract of *N. benthamiana* leaves infiltrated with *A. tumefaciens* LBA4404 pEAQ-HT-Sali3-2-[QAYGVYTW (SEQ ID NO: 198)] for six days. FIG. 22D is MS analysis of predicted [QAYGVYTW (SEQ ID NO: 198)]-lyciumin chemotype. FIG. 22E is MS/MS analysis of predicted [QAYGVYTW (SEQ ID NO: 198)]-lyciumin chemotype.

FIGS. 23A-B pertain to heterologous expression of Sali3-2-[QPAGVYTW (SEQ ID NO: 255)] in *Nicotiana benthamiana*. FIG. 23A is Sali3-2-[QPAGVYTW (SEQ ID NO: 255)] lyciumin precursor peptide (BURP domain underlined, core peptide highlighted in red). FIG. 23B is predicted [QPAGVYTW (SEQ ID NO: 255)]-lyciumin chemotype.

FIGS. 24A-B pertain to heterologous expression of Sali3-2-[QPYAVYTW (SEQ ID NO: 257)] in *Nicotiana benthamiana*. FIG. 24A is Sali3-2-[QPYAVYTW (SEQ ID NO: 257)] lyciumin precursor peptide (BURP domain underlined, core peptide highlighted in red). FIG. 24B is predicted [QPYAVYTW (SEQ ID NO: 257)]-lyciumin chemotype.

FIGS. 25A-B pertain to heterologous expression of Sali3-2-[QPYGAYTW (SEQ ID NO: 259)] in *Nicotiana benthamiana*. FIG. 25A is Sali3-2-[QPYGAYTW (SEQ ID NO: 259)] lyciumin precursor peptide (BURP domain underlined, core peptide highlighted in red). FIG. 25B is predicted [QPYGAYTW (SEQ ID NO: 259)]-lyciumin chemotype.

FIGS. 26A-B pertain to heterologous expression of Sali3-2-[QPYGVATW (SEQ ID NO: 261)] in *Nicotiana benthamiana*. FIG. 26A is Sali3-2-[QPYGVATW (SEQ ID NO: 261)] lyciumin precursor peptide (BURP domain underlined, core peptide highlighted in red). FIG. 26B is predicted [QPYGVATW (SEQ ID NO: 261)]-lyciumin chemotype.

FIGS. 27A-B pertain to heterologous expression of Sali3-2-[QPYGVYAW (SEQ ID NO: 263)] in *Nicotiana benthamiana*. FIG. 27A is Sali3-2-[QPYGVYAW (SEQ ID NO: 263)] lyciumin precursor peptide (BURP domain underlined, core peptide highlighted in red). FIG. 27B is predicted [QPYGVYAW (SEQ ID NO: 263)]-lyciumin chemotype.

FIGS. 28A-I pertain to heterologous expression of Sali3-2-[QPYTVYTW (SEQ ID NO: 265)] in *Nicotiana benthamiana*. FIG. 28A is Sali3-2-[QPYTVYTW (SEQ ID NO: 265)] lyciumin precursor peptide (BURP domain underlined, core peptide highlighted in red). FIG. 28B is predicted [QPYTVYTW (SEQ ID NO: 265)]-lyciumin chemotype. FIG. 28C is LC-MS chemotyping of predicted [QPYTVYTW (SEQ ID NO: 265)]-lyciumin in peptide extract of *N. benthamiana* leaves infiltrated with *A. tumefaciens* LBA4404 pEAQ-HT-Sali3-2-[QPYTVYTW (SEQ ID NO: 265)] for six days. FIG. 28D is MS analysis of predicted [QPYTVYTW (SEQ ID NO: 265)]-lyciumin chemotype. FIG. 28E is MS/MS analysis of predicted [QPYTVYTW (SEQ ID NO: 265)]-lyciumin chemotype. FIG. 28F is predicted [QPYTVYTW (SEQ ID NO: 265)]-dehydrothreonine lyciumin chemotype. FIG. 28G is LC-MS chemotyping of predicted [QPYTVYTW (SEQ ID NO: 265)]-dehydrothreonine lyciumin in peptide extract of *N. benthamiana* leaves infiltrated with *A. tumefaciens* LBA4404 pEAQHT-Sali3-2-[QPYTVYTW (SEQ ID NO: 265)] for six days. FIG. 28H is MS analysis of predicted [QPYTVYTW (SEQ ID NO: 265)]-dehydrothreonine lyciumin chemotype. FIG. 28I is MS/MS analysis of predicted [QPYTVYTW (SEQ ID NO: 265)]-dehydrothreonine lyciumin chemotype.

FIGS. 29A-B pertain to heterologous expression of Sali3-2-[QPYGVYTY (SEQ ID NO: 267)] in *Nicotiana benthamiana*. FIG. 29A is Sali3-2-[QPYGVYTY (SEQ ID NO: 267)] precursor peptide (BURP domain underlined, core peptide highlighted in red). FIG. 29B is predicted [QPYGVYTY (SEQ ID NO: 267)]-cyclic peptide chemotype with a putative C-terminal cyclization site.

FIGS. 30A-B pertain to heterologous expression of Sali3-2-[QPYGVYFY (SEQ ID NO: 268)] and CanBURP in *Nicotiana benthamiana* and MS characterization of putative cyclic lyciumin-type peptide in *Capsicum annuum*. FIG. 30A is *Capsicum annum* precursor peptide (BURP domain underlined, core peptide highlighted in red). FIG. 30B is predicted [QPYGVYFY (SEQ ID NO: 268)]-cyclic peptide chemotype with a putative C-terminal cyclization site.

FIGS. 31A-B pertain to heterologous expression of Sali3-2-[QPWGVGTW (SEQ ID NO: 61)] in *Nicotiana bentha-*

*miana*. FIG. 31A is Sali3-2-[QPWGVGTW (SEQ ID NO: 61)] lyciumin precursor peptide (BURP domain underlined, core peptide highlighted in red). FIG. 31B is predicted [QPWGVGTW (SEQ ID NO: 61)]-lyciumin chemotype.

FIGS. 32A-B pertain to heterologous expression of Sali3-2-[QPWGVGAW (SEQ ID NO: 87)] in *Nicotiana benthamiana*. FIG. 32A is Sali3-2-[QPWGVGAW (SEQ ID NO: 87)] lyciumin precursor peptide (BURP domain underlined, core peptide highlighted in red). FIG. 32B is predicted [QPWGVGAW (SEQ ID NO: 87)]-lyciumin chemotype.

FIGS. 33A-B pertain to heterologous expression of Sali3-2-[QPWGVYTW (SEQ ID NO: 279)] in *Nicotiana benthamiana*. FIG. 33A is Sali3-2-[QPWGVYTW (SEQ ID NO: 279)] lyciumin precursor peptide (BURP domain underlined, core peptide highlighted in red). FIG. 33B is predicted [QPWGVYTW (SEQ ID NO: 279)]-lyciumin chemotype.

FIGS. 34A-B pertain to heterologous expression of Sali3-2-[QPFGVYTW (SEQ ID NO: 280)] in *Nicotiana benthamiana*. FIG. 34A is Sali3-2-[QPFGVYTW (SEQ ID NO: 280)] lyciumin precursor peptide (BURP domain underlined, core peptide highlighted in red). FIG. 34B is predicted [QPFGVYTW (SEQ ID NO: 280)]-lyciumin chemotype.

FIGS. 35A-B pertain to heterologous expression of Sali3-2-[QPFGFFSW (SEQ ID NO: 69)] in *Nicotiana benthamiana*. FIG. 35A is Sali3-2-[QPFGFFSW (SEQ ID NO: 69)] lyciumin precursor peptide (BURP domain underlined, core peptide highlighted in red). FIG. 35B is predicted [QPFGFFSW (SEQ ID NO: 69)]-lyciumin chemotype.

FIGS. 36A-B pertain to heterologous expression of Sali3-2-[QPWGVYSW (SEQ ID NO: 77)] in *Nicotiana benthamiana*. FIG. 36A is Sali3-2-[QPWGVYSW (SEQ ID NO: 77)] lyciumin precursor peptide (BURP domain underlined, core peptide highlighted in red). FIG. 36B is predicted [QPWGVYSW (SEQ ID NO: 77)]-lyciumin chemotype.

FIGS. 37A-B pertain to heterologous expression of Sali3-2-[QPYGVYFW (SEQ ID NO: 63)] in *Nicotiana benthamiana*. FIG. 37A is Sali3-2-[QPYGVYFW (SEQ ID NO: 63)] lyciumin precursor peptide (BURP domain underlined, core peptide highlighted in red). FIG. 37B is predicted [QPYGVYFW (SEQ ID NO: 63)]-lyciumin chemotype.

FIG. 38B shows the nucleotide and amino acid sequences of an engineered lyciumin precursor containing one repeat of a single core peptide (SEQ ID NO: 50; QPWGVGSW=lyciumin B). FIG. 38C shows the nucleotide and amino acid sequences of an engineered lyciumin precursor containing five repeats of a single core peptide (SEQ ID NO: 50; QPWGVGSW=lyciumin B). FIG. 38D shows the nucleotide and amino acid sequences of an engineered lyciumin precursor containing ten repeats of a single core peptide (SEQ ID NO: 50; QPWGVGSW=lyciumin B).

FIGS. 39A-B show lyciumin chemotypes and types of precursor peptides in plants. FIG. 39A is a chemical structure of lyciumins. FIG. 39B show two types of BURP-domain lyciumin precursor peptides categorized based on primary structure (Abbreviation: Core-core lyciumin peptide domain).

FIGS. 40A-C show characterization of lyciumin chemo- and genotype in lycophyte *Selaginella uncinata*. FIG. 40A is a lyciumin precursor peptide from *S. uncinata*. The BURP domain sequence is underlined, the lyciumin core peptide motifs are highlighted in red, and the signaling peptide sequence is highlighted in blue. FIG. 40B is the predicted lyciumin-[QPYSVFAW (SEQ ID NO: 147)] chemotype from *S. uncinata*. FIG. 40C is LC-MS detection of predicted lyciumin-[QPYSVFAW (SEQ ID NO: 147)] chemotype in peptide extract of *S. uncinata* root.

FIGS. 41A-C show taxonomic distribution and phylogenetic relationship of lyciumin precursors in land plants. FIG. 41A is a simplified maximum-likelihood phylogenetic tree built using the BURP-domain sequences of lyciumin precursors predicted from plant genomes (Kersten and Weng, 2018) and plant transcriptomes (FIGS. 43A-I) and founding members of BURP-domain protein family. Bootstrap values (based on 1000 replicates) of key branches are displayed. The scale measures evolutionary distances in substitutions per amino acid. A large-scale neighbor-joining tree also including non-lyciumin-producing BURP-domain proteins from several sequenced plant genomes is shown in Dataset S2. FIG. 41B is a Venn diagram of core peptide sequences of predicted and characterized lyciumin chemotypes based on genome and transcriptome mining (Table 8). FIG. 41B discloses SEQ ID NOS 148, 83 and 78, respectively, in order of appearance. FIG. 41C is taxonomic distribution of predicted and characterized lyciumin chemotypes (both highlighted in red) in land plants. Plant families with characterized lyciumin chemotypes are denoted by asterisks.

FIGS. 42A-F show convergent evolution of lyciumin-[QPFGVFGW (SEQ ID NO: 83)] from nonhomologous precursor proteins in *Celtis occidentalis* (Cannabaceae) and *Achyranthes bidentata* (Amaranthaceae). FIG. 42A is a photograph of a *C. occidentalis* tree used for chemotyping experiments in Example 2. FIG. 42B is the predicted lyciumin-[QPFGVFGW (SEQ ID NO: 83)] precursor peptide from *C. occidentalis* with DUF2775 domain (type 3 lyciumin precursor). The DUF2775-domain sequence is underlined, the core peptide motifs are highlighted in red, and the signal peptide sequence is highlighted in blue. FIG. 42C is the predicted lyciumin-[QPFGVFGW (SEQ ID NO: 83)] (lyciumin Q) chemotype. FIG. 42D is a greenhouse-grown *A. bidentata* plant used in Example 2. FIG. 42E is the predicted lyciumin-[QPFGVFGW (SEQ ID NO: 83)] BURP-domain precursor peptide from *A. bidentata* transcriptome. The core peptide motifs are highlighted in red, orange and purple, the signal peptide is highlighted in blue, and the BURP domain is underlined. FIG. 42F is LC-MS characterization of lyciumin-[QPFGVFGW (SEQ ID NO: 83)] in peptide extracts of *C. occidentalis* leaves, *A. bidentata* seeds, and *N. benthamiana* leaves sampled six days after infiltration with *Agrobacterium tumefaciens* LBA4404 carrying the pEAQ-HT-Sali3-2-[QPFGVFGW (SEQ ID NO: 83)] construct. The detailed MS/MS analysis is shown in FIGS. 46A-G.

FIGS. 43A-I are Dataset S1. Candidate lyciumin precursor peptides from plant transcriptomes. Underlined-BURP domain, red-core peptide.

FIGS. 44A-B show characterization of lyciumin-[QPYGVFAW (SEQ ID NO: 78)] in *Selaginella uncinata*. FIG. 44A is heterologous expression of Sali3-2-[QPYGVFAW (SEQ ID NO: 78)] in *Nicotiana benthamiana*. Sali3-2-[QPYGVFAW (SEQ ID NO: 78)] lyciumin precursor peptide (BURP domain underlined, core peptide highlighted in red). FIG. 44B is predicted [QPYGVFAW (SEQ ID NO: 78)]-lyciumin chemotype.

FIGS. 45A-B pertain to CocDUF2775-homolog from *Paraspomia andersonii* (Cannabaceae). FIG. 45A is protein sequence of CocDUF2775-homolog from *Parasponia andersonii* (Cannabaceae). FIG. 45B is a sequence alignment of CocDUF2775 (SEQ ID NO: 250) and its closest NCBI-nr sequence database homolog (PON47930.1, SEQ ID NO: 278). Predicted core peptide sequences are highlighted in red.

FIGS. 46A-G pertain to characterization of lyciumin-[QPFGVFGW (SEQ ID NO: 83)] in *Celtis occidentalis* and *Achyranthes bidentata*. FIG. 46A is an MS analysis of predicted [QPFGVFGW (SEQ ID NO: 83)]-lyciumin chemotype in peptide extract of *Celtis occidentalis* leaves. FIG. 46B is an MS/MS analysis of predicted [QPFGVFGW (SEQ ID NO: 83)]-lyciumin chemotype in peptide extract of *Celtis occidentalis* leaves. FIG. 46C shows heterologous expression of Sali3-2-[QPFGVFGW (SEQ ID NO: 83)] in *Nicotiana benthamiana*. Sali3-2-[QPFGVFGW (SEQ ID NO: 83)] lyciumin precursor peptide (BURP domain underlined, core peptide highlighted in red). FIG. 46D is MS analysis of predicted [QPFGVFGW (SEQ ID NO: 83)]-lyciumin chemotype in peptide extract of *N. benthamiana* leaves infiltrated with *A. tumefaciens* LBA4404 pEAQ-HTSali3-2-[QPFGVFGW (SEQ ID NO: 83)] for six days. FIG. 46E is MS/MS analysis of predicted [QPFGVFGW (SEQ ID NO: 83)]-lyciumin chemotype in peptide extract of *N. benthamiana* leaves infiltrated with *A. tumefaciens* LBA4404 pEAQ-HT-Sali3-2-[QPFGVFGW (SEQ ID NO: 83)] for six days. FIG. 46F is MS analysis of predicted [QPFGVFGW (SEQ ID NO: 83)]-lyciumin chemotype in peptide extract of *Achyranthes bidentata* seeds. FIG. 46G is MS/MS analysis of predicted [QPFGVFGW (SEQ ID NO: 83)]-lyciumin chemotype in peptide extract of *Achyranthes bidentata* seeds.

DETAILED DESCRIPTION

Figure 1A:
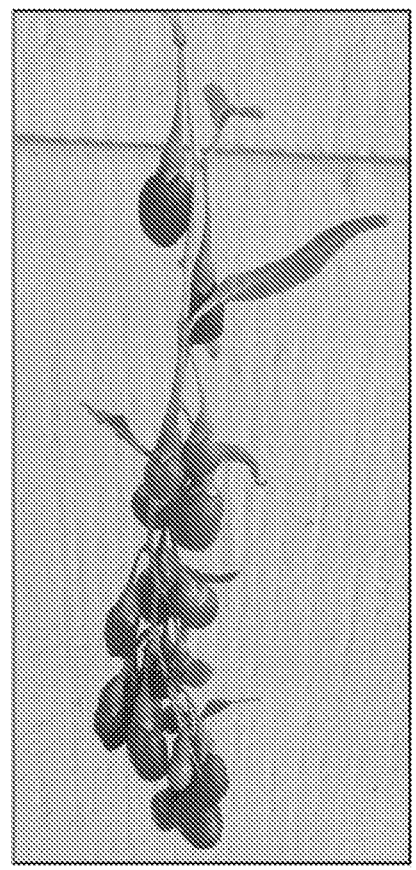

A description of example embodiments follows.

Ribosomally synthesized and post-translationally modified peptides (RiPPs) have been rapidly expanded in defined classes in the era of whole genome sequencing. While most RiPPs have been characterized from bacteria and fungi, few examples are known from plants. Described herein are lyciumins as a plant RiPP class. A lyciumin precursor gene was identified from the lyciumin producer *Lycium barbarum*. A precursor gene-guided genome mining approach was used to show that lyciumin genotypes and chemotypes are widely distributed in crop and forage plants. The promiscuity of the lyciumin pathway led to the discovery of peptide macrocyclization chemistry in lyciumin-type peptides from pepper seeds and suggests a largely untapped peptide chemical space in the plant kingdom. Based on the physical connection of lyciumin core peptides to protein domains associated with abiotic stress responses in plants, a platform for lyciumin expression and diversification was developed, which can be used to create a library of lyciumin cyclic peptides. The lyciumins described herein can be expressed in planta. The lyciumins cyclic peptides described herein can be used in agrochemical and pharmaceutical applications that aim to increase plant fitness towards abiotic and biotic stresses and treat human diseases, respectively.

Ribosomally synthesized and post-translationally modified peptides (RiPPs) are a rapidly growing class of natural products, since whole genome sequencing enabled the discovery of many RiPP precursor genes and corresponding biosynthetic pathways [8]. While most RiPPs have been discovered from bacteria and fungi, few examples are known from plants. The two biosynthetically defined classes of characterized plant RiPPs are cyclotides and orbitides, which are "head-to-tail" cyclic peptides with or without disulfide bonds, respectively [8-10]. Beyond "head-to-tail" cyclic peptides, the phytochemical repertoire of cyclic peptides suggests that there is a largely untapped diversity of branched cyclic plant peptide chemistry and underlying biochemistry to be discovered [11].

Discovery of peptide natural products and their biosynthetic pathways from microbes and fungi has been revolutionized by genome mining approaches using a vast resource of microbial and fungal genome sequences and biosynthetic knowledge of peptide natural product biosynthesis [12-16]. During the past decade, the number of publicly available plant genomes has exponentially increased due to the improvement of sequencing technologies and lowered genome sequencing costs [17]. In addition, characterization of plant biosynthetic pathways has accelerated due to synthetic biology approaches [18,19]. In analogy to microbial and fungal genomics, the growing plant genomic resource has inspired genome mining approaches for known classes of plant natural products [20-22] based on the current knowledge of plant natural product biosynthesis [23]. Generally, in a genome mining experiment predicted biosynthetic genotypes are connected with corresponding chemotypes based on applied biosynthetic knowledge in three steps: (A) Genotype prediction (the prediction of biosynthetic genes), (B) chemotype prediction (the prediction of structural features of a natural product from its biosynthetic genes) and (C) structure-guided chemotyping (the connection of an analyte structure with the predicted natural product structure) [13]. However, there are several challenges associated with plant natural product discovery by genome mining: (A) Genotype prediction is complicated by knowledge gaps in plant natural product biosynthesis and no or only partial clustering of biosynthetic genes in some plant natural product pathways, (B) chemotype prediction from biosynthetic genes can be difficult for certain natural product classes, and (C) structure-guided chemotyping can be problematic in terms of identification of structural information that can be connected to a predicted chemotype from given biosynthetic genes for a successful genome mining experiment. RiPPs have advantages to circumvent these general problems of plant genome mining because the peptide sequence is directly encoded in the genome as a core peptide within a precursor peptide [8]. Thus, identification of a precursor peptide gene specific to a chemically defined RiPP class yields structural information via the core peptide to enable the prediction of a RiPP structure for subsequent structure-guided chemotyping, for example by mass spectrometry [24]. Such a precursor gene-guided genome mining approach for plant RiPPs should not require knowledge of other biosynthetic genes encoding post-translationally modifying enzymes or proteases.

A precursor gene-guided genome mining approach was employed to identify a candidate class of plant RiPPs: the branched cyclic lyciumin peptides [25]. Lyciumins were originally isolated as inhibitors of the angiotensin-converting enzyme and renin from the roots of *Lycium barbarum* (Solanaceae, FIG. 1A), a Chinese herbal medicine for the treatment of hypertension [25]. Lyciumins are branched cyclic peptides with an N-terminal pyroglutamate and a macrocyclic linkage involving a C-terminal tryptophan or tyrosine residue. A lyciumin cyclic peptide typically consists of eight amino acids of a core lyciumin peptide domain. Typically, the C-terminal residue cyclizes with the α-carbon of the fourth residue. An example is a macrocyclic linkage between a C-terminal tryptophan indole-nitrogen and a glycine-α-carbon. Lyciumin A and C derivatives have also been isolated from the seeds of the medicinal plant *Celosia argentea* (Amaranthaceae) suggesting that these peptides are produced by multiple plant families [26].

Described herein is the discovery of lyciumin cyclic peptides from crop and forage plants by precursor gene-guided genome mining. Based on the physical connection of lyciumin biosynthesis and abiotic stress response reception in lyciumin precursor peptides, a platform is established to metabolically engineer and produce lyciumin peptide libraries, e.g., in planta. Such lyciumin peptide libraries can be used for, e.g., future engineering applications towards crops with increased stress tolerance. The discovery of lyciumins is a blueprint for peptide discovery by genome mining in the plant kingdom and lyciumin metabolic engineering sets the stage for their potential application as agrochemicals or pharmaceuticals to increase crop fitness and treat human diseases, respectively.

As used herein, the term "lyciumin precursor peptide" refers to a peptide that includes an N-terminal leader domain, one or more core lyciumin peptide domains, and, optionally, a C-terminal BURP domain or C-terminal DUF2775 domain. In some instances, one or more core lyciumin peptide domains can be within a BURP domain. In some instances, one or more core lyciumin peptide domains can be within a DUF2775 domain. In some instances, one or more core lyciumin peptide domains are not within (e.g., outside) a BURP domain. In some instances, one or more core lyciumin peptide domains can be within the N-terminal leader domain. In some instances, one or more core lyciumin peptide domains are not within (e.g., outside) the N-terminal leader domain. In some embodiments, a lyciumin precursor peptide includes from one to twenty core lyciumin peptide domains. In some embodiments, a lyciumin precursor peptide includes from one to ten core lyciumin peptide domains. In some instances, lyciumin precursor peptides can include more than twenty core lyciumin peptide domains. In some embodiments, the lyciumin precursor peptide includes a C-terminal BURP domain. In some embodiments, the lyciumin precursor peptide, or biologically-active fragment thereof, can include a signal peptide sequence. For example, a signal peptide sequence can direct a lyciumin precursor peptide, or biologically-active fragment thereof, through a portion of the secretory pathway and can facilitate localization to a particular organelle, such as a vacuole, which can be relevant for subsequent processing or conversion from a lyciumin precursor peptide to a lyciumin cyclic peptide. A signal peptide can be endogenous for a particular host cell or plant cell, or it can be heterologous. Typically, a signal peptide is located N-terminal to one or more core lyciumin peptide domains. In some instances, a signal peptide can be part of an N-terminal leader domain. In certain host cells (e.g., mammalian or plant host cells), expression and/or secretion of a protein can be increased by using a signal sequence, such as a heterologous signal sequence. Therefore, in some embodiments, the lyciumin precursor peptide includes a heterologous signal sequence at its N-terminus.

As used herein, the term "core lyciumin peptide domain" refers to a peptide domain that includes eight amino acids. The peptide is of the form QXX(G/A/T/S/P/E/F/L/R)XXX(Y/W) (SEQ ID NO: 294), where X is any amino acid. For example, in some embodiments of interest, the peptide is of the form QXX(G/A/T/S/P)XXX(Y/W) (SEQ ID NO: 295), where X is any amino acid. For example, in some embodiments of interest, the peptide is of the form QXX(G/A/T/S)XXX(Y/W) (SEQ ID NO: 296), where X is any amino acid. For example, in some embodiments of interest, the peptide is of the form QXX(G/A/T)XXX(Y/W) (SEQ ID NO: 297), where X is any amino acid. In particular embodiments, X is any of the twenty-two naturally occurring amino acids. In particular embodiments, X is any of the twenty amino acids encoded by the universal genetic code. In some embodiments, a core lyciumin peptide domain is a sequence listed in Table 1, Table 2, Table 3, or Table 4. In some embodiments, a core lyciumin peptide domain differs in sequence from a sequence listed in Table 1, Table 2, Table 3, or Table 4. For example, a core lyciumin peptide domain can have at least one substitution (e.g., 2, 3, 4, 5, etc. substitutions) relative to a sequence listed in Table 1, Table 2, Table 3, or Table 4. In some embodiments, the core lyciumin peptide domain differs in sequence from a naturally occurring core lyciumin peptide domain. In some embodiments, the sequence of the lyciumin precursor peptide, or biologically-active fragment thereof, differs from a naturally occurring sequence. In particular embodiments, as described herein, the variable X in the peptide QXX(G/A/T/S/P/E/F/L/R)XXX(Y/W) (SEQ ID NO: 294), the peptide QXX(G/A/T/S/P)XXX(Y/W) (SEQ ID NO: 295), the peptide QXX(G/A/T/S)XXX(Y/W) (SEQ ID NO: 296), or the peptide QXX(G/A/T)XXX(Y/W) (SEQ ID NO: 297) may be further restricted at individual positions, as described in the following paragraphs. A wide variety of core lyciumin peptide domains can be created. For example, in some embodiments, one of the X positions can be restricted. In other embodiments, two of the X positions can be restricted. In other embodiments, three of the X positions can be restricted. In other embodiments, four of the X positions can be restricted. In other embodiments, five of the X positions can be restricted.

In some embodiments of the core lyciumin peptide, the second position is proline or alanine. In some embodiments, the second position is proline. In some embodiments, the second position is not proline. In some embodiments, the second position is alanine. In some embodiments, the second position is not alanine.

In some embodiments of the core lyciumin peptide, the third position is tryptophan, alanine, tyrosine, phenylalanine, leucine, isoleucine, or serine. In some embodiments, the third position is tryptophan. In some embodiments, the third position is not tryptophan. In some embodiments, the third position is alanine. In some embodiments, the third position is not alanine. In some embodiments, the third position is tyrosine. In some embodiments, the third position is not tyrosine. In some embodiments, the third position is phenylalanine. In some embodiments, the third position is not phenylalanine. In some embodiments, the third position is leucine. In some embodiments, the third position is not leucine. In some embodiments, the third position is isoleucine. In some embodiments, the third position is not isoleucine. In some embodiments, the third position is serine. In some embodiments, the third position is not serine.

In some embodiments of the core lyciumin peptide, the fourth position is glycine. In some embodiments, the fourth position is not glycine. In some embodiments, the fourth position is alanine. In some embodiments, the fourth position is not alanine. In some embodiments, the fourth position is threonine. In some embodiments, the fourth position is not threonine. In some embodiments, the fourth position is serine. In some embodiments, the fourth position is not serine. In some embodiments, the fourth position is proline. In some embodiments, the fourth position is not proline. In some embodiments, the fourth position is glutamic acid. In some embodiments, the fourth position is not glutamic acid. In some embodiments, the fourth position is phenylalanine. In some embodiments, the fourth position is not phenylalanine. In some embodiments, the fourth position is leucine. In some embodiments, the fourth position is not leucine. In some embodiments, the fourth position is arginine. In some embodiments, the fourth position is not arginine.

In some embodiments of the core lyciumin peptide, the fifth position is valine, alanine, phenylalanine, serine, glycine, threonine, isoleucine, glutamine, or leucine. In some embodiments, the fifth position is valine. In some embodiments, the fifth position is not valine. In some embodiments, the fifth position is alanine. In some embodiments, the fifth position is not alanine. In some embodiments, the fifth position is phenylalanine. In some embodiments, the fifth position is not phenylalanine. In some embodiments, the fifth position is serine. In some embodiments, the fifth position is not serine. In some embodiments, the fifth position is glycine. In some embodiments, the fifth position is not glycine. In some embodiments, the fifth position is threonine. In some embodiments, the fifth position is not threonine. In some embodiments, the fifth position is isoleucine. In some embodiments, the fifth position is not isoleucine. In some embodiments, the fifth position is glutamine. In some embodiments, the fifth position is not glutamine. In some embodiments, the fifth position is leucine. In some embodiments, the fifth position is not leucine.

In some embodiments of the core lyciumin peptide, the sixth position is glycine, tyrosine, alanine, threonine, serine, phenylalanine, leucine, cysteine, methionine, isoleucine, arginine, histidine, asparagine, valine, or aspartate. In some embodiments, the sixth position is glycine. In some embodiments, the sixth position is not glycine. In some embodiments, the sixth position is tyrosine. In some embodiments, the sixth position is not tyrosine. In some embodiments, the sixth position is alanine. In some embodiments, the sixth position is not alanine. In some embodiments, the sixth position is threonine. In some embodiments, the sixth position is not threonine. In some embodiments, the sixth position is serine. In some embodiments, the sixth position is not serine. In some embodiments, the sixth position is phenylalanine. In some embodiments, the sixth position is not phenylalanine. In some embodiments, the sixth position is leucine. In some embodiments, the sixth position is not leucine. In some embodiments, the sixth position is cysteine. In some embodiments, the sixth position is not cysteine. In some embodiments, the sixth position is methionine. In some embodiments, the sixth position is not methionine. In some embodiments, the sixth position is isoleucine. In some embodiments, the sixth position is not isoleucine. In some embodiments, the sixth position is arginine. In some embodiments, the sixth position is not arginine. In some embodiments, the sixth position is histidine. In some embodiments, the sixth position is not histidine. In some embodiments, the sixth position is asparagine. In some embodiments, the sixth position is not asparagine. In some embodiments, the sixth position is valine. In some embodiments, the sixth position is not valine. In some embodiments, the sixth position is aspartate. In some embodiments, the sixth position is not aspartate.

In some embodiments of the core lyciumin peptide, the seventh position is serine, isoleucine, threonine, alanine, phenylalanine, glycine, tyrosine, methionine, lysine, valine, or arginine. In some embodiments, the seventh position is serine. In some embodiments, the seventh position is not serine. In some embodiments, the seventh position is isoleucine. In some embodiments, the seventh position is not isoleucine. In some embodiments, the seventh position is threonine. In some embodiments, the seventh position is not threonine. In some embodiments, the seventh position is alanine. In some embodiments, the seventh position is not alanine. In some embodiments, the seventh position is phenylalanine. In some embodiments, the seventh position is not phenylalanine. In some embodiments, the seventh position is glycine. In some embodiments, the seventh position is not glycine. In some embodiments, the seventh position is tyrosine. In some embodiments, the seventh position is not tyrosine. In some embodiments, the seventh position is methionine. In some embodiments, the seventh position is not methionine. In some embodiments, the seventh position is lysine. In some embodiments, the seventh position is not lysine. In some embodiments, the seventh position is valine. In some embodiments, the seventh position is not valine. In some embodiments, the seventh position is arginine. In some embodiments, the seventh position is not arginine.

In some embodiments of the core lyciumin peptide, the eighth position is tyrosine. In some embodiments, the eighth position is not tyrosine. In some embodiments, the eighth position is tryptophan. In some embodiments, the eighth position is not tryptophan.

As used herein, the term "biologically-active fragment," when referring to a lyciumin precursor peptide, refers to a fragment of a lyciumin precursor peptide that includes at least one core lyciumin peptide domain and that can be converted to a lyciumin cyclic peptide (e.g., in a host cell). Typically, the biologically-active fragment is cyclized in the host cell. In some instances, the biologically-active fragment may have shorter N-terminal or C-terminal domains compared to a lyciumin precursor peptide. In some instances, biologically-active fragments can be fragments of naturally-occurring lyciumin precursor peptides. In some instances, a biologically-active fragment can be a portion of a lyciumin precursor peptide having at least one core lyciumin peptide, which is embedded in, or linked to (e.g., at the N-terminus of, at the C-terminus of), a heterologous amino acid sequence that is not generally found in a lyciumin precursor peptide.

In some embodiments, the invention provides a method of producing one or more lyciumin cyclic peptides that includes: (a) providing a host cell that includes a transgene encoding a polypeptide that comprises one or more core lyciumin peptide domains; (b) expressing the transgene in the host cell to thereby produce a polypeptide that includes one or more core lyciumin peptide domains. In some embodiments, the polypeptide is converted to one or more lyciumin cyclic peptides in the host cell.

As used herein, the term "lyciumin cyclic peptide" refers to a branched cyclic peptide with an N-terminal pyroglutamate and a macrocyclic linkage involving a C-terminal tryptophan or tyrosine residue. A lyciumin cyclic peptide typically consists of the eight amino acids of the core lyciumin peptide domain. Typically, the C-terminal residue cyclizes with the α-carbon of the fourth residue. An example is a macrocyclic linkage between a C-terminal tryptophan indole-nitrogen and a glycine-α-carbon.

The BURP domain (Pfam 03181) is around 230 amino acid residues and has the following conserved features: two phenylalanine residues at its N-terminus; two cysteine residues; and four repeated cysteine-histidine motifs, arranged as: CH-X(10)-CH-X(25-27)-CH-X(25-26)-CH, where X can be any amino acid (SEQ ID NO: 282).

The DUF2775 domain (Pfam 10950) is a eukaryotic protein family which includes a number of plant organ-specific proteins. Their predicted amino acid sequence is often repetitive and suggests that these proteins could be exported and glycosylated. Multiple sequence alignment shows a highly conserved motif of 135 amino acids. This motif includes approximately 20 amino acids from the non-repeating area of the peptide, 2 tandem repeats and 1 truncated tandem repeat (Albornos et al., 2012). The first seven amino acids of the DUF2775 domain are typically KDXYXGW (SEQ ID NO: 281), where X can be any amino acid.

Embodiments described herein also include engineered nucleic acids that encode engineered lyciumin precursor peptides (and engineered lyciumin precursor peptides encoded by such engineered nucleic acids). An example is an engineered nucleic acid that encodes n number of core lyciumin peptide domains, wherein n is an integer. The core lyciumin peptide domains within an engineered lyciumin precursor peptide can be identical or non-identical. Multiple identical core lyciumin peptide domains can allow for increased production of a homogenous population of core lyciumin peptides and lyciumin cyclic peptides. Typically, n is an integer from 1 to 10, preferably from 5 to 10. In some instances, n can be greater than 10. In some instances, an engineered nucleic acid encodes from 5 to 10 identical lyciumin precursor peptides. The core lyciumin peptides domains are typically separated by an intervening sequence.

In the example shown in FIGS. 38B-D, the core lyciumin peptide domains, which are indicated in red, are separated by a thirteen amino acid sequence, though different lengths are permissible. In the embodiment of FIGS. 38B-D, arginine is immediately N-terminal to the core lyciumin peptide domain, except for an instance where serine is immediately N-terminal to the core lyciumin peptide domain. In the embodiment of FIGS. 38B-D, tyrosine is immediately C-terminal to the core lyciumin peptide domain. Other amino acids can be immediately N-terminal or C-terminal. A wide variety of core lyciumin peptide domains can be expressed from an engineered nucleic acid.

As used herein, "converting the lyciumin precursor peptide, or biologically-active fragment thereof, to one or more lyciumin cyclic peptides in a host cell," "converted to one or more lyciumin cyclic peptides in a host cell," and similar phrases refer to one or more enzymatic reactions that convert a lyciumin precursor peptide, or biologically-active fragment thereof, to one or more lyciumin cyclic peptides. In some instances, conversion is facilitated by one or more enzymes that cyclizes the lyciumin precursor peptide, or biologically-active fragment thereof. In some instances, conversion is catalyzed, in part, by one or more endopeptidases, such as an arginine endopeptidase, which acts N-terminal to a core lyciumin peptide domain. In some instances, conversion is catalyzed by one or more glutamine cyclotransferases, which cyclize an N-terminal glutamine in a core lyciumin peptide domain. In some instances, conversion is catalyzed by one or more exopeptidases. Conversion to a lyciumin cyclic peptide can, but need not, occur within in a host cell.

Host cells include cells that are capable of converting a lyciumin precursor peptide to a lyciumin cyclic peptide, as well as cells that are incapable of converting a lyciumin precursor peptide to a lyciumin cyclic peptide. For example, a host cell can express a lyciumin precursor peptide but lack one or more enzymes required to convert the lyciumin precursor peptide to a lyciumin cyclic peptide. In such circumstances, the lyciumin precursor peptide can be isolated or obtained from the host cell and then converted to a lyciumin cyclic peptide in another environment (e.g., in a cell free system, such as in a cell lysate (or fractionated cell lysate) from a source that is capable of converting a lyciumin precursor peptide to a lyciumin cyclic peptide).

In some embodiments, a lyciumin precursor peptide can include a tag, which can be used to isolate the lyciumin precursor peptide from a cell that expresses it. Such a tag can be useful for a manufacturing process that involves recombinant expression of a lyciumin precursor peptide and subsequent cyclization using purified enzyme. In some embodiments, a nucleotide sequence encoding a lyciumin precursor peptide is fused in-frame with a nucleotide sequence encoding an epitope tag, also known as an affinity tag, which can be useful for, e.g., protein purification. Examples of suitable epitope tags are known in the art and include FLAG, HA, His, GST, CBP, MBP, c-Myc, DHFR, GFP, CAT and others.

Nucleic Acids

As used herein, the term "nucleic acid" refers to a polymer comprising multiple nucleotide monomers (e.g., ribonucleotide monomers or deoxyribonucleotide monomers). "Nucleic acid" includes, for example, DNA (e.g., genomic DNA and cDNA), RNA, and DNA-RNA hybrid molecules. Nucleic acid molecules can be naturally occurring, recombinant, or synthetic. In addition, nucleic acid molecules can be single-stranded, double-stranded or triple-stranded. In certain embodiments, nucleic acid molecules can be modified. In the case of a double-stranded polymer, "nucleic acid" can refer to either or both strands of the molecule.

The terms "nucleotide" and "nucleotide monomer" refer to naturally occurring ribonucleotide or deoxyribonucleotide monomers, as well as non-naturally occurring derivatives and analogs thereof. Accordingly, nucleotides can include, for example, nucleotides comprising naturally occurring bases (e.g., adenosine, thymidine, guanosine, cytidine, uridine, inosine, deoxyadenosine, deoxythymidine, deoxyguanosine, or deoxycytidine) and nucleotides comprising modified bases known in the art.

As used herein, the term "sequence identity," refers to the extent to which two nucleotide sequences, or two amino acid sequences, have the same residues at the same positions when the sequences are aligned to achieve a maximal level of identity, expressed as a percentage. For sequence alignment and comparison, typically one sequence is designated as a reference sequence, to which a test sequences are compared. The sequence identity between reference and test sequences is expressed as the percentage of positions across the entire length of the reference sequence where the reference and test sequences share the same nucleotide or amino acid upon alignment of the reference and test sequences to achieve a maximal level of identity. As an example, two sequences are considered to have 70% sequence identity when, upon alignment to achieve a maximal level of identity, the test sequence has the same nucleotide or amino acid residue at 70% of the same positions over the entire length of the reference sequence.

Alignment of sequences for comparison to achieve maximal levels of identity can be readily performed by a person of ordinary skill in the art using an appropriate alignment method or algorithm. In some instances, the alignment can include introduced gaps to provide for the maximal level of identity. Examples include the local homology algorithm of Smith & Waterman, *Adv. Appl. Math.* 2:482 (1981), the homology alignment algorithm of Needleman & Wunsch, *J. Mol. Biol.* 48:443 (1970), the search for similarity method of Pearson & Lipman, *Proc. Nat'l. Acad. Sci. USA* 85:2444 (1988), computerized implementations of these algorithms (GAP, BESTFIT, FASTA, and TFASTA in the Wisconsin Genetics Software Package, Genetics Computer Group, 575 Science Dr., Madison, Wis.), and visual inspection (see generally Ausubel et al., Current Protocols in Molecular Biology).

When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters. A commonly used tool for determining percent sequence identity is Protein Basic Local Alignment Search Tool (BLASTP) available through National Center for Biotechnology Information, National Library of Medicine, of the United States National Institutes of Health. (Altschul et al., 1990).

In various embodiments, two nucleotide sequences, or two amino acid sequences, can have at least, e.g., 70%, 75%, 80%, 85%, 86%, 87%, 88%, 89%, 90%, 91%, 92%, 93%, 94%, 95%, 96%, 97%, 98%, 99%, or more, sequence identity. When ascertaining percent sequence identity to one or more sequences described herein, the sequences described herein are the reference sequences.

For many of the nucleotide sequences described herein, additional 5'- and 3'-nucleotides can be appended to the nucleotide sequence in order to perform Gibson cloning of the sequence into an expression vector. Gibson cloning utilizes Gibson assembly, an exonuclease-based method for joining DNA fragments. For example, a 5' adapter (see SEQ ID NO: 123) and a 3' adapter (see SEQ ID NO: 124) can be appended 5' and 3', respectively, to SEQ ID NOS: 9 through 33 for Gibson cloning and assembly into tobacco expression vector pEAQ-HT.

Vectors

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by, e.g., restriction enzyme technology. Some viral vectors comprise the RNA of a transmissible agent. A common type of vector is a "plasmid", which generally is a self-contained molecule of double-stranded DNA that can readily accept additional (foreign) DNA and which can readily introduced into a suitable host cell. A large number of vectors, including plasmid and fungal vectors, have been described for replication and/or expression in a variety of eukaryotic and prokaryotic hosts.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

Gene delivery vectors generally include a transgene (e.g., nucleic acid encoding an enzyme) operably linked to a promoter and other nucleic acid elements required for expression of the transgene in the host cells into which the vector is introduced. Suitable promoters for gene expression and delivery constructs are known in the art. For bacterial host cells, suitable promoters, include, but are not limited to promoters obtained from the E. coli lac operon, Streptomyces coelicolor agarase gene (dagA), Bacillus subtilis levansucrase gene (sacB), Bacillus licheniformis alpha-amylase gene (amyL), Bacillus stearothermophilus maltogenic amylase gene (amyM), Bacillus amyloliquefaciens alpha-amylase gene (amyQ), Bacillus licheniformis penicillinase gene (penP), Bacillus subtilis xylA and xylB genes, and prokaryotic beta-lactamase gene (See e.g., Villa-Kamaroff et al., Proc. Natl. Acad. Sci. USA 75:3727-3731, 1978), as well as the tac promoter (See e.g., DeBoer et al., Proc. Natl. Acad. Sci. USA 80:21-25, 1983). Examples of promoters for filamentous fungal host cells, include, but are not limited to promoters obtained from the genes for Aspergillus oryzae TAKA amylase, Rhizomucor miehei aspartic proteinase, Aspergillus niger neutral alpha-amylase, Aspergillus niger acid stable alpha-amylase, Aspergillus niger or Aspergillus awamori glucoamylase (glaA), Rhizomucor miehei lipase, Aspergillus oryzae alkaline protease, Aspergillus oryzae triose phosphate isomerase, Aspergillus nidulans acetamidase, and Fusarium oxysporum trypsin-like protease (See e.g., WO 96/00787), as well as the NA2-tpi promoter (a hybrid of the promoters from the genes for Aspergillus niger neutral alpha-amylase and Aspergillus oryzae triose phosphate isomerase), and mutant, truncated, and hybrid promoters thereof. Examples of yeast cell promoters can be from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH2/GAP), and Saccharomyces cerevisiae 3-phosphoglycerate kinase. Other useful promoters for yeast host cells are known in the art (See e.g., Romanos et al., Yeast 8:423-488, 1992). For plant host cells, examples of suitable promoters include the cauliflower mosaic virus 35S promoter (CaMV 35S), and promoters (e.g., constitutive promoters) of genes that are highly expressed in plants (e.g., plant housekeeping genes, genes encoding Ubiquitin, Actin, Tubulin, or EIF (eukaryotic initiation factor)). Plant virus promoters can also be used. Additional useful plant promoters include those discussed in [50, 51], the entire contents of which are incorporated herein by reference. The selection of a suitable promoter is within the skill in the art. The recombinant plasmids can also comprise inducible, or regulatable, promoters for expression of a lyciumin precursor peptide, or biologically-active fragment thereof, in cells.

Various gene delivery vehicles are known in the art and include both viral and non-viral (e.g., naked DNA, plasmid) vectors. Viral vectors suitable for gene delivery are known to those skilled in the art. Such viral vectors include, e.g., vector derived from the herpes virus, baculovirus vector, lentiviral vector, retroviral vector, adenoviral vector and adeno-associated viral vector (AAV). Vectors derived from plant viruses can also be used, such as the viral backbones of the RNA viruses Tobacco mosaic virus (TMV), Potato virus X (PVX) and Cowpea mosaic virus (CPMV), and the DNA geminivirus Bean yellow dwarf virus. The viral vector can be replicating or non-replicating.

Non-viral vectors include naked DNA and plasmids, among others. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and such vectors may be introduced into many appropriate host cells, using methods disclosed or cited herein or otherwise known to those skilled in the relevant art.

In certain embodiments, the vector comprises a transgene operably linked to a promoter. The transgene encodes a biologically-active molecule, such as a lyciumin precursor peptide described herein.

To facilitate the introduction of the gene delivery vector into host cells, the vector can be combined with different chemical means such as colloidal dispersion systems (macromolecular complex, nanocapsules, microspheres, beads) or lipid-based systems (oil-in-water emulsions, micelles, liposomes).

Some embodiments relate to a vector comprising a nucleic acid encoding lyciumin precursor peptide, or biologically-active fragment thereof, described herein. In certain embodiments, the vector is a plasmid, and includes any one or more plasmid sequences such as, e.g., a promoter sequence, a selection marker sequence, or a locus-targeting sequence. Suitable plasmid vectors include p423TEF 2μ, p425TEF 2μ, and p426TEF 2μ. Another suitable vector is pHis8-4 (Whitehead Institute, Cambridge, Massachusetts, United States of America). Another suitable vector is pEAQ-HT [50].

Although the genetic code is degenerate in that most amino acids are represented by multiple codons (called "synonyms" or "synonymous" codons), it is understood in the art that codon usage by particular organisms is nonrandom and biased towards particular codon triplets. Accordingly, in some embodiments, the vector includes a nucleotide sequence that has been optimized for expression in a particular type of host cell (e.g., through codon optimization). Codon optimization refers to a process in which a polynucleotide encoding a protein of interest is modified to replace particular codons in that polynucleotide with codons that encode the same amino acid(s), but are more commonly used/recognized in the host cell in which the nucleic acid is being expressed. In some aspects, the polynucleotides described herein are codon optimized for expression in a bacterial cell, e.g., *E. coli*. In some aspects, the polynucleotides described herein are codon optimized for expression in a yeast cell, e.g., *S. cerevisiae*. In some aspects, the polynucleotides described herein are codon optimized for expression in a tobacco cell, e.g., *N. benthamiana*.

Host Cells

A wide variety of host cells can be used in the present invention, including fungal cells, bacterial cells, plant cells, insect cells, and mammalian cells.

In some embodiments, the host cell is a fungal cell, such as a yeast cell and an *Aspergillus* spp cell. A wide variety of yeast cells are suitable, such as cells of the genus *Pichia*, including *Pichia pastoris* and *Pichia stipitis*; cells of the genus *Saccharomyces*, including *Saccharomyces cerevisiae*; cells of the genus *Schizosaccharomyces*, including *Schizosaccharomyces pombe*; and cells of the genus *Candida*, including *Candida albicans*.

In some embodiments, the host cell is a bacterial cell. A wide variety of bacterial cells are suitable, such as cells of the genus *Escherichia*, including *Escherichia coli*; cells of the genus *Bacillus*, including *Bacillus subtilis*; cells of the genus *Pseudomonas*, including *Pseudomonas aeruginosa*; and cells of the genus *Streptomyces*, including *Streptomyces griseus*.

In some embodiments, the host cell is a plant cell. A wide variety of cells from a plant are suitable, including cells from a *Nicotiana benthamiana* plant. In some embodiments, the plant belongs to a genus selected from the group consisting of *Arabidopsis*, *Beta*, *Glycine*, *Helianthus*, *Solanum*, *Triticum*, *Oryza*, *Brassica*, *Medicago*, *Prunus*, *Malus*, *Hordeum*, *Musa*, *Phaseolus*, *Citrus*, Piper, Sorghum, *Daucus*, *Manihot*, *Capsicum*, and *Zea*. In some embodiments, the host cell is a plant cell from the Amaranthaceae family. In some embodiments, the plant cell is an *Amaranthus* genus plant cell, such as an *Amaranthus hypochondriacus* plant cell. In some embodiments, the plant cell is a Beta genus plant cell, such as a *Beta vulgaris* plant cell. In some embodiments, the plant cell is a *Chenopodium* genus plant cell, such as a *Chenopodium quinoa* plant cell. In some embodiments, the plant cell is a Fabaceae family plant cell. In some embodiments, the plant cell is a Glycine genus plant cell, such as a *Glycine max* plant cell. In some embodiments, the plant cell is a *Medicago* genus plant cell, such as a *Medicago truncatula* plant cell. In some embodiments, the plant cell is a Solanaceae family plant cell. In some embodiments, the plant cell is a *Solanum* genus plant cell, such as a *Solanum melongena* plant cell or a *Solanum tuberosum* plant cell. In some embodiments, the plant cell is a *Nicotiana* genus plant cell, such as a *Nicotiana benthamiana* plant cell. In some embodiments, the plant cell is a *Capsicum* genus plant cell, such as a *Capsicum annuum* plant cell.

In some embodiments, the host cell is an insect cell, such as a *Spodoptera frugiperda* cell, such as *Spodoptera frugiperda* Sf9 cell line and *Spodoptera frugiperda* Sf21 In some embodiments, the host cell is a mammalian cell.

In some embodiments, the host cell is an *Escherichia coli* cell. In some embodiments, the host cell is a *Nicotiana benthamiana* cell. In some embodiments, the cell is a *Saccharomyces cerevisiae* cell.

As used herein, the term "host cell" encompasses cells in cell culture and also cells within an organism (e.g., a plant). In some embodiments, the host cell is part of a transgenic plant.

Some embodiments relate to a host cell comprising a vector as described herein. In certain embodiments, the host cell is an *Escherichia coli* cell, a *Nicotiana benthamiana* cell, or a *Saccharomyces cerevisiae* cell.

In some embodiments, the host cells are cultured in a cell culture medium, such as a standard cell culture medium known in the art to be suitable for the particular host cell.

Methods of Making Transgenic Host Cells

Described herein are methods of making a transgenic host cell. The transgenic host cells can be made, for example, by introducing one or more of the vector embodiments described herein into the host cell.

In some embodiments, the method comprises introducing into a host cell a vector that includes a nucleic acid transgene that encodes a lyciumin precursor peptide, or a biologically-active fragment thereof. The lyciumin precursor peptide, or biologically-active fragment thereof, can include one or more core lyciumin peptide domains.

In some embodiments, one or more of the nucleic acids are integrated into the genome of the host cell. In some embodiments, the nucleic acids to be integrated into a host genome can be introduced into the host cell using any of a variety of suitable methodologies known in the art, including, for example, CRISPR-based systems (e.g., CRISPR/Cas9; CRISPR/Cpf1), TALEN systems and *Agrobacterium*-mediated transformation. However, as those skilled in the art would recognize, transient transformation techniques can be used that do not require integration into the genome of the host cell. In some embodiments, nucleic acid (e.g., plasmids) can be introduced that are maintained as episomes, which need not be integrated into the host cell genome.

In certain embodiments, the nucleic acid is introduced into a tissue, cell, or seed of a plant cell. Various methods of introducing nucleic acid into the tissue, cell, or seed of plants are known to one of ordinary skill in the art, such as protoplast transformation. The particular method can be selected based on several considerations, such as, e.g., the type of plant used. For example, a floral dip method is a suitable method for introducing genetic material into a plant.

In other embodiments, agroinfiltration can be useful for transient expression in plants. In certain embodiments, the nucleic acid can be delivered into the plant by an *Agrobacterium*.

In some embodiments, a host cell is selected or engineered to have increased activity of the synthesis pathway.

Some of the methods described herein include assaying for an activity of interest. For example, crude extract from a host cell that expresses a lyciumin precursor peptide and/or lyciumin cyclic peptide, or a lyciumin cyclic peptide isolated from the host cell, can be assayed for an activity of interest. An example of an activity of interest is modulation (enhancement or inhibition) of fungal or bacterial growth, such as the ability to inhibit growth of a pathogenic fungal or bacterial species or the ability to promote growth of a potentially desirable fungal or bacterial species. Another example of an activity of interest is a protease inhibitor activity, which can include inhibition of a viral, bacterial, fungal, or mammalian protease.

Exemplification

Example 1

Results
Lyciumins are Plant RiPPs

The requirement for precursor gene-guided genome mining of a class of plant ribosomal peptides is the identification of a peptide-specific precursor gene, which provides the peptide sequence information via the core peptide. In order to identify the lyciumin precursor gene, a de novo transcriptome was generated of the roots of a *Lycium barbarum* plant, which produced lyciumin A, B and D based on liquid chromatography-mass spectrometry (LC-MS). Tblastn search of predicted core peptide sequences of lyciumin A (SEQ ID NO: 148; QPYGVGSW), lyciumin B (SEQ ID NO: 50; QPWGVGSW) and lyciumin D (SEQ ID NO: 174; QPYGVGIW) yielded three partial transcripts of candidate lyciumin precursor genes and a full length sequence of a candidate lyciumin precursor gene was obtained by cloning guided by these transcripts (FIGS. 1C and 5). The identified lyciumin precursor from *Lycium barbarum*, LbaLycA, consists of an N-terminal signal peptide indicating processing through the secretory pathway (FIG. 6) [27], an N-terminal domain with twelve repeats with each including a core peptide for lyciumin A, B or D and a C-terminal BURP domain (Pfam 03181) [28]. BURP domain proteins are terrestrial plant-specific proteins, which have diverse tempo-spatial expression patterns in plants and are often associated with abiotic stress responses of plants and exhibit diverse temporal and spatial expression patterns in plants. BURP domain proteins are named after their initial members: BNM2, a microspore protein from *Brassica rapus* [30], VfUSP, an unknown seed protein from *Vicia faba* [31], RD22, an *Arabidopsis thaliana* dehydration-responsive protein [32], and PG1B, a β-subunit of polygalacturonase isoenzyme 1 of tomato [33].

Figure 1D:
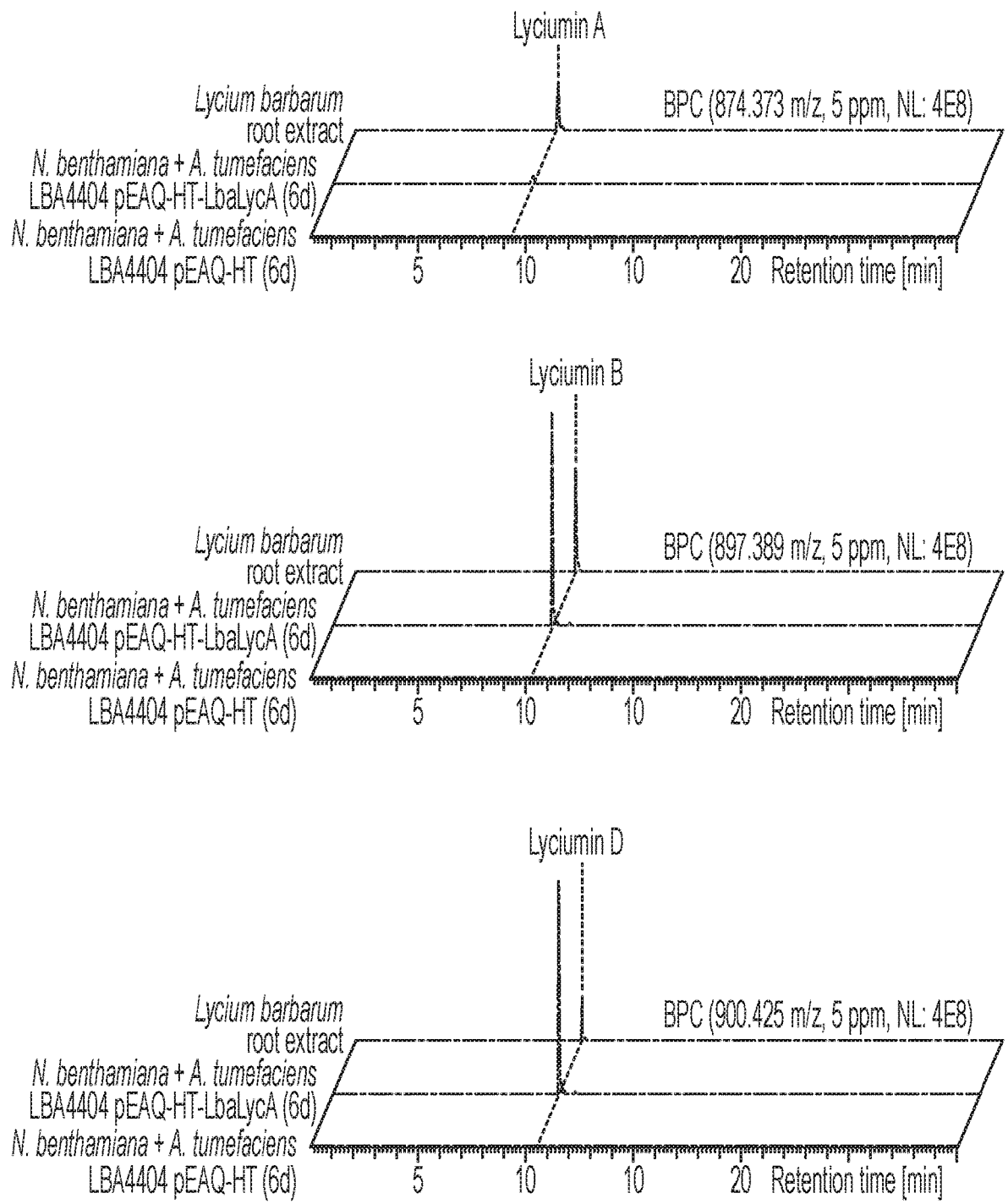

In order to test whether LbaLycA is a precursor peptide for lyciumin biosynthesis, LbaLycA was expressed heterologously in *Nicotiana benthamiana* via infiltration of *Agrobacterium tumefaciens* LBA4404 pEAQ-HT-LbaLycA. LC-MS analysis of an organic extract of *N. benthamiana* leaves six days after inoculation with *A. tumefaciens* LBA4404 pEAQ-HT-LbaLycA showed mass signals for lyciumin A, B and D, as detected in *Lycium barbarum* root extracts (FIG. 1D), while no lyciumin mass signals appeared in the empty vector control. This result showed that lyciumins are plant RiPPs. In addition, the reconstitution of lyciumin biosynthesis by sole expression of a lyciumin precursor gene in *N. benthamiana* (Solanaceae) leaves revealed that tobacco leaf cells must have the enzymes necessary to produce lyciumins.

TABLE 1

Genome mining of BURP domain proteins in plant genomes and predicted lyciumin core peptides. Asterisks indicate transcriptome-derived lyciumin core peptide sequences.

| Organism (Genome version) | Family | Database | Predicted BURP domain # | Predicted core peptides |
|---|---|---|---|---|
| Amaranthus hypochondriacus (v1.0) | Amaranthaceae | JGI Phytozome 12.1 | 19 | QPYTVGSW (SEQ ID NO: 41), QPYTVFSW (SEQ ID NO: 42) |
| Amborella trichopoda (v1.0) | Amborellaceae | JGI Phytozome 12.1 | 34 | |
| Anacardium occidentale (v0.9) | Anacardiaceae | JGI Phytozome pre-release species | 13 | |
| Ananas comosus (v3) | Bromeliaceae | JGI Phytozome 12.1 | 7 | |
| Aquilegia coerulea (v3.1) | Ranunculaceae | JGI Phytozome 12.1 | 5 | |
| Arabidopsis halleri (v1.1) | Brassicaceae | JGI Phytozome 12.1 | 5 | |
| Arabidopsis lyrata (v2.1) | Brassicaceae | JGI Phytozome 12.1 | 7 | |
| Arabidopsis thaliana (TAIR10) | Brassicaceae | JGI Phytozome 12.1 | 5 | |
| Arachis duranensis (Aradu1.1) | Fabaceae | NCBI (GenBank JQIN00000000.1) | 18 | QPYGVYTW (SEQ ID NO: 43) |
| Arachis ipaensis (Araip1.1) | Fabaceae | NCBI (GenBank JQIO00000000.1) | 17 | QPYGVYTW (SEQ ID NO: 43) |

TABLE 1-continued

Genome mining of BURP domain proteins in plant genomes and predicted lyciumin core peptides. Asterisks indicate transcriptome-derived lyciumin core peptide sequences.

| Organism (Genome version) | Family | Database | Predicted BURP domain # | Predicted core peptides |
|---|---|---|---|---|
| Aegilops tauschii (Aet_MR_1.0) | Poaceae | NCBI (GenBank MCGU00000000.1) | 24 | |
| Asparagus officinalls (V1.1) | Asparagaceae | JGI Phytozome pre-release species | 7 | |
| Beta vulgaris (RefBeet-1.2.2) | Amaranthaceae | NCBI (GenBank AYZS00000000.2) | 18 | QPWTVYGW (SEQ ID NO: 44), QPWTVAGW (SEQ ID NO: 45), QPFTISAW (SEQ ID NO: 46), QPWTVAAW (SEQ ID NO: 47) |
| Boechera stricta (v1.2) | Brassicaceae | JGI Phytozome 12.1 | 5 | |
| Brachypodium distachyon (v3.1) | Poaceae | JGI Phytozome 12.1 | 14 | |
| Brachypodium stacei (v1.1) | Poaceae | JGI Phytozome 12.1 | 16 | |
| Brachypodium sylvaticum (v1.1) | Poaceae | JGI Phytozome pre-release species | 19 | |
| Brassica oleracea capitata (v1.0) | Brassicaceae | JGI Phytozome 12.1 | 7 | |
| Brassica rapa FPsc (v1.3) | Brassicaceae | JGI Phytozome 12.1 | 9 | |
| Cajanus cajan (C.cajan_V1.0) | Fabaceae | NCBI (GenBank AGCT00000000.1) | 13 | |
| Camelina sativa (Cs) | Brassicaceae | NCBI (GenBank JFZQ00000000.1) | 17 | |
| Capsella grandiflora (v1.1) | Brassicaceae | JGI Phytozome 12.1 | 5 | |
| Capsella rubella (v1.0) | Brassicaceae | JGI Phytozome 12.1 | 5 | |
| Capsicum annuum (Zunla 1 Ref_v1.0) | Solanaceae | NCBI (GenBank ASJU00000000.1) | 23 | QPYGGLTW (SEQ ID NO: 48), QPWGVCLW (SEQ ID NO: 49), QPWGVGSW (SEQ ID NO: 50), QPWGVGFW (SEQ ID NO: 51) |
| Capsicum baccatum (ASM227188v2) | Solanaceae | NCBI (GenBank MLFT00000000.2) | 21 | |
| Capsicum chinense (ASM227189v2) | Solanaceae | NCBI (GenBank MCIT00000000.2) | 21 | QPWGVCFW (SEQ ID NO: 52), QPWGVGSW (SEQ ID NO: 50), QPWGVGFW (SEQ ID NO: 51) |
| Carica papaya (ASGPBv0.4) | Caricaceae | JGI Phytozome 12.1 | 11 | |
| Chenopodium quinoa (v1.0) | Amaranthaceae | JGI Phytozome pre-release species | 42 | QPFTVVGW (SEQ ID NO: 53), QPYTVMAW (SEQ ID NO: 54), QPYTVWGW (SEQ ID NO: 55), |

TABLE 1-continued

Genome mining of BURP domain proteins in plant genomes and predicted lyciumin core peptides. Asterisks indicate transcriptome-derived lyciumin core peptide sequences.

| Organism (Genome version) | Family | Database | Predicted BURP domain # | Predicted core peptides |
|---|---|---|---|---|
| | | | | QPYTVMGW (SEQ ID NO: 56), QPYTVYGW (SEQ ID NO: 57), QPFTVFGW (SEQ ID NO: 58), QPYTVDGW (SEQ ID NO: 59) |
| Cicer arietinum (v1.0) | Fabaceae | JGI Phytozome pre-release species | 15 | |
| Citrus clementina (v1.0) | Rutaceae | JGI Phytozome 12.1 | 11 | |
| Citrus sinensis (v1.1) | Rutaceae | JGI Phytozome 12.1 | 9 | |
| Coffea arabica (UCDv0.5) | Rubiaceae | JGI Phytozome pre-release species | 61 | |
| Cucumis melo (ASM31304v1) | Cucurbitaceae | NCBI (GenBank CAJI00000000.1) | 7 | |
| Cucumis sativus (v1.0) | Cucurbitaceae | JGI Phytozome 12.1 | 7 | |
| Cucurbita moschata (Cmos_1.0) | Cucurbitaceae | NCBI (GenBank NEWM00000000.1) | 10 | |
| Daucus carota (v2.0) | Apiaceae | JGI Phytozome 12.1 | 14 | |
| Dichanthelium oligosanthes (ASM163321v2) | Poaceae | NCBI (GenBank LWDX00000000.2) | 11 | |
| Durio zibethinus (Duzib1.0) | Malvaceae | NCBI (GenBank NSDW00000000.1) | 20 | |
| Elaeis guineensis (EG5) | Arecaceae | NCBI (GenBank ASJS00000000.1) | 21 | |
| Erythranthe guttata (Mimgu1_0) | Phrymaceae | NCBI (GenBank APLE00000000.1) | 6 | |
| Eucalyptus grandis (v2.0) | Myrtaceae | JGI Phytozome 12.1 | 14 | |
| Eutrema salsugineum (v1.0) | Brassicaceae | JGI Phytozome 12.1 | 5 | |
| Fragaria vesca (v1.1) | Rosaceae | JGI Phytozome 12.1 | 10 | |
| Glycine max (Wm82.a2.v1) | Fabaceae | JGI Phytozome 12.1 | 26 | QPFTVFAW (SEQ ID NO: 60), QPWGVGTW (SEQ ID NO: 61), QPYGVYTW (SEQ ID NO: 43) |
| Gossypium hirsutum (v1.1) | Malvaceae | JGI Phytozome pre-release species | 27 | |
| Gossypium raimondii (v2.1) | Malvaceae | JGI Phytozome 12.1 | 18 | |
| Hevea brasiliensis (ASM165405v1) | Euphorbiaceae | NCBI (GenBank LVXX00000000.1) | 19 | |
| Helianthus annuus (r1.2) | Asteraceae | JGI Phytozome pre-release species | 17 | |
| Hordeum vulgare (r1) | Poaceae | JGI Phytozome pre-release species | 15 | |
| Ipomoea nil (Asagao_1.1) | Convolvulaceae | NCBI (GenBank BDFN00000000.1) | 12 | |
| Jatropha curcas (JatCur_1.0) | Euphorbiaceae | NCBI (GenBank AFEW00000000.1) | 32 | |
| Juglans regia (wgs.5d) | Juglandaceae | NCBI (GenBank LIHL00000000.1) | 13 | |
| Kalanchoe fedtschenkoi (v1.1) | Crassulaceae | JGI Phytozome 12.1 | 32 | |
| Kalanchoe laxiflora (v1.1) | Crassulaceae | JGI Phytozome 12.1 | 31 | |

TABLE 1-continued

Genome mining of BURP domain proteins in plant genomes and predicted lyciumin core peptides. Asterisks indicate transcriptome-derived lyciumin core peptide sequences.

| Organism (Genome version) | Family | Database | Predicted BURP domain # | Predicted core peptides |
| --- | --- | --- | --- | --- |
| Lactuca sativa (V8) | Asteraceae | JGI Phytozome pre-release species | 12 | |
| Linum usitatissimum (v1.0) | Linaceae | JGI Phytozome 12.1 | 18 | |
| Lupinus angustifolius (LupAngTanjil_v1.0) | Fabaceae | NCBI (GenBank MLAU00000000.1) | 13 | |
| Malus domestica (v1.0) | Rosaceae | JGI Phytozome 12.1 | 28 | |
| Manihot esculenta (v6.1) | Euphorbiaceae | JGI Phytozome 12.1 | 31 | |
| Marchantia polymorpha (v3.1) | Marchantiaceae | JGI Phytozome 12.1 | 1 | |
| Medicago truncatula (Mt4.0v1) | Fabaceae | JGI Phytozome 12.1 | 52 | QPLLFIYW (SEQ ID NO: 62), QPYGVYFW (SEQ ID NO: 63), QPYGVYTW (SEQ ID NO: 43), QPLTTRMW (SEQ ID NO: 64), QPLITRMW (SEQ ID NO: 146), QPLTTSMW (SEQ ID NO: 65), QPITTHMW (SEQ ID NO: 66), QPFGINIW (SEQ ID NO: 67), QPFGVLTW (SEQ ID NO: 68), QPFGFFSW (SEQ ID NO: 69), QPLPAHKW (SEQ ID NO: 70), QPFRTIGW (SEQ ID NO: 71), QPLGAVKW (SEQ ID NO: 72), QPFGSLTW (SEQ ID NO: 73), QPFGVAAW (SEQ ID NO: 74), QPFGFRAW (SEQ ID NO: 75), QPFEAHTW (SEQ ID NO: 76) |
| Mimulus guttatus (v2.0) | Phrymaceae | JGI Phytozome 12.1 | 8 | |
| Miscanthus sinensis (v7.1) | Poaceae | JGI Phytozome pre-release species | 23 | |
| Morus notabilis (ASM41409v2) | Moraceae | NCBI (GenBank ATGF00000000.1) | 10 | |
| Musa acuminata (v1) | Musaceae | JGI Phytozome 12.1 | 7 | |

TABLE 1-continued

Genome mining of BURP domain proteins in plant genomes and predicted lyciumin core peptides. Asterisks indicate transcriptome-derived lyciumin core peptide sequences.

| Organism (Genome version) | Family | Database | Predicted BURP domain # | Predicted core peptides |
|---|---|---|---|---|
| Nelumbo nucifera (Chinese Lotus 1.1) | Nelumbonaceae | NCBI (GenBank AQOG00000000.1) | 8 | |
| Nicotiana attenuata (v2) | Solanaceae | NCBI (GenBank MJEQ00000000.1) | 14 | QPWGVYSW (SEQ ID NO: 77) |
| Nicotiana benthamiana (v1.0.1) | Solanaceae | Sol Genomics Network | 12 | |
| Nicotiana sylvestris (Nsyl) | Solanaceae | NCBI (GenBank ASAF00000000.1) | 10 | |
| Nicotiana tabacum (v1.0 Edwards 2017) | Solanaceae | Sol Genomics Network | 15 | |
| Nicotiana tomentosiformis (Ntom_v01) | Solanaceae | NCBI (GenBank ASAG00000000.1) | 10 | |
| Olea europaea var. sylvestris (v1.0) | Oleaceae | JGI Phytozome pre-release species | 16 | |
| Oropetium thomaeum (v1.0) | Poaceae | JGI Phytozome 12.1 | 4 | |
| Oryza sativa (v7_JGI) | Poaceae | JGI Phytozome 12.1 | 18 | |
| Panicum hallii (v2.0) | Poaceae | JGI Phytozome 12.1 | 13 | |
| Panicum virgatum (v1.1) | Poaceae | JGI Phytozome 12.1 | 36 | |
| Petunia axillaris (v1.6.2) | Solanaceae | Sol Genomics Network | 13 | QPYGVFAW (SEQ ID NO: 78), QPFGVFAW (SEQ ID NO: 79) |
| Petunia inflata (v1.0.1) | Solanaceae | Sol Genomics Network | 14 | QPYGPFGW (SEQ ID NO: 80), QPFGDYVW (SEQ ID NO: 81), QPYGVFGW (SEQ ID NO: 82), QPFGVFGW (SEQ ID NO: 83), QPFGVFVW (SEQ ID NO: 84) |
| Phalaenopsis equestris (ASM126359v1) | Orchidaceae | NCBI (GenBank APLD00000000.1) | 7 | |
| Phaseolus vulgaris (v2.1) | Fabaceae | JGI Phytozome 12.1 | 11 | |
| Phoenix dactylifera (DPV01) | Arecaceae | NCBI (GenBank ATBV00000000.1) | 11 | |
| Physcomitrella patens (v3.3) | Funariaceae | JGI Phytozome 12.1 | 9 | |
| Populus deltoides (WV94 v2.1) | Fabaceae | JGI Phytozome pre-release species | 21 | |
| Populus euphratica (PopEup_1.0) | Salicaceae | NCBI (GenBank AOFL00000000.1) | 14 | |
| Populus trichocarpa (v3.0) | Salicaceae | JGI Phytozome 12.1 | 20 | |
| Prunus avium (PAV_r1.0) | Rosaceae | NCBI (GenBank BDGV00000000.1) | 19 | QPAPQLYW (SEQ ID NO: 85) |
| Prunus persica (v2.1) | Rosaceae | JGI Phytozome 12.1 | 29 | QPAAQLYW (SEQ ID NO: 86), QPAPQLYW (SEQ ID NO: 85) |

TABLE 1-continued

Genome mining of BURP domain proteins in plant genomes and predicted lyciumin core peptides. Asterisks indicate transcriptome-derived lyciumin core peptide sequences.

| Organism (Genome version) | Family | Database | Predicted BURP domain # | Predicted core peptides |
|---|---|---|---|---|
| Pyrus x bretschneideri (Pbr_ v1.0) | Rosaceae | NCBI (GenBank AJSU00000000.1) | 21 | |
| Raphanus sativus (Rs1.0) | Brassicaceae | NCBI (GenBank JRUI00000000.2) | 11 | |
| Ricinus communis (v0.1) | Euphorbiaceae | JGI Phytozome 12.1 | 24 | |
| Salix purpurea (v1.0) | Salicaceae | JGI Phytozome 12.1 | 12 | |
| Selaginella moellendorffii (v1.0) | Selaginellaceae | JGI Phytozome 12.1 | 7 | |
| Sesamum indicum (v1.0) | Pedaliaceae | NCBI (GenBank APMJ00000000.1) | 9 | |
| Setaria italica (v2.2) | Poaceae | JGI Phytozome 12.1 | 15 | |
| Setaria viridis (v1.1) | Poaceae | JGI Phytozome 12.1 | 15 | |
| Solanum lycopersicum (iTAG2.4) | Solanaceae | JGI Phytozome 12.1 | 14 | QPWGVGAW (SEQ ID NO: 87), QPWGVYRW (SEQ ID NO: 88), QPYGVYRW (SEQ ID NO: 89), QPYGVYSW (SEQ ID NO: 90), QPWGVGSW (SEQ ID NO: 50) |
| Solanum melongena (v2.5.1) | Solanaceae | Sol Genomics Network | 10 | QPWGVNSW (SEQ ID NO: 91), QPWGVLRW (SEQ ID NO: 92), QPWGVGSW (SEQ ID NO: 50), QPWGVLGW (SEQ ID NO: 93), QPYGVYTW (SEQ ID NO: 43), |
| Solanum pennellii | Solanaceae | Sol Genomics Network | 13 | QPWGVGAW (SEQ ID NO: 87), QPFGVYRW (SEQ ID NO: 94), QPWGVFRW (SEQ ID NO: 95), QPWGVGSW (SEQ ID NO: 50) |
| Solanum pimpinellifolium (LA1589) | Solanaceae | Sol Genomics Network | 13 | QPWGVGAW (SEQ ID NO: 87), QPWGVYRW (SEQ ID NO: 88), QPYGVYRW (SEQ ID NO: 89), QPYGVYSW (SEQ ID NO: 90), |

TABLE 1-continued

Genome mining of BURP domain proteins in plant genomes and predicted lyciumin core peptides. Asterisks indicate transcriptome-derived lyciumin core peptide sequences.

| Organism (Genome version) | Family | Database | Predicted BURP domain # | Predicted core peptides |
|---|---|---|---|---|
| Solanum tuberosum (v4.03) | Solanaceae | JGI Phytozome 12.1 | 20 | QPWGVGSW (SEQ ID NO: 50) QPWGVDSW (SEQ ID NO: 97), QPYGVGVW (SEQ ID NO: 98), QPFGVGRW* (SEQ ID NO: 99), QPWGVGRW* (SEQ ID NO: 100), QPFGVVAW* (SEQ ID NO: 101), QPYGVLAW* (SEQ ID NO: 102), QPYGVSRW* (SEQ ID NO: 103), QPWGVVAW* (SEQ ID NO: 104), QPYGVFRW* (SEQ ID NO: 105), QPYGVFAW* (SEQ ID NO: 78), QPYGVDGW* (SEQ ID NO: 107), QPYGVYRW* (SEQ ID NO: 89), QPWGVGAW* (SEQ ID NO: 87), QPYGVFGW* (SEQ ID NO: 82), QPFGVFGW* (SEQ ID NO: 83), QPYGVFAW* (SEQ ID NO: 78), QPWGVGSW* (SEQ ID NO: 50) |
| Sorghum bicolor (v3.1.1) | Poaceae | JGI Phytozome 12.1 | 11 | |
| Sphagnum fallax (v0.5) | Sphagnaceae | JGI Phytozome 12.1 | 8 | |
| Spinacia oleracea (ASM200726v1) | Amaranthaceae | NCBI (GenBank LZYP00000000.1) | 16 | |
| Spirodela polyrhiza (v2) | Araceae | JGI Phytozome 12.1 | 11 | |
| Tarenaya hassleriana (ASM46358v1) | Cleomaceae | NCBI (GenBank AOUI00000000.1) | 8 | |
| Theobroma cacao (v1.1) | Malvaceae | JGI Phytozome 12.1 | 14 | |
| Trifolium pratense (v2) | Fabaceae | JGI Phytozome 12.1 | 36 | QPLGTWIW (SEQ ID NO: 108), QPFGIAAW (SEQ ID NO: 109), |

TABLE 1-continued

Genome mining of BURP domain proteins in plant genomes and predicted lyciumin core peptides. Asterisks indicate transcriptome-derived lyciumin core peptide sequences.

| Organism (Genome version) | Family | Database | Predicted BURP domain # | Predicted core peptides |
|---|---|---|---|---|
| | | | | QPSGVYIW (SEQ ID NO: 110), QPFGINIW (SEQ ID NO: 67), QPYGVYTW (SEQ ID NO: 43) |
| *Triticum aestivum* (v2.2) | Poaceae | JGI Phytozome pre-release species | 33 | |
| *Vicia faba* (VfEP_Reference-Unigene) | Fabaceae | NCBI (GenBank CSVX00000000.1) | 5 | |
| *Vigna angularis* (Vigan1.1) | Fabaceae | NCBI (GenBank JZJH00000000.1) | 13 | |
| *Vigna radiata* (release 101) | Fabaceae | NCBI (GenBank JJMO00000000.1) | 24 | |
| *Vigna unguiculata* (v1.1) | Fabaceae | JGI Phytozome pre-release species | 19 | QPATLLAW (SEQ ID NO: 111) |
| *Vitis vinifera* (Genoscope.12X) | Vitaceae | JGI Phytozome 12.1 | 7 | |
| *Zea mays* PH207 (v1.1) | Poaceae | JGI Phytozome 12.1 | 10 | |
| *Ziziphus jujuba* (ZizJuj_1.1) | Rhamnaceae | NCBI (GenBank JREP00000000.1) | 20 | |
| *Zostera marina* (v2.2) | Zosteraceae | JGI Phytozome 12.1 | 9 | |

Figure 2A:
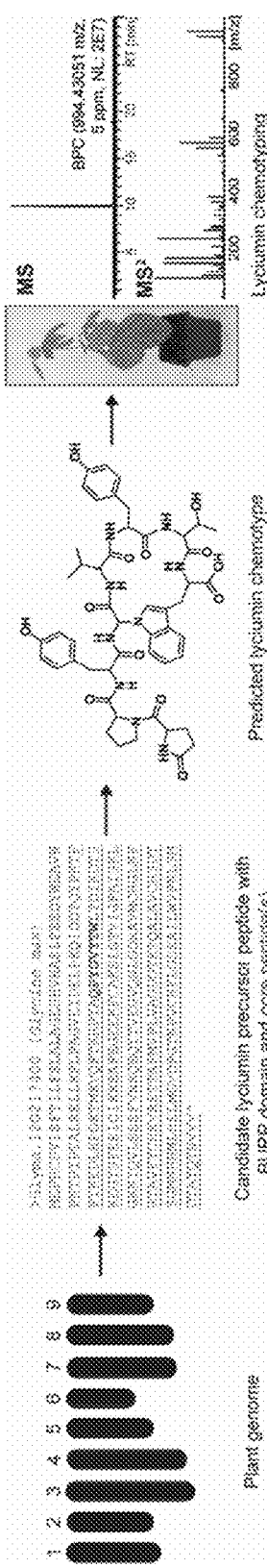
FIGS. 2A-B show lyciumin discovery by plant genome mining.
Figure 7A:
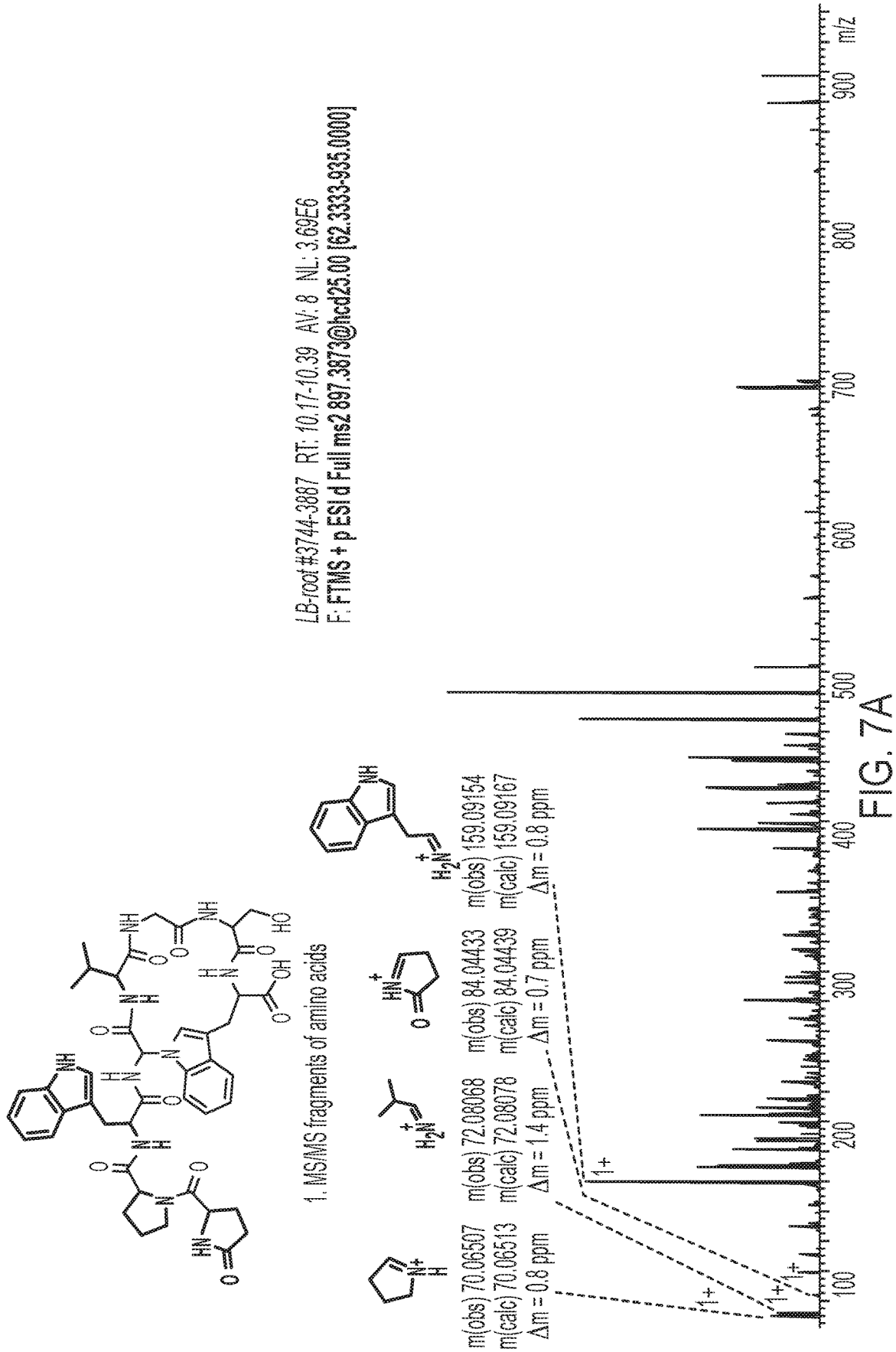
Figure 7B:
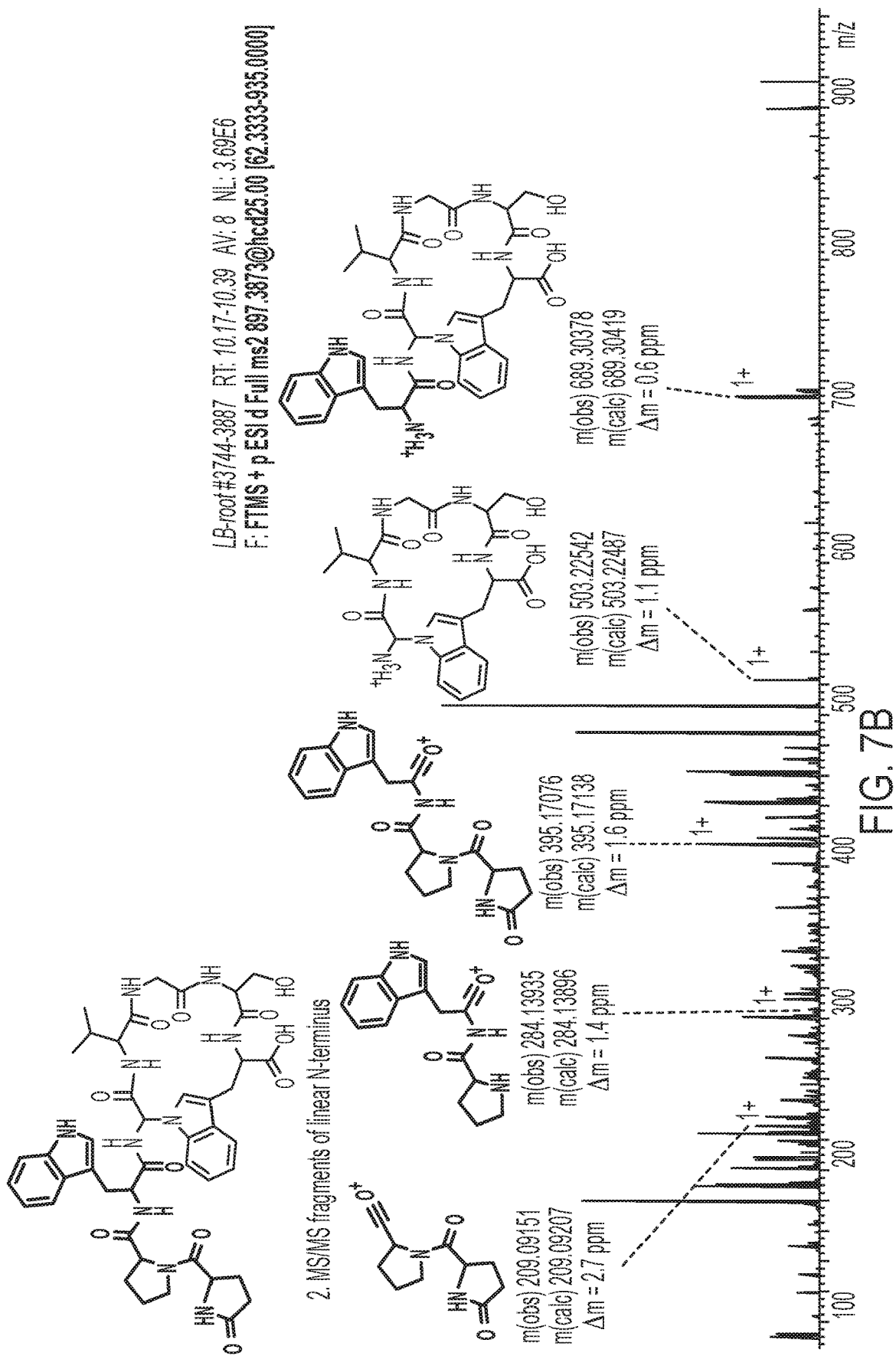
Figure 7C:
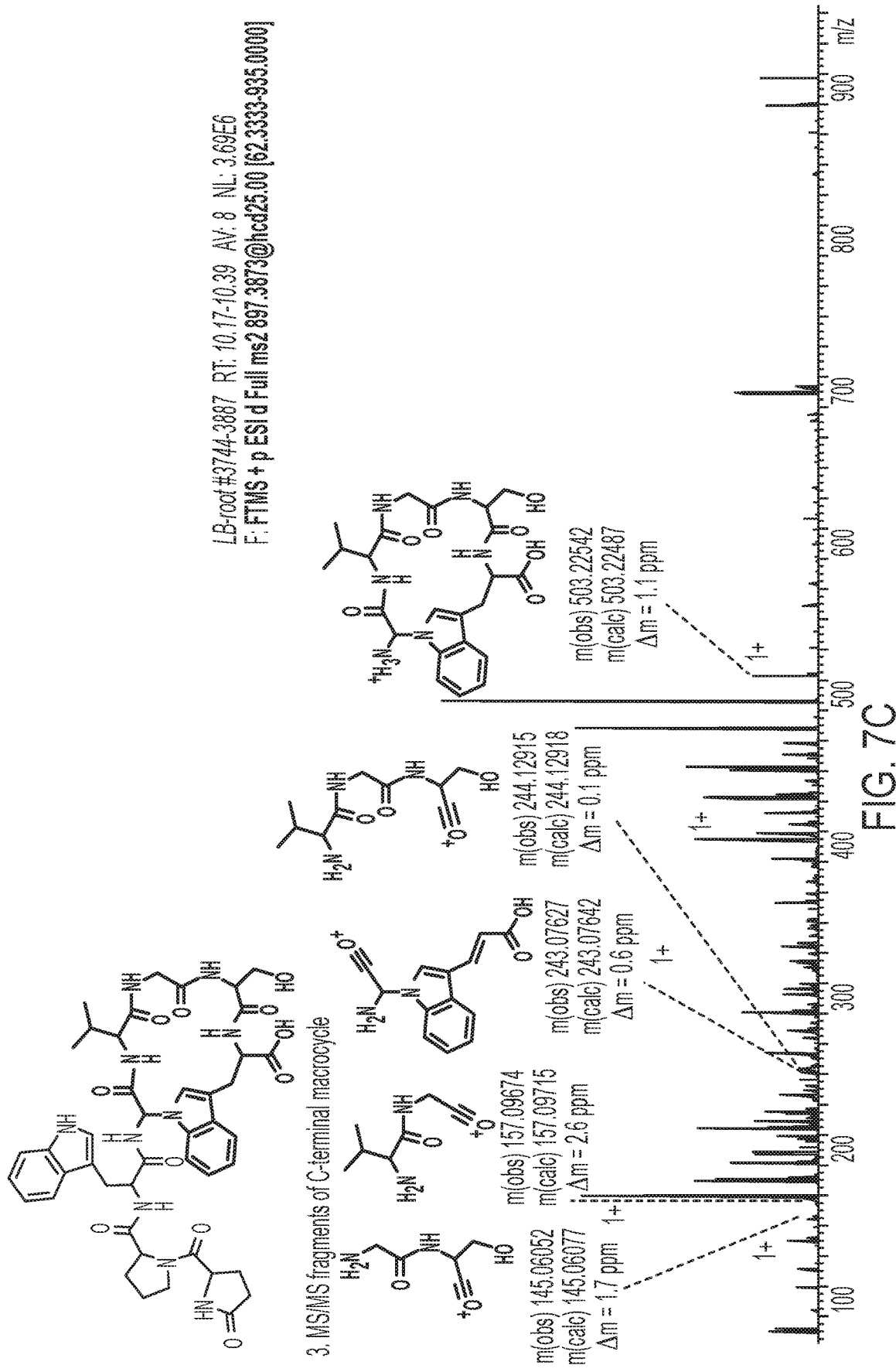

Genome Mining Reveals Hidden Chemical Diversity of Lyciumin Plant Ribosomal Peptides With a precursor gene for lyciumin biosynthesis in hand, lyciumin genotypes and chemotypes in genome sequenced plants were identified. The precursor gene-guided genome mining approach (FIG. 2A) started with tblastn-search of plant genomes for homologs of lyciumin precursor LbaLycA and, generally, BURP domain proteins (Pfam 03181). A candidate lyciumin precursor was identified by one or multiple candidate core peptide sequences of the motif QP(X)$_5$W (SEQ ID NO: 298) in its N-terminal half, i.e. the non-BURP domain. If a putative lyciumin precursor was identified from a plant genome, corresponding lyciumin structures were predicted based on its core peptide sequences. Herein, the N-terminal glutamine was transformed into a pyroglutamine and the C-terminal tryptophan-indole-nitrogen was linked to the α-carbon of the amino acid at the fourth position. Subsequently, these predicted lyciumin chemotypes were searched for in the LC-MS-based metabolomics dataset of peptide extracts prepared from the target plant host, by querying both peptide parent masses in MS data and predicted peptide fragment masses in MS/MS data (e.g. the pyroglutamate-proline-b-ion ([M+H]$^+$, 209.09207 m/z, or amino acid-iminium ions). Finally, MS/MS analysis of lyciumins enables the characterization of a planar structure (FIGS. 7A-C) and, thus, could verify a connection of a candidate lyciumin mass spectrum with a lyciumin genotype as a successful plant genome mining experiment.

Genome mining of LbaLycA homologs revealed that 21 of 116 analyzed plant genomes have a candidate lyciumin precursor peptide gene (Table 1). The putative lyciumin producing plants were Amaranthaceae, Fabaceae, Rosaceae or Solanaceae plants. Bioinformatic analysis of identified BURP domain proteins yielded 71 distinct core peptide sequences with 60 of them being species-specific (Table 2), indicating a large untapped diversity of lyciumin chemotypes, and several core peptide sequences, which are present in multiple species and families (QPYGVYTW (SEQ ID NO: 43) and QPWGVGSW (SEQ ID NO: 50)), indicating functional selection of their products. Subsequently, ten plants with candidate lyciumin genotypes were selected and their organic extracts were analyzed for predicted lyciumin chemotypes by LC-MS. For seven of those plants, predicted lyciumin analytes could be detected and verified by MS and MS/MS analysis including economically important crop and forage plants such as *Amaranthus hypochondriacus* (amaranth), *Beta vulgaris* (beet), *Chenopodium quinoa* (quinoa), *Glycine max* (soy), *Solanum melongena* (eggplant), and *Medicago truncatula* (FIGS. 2B, 12A-B, 13A-B, 14A-B, 15A-D, 16A-D, and 17A-B). Identities were verified by LC-MS, MS and MS/MS. No lyciumin peptides could be detected in peptide extracts of *Solanum lycopersicum* Heinz 1702 (tomato), *Capsicum annuum* (pepper) and *Trifolium pratens* (red clover). Characterized lyciumin precursor genes are differentially expressed in plant tissues and developmental stages with generally the highest expression in roots and embryo-developing tissues (FIGS. 8A-E). Accordingly, characterized lyciumin concentrations are generally the highest in roots and seeds, while some lyciumins are detected in the whole plant, such as in soy, *quinoa* and amaranth (FIGS. 9A-D).

Figure 6:
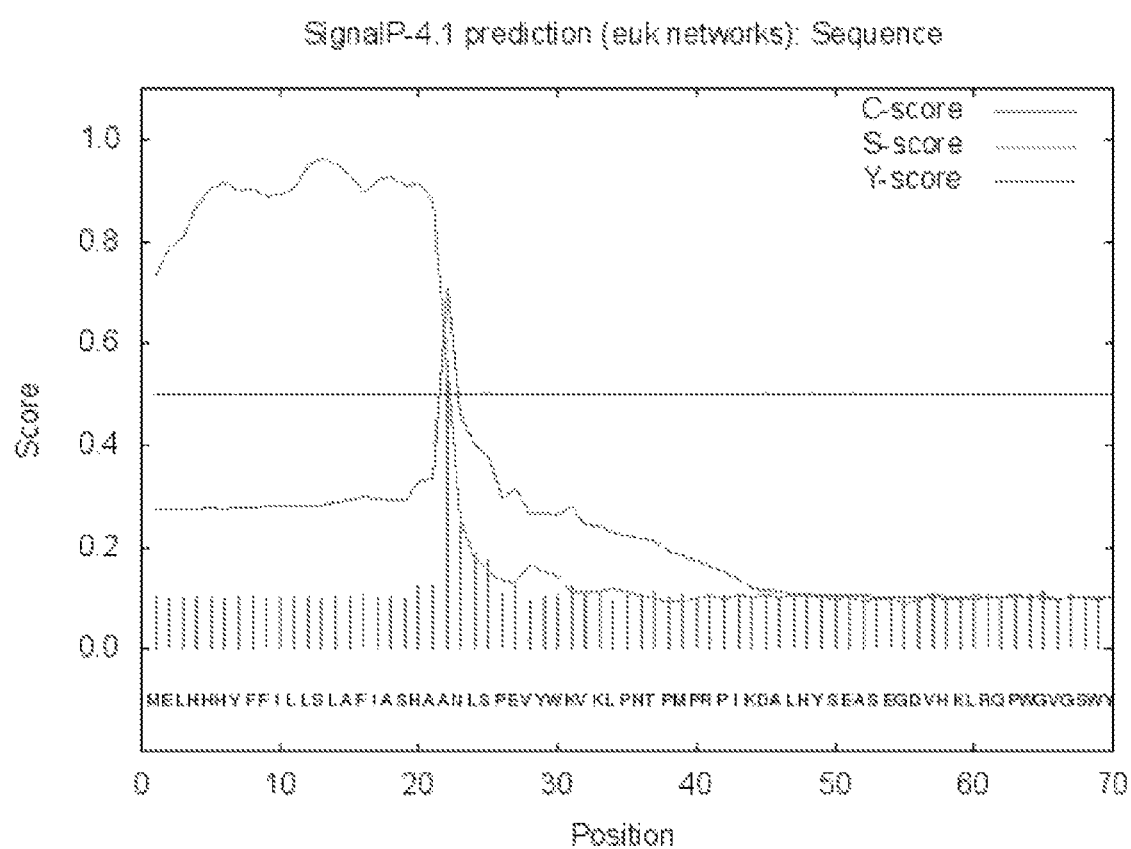

For *Solanum tuberosum* (potato), several lyciumin peptides could be characterized by LC-MS analysis. However, none of the detected peptides matched the predicted core peptide sequences from the genome derived lyciumin precursor. Analysis of the corresponding genome location showed that the 5'-region of the lyciumin precursor gene PGSC0003DMG400047074 was incomplete (FIGS. 18A-D and 19A-O). Therefore, a de novo transcriptome was assembled for a Russett potato tuber (NCBI SRA: SRR5970148) in order to recover the missing core peptide sequences of the predicted lyciumin precursor. Blast search in the transcriptome using LbaLycA as query yielded eleven additional core peptide sequences from candidate lyciumin precursor transcripts including all core peptide sequences that matched detected potato lyciumin peptides (FIGS. 18A-D, and 19A-O; Tables 1 and 2). To verify this result, one precursor peptide gene of a detected potato lyciumin, StuBURP, was cloned and transiently expressed in *N. benthamiana* leaves, which resulted in the detection of its predicted product, lyciumin J (StuBURP, FIGS. 18A-D and 19A-O). LC-MS, MS, and MS-MS were performed. The characterization of potato lyciumins indicates that peptide genome mining can be complicated by sequencing gaps in early or draft genomes and that de novo transcriptomics can complement plant RiPP genome mining. An issue of de novo transcriptome assembly for lyciumin precursor identification is that de novo transcriptome assembly programs such as Trinity and rnaSPADES have problems with complete assembly of short repeats such as the N-terminal domain of LbaLycA (FIGS. 6 and 19A-O).

TABLE 2

Examples of lyciumin core peptides; asterisks indicate detected peptides.

| Core peptide (SEQ ID NO:) | Chemotype | Single- vs. Multi-Species | Organism(s) |
|---|---|---|---|
| QPYTVGSW* (SEQ ID NO: 41) | Lyciumin A | Single-species | *Amaranthus hypochondriacus* |
| QPYTVFSW* (SEQ ID NO: 42) | Lyciumin C | Single-species | *Amaranthus hypochondriacus* |
| QPYGVYTW* (SEQ ID NO: 43) | Lyciumin I | Multi-species | *Arachis duranensis, Arachis ipaensis, Glycine max, Medicago truncatula, Solanum melongena, Trifolium pratens* |
| QPWTVYGW (SEQ ID NO: 44) | | Single-species | *Beta vulgaris* |
| QPWTVAGW (SEQ ID NO: 45) | | Single-species | *Beta vulgaris* |
| QPFTISAW (SEQ ID NO: 46) | | Single-species | *Beta vulgaris* |
| QPWTVAAW* (SEQ ID NO: 47) | Lyciumin E | Single-species | *Beta vulgaris* |
| QPYGGLTW (SEQ ID NO: 48) | | Single-species | *Capsicum annuum* |
| QPWGVCLW (SEQ ID NO: 49) | | Single-species | *Capsicum annuum* |
| QPWGVGSW* (SEQ ID NO: 50) | Lyciumin B | Multi-species | *Capsicum annuum, Capsicum chinense, Solanum lycopersicum, Solanum melongena, Solanum pennellii, Solanum pimpinellifolium, Solanum tuberosum* |
| QPWGVGFW (SEQ ID NO: 51) | | Multi-species | *Capsicum annuum, Capsicum chinense* |
| QPWGVCFW (SEQ ID NO: 52) | | Single-species | *Capsicum chinense* |
| QPFTVVGW* (SEQ ID NO: 53) | Lyciumin G | Single-species | *Chenopodium quinoa* |
| QPYTVMAW (SEQ ID NO: 54) | | Single-species | *Chenopodium quinoa* |
| QPYTVWGW* (SEQ ID NO: 55) | Lyciumin F | Single-species | *Chenopodium quinoa* |

TABLE 2-continued

Examples of lyciumin core peptides; asterisks indicate detected peptides.

| Core peptide (SEQ ID NO:) | Chemotype | Single- vs. Multi-Species | Organism(s) |
|---|---|---|---|
| QPYTVMGW (SEQ ID NO: 56) | | Single-species | *Chenopodium quinoa* |
| QPYTVYGW (SEQ ID NO: 57) | | Single-species | *Chenopodium quinoa* |
| QPFTVFGW (SEQ ID NO: 58) | | Single-species | *Chenopodium quinoa* |
| QPYTVDGW (SEQ ID NO: 59) | | Single-species | *Chenopodium quinoa* |
| QPFTVFAW (SEQ ID NO: 60) | | Single-species | *Glycine max* |
| QPWGVGTW* (SEQ ID NO: 61) | Lyciumin H | Single-species | *Glycine max* |
| QPLLFIYW (SEQ ID NO: 62) | | Single-species | *Medicago truncatula* |
| QPYGVYFW (SEQ ID NO: 63) | | Single-species | *Medicago truncatula* |
| QPLTTRMW (SEQ ID NO: 64) | | Single-species | *Medicago truncatula* |
| QPLTTSMW (SEQ ID NO: 65) | | Single-species | *Medicago truncatula* |
| QPITTHMW (SEQ ID NO: 66) | | Single-species | *Medicago truncatula* |
| QPFGINIW (SEQ ID NO: 67) | | Multi-species | *Medicago truncatula, Trifolium pratense* |
| QPFGVLTW (SEQ ID NO: 68) | | Single-species | *Medicago truncatula* |
| QPFGFFSW (SEQ ID NO: 69) | | Single-species | *Medicago truncatula* |
| QPLPAHKW (SEQ ID NO: 70) | | Single-species | *Medicago truncatula* |
| QPFRTIGW (SEQ ID NO: 71) | | Single-species | *Medicago truncatula* |
| QPLGAVKW (SEQ ID NO: 72) | | Single-species | *Medicago truncatula* |
| QPFGSLTW (SEQ ID NO: 73) | | Single-species | *Medicago truncatula* |
| QPFGVAAW (SEQ ID NO: 74) | | Single-species | *Medicago truncatula* |
| QPFGFRAW (SEQ ID NO: 75) | | Single-species | *Medicago truncatula* |
| QPFEAHTW (SEQ ID NO: 76) | | Single-species | *Medicago truncatula* |
| QPWGVYSW (SEQ ID NO: 77) | | Single-species | *Nicotiana attenuata* |
| QPYGVFAW* (SEQ ID NO: 78) | Lyciumin J | Multi-species | *Petunia axillaris, Solanum tuberosum* |
| QPFGVFAW (SEQ ID NO: 79) | | Single-species | *Petunia axillaris* |

TABLE 2-continued

Examples of lyciumin core peptides;
asterisks indicate detected peptides.

| Core peptide (SEQ ID NO:) | Chemotype | Single- vs. Multi-Species | Organism(s) |
|---|---|---|---|
| QPYGPFGW (SEQ ID NO: 80) | | Single-species | *Petunia inflata* |
| QPFGDYVW (SEQ ID NO: 81) | | Single-species | *Petunia inflata* |
| QPYGVFGW (SEQ ID NO: 82) | | Multi-species | *Petunia inflata, Solanum tuberosum* |
| QPFGVFGW (SEQ ID NO: 83) | | Multi-species | *Petunia inflata, Solanum tuberosum* |
| QPFGVFVW (SEQ ID NO: 84) | | Single-species | *Petunia inflata* |
| QPAPQLYW (SEQ ID NO: 85) | | Multi-species | *Prunus avium, Prunus persica* |
| QPAAQLYW (SEQ ID NO: 86) | | Single-species | *Prunus persica* |
| QPWGVGAW* (SEQ ID NO: 87) | Lyciumin K | Multi-species | *Solanum lycopersicum, Solanum pennellii, Solanum pimpinellifolium, Solanum tuberosum* |
| QPWGVYRW (SEQ ID NO: 88) | | Single-species | *Solanum lycopersicum* |
| QPYGVYRW* (SEQ ID NO: 89) | Lyciumin M | Multi-species | *Solanum lycopersicum, Solanum pimpinellifolium, Solanum tuberosum* |
| QPYGVYSW (SEQ ID NO: 90) | | Multi-species | *Solanum lycopersicum, Solanum pimpinellifolium* |
| QPWGVNSW (SEQ ID NO: 91) | | Single-species | *Solanum melongena* |
| QPWGVLRW (SEQ ID NO: 92) | | Single-species | *Solanum melongena* |
| QPWGVLGW (SEQ ID NO: 93) | | Single-species | *Solanum melongena* |
| QPFGVYRW (SEQ ID NO: 94) | | Single-species | *Solanum pennellii* |
| QPWGVFRW (SEQ ID NO: 95) | | Single-species | *Solanum pennellii* |
| QPYGVYSW (SEQ ID NO: 90) | | Single-species | *Solanum pimpinellifolium* |
| QPWGVDSW (SEQ ID NO: 97) | | Single-species | *Solanum tuberosum* |
| QPYGVGVW (SEQ ID NO: 98) | | Single-species | *Solanum tuberosum* |
| QPFGVGRW (SEQ ID NO: 99) | | Single-species | *Solanum tuberosum* |
| QPWGVGRW* (SEQ ID NO: 100) | Lyciumin O | Single-species | *Solanum tuberosum* |
| QPFGVVAW (SEQ ID NO: 101) | | Single-species | *Solanum tuberosum* |

TABLE 2-continued

Examples of lyciumin core peptides;
asterisks indicate detected peptides.

| Core peptide (SEQ ID NO:) | Chemotype | Single- vs. Multi-Species | Organism(s) |
| --- | --- | --- | --- |
| QPYGVLAW (SEQ ID NO: 102) | | Single-species | Solanum tuberosum |
| QPYGVSRW* (SEQ ID NO: 103) | Lyciumin N | Single-species | Solanum tuberosum |
| QPWGVVAW* (SEQ ID NO: 104) | Lyciumin L | Single-species | Solanum tuberosum |
| QPYGVFRW (SEQ ID NO: 105) | | Single-species | Solanum tuberosum |
| QPYGVFAW (SEQ ID NO: 78) | | Single-species | Solanum tuberosum |
| QPYGVDGW (SEQ ID NO: 107) | | Single-species | Solanum tuberosum |
| QPLGTWIW (SEQ ID NO: 108) | | Single-species | Trifolium pratense |
| QPFGIAAW (SEQ ID NO: 109) | | Single-species | Trifolium pratense |
| QPSGVYIW (SEQ ID NO: 110) | | Single-species | Trifolium pratense |
| QPATLLAW (SEQ ID NO: 111) | | Single-species | Vigna unguiculata |

The Sequence Rules of Naturally Occurring Lyciumins

Figure 2B:
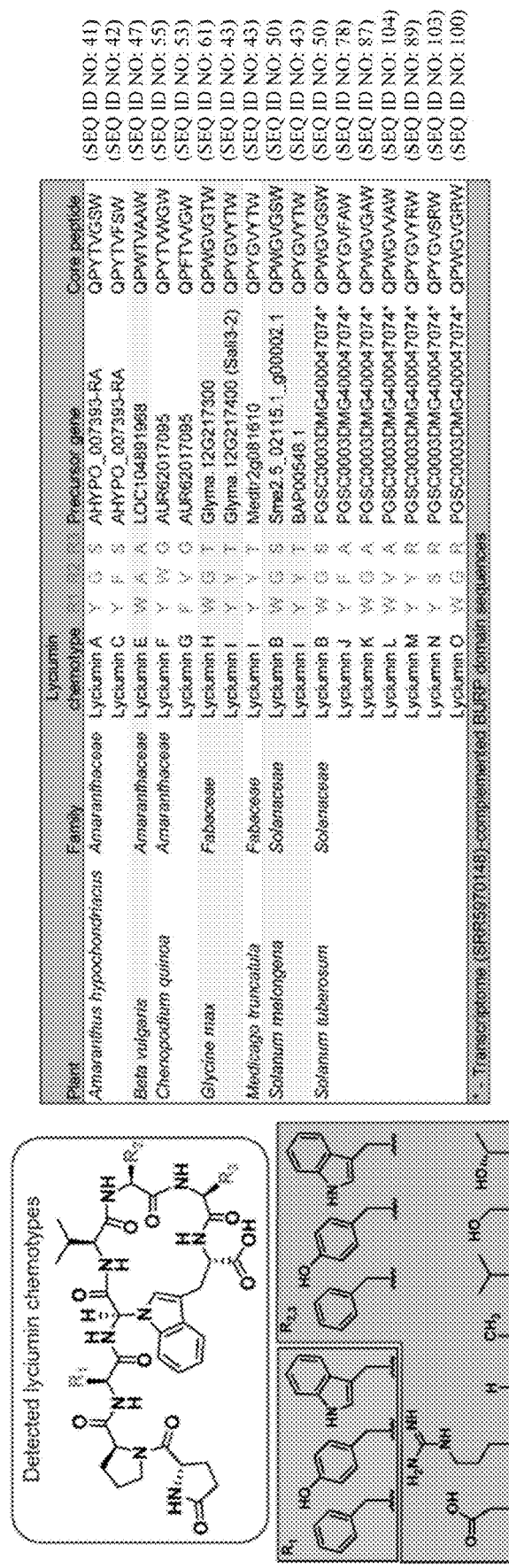

Next, the observed lyciumins were analyzed in their structural diversity (FIGS. 1B and 2B). In this example, all detected lyciumins have an aromatic amino acid (Phe, Tyr, Trp) at the third position and a valine at the fifth position. The sixth and seventh residues vary greatly with ten different amino acids including aromatic, polar and charged residues. In this example, the cyclization site is a glycine at the fourth position of all detected lyciumins, except for the identified Amaranthaceae lyciumin precursor peptides which contain a threonine at the fourth residue of the core peptides (FIG. 2B and Table 2). In organic extracts of investigated Amaranthaceae plants, several lyciumin derivatives were detected, which show a mass shift at the fourth residue corresponding to $C_2H_3O$ or a putative dehydrothreonine, supporting a biosynthetic route via a threonine cyclization site. Predicted and characterized lyciumin genotypes can be divided into two types based on primary structure. Type 1 lyciumin precursors have core peptides within the BURP domain (e.g. in Fabaceae), while type 2 lyciumin precursors contain core peptides N-terminally of the BURP domain (e.g. in Amaranthaceae and Solanaceae) (FIG. 10A).

Parallel Evolution of Lyciumin Biosynthesis in Angiosperms and Lycophytes

The discovery of lyciumin biosynthesis in three plant families via genome mining motivated a more detailed exploration of the distribution of lyciumin genotypes in the plant kingdom. To do this, plant transcriptomes were targeted as an alternative source for the discovery of lyciumins in plants, as the analysis of the sequenced plant genomes only represented 42 of the estimated 667 plant families. Given success in improving BURP domain precursor gene assembly for lyciumin discovery from the potato transcriptome, large-scale de novo re-assembly of transcriptomes of 793 plants species representing 317 plant families was performed using rnaSPAdes [35], starting from raw sequencing reads generated as part of the 1kp project. Subsequently, tblastn searches of type 1 and type 2 lyciumin precursors in the assembled transcriptomes identified candidate lyciumin precursors in multiple plant families, including Aizoaceae, Mollunginaceae, Nyctaginaceae, Petiveriaceae, Phytolaccaceae (all Caryophyllales) and Selaginellaceae (Table 3). Corresponding to these transcriptome predictions, a lyciumin chemotype was detected in the peptide extract of Selaginella uncinata roots, showcasing that lyciumins can also be discovered by mining transcriptomes. The putative Selaginella peptide lyciumin P is derived from the core peptide QPYSVFAW (SEQ ID NO: 147) and features a serine as the putative cyclization site (FIGS. 20A-B), in contrast to the glycine and threonine residues found in other plants. It is noteworthy that Selaginellaceae represents lycophytes, which are basal vascular plants diverged from the rest of the vascular plant lineages over 400 million years ago.

Several observations support independent diversification of lyciumin peptides in Selaginellaceae, Fabaceae, Solanaceae and Caryophyllales families with a few cases of parallel evolution of the identical lyciumin peptide natural products in distantly related plant families. First, the phylogenetic analysis of the BURP domains of the predicted and characterized lyciumin precursor proteins reveals five well-defined clades of sequences from Caryophyllales, Fabaceae, Rosaceae, Solanaceae, and Selaginellaceae (FIG. 10B), suggesting the diversity of lyciumin biosynthesis arose after these plant families have split from each other. Second, both Fabaceae and Selaginellaceae contain type 1 lyciumin precursors, while Caryophyllales and Solanaceae contain type 2 lyciumin precursors (FIG. 10B, Table 3), implicating possible independent recruitments of non-peptide-producing ancestral BURP domain proteins for lyciumin biosynthesis in various plant families. Third, the predicted cyclization site at the fourth position of lyciumin core peptides is a threonine in most Caryophyllales precursors, a glycine in most Fabaceae and Solanaceae precursors, and a serine or a glycine in Selaginellaceae precursors (FIG. 10B), which suggests independent diversification and potentially independent occurrences of the lyciumin biosynthetic machineries in these plant families. Finally, core peptides of predicted and characterized lyciumin precursors are mostly unique to each of these clades (75% of core peptides are found in one plant family, FIG. 10C, Table 4). However, two lyciumin chemotypes (lyciumin A and J) are predicted to occur in three of the five clade, presenting exemplary cases of parallel evolution of identical metabolic traits from homologous ancestral states (FIG. 10C). The repeated occurrences of lyciumin A and J in distantly related plant lineages also imply important biological functions contained in these natural products for their plant hosts. Given these results in the context of phylogenetic relationship among the predicted and characterized lyciumin-producing plants, it is reasonable to conclude that homologous BURP domain protein progenitors likely gave rise to independent occurrences of lyciumin biosynthesis at least twice in lycophytes and angiosperms during land plant evolution, and that the diversity of lyciumin genotypes and chemotypes present in extant plants largely arose through independent divergent evolution within the host plant families (FIG. 10D).

TABLE 3

Transcriptome mining of lyciumin precursor genes in 1 kp database of plant transcriptomes (de novo rnaSPADES re-assembly)

| Organism | NCBI SRA | Transcript product (Dataset S3) | Lyciumin precursor type | Predicted core peptides (QP(X)$_5$W) | Predicted lyciumin chemotype (threonine at fourth position from predicted core peptide converted to glycine) |
|---|---|---|---|---|---|
| Selaginella willdenowii | ERR2040880 | SwiBURP | 1 | QPYSVFAW (SEQ ID NO: 147) | QPYSVFAW (SEQ ID NO: 147) |
| Selaginella bryopteris | SRR3136708 | SbrBURP | 1 | QPYGVGSW (SEQ ID NO: 148), QPYGVIRW (SEQ ID NO: 149) | QPYGVGSW (SEQ ID NO: 148), QPYGVIRW (SEQ ID NO: 149) |
| Selaginella moellendorffii | SRR7132766 | SmoBURP | 1 | QPYGVGAW (SEQ ID NO: 150) | QPYGVGAW (SEQ ID NO: 150) |
| Selaginella uncinata | SRR7132763 | SunBURP | 1 | QPYSVFAW (SEQ ID NO: 147) | QPYSVFAW (SEQ ID NO: 147) |
| Acacia argyrophylla | ERR2040348 | AarBURP | 1 | QPWGVGTW (SEQ ID NO: 61) | QPWGVGTW (SEQ ID NO: 61) |
| Acacia pycnantha | ERR2040344 | ApyBURP | 1 | QPWGVGTW (SEQ ID NO: 61) | QPWGVGTW (SEQ ID NO: 61) |
| Apios americana | ERR706837 | AamBURP | 1 | QPYGVYAW (SEQ ID NO: 151) | QPYGVYAW (SEQ ID NO: 151) |
| Astragalus membranaceus | ERR706814 | AmeBURP1 | 1 | QPFGARTW (SEQ ID NO: 152) | QPFGARTW (SEQ ID NO: 152) |
| | | AmeBURP2 | 1 | QPFGALVW (SEQ ID NO: 153), QPFGGFAW (SEQ ID NO: 154) | QPFGALVW (SEQ ID NO: 153), QPFGGFAW (SEQ ID NO: 154) |
| | | AmeBURP3 | 1 | QPFGFLIW (SEQ ID NO: 155) | QPFGFLIW (SEQ ID NO: 155) |

TABLE 3-continued

Transcriptome mining of lyciumin precursor genes in 1 kp database of plant transcriptomes (de novo rnaSPADES re-assembly)

| Organism | NCBI SRA | Transcript product (Dataset S3) | Lyciumin precursor type | Predicted core peptides (QP(X)₅W) | Predicted lyciumin chemotype (threonine at fourth position from predicted core peptide converted to glycine) |
|---|---|---|---|---|---|
| Bituminaria bituminosa | ERR2040332 | BbiBURP | 1 | QPYGVLYW (SEQ ID NO: 156) | QPYGVLYW (SEQ ID NO: 156) |
| Glycine soja | ERR2040335 | GsoBURP1 | 1 | QPWGVGTW (SEQ ID NO: 61) | QPWGVGTW (SEQ ID NO: 61) |
|  |  | GsoBURP2 | 1 | QPYGVYTW (SEQ ID NO: 43) | QPYGVYTW (SEQ ID NO: 43) |
| Glycyrrhiza lepidota | ERR2040333 | GleBURP | 1 | QPYGVYTW (SEQ ID NO: 43) | QPYGVYTW (SEQ ID NO: 43) |
| Lathyrus sativus | ERR706828 | LsaBURP | 1 | QPFGINSW (SEQ ID NO: 157) | QPFGINSW (SEQ ID NO: 157) |
| Senna hebecarpa | ERR706829 | SheBURP1 | 1 | QPFGVFAW (SEQ ID NO: 79) | QPFGVFAW (SEQ ID NO: 79) |
|  | ERR706829 | SheBURP2 | 1 | QPYGVFAW (SEQ ID NO: 78) | QPYGVFAW (SEQ ID NO: 78) |
| Xanthocercis zambesiaca | ERR706865 | XzaBURP | 1 | QPYGVYSW (SEQ ID NO: 90) | QPYGVYSW (SEQ ID NO: 90) |
| Delosperma echinatum | ERR2040192 | DecBURP1 | 2 | QPWTVSLW (SEQ ID NO: 158) | QPWGVSLW (SEQ ID NO: 159) |
|  |  | DecBURP2 | 2 | QPWTVSSW (SEQ ID NO: 160) | QPWGVSSW (SEQ ID NO: 161) |
| Alternanthera brasiliana | ERR2040215 | AbrBURP | 2 | QPYTVGAW (SEQ ID NO: 162) | QPYGVGAW (SEQ ID NO: 150) |
| Alternanthera sessilis | ERR2040219 | AseBURP | 2 | QPFTVGAW (SEQ ID NO: 163) | QPFGVGAW (SEQ ID NO: 164) |
| Amaranthus tricolor | ERR2040205 | AtrBURP1 | 2 | QPYTVGSW (SEQ ID NO: 41), QPFTVGSW (SEQ ID NO: 165) | QPYGVGSW (SEQ ID NO: 148), QPFGVGSW (SEQ ID NO: 166) |
|  |  | AtrBURP2 | 2 | QPYTVGSW (SEQ ID NO: 41), QPFTVGSW (SEQ ID NO: 165) | QPYGVGSW (SEQ ID NO: 148), QPFGVGSW (SEQ ID NO: 166) |
| Atriplex hortensis | ERR2040208 | AhoBURP | 2 | QPFTVGAW (SEQ ID NO: 163) | QPFGVGAW (SEQ ID NO: 164) |

TABLE 3-continued

Transcriptome mining of lyciumin precursor genes in 1 kp database of plant transcriptomes (de novo rnaSPADES re-assembly)

| Organism | NCBI SRA | Transcript product (Dataset S3) | Lyciumin precursor type | Predicted core peptides (QP(X)$_5$W) | Predicted lyciumin chemotype (threonine at fourth position from predicted core peptide converted to glycine) |
|---|---|---|---|---|---|
| Atriplex prostrata | ERR2040210 | AprBURP1 | 2 | QPFTVGAW (SEQ ID NO: 163) | QPFGVGAW (SEQ ID NO: 164) |
| | | AprBURP2 | 2 | QPFTVGAW (SEQ ID NO: 163) | QPFGVGAW (SEQ ID NO: 164) |
| | | AprBURP3 | 2 | QPFTVGAW (SEQ ID NO: 163), QPFTFRAW (SEQ ID NO: 167) | QPFGVGAW (SEQ ID NO: 164), QPFGFRAW (SEQ ID NO: 75) |
| Chenopodium quinoa | ERR2040214 | CquBURP | 2 | QPFTVVGW (SEQ ID NO: 53), QPYTVMAW (SEQ ID NO: 54), QPYTVWGW (SEQ ID NO: 55), QPYTVMGW (SEQ ID NO: 56) | QPFGVVGW (SEQ ID NO: 168), QPYGVMAW (SEQ ID NO: 169), QPYGVWGW (SEQ ID NO: 170), QPYGVMGW (SEQ ID NO: 171) |
| Hypertelis cerviana | ERR2040235 | HceBURP | 2 | QPFTVLGW (SEQ ID NO: 179), QPFTVFGW (SEQ ID NO: 58) | QPFGVLGW (SEQ ID NO: 180), QPFGVFGW (SEQ ID NO: 83) |
| Bougainvillea spectabilis | ERR2040242 | BspBURP1 | 2 | QPFTVGSW (SEQ ID NO: 165), QPYTVGSW (SEQ ID NO: 41), QPYTVGAW (SEQ ID NO: 162) | QPFGVGSW (SEQ ID NO: 166), QPYGVGSW (SEQ ID NO: 148), QPYGVGAW (SEQ ID NO: 150) |
| | | BspBURP2 | 2 | (Q)PYTVGAW (SEQ ID NO: 162) | (Q)PYGVGAW (SEQ ID NO: 150) |
| | | BspBURP3 | 2 | QPYTVGGW (SEQ ID NO: 181), QPYTVGAW (SEQ ID NO: 162), QPCTVGAW (SEQ ID NO: 183) | QPYGVGGW (SEQ ID NO: 182), QPYGVGAW (SEQ ID NO: 150), QPCGVGAW (SEQ ID NO: 184) |
| Petiveria alliacea | ERR2040253 | PalBURP | 2 | QPYTVGAW (SEQ ID NO: 162) | QPYGVGAW (SEQ ID NO: 150) |
| Phytolacca bogotensis | ERR2040254 | PboBURP | 2 | QPYTVFAW (SEQ ID NO: 185), | QPYGVFAW (SEQ ID NO: 78), |

TABLE 3-continued

Transcriptome mining of lyciumin precursor genes in 1 kp database of plant transcriptomes (de novo rnaSPADES re-assembly)

| Organism | NCBI SRA | Transcript product (Dataset S3) | Lyciumin precursor type | Predicted core peptides (QP(X)₅W) | Predicted lyciumin chemotype (threonine at fourth position from predicted core peptide converted to glycine) |
|---|---|---|---|---|---|
| | | | | QPYTVFSW (SEQ ID NO: 42) | QPYGVFSW (SEQ ID NO: 175) |
| Microtea debilis | ERR2040255 | MdeBURP | 2 | QPYTVFAW (SEQ ID NO: 185) | QPYGVFAW (SEQ ID NO: 78) |
| Hilleria latifolia | ERR2040256 | HlaBURP | 2 | QPYTVGSW (SEQ ID NO: 41), QPYIAILW (SEQ ID NO: 186) | QPYGVGSW (SEQ ID NO: 148), QPYIAILW (SEQ ID NO: 186) |
| Atropa belladonna | ERR2040625 | AbeBURP1 | 2 | QPYGVFSW (SEQ ID NO: 175), QPYGVGFW (SEQ ID NO: 176), QPYGVGSW (SEQ ID NO: 148) | QPYGVFSW (SEQ ID NO: 175), QPYGVGFW (SEQ ID NO: 176), QPYGVGSW (SEQ ID NO: 148) |
| | | AbeBURP2 | 2 | QPWEVFSW (SEQ ID NO: 177) | QPWEVFSW (SEQ ID NO: 177) |
| Lycium barbarum | ERR2040629 | LbaBURP1 | 2 | QPYGVGSW (SEQ ID NO: 148) | QPYGVGSW (SEQ ID NO: 148) |
| | | LbaBURP2 | 2 | QPYGVGSW (SEQ ID NO: 148), QPYGVFSW (SEQ ID NO: 175), QPWGVGSW (SEQ ID NO: 50) | QPYGVGSW (SEQ ID NO: 148), QPYGVFSW (SEQ ID NO: 175), QPWGVGSW (SEQ ID NO: 50), QPFGVGSW (SEQ ID NO: 166) |
| Solanum cheesmaniae | ERR2040630 | SchBURP1 | 2 | QPYGVYTW (SEQ ID NO: 43) | QPYGVYTW (SEQ ID NO: 43) |
| | | SchBURP2 | 2 | QPWGVGSW (SEQ ID NO: 50) | QPWGVGSW (SEQ ID NO: 50) |
| Solanum dulcamara | ERR2040627 | SduBURP | 2 | QPYGVSIW (SEQ ID NO: 173), QPWGVGSW (SEQ ID NO: 50), QPYGVFSW (SEQ ID NO: 175), QPYGVGIW (SEQ ID NO: 174) | QPYGVSIW (SEQ ID NO: 173), QPWGVGSW (SEQ ID NO: 50), QPYGVFSW (SEQ ID NO: 175), QPYGVGIW (SEQ ID NO: 174) |

TABLE 3-continued

Transcriptome mining of lyciumin precursor genes in 1 kp database of plant transcriptomes (de novo rnaSPADES re-assembly)

| Organism | NCBI SRA | Transcript product (Dataset S3) | Lyciumin precursor type | Predicted core peptides (QP(X)$_5$W) | Predicted lyciumin chemotype (threonine at fourth position from predicted core peptide converted to glycine) |
|---|---|---|---|---|---|
| Solanum lasiophyllum | ERR2040632 | SlaBURP1 | 2 | QPWGVGAW (SEQ ID NO: 87), QPYGVYSW (SEQ ID NO: 90), QPWGVGSW (SEQ ID NO: 50) | QPWGVGAW (SEQ ID NO: 87), QPYGVYSW (SEQ ID NO: 90), QPWGVGSW (SEQ ID NO: 50) |
| | | SlaBURP2 | 2 | QPWGVYRW (SEQ ID NO: 88), QPYGVYRW (SEQ ID NO: 89), QPWGVGAW (SEQ ID NO: 87) | QPWGVYRW (SEQ ID NO: 88), QPYGVYRW (SEQ ID NO: 89), QPWGVGAW (SEQ ID NO: 87) |
| Solanum ptychanthum | ERR2040626 | SptBURP | 2 | QPYGVFAW (SEQ ID NO: 78) | QPYGVFAW (SEQ ID NO: 78) |
| Solanum sisymbriifolium | ERR2040632 | SsiBURP | 2 | QPYDAYSW (SEQ ID NO: 178) | QPYDAYSW (SEQ ID NO: 178) |
| Solanum virginianum | ERR2040628 | SviBURP1 | 2 | QPYGVYSW (SEQ ID NO: 90) | QPYGVYSW (SEQ ID NO: 90) |
| | | SviBURP2 | 2 | QPYGVYGW (SEQ ID NO: 172), QPYGVYVW (SEQ ID NO: 251) | QPYGVYGW (SEQ ID NO: 172), QPYGVYVW (SEQ ID NO: 251) |

TABLE 4

Core peptide analysis of lyciumin chemotypes predicted from genomes and transcriptomes.

| Core peptide | Chemotype | Organism(s) | Plant family | Plant order |
|---|---|---|---|---|
| QPYGVGSW* (SEQ ID NO: 148) | Lyciumin A | Amaranthus hypochondriacus, Amaranthus tricolor, Atropa belladonna, Bougainvillea spectabilis, Hilleria latifolia, Lycium barbarum, Selaginella bryopteris | Amaranthaceae, Phytolaccaceae, Nyctaginaceae, Selaginellaceae, Solanaceae | Caryophyllales, Selaginellales, Solanales |

TABLE 4-continued

Core peptide analysis of lyciumin chemotypes predicted from genomes and transcriptomes.

| Core peptide | Chemotype | Organism(s) | Plant family | Plant order |
|---|---|---|---|---|
| QPYGVFSW* (SEQ ID NO: 175) | Lyciumin C | Amaranthus hypochondriacus, Phytolacca bogotensis, Atropa belladonna, Lycium barbarum, Solanum dulcamara, | Amaranthaceae, Phytolaccaceae, Solanaceae | Caryophyllales, Solanales |
| QPYGVYTW* (SEQ ID NO: 43) | Lyciumin I | Arachis duranensis, Arachis ipaensis, Glycine max, Glycine soja, Glycyrrhiza lepidota, Medicago truncatula, Solanum cheesmaniae, Solanum melongena, Trifolium pratens | Fabaceae, Solanaceae | Fabales, Solanales |
| QPWGVYGW (SEQ ID NO: 187) | | Beta vulgaris | Amaranthaceae | Caryophyllales |
| QPWGVAGW (SEQ ID NO: 188) | | Beta vulgaris | Amaranthaceae | Caryophyllales |
| QPFGISAW (SEQ ID NO: 189) | | Beta vulgaris | Amaranthaceae | Caryophyllales |
| QPWGVAAW* (SEQ ID NO: 190) | Lyciumin E | Beta vulgaris | Amaranthaceae | Caryophyllales |
| QPYGGLTW (SEQ ID NO: 48) | | Capsicum annuum | Solanaceae | Solanales |
| QPWGVCLW (SEQ ID NO: 49) | | Capsicum annuum | Solanaceae | Solanales |
| QPWGVGSW* (SEQ ID NO: 50) | Lyciumin B | Capsicum annuum, Capsicum chinense, Lycium barbarum, Solanum cheesmaniae, Solanum dulcamara, Solanum lasiophyllum, Solanum lycopersicum, Solanum melongena, Solanum pennellii, Solanum pimpinellifolium, Solanum tuberosum | Solanaceae | Solanales |
| QPWGVGFW (SEQ ID NO: 51) | | Capsicum annuum, Capsicum chinense | Solanaceae | Solanales |

TABLE 4-continued

Core peptide analysis of lyciumin chemotypes predicted from genomes and transcriptomes.

| Core peptide | Chemotype | Organism(s) | Plant family | Plant order |
|---|---|---|---|---|
| QPWGVCFW (SEQ ID NO: 52) | | Capsicum chinense | Solanaceae | Solanales |
| QPFGVVGW* (SEQ ID NO: 168) | Lyciumin G | Chenopodium quinoa | Amaranthaceae | Caryophyllales |
| QPYGVMAW (SEQ ID NO: 169) | | Chenopodium quinoa | Amaranthaceae | Caryophyllales |
| QPYGVWGW* (SEQ ID NO: 170) | Lyciumin F | Chenopodium quinoa | Amaranthaceae | Caryophyllales |
| QPYGVMGW (SEQ ID NO: 171) | | Chenopodium quinoa | Amaranthaceae | Caryophyllales |
| QPYGVYGW (SEQ ID NO: 172) | | Chenopodium quinoa, Solanum virginianum | Amaranthaceae, Solanaceae | Caryophyllales, Solanales |
| QPFGVFGW (SEQ ID NO: 83) | | Chenopodium quinoa, Hypertelis cerviana, Petunia inflata, Solanum tuberosum | Amaranthaceae, Molluginaceae, Solanaceae | Caryophyllales, Solanales |
| QPYGVDGW (SEQ ID NO: 107) | | Chenopodium quinoa, Solanum tuberosum | Amaranthaceae, Solanaceae | Caryophyllales, Solanales |
| QPFGVFAW (SEQ ID NO: 79) | | Glycine max, Petunia axillaris, Senna hebecarpa | Fabaceae, Solanaceae | Fabales, Solanales |
| QPWGVGTW* (SEQ ID NO: 61) | Lyciumin H | Glycine max, Acacia argyrophylla, Acacia pycnantha, Glycine soja | Fabaceae | Fabales |
| QPLLFIYW (SEQ ID NO: 62) | | Medicago truncatula | Fabaceae | Fabales |
| QPYGVYFW (SEQ ID NO: 63) | | Medicago truncatula | Fabaceae | Fabales |
| QPLGTRMW (SEQ ID NO: 191) | | Medicago truncatula | Fabaceae | Fabales |
| QPLGTSMW (SEQ ID NO: 192) | | Medicago truncatula | Fabaceae | Fabales |
| QPIGTHMW (SEQ ID NO: 193) | | Medicago truncatula | Fabaceae | Fabales |
| QPFGINIW (SEQ ID NO: 67) | | Medicago truncatula, Trifolium pratense | Fabaceae | Fabales |
| QPFGVLTW (SEQ ID NO: 68) | | Medicago truncatula | Fabaceae | Fabales |

TABLE 4-continued

Core peptide analysis of lyciumin chemotypes predicted from genomes and transcriptomes.

| Core peptide | Chemotype | Organism(s) | Plant family | Plant order |
|---|---|---|---|---|
| QPFGFFSW (SEQ ID NO: 69) | | Medicago truncatula | Fabaceae | Fabales |
| QPLPAHKW (SEQ ID NO: 70) | | Medicago truncatula | Fabaceae | Fabales |
| QPFRTIGW (SEQ ID NO: 71) | | Medicago truncatula | Fabaceae | Fabales |
| QPLGAVKW (SEQ ID NO: 72) | | Medicago truncatula | Fabaceae | Fabales |
| QPFGSLTW (SEQ ID NO: 73) | | Medicago truncatula | Fabaceae | Fabales |
| QPFGVAAW (SEQ ID NO: 74) | | Medicago truncatula | Fabaceae | Fabales |
| QPFGFRAW (SEQ ID NO: 75) | | Atriplex prostrata, Medicago truncatula | Amaranthaceae, Fabaceae | Caryophyllales, Fabales |
| QPFEAHTW (SEQ ID NO: 76) | | Medicago truncatula | Fabaceae | Fabales |
| QPWGVYSW (SEQ ID NO: 77) | | Nicotiana attenuata | Solanaceae | Solanales |
| QPYGVFAW* (SEQ ID NO: 78) | Lyciumin J | Microtea debilis, Petunia axillaris, Phytolacca bogotensis, Senna hebecarpa, Solanum ptychanthum, Solanum tuberosum | Phytolaccaceae, Fabaceae, Solanaceae | Caryophyllales, Fabales, Solanales |
| QPYGPFGW (SEQ ID NO: 80) | | Petunia inflata | Solanaceae | Solanales |
| QPFGDYVW (SEQ ID NO: 81) | | Petunia inflata | Solanaceae | Solanales |
| QPYGVFGW (SEQ ID NO: 82) | | Petunia inflata, Solanum tuberosum | Solanaceae | Solanales |
| QPFGVFVW (SEQ ID NO: 84) | | Petunia inflata | Solanaceae | Solanales |
| QPAPQLYW (SEQ ID NO: 85) | | Prunus avium, Prunus persica | Rosaceae | Rosales |
| QPAAQLYW (SEQ ID NO: 86) | | Prunus persica | Rosaceae | Rosales |

TABLE 4-continued

Core peptide analysis of lyciumin chemotypes predicted from genomes and transcriptomes.

| Core peptide | Chemotype | Organism(s) | Plant family | Plant order |
| --- | --- | --- | --- | --- |
| QPWGVGAW* (SEQ ID NO: 87) | Lyciumin K | *Solanum lasiophyllum, Solanum lycopersicum, Solanum pennellii, Solanum pimpinellifolium, Solanum tuberosum* | *Solanaceae* | *Solanales* |
| QPWGVYRW (SEQ ID NO: 88) | | *Solanum lasiophyllum, Solanum lycopersicum* | *Solanaceae* | *Solanales* |
| QPYGVYRW* (SEQ ID NO: 89) | Lyciumin M | *Solanum lasiophyllum, Solanum lycopersicum, Solanum pimpinellifolium, Solanum tuberosum* | *Solanaceae* | *Solanales* |
| QPYGVYSW (SEQ ID NO: 90) | | *Solanum lasiophyllum, Solanum lycopersicum, Solanum pimpinellifolium, Solanum virginianum, Xanthocercis zambesiaca* | *Fabaceae, Solanaceae* | *Fabales, Solanales* |
| QPWGVNSW (SEQ ID NO: 91) | | *Solanum melongena* | *Solanaceae* | *Solanales* |
| QPWGVSSW (SEQ ID NO: 161) | | *Delosperma echinatum* | *Aizoaceae* | *Caryophyllales* |
| QPWGVLRW (SEQ ID NO: 92) | | *Solanum melongena* | *Solanaceae* | *Solanales* |
| QPWGVLGW (SEQ ID NO: 93) | | *Solanum melongena* | *Solanaceae* | *Solanales* |
| QPFGVYRW (SEQ ID NO: 94) | | *Solanum pennellii* | *Solanaceae* | *Solanales* |
| QPWGVFRW (SEQ ID NO: 95) | | *Solanum pennellii* | *Solanaceae* | *Solanales* |
| QPWGVDSW (SEQ ID NO: 97) | | *Solanum tuberosum* | *Solanaceae* | *Solanales* |
| QPYGVGVW (SEQ ID NO: 98) | | *Solanum tuberosum* | *Solanaceae* | *Solanales* |
| QPFGVGRW (SEQ ID NO: 99) | | *Solanum tuberosum* | *Solanaceae* | *Solanales* |
| QPWGVGRW* (SEQ ID NO: 100) | Lyciumin O | *Solanum tuberosum* | *Solanaceae* | *Solanales* |

TABLE 4-continued

Core peptide analysis of lyciumin chemotypes predicted from genomes and transcriptomes.

| Core peptide | Chemotype | Organism(s) | Plant family | Plant order |
|---|---|---|---|---|
| QPFGVVAW (SEQ ID NO: 101) | | *Solanum tuberosum* | *Solanaceae* | *Solanales* |
| QPYGVLAW (SEQ ID NO: 102) | | *Solanum tuberosum* | *Solanaceae* | *Solanales* |
| QPYGVSRW* (SEQ ID NO: 103) | Lyciumin N | *Solanum tuberosum* | *Solanaceae* | *Solanales* |
| QPWGVVAW* (SEQ ID NO: 104) | Lyciumin L | *Solanum tuberosum* | *Solanaceae* | *Solanales* |
| QPYGVFRW (SEQ ID NO: 105) | | *Solanum tuberosum* | *Solanaceae* | *Solanales* |
| QPLGTWIW (SEQ ID NO: 108) | | *Trifolium pratense* | *Fabaceae* | *Fabales* |
| QPFGIAAW (SEQ ID NO: 109) | | *Trifolium pratense* | *Fabaceae* | *Fabales* |
| QPSGVYIW (SEQ ID NO: 110) | | *Trifolium pratense* | *Fabaceae* | *Fabales* |
| QPAGLLAW (SEQ ID NO: 194) | | *Vigna unguiculata* | *Fabaceae* | *Fabales* |
| QPYGVIRW (SEQ ID NO: 149) | | *Selaginella bryopteris* | *Selaginellaceae* | *Selaginellales* |
| QPYGVGAW (SEQ ID NO: 150) | | *Alternanthera brasiliana, Bougainvillea spectabilis, Petiveria alliacea, Selaginella moellendorffii* | *Amaranthaceae, Nyctaginaceae, Petiveriaceae, Selaginellaceae* | *Caryophyllales, Selaginellales* |
| QPYGVYAW (SEQ ID NO: 151) | | *Apios americana* | *Fabaceae* | *Fabales* |
| QPFGARTW (SEQ ID NO: 152) | | *Astragalus membranaceus* | *Fabaceae* | *Fabales* |
| QPFGALVW (SEQ ID NO: 153) | | *Astragalus membranaceus* | *Fabaceae* | *Fabales* |
| QPFGGFAW (SEQ ID NO: 154) | | *Astragalus membranaceus* | *Fabaceae* | *Fabales* |
| QPFGFLIW (SEQ ID NO: 155) | | *Astragalus membranaceus* | *Fabaceae* | *Fabales* |
| QPFGFLIW (SEQ ID NO: 155) | | *Astragalus membranaceus* | *Fabaceae* | *Fabales* |

TABLE 4-continued

Core peptide analysis of lyciumin chemotypes predicted from genomes and transcriptomes.

| Core peptide | Chemotype | Organism(s) | Plant family | Plant order |
|---|---|---|---|---|
| QPYGVLYW (SEQ ID NO: 156) | | Bituminaria bituminosa | Fabaceae | Fabales |
| QPFGINSW (SEQ ID NO: 157) | | Lathyrus sativus | Fabaceae | Fabales |
| QPWGVSLW (SEQ ID NO: 159) | | Delosperma echinatum | Aizoaceae | Caryophyllales |
| QPFGVGAW (SEQ ID NO: 164) | | Atriplex hortensis, Atriplex prostrata, Alternanthera sessilis | Amaranthaceae | Caryophyllales |
| QPFGVLGW (SEQ ID NO: 195) | | Hypertelis cerviana | Molluginaceae | Caryophyllales |
| QPYGVGGW (SEQ ID NO: 182) | | Bougainvillea spectabilis | Nyctaginaceae | Caryophyllales |
| QPCGVGAW (SEQ ID NO: 184) | | Bougainvillea spectabilis | Nyctaginaceae | Caryophyllales |
| QPYGVGFW (SEQ ID NO: 176) | | Atropa belladonna | Solanaceae | Solanales |
| QPWEVFSW (SEQ ID NO: 177) | | Atropa belladonna | Solanaceae | Solanales |
| QPFGVGSW (SEQ ID NO: 166) | | Amaranthus tricolor, Bougainvillea spectabilis, Lycium barbarum | Solanaceae | Solanales |
| QPYGVSIW (SEQ ID NO: 173) | | Solanum dulcamara | Solanaceae | Solanales |
| QPYGVGIW (SEQ ID NO: 174) | | Solanum dulcamara | Solanaceae | Solanales |
| QPYGVYGW (SEQ ID NO: 172) | | Solanum virginianum | Solanaceae | Solanales |
| QPYSVFAW* (SEQ ID NO: 147) | Lyciumin P | Selaginella uncinata, Selaginella willdenowii | Selaginellaceae | Selaginellales |
| QPYDAYSW (SEQ ID NO: 178) | | Solanum sisymbriifolium | Solanaceae | Solanales |

If fourth amino acid is a threonine, it is converted to glycine based on sequence rules of naturally occurring lyciumins (FIG. 2B) from predicted and characterized lyciumin precursors from genome and transcriptome mining.
Astericks note characterized lyciumin chemotypes.

Figure 3A:
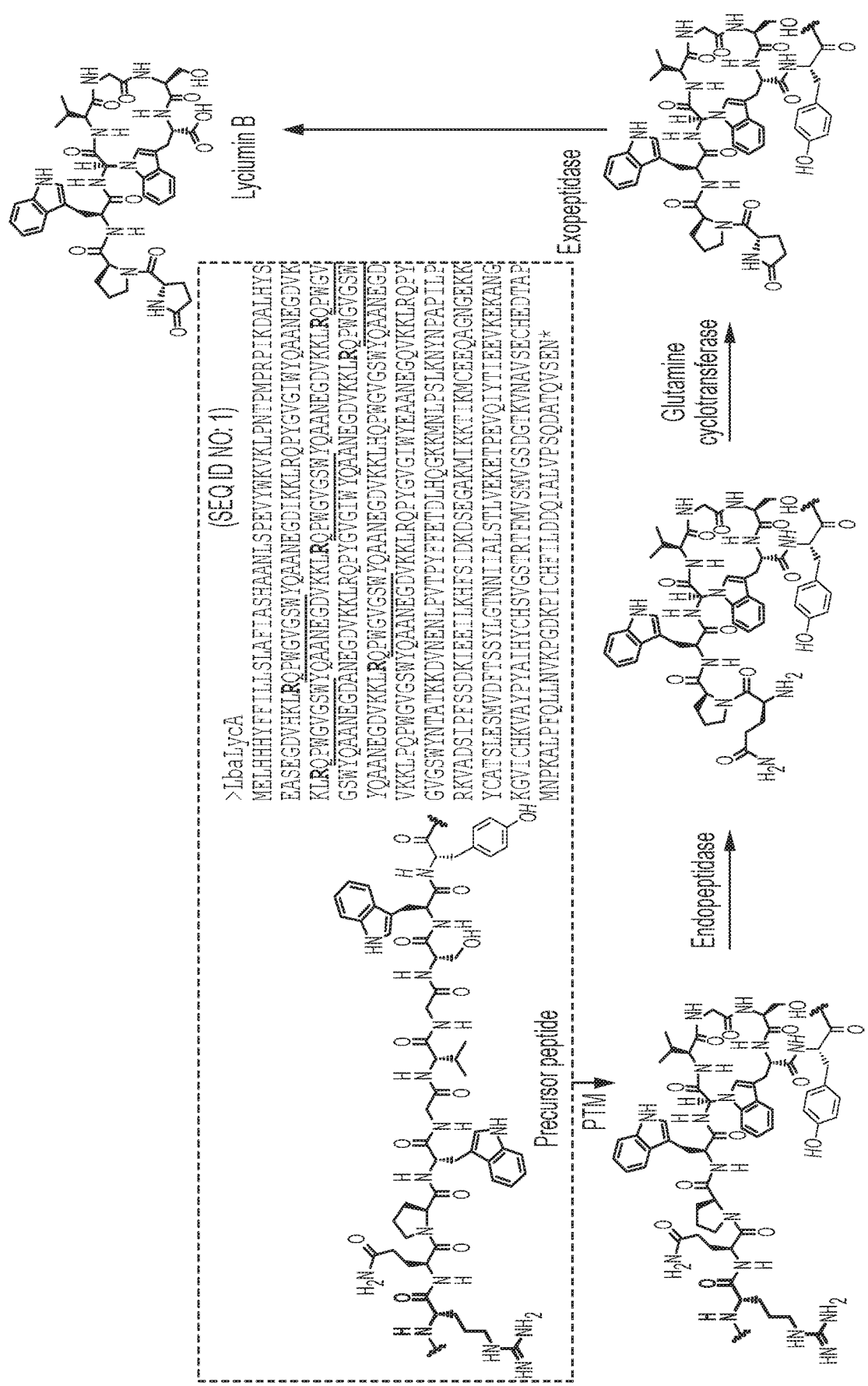

The Lyciumin Biosynthetic Pathway is Promiscuous in Substrate and Macrocyclization A biosynthetic proposal for lyciumins was established from heterologous expression, sequences and genome locations of precursor peptide genes. Following the general dogma of RiPP biosynthesis, lyciumin biosynthesis starts with translation of a precursor peptide gene such as LbaLycA by the ribosome (FIG. 3A) [8]. The precursor peptide is then cyclized between the tryptophan and glycine in each core peptide, which is supported by no detection of the linear core peptides in the LbaLycA heterologous expression experiments in N. benthamiana or in L. barbarum root extracts. Cyclization of the tryptophan-indole nitrogen to an unactivated α-carbon suggests a radical-oxidative cyclization mechanism (36), although candidate lyciumin cyclases have yet to be identified. In the next step, the modified LbaLycA is cleaved by an endopeptidase, N-terminally of the core peptide. This is supported by the detection of lyciumin derivatives with an N-terminal glutamine in leaf extracts of N. benthamiana transiently expressing LbaLycA, and in L. barbarum root extracts (FIG. 3B). Subsequently, core peptides are N-terminally protected by pyroglutamate formation, which can be catalyzed by a glutamine cyclotransferase (QC). Indeed, QC-encoding genes were identified next to the lyciumin precursor genes in the genomes of Chenopodium quinoa and Beta vulgaris (FIG. 3C, Table 5). Furthermore, co-expression of LbaLycA with a L. barbarum homolog of these QCs in N. benthamiana resulted in the loss of mass signals of N-terminally unprotected lyciumins, confirming their enzymatic role in forming the N-terminal pyroglutamate moiety in lyciumins (FIGS. 3D and 21A-B). In the final step, lyciumins are produced by C-terminal exoproteolytic maturation. This step is supported by the detection of multiple C-terminally extended lyciumin derivatives in leaf extracts of N. benthamiana transiently expressing LbaLycA, and in L. barbarum root extracts (FIG. 3E). See also FIG. 4E.

max with only one core 3644899.31 peptide (QPYGVYTW (SEQ ID NO: 43)) in the N-terminal domain was characterized. Heterologous expression of this precursor, namely Sali3-2 (Glyma. 12G217400) [39], in N. benthamiana resulted in the formation of its predicted lyciumin product, lyciumin I (FIGS. 2B and 4A). With a single core peptide precursor in hand, an alanine scan was first performed through its core peptide region to identify mutable positions (FIG. 4B). Based on MS analysis, mutations of all residues, except the N-terminal glutamine and the C-terminal tryptophan of the Sali3-2 core peptide, to alanine resulted in lyciumin formation, indicating core peptide promiscuity of the lyciumin pathway (FIGS. 4B, 22A-E, 23A-B, 24A-B, 25A-B, 26A-B, and 27A-B).

Next, it was tested whether the length of the linear N-terminus or the size of the peptide macrocycle could be modified in the N. benthamiana heterologous expression system (FIG. 4B). No lyciumin production was observed for a four-, two-, or one-amino acid-long N-terminal branch, suggesting a conserved N-terminus length of three amino acids (FIG. 4B). Similarly, no lyciumin formation occurred from core peptides with four- or six-amino acid-long C-termini, indicating a conserved C-terminal macrocycle of five amino acids (FIG. 4B). Finally, whether the cyclization residues could be altered was tested. Based on Amaranthaceae lyciumin precursors, mutation of Sali3-2 core peptide from glycine to threonine at the fourth position resulted

TABLE 5

Bioinformatic analysis of lyciumin precursor genes and co-clustered glutamine cyclotransferase genes in genomes of Beta vulgaris and Chenopodium quinoa (FIG. 3C).

| Gene | Predicted function | Reference | Gene product length [aa] | Closest functional blastp homolog (organism) [Similarity/Identity, %/%] |
|---|---|---|---|---|
| *Chenopodium quinoa* (v1.0) locus | | | | |
| AUR62017095-RA (CquBURP1) | BURP domain lyciumin precursor | XP_021740703.1 | 619 | XP_010675925.1\|PREDICTED: BURP domain protein USPL1 [*Beta vulgaris* subsp. *vulgaris*] [68/57] |
| AUR62017096-RA | Glutamine cyclotransferase | XP_021740704.1 | 286 | XP_010675927.1\|PREDICTED: glutaminyl-peptide cyclotransferase isoform X1 (*Beta vulgaris* subsp. *vulgaris*) [80/71] |
| *Beta vulgaris* locus (RefBeet-1.2.2) | | | | |
| LOC104891851 (BvuBURP2) | BURP domain lyciumin precursor | XP_010675925.1 | 446 | XP_010676059.1\|PREDICTED: BURP domain protein USPL1-like (*Beta vulgaris* subsp. *vulgaris*) [93/89] |
| LOC104891854 | Glutamine cyclotransferase | XP_010675927.1 | 306 | XP_021771347.1\|glutaminyl-peptide cyclotransferase-like isoform X1 [*Chenopodium quinoa*] |
| LOC104891968 (BvuBURP1) | BURP domain lyciumin precursor | XP_010676059.1 | 404 | XP_010675925.1\|PREDICTED: BURP domain protein USPL1 (*Beta vulgaris* subsp. *vulgaris*) [93/89] |
| LOC104891853 | Glutamine cyclotransferase | XP_010675926.1 | 201 | XP_021740704.1\|glutaminyl-peptide cyclotransferase-like (*Chenopodium quinoa*) [73/68] |

Despite the lack of a characterized lyciumin cyclase, the promiscuity of the lyciumin biosynthetic pathway in N. benthamiana was investigated. In order to generate lyciumin core peptide mutants, a lyciumin precursor from *Glycine* in lyciumin I production. When this mutant precursor peptide gene was expressed in N. benthamiana, production of a putative dehydrothreonine-derivative was detected, as observed for Amaranthaceae lyciumin chemotypes with corresponding [Thr4]-core peptides (FIG. 2B) in addition to lyciumin I (FIGS. 28A-I). Mutation of the C-terminal tryptophan to the other aromatic amino acids, phenylalanine and histidine, led to abolishment of lyciumin formation (FIG. 4B). Surprisingly, mutation to tyrosine yielded a cyclic peptide with a putative new tyrosine [Tyr8] macrocyclization based on MS analysis, thus, suggesting the discovery of a new peptide macrocyclization (FIG. 4B).

In order to investigate whether the lyciumin pathway can produce unknown peptide macrocyclizations, the BURP domain sequences from genome sequenced plants for core peptides with the motif QP(X)$_5$Y (SEQ ID NO: 299), i.e. a C-terminal tyrosine instead of a tryptophan, were revisited. This search identified a candidate precursor peptide from Capsicum anmum, CanBURP, with a predicted QPYGVYFY (SEQ ID NO: 268) core peptide was transiently expressed in N. benthamiana, which suggested a lyciumin derivative with a tyrosine macrocyclization. In a parallel experiment, Sali3-2 was transiently expressed with the same core peptide sequence. Furthermore, peptide metabolic profiling was also conducted with C. annuum seed extract. In all three experiments, analytes were detected suggesting cyclic peptide chemistry derived from the tyrosine-terminal core peptide (FIGS. 30A-F). Ultimately, the investigation of the lyciumin pathway in tobacco with a soybean precursor peptide shows specificity in peptide architecture but promiscuity in peptide sequence and macrocyclization, allowing for the discovery of a new RiPP class by genome mining.

Taken together, these structure-function relationship studies varying precursor core peptide sequence in heterologously reconstituted lyciumin pathway in N. benthamiana suggest restriction in peptide length but promiscuity in peptide sequence and macrocyclization, presenting tremendous opportunity for branched cyclic RiPP diversification via metabolic engineering. Several lyciumins have been produced, such as lyciumin H and K (FIGS. 2C, 4B, 31A-B, and 32A-B), "unnatural" lyciumins such as lyciumin-[QPFGVYTW (SEQ ID NO: 280)] and lyciumin-[QPWGVYTW (SEQ ID NO: 279)] (FIGS. 4B, 33A-B, and 34A-B), and predicted lyciumins with up to four mutations from genome-derived BURP domain sequences such as lyciumin-[QPFGFFSW (SEQ ID NO: 69)] and lyciumin-[QPYGVYFW (SEQ ID NO: 63)] from M. truncatula (FIGS. 4B, 35A-B, and 36A-B) and lyciumin-[QPYGVYSW (SEQ ID NO: 90)] from Nicotiana attenuata (FIGS. 4B and 37A-B) via the Sali3-2-based heterologous expression system in N. benthamiana. These results highlight the utility of this expression platform for unlocking cryptic peptide chemotypes from diverse plant species and producing peptide libraries based on existing, predicted or unknown lyciumin chemical space.

Heterologous Lyciumin Production in Tobacco Vs. Source Plant (Lycium barbarum)

Transient expression was measured for engineered lyciumin precursor from Lycium barbarum (LbaLycA) with one, five or ten repeats of a single core peptide (QPWGVGSW=lyciumin B (SEQ ID NO: 50)) after infiltration of six week old tobacco leaves with A. tumefaciens LBA4404 pEAQ-HT-LycA-1×/5×/10× (three plants per construct). See SEQ ID NOS: 112-117, FIGS. 38B-D.

Peptide extraction of freeze-dried, infiltrated leaf samples of each plant (0.1 g) occurred six days after infiltration and peptide extraction of freeze-dried Lycium barbarum roots was done with plant material from 6 month old plants (0.1 g).

LC-MS analysis for lyciumin B mass signal (single ion monitoring: 896.3-897.3 m/z) and manual peak integration was performed in QualBrowser (Thermo).

Figure 38A:
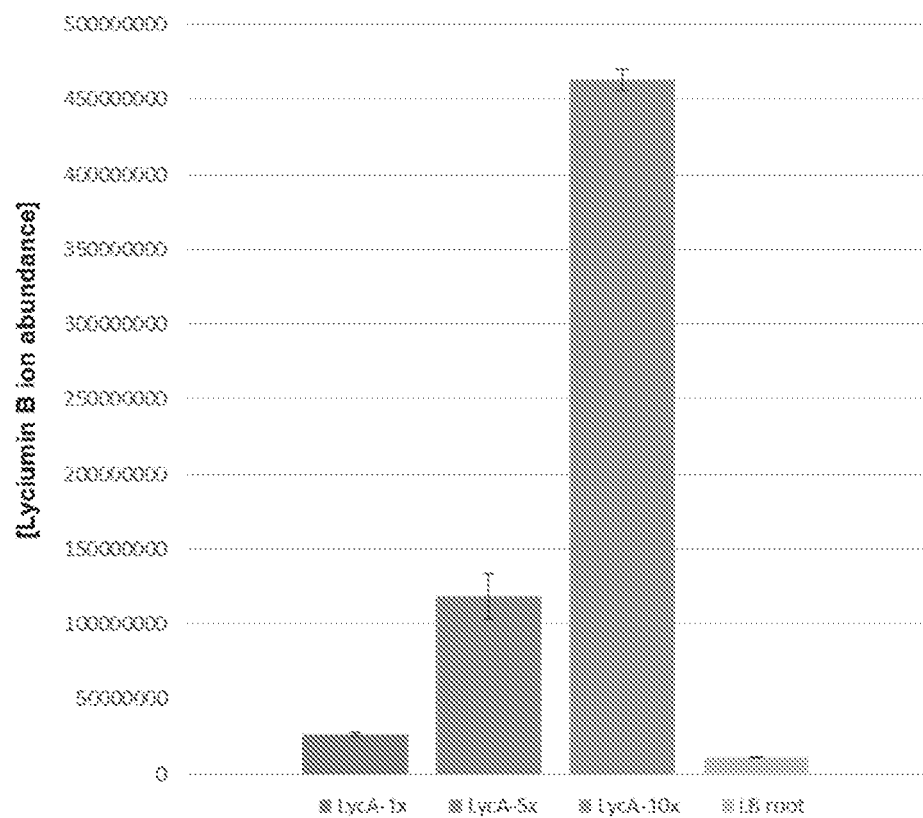
FIG. 38A is a chart showing Lyciumin B production in tobacco and source plant (*Lycium barbarum*).

The results are shown in FIG. 38A, which indicate detection of increasing lyciumin B concentration in tobacco transiently expressing engineered lyciumin precursors with increasing lyciumin B repeats (1<5<10); and detection of higher lyciumin B concentration in tobacco transiently expressing lyciumin precursors than in lyciumin B source plant tissue (Lycium barbarum root).

Discussion

Here, lyciumins are described as a branched cyclic plant RiPP class that is characterized by an N-terminal pyroglutamate and a macrocyclic bond between a C-terminal tryptophan or tyrosine residue, e.g., C-terminal tryptophan-indole-nitrogen and a glycine-α-carbon. Lyciumins were determined to be RiPPs by identification of their precursor peptide from Lycium barbarum. The characterized precursor peptide of this RiPP class enabled successful genome mining of other lyciumin genotypes and chemotypes in genome sequenced crop and forage plants. Biosynthetic investigation of the lyciumin pathway in tobacco indicates promiscuity in peptide sequence, but not in peptide architecture. The pathway tolerates mutation of the C-terminal tryptophan to a tyrosine to form a putative new peptide macrocyclization found in lyciumin-[QPYGVYFY (SEQ ID NO: 268)] from pepper seeds by genome mining. The connection of lyciumin core peptides with BURP domains suggests a physical connection of abiotic stress responses via heavy metal-binding BURP domains in plant vacuoles and lyciumin peptide signaling from roots and young plants for potential rhizosphere modulation to alleviate stress such as drought and acidic soil. As rhizosphere engineering has potential to increase crop and forage plant fitness in changing climates and growth conditions, a platform was engineered to produce lyciumin peptide libraries in planta for potential agricultural applications of the lyciumin pathway as transgenes or gene editing targets. Lyciumin cyclic peptide libraries may be used for other purposes, such as development of peptide based-drugs such as protease inhibitors.

Genome mining for plant natural product discovery has been realized for multiple natural product classes on a single-pathway scale and on a multi-pathway scale [21,22, 41,42]. Increasing biosynthetic knowledge catalyzed by synthetic biology [18,23] and increasing genomic plant resources prime the field of plant natural products for automated natural product discovery by genome mining. Plant RiPPs such as the lyciumins are a suitable class to be added to plant genome mining pipelines as they could be readily connected from a genotype to a chemotype in a similar fashion as microbial peptide natural products [43].

Overall, described herein is a blueprint for genome mining of branched cyclic RiPPs in plants by identification of pathway-specific precursor peptides. These cyclic lyciumin peptides have potential utility for increasing crop fitness and developing peptide-based drugs.

Materials and Methods

Materials and Instruments

All chemicals were purchased from Sigma-Aldrich, unless otherwise specified. Oligonucleotide primers and synthetic genes were purchased as gBlocks® from Integrated DNA Technologies, Inc. Solvents for liquid chromatography high-resolution mass spectrometry were Optima® LC-MS grade (Fisher Scientific) or LiChrosolv® LC-MS grade (Millipore). High resolution mass spectrometry analysis was performed on a Thermo ESI-Q-Exactive Orbitrap MS coupled to a Thermo Ultimate 3000 UHPLC system.

Low-resolution mass spectrometry analysis was done on a Thermo ESI-QQQ MS coupled to a Thermo Ultimate 3000 UHPLC system. NMR analysis was performed on a Bruker Avance II 600 MHz NMR spectrometer equipped with a High Sensitivity Prodigy Cryoprobe. Preparative HPLC was performed on a Shimadzu LC-20AP liquid chromatograph equipped with a SPD-20A UV/VIS detector and a FRC-10A fraction collector.

Plant Material

*Lycium barbarum* was purchased as three year-old plants for extraction and cultivation. *Amaranthus hypochondriacus* seeds for cultivation were purchased from Strictly Medicinal® Seeds. Amaranth grain for extraction was Arrowhead Mills® amaranth. *Chenopodium quinoa* seeds for cultivation were purchased from Earthcare Seeds. Quinoa for extraction was Trader Joe's® Tricolor *quinoa*. *Beta vulgaris* seeds (Detroit Dark Red cultivar) for cultivation and extraction were purchased from David's Garden Seeds. *Glycine max* seeds (Chiba green soybean) for cultivation and extraction were purchased from High Mowing Organic Seeds®. Seeds of wild-type *Medicago truncatula* for cultivation were a gift by Prof. Dong Wang (U Mass Amherst). *Capsicum annuum* seeds (Jalapeno Early) for cultivation and extraction were purchased from EdenBrothers®. *Solanum lycopersicum* seeds (cultivar Heinz 1706-BG) for cultivation were provided by the Tomato Genetics Resource Center (UC Davis). *Solanum melongena* seeds for cultivation were purchased from Seedz®. *Solanum tuberosum* tubers for cultivation (Russett or Red potato) were purchased from Trader Joe's®. *Trifolium pratense* seeds were purchased from OutsidePride.com®. *Nicotiana benthamiana* seeds for cultivation were a gift from the Lindquist lab (Whitehead Institute, MIT). *Selaginella uncinata* plant was purchased from Plant Delights Nursery®.

Plant Cultivation

*Lycium barbarum* was grown from three year-old live roots in MiracleGro® potting soil as a potted plant in full sun with occasional application of organic fertilizer. *Lycium barbarum* seeds from fruits of the three year-old plant, were grown in Sun Gro® Propagation Mix soil with added vermiculite (Whittemore Inc.) and added fertilizer in a greenhouse with a 16 h light/8 h dark cycle for six months. *Amaranthus hypochondriacus, Chenopodium quinoa, Beta vulgaris, Glycine max, Medicago truncatula, Capsicum annuum, Solanum lycopersicum, Solanum melongena* and *Trifolium pratense* were grown from seeds in Sun Gro® Propagation Mix soil with added vermiculite (Whittemore Inc.) and added fertilizer in a greenhouse with a 16 h light/8 h dark cycle for six months. *Nicotiana benthamiana* was grown from seeds in Sun Gro® Propagation Mix soil with added vermiculite (Whittemore Inc.) and added fertilizer in a greenhouse with a 16 h light/8 h dark cycle for three months. *Solanum tuberosum* tubers were sprouted under natural light for three weeks.

Transcriptomic Analysis of *Lycium barbarum* and Identification of Candidate Precursor Gene LbaLycA

*Lycium barbarum* roots were removed from a three year-old plant, washed with sterile water, and total RNA was extracted with the QIAGEN RNeasy Plant Mini kit. RNA quality was assessed by Agilent Bioanalyzer. A strand-specific mRNA library was prepared (TruSeq Stranded Total RNA with Ribo Zero Library Preparation Kit, Illumina) and sequenced with a HiSeq2000 Illumina sequencer in HISEQRAPID mode (100×100). Illumina sequence raw-files were combined and assembled by the Trinity package [34]. Gene expression was estimated by mapping raw sequencing reads to the assembled transcriptomes using RSEM [37]. The *Lycium barbarum* root transcriptome was analyzed for lyciumin precursors by searching predicted core peptide sequences for known lyciumin A (SEQ ID NO: 148; QPYGVGSW), lyciumin B (SEQ ID NO: 50; QPWGVGSW), lyciumin C (SEQ ID NO: 175; QPYGVFSW), and lyciumin D (SEQ ID NO: 174; QPYGVGIW) by blastp algorithm on an internal Blast server. In order to clone and sequence a lyciumin precursor gene from *Lycium barbarum*, cDNA was prepared from root total RNA with SuperScript® III First-Strand Synthesis System (Invitrogen). Transcripts with lyciumin core peptide sequences were used to design cloning primers (LbaLycA-pEAQ-AgeI (SEQ ID NO: 118): AGACCGGTATG-GAGTTGCATCACCATTAC, LbaLycA-pEAQ-XhoI (SEQ ID NO: 119): AGCTCGAGTTAGTTTTCAGACACTT-GAGTTGCG) for amplification of precursor peptide gene LbaLycA with Phusion® High-Fidelity DNA polymerase (New England Biolabs) and directional cloning with restriction enzymes AgeI and XhoI (New England Biolabs) and T4 DNA ligase (New England Biolabs) into pEAQ-HT, which was linearized by restriction enzymes AgeI and XhoI [38]. Cloned LbaLycA was sequenced by Sanger sequencing from pEAQ-HT-LbaLycA.

Cloning of Lyciumin Precursor Gene StuBURP from *Solanum tuberosum*

Tuber sprout tissue was removed from a sprouting potato tuber and total RNA was extracted with the QIAGEN RNeasy Plant Mini kit. cDNA was prepared from sprout total RNA with SuperScript® III First-Strand Synthesis System (Invitrogen). A de novo transcriptome was assembled from a Russett potato RNA-seq dataset (NCBI SRA: SRR5970148) and transcripts homologous to target lyciumin precursor PGSC0003DMG400047074 were used to design cloning primers (StuBURP-pEAQ-fwd (SEQ ID NO: 120): TGCCCAAATTCGCGACCGGTATG-GAGTTGCATCACCAATA; StuBURP-pEAQ-rev (SEQ ID NO: 121): CCAGAGTTAAAGGCCTCGAGT-TAGTTTTCAGCCACTTGAAGAACTG) for amplification of precursor gene StuBURP with Phusion® High-Fidelity DNA polymerase (New England Biolabs). StuBURP was cloned into pEAQ-HT, which was linearized by restriction enzymes AgeI and XhoI, by Gibson cloning assembly (New England Biolabs). Cloned StuBURP (SEQ ID NO. 126) was sequenced by Sanger sequencing from pEAQ-HT-StuBURP.

Heterologous Expression of Lyciumin Precursor Genes in *Nicotiana benthamiana*

*Agrobacterium tumefaciens* LBA4404 was transformed with pEAQ-HT-LbaLycA, other pEAQ-HT constructs with lyciumin precursor genes (pEAQ-HT-StuBURP, pEAQ-HT-CanBURP, pEAQ-HT-Sali3-2, pEAQ-HT-Sali-3-2-mutants) or pEAQ-HT-LbaQC by electroporation (2.5 kV), plated on YM agar (0.4 g yeast extract, 10 g mannitol, 0.1 g sodium chloride, 0.2 g magnesium sulfate (heptahydrate), 0.5 g potassium phosphate, (dibasic, trihydrate), 15 g agar, ad 1 L Milli-Q Millipore water, adjusted pH 7) with 100 µg/mL rifampicin, 50 µg/mL kanamycin and 100 µg/mL streptomycin and incubated for two days at 30° C. A 5 mL starter culture of YM medium with 100 µg/mL rifampicin, 50 µg/mL kanamycin and 100 µg/mL streptomycin was inoculated with a clone of *Agrobacterium tumefaciens* LBA4404 pEAQ-HT-LbaLycA and incubated for 24-36 h at 30° C. on a shaker at 225 rpm Subsequently, the starter culture was used to inoculate a 50 mL culture of YM medium with 100 µg/mL rifampicin, 50 µg/mL kanamycin and 100 µg/mL streptomycin, which was incubated for 24 h at 30° C. on a shaker at 225 rpm. The cells from the 50 mL culture were centrifuged for 30 min at 3000 g, the YM medium was discarded and cells were resuspended in MMA medium (10 mM MES KOH buffer (pH 5.6), 10 mM magnesium chloride, 100 µM acetosyringone) to give a final optical density of 0.8. The Agrobacterium suspension was infiltrated into the bottom of Nicotiana benthamiana plants (six weeks old). N. benthamiana plants were placed in the shade two hours before infiltration. After infiltration, N. benthamiana plants were grown as described above for six days. Subsequently, infiltrated leaves were collected and subjected to chemotyping.

Chemotyping of Lyciumin Peptides from Plant Material

For peptide chemotyping, 0.2 g plant material (fresh weight) were frozen in liquid nitrogen and ground with mortar and pestle. Ground plant material was extracted with 10 mL methanol for 1 h at 37° C. in a glass vial. Plant methanol extract was dried under nitrogen gas in a separate glass vial. Dried plant methanol extract was resuspended in water (10 mL) and partitioned with hexane (2×10 mL) and ethyl acetate (2×10 mL), and subsequently extracted with n-butanol (10 mL). The n-butanol extract was dried in vacuo and resuspended in 2 mL methanol for liquid chromatography-mass spectrometry (LC-MS) analysis. Peptide extracts were subjected to high resolution MS analysis with the following LC-MS parameters: LC-Phenomenex Kinetex® 2.6 µm C18 reverse phase 100 Å 150×3 mm LC column, LC gradient: solvent A—0.1% formic acid, solvent B—acetonitrile (0.1% formic acid), 0-2 min—5% B, 2-23 min—5-95% B, 23-25 min—95% B, 25-30 min—5% B, 0.5 mL/min, MS—positive ion mode, Full MS: Resolution 70000, mass range 425-1250 m/z, dd-MS$^2$ (data-dependent MS/MS): resolution 17500, Loop count 5, Collision energy 15-35 eV (stepped), dynamic exclusion 1 s. LC-MS data was analyzed with QualBrowser in the Thermo Xcalibur software package (version 3.0.63, ThermoScientific).

For comparative chemotyping of lyciumin concentrations in different plant tissues, peptides were extracted from plant tissues as described above from three different plants of the same age. Analyzed tissues of Amaranthus hypochondriacus and Chenopodium quinoa (three month old) were flower, leaf, root, seed and stem. Analyzed tissues of Beta vulgaris (three month old) were leaf, root, seed and stem. Analyzed tissues of Glycine max (three month old) were bean, leaf, pod, root and stem. Analyzed tissues for Solanum tuberosum (three week old) were sprout and tuber. Peptide extracts were subjected to low resolution MS analysis by selected-ion monitoring (SIM) of lyciumin masses specific to each plant and the following LC-MS parameters: LC—Phenomenex Kinetex® 2.6 µm C18 reverse phase 100 Å 150×3 mm LC column, LC gradient: solvent A—0.1% formic acid, solvent B—acetonitrile (0.1% formic acid), 0-1 min: 5% B, 1-8 min: 5-95% B, 8-10 min: 95% B, 10-15 min: 5% B, MS—positive ion mode, SIM (Amaranthus hypochondriacus: 872.8-873.8 m/z and 963.8-964.8 m/z, Chenopodium quinoa: 869.8-870.8 m/z and 972.8-973.8 m/z, Beta vulgaris: 894.8-895.8 m/z, Glycine max: 910.8-911.8 m/z and 993.8-994.8 m/z, Solanum tuberosum: 880.8-881.8 m/z, 896.8-897.8 m/z, 913.8-914.8 m/z, 922.8-923.8 m/z, 947.8-948.8 m/z, 972.8-973.8 m/z and 1048.8-1049.8 m/z). Lyciumin ion abundance values were determined by peak area integration from each lyciumin SIM chromatogram in QualBrowser in the Thermo Xcalibur software package (version 3.0.63, ThermoScientific).

Lyciumin Genome Mining

Prediction of lyciumin genotypes: For prediction of lyciumin precursor peptide genes in a plant genome, LbaLycA homologs were searched by tblastn in the 6-frame translated genome sequence (JGI Phytozome v12.1 and pre-release genomes) or by blastp of Refseq protein sequences (NCBI genomes, Table 1). In addition, annotated BURP domains were identified by 'BURP domain' Keyword search (JGI Phytozome v12.1 and pre-release genomes). All identified BURP domain proteins from a plant genome were then searched for lyciumin core peptide sequences with the search criteria of a glutamine and proline as the first and second amino acid, respectively, in the core peptide sequence and a tryptophan at the eighth position of the core peptide sequence. A BURP domain protein, which contained one or multiple sequences matching these lyciumin core peptide criteria, was a candidate lyciumin precursor peptide and, thus, its gene a predicted lyciumin genotype in the target plant genome.

In order to complement missing core peptide sequences from a lyciumin precursor gene with a sequence gap in the potato genome (PGSC0003DMG400047074), a Russett potato tuber transcriptome (NCBI SRA: SRR5970148) was assembled by Trinity (v2.4) and rnaSPAdes (v1.0, kmer 25, 75) [35]. Precursor peptide transcripts with missing core peptide sequences were searched in both de novo transcriptome assemblies by LbaLycA tblastn search.

Prediction of lyciumin chemotypes: A lyciumin structure was predicted from a putative lyciumin core peptide sequence by transformation of the glutamine at the first position to a pyroglutamate and formation of a covalent bond between the indole-nitrogen of the tryptophan at the eighth position with the α-carbon of the residue at the fourth position by loss of two hydrogens.

Lyciumin chemotyping: LC-MS data of peptide extracts from a predicted lyciumin producing plant was analyzed for lyciumin mass signals by (a) parent mass search (base peak chromatogram of calculated [M+H]$^+$ of predicted lyciumin structure, Δm=5 ppm), (b) fragment mass search of pyroglutamate-proline-b-ion in MS/MS data ($C_{10}H_{13}N_2O^+$, 209.09207 m/z, Δm=5 ppm), and (c) iminium ion mass search of specific amino acids of predicted structure in MS/MS data (for example, pyroglutamate iminium ion [M+H]$^+$ 84.04439 m/z) with QualBrowser in the Thermo Xcalibur software package (version 3.0.63, ThermoScientific). Putative mass signals of predicted lyciumin structures were confirmed by MS/MS data analysis.

Lyciumin Transcriptome Mining

For lyciumin transcriptome mining, transcriptomes of terrestrial plants from the 1kp database were assembled by rnaSPAdes (v1.0, kmer 25, 75 or, if failed, default kmer 55). De novo assembled transcriptomes were searched for LbaLycA homologs (type 1 lyciumin precursor) and Sali3-2 (Glycine max, AAB66369.1, type 2 lyciumin precursor) by tblastn search on an internal Blast server. Candidate lyciumin precursors were predicted with the same core peptide search criteria as for lyciumin genome mining with some precursors being partial sequences due to failed complete de novo assembly (Table 3). In order to verify lyciumin genotype prediction in Selaginellaceae (1kp dataset: ERR2040880-Selaginella willdenowii), other Selaginella transcriptomes from the NCBI SRA were de novo assembled (rnaSPAdes, v1.0, kmer 25, 75, SRR3136708—Selaginella bryopteris, SRR4762537—Selaginella martensii, SRR5499403—Selaginella uncinata, SRR7132763—Selaginella uncinata, SRR7132764—Selaginella rupestris, SRR7132766—Selaginella moellendorffii, SRR7132767—Selaginella peruviana, SRR7132768—Selaginella borealis, SRR7132769—Selaginella braunii), and searched for lyciumin genotypes as described above. For core peptide analysis of predicted lyciumin genotypes (Table 4, FIG. 10C) from genomes and transcriptomes, predicted core peptides from predicted lyciumin precursor protein sequences were transformed at the fourth position to a glycine in case of a fourth position threonine based on glycine as the common cyclization residue in Amaranthaceae lyciumin chemotypes (FIG. 2C).

Phylogenetic Analysis of Lyciumin Precursor Peptides

Protein sequences of characterized and predicted lyciumin precursors from genomes and transcriptomes (except 3'-partial sequences) and four founding members of the BURP domain family (NP_001303011.1—BURP domain-containing protein BNM2A precursor [*Brassica napus*], NP_001234835.1-Polygalacturonase-1 non-catalytic subunit beta precursor [*Solanum lycopersicum*], CAA31603.1/CAA31602.1-Embryonic abundant protein USP87/Embryonic abundant protein USP92 [*Vicia faba*], NP_197943.1—BURP domain protein RD22 [*Arabidopsis thaliana*]) [30-33] were reduced to their BURP domain (Pfam PF03181) and aligned using Muscle algorithm in MEGA (ver. 7.0.9). A neighbor-joining phylogenetic tree was generated with 2000 bootstrap generations using the p-distance method in MEGA.

Lyciumin Metabolic Engineering in *Nicotiana benthamiana*

Predicted lyciumin precursor Sali3-2 (Glyma.12G217400) was synthesized as an IDT gBlock® with a 5'-adapter (TGCCCAAATTCGCGACCGGT (SEQ ID NO: 252)) and a 3'-adapter (CTCGAGGCCTTTAACTCTGG (SEQ ID NO: 253) for Gibson assembly. pEAQ-HT was digested by AgeI and XhoI restriction enzymes and the Sali3-2 gBlock® was cloned into the digested pEAQ-HT with Gibson Assembly Master Mix (New England Biolabs). pEAQ-HT-Sali3-2 was verified by Sanger sequencing and transformed into *Agrobacterium tumefaciens* LBA4404 for heterologous expression as described above. Constructs for metabolic engineering of lyciumins were Sali3-2 mutants of its core peptide sequence (SEQ ID NOS: 8-33). Sali3-2 mutants were synthesized as gBlocks® and cloned into pEAQ-HT for heterologous expression in *N. benthamiana* as described above. Chemotyping of infiltrated *N. benthamiana* leafs for lyciumins was done as described above.

Purification and Structure Elucidation of Lyciumins

For lyciumin A, B and D isolation, *Lycium barbarum* roots (100 g wet weight) were ground with a tissue homogenizer and extracted for 16 h with methanol shaking at 225 rpm and 37° C. For lyciumin C isolation, amaranth grain (4.5 kg) was ground in a tissue homogenizer and extracted for 16 h with methanol shaking at 225 rpm and 37° C. Methanol extracts were filtered and dried in vacuo. Dried methanol extracts were resuspended in water and partitioned twice with hexane and twice with ethylacetate and then extracted twice with n-butanol. n-butanol extracts were dried in vacuo. Dried n-butanol extracts were resuspended in 10% methanol and separated by flash liquid chromatography with Sephadex LH20 as a stationary phase and a gradient of 10-100% methanol as a mobile phase. Fractions were collected with a fraction collector and analyzed for lyciumin content by LC-QQQ-MS with the following LC-MS settings: LC—Phenomenex Kinetex® 2.6 μm C18 reverse phase 100 Å 150×3 mm LC column, LC gradient: solvent A—0.1% formic acid, solvent B—acetonitrile (0.1% formic acid), 0.5 mL/min, 0-1 min: 5% B, 1-8 min: 5-95% B, 8-10 min: 95% B, 10-15 min: 5% B, MS—positive ion mode, Full MS: Lyciumin A/B/D—860-920 m/z, Lyciumin C/I—950-1010 m/z. LH20 fractions with lyciumins were combined, dried in vacuo, resuspended in 10% acetonitrile (0.1% trifluoroacetic acid) and subjected to preparative HPLC with a Phenomenex Kinetex® 5 μm C18 reverse phase 100 Å 150×21.2 mm LC column as a stationary phase for two rounds of separation. LC settings were as follows: solvent A—0.1% trifluoroacetic acid, solvent B—acetonitrile (0.1% trifluoroacetic acid), 10 mL/min, Lyciumin A (20 mg)—1.LC: 0-3 min: 10% B, 3-43 min: 10-50% B, 43-45 min: 50-95% B, 45-48 min: 95% B, 48-49 min: 95-10% B, 49-69 min: 10% B, 2.LC: 0-5 min: 35% B, 5-35 min: 35-50% B, 35-38 min: 50-95% B, 38-40 min: 95% B, 40-40.1 min: 95-35% B, 40.1-60 min: 35% B, Lyciumin B (13 mg)—1.LC: 0-3 min: 20% B, 3-48 min: 20-40% B, 48-50 min: 40-95% B, 50-54 min: 95% B, 54-55 min: 95-20% B, 55-70 min: 20% B, 2.LC: 0-3 min: 30% B, 3-35 min: 30-45% B, 35-38 min: 45-95% B, 38-40 min: 95% B, 40-40.1 min: 95-30% B, 40.1-60 min: 30% B, Lyciumin C—1.LC: 0-3 min: 10% B, 3-43 min. 10-50% B, 43-45 min: 50-95% B, 45-48 min: 95% B, 48-49 min: 95-10% B, 49-69 min: 10% B, 2.LC: 0-3 min: 40% B, 3-48 min: 40-55% B, 48-50 min: 55-95% B, 50-54 min: 95% B, 54-55 min: 95-40%, 55-70 min: 40% B, Lyciumin D (5 mg)—1.LC: 0-3 min: 20% B, 3-48 min: 20-40% B, 48-50 min: 40-95% B, 50-54 min: 95% B, 54-55 min: 95-20% B, 55-70 min: 20% B. 2.LC: 0-3 min: 30% B, 3-48 min: 30-50% B, 48-50 min: 50-95% B, 50-54 min: 95% B, 54-55 min: 95-30% B, 55-70 min: 30% B, Lyciumin I—1.LC: 0-3 min: 20% B, 3-48 min: 20-50% B, 48-50 min: 50-95% B, 50-54 min: 95% B, 54-55 min: 95-20% B, 55-70 min: 20% B, 2 LC: 0-3 min. 25% B, 3-48 min: 25-45% B, 48-50 min: 45-95% B, 50-54 min: 95% B, 54-55 min: 95-25% B, 55-70 min: 25% B. Preparative HPLC fractions with lyciumin C and lyciumin I, respectively, were combined, dried in vacuo, resuspended in 30% acetonitrile (0.1% trifluoroacetic acid) and subjected to semipreparative HPLC with a Phenomenex Kinetex® 5 μm C18 reverse phase 100 Å 250×10 mm LC column as a stationary phase. LC settings were as follows: Solvent A—0.1% trifluoroacetic acid, solvent B—acetonitrile (0.1% trifluoroacetic acid), 1.5 mL/min, Lyciumin C (25 mg)—0-5 min: 40% B, 5-15 min: 40-42% B, 15-17 min: 42-95% B, 17-20 min, 95% B, 20-20.1 min: 95-40% B, and lyciumin I (2.5 mg)—0-5 min: 30% B, 5-30 min: 30-35% B, 30-32 min: 35-95% B, 32-36 min: 95% B, 36-40 min: 95-30% B, 40-60 min. 30% B. For NMR analysis, lyciumin A, B, C, D and I were each dissolved in DMSO-d6. Lyciumin A was analyzed for 1H and 13C NMR data, lyciumin B, D and C were analyzed for $^1$H NMR data. Lyciumin I was analyzed for $^1$H NMR, $^1$H-$^1$H COSY, $^1$H-$^1$H TOCSY, HSQC, HMBC and ROESY data. NMR data was analyzed with TopSpin software (v3.5) from Bruker. Stereochemistry of crosslinked glycine α-carbons at the fourth position of lyciumins was inferred as (R) based on lyciumin A analysis and same ROESY correlations of lyciumin I glycine-Hα as reported for lyciumin A [52]. Stereochemistry of other amino acids of lyciumin I was inferred as (L)-amino acids because of its ribosomal biosynthesis and (L)-amino acid stereochemistry in all reported lyciumins [25,26,52].

Gene Expression Analysis of Characterized Lyciumin Precursors

Figure 8C:
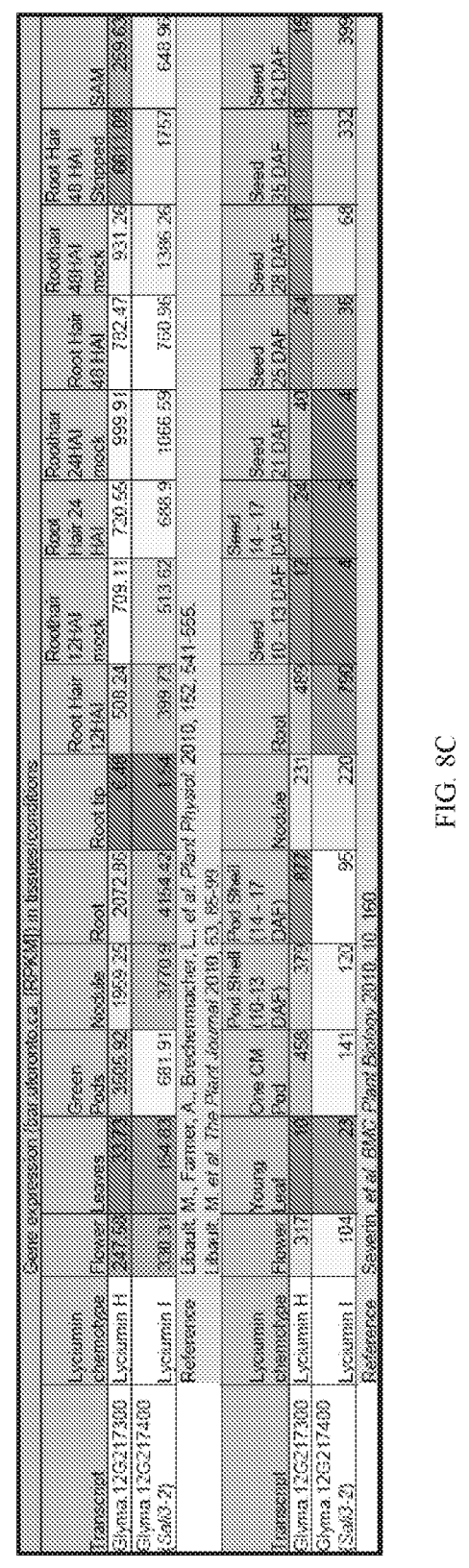
Figures 8D, 8E:
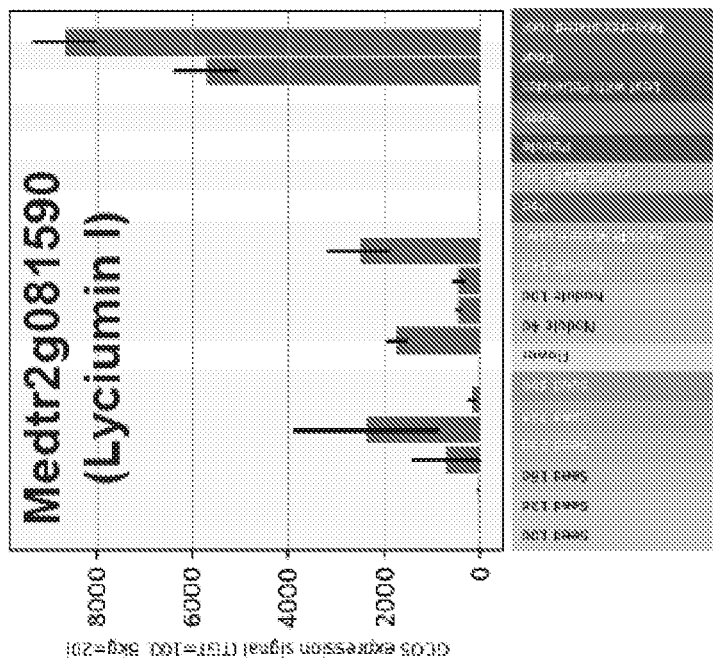
Figure 11:
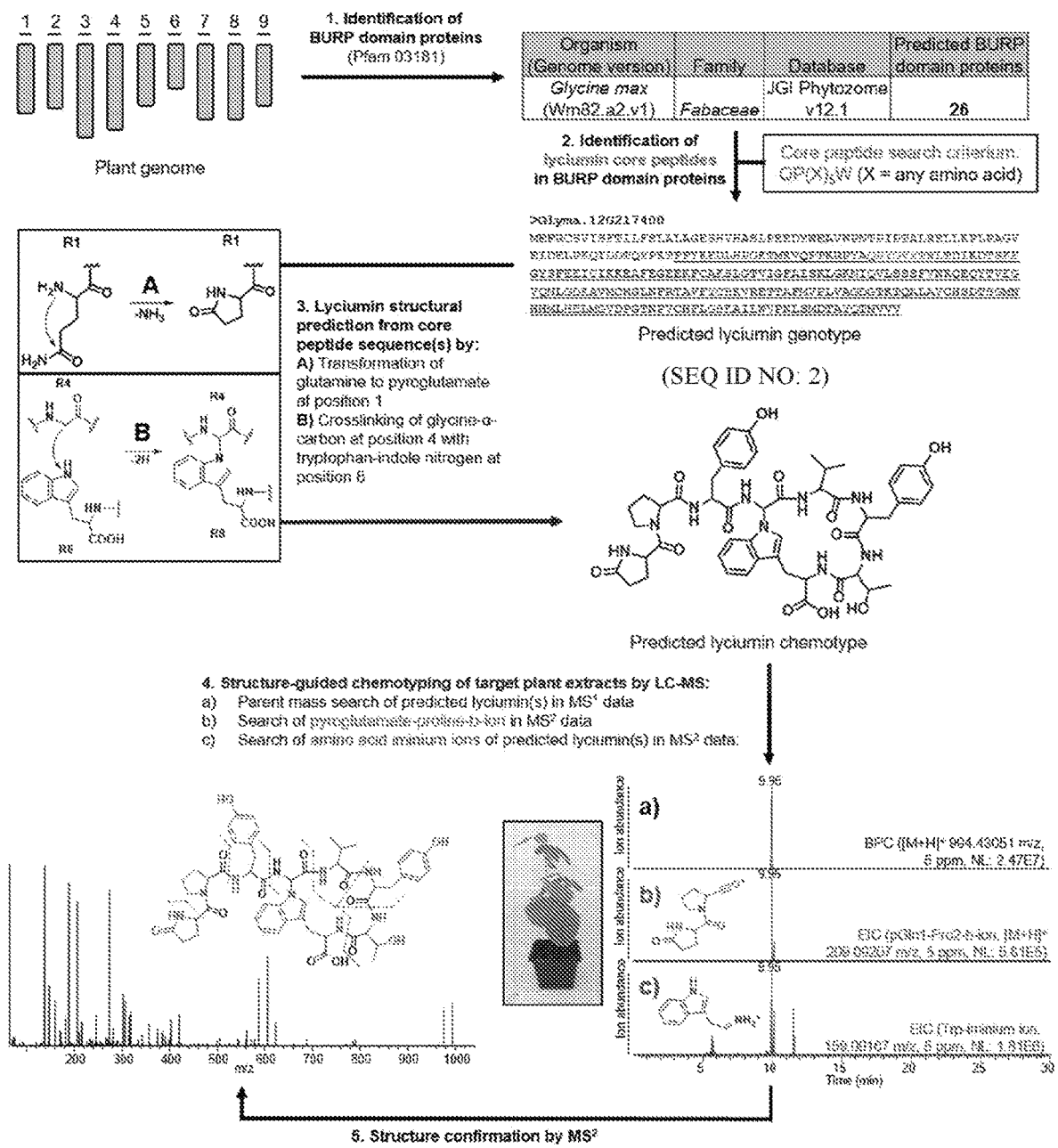

Gene expression of characterized lyciumin precursors was estimated by mapping raw sequencing reads to de novo assembled transcriptomes using RSEM [37]. For *Solanum tuberosum*, gene expression of lyciumin precursor peptide gene (PGSC0003DMG400047074, SEQ ID NO: 38) was analyzed in 16 tissue samples (NCBI SRA datasets: ERR029909, ERR029910, ERR029911, ERR029912, ERR029913, ERR029914, ERR029915, ERR029916, ERR029917, ERR029918, ERR029919, ERR029920, ERR029921, ERR029922, ERR029923, ERR029924) by RSEM against the combined de novo Trinity-assembled transcriptome of all 16 samples (FIG. 8E). For *Amaranthus*

*hypochondriacus*, gene expression of lyciumin precursor peptide gene AHYPO_007393-RA was analyzed in eight tissues and conditions (NCBI SRA: SRR1598916, SRR1598915, SRR1598914, SRR1598913, SRR1598912, SRR1598911, SRR1598910, SRR1598909) by RSEM against the combined de novo Trinity-assembled transcriptome of all eight samples. (FIG. 8A). For *Chenopodium quinoa*, gene expression of lyciumin precursor peptide AUR62017095 was analyzed in 15 tissue samples (NCBI: SRA: SRR5974430, SRR5974427, SRR5974436, SRR5974438, SRR5974437, SRR5974435, SRR5974432, SRR5974433, SRR5974425, SRR5974426, SRR5974424, SRR5974431, SRR5974428, SRR5974429, SRR5974434) against the combined de novo Trinity-assembled transcriptome of all 15 samples (FIG. 8B). For *Medicago truncatula*, gene expression of lyciumin precursor peptide Medtr2g081610 (SEQ ID NO: 40) was assessed by the eFP bar.utoronto.ca webbrowser of gene expression data from *Medicago truncatula* RNA-seq dataset and displayed (FIG. 8D). For *Glycine max*, gene expression of lyciumin precursor peptides Sali3-2 (SEQ ID NO: 8) and Glyma. 12G217300 (SEQ ID NO: 36) was assessed by the eFP bar.utoronto.ca webbrowser of gene expression data from *Glycine max* RNA-seq datasets and displayed (FIG. 8C).

Glutamine Cyclotransferase Co-Expression Assays with LbaLycA in *Nicotiana benthamiana*

Glutamine cyclotransferase LbaQC was characterized as the closest homolog of *Chenopodium quinoa* glutamine cyclotransferase (AUR62017096, Phytozome 12.1) by blastp search of *L. barbarum* root transcriptome on an internal Blast server. LbaQC was synthesized as a gBlock® (ATGGTTTCTTCTACTTCATATCTACCTACCAAT-CACACAAAAATGCCTCTGCTAA ATCCAAGGTT-TCTAGTCATAAGCTTGATTGTTCTACTGAGCAT-CACCGTATTCAGA GAAGCTGAAGCATCATATAGA-GTTTACAAAGTCAAAGTAGTCAATGAATTCCCTC ACGACCCCCAAGCCTACACTCAGGGGCTTCTC-TATGCAGAAAATAATACACTCTT TGAATCAACTG-GACTTTACGGACGTTCATCTGTTCGAAAAGTTG-CATTGCTGGAC GGTAAGGTTGAGAGACTTCAT-GAAATGGAGTCTTCTTACTTTGGAGAGGGTCTAA CTCTTCTTGGTGAGAGGTTGTTCCAACTAA-CATGGTTGCTGGATACAGGTTTCATA TATGATCGA-TACAACTTCAGCAAATTCAAAAAGTTTACTCATCA-CATGCAAGATG GTTGGGGATTGGCAACC-GATGGGAAAGTACTTTTTGGAAGTGATGGAACAT-CAA CATTATATAAGATTGACCCTAAAACAAT-GAAAGTCATCAGAAAACAAGTIGTCAA GTCT-CAAGGGCATGAAGTGCGCTACCTGAATGAGCTGG-AGTATGTGAAAGCTGA AGTCTGGGCAAATGTT-TATGTGACTGATTGCATTGCTAGAATTTCAC-CAAAAGAT GGCACTGTGATCGGGTGGATTCTCCTT-CAATCTCTAAGAGAAGAGTTAATATCAA GAGGATATAAGGACTTCGAGGTCCTGAATG-GAATCGCATGGGACAGAGATGGTG ACCGTAT-TTTTGTGACAGGGAAACTATGGCCAAAGCTCTTT-GAGATCAAGTTGCT CCCCCTCACACCGAATGA-TCCATTGGCTGGAGAAATCAATAACTTGTGCATC-CCG AAAACCAGTTTTCTCTTGGAAATTTAG (SEQ ID NO: 122)) with a 5'-adapter (TGCCCAAAT-TCGCGACCGGT) (SEQ ID NO: 123) and a 3'-adapter (CTCGAGGCCTTTAACTCTGG) (SEQ ID NO: 124) for Gibson assembly. pEAQ-HT was digested by AgeI and XhoI restriction enzymes and the LbaQC gBlock® was cloned into linearized pEAQ-HT with Gibson Assembly Master Mix (New England Biolabs). pEAQ-HT-LbaQC was verified by Sanger sequencing. For glutamine cyclotransferase co-expression assays, pEAQ-HT-LbaQC and pEAQ-HT-LbaLycA were transformed into *Agrobacterium tumefaciens* LBA4404 for heterologous expression as described above. For co-expression assay, leaves of three plants of *Nicotiana benthamiana* (six week old) were infiltrated with a 1:1 mixture of resuspended *A. tumefaciens* LBA4404 pEAQ-HT-LbaQC (OD 0.8) and *A. tumefaciens* LBA4404 pEAQ-HT-LbaLycA (OD 0.8). For LbaLycA control expression without LbaQC, leaves of three plants of *Nicotiana benthamiana* (six week old) were infiltrated with resuspended *A. tumefaciens* LBA4404 pEAQ-HT-LbaLycA (OD 0.4). Infiltrated plants were cultivated as described before for six days for heterologous expression. After six days, leaves of three plants of the LbaQC-LbaLycA co-expression and leaves of three plants of LbaLycA expression control were collected and freeze-dried. For comparative chemotyping of [Gln1]-lyciumin B, [Gln1]-lyciumin D, lyciumin B and lyciumin D, peptides were extracted from 0.1 g of freeze-dried tobacco leaves as described above for peptide chemotyping from the LbaQC-LbaLycA co-expression plants and from the LbaLycA expression plants. Peptide extracts were subjected to low resolution MS analysis by selected-ion monitoring (SIM) of masses of [Gln1]-lyciumins and lyciumins with the following LC-MS parameters: LC—Phenomenex Kinetex® 2.6 μm C18 reverse phase 100 Å 150×3 mm LC column, LC gradient: solvent A—0.1% formic acid, solvent B—acetonitrile (0.1% formic acid), 0.5 mL/min, 0-1 min: 5% B, 1-8 min: 5-95% B, 8-10 min. 95% B, 10-15 min: 5% B, MS—positive ion mode, SIM: 896.8-897.8 m/z (lyciumin B), 899.8-900.8 m/z (lyciumin D), 913.8-914.8 m/z ([Gln1]-lyciumin B), 916.8-917.8 m/z ([Gln1]-lyciumin D). Lyciumin and [Gln1]-lyciumin ion abundance values were determined by peak area integration from each peptide SIM chromatogram in QualBrowser in the Thermo Xcalibur software package (version 3.0.63, ThermoScientific).

Example 2

Results

This experiment investigates the taxonomic distribution of lyciumin-type RiPPs in the plant kingdom and further probes into the evolutionary mechanisms that could explain the observed distribution pattern. This endeavour was greatly facilitated by the extensive plant transcriptome sequencing effort in the recent years, e.g., the 1kp project, which covers more than half of the extent plant families on earth (Matasci et al., 2014). This experiment establishes an evolutionary framework of how lyciumin-type RiPPs have emerged over the last 450 million years of land plant evolution.

Example 2 is an extension of the results described in Example 1 under the subheading "Parallel evolution of lyciumin biosynthesis in angiosperms and lycophytes." Some of the results presented under that subheading of Example 1 may be repeated in Example 2 for clarity.

Lyciumin Genotypes are Present in Multiple Angiosperm Families and in the Lycophyte Family Selaginellaceae With the recently revealed knowledge of the lyciumin precursor protein (Kersten and Weng, 2018), the distribution of lyciumin genotypes in the plant kingdom was explored using available transcriptome resources generated by the plant community in recent years (Matasci et al., 2014).

However, an apparent issue of identification of lyciumin precursor genes from plant transcriptomes is the repetitive nature of most of the lyciumin-precursor-peptide-encoding genes, which causes misassembly of these genes from short-read RNA-seq data using de novo transcriptome assembly programs. For example, known lyciumin precursor peptides from Amaranthaceae, Fabaceae and Solanaceae comprise repeating motifs of lyciumin core peptides either in the N-terminal domain (type 1 lyciumin precursor) or within the BURP domain (type 2 lyciumin precursor) (FIG. 39B) (Kersten and Weng, 2018). Surveying among numerous de novo transcriptome assembly softwares, it was observed that rnaSPAdes (Grabherr et al., 2011; Bankevich et al., 2012; Bushmanova et al., 2018) is generally more robust in de novo assembly of lyciumin precursor genes containing repetitive core-peptide motif compared to other assemblers (Grabherr et al., 2011; Bankevich et al., 2012; Bushmanova et al., 2018). To further assess whether rnaS-PAdes is more suitable for lyciumin genotype identification from transcriptome data, RNA-seq datasets of characterized and predicted lyciumin producers based on genome mining were assembled by rnaSPAdes (v1.0) and by Trinity (v2.6.6) in three repeated runs. Trinity was selected for this comparison as it was the second best assembler for repetitive lyciumin precursor peptide genes in the initial survey. Assembly of previously characterized and predicted lyciumin precursor peptides were then compared between the rnaSPAdes assembly and Trinity assembly. Whereas Trinity assembly yielded only one fully assembled precursor gene sequence in six test cases, rnaSPAdes enabled the complete assembly of five precursor gene sequences of the six test cases. Both assemblers yielded the correct core peptide gene sequences in each successfully assembled test case with the exception that rnaSPAdes missed one core peptide sequence in one assembled *Solanum melongena* precursor compared to Trinity (Sme2.5_02115.1_g00002.1). Whereas Trinity showed small variations in assembly between repeated runs, e.g., in repeat number per lyciumin precursor (*Nicotiana attenuata* OIT08186.1), rnaSPAdes assembly of lyciumin precursors was consistent over repeated runs.

Given the results of improved BURP-domain precursor gene assembly using rnaSPAdes at the time of the transcriptome analysis, de novo reassembly of transcriptomes of 793 plant species was performed using maSPAdes starting from raw sequencing reads generated as part of the 1kp project (Matasci et al., 2014), which represent a total of 317 land plant families. Subsequently, lyciumin genotypes were searched for in these reassembled transcriptomes by tblastn using type 1 (LbaLycA, GenBank: MH124242) and type 2 (Sali3-2, GenBank: AAB66369) lyciumin precursors as queries. This exercise readily identified a battery of candidate lyciumin precursor genes distributed across diverse plant families that extend beyond the previously reported Amaranthaceae, Fabaceae and Solanaceae (Kersten and Weng, 2018). These newly identified lyciumin-genotype-containing plant families include Aizoaceae, Molluginaceae, Nyctaginaceae, Petiveriaceae and Phytolaccaceae, which are all under the order of Caryophyllales, as well as Selaginellaceae. It is noteworthy that Selaginellaceae is one of the three extant families of lycophytes which are basal vascular plants separated from all other euphyllophytes over 400 million years ago (Banks, 2009).

Lyciumin Chemotyping Confirms Lyciumin Biogenesis in Lycophytes

Since RiPPs have only been reported in angiosperms, we sought to confirm the predicted lyciumin production in *Selaginella*. To do this, several additional transcriptomes of *Selaginella* species were assembled starting from RNA-seq raw reads available from the NCBI SRA using rnaSPAdes, and searched for lyciumin genotypes. In addition to *Selaginella willdenowii* (1kp dataset, NCBI SRA: ERR2040880) (Matasci et al., 2014), lyciumin precursor genes were found in three other *Selaginella* species: *S. uncinata*, *S. moellendorffii* and *S. bryopteris* (FIGS. 43A-I). One predicted lyciumin precursor gene was cloned and sequenced from root cDNA of *S. uncinata* (FIG. 40A, SunBURP, GenBank: MK089798). The corresponding lyciumin precursor peptide has five repeats including the putative lyciumin core peptide QPYSVFAW (SEQ ID NO: 147), indicating a serine serving as a lyciumin cyclization residue (FIG. 30B). Subsequent metabolic profiling experiments using liquid chromatography-mass spectrometry (LC-MS) further revealed an analyte in the peptide extract of *S. uncinata* roots that matched the mass of a predicted lyciumin—[QPYSVFAW (SEQ ID NO: 147)] peptide (FIGS. 40C and 40D) and had a lyciumin-characteristic pyroglutamate-proline b-ion in its MS/MS spectrum (FIG. 40D, Figure S3) (Kersten and Weng, 2018). Further MS/MS analysis of the candidate lyciumin—[QPYSVFAW (SEQ ID NO: 147)] peptide confirmed the cyclization site at the fourth amino acid, enabling the prediction of a new peptide macrocyclization between the tryptophan-indole nitrogen and the α-carbon of a serine (FIG. 40C) based on MS/MS data, core peptide sequence and comparative MS/MS analysis of lyciumin—[QPYGVFAW (SEQ ID NO: 78)] (FIGS. 44A-B). This newly identified lyciumin—[QPYSVFAW (SEQ ID NO: 147)] (lyciumin P) represents the first RiPP from a non-seed plant and highlights that new RiPP chemistry could be discovered by large-scale transcriptome mining in plants.

Phylogenetic and Sequence Analysis of BURP-Domain Lyciumin Precursors Suggests Divergent and Parallel Evolution of Lyciumins in Land Plants Given the occurrence of lyciumins in multiple families of angiosperms and lycophytes, the evolutionary history of the characterized and predicted lyciumin precursor genes was examined (FIGS. 43A-I) (Kersten and Weng, 2018). Two general scenarios of lyciumin evolution are plausible. In the first scenario, the ability to produce lyciumin-type cyclic peptides from BURP-domain-containing genes evolved prior to the bifurcation of lycophytes and euphyllophytes. This trait was independently lost in plant families that do not contain lyciumin genotypes (Griesmann et al., 2018). Alternatively, ancestral non-peptide-producing BURP-domain genes could be independently recruited as lyciumin-type peptide precursor genes in distantly related plant families.

To test these alternative evolutionary hypotheses, phylogenetic analyses were performed of BURP-domain proteins from several sequenced plant genomes together with BURP domains of the predicted and characterized lyciumin-producing precursor proteins or BURP domains of the predicted and characterized lyciumin-producing precursor proteins alone (FIG. 31A). The resulted phylogenies show five well-resolved clades of sequences from Caryophyllales, Fabaceae, Rosaceae, Solanaceae, and Selaginellaceae with no support of shared ancestry for any of the two or more families, suggesting that ancestral BURP-domain proteins were likely recruited independently to serve as lyciumin precursor peptides within each of these five plant lineages.

Lyciumin Chemotyping Confirms Lyciumin Biogenesis in Lycophytes

The core peptide motif sequences of all the predicted and characterized lyciumin precursors were systematically examined, and it was found that the lyciumin core-peptide motifs are mostly unique to each of the phylogenetic clades (75% of core peptides are found in one plant family, FIG. 41B), suggesting extensive diversification of lyciumin peptide chemistry within each of the lyciumin-producing plant families. Notably, several lyciumin chemotypes are predicted to occur in three of the five clades: lyciumin A in Caryophyllales, Selaginellales and Solanales, lyciumin J and lyciumin—[QPFGVFAW (SEQ ID NO: 79)] in Caryophyllales, Fabales and Solanales, and lyciumin—[QPFGVFGW (SEQ ID NO: 83)] in Caryophyllales, Rosales and Solanales (FIG. 41B). A number of lyciumins are present in two plant orders. These include lyciumin C, lyciumin I, lyciumin—[QPYGVYGW (SEQ ID NO: 172)] and lyciumin—[QPFGVGSW (SEQ ID NO: 166)] in Caryophyllales and Solanales, lyciumin—[QPFGFRAW (SEQ ID NO: 75)] in Caryophyllales and Fabales, lyciumin—[QPYGVYSW (SEQ ID NO: 90)] in Fabales and Solanales, and lyciumin—[QPYGVGAW (SEQ ID NO: 150)] in Caryophyllales and Selaginellales. These observations suggest that those chemotypes shared between distantly related plant families are exemplary cases of metabolic trait convergence against the backdrop of extensive parallel divergence. Previous structure-function exploration of the sequence rules of lyciumin core peptides suggests that over 3,000,000 lyciumin chemotypes are theoretically possible (Kersten and Weng, 2018). The fact that several identical lyciumin chemotypes evolved repeatedly in multiple plant families implicates that these peptides likely play some generally important biological functions in their host plants (FIG. 41B).

From the perspective of lyciumin precursor gene structure, both Fabaceae and Selaginellaceae contain type 1 lyciumin precursors, while Caryophyllales and Solanaceae contain type 2 lyciumin precursors (FIG. 41A and FIGS. 43A-I) (Kersten and Weng, 2018). The predicted cyclization site at the fourth position of lyciumin core peptides is a threonine in most Caryophyllales precursors, a glycine in most Fabaceae precursors, a glycine in most Solanaceae precursors, a proline in most Rosaceae precursors, and a serine or a glycine in Selaginellaceae precursors (FIGS. 43A-1).

Given these results in the context of the taxonomic relationship of the predicted and characterized lyciumin-producing plants, homologous non-lyciumin-producing BURP-domain protein progenitors likely gave rise to independent occurrences of lyciumin biogenesis at least once in lycophytes and four times in eudicots followed by extensive divergent and parallel evolution to yield the extant lyciumin chemodiversity (FIG. 41C).

Figure 46A:
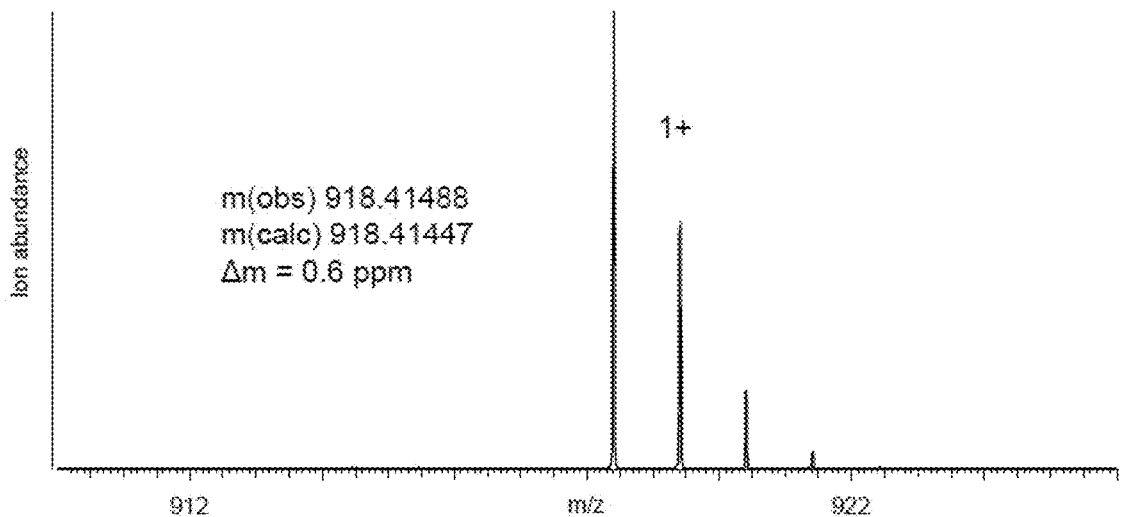
Figure 46B:
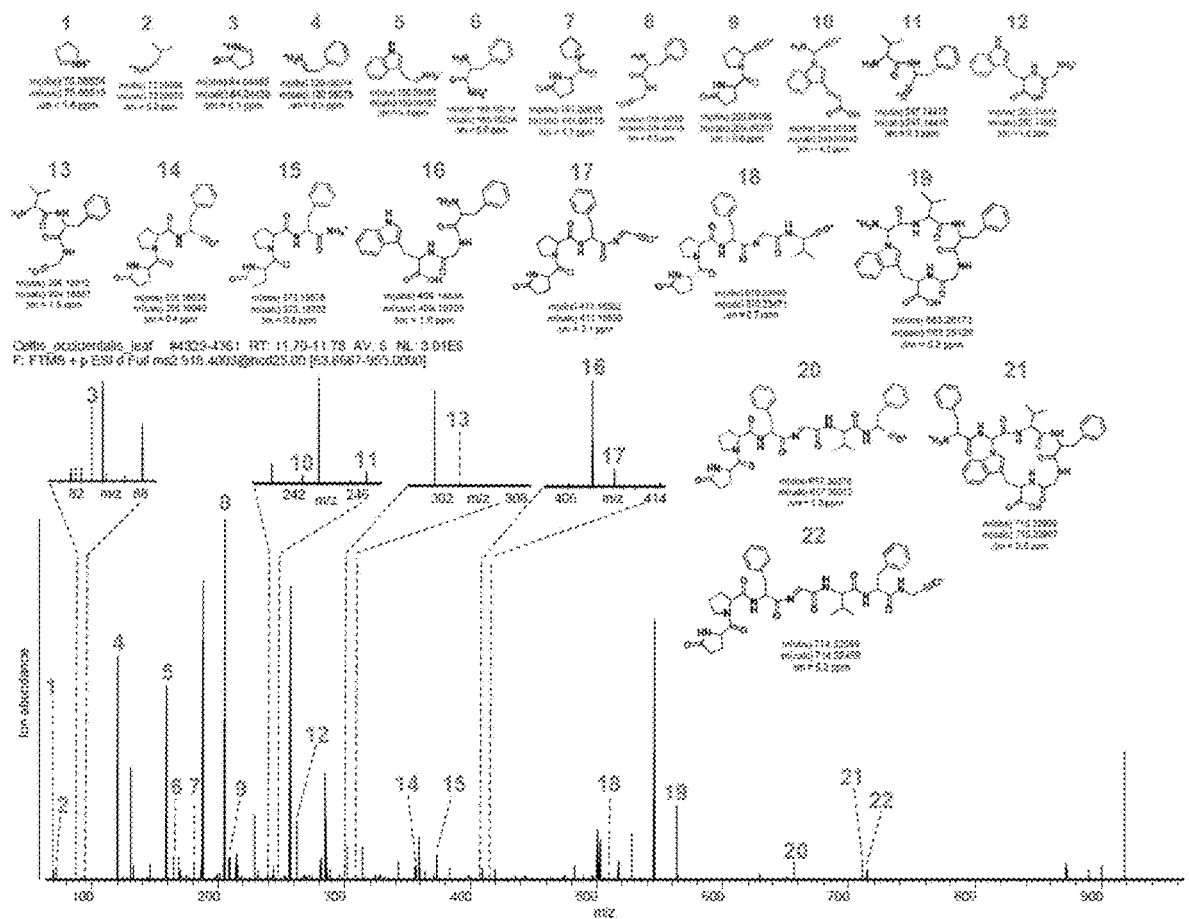
Figure 46F:
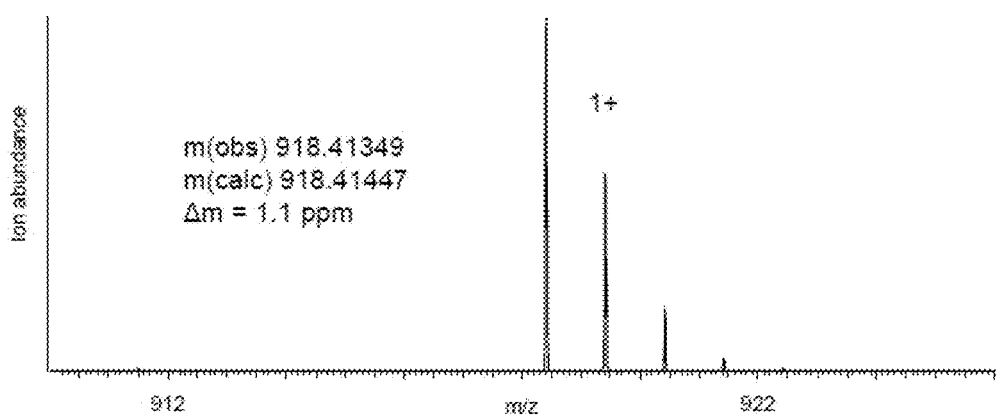
Figure 46G:
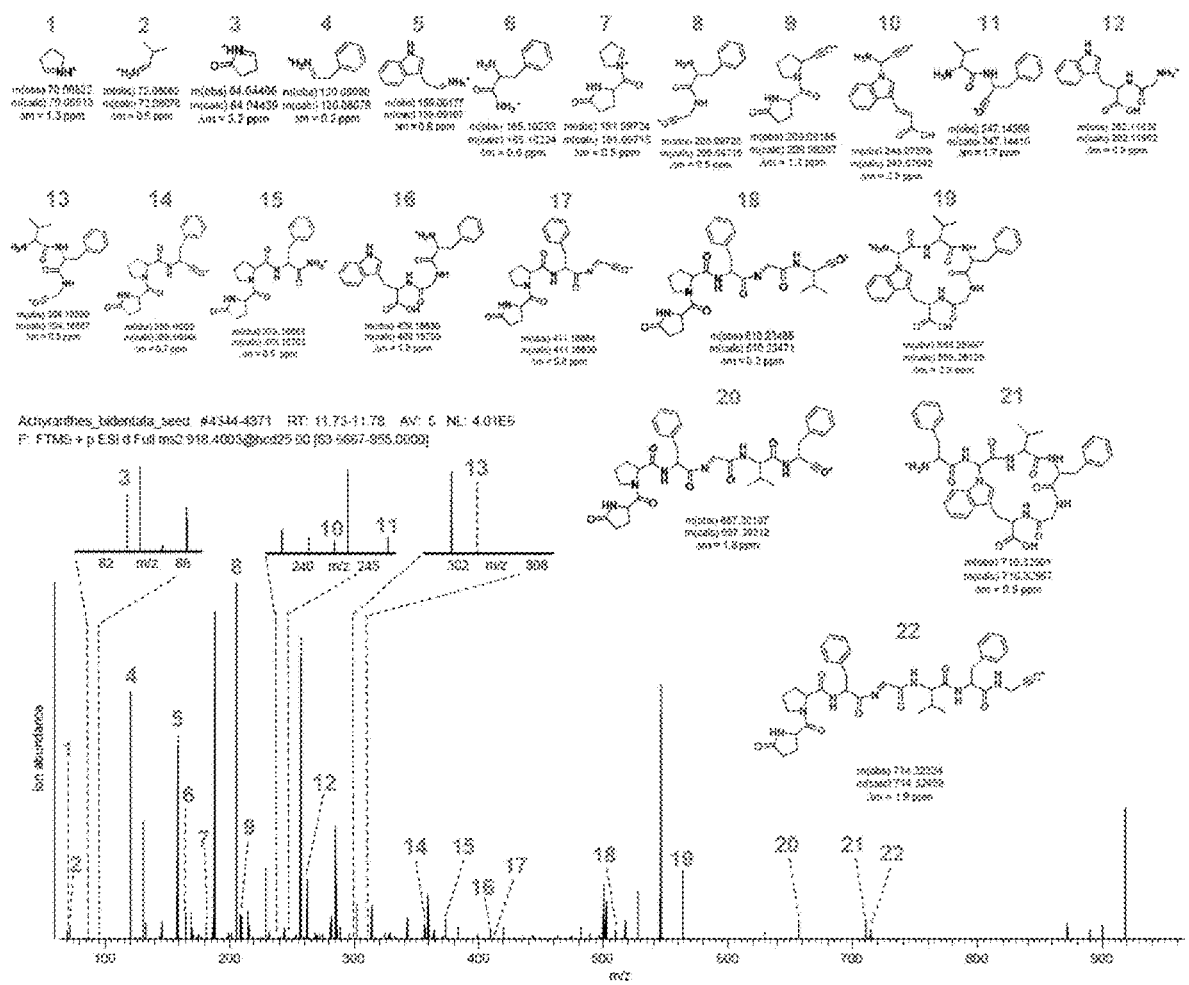

A Shared Lyciumin Chemotype in Hemp Plant Celtis occidentalis and Amaranth Plant Achyranthes bidentata is Derived from Two Disparate Families of Precursor Peptides When mining new lyciumin genotypes from diverse plant transcriptomes, a lyciumin core-peptide-containing gene from hackberry (Celtis occidentalis, Cannabaceae, FIG. 42A, NCBI SRA: ERR2040412) was serendipitously identified, which does not contain a C-terminal BURP domain. Instead, this putative lyciumin precursor is a DUF2775-domain protein (PF10950) with three repeats including the putative lyciumin core peptide QPFGVFGW (SEQ ID NO: 83) (FIG. 42B). Searching proteins related to this newly discovered candidate C. occidentalis lyciumin precursor CocDUF2775 identified an organ-specific protein (PF10950) from Cannabaceae plant Parasponia andersonii as the closest homolog which does not contain lyciumin core peptides (FIGS. 45A-B). Intrigued by the possibility of a new lyciumin precursor gene family in plants, several tissues of a C. occidentalis tree were analyzed by LC-MS and to look for the predicted lyciumin—[QPFGVFGW (SEQ ID NO: 83)] (lyciumin Q) chemotype (FIG. 42C). The peptide extract of C. occidentalis leaves indeed contained an analyte that matches the predicted lyciumin—[QPFGVFGW (SEQ ID NO: 83)] chemotype by MS and MS/MS analysis (FIGS. 42F and 46A-B). To further verify the detected lyciumin—[QPFGVFGW (SEQ ID NO: 83)] chemotype, lyciumin—[QPFGVFGW (SEQ ID NO: 83)] was generated in transgenic Nicotiana benthamiana via a previously described lyciumin expression platform (Kersten and Weng, 2018) with all chromatographic and MS features identical to the isolated lyciumin—[QPFGVFGW (SEQ ID NO: 83)] from C. occidentalis (FIGS. 42F and 46A-B). In brief, this platform is based on the Glycine max lyciumin precursor gene Sali3-2 (Tang et al., 2014). Sali3-2 harbors a single core peptide sequence, which allows for convenient production of any lyciumin chemotypes of interest in N. benthamiana via transient expression of Sali3-2 with engineered core peptide sequence. Since the reassembled C. occidentalis transcriptome does not encode any BURP-domain proteins that contain the core peptide QPFGVFGW (SEQ ID NO: 83) (FIG. 46A-B), it was concluded that CocDUF2775 is a new type of lyciumin precursor peptide defined by its DUF2775 domain, which was dubbed the type 3 lyciumin precursor (FIG. 42B) (Albornos et al., 2012).

The emergence of lyciumins from precursor peptides unrelated to the BURP-domain proteins indicates a potential case of convergent evolution of lyciumins in plants. To probe this hypothesis further, all characterized and predicted BURP-domain lyciumin precursor peptides were queried for potential lyciumin—[QPFGVFGW (SEQ ID NO: 83)] producers. This exercise identified several BURP-domain lyciumin precursor genes from Chenopodium quinoa (Amaranthaceae), Hypertelis (Kewa) cerviana (Molluginaceae), Petunia inflata and Solanum tuberosum (both Solanaceae) that harbor the capacity to produce lyciumin—[QPFGVFGW (SEQ ID NO: 83)]. Because lyciumin—[QPFGVFGW (SEQ ID NO: 83)] could not be detected in peptide extracts of greenhouse-grown C. quinoa and S. tuberosum plants, whereas H. cerviana and P. inflata plants were not available for chemical analysis, additional Amaranthaceae transcriptomes were further queried to search for BURP-domain precursor genes containing lyciumin—[QPFGVFGW (SEQ ID NO: 83)] motifs. One such candidate gene was identified in the transcriptome of ox knee (Achyranthes bidentata) (FIGS. 42D and 42E), which contains several repeats with QPFTVFGW (SEQ ID NO: 58) core peptides. Example 1 shows that lyciumin-producing plants of the Amaranthaceae family have a threonine at the fourth position of the lyciumin core peptide which is transformed into a glycine during lyciumin biosynthesis (Kersten and Weng, 2018). Therefore, the identified core peptide QPFTVFGW (SEQ ID NO: 58) in a lyciumin precursor protein from A. bidentata indicates the formation of a putative lyciumin—[QPFGVFGW (SEQ ID NO: 83)] chemotype. Peptide chemotyping of multiple tissues of a greenhouse-grown A. bidentata plant revealed the accumulation of lyciumin—[QPFGVFGW (SEQ ID NO: 83)] (lyciumin Q) in seeds (FIGS. 42F and 46A-G). The biogenesis of the same lyciumin chemotype from nonhomologous precursor proteins, i.e., DUF2775-domain and BURP-domain proteins, in two distantly related angiosperm families illustrates a classic case of convergent evolution of a metabolic trait (Weng, 2014).

Discussion

Knowledge of plant specialized metabolism is incomplete. The increase of genomic and transcriptomic data from taxonomically diverse plants can greatly accelerate the discovery of new plant chemotypes and unlock the trajectories of metabolic evolution towards these chemical adaptations. In Example 2, large-scale transcriptome mining followed by peptide chemotyping was carried out, which revealed that the branched cyclic lyciumin RiPPs most likely evolved independently at least once in lycophytes and four times in angiosperms. The results also suggest that lyciumins have emerged in BURP-domain precursor genes and DUF2775-domain precursor genes via convergent evolution.

Lyciumins share several similar features in terms of their biosynthetic origin and taxonomic distribution with head-to-tail cyclic RiPPs such as cyclotides and orbitides. Like other classes of plant cyclic RiPPS, lyciumins might have occurred through serendipitous emergence of a single lyciumin core peptide motif sequence in progenitor BURP domain proteins or DUF2775 domain proteins, which could be processed into small stable branched cyclic peptides by post-translationally modifying enzymes and proteases already present in the host plant cells. Lyciumins with favorable properties that render selective advantage to the plant host were more likely to be retained. Through core peptide mutagenesis and internal motif duplication, the ancestral lyciumins could undergo subsequent chemical optimization, amplification and diversification to yield extant lyciumins (Mylne et al., 2012). Indeed, lyciumin precursor peptides have diverse core peptide sequences that often exist as repetitive motifs in one precursor gene (FIGS. 43A-I) (Kersten and Weng, 2018). Lyciumin genotypes and chemotypes were mainly found in angiosperms prior to this study, which is also the case for cyclotides and orbitides discovered to date. Moreover, like cyclotide and orbitide precursors, all three types of lyciumin precursors contain N-terminal signaling peptides targeting to the secretory pathway (FIGS. 39B and 42B), suggesting that lyciumin precursor proteins are likely directed to the vacuole to complete RiPP biosynthesis similar to cyclotides (Conlan et al., 2011).

There are several unique aspects of lyciumins in the context of plant RiPP evolution. First, lyciumins occurred in non-angiosperms, i.e., *Selaginella* plants, and, therefore, represent the only known RiPP family from non-angiosperms to date. Nevertheless, a report of a cyclotide-like protein domain with protease inhibitory activity in *S. moellendorffii* (James et al., 2017) implies that head-to-tail cyclic RiPPs may also exist in non-angiosperms and await to be discovered. Second, lyciumins have evolved from different precursor peptides than those that give rise to head-to-tail cyclic RiPPs. Whereas precursor peptides of cyclotides and orbitides are mainly stand-alone proteins (Jennings et al., 2001; Mylne et al., 2012) or seed storage albumins (Poth et al., 2011), lyciumin precursors are either BURP-domain proteins or DUF2775-domain proteins. The full elucidation of lyciumin biosynthetic steps such as proteolytic cleavage and cyclization in characterized lyciumin-producing plant families will further reveal additional differences and similarities between the evolutionary trajectories underlying the head-to-tail cyclic RiPPs and the branched cyclic RiPPs in plants.

This study reveals a complex history of lyciumin evolution within land plants. First, lyciumin genotypes and the corresponding chemotypes were identified in distantly related lycophytes (i.e., Selaginellaceae) and angiosperms (i.e., Cannabaceae, Caryophyllales families, Fabaceae, Solanaceae), whereas no lyciumin genotypes were found in taxa immediately sister to these lyciumin-producing plant lineages nor in any ferns and gymnosperms which are two major vascular plant lineages intermediate between lycophytes and angiosperms. Specifically, no BURP-domain proteins with lyciumin-like core peptide motifs were found in the transcriptomes of the families Lycopodiaceae and Isoetaceae, the only two other extant lycophyte families besides Selaginellaceae. Similarly, lyciumin-producing BURP-domain proteins are absent from plant orders neighboring Fabales (i.e., Malpighiales and Rosales), Caryophyllales (i.e., Berberidopsidales and Cornales), and Solanales (i.e., Gentianales and Lamiales). Moreover, no lyciumin-producing DUF2775-domain proteins were found in plant orders neighboring Rosales (i.e., Fabales and Cucurbitales). Based on these observations, it is most likely that the ability to produce lyciumins arose independently in lycophytes and angiosperms. Phylogenetic reconstruction of lyciumin-producing and non-lyciumin-producing BURP-domain sequences and analysis of the cyclization residues further suggest that the recruitment of BURP-domain proteins for lyciumin biogenesis occurred independently at least four times within angiosperms. Second, although lyciumin chemotypes vary greatly between lyciumin-producing plant families, a few overlapping lyciumin chemotypes were also found (FIG. 41B), illustrating potential cases of parallel evolution. Third, the occurrence of identical lyciumins from unrelated BURP-domain and DUF2775-domain precursor proteins demonstrates a case of convergent evolution (Weng, 2014) in terms of the RiPP precursor peptide recruitment. Future analysis of increasing plant transcriptomes and genomes from all plant lineages (Cheng et al., 2018) will continue to test and refine the model of branched cyclic RiPP evolution in plants.

Lyciumins have been characterized as protease inhibitors, which implicates their potential physiological functions in host defense similar to other plant RiPP classes (Hernandez et al., 2000). While specific functions of DUF2775 proteins in plants are unknown (Albornos et al., 2012), BURP domains have been associated with plant responses to abiotic stresses such as drought (Wang et al., 2012). For example, the lyciumin I precursor peptide Sali3-2 is highly expressed in Gi. max roots under acidic soil conditions (Ragland and Soliman, 1997), and its overexpression in *Arabidopsis* alleviates heavy metal stress (Tang et al., 2014). Future research will help elucidate why lyciumins evolved from BURP-domain or DUF2775-domain proteins. It is possible that lyciymins first evolved to enhance host defense or metal-chelation when host plants were under certain abiotic stresses. A comprehensive understanding of the biosynthetic mechanism and evolution of lyciumin-type RiPPs in the plant kingdom will ultimately facilitate engineering of this cyclic peptide class for crop improvement and drug development.

Methods

Materials and Methods

All chemicals were purchased from Sigma-Aldrich, unless otherwise specified. Oligonucleotide primers and synthetic genes were purchased as gBlocks® from Integrated DNA Technologies, Inc. Solvents for liquid chromatography high-resolution mass spectrometry were Optima® LC-MS grade (Fisher Scientific) or LiChrosolv® LC-MS grade (Millipore). High resolution mass spectrometry analysis was performed on a Thermo ESI-Q-Exactive Orbitrap MS coupled to a Thermo Ultimate 3000 UHPLC system. Low-resolution mass spectrometry analysis was done on a Thermo ESI-QQQ MS coupled to a Thermo Ultimate 3000 UHPLC system.

Plant Material

*Nicotiana benthamiana* seeds for cultivation were a gift from the Lindquist lab (Whitehead Institute, MIT). *Selag-*

*inella uncinata* plants were purchased from Plant Delights Nursery, Inc. *Celtis occidentalis* leaves were collected from a living tree (Accession No. 7894*A) on Aug. 3, 2018 in the Arnold Arboretum of Harvard University (Project No. 25-2018). *Achyranthes bidentata* seeds for cultivation were purchased from Frozen Seed Capsules™. *Chenopodium quinoa* seeds for cultivation were purchased from Earthcare Seeds.

Plant Cultivation

*Achyranthes bidentata, Chenopodium quinoa* and *Nicotiana benthamiana* were grown in Sun Gro® Propagation Mix soil with added vermiculite (Whittemore Inc.) and added fertilizer in a greenhouse with a 16 h light/8 h dark cycle for two to six months.

Transcriptome Assembly and Transcriptome Mining of Lyciumin Precursor Genes

For comparative assembly of lyciumin precursor genes, selected plant transcriptome datasets from the NCBI Sequence Read Archive (*Lycium barbarum*—SRR6896657, *Amaranthus hypochondriacus*—SRR1598913, *Chenopodium quinoa*—ERR2040214, *Solanum melongena*—SRR1104129, *Medicago truncatula*—SRR5732302, *Nicotiana attenuata*—SRR1950612) were assembled in triplicate with Trinity (v2.6.6, Grabherr et al., 2011) or rnaSPAdes (v1.0, kmer=25, 75 or 55, Bankevich et al., 2012; Bushmanova et al., 2018). Target lyciumin precursor peptides (*Lycium barbarum*—MH124242, *Amaranthus hypochondriacus*—AHYPO_007393, *Chenopodium quinoa*—XP_021740703.1, *Solanum melongena*—Sme2.5_02115.1_g00002.1, *Medicago truncatula*—Medtr8g045890, *Nicotiana attenuata*—OIT08186.1) were searched in the corresponding de novo transcriptome assemblies by tblastn on an internal Blast server (Priyam et al., 2015).

For large-scale transcriptome mining of lyciumin precursor genes, land plant transcriptome datasets from the 1kp database (Matasci et al. 2014, Table S1) were assembled by rnaSPAdes (v1.0, kmer=25, 75). If an rnaSPAdes (kmer=25, 75) assembly failed, the transcriptome was assembled with rnaSPAdes (kmer=55) if possible. Resulting maSPAdes-contig files of the 1kp transcriptomes were searched on an internal Blast server by blastn for (A) homologs of type 1 lyciumin precursor Sali3-2 (GenBank: AAB66369) or (B) homologs of type 2 lyciumin precursor LbaLycA (GenBank: MH124242). Candidate lyciumin precursors were identified by the presence of a lyciumin core peptide motif defined as QP(X)$_5$W (SEQ ID NO: 298), where X is any amino acid, in the N-terminal domain (type 2 lyciumin precursor) or within the BURP domain (type 1 lyciumin precursor).

Cloning of *Selaginella uncinata* Lyciumin Precursor Gene SunBURP

Illumina sequence raw-files of a *Selaginella uncinata* transcriptome (NCBI-SRA: SRR7132763) were combined and assembled by rnaSPAdes (v1.0, kmer 25, 75, Bankevich et al., 2012; Bushmanova et al., 2018). The *Selaginella uncinata* root transcriptome was analyzed for lyciumin precursor genes by blastp algorithm on an internal Blast server (Priyam et al., 2015). Root tissue was removed from a *Selaginella uncinata* plant and total RNA was extracted with the QIAGEN RNeasy Plant Mini kit. cDNA was prepared from root total RNA with SuperScript® III First-Strand Synthesis System (Invitrogen). Transcripts homologous to target lyciumin precursor LbaLycA were used to design cloning primers (SunBURP-pEAQ-fwd (SEQ ID NO: 128): TGCCCAAATTCGCGACCGGTATGG-CATCTAATCTCCTTTACTTGC, SunBURP-pEAQ-rev (SEQ ID NO: 129): CCAGAGTTAAAGGCCTCGAGT-TACCACACAATGGTTTCGTACC) for amplification of precursor peptide gene SunBURP with Phusion® High-Fidelity DNA polymerase (New England Biolabs). SunBURP was cloned into pEAQ-HT (Sainsbury et al., 2009), which was linearized by restriction enzymes AgeI and XhoI, by Gibson cloning assembly (New England Biolabs) (Gibson et al., 2009). Cloned SunBURP was sequenced by Sanger sequencing from pEAQ-HT-SunBURP.

Peptide Chemotyping

For peptide chemotyping, 0.2 g plant material (fresh weight) were frozen and ground with mortar and pestle. Ground plant material was extracted with 10 mL methanol for 1 h at 37° C. in a glass vial. Plant methanol extract was dried under nitrogen gas in a separate glass vial. Dried plant methanol extract was resuspended in water (10 mL) and partitioned with hexane (2×10 mL) and ethyl acetate (2×10 mL), and subsequently extracted with n-butanol (10 mL). The n-butanol extract was dried in vacuo and resuspended in 2 mL methanol for liquid chromatography-mass spectrometry (LC-MS) analysis. Peptide extracts were subjected to high resolution MS analysis with the following LC-MS parameters: LC—Phenomenex Kinetex® 2.6 µm C18 reverse phase 100 Å 150×3 mm LC column, LC gradient: solvent A—0.1% formic acid, solvent B—acetonitrile (0.1% formic acid), 0-2 min: 5% B, 2-23 min: 5-95% B, 23-25 min: 95% B, 25-30 min: 5% B, 0.5 mL/min, MS—positive ion mode, Full MS: Resolution 70000, mass range 425-1250 m/z, dd-MS$^2$ (data-dependent MS/MS): resolution 17500, Loop count 5, Collision energy 15-35 eV (stepped), dynamic exclusion 1 s. LC-MS data of peptide extracts from a predicted lyciumin producing plant was analyzed for lyciumin mass signals by (a) parent mass search (base peak chromatogram of calculated [M+H]$^+$ of predicted lyciumin structure, Δm=5 ppm), (b) fragment mass search of pyroglutamate-proline-b-ion in MS/MS data ($C_{10}H_{13}N_2O_3^+$, 209.09207 m/z, Δm=5 ppm), and (c) iminium ion mass search of specific amino acids of predicted structure in MS/MS data (for example, pyroglutamate iminium ion [M+H]$^+$ 84.04439 m/z). Putative mass signals of predicted lyciumin structures were confirmed by MS/MS data analysis with QualBrowser in the Thermo Xcalibur software package (version 3.0.63, ThermoScientific).

Transient Expression of Lyciumin Precursor Genes Sali3-2-[QPFGVFGW (SEQ ID) NO: 83)] and Sali3-2-[QPYGVFAW (SEQ ID) NO: 78)] in *Nicotiana benthamiana*

Sali3-2-[QPFGVFGW (SEQ ID NO: 83)] and Sali3-2-[QPYGVFAW (SEQ ID NO: 78)] were cloned into pEAQ-HT (Sainsbury et al., 2009), which was linearized by restriction enzymes AgeI and XhoI, by Gibson cloning assembly (New England Biolabs) (Gibson et al., 2009). *Agrobacterium tumefaciens* LBA4404 was transformed with pEAQ-HT-Sali3-2-[QPFGVFGW (SEQ ID NO: 83)] or pEAQ-HT-Sali3-2-[QPYGVFAW (SEQ ID NO: 78)] by electroporation (2.5 kV), plated on YM agar (0.4 g yeast extract, 10 g mannitol, 0.1 g sodium chloride, 0.2 g magnesium sulfate (heptahydrate), 0.5 g potassium phosphate, (dibasic, trihydrate), 15 g agar, ad 1 L Milli-Q Millipore water, adjusted pH 7) with 100 µg/mL rifampicin, 50 µg/mL kanamycin and 100 µg/mL streptomycin and incubated for two days at 30° C. A 5 mL starter culture of YM medium with 100 µg/mL rifampicin, 50 µg/mL kanamycin and 100 µg/mL streptomycin was inoculated with a clone of *Agrobacterium tumefaciens* LBA4404 pEAQ-HT-Sali3-2-[QPFGVFGW (SEQ ID NO: 83)] or pEAQ-HT-Sali3-2-[QPYGVFAW (SEQ ID NO: 78)] and incubated for 24-36 h at 30° C. on a shaker at 225 rpm. Subsequently, the starter culture was used to inoculate a 50 mL culture of YM medium with 100 µg/mL rifampicin, 50 µg/mL kanamycin and 100 µg/mL streptomycin, which was incubated for 24 h at 30° C. on a shaker at 225 rpm. The cells from the 50 mL culture were centrifuged for 30 min at 3000 g, the YM medium was discarded and cells were resuspended in MMA medium (10 mM MES KOH buffer (pH 5.6), 10 mM magnesium chloride, 100 µM acetosyringone) to give a final optical density of 0.8. The *Agrobacterium* suspension was infiltrated into the bottom of leaves of *Nicotiana benthamiana* plants (six week old). *N. benthamiana* plants were placed in the shade two hours before infiltration. After infiltration, *N. benthamiana* plants were grown as described above for six days. Subsequently, infiltrated leaves were collected and subjected to chemotyping.

Phylogenetic Analysis of Lyciumin Precursor Genes (BURP Domains)

Protein sequences of characterized and predicted lyciumin precursors from genomes (Kersten et al., 2018, except 3'-partial sequences) and transcriptomes (FIGS. 43A-I, precursors with full length BURP domains only) and four founding members of the BURP domain family (NP_001303011.1—BURP domain-containing protein BNM2A precursor [*Brassica napus*], NP 001234835.1—Polygalacturonase-1 non-catalytic subunit beta precursor [*Solanum lycopersicum*], CAA31603.1/CAA31602.1—Embryonic abundant protein USP87/Embryonic abundant protein USP92 [*Vicia faba*], NP_197943.1—BURP domain protein RD22 [*Arabidopsis thaliana*]) (Bassüner et al., 1988, Yamaguchi-Shinozaki et al., 1993, Zheng et al., 1992, Boutilier et al., 1994) were reduced to their BURP domain (Pfam PF03181) and aligned using Muscle algorithm (Edgar, 2004) in MEGA (ver. 7.0.9) (Kumar et al., 2016). A maximum-likelihood phylogenetic tree was generated with 1000 bootstrap generations using the p-distance method (Nei et al., 2000) in MEGA.

Accession Numbers

LC-MS datasets (MassIVE) (Wang et al., 2016): MSV000083215 (*Celtis occidentalis* leaf), MSV000083216 (*Achyranthes bidentata* seed), MSV000083217 (*Selaginella uncinata* root). GenBank: SunBURP-MK089798.

```
SEQUENCES
LbaLycA (SEQ ID NO: 1):
MELHHHYFFILLSLAFIASHAANLSPEVYWKVKLPNTPMPRPIKDALHYSEASEGDV

HKLRQPWGVGSWYQAANEGDIKKLRQPYGVGIWYQAANEGDVKKLRQPWGVGS

WYQAANEGDVKKLRQPWGVGSWYQAANEGDVKKLRQPWGVGSWYQAANEGDA

NEGDVKKLRQPYGVGIWYQAANEGDVKKLRQPWGVGSWYQAANEGDVKKLRQP

WGVGSWYQAANEGDVKKLHQPWGVGSWYQAANEGDVKKLPQPWGVGSWYQAA

NEGDVKKLRQPYGVGIWYEAANEGQVKKLRQPYGVGSWYNTATKKDVNENLPVT

PYFFETDLHQGKKMNLPSLKNYNPAPILPRKVADSIPFSSDKIEEILKHFSIDKDSEGA

KMIKKTIKMCEEQAGNGEKKYCATSLESMVDFTSSYLGTNNIIALSTLVEKETPEVQI

YTIEEVKEKANGKGVICHKVAYPYAIHYCHSVGSTRTFMVSMVGSDGTKVNAVSEC

HEDTAPMNPKALPFQLLNVKPGDKPICHFILDDQIALVPSQDATQVSEN

Glycine max: Glyma.12G217400 Org_Gmax peptide: Glyma.12G217400.1.p
(1 of 11) PTHR31236:SF2-DEHYDRATION-RESPONSIVE PROTEIN RD22
(PAC:30547846) (SEQ ID NO: 2):
MEFRCSVISFTILFSLALAGESHVHASLPEEDYWEAVWPNTPIPTALRELLKPLPAGVE

IDELPKQIDDTQYPKTFFYKEDLHPGKTMKVQFTKRPYAQPYGVYTWLTDIKDTSKE

GYSFEEICIKKEAFEGEEKFCAKSLGTVIGFAISKLGKNIQVLSSSFVNKQEQYTVEGV

QNLGDKAVMCHGLNFRTAVFYCHKVRETTAFMVPLVAGDGTKTQALAVCHSDTSG

MNHHMLHELMGVDPGTNPVCHFLGSKAILWVPNLSMDTAYQTNVVV

BURP domain-containing protein 5-like (CanBURP, Capsicum annuum)
(SEQ ID NO: 3):
MAMLYQYYFFTLLSLVFVVISHAANLSPEVYWKIKLPNTPMPKPIKDALHISEKTSQP

YGGLTWDWFHVFSKNELHKLHQLSQPYGVYFYGVSLKNLNEDHLVTRFFFETDLH

QGKKVNLKSLKNNNPAPLLPRKVVDSISFSSNRIEEILDHFSVDNNSEDAKVIKRTVE

LCEQPAADGEIKYCATSLESIIDFASSRLETNNILAIHTEVEKETPVLQTYTIKEVKEKA

NGKCVICHKVPYPYAVHFCHDVGSTRAFRVTMVGADGTKVNAVSVCHEDTASMNP

KALVFQLLNIKPGDKPICHFIMDDQIALFPSQNAVLQMAEG

AUR62017096-RA [CquBURP1, Chenopodium quinoa] [glutamine
cyclotransferase] (SEQ ID NO: 4):
MLKFLYFPFAYYLHSLAEVEAFLVMSSSYFGEGLTLVGERLYQLTYDQNTGFIYDRT

TLSKVSNSGVPLLLTIGIFNHQMKDGWGLTTDGKIMFGSDGSSTLYHIDPRTMKVIKR
```

-continued

QNVRYKDLDVHYLNELEYVHGEVWANVFRTDCIIRISPEDGTVLGWILLPMLRERLE

AAGEIESEDVLNGIAWDSDGKRIFVTGKLWPKLFEIKVHSSNDHSQVDIERMCIQML

TRLEGMK

XP_010675926.1 PREDICTED: glutaminyl-peptide cyclotransferase
isoform X1 [*Beta vulgaris* subsp. *vulgaris*] (SEQ ID NO: 5):
MASECILVPCYKRLSRAVSIACLLGFLVPLSILSNTLSALPLDSQKNIQLPQIYTIEVVN

VYPHDPRAFTEGLLYGGNNTLYESTGLYGMSTVRRVTLQTGKVEALQTMDLSYFGE

GLTLVDERLYQLTYEHNTGFIHDRSNLSKVRNSGNPFLFCWNLSFEHSCSPTGHFCLD

LDLSRVGMLQEDELIDFYTLQSPCYSR

XP_010675927.1 PREDICTED: glutaminyl-peptide cyclotransferase
isoform X1 [*Beta vulgaris* subsp. *vulgaris*] (SEQ ID NO: 6):
MASECILAPCYKRLSRAVSIACLLGFLVPLSILSNTLSALPLDSQKNIQLPQIYTIEVVN

VYPHDPRAFTEGLLYGGNNTLYESTGLYGMSTVRRVTLQTGKVEAFQTMDLSYFGE

GLTLVDERLYQLTYEHNTGFIYDRSNLSKIGQFTHQMADGWGLASDGKVLFGSDGS

STLYQIDPKTMKEIQRQTVRYMDLDVPYLNELEYVNGEVWANVATTDCIVRISPEDG

TVLGWILLPILRERMMADGELDVFDILNGIAWDKDEQRVFVTGKCWPKVFEIKVNQ

SKDHSDADVRRLCIPVPASVEAMK

LbaQC1 [*Lycium barbarum*][glutamine cyclotransferase]
(SEQ ID NO: 7):
MPLLNPRFLVISLIVLLSITVFREAEASYRVYKVKVVNEFPHDPQAYTQGLLYAENNT

LFESTGLYGRSSVRKVALLDGKVERLHEMESSYFGEGLTLLGERLFQLTWLLDTGFI

YDRYNFSKFKKFTHhMQDGWGLATDGKVLFGSDGTSTLYKIDPKTMKVIRKQVVK

SQGHEVRYLNELEYVKAEVWANVYTDCIARISPKDGTVIGWILLQSLREELISRGY

KDFEVLNGIAWDRDGDRIFVTGKLWPKLFEIKLLPLTPNDPLAGEINNLCIPKTSFL

LEI

Sali3-2 (SEQ ID NO: 8):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTATGGTGTATATACATGGTTAACGGATAT

TAAAGACACCTCTAAAGAAGGATATAGTTTTGAAGAGATATGCATCAAGAAGA

AGCGTTTGAGGGAGAAGAGAAGTTTTGTGCAAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCATCAGACTAACGT

TGTTGTTTAA

-continued

Sali3-2-[QPWGVYTW] (SEQ ID NO: 9):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTGGGGTGTATATACATGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

Sali3-2-[QPYGVYFW] (SEQ ID NO: 10):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTATGGTGTATATTTCTGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

Sali3-2-[QPWGVGAW] (SEQ ID NO: 11):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTGGGGTGTAGGTGCATGGTTAACGGATAT

TAAAGACACCTCTAAAGAAGGATATAGTTTTGAAGAGATATGCATCAAGAAAGA

-continued

```
AGCGTTTGAGGGAGAAGAGAAGTTTTGTGCAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA
```

Sali3-2-[QPFGVYTW] (SEQ ID NO: 12):
```
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTTTGGTGTATATACATGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA
```

Sali3-2-[QPWGVGTW] (SEQ ID NO: 13):
```
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTGGGGTGTAGGTACATGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA
```

-continued

AGGCCATTTTATGGGTACCCAATTTATCTATGGACACTGCCTATCAGACTAACGT

TGTTGTTTAA

Sali3-2-[EPYGVYTW] (SEQ ID NO: 14):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCAGAACCTTATGGTGTATATACATGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

Sali3-2-[QAYGVYTW] (SEQ ID NO: 15):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAAGCTTATGGTGTATATACATGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

Sali3-2-[QPAGVYTW] (SEQ ID NO: 16):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

-continued

TCACCAAGCGTCCCTATGCACAACCTGCTGGTGTATATACATGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

Sali3-2-[QPFGFFSW] (SEQ ID NO: 17):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTTTGGTTTCTTCTCATGGTTAACGGATATT

AAAGACACCTCTAAAGAAGGATATAGTTTTGAAGAGATATGCATCAAGAAAGAA

GCGTTTGAGGGAGAAGAGAAGTTTTGTGCAAAATCCTTGGGAACAGTAATTGGT

TTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

Sali3-2-[QPYGVYW] (SEQ ID NO: 18):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTATGGTGTATATTGGTTAACGGATATTAA

AGACACCTCTAAAGAAGGATATAGTTTTGAAGAGATATGCATCAAGAAAGAAGC

GTTTGAGGGAGAAGAGAAGTTTTGTGCAAAATCCTTGGGAACAGTAATTGGTTTT

GCCATTTCAAAGCTGGGAAAGAACATTCAAGTACTTTCAAGTTCCTTTGTCAATA

AGCAAGAGCAATACACTGTGGAAGGAGTGCAGAATCTTGGAGACAAAGCAGTG

ATGTGTCATGGGCTAAATTTCAGAACTGCAGTATTTTACTGCCATAAAGTCCGTG

AAACAACAGCTTTCATGGTTCCATTGGTGGCTGGTGATGGAACCAAAACTCAGG

CACTTGCTGTTTGCCACTCAGATACTTCTGGAATGAATCATCACATGCTTCATGA

```
ACTCATGGGAGTTGATCCTGGAACTAACCCTGTTTGCCATTTCCTTGGAAGCAAG

GCCATTTTATGGGTACCCAATTTATCTATGGACACTGCCTATCAGACTAACGTTG

TTGTTTAA

Sali3-2-[QPYGVYTAW] (SEQ ID NO: 19):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTATGGTGTATATACAGCATGGTTAACGGA

TATTAAAGACACCTCTAAAGAAGGATATAGTTTTGAAGAGATATGCATCAAGAA

AGAAGCGTTTGAGGGAGAAGAGAAGTTTTGTGCAAAATCCTTGGGAACAGTAAT

TGGTTTTGCCATTTCAAAGCTGGGAAAGAACATTCAAGTACTTTCAAGTTCCTTT

GTCAATAAGCAAGAGCAATACACTGTGGAAGGAGTGCAGAATCTTGGAGACAAA

GCAGTGATGTGTCATGGGCTAAATTTCAGAACTGCAGTATTTTACTGCCATAAAG

TCCGTGAAACAACAGCTTTCATGGTTCCATTGGTGGCTGGTGATGGAACCAAAAC

TCAGGCACTTGCTGTTTGCCACTCAGATACTTCTGGAATGAATCATCACATGCTT

CATGAACTCATGGGAGTTGATCCTGGAACTAACCCTGTTTGCCATTTCCTTGGAA

GCAAGGCCATTTTATGGGTACCCAATTTATCTATGGACACTGCCTATCAGACTAA

CGTTGTTGTTTAA

Sali3-2-[QPWGVYSW] (SEQ ID NO: 20):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTGGGGTGTATATTCATGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

Sali3-2-[QPYAVYTW] (SEQ ID NO: 21):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA
```

```
AAACATTCTTCTATAAAGAAGACCTTCATCCAGGCAAAACAATGAAAGTACAAT

TCACCAAGCGTCCCTATGCACAACCTTATGCTGTATATACATGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

Sali3-2-[QPYTVYTW] (SEQ ID NO: 22):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTATACTGTATATACATGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

Sali3-2-[QPYGAYTW] (SEQ ID NO: 23):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTATGGTGCATATACATGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC
```

-continued

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

Sali3-2-[QPYGVATW] (SEQ ID NO: 24):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTATGGTGTAGCTACATGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

Sali3-2-[QPYGVYAW] (SEQ ID NO: 25):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTATGGTGTATATGCATGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

Sali3-2-[QPYGVYTA] (SEQ ID NO: 26):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

-continued

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTATGGTGTATATACAGCGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCATCAGACTAACGT

TGTTGTTTAA

Sali3-2-[QPYGVYTY] (SEQ ID NO: 27):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTATGGTGTATATACATACTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCATCAGACTAACGT

TGTTGTTTAA

Sali3-2-[QYGVYTW] (SEQ ID NO: 28):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAATATGGTGTATATACATGGTTAACGGATATTAA

AGACACCTCTAAAGAAGGATATAGTTTTGAAGAGATATGCATCAAGAAAGAAGC

GTTTGAGGGAGAAGAGAAGTTTTGTGCAAAATCCTTGGGAACAGTAATTGGTTTT

GCCATTTCAAAGCTGGGAAGAACATTCAAGTACTTTCAAGTTCCTTTGTCAATA

AGCAAGAGCAATACACTGTGGAAGGAGTGCAGAATCTTGGAGACAAAGCAGTG

-continued

ATGTGTCATGGGCTAAATTTCAGAACTGCAGTATTTTACTGCCATAAAGTCCGTG

AAACAACAGCTTTCATGGTTCCATTGGTGGCTGGTGATGGAACCAAAACTCAGG

CACTTGCTGTTTGCCACTCAGATACTTCTGGAATGAATCATCACATGCTTCATGA

ACTCATGGGAGTTGATCCTGGAACTAACCCTGTTTGCCATTTCCTTGGAAGCAAG

GCCATTTTATGGGTACCCAATTTATCTATGGACACTGCCTATCAGACTAACGTTG

TTGTTTAA

Sali3-2-[QGVYTW] (SEQ ID NO: 29):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAAGGTGTATATACATGGTTAACGGATATTAAAGA

CACCTCTAAAGAAGGATATAGTTTTGAAGAGATATGCATCAAGAAAGAAGCGTT

TGAGGGAGAAGAGAAGTTTTGTGCAAAATCCTTGGGAACAGTAATTGGTTTTGCC

ATTTCAAAGCTGGGAAAGAACATTCAAGTACTTTCAAGTTCCTTTGTCAATAAGC

AAGAGCAATACACTGTGGAAGGAGTGCAGAATCTTGGAGACAAAGCAGTGATGT

GTCATGGGCTAAATTTCAGAACTGCAGTATTTTACTGCCATAAAGTCCGTGAAAC

AACAGCTTTCATGGTTCCATTGGTGGCTGGTGATGGAACCAAAACTCAGGCACTT

GCTGTTTGCCACTCAGATACTTCTGGAATGAATCATCACATGCTTCATGAACTCA

TGGGAGTTGATCCTGGAACTAACCCTGTTTGCCATTTCCTTGGAAGCAAGGCCAT

TTTATGGGTACCCAATTTATCTATGGACACTGCCTATCAGACTAACGTTGTTGTTT

AA

Sali3-2-[QAPYGVYTW] (SEQ ID NO: 30):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAAGCACCTTATGGTGTATATACATGGTTAACGGA

TATTAAAGACACCTCTAAAGAAGGATATAGTTTTGAAGAGATATGCATCAAGAA

AGAAGCGTTTGAGGGAGAAGAGAAGTTTTGTGCAAAATCCTTGGGAACAGTAAT

TGGTTTTGCCATTTCAAAGCTGGGAAAGAACATTCAAGTACTTTCAAGTTCCTTT

GTCAATAAGCAAGAGCAATACACTGTGGAAGGAGTGCAGAATCTTGGAGACAAA

GCAGTGATGTGTCATGGGCTAAATTTCAGAACTGCAGTATTTTACTGCCATAAAG

TCCGTGAAACAACAGCTTTCATGGTTCCATTGGTGGCTGGTGATGGAACCAAAAC

TCAGGCACTTGCTGTTTGCCACTCAGATACTTCTGGAATGAATCATCACATGCTT

CATGAACTCATGGGAGTTGATCCTGGAACTAACCCTGTTTGCCATTTCCTTGGAA

GCAAGGCCATTTTATGGGTACCCAATTTATCTATGGACACTGCCTATCAGACTAA

CGTTGTTGTTTAA

Sali3-2-[QPYGVYTF] (SEQ ID NO: 31):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTATGGTGTATATACATTCTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

Sali3-2-[QPYGVYTH] (SEQ ID NO: 32):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTATGGTGTATATACACACTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

Sali3-2-[QPYGVYFY] (SEQ ID NO: 33):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTATGGTGTATATTTCTACTTAACGGATATT

AAAGACACCTCTAAAGAAGGATATAGTTTTGAAGAGATATGCATCAAGAAAGAA

```
GCGTTTGAGGGAGAAGAGAAGTTTTGTGCAAAATCCTTGGGAACAGTAATTGGT

TTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

AHYPO_007393 Org_Ahypochondriacus peptide: AHYPO_007393-RA (1 of 19)
PF03181-BURP domain (BURP) (PAC:32833029) (SEQ ID NO: 34)
MAMDLRLQFPALFLLTFLALHASSCKQEDYWKMKLPKVPMPEAIKQSLLHSGGENK

LKDDSALKQPYTVGSWKYDVDTNKVKDDSVVKQPYTVGSWKYDADKNKVPDESA

LKQPYTVFSWKYDAGENKVKDESALKQPYTVFSWKYDAGENKVKDESALKQPYTV

FSWKYDAGENKVKDESALKQPYTVFSWKYDAGENKVKDESALKQPYTVFSWKYD

AGENKVKDESALKQPYTVFSWKYDAGENKVKDESALKQPYTVFSWKYDAGENKV

KDESALKQPYTVFSWKYDAGENKVKDESALKQPYTVFSWKYDAGENKVKDESALK

QPYTVFSWKYDAGENKVKDESALKQPYTVFSWKYDAGENKVKDESALKQPYTVGS

WKYDAGENKVKDESALKQPYTVGSWKYNENDESKQASPHHLHHHKLMHDNVNSK

DQEDLTDGSVFFVEKSLHIGSKLKHDFQKTPKTSFLSKQEAQSIPFSMEKIGDILNLTC

AQSMEDIVDFVVGELGTNEVEIKMMNNNIEVPNGIQDYVLSKVEKLVVPGNTAVAC

HRMSYPYIVYYCHHQQDIGQYNVTLVSPSTGAAFQTTAVCHYDTYAWQPDVVALK

YLGIRPGDAPVCHFSAINDMFWNRKNNDFKSLDMVQ*

AUR62017095 Org_Cquinoaearly-release peptide: AUR62017095-RA BURP5:
BURP domain-containing protein 5 (PAC:36309717) (SEQ ID NO: 35)
MSLYSNDADKAKKANTNQPFTVVGWKYNADGAKERVGMSQPYTVMAWKYNVD

DAKERVGIDQPYTVWGWNYNTDSANKEKVKEAYKPLSIETNTKKTGIDQPYTVWG

WNYNTNSANKEKVKEAEKPLSIETNTKKTGVDQPYTVWGWNYNTNNANKEKVKE

AEKPLSIETNTKKTGIDQPYTVWGWNYNTDSANKEKVKEANKPLSIETDTKKTGIDQ

PYTVWGWNYNTDSANKEKVKEAEKSLSIETNTKKTGIDQPYTVWGWNYNTNSGNK

EKVKEADKVFTMDTSTKKAGTKQPYTVMGWKYNADNGKREKVGHEVSVGSVFFIE

KSLRLGDKLKHDFQKTPSVPFLPKHIAKSIPFSEDKFTEILNLFSIKPGSVEATGIKGTL

DVCLHRPKVEKENRTCAQSMEDVVDFVVRELGSNDVELRMMKNDIEVPKGIQDYVI

TKVKKLVVPGNTAAACHRMSYPYVVVYYCHHQQDIGHYDVTLVSPTTGNAIQTTAV

CHYDTYAWKPNVPALQYLGIRPGDAPVCHFSAINDMFWSLKANSKSLDMVV*

Glyma.12G217300 Org_Gmax peptide: Glyma.12G217300 PTHR31236:SF2-
DEHYDRATION-RESPONSIVE PROTEIN RD22 (PAC:30548760) (SEQ ID NO: 36)
MALRCLVMSLSVLFTLGLARESHARDEDFWHAVWPNTPIPSSLRDLLKPGPASVEID

DHPMQIEETQYPKTFFYKEDLHPGKTMKVQFSKPPFQQPWGVGTWLKEIKDTTKEG

YSFEELCIKKEAIEGEEKFCAKSLGTVIGFAISKLGKNIQVLSSSFVNKQDQYTVEGVQ

NLGDKAVMCHRLNFRTAVFYCHEVRETTAFMVPLVAGDGTKTQALAICHSNTSGM

NHQMLHQLMGVDPGTNPVCHFLGSKAILWVPNLSVDTAYQTNIVA*
```

PGSC0003DMG400047074 Org_Stuberosum peptide:
PGSC0003DMP400069178 BURP domain-containing protein
(PAC:37467747, SEQ ID NO: 38):
MELHHQYYFFTFFSVIFVVSHAANLSPEVYWRVKLPNTPMPTPIKDALHISDGIRLPL

RTSFTKYANHGEWVDGIRLPFENELHKVRQPWGVDSWYQAAPENELHKVRQPYGV

GVWYNDAAKKDLNDNHPVTPYFFETDLHQGKKMNLQSLKNYNPAPILPRKVVDSI

AFSSDKIEEILNHFSVDKDSERAKDIKKTIKTCEEPAGNGEVKHCATSLESMIDFTLSH

LGTNNIIAMSTEVEKETPEVQAYTIEKVEEKANGKGVVCHKVAYPYAVHFCHDVGS

TRTFMVSMVGADGTKVNAVSVCHEDTASMNPKALPFQLLNVKPGDKPICHFTLDD

QIALFPSQNAVLQVAEN*

Medtr2g081590 Org_Mtruncatula peptide: Medtr2g081590.1 PTHR31236:SF2-
DEHYDRATION-RESPONSIVE PROTEIN RD22 (PAC:31067976, SEQ ID NO: 39):
MGFQHLLIFISVLSLALAGGSHASVPEEEYWEAVWPNTPIPTSLLELLKPGPKGVEID

DLPTEIDDTQFPTNFFYEHELYPGKTMNMQFSKRPLAQPYGVYFWMHDIKDLQKEG

YTIDEMCVKNKPKKVEEKFCAKSLGTLIGFAISKLGKNIQSLSSSFIDKHEQYKIESVQ

NLGDKAVMCHRLNFQKVVFYCHEVHGTTAFKVPLVANDGTKTHAIATCHADISGM

NQHMLHQIMKGDPGSNHVCHFLGNKAILWVPNLGLDNAYGANAAL*

Medtr2g081610 Org_Mtruncatula peptide: Medtr2g081610.1 PTHR31236:SF2-
DEHYDRATION-RESPONSIVE PROTEIN RD22 (PAC:31064010, SEQ ID NO: 40):
MELKHILIFISVLSLALAGGSHASLPEEEYWEAVWPNTPIPSSLRELLKPGPEGVEIDD

LPMEVDDTQYPKTFFYEHELYPGKTMKVQFSKRPFAQPYGVYTWMREIKDIEKEGY

TFNEVCVKKAAAEGEQKFCAKSLGTLIGFSISKLGKNIQALSSSFIDKHEQYKIESVQN

LGEKAVMCHRLNFQKVVFYCHEIHGTTAFMVPLVANDGRKTQALAVCHTDTSGMN

HEMLQQIMKADPGSKPVCHFLGNKAILWVPNLGLDNAYGANAAV*

CanBURP nucleotide sequence (SEQ ID NO: 37):
ATGGCGATGCTTTACCAATATTACTTCTTCACACTTCTTTCTCTTGTTTTTGTCGTA

ATTAGTCATGCAGCAAATTTATCTCCTGAGGTGTATTGGAAAATCAAACTACCC

AATACTCCTATGCCCAAACCTATCAAGGATGCCCTACACATTTCTGAGAAAACGT

CCCAACCATATGGAGGTCTTACTTGGGATTGGTTTCACGTTTTCTCCAAGAACGAG

CTACACAAATTACACCAATTAAGCCAACCATATGGAGTGTACTTTTATGGTGTTT

CTTTGAAAAACCTTAATGAAGATCACCTAGTTACACGTTTCTTTTTTGAAACCGAT

TTACATCAAGGGAAAAAGTGAATCTTAAGTCGCTCAAAAACAACAATCCAGCT

CCCCTTTTGCCTCGCAAAGTTGTAGATTCCATCTCTTTCTCATCGAACAGAATTGA

GGAAATTCTTGATCACTTTTCTGTTGACAACAATTCAGAAGATGCTAAAGTGATCA

AGAGAACAGTCGAACTCTGTGAACAGCCCGCAGCTGATGGAGAGATAAAATATTGT

GCCACTTCCTTGGAATCTATAATTGATTTCGCCTCATCTCGCTTGGAAACAAACA

ATATTTTGGCAATTCACACCGAGGTAGAGAAGGAAACTCCAGTGCTGCAAACATAT

ACTATCAAAGAAGTGAAAGAGAAAGCAAACGGTAAATGTGTCATATGCCACAAA

GTACCTTACCCATATGCAGTACACTTTTGCCATGATGTAGGAAGCACCAGGGCTT

TTAGGGTCACTATGGTGGGTGCTGATGGAACAAAAGTTAATGCAGTATCAGTCTGC

CATGAGGATACTGCATCCATGAATCCTAAGGCATTGGTTTTTCAGTTGCTCAATA

TTAAGCCCGGAGATAAGCCTATTTGCCATTTTATTATGGATGATCAAATTGCCCTGT

TTCCTTCACAAAACGCAGTTCTTCAAATGGCTGAAGGCTAA

LbaLycA (*Lycium barbarum*) nucleotide sequence (SEQ ID NO: 125):
ATGGAGTTGCATCACCATTACTTCTTCATACTTCTTTCTCTTGCTTTTATAGCAAG

TCATGCAGCTAATTTATCTCCTGAGGTGTATTGGAAAGTCAAGCTGCCCAACACT

CCTATGCCCAGACCCATTAAGGATGCTCTACACTATTCTGAAGCCTCCGAGGGTG

ACGTTCACAAGTTGCGCCAACCATGGGGAGTGGGTTCGTGGTATCAAGCAGCAA

ACGAGGGTGATATTAAAAAATTACGCCAACCATATGGAGTTGGTATATGGTATC

AAGCAGCAAACGAGGGTGATGTTAAAAAATTACGCCAACCATGGGGAGTTGGTT

CCTGGTATCAAGCAGCAAACGAGGGTGATGTTAAAAAATTACGCCAACCATGGG

GAGTGGGTTCCTGGTATCAAGCAGCAAACGAGGGTGATGTTAAAAAATTACGCC

AACCATGGGGAGTGGGTTCCTGGTATCAAGCAGCAAACGAGGGTGATGCAAATG

AGGGTGATGTTAAAAAATTACGCCAACCATATGGAGTTGGTATATGGTATCAAG

CAGCAAACGAGGGTGATGTTAAAAAATTACGCCAACCATGGGGAGTGGGTTCTT

GGTATCAAGCAGCAAACGAGGGTGATGTTAAAAAATTACGCCAACCATGGGGAG

TGGGTTCCTGGTATCAAGCAGCAAACGAGGGTGATGTTAAAAAATTACACCAAC

CATGGGGAGTGGGTTCCTGGTATCAAGCAGCAAACGAGGGTGATGTTAAAAAAT

TACCCCAACCATGGGGAGTGGGTTCCTGGTATCAAGCAGCAAACGAGGGTGATG

TTAAAAAATTACGCCAACCATATGGAGTTGGTATATGGTATGAAGCAGCAAACG

AGGGTCAAGTTAAAAAATTACGCCAACCCTATGGAGTGGGTTCGTGGTATAATA

CTGCTACAAAGAAAGATGTTAATGAAAACCTCCCAGTCACCCCTTACTTTTTTGA

AACAGATTTACATCAAGGGAAAAAGATGAATCTTCCATCTCTCAAAAATTATAAT

CCAGCTCCCATTTTGCCTCGCAAAGTTGCAGATTCCATCCCCTTCTCATCAGACA

AGATTGAAGAAATTCTAAAGCACTTTTCCATTGATAAGGACTCAGAGGGGGCTA

AAATGATCAAGAAAACTATCAAATGTGTGAGGAGCAAGCGGGTAATGGCGAG

AAGAAATATTGTGCCACTTCCTTAGAATCAATGGTTGATTTCACCTCATCTTATCT

GGGAACAAATAATATTATAGCACTTTCCACTTTAGTAGAGAAGGAAACTCCAGA

GGTGCAAATATATACCATCGAAGAAGTGAAAGAGAAAGCAAATGGCAAAGGCG

TGATATGCCACAAAGTGGCTTACCCGTATGCGATACATTATTGCCATAGTGTAGG

AAGCACAAGGACCTTTATGGTCTCAATGGTGGGTTCTGATGGAACAAAAGTTAAT

GCAGTATCAGAGTGTCATGAGGATACTGCACCCATGAACCCTAAGGCATTGCCTT

TTCAATTGCTCAACGTTAAGCCAGGAGATAAACCTATTTGCCATTTCATATTGGA

TGATCAGATTGCCTTAGTTCCTTCTCAAGACGCAACTCAAGTGTCTGAAAACTAA

StuBURP (*Solanum tuberosum*) nucleotide sequence (SEQ ID NO: 126):
ATGGAGTTGCTTCACCAATATTATTTCTTCACATTTTTTTCTGTAATTTTTGTGGTA

AGTCATGCAGCAAATTTATCTCCTGAGGTGTATTGGAGAGTCAAATTGCCTAATA

CTCCCATGCCCACACCTATCAAAGATGCACTACACATTTCTGAGAAAACTGCATA

TAATGGAGATGGAAACACCAAAATATCCCAACCATATGGAGTGTTTGCATGGTA

TCAGGCTGCCTCCGAGAATGAGCTTCACAAAGTACGCCAACCATATGGAGTGGA

TGGATGGTACAAGGCTGCCTCCGAGAATGAGCTTCACAAAGTACGCCAACCATA

TGGAGTGTTTGCATGGTACAAGGCTATCACCGAGAATGAGCTTCACAAAGTACG

CCAACCATATGGAGTGTTTGCATGGTACAAGGCTGCCACCGAGAATGAGCTTCA

CAAAGTACGCCAACCATATGGAGTGTTTGCATGGTACAAGGCTGCCTCCGAGAA

```
TGTGCTTCACAAAGTACGCCAACCATATGGAGTGTTTGCATGGTACAATGATGCT

GCTAAGAAAGATCTTAATGACAATCACCCAGTGACGCCATACTTCTTTGAAACAG

ATTTACATCAAGGGAAAAAAATGAATCTTCAGTCTCTCAAAAACTACAATCCAG

CACCCATTTTGCCACGCAAAGTTGTAGATTCAATTGCTTTCTCATCGGACAAAAT

TGAGGAAATTCTTAATCACTTCTCTGTTGATAAGGACTCGGAACGTGCTAAAGAC

ATCAAGAAAACAATCAAAATGTGTGAAGAGCCTGCGGGTAACGGAGAGGTAAA

ACATTGTGCCACTTCTTTGGAATCTATGATTGATTTCACCTTATCTCACCTGGGAA

CAAACAATATTGTAGCAATTTCCACTGAAGTAGACAAGGAAACTCCAGAGGTGC

AAACATATACCATCGAAAAAGTGGAAGAGAAAGCAAATGGCAAAGGTGTTGTAT

GTCACAAAGTAGCTTACCCATATGCAGTACACTTTTGCCATGATGTAGGAAGCAC

TAGGACATTTGTGGTGTCTATGGTGGGTGCTGACGGAACAAAAGTTAATGCAGTA

TCAGTCTGCCATGAGGATACTGCATCCATGAACCCTAAGGCATTGCCTTTTCAGT

TGCTCAACGTTAAGCCTGGAGACAAGCCTATTTGCCATTTCACTTTGGACGATCA

AATTGCCCTGTTTCCTTCTCAAAACGCACTTCTTCAAGTGGCTGAAAACTAA

StuBURP (Solanum tuberosum) (SEQ ID NO: 127):
MELLHQYYFFTFFSVIFVVSHAANLSPEVYWRVKLPNTPMPTPIKDALHISEKTAYNG

DGNTKISQPYGVFAWYQAASENELHKVRQPYGVDGWYKAASENELHKVRQPYGVF

AWYKAITENELHKVRQPYGVFAWYKAATENELHKVRQPYGVFAWYKAASENVLH

KVRQPYGVFAWYNDAAKKDLNDNHPVTPYFFETDLHQGKKMNLQSLKNYNPAPIL

PRKVVDSIAFSSDKIEEILNHFSVDKDSERAKDIKKTIKMCEEPAGNGEVKHCATSLES

MIDFTLSHLGTNNIVAISTEVDKETPEVQTYTIEKVEEKANGKGVVCHKVAYPYAVH

FCHDVGSTRTFVVSMVGADGTKVNAVSVCHEDTASMNPKALPFQLLNVKPGDKPIC

HFTLDDQIALFPSQNALLQVAEN

Sali3-2-[QPFGVFGW] ordered from IDT as gblocks® (SEQ ID NO: 196):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCGTTTGGAGTATTTGGTTGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA
```

-continued

Sali3-2-[QPYGVFAW] ordered from IDT as gblocks® (SEQ ID NO: 197):
ATGGAATTTCGATGCTCAGTCATCTCTTTTACCATTCTCTTCTCTCTTGCTCTTGCA

GGAGAGAGCCATGTCCATGCATCGCTACCTGAGGAAGATTATTGGGAAGCTGTT

TGGCCAAACACTCCCATTCCCACTGCACTGCGAGAGCTTCTAAAGCCTCTCCCTG

CAGGTGTTGAAATCGATGAACTCCCTAAGCAAATTGATGATACACAGTACCCAA

AAACATTCTTCTATAAAGAAGACCTTCATCCAGGCAAAACAATGAAAGTACAAT

TCACCAAGCGTCCCTATGCACAACCTTATGGTGTATTCGCCTGGTTAACGGATAT

TAAAGACACCTCTAAAGAAGGATATAGTTTTGAAGAGATATGCATCAAGAAAGA

AGCGTTTGAGGGAGAAGAGAAGTTTTGTGCAAAATCCTTGGGAACAGTAATTGG

TTTTGCCATTTCAAAGCTGGGAAAGAACATTCAAGTACTTTCAAGTTCCTTTGTCA

ATAAGCAAGAGCAATACACTGTGGAAGGAGTGCAGAATCTTGGAGACAAAGCA

GTGATGTGTCATGGGCTAAATTTCAGAACTGCAGTATTTTACTGCCATAAAGTCC

GTGAAACAACAGCTTTCATGGTTCCATTGGTGGCTGGTGATGGAACCAAAACTCA

GGCACTTGCTGTTTGCCACTCAGATACTTCTGGAATGAATCATCACATGCTTCAT

GAACTCATGGGAGTTGATCCTGGAACTAACCCTGTTTGCCATTTCCTTGGAAGCA

AGGCCATTTTATGGGTACCCAATTTATCTATGGACACTGCCTATCAGACTAACGT

TGTTGTTTAA

References for Example 1

1. Craik, D. J., Fairlie, D. P., Liras, S. and Price, D., 2013. The future of peptide-based drugs. Chemical biology & drug design, 81 (1), pp. 136-147.
2. Nolan, E. M. & Walsh, C. T. How nature morphs peptide scaffolds into antibiotics. ChemBioChem 10, 34-53 (2009).
3. Gao, A. G., Hakimi, S. M., Mittanck, C. A., Wu, Y., Woerner, B. M., Stark, D. M., Shah, D. M., Liang, J. and Rommens, C. M., 2000. Fungal pathogen protection in potato by expression of a plant defensin peptide. Nature biotechnology, 18 (12), pp. 1307-1310.
4. Ventola, C. L., 2015. The antibiotic resistance crisis: part 1: causes and threats. Pharmacy and Therapeutics, 40 (4), p.277.
5. Tabashnik, B. E. and Carrière, Y., 2017. Surge in insect resistance to transgenic crops and prospects for sustainability. Nature biotechnology, 35 (10), p.926.
6. Chaparro, J. M., Badri, D. V. and Vivanco, J. M., 2014. Rhizosphere microbiome assemblage is affected by plant development. The ISME journal, 8 (4), pp. 790-803.
7. Dimkpa, C., Weinand, T. and Asch, F., 2009. Plant-rhizobacteria interactions alleviate abiotic stress conditions. Plant, cell & environment, 32 (12), pp. 1682-1694.
8 Arnison, P. G., Bibb, M. J., Bierbaum, G., Bowers, A. A., Bugni, T. S., Bulaj, G., Camarero, J. A., Campopiano, D. J., Challis, G. L., Clardy, J. and Cotter, P. D., 2013. Ribosomally synthesized and post-translationally modified peptide natural products: overview and recommendations for a universal nomenclature. Natural product reports, 30 (1), pp. 108-160.
9. Craik, D. J., Daly, N. L., Bond, T. and Waine, C., 1999. Plant cyclotides: a unique family of cyclic and knotted proteins that defines the cyclic cystine knot structural motif. Journal of molecular biology, 294 (5), pp. 1327-1336.
10. Craik, D. J., Lee, M. H., Rehm, F. B., Tombling, B., Doffek, B. and Peacock, H., 2017. Ribosomally-synthesised cyclic peptides from plants as drug leads and pharmaceutical scaffolds. Bioorganic & medicinal chemistry.
11. Tan, N. H. and Zhou, J., 2006. Plant cyclopeptides. Chemical reviews, 106 (3), pp. 840-895.
12. Lautru, S., Deeth, R. J., Bailey, L. M. and Challis, G. L., 2005. Discovery of a new peptide natural product by *Streptomyces coelicolor* genome mining. Nature chemical biology, 1 (5), pp. 265-269.
13. Kersten, R. D., Yang, Y. L., Xu, Y., Cimermancic, P., Nam, S. J., Fenical, W., Fischbach, M. A., Moore, B. S. and Dorrestein, P. C., 2011. A mass spectrometry-guided genome mining approach for natural product peptidogenomics. Nature chemical biology, 7 (11), pp. 794-802.
14. Winter, J. M., Behnken, S. and Hertweck, C., 2011. Genomics-inspired discovery of natural products. Current opinion in chemical biology, 15 (1), pp. 22-31.
15. Ziemert, N., Alanjary, M. and Weber, T., 2016. The evolution of genome mining in microbes—a review. Natural product reports, 33 (8), pp. 988-1005.
16. Hetrick, K. J. and van der Donk, W. A., 2017. Ribosomally synthesized and post-translationally modified peptide natural product discovery in the genomic era. Current Opinion in Chemical Biology, 38, pp. 36-44.
17. Goodstein, D. M., Shu, S., Howson, R., Neupane, R., Hayes, R. D., Fazo, J., Mitros, T., Dirks, W., Hellsten, U., Putnam, N. and Rokhsar, D. S., 2011. Phytozome: a comparative platform for green plant genomics. Nucleic acids research, 40 (D1), pp. D1178-D1186.
18. Lau, W. and Sattely, E. S., 2015. Six enzymes from mayapple that complete the biosynthetic pathway to the etoposide aglycone. Science, 349 (6253), pp. 1224-1228.
19. Owen, C., Patron, N. J., Huang, A. and Osbourn, A., 2017. Harnessing plant metabolic diversity. Current Opinion in Chemical Biology, 40, pp. 24-30.

20. Medema, M. H. and Osbourn, A., 2016. Computational genomic identification and functional reconstitution of plant natural product biosynthetic pathways. Natural product reports, 33 (8), pp. 951-962.
21. Kautsar, S. A., Suarez Duran, H. G., Blin, K., Osbourn, A. and Medema, M. H., 2017. plantiSMASH: automated identification, annotation and expression analysis of plant biosynthetic gene clusters. Nucleic acids research, 45 (W1), pp. W55-W63.
22. Topfer, N., Fuchs, L. M. and Aharoni, A., 2017. The PhytoClust tool for metabolic gene clusters discovery in plant genomes. Nucleic acids research, 45 (12), pp. 7049-7063.
23. Anarat-Cappillino, G. and Sattely, E. S., 2014. The chemical logic of plant natural product biosynthesis. Current opinion in plant biology, 19, pp. 51-58.
24. Mohimani, H. and Pevzner, P. A., 2016. Dereplication, sequencing and identification of peptidic natural products: from genome mining to peptidogenomics to spectral networks. Natural product reports, 33 (1), pp. 73-86.
25. Yahara S, Shigeyama C, Nohara T. Tetrahedron Lett. (1989)
26. Morita, H., Suzuki, H. and Kobayashi, J. I., 2004. Celogenamide A, a New Cyclic Peptide from the Seeds of *Celosia* a rgentea. Journal of natural products, 67 (9), pp. 1628-1630.
27. Petersen T N., Brunak S., von Heijne G. & Nielsen H. SignalP 4.0: discriminating signal peptides from transmembrane regions Nature Methods, 8:785-786, 2011
28. Hattori, J., Boutilier, K. A., Campagne, M. L. and Miki, B. L., 1998. A conserved BURP domain defines a novel group of plant proteins with unusual primary structures. Molecular and General Genetics MGG, 259 (4), pp. 424-428.
29. Ding, X., Hou, X., Xie, K. and Xiong, L., 2009. Genome-wide identification of BURP domain-containing genes in rice reveals a gene family with diverse structures and responses to abiotic stresses. Planta, 230 (1), pp. 149-163.
30. Boutilier, K. A., Gines, M. J., DeMoor, J. M., Huang, B., Baszczynski, C. L., Iyer, V. N. and Miki, B. L., 1994. Expression of the BnmNAP subfamily of napin genes coincides with the induction of *Brassica* microspore embryogenesis. Plant molecular biology, 26 (6), pp. 1711-1723.
31. Bassüner, R., Bäumlein, H., Huth, A., Jung, R., Wobus, U., Rapoport, T. A., Saalbach, G. and Müntz, K., 1988. Abundant embryonic mRNA in field bean (*Vicia faba* L.) codes for a new class of seed proteins: cDNA cloning and characterization of the primary translation product. Plant molecular biology, 11 (3), pp. 321-334.
32. Yamaguchi-Shinozaki, K. and Shinozaki, K., 1993. The plant hormone abscisic acid mediates the drought-induced expression but not the seed-specific expression of rd22, a gene responsive to dehydration stress in *Arabidopsis thaliana*. Molecular and General Genetics MGG, 238 (1), pp. 17-25.
33. Zheng, L., Heupel, R. C. and DellaPenna, D., 1992. The beta subunit of tomato fruit polygalacturonase isoenzyme 1: isolation, characterization, and identification of unique structural features. The plant cell, 4 (9), pp. 1147-1156.
34. Grabherr, M. G., Haas, B. J., Yassour, M., Levin, J. Z., Thompson, D. A., Amit, I., Adiconis, X., Fan, L., Raychowdhury, R., Zeng, Q. and Chen, Z., 2011. Full-length transcriptome assembly from RNA-Seq data without a reference genome. Nature biotechnology, 29 (7), pp. 644-652.
35. Bankevich, A., Nurk, S., Antipov, D., Gurevich, A. A., Dvorkin, M., Kulikov, A. S., Lesin, V. M., Nikolenko, S. I., Pham, S., Prjibelski, A. D. and Pyshkin, A. V., 2012. SPAdes: a new genome assembly algorithm and its applications to single-cell sequencing. Journal of computational biology, 19 (5), pp. 455-477.
36. Tang, M. C., Zou, Y., Watanabe, K., Walsh, C. T. and Tang, Y., 2016. Oxidative cyclization in natural product biosynthesis. Chemical reviews, 117 (8), pp. 5226-5333.
37. Li, B. and Dewey, C. N., 2011. RSEM: accurate transcript quantification from RNA-Seq data with or without a reference genome. *BMC bioinformatics*, 12 (1), p.323.
38. Sainsbury, F., Thuenemann, E. C. and Lomonossoff, G. P., 2009. pEAQ: versatile expression vectors for easy and quick transient expression of heterologous proteins in plants. *Plant biotechnology journal*, 7 (7), pp. 682-693.
39. Ragland M, Soliman K M (1997) Sali5±4a and Sali3±2, two genes induced by aluminum in soybean roots. Plant Physiol 114:395
40. Tang, Y., Cao, Y., Qiu, J., Gao, Z., Ou, Z., Wang, Y. and Zheng, Y., 2014. Expression of a vacuole-localized BURP-domain protein from soybean (SALI3-2) enhances tolerance to cadmium and copper stresses. PloS one, 9 (6), p.e98830
41. Fazio, G. C., Xu, R. and Matsuda, S. P., 2004. Genome mining to identify new plant triterpenoids. Journal of the American Chemical Society, 126 (18), pp. 5678-5679.
42. Huang, A. C., Kautsar, S. A., Hong, Y. J., Medema, M. H., Bond, A. D., Tantillo, D. J. and Osbourn, A., 2017. Unearthing a sesterterpene biosynthetic repertoire in the Brassicaceae through genome mining reveals convergent evolution. Proceedings of the National Academy of Sciences, p.201705567.
43. Mohimani, H., Kersten, R. D., Liu, W. T., Wang, M., Purvine, S. O., Wu, S., Brewer, H. M., Pasa-Tolic, L., Bandeira, N., Moore, B. S. and Pevzner, P. A., 2014. Automated genome mining of ribosomal peptide natural products. ACS chemical biology, 9 (7), pp. 1545-1551.
44. Mylne, J. S., Chan, L. Y., Chanson, A. H., Daly, N. L., Schaefer, H., Bailey, T. L., Nguyencong, P., Cascales, L. and Craik, D. J., 2012. Cyclic peptides arising by evolutionary parallelism via asparaginyl-endopeptidase-mediated biosynthesis. The Plant Cell, 24 (7), pp. 2765-2778.
45. J. A. Condie, G. Nowak, D. W. Reed, J. J. Balsevich, M. J. Reaney, P. G. Arnison and P. S. Covello, Plant J., 2011, 67, 682.
46. Mylne, J. S., Colgrave, M. L., Daly, N. L., Chanson, A. H., Elliott, A. G., McCallum, E. J., Jones, A. and Craik, D. J., 2011. Albumins and their processing machinery are hijacked for cyclic peptides in sunflower. Nature Chemical Biology, 7 (5), pp. 257-259.
47. Saska, I., Gillon, A. D., Hatsugai, N., Dietzgen, R. G., Hara-Nishimura, I., Anderson, M. A. and Craik, D. J., 2007. An asparaginyl endopeptidase mediates in vivo protein backbone cyclization. Journal of Biological Chemistry, 282 (40), pp. 29721-29728.
48. Goodbody, A. E., Endo, T., Vukovic, J., Kutney, J. P., Choi, L. S. and Misawa, M., 1988. Enzymic coupling of catharanthine and vindoline to form 3',4'-anhydrovinblastine by horseradish peroxidase. Planta *medica*, 54 (02), pp. 136-140.
49. Sterjiades, R., Dean, J. F. and Eriksson, K. E. L., 1992. Laccase from sycamore maple (*Acer pseudoplatanus*) polymerizes monolignols. *Plant Physiology*, 99 (3), pp. 1162-1168.
50. Sainsbury, F., Thuenemann, E. C., and Lomonossoff, G. P. pEAQ: versatile expression vectors for easy and quick transient expression of heterologous proteins in plants. *Plant Biotechnol J.* 7 (7): 682-93 (2009).

51. Hernandez-Garcia, C. M. and Finer, J. J. Identification and validation of promoters and cis-acting regulatory elements. *Plant Sci.* 217-218 (2014) 109-119.

52. Morita, H., Yoshida, N., Takeya, K., Itokawa, H. & Shirota, O. Configurational and conformational analyses of a cyclic octapeptide, lyciumin A, from *Lycium chinense* Mill. *Tetrahedron* 52, 2795-2802 (1996).

References for Example 2

53. Albornos, L., Martín, I., Iglesias, R., Jiménez, T., Labrador, E., and Dopico, B. (2012). ST proteins, a new family of plant tandem repeat proteins with a DUF2775 domain mainly found in Fabaceae and Asteraceae. BMC Plant Biol. 12:207.

54. Arnison, P. G., Bibb, M. J., Bierbaum, G., Bowers, A. A., Bugni, T. S., Bulaj, G., Camarero, J. A., Campopiano, D. J., Challis, G. L., Clardy, J., et al. (2013). Ribosomally synthesized and post-translationally modified peptide natural products: overview and recommendations for a universal nomenclature. Nat. Prod. Rep. 30:108-160.

55. Bankevich, A., Nurk, S., Antipov, D., Gurevich, A. A., Dvorkin, M., Kulikov, A. S., Lesin, V. M., Nikolenko, S. I., Pham, S., Prjibelski, A. D., et al. (2012). SPAdes: a new genome assembly algorithm and its applications to single-cell sequencing. J. Comput. Biol. 19:455-477.

56. Banks, J. A. (2009). *Selaginella* and 400 million years of separation. Annu. Rev. Plant Biol. 60:223-238.

57. Barber, C. J. S., Pujara, P. T., Reed, D. W., Chiwocha, S., Zhang, H., and Covello, P. S. (2013). The Two-step Biosynthesis of Cyclic Peptides from Linear Precursors in a Member of the Plant Family Caryophyllaceae Involves Cyclization by a Serine Protease-like Enzyme. J. Biol. Chem. 288:12500-12510.

58. Bassüner, R., Bäumlein, H., Huth, A., Jung, R., Wobus, U., Rapoport, T. A., Saalbach, G., and Müntz, K. (1988). Abundant embryonic mRNA in field bean (*Vicia faba* L.) codes for a new class of seed proteins: cDNA cloning and characterization of the primary translation product. Plant Mol. Biol. 11:321-334.

59. Belknap, W. R., McCue, K. F., Harden, L. A., Vensel, W. H., Bausher, M. G., and Stover, E. (2015). A family of small cyclic amphipathic peptides (SCAmpPs) genes in citrus. BMC Genomics 16:303.

60. Boutilier, K. A., Ginés, M. J., DeMoor, J. M., Huang, B., Baszczynski, C. L., Iyer, V. N., and Miki, B. L. (1994). Expression of the BnmNAP subfamily of napin genes coincides with the induction of *Brassica* microspore embryogenesis. Plant Mol. Biol. 26:1711-1723.

61. Bushmanova, E., Antipov, D., Lapidus, A., and Przhibelskiy, A. D. (2018). rnaSPAdes: a de novo transcriptome assembler and its application to RNA-Seq data Advance Access published 2018, doi: 10.1101/420208.

62. Chekan, J. R., Estrada, P., Covello, P. S., and Nair, S. K. (2017). Characterization of the macrocyclase involved in the biosynthesis of RiPP cyclic peptides in plants. Proc. Natl. Acad. Sci. U.S.A 114:6551-6556.

63. Cheng, S., Melkonian, M., Smith, S. A., Brockington, S., Archibald, J. M., Delaux, P.-M., Li, F.-W., Melkonian, B., Mavrodiev, E. V., Sun, W., et al. (2018). 10KP: A phylodiverse genome sequencing plan. Gigascience 7:1-9.

64. Claeson, P., Göransson, U., Johansson, S., Luijendijk, T., and Bohlin, L. (1998). Fractionation Protocol for the Isolation of Polypeptides from Plant Biomass. J. Nat. Prod. 61:77-81.

65. Condie, J. A., Nowak, G., Reed, D. W., Balsevich, J. J., Reaney, M. J. T., Arnison, P. G., and Covello, P. S. (2011). The biosynthesis of Caryophyllaceae-like cyclic peptides in *Saponaria vaccaria* L. from DNA-encoded precursors. Plant J. 67:682-690.

66. Conlan, B. F., Gillon, A. D., Barbeta, B. L., and Anderson, M. A. (2011). Subcellular targeting and biosynthesis of cyclotides in plant cells. Am. J. Bot. 98:2018-2026.

67. Craik, D. J., Lee, M.-H., Rehm, F. B. H., Tombling, B., Doffek, B., and Peacock, H. (2018). Ribosomally-synthesised cyclic peptides from plants as drug leads and pharmaceutical scaffolds. Bioorg. Med. Chem. 26:2727-2737.

68. Dutton, J. L., Renda, R. F., Waine, C., Clark, R. J., Daly, N. L., Jennings, C. V., Anderson, M. A., and Craik, D. J. (2004). Conserved structural and sequence elements implicated in the processing of gene-encoded circular proteins. J. Biol. Chem. 279:46858-46867.

69. Edgar, R. C. (2004). MUSCLE: multiple sequence alignment with high accuracy and high throughput. Nucleic Acids Res. 32:1792-1797.

70. Gibson, D. G., Young, L., Chuang, R.-Y., Venter, J. C., Hutchison, C. A., 3rd, and Smith, H. O. (2009). Enzymatic assembly of DNA molecules up to several hundred kilobases. Nat. Methods 6:343-345.

71. Grabherr, M. G., Haas, B. J., Yassour, M., Levin, J. Z., Thompson, D. A., Amit, I., Adiconis, X., Fan, L., Raychowdhury, R., Zeng, Q., et al. (2011). Full-length transcriptome assembly from RNA-Seq data without a reference genome. Nat. Biotechnol. 29:644-652.

72. Griesmann, M., Chang, Y., Liu, X., Song, Y., Haberer, G., Crook, M. B., Billault-Penneteau, B., Lauressergues, D., Keller, J., Imanishi, L., et al. (2018). Phylogenomics reveals multiple losses of nitrogen-fixing root nodule symbiosis. Science 361.

73. Gruber, C. W., Cemazar, M., Clark, R. J., Horibe, T., Renda, R. F., Anderson, M. A., and Craik, D. J. (2007). A novel plant protein-disulfide isomerase involved in the oxidative folding of cystine knot defense proteins. J. Biol. Chem. 282:20435-20446.

74. Gui, B., Shim, Y. Y., Datla, R. S. S., Covello, P. S., Stone, S. L., and Reaney, M. J. T. (2012). Identification and Quantification of Cyclolinopeptides in Five Flaxseed Cultivars. J. Agric. Food Chem. 60:8571-8579.

75. Hernandez, J. F., Gagnon, J., Chiche, L., Nguyen, T. M., Andrieu, J. P., Heitz, A., Trinh Hong, T., Pham, T. T., and Le Nguyen, D. (2000). Squash trypsin inhibitors from *Momordica cochinchinensis* exhibit an atypical macrocyclic structure. Biochemistry 39:5722-5730.

76. James, A. M., Jayasena, A. S., Zhang, J., Berkowitz, O., Secco, D., Knott, G. J., Whelan, J., Bond, C. S., and Mylne, J. S. (2017). Evidence for Ancient Origins of Bowman-Birk Inhibitors from *Selaginella moellendorffii*. Plant Cell 29:461-473.

77. Jayasena, A. S., Fisher, M. F., Panero, J. L., Secco, D., Bernath-Levin, K., Berkowitz, O., Taylor, N. L., Schilling, E. E., Whelan, J., and Mylne, J. S. (2017). Stepwise Evolution of a Buried Inhibitor Peptide over 45 My. Mol. Biol. Evol. 34:1505-1516.

78. Jennings, C., West, J., Waine, C., Craik, D., and Anderson, M. (2001). Biosynthesis and insecticidal properties of plant cyclotides: the cyclic knotted proteins from *Oldenlandia affinis*. Proc. Natl. Acad. Sci. U.S.A 98:10614-10619.

79. Kaufmann, H. P., and Tobschirbel, A. (1959). Über ein Oligopeptid aus Leinsamen. Chem. Ber. 92:2805-2809.

80. Kersten, R. D., and Weng, J.-K. (2018). Gene-guided discovery and engineering of branched cyclic peptides in plants. Proc. Natl. Acad. Sci. U.S.A 115: E10961-E10969.
81. Koehbach, J., O'Brien, M., Muttenthaler, M., Miazzo, M., Akcan, M., Elliott, A. G., Daly, N. L., Harvey, P. J., Arrowsmith, S., Gunasekera, S., et al. (2013). Oxytocic plant cyclotides as templates for peptide G protein-coupled receptor ligand design. Proc. Natl. Acad. Sci. U.S.A 110:21183-21188.
82. Kumar, S., Stecher, G., and Tamura, K. (2016). MEGA7: Molecular Evolutionary Genetics Analysis Version 7.0 for Bigger Datasets. Mol. Biol. Evol. 33:1870-1874.
83. Luckett, S., Garcia, R. S., Barker, J. J., Konarev, A. V., Shewry, P. R., Clarke, A. R., and Brady, R. L. (1999). High-resolution structure of a potent, cyclic proteinase inhibitor from sunflower seeds. J. Mol. Biol. 290:525-533.
84. Matasci, N., Hung, L.-H., Yan, Z., Carpenter, E. J., Wickett, N. J., Mirarab, S., Nguyen, N., Warnow, T., Ayyampalayam, S., Barker, M., et al. (2014). Data access for the 1,000 Plants (1KP) project. Gigascience 3:17.
85. Mylne, J. S., Colgrave, M. L., Daly, N. L., Chanson, A. H., Elliott, A. G., McCallum, E. J., Jones, A., and Craik, D. J. (2011). Albumins and their processing machinery are hijacked for cyclic peptides in sunflower. Nat. Chem. Biol. 7:257-259.
86. Mylne, J. S., Chan, L. Y., Chanson, A. H., Daly, N. L., Schaefer, H., Bailey, T. L., Nguyencong, P., Cascales, L., and Craik, D. J. (2012). Cyclic peptides arising by evolutionary parallelism via asparaginyl-endopeptidase-mediated biosynthesis. Plant Cell 24:2765-2778.
87. Nei, M., and Kumar, S. (2000). Molecular Evolution and Phylogenetics. Oxford University Press, USA.
88. Nguyen, G. K. T., Lian, Y., Pang, E. W. H., Nguyen, P. Q. T., Tran, T. D., and Tam, J. P. (2013). Discovery of linear cyclotides in monocot plant Panicum laxum of Poaceae family provides new insights into evolution and distribution of cyclotides in plants. J. Biol. Chem. 288: 3370-3380.
89. Nguyen, G. K. T., Wang, S., Qiu, Y., Hemu, X., Lian, Y., and Tam, J. P. (2014). Butelase 1 is an Asx-specific ligase enabling peptide macrocyclization and synthesis. Nat. Chem. Biol. 10:732-738.
90. Park, S., Yoo, K.-O., Marcussen, T., Backlund, A., Jacobsson, E., Rosengren, K. J., Doo, I., and Göransson, U. (2017). Cyclotide Evolution: Insights from the Analyses of Their Precursor Sequences, Structures and Distribution in Violets ( ). Front. Plant Sci. 8:2058.
91. Poth, A. G., Colgrave, M. L., Lyons, R. E., Daly, N. L., and Craik, D. J. (2011). Discovery of an unusual biosynthetic origin for circular proteins in legumes. Proc. Natl. Acad. Sci. U.S.A 108:10127-10132.
92. Poth, A. G., Mylne, J. S., Grassl, J., Lyons, R. E., Millar, A. H., Colgrave, M. L., and Craik, D. J. (2012). Cyclotides associate with leaf vasculature and are the products of a novel precursor in petunia (Solanaceae). J. Biol. Chem. 287:27033-27046.
93. Priyam, A., Woodcroft, B. J., Rai, V., Munagala, A., Moghul, I., Ter, F., Gibbins, M. A., Moon, H., Leonard, G., Rumpf, W., et al. (2015). Sequenceserver: a modern graphical user interface for custom BLAST databases Advance Access published 2015, doi: 10.1101/033142.
94. Ragland, M., and Soliman, K. M. (1997). A molecular approach to understanding aluminum tolerance in soybean (Glycine max L.). In Global Environmental Biotechnology, pp. 125-138.
95. Saether, O., Craik, D. J., Campbell, I. D., Sletten, K., Juul, J., and Norman, D. G. (1995). Elucidation of the primary and three-dimensional structure of the uterotonic polypeptide kalata B1. Biochemistry 34:4147-4158.
96. Sainsbury, F., Thuenemann, E. C., and Lomonossoff, G. P. (2009). pEAQ: versatile expression vectors for easy and quick transient expression of heterologous proteins in plants. Plant Biotechnol. J. 7:682-693.
97. Saska, I., Gillon, A. D., Hatsugai, N., Dietzgen, R. G., Hara-Nishimura, I., Anderson, M. A., and Craik, D. J. (2007). An asparaginyl endopeptidase mediates in vivo protein backbone cyclization. J. Biol. Chem. 282:29721-29728.
98. Tan, N.-H., and Zhou, J. (2006). Plant Cyclopeptides. Chem. Rev. 106:840-895.
99. Tang, Y., Cao, Y., Gao, Z., Ou, Z., Wang, Y., Qiu, J., and Zheng, Y. (2014). Expression of a vacuole-localized BURP-domain protein from soybean (SALI3-2) enhances tolerance to cadmium and copper stresses. PLOS One 9: e98830.
100. van den Berg, A. J. J., S F A, den Bosch, J. J. K., Kroes, B. H., Beukelman, C. J., Leeflang, B. R., and Labadie, R. P. (1995). Curcacycline A—a novel cyclic octapeptide isolated from the latex of Jatropha curcasL. FEBS Lett. 358:215-218.
101. Wang, H., Zhou, L., Fu, Y., Cheung, M.-Y., Wong, F.-L., Phang, T.-H., Sun, Z., and Lam, H.-M. (2012). Expression of an apoplast-localized BURP-domain protein from soybean (GmRD22) enhances tolerance towards abiotic stress. Plant Cell Environ. 35:1932-1947. 102. Wang, M., Carver, J. J., Phelan, V. V., Sanchez, L. M., Garg, N., Peng, Y., Nguyen, D. D., Watrous, J., Kapono, C. A., Luzzatto-Knaan, T., et al. (2016). Sharing and community curation of mass spectrometry data with Global Natural Products Social Molecular Networking. Nat. Biotechnol. 34:828-837.
103. Weng, J.-K. (2014). The evolutionary paths towards complexity: a metabolic perspective. New Phytol. 201: 1141-1149.
104. Weng, J.-K., and Chapple, C. (2010). The origin and evolution of lignin biosynthesis. New Phytol. 187:273-285.
105. Weng, J.-K., Philippe, R. N., and Noel, J. P. (2012). The rise of chemodiversity in plants. Science 336:1667-1670.
106. Yamaguchi-Shinozaki, K., and Shinozaki, K. (1993). The plant hormone abscisic acid mediates the drought-induced expression but not the seed-specific expression of rd22, a gene responsive to dehydration stress in Arabidopsis thaliana. Mol. Gen. Genet. 238:17-25.
107. Zheng, L., Heupel, R. C., and DellaPenna, D. (1992). The b Subunit of Tomato Fruit Polygalacturonase Isoenzyme 1: Isolation, Characterization, and Identification of Unique Structural Features. Plant Cell 4:1147.

INCORPORATION BY REFERENCE; EQUIVALENTS

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method of producing one or more lyciumin cyclic peptides, the method comprising:
   a) providing a host cell comprising a transgene encoding a precursor peptide comprising: i) a signal peptide; ii) one or more peptide domains of eight amino acids comprising SEQ ID NO: 294; and iii) a BURP domain comprising two phenylalanine residues at its N-terminus, two cysteine residues, and four repeated cysteine-histidine motifs, arranged as SEQ ID NO: 282;
   b) expressing the transgene in the host cell to thereby produce the precursor peptide, wherein the precursor peptide is converted to one or more lyciumin cyclic peptides in the host cell; and
   c) isolating one or more of the lyciumin cyclic peptides from the host cell.

2. The method of claim 1, wherein the transgene is operably linked to a heterologous promoter in the host cell.

3. The method of claim 1, wherein the transgene is introduced in a vector.

4. The method of claim 1, further comprising introducing the transgene into the host cell.

5. The method of claim 1, wherein the precursor peptide comprises a plurality of peptide domains of eight amino acids comprising SEQ ID NO: 294.

6. The method of claim 5, wherein the plurality of peptide domains of eight amino acids comprising SEQ ID NO: 294 encode two or more lyciumin cyclic peptides having different amino acid sequences.

7. The method of claim 1, wherein the host cell expresses one or more enzymes that cyclize the precursor peptide; one or more endopeptidases; one or more glutamine cyclotransferases; and one or more exopeptidases, or a combination thereof.

8. The method of claim 1, wherein arginine is immediately N-terminal to the one or more peptide domains of eight amino acids comprising SEQ ID NO: 294.

9. The method of claim 7, wherein the endopeptidase is an arginine endopeptidase.

10. The method of claim 1, wherein tyrosine is immediately C-terminal to the one or more peptide domains of eight amino acids comprising SEQ ID NO: 294.

11. The method of claim 1, wherein the host cell is a plant cell.

12. The method of claim 11, wherein the plant cell is a Fabaceae family plant cell.

13. The method of claim 11, wherein the plant cell is a Solanaceae family plant cell.

14. The method of claim 13, wherein the plant cell is a *Nicotiana* genus plant cell.

15. The method of claim 14, wherein the plant cell is a *Nicotiana benthamiana* plant cell.

16. The method of claim 1, wherein the one or more peptide domains of eight amino acids comprises SEQ ID NO: 295.

17. The method of claim 1, wherein the one or more peptide domains of eight amino acids comprises SEQ ID NO: 296.

18. The method of claim 1, wherein the one or more peptide domains of eight amino acids comprises SEQ ID NO: 297.

19. The method of claim 1, wherein the one or more peptide domains of eight amino acids comprises proline or an alanine in the second position.

20. The method of claim 1, wherein the one or more peptide domains of eight amino acids comprises tyrosine, alanine, tryptophan, or phenylalanine in the third position.

21. The method of claim 1, wherein the one or more peptide domains of eight amino acids comprises glycine or threonine in the fourth position.

22. The method of claim 1, wherein the one or more peptide domains of eight amino acids comprises valine, alanine, or phenylalanine in the fifth position.

23. The method of claim 1, wherein the one or more peptide domains of eight amino acids comprises tyrosine, alanine, glycine, or phenylalanine in the sixth position.

24. The method of claim 1, wherein the one or more peptide domains of eight amino acids comprises threonine, alanine, serine, or phenylalanine in the seventh position.

25. The method of claim 1, wherein the one or more peptide domains of eight amino acids comprises tryptophan in the eighth position.

26. The method of claim 1, wherein the method further comprises assaying for an activity of interest the lyciumin peptide isolated from the host cell.

* * * * *